United States Patent
Wan et al.

(10) Patent No.: US 11,999,746 B2
(45) Date of Patent: *Jun. 4, 2024

(54) COMPOUNDS

(71) Applicant: GlaxoSmithKline Intellectual Property Development Limited, Brentford (GB)

(72) Inventors: Zehong Wan, Shanghai (CN); Xiaomin Zhang, Shanghai (CN); Jian Wang, Shanghai (CN); Matthew Robert Sender, Collegeville, PA (US); Eric Steven Manas, Collegeville, PA (US); Raphael Anthony Rivero, Collegeville, PA (US); Joseph E Pero, Collegeville, PA (US); Christopher Ernst Neipp, Collegeville, PA (US); Vipulkumar Kantibhai Patel, Stevenage (GB)

(73) Assignee: GlaxoSmithKline Intellectual Property Development Limited (GB)

( * ) Notice: Subject to any disclaimer, the term of this patent is extended or adjusted under 35 U.S.C. 154(b) by 1315 days.

This patent is subject to a terminal disclaimer.

(21) Appl. No.: 16/524,238

(22) Filed: Jul. 29, 2019

(65) Prior Publication Data

US 2020/0055863 A1 Feb. 20, 2020

Related U.S. Application Data

(63) Continuation of application No. 16/143,788, filed on Sep. 27, 2018, now Pat. No. 10,428,078, which is a continuation of application No. 15/327,706, filed as application No. PCT/CN2015/084606 on Jul. 21, 2015, now Pat. No. 10,125,141.

(30) Foreign Application Priority Data

Jul. 22, 2014 (WO) ............... PCT/CN2014/000695

(51) Int. Cl.
| | | |
|---|---|---|
| *C07D 487/14* | (2006.01) | |
| *C07D 471/14* | (2006.01) | |
| *C07D 471/20* | (2006.01) | |
| *C07D 487/04* | (2006.01) | |
| *C07D 491/20* | (2006.01) | |
| *C07D 498/14* | (2006.01) | |
| *C07D 513/14* | (2006.01) | |

(52) U.S. Cl.
CPC ......... *C07D 487/14* (2013.01); *C07D 471/14* (2013.01); *C07D 471/20* (2013.01); *C07D 487/04* (2013.01); *C07D 491/20* (2013.01); *C07D 498/14* (2013.01); *C07D 513/14* (2013.01); *H05K 999/99* (2013.01)

(58) Field of Classification Search
None
See application file for complete search history.

(56) References Cited

U.S. PATENT DOCUMENTS

| | | |
|---|---|---|
| 6,828,326 B2 | 12/2004 | Picard et al. |
| 8,772,303 B2 | 7/2014 | Van Schie |
| 8,975,400 B2 | 3/2015 | Wan et al. |
| 9,783,546 B2 | 10/2017 | Wan et al. |
| 10,125,141 B2 | 11/2018 | Wan et al. |
| 2013/0178488 A1 | 7/2013 | Wan et al. |
| 2014/0080055 A1 | 3/2014 | Hatakeyama et al. |
| 2019/0023715 A1 | 1/2019 | Wan et al. |

FOREIGN PATENT DOCUMENTS

| | | |
|---|---|---|
| CN | 103827118 | 5/2014 |
| CN | 103927116 A | 5/2014 |
| CN | 103842362 A | 6/2014 |
| WO | WO 2003/041712 A1 | 5/2003 |
| WO | WO 2009/147476 A1 | 12/2009 |
| WO | WO 2012/037782 A1 | 3/2012 |
| WO | WO 2013/013503 | 1/2013 |
| WO | WO 2013/014185 A1 | 1/2013 |
| WO | WO 2013/059278 A2 | 4/2013 |
| WO | WO 2014/114249 A1 | 7/2014 |
| WO | WO 2014/114694 A1 | 7/2014 |
| WO | WO 2016/011930 A1 | 1/2016 |
| WO | WO 2016/011931 A1 | 1/2016 |

*Primary Examiner* — Michael Barker
(74) *Attorney, Agent, or Firm* — Hao Yin

(57) ABSTRACT

The present invention relates to novel compounds that inhibit Lp-PLA$_2$ activity, processes for their preparation, to compositions containing them and to their use in the treatment of diseases associated with the activity of Lp-PLA$_2$, for example Alzheimer's disease.

14 Claims, No Drawings

COMPOUNDS

RELATED APPLICATION

The present application claims priority from PCT International Application No. PCT/CN2014/000695 filed on Jul. 22, 2014 at the State Intellectual Property Office of the People's Republic of China, the entire contents of which is incorporated herein by reference.

FIELD OF THE INVENTION

The present invention relates to novel tricyclic imidazopyrimidinone compounds, processes for their preparation, intermediates useful in their preparation, pharmaceutical compositions containing them, and their use in therapy for the treatment of diseases mediated by Lp-PLA$_2$.

BACKGROUND OF THE INVENTION

Lipoprotein-associated phospholipase A2 (Lp-PLA$_2$) previously known as platelet-activating factor acetylhydrolase (PAF-AH), is a phospholipase A2 enzyme involved in hydrolysis of lipoprotein lipids or phospholipids. Lp-PLA$_2$ travels with low-density lipoprotein (LDL) and rapidly cleaves oxidized phosphatidylcholine molecules derived from the oxidation of LDL. (See e.g., Zalewski A, et al., *Arterioscler. Thromb. Vasc. Biol.*, 25, 5, 923-31 (2005)). Lp-PLA$_2$ hydrolyzes the sn-2 ester of the oxidized phosphatidylcholines to give lipid mediators, lyso-phosphatidylcholine (lysoPC) and oxidized nonesterified fatty acids (NEFAs). It has been observed that lysoPC and NEFAs elicit inflammatory responses. (See e.g., Zalewski A, et al. (2005)).

A number of Lp-PLA$_2$ inhibitors and/or uses thereof have been previously described. (See. for example, published patent application nos. WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, and WO08/048866.) Disclosed uses include treating disease that involves or is associated with endothelial dysfunction, disease that involves lipid oxidation in conjunction with Lp-PLA$_2$ activity (e.g., associated with the formation of lysophosphatidylcholine and oxidized free fatty acids), and disease that involves activated monocytes, macrophages or lymphocytes or which is associated with increased involvement of monocytes, macrophages or lymphocytes. Examples of diseases include atherosclerosis (e.g. peripheral vascular atherosclerosis and cerebrovascular atherosclerosis), diabetes, hypertension, angina pectoris, after ischaemia and reperfusion, rheumatoid arthritis, stroke, inflammatory conditions of the brain such as Alzheimer's Disease, various neuropsychiatric disease such as schizophrenia, myocardial infarction, ischaemia, reperfusion injury, sepsis, acute and chronic inflammation, and psoriasis.

Lp-PLA$_2$ inhibitors and/or uses thereof are also reported, for example, in PCT Publication Nos. WO05/003118 (and its Canadian family member CA 2530816A1); WO06/063811; WO06/063813 and WO 2008/141176; JP 200188847; and US Published Patent Application Nos. US 2008/0279846 A1, US 2010/0239565 A1, and US 2008/0280829 A1.

Other researchers have studied the effects related to Lp-PLA$_2$ and inhibitors thereof. For example, research data has also indicated that LysoPC promotes atherosclerotic plaque development, which can ultimately lead to the formation of a necrotic core. (See e.g., Wlensky et al., *Current Opinion in Lipidology*, 20, 415-420 (2009)). In addition, the effect of Lp-PLA$_2$ inhibitors on atherosclerotic plaque composition was demonstrated in a diabetic and hypercholesterolemic porcine model of accelerated coronary atherosclerosis. (See e.g., Wilensky et al., *Nature Medicine*, 10, 1015-1016 (2008)). These research results provided further evidence that Lp-PLA$_2$ inhibitors may be used to treat atherosclerosis.

Additional studies indicate that high Lp-PLA$_2$ activity is associated with high risk of dementia, including Alzheimer's disease (AD) (See e.g., Van Oijen, et al. Annals of Neurology, 59,139 (2006)). Higher levels of oxidized LDL have also been observed in AD patients (See e.g., Kassner et al. *Current Alzheimer Research*, 5, 358-366 (2008); Dildar, et al., *Alzheimer Dis Assoc Disord*, 24, April-June (2010); Sinem, et al. *Current Alzheimer Research*, 7, 463-469 (2010)). Further, studies show that neuroinflammation is present in AD patients and multiple cytotoxic inflammatory cytokines are up-regulated in AD patients. (See e.g., Colangelo, et al., *Journal of Neuroscience Research*, 70, 462-473 (2002); Wyss-Coray, *Nature Medicine*, 12, September (2006)). Research has shown that LysoPC function is a pro-inflammatory factor inducing multiple cytotoxic inflammatory cytokine release (See Shi, et al. *Atherosclerosis*, 191, 54-62 (2007)). Therefore, these studies provide additional evidence that that the inhibitors of Lp-PLA$_2$ can be used to treat AD by inhibiting activity of Lp-PLA$_2$ and reducing lysoPC production.

In addition, use of an Lp-PLA$_2$ inhibitor in a diabetic and hypercholesterolemia swine model demonstrated that blood-brain-barrier leakage and brain amyloid beta protein (Aβ) burden, the pathological hallmarks of Alzheimer's disease, were reduced. (See U.S. Patent Application Publication No. 2008/0279846). This publication describes several uses of Lp-PLA$_2$ inhibitors for treating diseases associated with blood-brain-barrier leakage, including, e.g., Alzheimer's disease and vascular dementia.

Further, neuroinflammation, including multiple cytotoxic cytokine release, is a common feature of all neurodegenerative diseases including multiple sclerosis, amyotrophic lateral sclerosis, Parkinson's disease, Alzheimer's disease, etc. (See e.g., Perry, *Acta Neuropathol*, 120, 277-286 (2010)). As discussed above, Lp-PLA$_2$ inhibitors can reduce inflammation, for example, reducing multiple cytokine release by suppressing lysoPC production. (See e.g., Shi, et al. *Atherosclerosis* 191, 54-62 (2007)). Thus, inhibiting Lp-PLA$_2$ is a potential therapeutic treatment for neurodegenerative diseases including multiple sclerosis, amyotrophic lateral sclerosis, Parkinson's disease, etc.

In addition to the inflammatory effect, LysoPC has been implicated in leukocyte activation, induction of apoptosis and mediation of endothelial dysfunction (See, e.g., Wlensky et al., *Current Opinion in Lipidology*, 20, 415-420 (2009)). Therefore, it is believed that Lp-PLA$_2$ inhibitors can be used to treat tissue damage associated with diabetes by reducing the production of lysoPC, which can cause a continuous cycle of vascular inflammation and increased reactive oxygen species (ROS) production. In light of the inflammatory roles of Lp-PLA$_2$ and the association between localized inflammatory processes and diabetic retinopathy, it is postulated that Lp-PLA$_2$ can be used to treat diabetic ocular disease.

Glaucoma and age-related macular degeneration (AMD) are retina neurodegenerative diseases. Studies suggest that inflammation, including TNF-alpha signaling, may play an important role in the pathogenesis of glaucoma and AMD (See e.g., Buschini et al., *Progress in Neurobiology*, 95, 14-25 (2011); Tezel, *Progress in Brain Research*, vol. 173, ISSN0079-6123, Chapter 28). Thus, considering Lp-PLA$_2$ inhibitors' function of blocking inflammatory cytokine release (See e.g., Shi, et al. *Atherosclerosis*, 191, 54-62 (2007)), it is believed that Lp-PLA$_2$ inhibitors can provide a potential therapeutic application for both glaucoma and AMD.

In view of the number of pathological responses that are mediated by Lp-PLA$_2$, attempts have been made to prepare compounds that inhibit its activity. Though a number of such compounds have been disclosed in the art, there remains a continuing need for inhibitors of Lp-PLA$_2$ which can be used in the treatment of a variety of conditions.

SUMMARY OF THE INVENTION

In a first aspect, this invention relates to compounds of Formula (I-1) and salts (e.g., pharmaceutically acceptable salts) thereof,

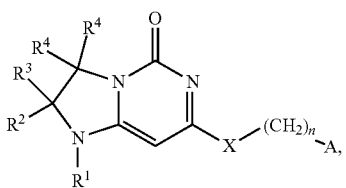

Formula (I-1)

wherein
- $R^1$ is selected from the group consisting of H, $C_{1-3}$alkyl and —C(O)—$C_{1-3}$alkyl; and
- $R^2$ and $R^3$ together with the carbon to which they are attached form a 4, 5 or 6 membered saturated ring, which ring
  - optionally contains one heteroatom ring member selected from N or O, and
  - is optionally substituted with one substituent of -L-K, wherein
    - L is selected from the group consisting of C(O), CH$_2$, and S(O)$_2$, and
    - K is selected from the group consisting of $C_{1-3}$alkyl, phenyl, and $C_{3-6}$cycloalkyl;
- or $R^1$ and $R^2$ together with the nitrogen and carbon to which they are attached form a 5 or 6-membered heterocyclic saturated ring, which ring
  - optionally contains one or two additional heteroatom ring member independently selected from the group consisting of N, O, C(O), S, S(O), and S(O)$_2$, and
  - is optionally substituted with one or more substituents independently selected from the group consisting of OH, halo, NR$^{1a}$R$^{1b}$, COOH, and —Y—R$^c$, wherein
    - Y is absent or is selected from the group consisting of C(O), S(O)$_2$, —C(O)—C(O)—, and CH$_2$, and
    - R$^c$ is selected from the group consisting of
      - $C_{1-5}$alkyl optionally substituted with one or more substituents independently selected from the group consisting of NR$^{2a}$R$^{2b}$, $C_{3-6}$ cycloalkyl, and —COOH,
      - $C_{1-3}$haloalkyl,
      - $C_{1-3}$ alkoxyl,
      - NR$^{3a}$R$^{3b}$,
      - —(CH$_2$)$_p$—C(O)—O—$C_{1-3}$ alkyl, wherein p is 1, 2, or 3 and the —(CH$_2$)$_p$— is optionally substituted by one or more methyl,
      - —(CH$_2$)$_q$—$C_{3-6}$cycloalkyl wherein q is 1, 2, or 3, wherein the cycloalkyl is optionally substituted with NR$^{4a}$R$^{4b}$ and the —(CH$_2$)$_q$— is optionally substituted by one or more methyl, and
      - heterocyclyl optionally substituted with one or more substituents independently selected from the group consisting of halo and NR$^{5a}$R$^{5b}$,
    - wherein R$^{1a}$, R$^{1b}$, R$^{2a}$, R$^{2b}$, R$^{3a}$, R$^{3b}$, R$^{4a}$, R$^{5b}$, R$^{5a}$, and R$^{5b}$ are independently H or $C_{1-3}$alkyl; and
- $R^3$ is H;
- each occurrence of $R^4$ is independently H or D;
- X is absent or is selected from the group consisting of
  - —O—,
  - —NH—, and
  - N—(C$_{1-3}$alkyl)-,
- n is 1 or 2;
- or X is —O—CH$_2$-bicyclo[1.1.1]pentanyl-CH$_2$—O— and n is 0; and
- A is unsubstituted thiophenyl, or
- A is

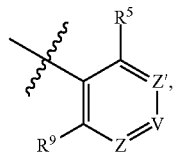

wherein
- $R^5$ and $R^9$ are independently H or halo,
- Z' is N or CR$^6$,
- Z is N or CR$^8$,
  - wherein R$^6$ and R$^8$ are independently selected from the group consisting of H, CN, halo, C$_{1-3}$alkyl, C$_{1-3}$haloalkyl, —S(O)$_2$—C$_{1-3}$alkyl and —S(O)—O$_{1-3}$alkyl, and
- V is N or CR$^7$, wherein R$^7$ is selected from the group consisting of H, halo, CN, C$_{1-3}$alkyl, C$_{1-3}$haloalkyl, and —S(O)$_2$—C$_{1-3}$ alkyl, or R$^7$ is -Q-(CH$_2$)$_m$—W, wherein
  - Q is O, N, or CH$_2$,
  - m is 0 or 1, and
  - W is selected from the group consisting of $C_{3-6}$ cycloalkyl, heterocyclyl, 5 or 6 membered heteroaryl and phenyl, wherein said cycloalkyl, heterocyclyl, heteroaryl or phenyl is optionally substituted with one or more substituents independently selected from the group consisting of C$_{1-3}$haloalkyl, CN, halo and C$_{1-5}$ alkyl;
- or when Z or Z' is CR$^6$ and V is CR$^7$, R$^6$ and R$^7$ together may form a 4,7-dioxaspiro[2.6]nonane;

with the proviso that the compound of Formula (I-1) is not
- 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
- 7-(2,3-difluorophenethyl)-3,4,11,11a-tetrahydro-1H-pyrazino[1',2':3,4]imidazo[1,2-c]pyrimidin-9(2H)-one,
- 7-((2,3-difluorobenzyl)amino)-11,11a-dihydro-1H-pyrazino[1',2':3,4]imidazo[1,2-c]pyrimidine-3,9(2H, 4H)-dione, 7-((3,4-difluorobenzyl)amino)-3,4,11,11a-tetrahydropyrimido[6',1':2,3]imidazo[5,1-c][1,4]thiazin-9(1H)-one 2,2-dioxide, 7-((2,3-difluorobenzyl)amino)-3,4,11,11a-tetrahydropyrimido[6',1':2,3]imidazo[5,1-c][1,4]thiazin-9(1H)-one-2-oxide, 7-((2,3-difluorobenzyl)amino)-3,4,11,11a-tetrahydropyrimido[6',1':2,3]imidazo[5,1-c][1,4]thiazin-9(1H)-one-2,2-dioxide, 7-(2,3-difluorophenethyl)-3,4,11,11a-tetrahydropyrimido[6',1':2,3]imidazo[5,1-c][1,4]thiazin-9(1H)-one, 4-(((1'-methyl-5'-oxo-3',5'-dihydro-1'H-spiro[cyclobutane-1,2'-imidazo[1,2-c]pyrimidin]-7'-yl)oxy)methyl)benzonitrile, 4-(((1'-methyl-5'-oxo-3',5'-dihydro-1'H-spiro[cyclopentane-1,2'-imidazo[1,2-c]pyrimidin]-7'-yl)oxy)methyl)benzonitrile, or 4-(((1'-methyl-5'-oxo-3',5'-dihydro-1'H-spiro[cyclohexane-1,2'-imidazo[1,2-c]pyrimidin]-7'-yl)oxy)methyl)benzonitrile.

This invention also relates to a pharmaceutical composition comprising compounds of this invention and a pharmaceutically acceptable excipient.

The invention also relates to methods of treating or preventing a disease associated with the activity of Lp-PLA$_2$, which comprises administering to a subject in need thereof with a therapeutically effective amount of a compound of the invention described herein. The disease may be associated with the increased involvement of monocytes, macrophages or lymphocytes; with the formation of lysophosphatidylcholine and oxidized free fatty acids; with lipid oxidation in conjunction with Lp-PLA$_2$ activity; or with endothelial dysfunction.

This invention also provides methods of treating or preventing a disease by inhibiting Lp-PLA$_2$ activity. Exemplary diseases include, but are not limited to, neurodegeneration disease (e.g., Alzheimer's disease, Parkinson's disease, Huntington's disease, vascular dementia), atherosclerosis, stroke, metabolic bone disorder (e.g., bone marrow abnormalities), dyslipidemia, Paget's diseases, type II diabetes, metabolic syndrome, insulin resistance, and hyperparathyroidism, diabetic ocular disorder (e.g., macular edema, diabetic retinopathy, and posterior uveitis), macular edema, wound healing, rheumatoid arthritis, chronic obstructive pulmonary disease (COPD), psoriasis, and multiple sclerosis. The methods comprise administering a therapeutically effective amount of a compound of this invention to a subject in need thereof. It is not intended that the present invention is limited to any particular stage of the disease (e.g. early or advanced).

This invention also provides methods of treating or preventing Alzheimer's disease. The methods comprise administering to a subject in need thereof a therapeutically effective amount of a compound of this invention.

This invention also provides methods of treating or preventing atherosclerosis. The methods comprise administering to a subject in need thereof a therapeutically effective amount of a compound of this invention.

This invention also provides methods of decreasing beta amyloid (also referred to as "Aβ") accumulation in the brain of a subject. The methods comprise administering to a subject in need thereof a therapeutically effective amount of a compound of the present invention. In certain embodiment, the beta amyloid is Abeta-42.

This invention also provides methods for treating or preventing ocular diseases by administering a compound of this invention. In certain embodiment, this invention provides methods of treating macular edema, which comprises administering to the subject a therapeutically effective amount of a compound of this invention. In certain embodiment, the macular edema is associated with diabetic ocular disease, for example, diabetic macular edema or diabetic retinopathy. In one embodiment, the macular edema is associated with posterior uveitis.

This invention also provides a use of compounds of this invention in the manufacture of a medicament for treating or preventing diseases described herein.

This invention also provides compounds of this invention for use in the treatment or prevention described herein.

DETAILED DESCRIPTION OF THE INVENTION

As used in the description of the embodiments of the invention and the appended claims, the singular forms "a", "an" and "the" are intended to include the plural forms as well, unless the context clearly indicates otherwise. Also, as used herein, "and/or" refers to encompasses any and all possible combinations of one or more of the associated listed items. It will be further understood that the terms "comprises" and/or "comprising" when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

A. Definitions

As used herein, unless otherwise indicated, "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complaint, interdisposition and/or affectation.

As used herein, unless otherwise indicated, "neurodegeneration disease" as used herein refers to a varied assortment of central nervous system disorder characterized by gradual and progressive loss of neural tissue and/or neural tissue function. A neurodegeneration disease is a class of neurological disease where the neurological disease is characterized by a gradual and progressive loss of neural tissue, and/or altered neurological function, typically reduced neurological function as a result of a gradual and progressive loss of neural tissue. In certain embodiments, the neurodegeneration diseases described herein include neurodegeneration diseases where there is a defective blood brain barrier, for example a permeable blood brain barrier. Examples of neurodegeneration diseases where there is a defective blood brain barrier include, but are not limited to, Alzheimer's disease, Huntington's disease, Parkinson's disease, vascular dementia and the like.

As used herein, unless otherwise indicated, "vascular dementia" is also referred to as "multi-infarct dementia", which refers to a group of syndromes caused by different mechanisms, which all result in vascular lesions in the brain. The main subtypes of vascular dementia are, for example, vascular mild cognitive impairment, multi-infarct dementia, vascular dementia due to a strategic single infarct, (affecting the thalamus, the anterior cerebral artery, the parietal lobes or the cingulated gyrus), vascular dementia due to hemorrhagic lesions, small vessel disease (including, e.g. vascular dementia due to lacunar lesions and Binswanger disease), and mixed dementia.

As used herein, unless otherwise indicated, "blood-brain barrier" or "BBB" are used interchangeably herein, and are used to refer to the permeable barrier that exists in blood vessels as they travel through the brain tissue that severely restricts and closely regulates what is exchanged between the blood and the brain tissue. The blood brain barrier components include the endothelial cells that form the innermost lining of all blood vessels, the tight junctions between adjacent endothelial cells that are structural correlate of the BBB, the basement membrane of endothelial cells and the expanded foot process of nearby astrocytes which cover nearly all of the exposed outer surface of the blood vessel.

As used herein, unless otherwise indicated, "metabolic bone disease" as used herein refers to a varied assortment of bone diseases characterized by gradual and progressive loss of bone tissue. Metabolic bone diseases described herein are metabolic bone diseases where there is a condition of diffusely decreased bone density and/or diminished bone strength. Such diseases are characterized by histological appearance. Exemplary metabolic bone diseases include, but are not limited to, osteoporosis which is characterized by decreased mineral and bone matrix, and osteomalacia which is characterized by decreased mineral but intact bone matrix.

As used herein, unless otherwise indicated, "osteopenic diseases" or "osteopenia" are used interchangeably herein, and refer to conditions with decreased calcification and/or bone density, and is a descriptive term used to refer to all skeletal systems in which decreased calcification and/or bone density is observed. Osteopenia also refers to a reduced bone mass due to inadequate osteoid synthesis.

As used herein, unless otherwise indicated, "osteoporosis" refers to conditions in which mineral and/or bone matrix are decreased and/or bone mass is reduced.

As used herein, unless otherwise indicated, "alkyl" is a monovalent, saturated hydrocarbon chain having a specified number of carbon atoms. For example, $C_{1-3}$alkyl refers to an alkyl group having from 1 to 3 carbon atoms. $C_{1-5}$alkyl refers to an alkyl group having from 1 to 5 carbon atoms. Alkyl groups may be straight or branched. In some embodiments, branched alkyl groups may have one, two, or three branches. Exemplary alkyl groups include, but are not limited to, methyl, methylethyl, ethyl, propyl (n-propyl and isopropyl), butyl (n-butyl, isobutyl, and tert-butyl).

As used herein unless otherwise indicated, "alkoxy" substituent is a group of formula "R—O—", where R is alkyl as defined above. For example, $C_{1-3}$alkoxy refers to such an alkoxy substituent containing 1 to 3 carbons. Exemplary alkoxy substituents include, but are not limited to, methoxy, ethoxy, n-propoxy, n-butoxy, n-pentoxy, n-hexyloxy, isopropoxy, isobutoxy, secbutoxy, tert-butoxy, isopentoxy and neopentoxy. In one embodiment, $C_{1-3}$alkoxy refers to methoxy, ethoxy, n-propoxy and isopropoxy.

As used herein, unless otherwise indicated, "$C_{3-6}$cycloalkyl" is a monovalent radical derived by removal of a hydrogen atom from a 3, 4, 5 or 6-membered monocyclic cycloalkane. Exemplary cycloalkyl include, but are not limited to, cyclopropyl, cyclobutyl, cyclopentyl and cyclohexyl.

As used herein, unless otherwise indicated, "heteroaryl" is a monovalent radical derived by removal of a hydrogen atom from a monocyclic 5 or 6-membered heteroaromatic ring, which ring consists of ring-carbon atoms and ring-heteroatoms selected from the group consisting of nitrogen, oxygen and sulphur, and which ring is aromatic. For example, heteroaryl is monocyclic heteroaryl consisting of 5 or 6 ring-atoms, 1 to 3 of which are ring-heteroatoms. Exemplary heteroaryls include, but are not limited to, furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, triazinyl, azepinyl, oxazepinyl, thiazepinyl and diazepinyl. In one embodiment, the heteroaryl refers to pyridinyl, primidinyl and pyrazolyl.

As used herein, unless otherwise indicated, "heterocyclyl" is a monovalent radical derived by removal of a hydrogen atom from a 3, 4, 5 or 6-membered saturated monocyclic heterocyclic ring, which ring consists of ring-carbon atoms and ring-heteroatoms selected from the group consisting of nitrogen, oxygen and sulfur. In one embodiment, heterocyclyl is monocyclic saturated heterocyclyl consisting of 3 to 6 ring-atoms, and 1 or 2 of which are ring-heteroatoms. Exemplary monocyclic saturated heterocyclyl substituents include, but are not limited to, pyrrolidinyl, dioxolanyl, imidazolidinyl, pyrazolidinyl, piperidinyl, dioxanyl, morpholino, dithianyl, thiomorpholino and piperazinyl. In an embodiment, the heterocycly refers to azetidinyl, piperidinyl, pyrrolidinyl and tetrahydro-2H-pyranyl.

As used herein, unless otherwise indicated, "halogen" refers to fluorine (F), chlorine (Cl), bromine (Br), or iodine (I). Halo refers to the halogen radicals: fluoro (—F), chloro (—Cl), bromo (—Br), or iodo (—I). In one embodiment, halo refers to F.

As used herein, unless otherwise indicated, "haloalkyl" is an alkyl group substituted by one or more halo substituents, which halo substituents may be the same or different. For example, $C_{1-3}$haloalkyl refers to a haloalkyl substituent containing 1 to 3 carbons. Exemplary haloalkyl substituents include, but are not limited to, monofluoromethyl, difluoromethyl, trifluoromethyl, 1-chloro-2-fluoroethyl, trifluoropropyl, 3-fluoropropyl, and 2-fluoroethyl. In one embodiment, $C_{1-3}$haloalkyl refers to trifluoromethyl, trifluoropropyl, 3-fluoropropyl and 2-fluoroethyl.

As used herein, unless otherwise indicated, when two substituents on a ring together with their interconnecting atom(s) combine to form a further ring, this ring may be spiro fused or orthofused. A spiro-fused ring system consists of two rings which have only one carbon atom in common. An ortho-fused ring system consists of two rings which have only two atoms and one bond in common.

As used herein, unless otherwise indicated, "optionally substituted" indicates that a group or a ring may be unsubstituted, or the group or a ring may be substituted with one or more substituent as defined herein.

As used herein, unless otherwise indicated, "4, 5 or 6 membered saturated ring, which ring optionally contains one heteroatom ring member selected from N or O" reference to 4, 5 or 6 membered saturated carbon ring and one carbon atom ring member can be optionally replaced with one heteroatom selected from N or O, for example, cyclobutanyl, cyclopentanyl, cyclohexanyl, azitidinyl, pyrrolidinyl, piperidinyl, oxetanyl, tetrahydrofuranyl, and tetrahydro-2H-pyranyl.

As used herein, unless otherwise indicated, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom. Suitable substituents are defined herein for each substituted or optionally substituted group.

As used herein, unless otherwise indicated, "treat", "treating" or "treatment" in reference to a disease means: (1) to ameliorate the disease or one or more of the biological manifestations of the disease (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease. In one embodiment, "treat" "treating" or "treatment" in reference to Alzheimer's disease means: to slow the progression of congnitive function decline.

As used herein, unless otherwise indicated, "prevent", "preventing" or "prevention" means the prophylactic administration of a drug to diminish the likelihood of the onset of or to delay the onset of a disease or biological manifestation thereof.

As used herein, unless otherwise indicated, "subject" means a mammalian subject (e.g., dog, cat, horse, cow, sheep, goat, monkey, etc.), and particularly human subjects including both male and female subjects, and including neonatal, infant, juvenile, adolescent, adult and geriatric subjects, and further including various races and ethnicities including, but not limited to, white, black, Asian, American Indian and Hispanic.

As used herein, unless otherwise indicated, "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, unless otherwise indicated, the term "therapeutically effective amount" means any amount which, as compared to a corresponding subject who has not received such amount, results in treating or preventing a disease, but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

B. Compounds

In a first aspect, this invention relates to compounds of Formula (I) and salts (e.g., pharmaceutically acceptable salts) thereof,

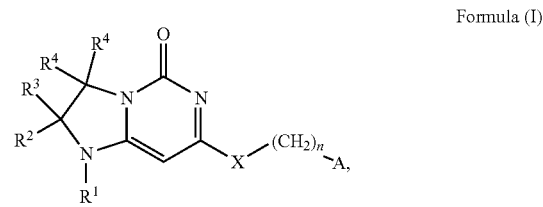

Formula (I)

wherein
$R^1$ is selected from the group consisting of H, $C_{1-3}$alkyl and —C(O)—$C_{1-3}$alkyl; and
$R^2$ and $R^3$ together with the carbon to which they are attached form a 4, 5 or 6 membered saturated ring, which ring
optionally contains one heteroatom ring member selected from N or O, and
is optionally substituted with one substituent of -L-K, wherein
L is selected from the group consisting of C(O), $CH_2$, and $S(O)_2$, and
K is selected from the group consisting of $C_{1-3}$alkyl, phenyl, and $C_{3-6}$cycloalkyl;
or $R^1$ and $R^2$ together with the nitrogen and carbon to which they are attached form a 5 or 6-membered heterocyclic saturated ring, which ring
optionally contains one or two additional heteroatom ring member independently selected from the group consisting of N, O, C(O), S, S(O), and $S(O)_2$, and
is optionally substituted with one or more (e.g., one, or one or two) substituents independently selected from the group consisting of OH, halo, $NR^{1a}R^{1b}$, COOH, and —Y—$R^c$, wherein
Y is absent or is selected from the group consisting of C(O), $S(O)_2$, —C(O)—C(O)—, and $CH_2$, and
$R^c$ is selected from the group consisting of
$C_{1-5}$alkyl optionally substituted with one or more (e.g., one, one or two, or one, two or three) substituents independently selected from the group consisting of $NR^{2a}R^{2b}$, $C_{3-6}$ cycloalkyl, and —COOH,
$C_{1-3}$haloalkyl,
$C_{1-3}$alkoxyl,
$NR^{3a}R^{3b}$,
—$(CH_2)_p$—C(O)—O—$C_{1-3}$alkyl, wherein p is 1, 2, or 3 and the —$(CH_2)_p$— is optionally substituted by one or more (e.g., one or one or two) methyl,
—$(CH_2)_q$—$C_{3-6}$cycloalkyl, wherein q is 1, 2, or 3, wherein the cycloalkyl is optionally substituted with NR$^{4a}$R$^{4b}$, and the —(CH$_2$)$_q$— is optionally substituted by one or more (e.g., one or one or two) methyl, and heterocyclyl optionally substituted with one or more (e.g., one or one or two) substituents independently selected from the group consisting of halo and NR$^{5a}$R$^{5b}$, wherein R$^{1a}$, R$^{1b}$, R$^{2a}$, R$^{2b}$, R$^{3a}$, R$^{3b}$, R$^{4a}$, R$^{4b}$, R$^{5a}$, and R$^{5b}$ are independently H or C$_{1-3}$alkyl; and R$^3$ is H;

each occurrence of R$^4$ is independently H or D;

X is absent or is selected from the group consisting of
—O—,
—NH—, and
N—(O$_{1-3}$alkyl)-, n is 1 or 2;

or X is —O—CH$_2$-bicyclo[1.1.1]pentanyl-CH$_2$—O— and n is 0; and

A is unsubstituted thiophenyl, or

A is

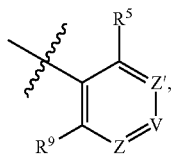

wherein
R$^5$ and R$^9$ are independently H or halo,
Z' is N or CR$^6$,
Z is N or CR$^8$,
wherein R$^6$ and R$^8$ are independently selected from the group consisting of H, CN, halo, C$_{1-3}$alkyl, C$_{1-3}$haloalkyl, —S(O)$_2$—O$_{1-3}$alkyl and —S(O)—C$_{1-3}$alkyl, and
V is N or CR$^7$, wherein R$^7$ is selected from the group consisting of H, halo, CN, C$_{1-3}$ alkyl, C$_{1-3}$haloalkyl, and —S(O)$_2$—C$_{1-3}$ alkyl, or R$^7$ is -Q-(CH$_2$)$_m$—W, wherein
Q is O, N, or CH$_2$,
m is 0 or 1, and
W is selected from the group consisting of 03.6 cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of C$_{1-3}$haloalkyl, CN, halo and C$_{1-5}$ alkyl;
or when Z or Z' is CR$^6$ and V is CR$^7$, R$^6$ and R$^7$ together may form a 4,7-dioxaspiro[2.6]nonane;

with the proviso that the compound of Formula (I) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2':3,4]imidazo[1,2-c]pyrimidine-3,9(2H,4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide, or
7-((2,3-difluorobenzyl)amino)-3,4,11,11a-tetrahydropyrimido[6',1':2,3]imidazo[5,1-c][1,4]thiazin-9(1H)-one-2,2-dioxide.

This invention provides, in a further aspect, compounds of Formula (I-1) and pharmaceutically acceptable salts thereof:

Formula (I-1)

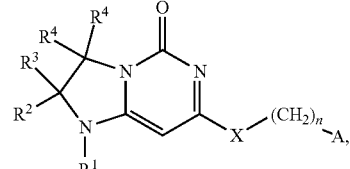

wherein
R$^1$ is selected from the group consisting of H, C$_{1-3}$alkyl and —C(O)—C$_{1-3}$alkyl; and R$^2$ and R$^3$ together with the carbon to which they are attached form a 4, 5 or 6 membered saturated ring, which ring
optionally contains one heteroatom ring member selected from N or O, and
is optionally substituted with one substituent of -L-K, wherein
L is selected from the group consisting of C(O), CH$_2$, and S(O)$_2$, and
K is selected from the group consisting of C$_{1-3}$alkyl, phenyl, and C$_{3-6}$cycloalkyl;

or R$^1$ and R$^2$ together with the nitrogen and carbon to which they are attached form a 5 or 6-membered heterocyclic saturated ring, which ring
optionally contains one or two additional heteroatom ring member independently selected from the group consisting of N, O, C(O), S, S(O), and S(O)$_2$, and
is optionally substituted with one or more (e.g., one, or one or two) substituents independently selected from the group consisting of OH, halo, NR$^{1a}$R$^{1b}$, COOH, and —Y—R$^c$, wherein
Y is absent or is selected from the group consisting of C(O), S(O)$_2$, —C(O)—C(O)—, and CH$_2$, and
R$^c$ is selected from the group consisting of
C$_{1-5}$alkyl optionally substituted with one or more (e.g., one, one or two, or one, two or three) substituents independently selected from the group consisting of NR$^{2a}$R$^{2b}$, C$_{3-6}$ cycloalkyl, and —COOH,
C$_{1-3}$ haloalkyl,
C$_{1-3}$ alkoxyl,
NR$^{3a}$R$^{3b}$,
—(CH$_2$)$_p$—C(O)—O—C$_{1-3}$ alkyl, wherein p is 1, 2, or 3 and the —(CH$_2$)$_p$— is optionally substituted by one or more (e.g., one or one or two) methyl,
—(CH$_2$)$_q$—C$_{3-6}$ cycloalkyl wherein q is 1, 2, or 3, wherein the cycloalkyl is optionally substituted with NR$^{4a}$R$^{4b}$, and the —(CH$_2$)$_q$— is optionally substituted by one or more (e.g., one or one or two) methyl, and
heterocyclyl optionally substituted with one or more (e.g., one or one or two) substituents independently selected from the group consisting of halo and NR$^{5a}$R$^{5b}$,
wherein R$^{1a}$, R$^{1b}$, R$^{2a}$, R$^{2b}$, R$^{3a}$, R$^{3b}$, R$^{4a}$, R$^{4b}$, R$^{5a}$, and R$^{5b}$ are independently H or C$_{1-3}$alkyl; and R³ is H;
each occurrence of R⁴ is independently H or D;
X is absent or is selected from the group consisting of
—O—,
—NH—, and
—N (C₁₋₃ alkyl)-,
n is 1 or 2;
or X is —O—CH₂-bicyclo[1.1.1]pentanyl-CH₂—O— and n is 0; and
A is unsubstituted thiophenyl, or
A is

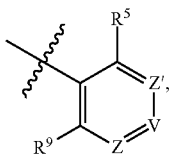

wherein
R⁵ and R⁹ are independently H or halo,
Z' is N or CR⁶,
Z is N or CR⁸,
  wherein R⁶ and R⁸ are independently selected from the group consisting of H, CN, halo, C₁₋₃alkyl, C₁₋₃haloalkyl, —S(O)₂—C₁₋₃ alkyl and —S(O)—C₁₋₃alkyl, and
V is N or CR⁷, wherein R⁷ is selected from the group consisting of H, halo, CN, C₁₋₃alkyl, C₁₋₃haloalkyl, and —S(O)₂—C₁₋₃ alkyl, or R⁷ is -Q-(CH₂)ₘ—W, wherein
  Q is O, N, or CH₂,
  m is 0 or 1, and
  W is selected from the group consisting of C₃₋₆cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of C₁₋₃haloalkyl, CN, halo and C₁₋₅alkyl;
  or when Z or Z' is CR⁶ and V is CR⁷, R⁶ and R⁷ together may form a 4,7-dioxaspiro[2.6]nonane;
with the proviso that the compound of Formula (I-1) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2':3,4]imidazo[1,2-c]pyrimidine-3,9(2H,4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide,
7-((2,3-difluorobenzyl)amino)-3,4,11,11a-tetrahydropyrimido[6',1':2,3]imidazo[5,1-c][1,4]thiazin-9(1H)-one-2,2-dioxide,
7-(2,3-difluorophenethyl)-3,4,11,11a-tetrahydropyrimido[6',1':2,3]imidazo[5,1-c][1,4]thiazin-9(1H)-one,
4-(((1'-methyl-5'-oxo-3',5'-dihydro-1'H-spiro[cyclobutane-1,2'-imidazo[1,2-c]pyrimidin]-7'-yl)oxy)methyl)benzonitrile,
4-(((1'-methyl-5'-oxo-3',5'-dihydro-1'H-spiro[cyclopentane-1,2'-imidazo[1,2-c]pyrimidin]-7'-yl)oxy)methyl)benzonitrile, or
4-(((1'-methyl-5'-oxo-3',5'-dihydro-1'H-spiro[cyclohexane-1,2'-imidazo[1,2-c]pyrimidin]-7'-yl)oxy)methyl)benzonitrile.

In one embodiment, this invention relates to compounds of Formula (I-2) and pharmaceutically acceptable salts thereof:

Formula (I-2)

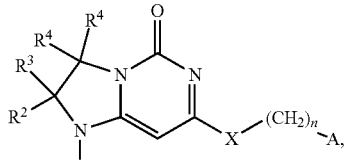

wherein
R¹ is selected from the group consisting of H, C₁₋₃alkyl and —C(O)—C₁₋₃alkyl; and
R² and R³ together with the carbon to which they are attached form a 4, 5 or 6 membered saturated ring, which ring
  optionally contains one heteroatom ring member selected from N or O, and
  is optionally substituted with one substituent of -L-K, wherein
    L is selected from the group consisting of C(O), CH₂, and S(O)₂, and
    K is selected from the group consisting of C₁₋₃alkyl, phenyl, and C₃₋₆cycloalkyl;
or R¹ and R² together with the nitrogen and carbon to which they are attached form a 5 or 6-membered heterocyclic saturated ring, which ring
  optionally contains one or two additional heteroatom ring member independently selected from the group consisting of N, O, C(O), S, S(O), and S(O)₂, and
  is optionally substituted with one or more (e.g., one, or one or two) substituents independently selected from the group consisting of OH, halo, NR¹ᵃR¹ᵇ, COOH, and —Y—Rᶜ, wherein
    Y is absent or is selected from the group consisting of C(O), S(O)₂, —C(O)—C(O)—, and CH₂, and
    Rᶜ is selected from the group consisting of
      C₁₋₅alkyl optionally substituted with one or more (e.g., one, one or two, or one, two or three) substituents independently selected from the group consisting of NR²ᵃR²ᵇ, C₃₋₆ cycloalkyl, and —COOH,
      C₁₋₃ haloalkyl,
      C₁₋₃ alkoxyl,
      NR³ᵃR³ᵇ,
      —(CH₂)ₚ—C(O)—O—C₁₋₃alkyl, wherein p is 1, 2, or 3 and the —(CH₂)ₚ— is optionally substituted by one or more (e.g., one or one or two) methyl,
      —(CH₂)_q—C₃₋₆ cycloalkyl, wherein q is 1, 2, or 3, wherein the cycloalkyl is optionally substituted with NR⁴ᵃR⁴ᵇ and the —(CH₂)_q— is optionally substituted by one or more (e.g., one or one or two) methyl, and
      heterocyclyl optionally substituted with one or more (e.g., one or one or two) substituents independently selected from the group consisting of halo and $NR^{5a}R^{5b}$,
wherein $R^{1a}$, $R^{1b}$, $R^{2a}$, $R^{2b}$, $R^{3a}$, $R^{3b}$, $R^{4a}$, $R^{5b}$, $R^{5a}$, and $R^{5b}$ are independently H or $C_{1-3}$alkyl; and $R^3$ is H;
each occurrence of $R^4$ is independently H or D;
X is absent or is selected from the group consisting of
—O—,
—NH—, and
—N ($C_{1-3}$ alkyl)-,
n is 1 or 2;
or X is —O—CH$_2$-bicyclo[1.1.1]pentanyl-CH$_2$—O— and n is 0; and
A is unsubstituted thiophenyl, or
A is

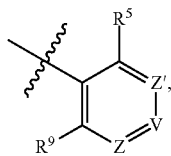

wherein
$R^5$ and $R^9$ are independently H or halo,
Z' is N or $CR^6$,
Z is N or $CR^8$,
wherein $R^6$ and $R^8$ are independently selected from the group consisting of H, CN, halo, $C_{1-3}$alkyl, $C_{1-3}$haloalkyl, —S(O)$_2$—$C_{1-3}$ alkyl and —S(O)—$C_{1-3}$alkyl, and
V is N or $CR^7$, wherein $R^7$ is selected from the group consisting of H, halo, CN, $C_{1-3}$alkyl, $C_{1-3}$haloalkyl, and —S(O)$_2$—$C_{1-3}$ alkyl, or $R^7$ is -Q-(CH$_2$)$_m$—W, wherein
Q is O, N, or CH$_2$,
m is 0 or 1, and
W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$alkyl;
or when Z or Z' is $CR^6$ and V is $CR^7$, $R^6$ and $R^7$ together may form a 4,7-dioxaspiro[2.6]nonane;
with the proviso that the compound of Formula (I-2) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2':3,4]imidazo[1,2-c]pyrimidine-3,9(2H,4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide,
7-((2,3-difluorobenzyl)amino)-3,4,11,11a-tetrahydropyrimido[6',1':2,3]imidazo[5,1-c][1,4]thiazin-9(1H)-one-2,2-dioxide,
7-(2,3-difluorophenethyl)-3,4,11,11a-tetrahydropyrimido[6',1':2,3]imidazo[5,1-c][1,4]thiazin-9(1H)-one,
4-(((1'-methyl-5'-oxo-3',5'-dihydro-1'H-spiro[cyclobutane-1,2'-imidazo[1,2-c]pyrimidin]-7'-yl)oxy)methyl)benzonitrile,
4-(((1'-methyl-5'-oxo-3',5'-dihydro-1'H-spiro[cyclopentane-1,2'-imidazo[1,2-c]pyrimidin]-7'-yl)oxy)methyl)benzonitrile, or
4-(((1'-methyl-5'-oxo-3',5'-dihydro-1'H-spiro[cyclohexane-1,2'-imidazo[1,2-c]pyrimidin]-7'-yl)oxy)methyl)benzonitrile,
and the compound of Formula (I-2) is not

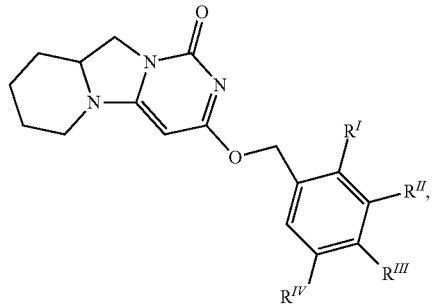

Formula (Z)

wherein
$R^I$ is H or F;
$R^{II}$ is selected from the group consisting of H, halo, CN, and $CF_3$;
$R^{III}$ is selected from the group consisting of H, F, CN, $CF_3$, $CH_3$, and —O—Y, wherein
Y is a phenyl, pyridinyl or pyrimidinyl, wherein the phenyl, pyridinyl or pyrimidinyl is substituted with one or more substituents independently selected from the group consisting of halo, $CF_3$ and CN; and
$R^{IV}$ is selected from the group consisting of CN, H, F and $CH_3$.

This invention provides, in a further aspect, compounds of Formula (I-3) and pharmaceutically acceptable salts thereof:

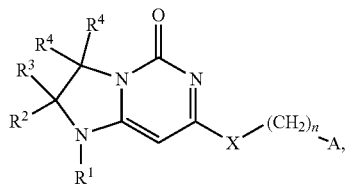

Formula (I-3)

wherein
$R^1$ is selected from the group consisting of H, $C_{1-3}$alkyl and —C(O)—$C_{1-3}$alkyl; and
$R^2$ and $R^3$ together with the carbon to which they are attached form a 4, 5 or 6 membered saturated ring, which ring
optionally contains one heteroatom ring member selected from N or O, and
is optionally substituted with one substituent of -L-K, wherein
L is selected from the group consisting of C(O), CH$_2$, and S(O)$_2$, and K is selected from the group consisting of $C_{1-3}$alkyl, phenyl, and $C_{3-6}$cycloalkyl;

or $R^1$ and $R^2$ together with the nitrogen and carbon to which they are attached form a 5-membered heterocyclic saturated ring, which ring optionally contains one or two additional heteroatom ring member independently selected from the group consisting of N, O, C(O), S, S(O), and $S(O)_2$, and is optionally substituted with one or more (e.g., one, or one or two) substituents independently selected from the group consisting of OH, halo, $NR^{1a}R^{1b}$, COOH, and —Y—$R^c$, wherein Y is absent or is selected from the group consisting of C(O), $S(O)_2$, —C(O)—C(O)—, and $CH_2$, and $R^c$ is selected from the group consisting of $C_{1-5}$alkyl optionally substituted with one or more (e.g., one, one or two, or one, two or three) substituents independently selected from the group consisting of $NR^{2a}R^{2b}$, $C_{3-6}$cycloalkyl, and —COOH, $C_{1-3}$haloalkyl, $C_{1-3}$alkoxyl, $NR^{3a}R^{3b}$, —$(CH_2)_p$—C(O)—O—$C_{1-3}$ alkyl, wherein p is 1, 2, or 3 and the —$(CH_2)_p$— is optionally substituted by one or more (e.g., one or one or two) methyl, —$(CH_2)_q$—$C_{3-6}$cycloalkyl, wherein q is 1, 2, or 3 wherein the cycloalkyl is optionally substituted with $NR^{4a}R^{4b}$ and the —$(CH_2)_q$— is optionally substituted by one or more (e.g., one or one or two) methyl, and heterocyclyl optionally substituted with one or more (e.g., one or one or two) substituents independently selected from the group consisting of halo and $NR^{5a}R^{5b}$, wherein $R^{1a}$, $R^{1b}$, $R^{2a}$, $R^{2b}$, $R^{3a}$, $R^{3b}$, $R^{4a}$, $R^{5b}$, $R^{5a}$, and $R^{5b}$ are independently H or $C_{1-3}$alkyl; and $R^3$ is H;

each occurrence of $R^4$ is independently H or D;

X is absent or is selected from the group consisting of —O—,

—NH—, and

—N ($C_{1-3}$ alkyl)-, n is 1 or 2;

or X is —O—$CH_2$-bicyclo[1.1.1]pentanyl-$CH_2$—O— and n is 0; and

A is unsubstituted thiophenyl, or

A is

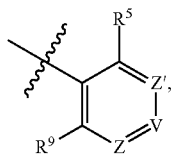

wherein $R^5$ and $R^9$ are independently H or halo,

Z' is N or $CR^6$,

Z is N or $CR^8$, wherein $R^6$ and $R^8$ are independently selected from the group consisting of H, CN, halo, $C_{1-3}$alkyl, $C_{1-3}$haloalkyl, —$S(O)_2$—$C_{1-3}$alkyl and —S(O)—$C_{1-3}$alkyl, and V is N or $CR^7$, wherein $R^7$ is selected from the group consisting of H, halo, CN, $C_{1-3}$alkyl, $C_{1-3}$haloalkyl, and —$S(O)_2$—$C_{1-3}$alkyl, or $R^7$ is -Q-$(CH_2)_m$—W, wherein Q is O, N, or $CH_2$, m is 0 or 1, and W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$alkyl;

or when Z or Z' is $CR^6$ and V is $CR^7$, $R^6$ and $R^7$ together may form a 4,7-dioxaspiro[2.6]nonane, with the proviso that the compound of Formula (I-2) is not 4-(((1'-methyl-5'-oxo-3',5'-dihydro-1'H-spiro[cyclobutane-1,2'-imidazo[1,2-c]pyrimidin]-7'-yl)oxy)methyl)benzonitrile, 4-(((1'-methyl-5'-oxo-3',5'-dihydro-1'H-spiro[cyclopentane-1,2'-imidazo[1,2-c]pyrimidin]-7'-yl)oxy)methyl)benzonitrile, or 4-(((1'-methyl-5'-oxo-3',5'-dihydro-1'H-spiro[cyclohexane-1,2'-imidazo[1,2-c]pyrimidin]-7'-yl)oxy)methyl)benzonitrile.

This invention provides, in a further aspect, compounds of Formula (I-4) and pharmaceutically acceptable salts thereof:

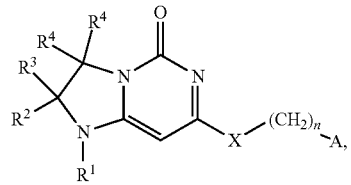

Formula (I-4)

wherein $R^1$ is selected from the group consisting of H, $C_{1-3}$alkyl and —C(O)—$C_{1-3}$alkyl; and $R^2$ and $R^3$ together with the carbon to which they are attached form a 4, 5 or 6 membered saturated ring, which ring optionally contains one heteroatom ring member selected from N or O, and is optionally substituted with one substituent of -L-K, wherein L is selected from the group consisting of C(O), $CH_2$, and $S(O)_2$, and K is selected from the group consisting of $C_{1-3}$alkyl, phenyl, and $C_{3-6}$cycloalkyl;

or $R^1$ and $R^2$ together with the nitrogen and carbon to which they are attached form a 6-membered heterocyclic saturated ring, which ring optionally contains one or two additional heteroatom ring member independently selected from the group consisting of N, O, C(O), S, S(O), and $S(O)_2$, and is optionally substituted with one or more (e.g., one, or one or two) substituents independently selected from the group consisting of OH, halo, $NR^{1a}R^{1b}$, COOH, and —Y—$R^c$, wherein Y is absent or is selected from the group consisting of C(O), $S(O)_2$, —C(O)—C(O)—, and $CH_2$, and R$^c$ is selected from the group consisting of
C$_{1-5}$alkyl optionally substituted with one or more (e.g., one, one or two, or one, two or three) substituents independently selected from the group consisting of NR$^{2a}$R$^{2b}$, C$_{3-6}$ cycloalkyl, and —COOH,
C$_{1-3}$ haloalkyl,
C$_{1-3}$ alkoxyl,
NR$^{3a}$R$^{3b}$,
—(CH$_2$)$_p$—C(O)—O—C$_{1-3}$ alkyl, wherein p is 1, 2, or 3 and the —(CH$_2$)$_p$— is optionally substituted by one or more (e.g., one or one or two) methyl,
—(CH$_2$)$_q$—C$_{3-6}$ cycloalkyl, wherein q is 1, 2, or 3 wherein the cycloalkyl is optionally substituted with NR$^{4a}$R$^{4b}$, and the —(CH$_2$)$_q$— is optionally substituted by one or more (e.g., one or one or two) methyl, and
heterocyclyl optionally substituted with one or more (e.g., one or one or two) substituents independently selected from the group consisting of halo and NR$^{5a}$R$^{5b}$,
wherein R$^{1a}$, R$^{1b}$, R$^{2a}$, R$^{2b}$, R$^{3a}$, R$^{3b}$, R$^{4a}$, R$^{5b}$, R$^{5a}$, and R$^{5b}$ are independently H or C$_{1-3}$alkyl; and
R$^3$ is H;
each occurrence of R$^4$ is independently H or D;
X is absent or is selected from the group consisting of
—O—,
—NH—, and
—N (C$_{1-3}$alkyl)-,
n is 1 or 2;
or X is —O—CH$_2$-bicyclo[1.1.1]pentanyl-CH$_2$—O— and n is 0; and
A is unsubstituted thiophenyl, or
A is

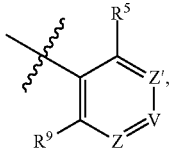

wherein
R$^5$ and R$^9$ are independently H or halo,
Z' is N or CR$^6$,
Z is N or CR$^8$,
wherein R$^6$ and R$^8$ are independently selected from the group consisting of H, CN, halo, C$_{1-3}$alkyl, C$_{1-3}$haloalkyl, —S(O)$_2$—C$_{1-3}$alkyl and —S(O)—C$_{1-3}$alkyl, and
V is N or CR$^7$, wherein R$^7$ is selected from the group consisting of H, halo, CN, C$_{1-3}$alkyl, C$_{1-3}$haloalkyl, and —S(O)$_2$—C$_{1-3}$ alkyl, or R$^7$ is -Q-(CH$_2$)$_m$—W, wherein
Q is O, N, or CH$_2$,
m is 0 or 1, and
W is selected from the group consisting of C$_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, one or one or two) substituents independently selected from the group consisting of C$_{1-3}$haloalkyl, CN, halo and C$_{1-5}$alkyl;

or when Z or Z' is CR$^6$ and V is CR$^7$, R$^6$ and R$^7$ together may form a 4,7-dioxaspiro[2.6]nonane;
with the proviso that the compound of Formula (I-4) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2':3,4]imidazo[1,2-c]pyrimidine-3,9(2H,4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide,
7-((2,3-difluorobenzyl)amino)-3,4,11,11a-tetrahydropyrimido[6',1':2,3]imidazo[5,1-c][1,4]thiazin-9(1H)-one-2,2-dioxide,
7-(2,3-Difluorophenethyl)-3,4,11,11a-tetrahydropyrimido[6',1':2,3]imidazo[5,1-c][1,4]thiazin-9(1H)-one,
4-(((1'-methyl-5'-oxo-3',5'-dihydro-1'H-spiro[cyclobutane-1,2'-imidazo[1,2-c]pyrimidin]-7'-yl)oxy)methyl)benzonitrile,
4-(((1'-methyl-5'-oxo-3',5'-dihydro-1'H-spiro[cyclopentane-1,2'-imidazo[1,2-c]pyrimidin]-7'-yl)oxy)methyl)benzonitrile, or
4-(((1'-methyl-5'-oxo-3',5'-dihydro-1'H-spiro[cyclohexane-1,2'-imidazo[1,2-c]pyrimidin]-7'-yl)oxy)methyl)benzonitrile.

In one embodiment, this invention relates to compounds of Formula (I-5) and pharmaceutically acceptable salts thereof:

Formula (I-5)

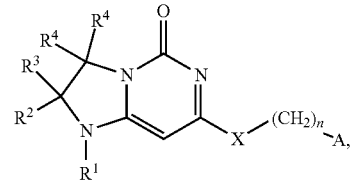

wherein
R$^1$ is selected from the group consisting of H, C$_{1-3}$alkyl and —C(O)—C$_{1-3}$alkyl; and
R$^2$ and R$^3$ together with the carbon to which they are attached form a 4, 5 or 6 membered saturated ring, which ring
optionally contains one heteroatom ring member selected from N or O, and
is optionally substituted with one substituent of -L-K, wherein
L is selected from the group consisting of C(O), CH$_2$, and S(O)$_2$, and
K is selected from the group consisting of C$_{1-3}$alkyl, phenyl, and C$_{3-6}$cycloalkyl;
or R$^1$ and R$^2$ together with the nitrogen and carbon to which they are attached form a 6-membered heterocyclic saturated ring, which ring
optionally contains one or two additional heteroatom ring member independently selected from the group consisting of N, O, C(O), S, S(O), and S(O)$_2$, and is optionally substituted with one or more (e.g., one, or one or two) substituents independently selected from the group consisting of OH, halo, $NR^{1a}R^{1b}$, COOH, and —Y—$R^c$, wherein
  Y is absent or is selected from the group consisting of C(O), S(O)$_2$, —C(O)—C(O)—, and CH$_2$, and $R^c$ is selected from the group consisting of
    $C_{1-5}$alkyl optionally substituted with one or more (e.g., one, one or two, or one, two or three) substituents independently selected from the group consisting of $NR^{2a}R^{2b}$, $C_{3-6}$ cycloalkyl, and —COOH,
    $C_{1-3}$haloalkyl,
    $C_{1-3}$alkoxyl,
    $NR^{3a}R^{3b}$,
    —(CH$_2$)$_p$—C(O)—O—$C_{1-3}$ alkyl, wherein p is 1, 2, or 3 and the —(CH$_2$)$_p$— is optionally substituted by one or more (e.g., one or one or two) methyl,
    —(CH$_2$)$_q$—$C_{3-6}$ cycloalkyl, wherein q is 1, 2, or 3 wherein the cycloalkyl is optionally substituted with $NR^{4a}R^{4b}$ and the —(CH$_2$)$_q$— is optionally substituted by one or more (e.g., one or one or two) methyl, and
    heterocyclyl optionally substituted with one or more (e.g., one or one or two) substituents independently selected from the group consisting of halo and $NR^{5a}R^{5b}$,
    wherein $R^{1a}$, $R^{1b}$, $R^{2a}$, $R^{2b}$, $R^{3a}$, $R^{3b}$, $R^{4a}$, $R^{5b}$, $R^{5a}$, and $R^{5b}$ are independently H or $C_{1-3}$alkyl; and
$R^3$ is H;
each occurrence of $R^4$ is independently H or D;
X is absent or is selected from the group consisting of
  —O—,
  —NH—, and
  —N ($C_{1-3}$ alkyl)-,
n is 1 or 2;
or X is —O—CH$_2$— bicyclo[1.1.1]pentanyl-CH$_2$—O— and n is 0; and
A is unsubstituted thiophenyl, or
A is

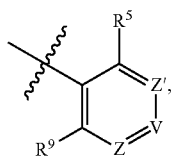

wherein
$R^5$ and $R^9$ are independently H or halo,
Z' is N or $CR^6$,
Z is N or $CR^8$,
  wherein $R^6$ and $R^8$ are independently selected from the group consisting of H, CN, halo, $C_{1-3}$alkyl, $C_{1-3}$haloalkyl, —S(O)$_2$—$C_{1-3}$ alkyl and —S(O)—$C_{1-3}$alkyl, and
V is N or $CR^7$, wherein $R^7$ is selected from the group consisting of H, halo, CN, $C_{1-3}$alkyl, $C_{1-3}$haloalkyl, and —S(O)$_2$—$C_{1-3}$ alkyl, or $R^7$ is -Q-(CH$_2$)$_m$—W, wherein
  Q is O, N, or CH$_2$,
  m is 0 or 1, and
  W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$alkyl;
  or when Z or Z' is $CR^6$ and V is $CR^7$, $R^6$ and $R^7$ together may form a 4,7-dioxaspiro[2.6]nonane;
with the proviso that the compound of Formula (I-5) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2':3,4]imidazo[1,2-c]pyrimidine-3,9(2H,4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide,
7-((2,3-difluorobenzyl)amino)-3,4,11,11a-tetrahydropyrimido[6',1':2,3]imidazo[5,1-c][1,4]thiazin-9(1H)-one-2,2-dioxide,
7-(2,3-Difluorophenethyl)-3,4,11,11a-tetrahydropyrimido[6',1':2,3]imidazo[5,1-c][1,4]thiazin-9(1H)-one,
4-(((1'-methyl-5'-oxo-3',5'-dihydro-1'H-spiro[cyclobutane-1,2'-imidazo[1,2-c]pyrimidin]-7'-yl)oxy)methyl)benzonitrile,
4-(((1'-methyl-5'-oxo-3',5'-dihydro-1'H-spiro[cyclopentane-1,2'-imidazo[1,2-c]pyrimidin]-7'-yl)oxy)methyl)benzonitrile, or
4-(((1'-methyl-5'-oxo-3',5'-dihydro-1'H-spiro[cyclohexane-1,2'-imidazo[1,2-c]pyrimidin]-7'-yl)oxy)methyl)benzonitrile,
and the compound of Formula (I-5) is not Formula (Z)

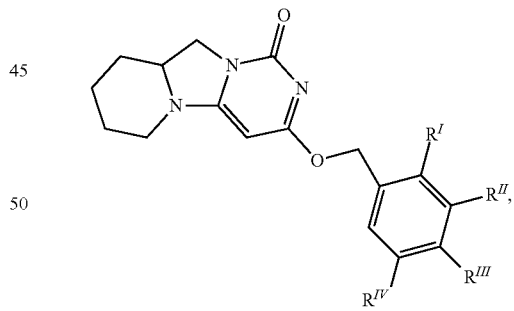

wherein
$R^I$ is H or F;
$R^{II}$ is selected from the group consisting of H, halo, CN, and $CF_3$;
$R^{III}$ is selected from the group consisting of H, F, CN, $CF_3$, $CH_3$, and —O—Y, wherein Y is a phenyl, pyridinyl or pyrimidinyl, wherein the phenyl, pyridinyl or pyrimidinyl is substituted with one or more substituents independently selected from the group consisting of halo, $CF_3$ and CN; and
$R^{IV}$ is selected from the group consisting of CN, H, F and $CH_3$.

In a further embodiment, the present invention provides compounds of Formula (II-1) and pharmaceutically acceptable salts thereof

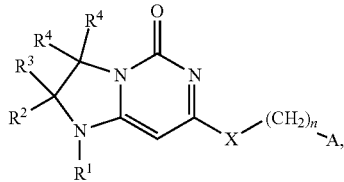

Formula (II-1)

wherein $R^1$ and $R^2$ together with the nitrogen and carbon to which they are attached form a 5 or 6-membered heterocyclic saturated ring, which ring optionally contains one or two additional heteroatom ring member independently selected from the group consisting of N, O, C(O), S, S(O), and S(O)$_2$, and is optionally substituted with one or more (e.g., one, or one or two) substituents independently selected from the group consisting of OH, halo, NR$^{1a}$R$^{1b}$, COOH, and —Y—R$^c$, wherein Y is absent or is selected from the group consisting of C(O), S(O)$_2$, —C(O)—C(O)—, and CH$_2$, and R$^c$ is selected from the group consisting of $C_{1-5}$alkyl optionally substituted with one or more (e.g., one, one or two, or one, two or three) substituents independently selected from the group consisting of NR$^{2a}$R$^{2b}$, $C_{3-6}$cycloalkyl, and —COOH, $C_{1-3}$ haloalkyl, $C_{1-3}$ alkoxyl, NR$^{3a}$R$^{3b}$, —(CH$_2$)$_p$—C(O)—O—$C_{1-3}$ alkyl, wherein p is 1, 2, or 3 and the —(CH$_2$)$_p$— is optionally substituted by one or more (e.g., one or one or two) methyl, —(CH$_2$)$_q$—$C_{3-6}$cycloalkyl, wherein q is 1, 2, or 3, wherein the cycloalkyl is optionally substituted with NR$^{4a}$R$^{4b}$, and the —(CH$_2$)$_q$— is optionally substituted by one or more (e.g., one or one or two) methyl, and heterocyclyl optionally substituted with one or more (e.g., one or one or two) substituents independently selected from the group consisting of halo and NR$^{5a}$R$^{5b}$, wherein R$^{1a}$, R$^{1b}$, R$^{2a}$, R$^{2b}$, R$^{3a}$, R$^{3b}$, R$^{4a}$, R$^{5b}$, R$^{5a}$, and R$^{5b}$ are independently H or $C_{1-3}$alkyl; and R$^3$ is H;

each occurrence of R$^4$ is independently H or D;

X is absent or is selected from the group consisting of

—O—,

—NH—, and

—N (C$_{1-3}$alkyl)-, n is 0, 1 or 2;

or X is —O—CH$_2$-bicyclo[1.1.1]pentanyl-CH$_2$—O— and n is 0; and

A is unsubstituted thiophenyl, or

A is

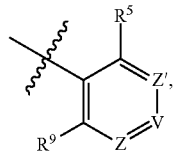

wherein

R$^5$ and R$^9$ are independently H or halo,

Z' is N or CR$^6$,

Z is N or CR$^8$, wherein R$^6$ and R$^8$ are independently selected from the group consisting of H, CN, halo, $C_{1-3}$alkyl, $C_{1-3}$haloalkyl, —S(O)$_2$—$C_{1-3}$alkyl and —S(O)—$C_{1-3}$alkyl, and V is N or CR$^7$, wherein R$^7$ is selected from the group consisting of H, halo, CN, $C_{1-3}$alkyl, $C_{1-3}$ alkyl, $C_{1-3}$haloalkyl, and —S(O)$_2$—$C_{1-3}$ alkyl, or R$^7$ is -Q-(CH$_2$)$_m$—W, wherein Q is O, N, or CH$_2$, m is 0 or 1, and W is selected from the group consisting of $C_{3-6}$ cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$alkyl;

or when Z or Z' is CR$^6$ and V is CR$^7$, R$^6$ and R$^7$ together may form a 4,7-dioxaspiro[2.6]nonane, with the proviso that the compound of Formula (II-1) is not 2-fluoro-5-(((9-oxo-2,3,4,9,11,11a-hexahydro-1H-pyrazino[1',2':3,4]imidazo[1,2-c]pyrimidin-7-yl)oxy) methyl)benzonitrile, 7-(2,3-difluorophenethyl)-3,4,11,11a-tetrahydro-1H-pyrazino[1',2':3,4]imidazo[1,2-c]pyrimidin-9(2H)-one, 7-((2,3-difluorobenzyl)amino)-11,11a-dihydro-1H-pyrazino[1',2':3,4]imidazo[1,2-c]pyrimidine-3,9(2H, 4H)-dione, 7-((3,4-difluorobenzyl)amino)-3,4,11,11a-tetrahydropyrimido[6',1':2,3]imidazo[5,1-c][1,4]thiazin-9(1H)-one 2,2-dioxide, 7-((2,3-difluorobenzyl)amino)-3,4,11,11a-tetrahydropyrimido[6',1':2,3]imidazo[5,1-c][1,4]thiazin-9(1H)-one-2-oxide, 7-((2,3-difluorobenzyl)amino)-3,4,11,11a-tetrahydropyrimido[6',1':2,3]imidazo[5,1-c][1,4]thiazin-9(1H)-one-2,2-dioxide, and 7-(2,3-Difluorophenethyl)-3,4,11,11a-tetrahydropyrimido[6',1':2,3]imidazo[5,1-c][1,4]thiazin-9(1H)-one.

In a further embodiment, the present invention provides compounds of Formula (II-2) and pharmaceutically acceptable salts thereof

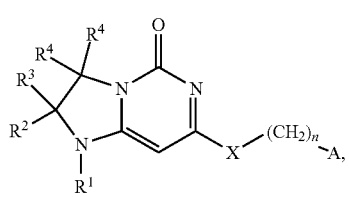

Formula (II-2)

wherein
R$^1$ and R$^2$ together with the nitrogen and carbon to which they are attached form a 5 or 6-membered heterocyclic saturated ring, which ring
optionally contains one or two additional heteroatom ring member independently selected from the group consisting of N, O, C(O), S, S(O), and S(O)$_2$, and
is optionally substituted with one or more (e.g., one, or one or two) substituents independently selected from the group consisting of OH, halo, NR$^{1a}$R$^{1b}$, COOH, and —Y—R$^c$, wherein
Y is absent or is selected from the group consisting of C(O), S(O)$_2$, —C(O)—C(O)—, and CH$_2$, and R$^c$ is selected from the group consisting of
C$_{1-5}$alkyl optionally substituted with one or more (e.g., one, one or two, or one, two or three) substituents independently selected from the group consisting of NR$^{2a}$R$^{2b}$, C$_{3-6}$ cycloalkyl, and —COOH,
C$_{1-3}$haloalkyl,
C$_{1-3}$alkoxyl,
NR$^{3a}$R$^{3b}$,
—(CH$_2$)$_p$—C(O)—O—C$_{1-3}$ alkyl, wherein p is 1, 2, or 3 and the —(CH$_2$)$_p$— is optionally substituted by one or more (e.g., one or one or two) methyl,
—(CH$_2$)$_q$—C$_{3-6}$ cycloalkyl, wherein q is 1, 2, or 3, wherein the cycloalkyl is optionally substituted with NR$^{4a}$R$^{4b}$ and the —(CH$_2$)$_q$— is optionally substituted by one or more (e.g., one or one or two) methyl, and
heterocyclyl optionally substituted with one or more (e.g., one or one or two) substituents independently selected from the group consisting of halo and NR$^{5a}$R$^{5b}$,
wherein R$^{1a}$, R$^{1b}$, R$^{2a}$, R$^{2b}$, R$^{3a}$, R$^{3b}$, R$^{4a}$, R$^{5b}$, R$^{5a}$, and R$^{5b}$ are independently H or C$_{1-3}$alkyl; and
R$^3$ is H;
each occurrence of R$^4$ is independently H or D;
X is absent or is selected from the group consisting of
—O—,
—NH—, and
—N (C$_{1-3}$ alkyl)-,
n is 0, 1 or 2;
or X is —O—CH$_2$— bicyclo[1.1.1]pentanyl-CH$_2$—O—, and n is 0; and
A is unsubstituted thiophenyl, or
A is

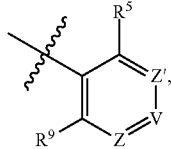

wherein
R$^5$ and R$^9$ are independently H or halo,
Z' is N or CR$^6$,
Z is N or CR$^8$,
wherein R$^6$ and R$^8$ are independently selected from the group consisting of H, CN, halo, C$_{1-3}$alkyl, C$_{1-3}$haloalkyl, —S(O)$_2$—C$_{1-3}$ alkyl and —S(O)—C$_{1-3}$alkyl, and V is N or CR$^7$, wherein R$^7$ is selected from the group consisting of H, halo, CN, C$_{1-3}$alkyl, C$_{1-3}$ alkyl, C$_{1-3}$haloalkyl, and —S(O)$_2$—C$_{1-3}$ alkyl, or R$^7$ is -Q-(CH$_2$)$_m$—W, wherein
Q is O, N, or CH$_2$,
m is 0 or 1, and
W is selected from the group consisting of C$_{3-6}$ cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of C$_{1-3}$haloalkyl, CN, halo and C$_{1-5}$alkyl;
or when Z or Z' is CR$^6$ and V is CR$^7$, R$^6$ and R$^7$ together may form a 4,7-dioxaspiro[2.6]nonane,
with the proviso that the compound of Formula (II-2) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile,
7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2':3,4]imidazo[1,2-c]pyrimidine-3,9(2H, 4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide,
7-((2,3-difluorobenzyl)amino)-3,4,11,11a-tetrahydropyrimido[6',1':2,3]imidazo[5,1-c][1,4]thiazin-9(1H)-one-2,2-dioxide, or
7-(2,3-Difluorophenethyl)-3,4,11,11a-tetrahydropyrimido[6',1':2,3]imidazo[5,1-c][1,4]thiazin-9(1H)-one,
and the compound of Formula (II-2) is not Formula (Z)

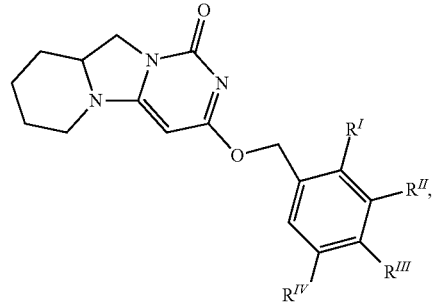

wherein
R$^I$ is H or F;
R$^{II}$ is selected from the group consisting of H, halo, CN, and CF$_3$;
R$^{III}$ is selected from the group consisting of H, F, CN, CF$_3$, CH$_3$, and —O—Y, wherein
Y is a phenyl, pyridinyl or pyrimidinyl, wherein the phenyl, pyridinyl or pyrimidinyl is substituted with one or more substituents independently selected from the group consisting of halo, CF$_3$ and CN; and
R$^{IV}$ is selected from the group consisting of CN, H, F and CH$_3$.

In a further embodiment, the present invention provides compounds of Formula (II-3) and pharmaceutically acceptable salts thereof

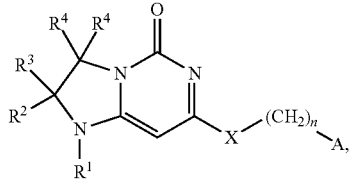

Formula (II-3)

wherein
$R^1$ and $R^2$ together with the nitrogen and carbon to which they are attached form a 5-membered heterocyclic saturated ring, which ring
  optionally contains one or two additional heteroatom ring member independently selected from the group consisting of N, O, C(O), S, S(O), and S(O)$_2$, and
  is optionally substituted with one or more (e.g., one, or one or two) substituents independently selected from the group consisting of OH, halo, $NR^{1a}R^{1b}$, COOH, and —Y—$R^c$, wherein
    Y is absent or is selected from the group consisting of C(O), S(O)$_2$, —C(O)—C(O)—, and CH$_2$, and
    $R^c$ is selected from the group consisting of
      C$_{1-5}$alkyl optionally substituted with one or more (e.g., one, one or two, or one, two or three) substituents independently selected from the group consisting of $NR^{2a}R^{2b}$, C$_{3-6}$cycloalkyl, and —COOH,
      C$_{1-3}$ haloalkyl,
      C$_{1-3}$ alkoxyl,
      $NR^{3a}R^{3b}$,
      —(CH$_2$)$_p$—C(O)—O—C$_{1-3}$ alkyl, wherein p is 1, 2, or 3 and the —(CH$_2$)$_p$— is optionally substituted by one or more (e.g., one or one or two) methyl,
      —(CH$_2$)$_q$—C$_{3-6}$cycloalkyl, wherein q is 1, 2, or 3, wherein the cycloalkyl is optionally substituted with $NR^{4a}R^{4b}$ and the —(CH$_2$)$_q$— is optionally substituted by one or more (e.g., one or one or two) methyl, and
      heterocyclyl optionally substituted with one or more (e.g., one or one or two) substituents independently selected from the group consisting of halo and $NR^{5a}R^{5b}$,
    wherein $R^{1a}$, $R^{1b}$, $R^{2a}$, $R^{2b}$, $R^{3a}$, $R^{3b}$, $R^{4a}$, $R^{5b}$, $R^{5a}$, and $R^{5b}$ are independently H or C$_{1-3}$alkyl; and
$R^3$ is H;
each occurrence of $R^4$ is independently H or D;
X is absent or is selected from the group consisting of
  —O—,
  —NH—, and
  —N(C$_{1-3}$alkyl)-,
n is 0, 1 or 2;
or X is —O—CH$_2$-bicyclo[1.1.1]pentanyl-CH$_2$—O—, and n is 0; and A is unsubstituted thiophenyl, or
A is

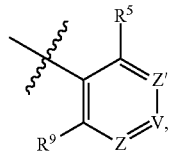

wherein
$R^5$ and $R^9$ are independently H or halo,
Z' is N or CR$^6$,
Z is N or CR$^8$,
wherein $R^6$ and $R^8$ are independently selected from the group consisting of H, CN, halo, C$_{1-3}$alkyl, C$_{1-3}$haloalkyl, —S(O)$_2$—C$_{1-3}$alkyl and —S(O)—O$_{1-3}$alkyl, and
V is N or CR$^7$, wherein $R^7$ is selected from the group consisting of H, halo, CN, C$_{1-3}$alkyl, C$_{1-3}$ alkyl, C$_{1-3}$haloalkyl, and —S(O)$_2$—C$_{1-3}$ alkyl, or $R^7$ is -Q-(CH$_2$)$_m$—W, wherein
  Q is O, N, or CH$_2$,
  m is 0 or 1, and
  W is selected from the group consisting of C$_{3-6}$ cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of C$_{1-3}$haloalkyl, CN, halo and C$_{1-5}$ alkyl;
or when Z or Z' is CR$^6$ and V is CR$^7$, $R^6$ and $R^7$ together may form a 4,7-dioxaspiro[2.6]nonane, In a further embodiment, the present invention provides compounds of Formula (II-4) and pharmaceutically acceptable salts thereof

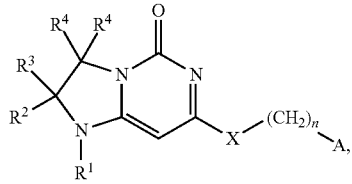

Formula (II-4)

wherein
$R^1$ and $R^2$ together with the nitrogen and carbon to which they are attached form a 6-membered heterocyclic saturated ring, which ring optionally contains one or two additional heteroatom ring member independently selected from the group consisting of N, O, C(O), S, S(O), and S(O)$_2$, and
is optionally substituted with one or more (e.g., one, or one or two) substituents independently selected from the group consisting of OH, halo, $NR^{1a}R^{1b}$, COOH, and —Y—$R^c$, wherein
  Y is absent or is selected from the group consisting of C(O), S(O)$_2$, —C(O)—C(O)—, and CH$_2$, and
  $R^c$ is selected from the group consisting of
    C$_{1-5}$alkyl optionally substituted with one or more (e.g., one, one or two, or one, two or three) substituents independently selected from the group consisting of $NR^{2a}R^{2b}$, C$_{3-6}$cycloalkyl, and —COOH,
    C$_{1-3}$ haloalkyl, $C_{1-3}$ alkoxyl,
$NR^{3a}R^{3b}$,
—$(CH_2)_p$—C(O)—O—$C_{1-3}$ alkyl, wherein p is 1, 2, or 3 and the —$(CH_2)_p$— is optionally substituted by one or more (e.g., one or one or two) methyl,
—$(CH_2)_q$—$C_{3-6}$ cycloalkyl, wherein q is 1, 2, or 3, wherein the cycloalkyl is optionally substituted with $NR^{4a}R^{4b}$ and the —$(CH_2)_q$— is optionally substituted by one or more (e.g., one or one or two) methyl, and
heterocyclyl optionally substituted with one or more (e.g., one or one or two) substituents independently selected from the group consisting of halo and $NR^{5a}R^{5b}$,
wherein $R^{1a}$, $R^{1b}$, $R^{2a}$, $R^{2b}$, $R^{3a}$, $R^{3b}$, $R^{4a}$, $R^{5b}$, $R^{5a}$, and $R^{5b}$ are independently H or $C_{1-3}$alkyl; and
$R^3$ is H;
each occurrence of $R^4$ is independently H or D;
X is absent or is selected from the group consisting of
—O—,
—NH—, and
—N ($C_{1-3}$ alkyl)-,
n is 0, 1 or 2;
or X is —O—$CH_2$-bicyclo[1.1.1]pentanyl-$CH_2$—O— and n is 0; and
A is unsubstituted thiophenyl, or
A is

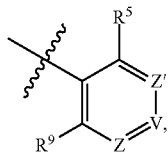

wherein
$R^5$ and $R^9$ are independently H or halo,
Z' is N or $CR^6$,
Z is N or $CR^8$,
wherein $R^6$ and $R^8$ are independently selected from the group consisting of H, CN, halo, $C_{1-3}$alkyl, $C_{1-3}$haloalkyl, —$S(O)_2$—$C_{1-3}$ alkyl and —$S(O)$—$C_{1-3}$alkyl, and
V is N or $CR^7$, wherein $R^7$ is selected from the group consisting of H, halo, CN, $C_{1-3}$alkyl, $C_{1-3}$ alkyl, $C_{1-3}$haloalkyl, and —$S(O)_2$—$C_{1-3}$ alkyl, or $R^7$ is -Q-$(CH_2)_m$—W, wherein
Q is O, N, or $CH_2$,
m is 0 or 1, and
W is selected from the group consisting of $C_{3-6}$ cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$alkyl;
or when Z or Z' is $CR^6$ and V is $CR^7$, $R^6$ and $R^7$ together may form a 4,7-dioxaspiro[2.6]nonane,
with the proviso that the compound of Formula (II-4) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile, 7-(2,3-difluorophenethyl)-3,4,11,11a-tetrahydro-1H-pyrazino[1',2':3,4]imidazo[1,2-c]pyrimidin-9(2H)-one,
7-((2,3-difluorobenzyl)amino)-11,11a-dihydro-1H-pyrazino[1',2': 3,4]imidazo[1,2-c]pyrimidine-3,9(2H,4H)-dione,
7-((3,4-difluorobenzyl)amino)-3,4,11,11a-tetrahydropyrimido[6',1':2,3]imidazo[5,1-c][1,4]thiazin-9(1H)-one 2,2-dioxide,
7-((2,3-difluorobenzyl)amino)-3,4,11,11a-tetrahydropyrimido[6',1':2,3]imidazo[5,1-c][1,4]thiazin-9(1H)-one-2-oxide,
7-((2,3-difluorobenzyl)amino)-3,4,11,11a-tetrahydropyrimido[6',1':2,3]imidazo[5,1-c][1,4]thiazin-9(1H)-one-2,2-dioxide, or
7-(2,3-difluorophenethyl)-3,4,11,11a-tetrahydropyrimido[6',1':2,3]imidazo[5,1-c][1,4]thiazin-9(1H)-one.

In a further embodiment, the present invention provides compounds of Formula (II-5) and pharmaceutically acceptable salts thereof Formula (II-5)

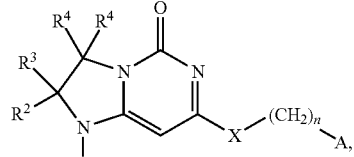

wherein
$R^1$ and $R^2$ together with the nitrogen and carbon to which they are attached form a 6-membered heterocyclic saturated ring, which ring
optionally contains one or two additional heteroatom ring member independently selected from the group consisting of N, O, C(O), S, S(O), and $S(O)_2$, and
is optionally substituted with one or more (e.g., one, or one or two) substituents independently selected from the group consisting of OH, halo, $NR^{1a}R^{1b}$, COOH, and —Y—$R^c$, wherein
Y is absent or is selected from the group consisting of C(O), $S(O)_2$, —C(O)—C(O)—, and $CH_2$, and
$R^c$ is selected from the group consisting of
$C_{1-5}$alkyl optionally substituted with one or more (e.g., one, one or two, or one, two or three) substituents independently selected from the group consisting of $NR^{2a}R^{2b}$, $C_{3-6}$cycloalkyl, and —COOH,
$C_{1-3}$ haloalkyl,
$C_{1-3}$alkoxyl,
$NR^{3a}R^{3b}$,
—$(CH_2)_p$—C(O)—O—$C_{1-3}$alkyl, wherein p is 1, 2, or 3 and the —$(CH_2)_p$— is optionally substituted by one or more (e.g., one or one or two) methyl,
—$(CH_2)_q$—$C_{3-6}$cycloalkyl, wherein q is 1, 2, or 3, wherein the cycloalkyl is optionally substituted with $NR^{4a}R^{4b}$ and the —$(CH_2)_q$— is optionally substituted by one or more (e.g., one or one or two) methyl, and
heterocyclyl optionally substituted with one or more (e.g., one or one or two) substituents independently selected from the group consisting of halo and $NR^{5a}R^{5b}$, wherein $R^{1a}$, $R^{1b}$, $R^{2a}$, $R^{2b}$, $R^{3a}$, $R^{3b}$, $R^{4a}$, $R^{5b}$, $R^{5a}$, and $R^{5b}$ are independently H or $C_{1-3}$alkyl; and $R^3$ is H;

each occurrence of $R^4$ is independently H or D;

X is absent or is selected from the group consisting of
—O—,
—NH—, and
—N ($C_{1-3}$ alkyl)-, n is 0, 1 or 2;

or X is —O—$CH_2$-bicyclo[1.1.1]pentanyl-$CH_2$—O—, and n is 0; and

A is unsubstituted thiophenyl, or

A is

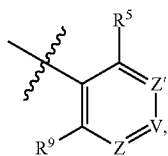

wherein
$R^5$ and $R^9$ are independently H or halo,
Z' is N or $CR^6$,
Z is N or $CR^8$,
wherein $R^6$ and $R^8$ are independently selected from the group consisting of H, CN, halo, $C_{1-3}$alkyl, $C_{1-3}$haloalkyl, —$S(O)_2$—$C_{1-3}$ alkyl and —$S(O)$—$C_{1-3}$alkyl, and
V is N or $CR^7$, wherein $R^7$ is selected from the group consisting of H, halo, CN, $C_{1-3}$alkyl, $C_{1-3}$ alkyl, $C_{1-3}$haloalkyl, and —$S(O)_2$—$C_{1-3}$alkyl, or $R^7$ is -Q-$(CH_2)_m$—W, wherein
Q is O, N, or $CH_2$,
m is 0 or 1, and
W is selected from the group consisting of $C_{3-6}$ cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$alkyl;

or when Z or Z' is $CR^6$ and V is $CR^7$, $R^6$ and $R^7$ together may form a 4,7-dioxaspiro[2.6]nonane, with the proviso that the compound of Formula (II-5) is not 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile, 7-(2,3-difluorophenethyl)-3,4,11,11a-tetrahydro-1H-pyrazino[1',2':3,4]imidazo[1,2-c]pyrimidin-9(2H)-one, 7-((2,3-difluorobenzyl)amino)-11,11a-dihydro-1H-pyrazino[1',2':3,4]imidazo[1,2-c]pyrimidine-3,9(2H, 4H)-dione, 7-((3,4-difluorobenzyl)amino)-3,4,11,11a-tetrahydropyrimido[6',1':2,3]imidazo[5,1-c][1,4]thiazin-9(1H)-one 2,2-dioxide, 7-((2,3-difluorobenzyl)amino)-3,4,11,11a-tetrahydropyrimido[6',1':2,3]imidazo[5,1-c][1,4]thiazin-9(1H)-one-2-oxide, 7-((2,3-difluorobenzyl)amino)-3,4,11,11a-tetrahydropyrimido[6',1':2,3]imidazo[5,1-c][1,4]thiazin-9(1H)-one-2,2-dioxide, or 7-(2,3-Difluorophenethyl)-3,4,11,11a-tetrahydropyrimido[6',1':2,3]imidazo[5,1-c][1,4]thiazin-9(1H)-one, and the compound of Formula (II-5) is not

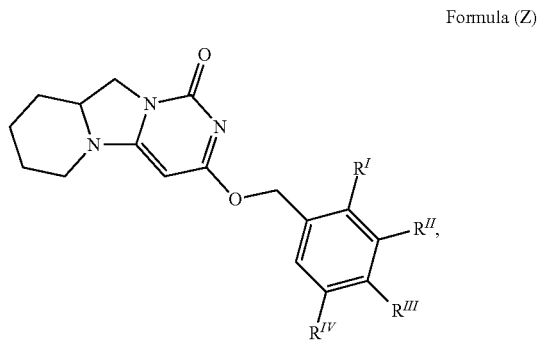

Formula (Z)

wherein
$R^I$ is H or F;
$R^{II}$ is selected from the group consisting of H, halo, CN, and $CF_3$;
$R^{III}$ is selected from the group consisting of H, F, CN, $CF_3$, $CH_3$, and —O—Y, wherein Y is a phenyl, pyridinyl or pyrimidinyl, wherein the phenyl, pyridinyl or pyrimidinyl is substituted with one or more substituents independently selected from the group consisting of halo, $CF_3$ and CN; and
$R^{Iv}$ is selected from the group consisting of CN, H, F and $CH_3$.

In other embodiments, the present invention provides compounds of Formula (III-1) and pharmaceutically acceptable salts thereof,

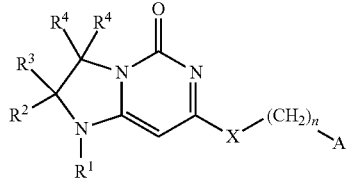

Formula (III-1)

wherein
$R^1$ and $R^2$ together with the nitrogen and carbon to which they are attached form a 5 or 6-membered heterocyclic saturated, unsubstituted ring, which ring optionally contains one additional heteroatom ring member selected from N, O and C(O); and
$R^3$ is H;
$R^4$ is H;
X is O;
n is 1 or 2; and
A is

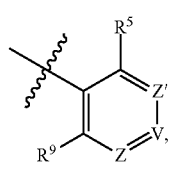

wherein
$R^5$ and $R^9$ are independently H or halo,
Z' is N or $CR^6$,
Z is N or $CR^8$,
  wherein $R^6$ and $R^8$ are independently selected from the group consisting of H, CN, halo, $C_{1-3}$alkyl, $C_{1-3}$haloalkyl, —$S(O)_2$—$C_{1-3}$alkyl and —$S(O)$—$C_{1-3}$alkyl, and
V is N or $CR^7$, wherein $R^7$ is selected from the group consisting of H, halo, CN, $C_{1-3}$ alkyl, $C_{1-3}$haloalkyl, and —$S(O)_2$—$C_{1-3}$ alkyl, or $R^7$ is -Q-$(CH_2)_m$—W, wherein
Q is O, N, or $CH_2$,
m is 0 or 1, and
W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$ alkyl,
with the proviso that the compound of Formula (III-1) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile or
7-(2,3-difluorophenethyl)-3,4,11,11a-tetrahydro-1H-pyrazino[1',2':3,4]imidazo[1,2-c]pyrimidin-9(2H)-one.

In other embodiments, the present invention provides compounds of Formula (III-2) and pharmaceutically acceptable salts thereof,

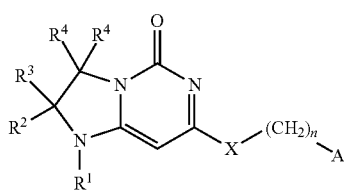

Formula (III-2)

wherein
$R^1$ and $R^2$ together with the nitrogen and carbon to which they are attached form a 5 or 6-membered heterocyclic saturated, unsubstituted ring, which ring optionally contains one additional heteroatom ring member selected from N, O and C(O); and
$R^3$ is H;
$R^4$ is H;
X is O;
n is 1 or 2; and
A is

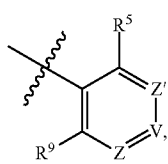

wherein
$R^5$ and $R^9$ are independently H or halo,
Z' is N or $CR^6$,
Z is N or $CR^8$,
  wherein $R^6$ and $R^8$ are independently selected from the group consisting of H, CN, halo, $C_{1-3}$alkyl, $C_{1-3}$haloalkyl, —$S(O)_2$—$C_{1-3}$alkyl and —$S(O)$—$C_{1-3}$alkyl, and
V is N or $CR^7$, wherein $R^7$ is selected from the group consisting of H, halo, CN, $C_{1-3}$ alkyl, $C_{1-3}$haloalkyl, and —$S(O)_2$—$C_{1-3}$ alkyl, or $R^7$ is -Q-$(CH_2)_m$—W, wherein
Q is O, N, or $CH_2$,
m is 0 or 1, and
W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$ alkyl,
with the proviso that the compound of Formula (III-2) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile or
7-(2,3-difluorophenethyl)-3,4,11,11a-tetrahydro-1H-pyrazino[1',2':3,4]imidazo[1,2-c]pyrimidin-9(2H)-one,
and with the proviso that the compound of Formula (III-2) is not

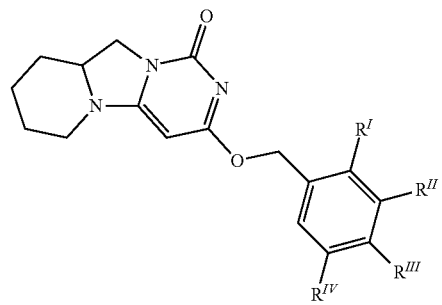

Formula (Z)

wherein
$R^I$ is H or F;
$R^{II}$ is selected from the group consisting of H, halo, CN, and $CF_3$;
$R^{III}$ is selected from the group consisting of H, F, CN, $CF_3$, $CH_3$, and —O—Y, wherein Y is a phenyl, pyridinyl or pyrimidinyl, wherein the phenyl, pyridinyl or pyrimidinyl is substituted with one or more substituents independently selected from the group consisting of halo, $CF_3$ and CN; and
$R^{IV}$ is selected from the group consisting of CN, H, F and $CH_3$.

In other embodiments, the present invention provides compounds of Formula (III-3) and pharmaceutically acceptable salts thereof, Formula (III-3)

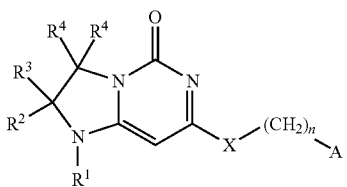

wherein
R[1] and R[2] together with the nitrogen and carbon to which they are attached form a 5-membered heterocyclic saturated, unsubstituted ring, which ring optionally contains one additional heteroatom ring member selected from N, O and C(O); and
R[3] is H;
R[4] is H;
X is O;
n is 1 or 2; and
A is

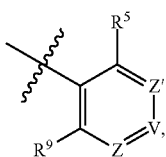

wherein
R[5] and R[9] are independently H or halo,
Z' is N or CR[6],
Z is N or CR[8],
  wherein R[6] and R[8] are independently selected from the group consisting of H, CN, halo, $C_{1-3}$alkyl, $C_{1-3}$haloalkyl, —S(O)$_2$—$C_{1-3}$alkyl and —S(O)—$C_{1-3}$alkyl, and
V is N or CR[7], wherein R[7] is selected from the group consisting of H, halo, CN, $C_{1-3}$ alkyl, $C_{1-3}$haloalkyl, and —S(O)$_2$—$C_{1-3}$ alkyl, or R[7] is -Q-(CH$_2$)$_m$—W, wherein
  Q is O, N, or CH$_2$,
  m is 0 or 1, and
  W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$ alkyl.

In other embodiments, the present invention provides compounds of Formula (III-4) and pharmaceutically acceptable salts thereof, Formula (III-4)

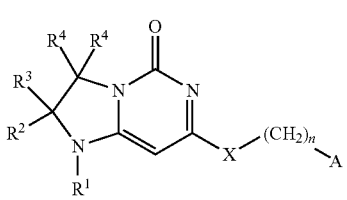

wherein
R[1] and R[2] together with the nitrogen and carbon to which they are attached form a 6-membered heterocyclic saturated, unsubstituted ring, which ring optionally contains one additional heteroatom ring member selected from N, O and C(O); and
R[3] is H;
R[4] is H;
X is O;
n is 1 or 2; and
A is

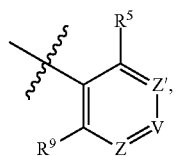

wherein
R[5] and R[9] are independently H or halo,
Z' is N or CR[6],
Z is N or CR[8],
  wherein R[6] and R[8] are independently selected from the group consisting of H, CN, halo, $C_{1-3}$alkyl, $C_{1-3}$haloalkyl, —S(O)$_2$—$C_{1-3}$alkyl and —S(O)—$C_{1-3}$alkyl, and
V is N or CR[7], wherein R[7] is selected from the group consisting of H, halo, CN, $C_{1-3}$ alkyl, $C_{1-3}$haloalkyl, and —S(O)$_2$—$C_{1-3}$ alkyl, or R[7] is -Q-(CH$_2$)$_m$—W, wherein
  Q is O, N, or CH$_2$,
  m is 0 or 1, and
  W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$ alkyl,
with the proviso that the compound of Formula (III-4) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile, or
7-(2,3-difluorophenethyl)-3,4,11,11a-tetrahydro-1H-pyrazino[1',2':3,4]imidazo[1,2-c]pyrimidin-9(2H)-one.

In other embodiments, the present invention provides compounds of Formula (III-5) and pharmaceutically acceptable salts thereof, Formula (III-5)

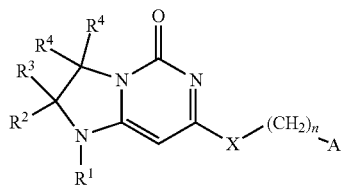

wherein
R[1] and R[2] together with the nitrogen and carbon to which they are attached form a 6-membered heterocyclic saturated, unsubstituted ring, which ring optionally contains one additional heteroatom ring member selected from N, O and C(O); and
$R^3$ is H;
$R^4$ is H;
X is O;
n is 1 or 2; and
A is

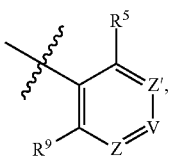

wherein
$R^5$ and $R^9$ are independently H or halo,
Z' is N or $CR^6$,
Z is N or $CR^8$,
  wherein $R^6$ and $R^8$ are independently selected from the group consisting of H, CN, halo, $C_{1-3}$alkyl, $C_{1-3}$haloalkyl, —S(O)$_2$—$C_{1-3}$alkyl and —S(O)—$C_{1-3}$alkyl, and
V is N or $CR^7$, wherein $R^7$ is selected from the group consisting of H, halo, CN, $C_{1-3}$ alkyl, $C_{1-3}$haloalkyl, and —S(O)$_2$—$C_{1-3}$ alkyl, or $R^7$ is -Q-(CH$_2$)$_m$—W, wherein
  Q is O, N, or CH$_2$,
  m is 0 or 1, and
  W is selected from the group consisting of $C_{3-6}$cycloalkyl, heterocyclyl, 5 or 6 membered heteroaryl and phenyl, wherein said cycloalkyl, heterocyclyl, heteroaryl or phenyl is optionally substituted with one or more (e.g., one, or one or two) substituents independently selected from the group consisting of $C_{1-3}$haloalkyl, CN, halo and $C_{1-5}$ alkyl,
  with the proviso that the compound of Formula (III-5) is not
2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile, or
7-(2,3-difluorophenethyl)-3,4,11,11a-tetrahydro-1H-pyrazino[1',2':3,4]imidazo[1,2-c]pyrimidin-9(2H)-one, and the compound of Formula (III-5) is not Formula (Z)

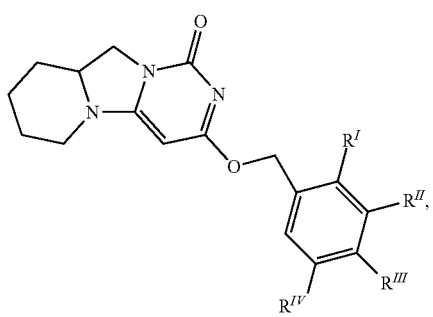

wherein
$R^I$ is H or F;
$R^{II}$ is selected from the group consisting of H, halo, CN, and CF$_3$;
$R^{III}$ is selected from the group consisting of H, F, CN, CF$_3$, CH$_3$, and —O—Y, wherein Y is a phenyl, pyridinyl or pyrimidinyl, wherein the phenyl, pyridinyl or pyrimidinyl is substituted with one or more substituents independently selected from the group consisting of halo, CF$_3$ and CN; and
$R^{IV}$ is selected from the group consisting of CN, H, F and CH$_3$.

In other embodiments, the present invention provides compounds of Formula Z and pharmaceutically acceptable salts thereof, Formula (Z)

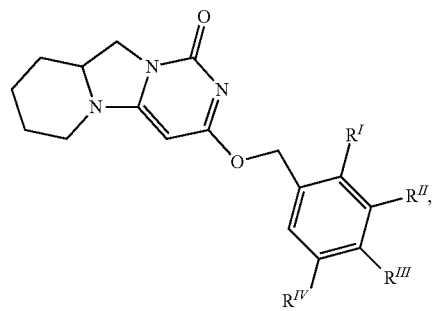

$R^I$ is H or F;
$R^{II}$ is selected from the group consisting of H, halo, CN, and CF$_3$;
$R^{III}$ is selected from the group consisting of H, F, CN, CF$_3$, CH$_3$, and —O—Y, wherein Y is a phenyl, pyridinyl or pyrimidinyl, wherein the phenyl, pyridinyl or pyrimidinyl is substituted with one or more substituents independently selected from the group consisting of halo, CF$_3$ and CN; and
$R^{IV}$ is selected from the group consisting of CN, H, F and CH$_3$.
$R^4$ is selected from the group consisting of CN, H, F and CH$_3$.

In one embodiment, this invention relates to compounds of above referenced Formulas and any of the above applicable embodiments, wherein $R^1$ and $R^2$ together with the nitrogen and carbon to which they are attached form a 5 or 6-membered heterocyclic saturated ring, which ring optionally contains one additional heteroatom ring member selected from N, O and C(O), and $R^3$ is H, and pharmaceutically acceptable salts thereof.

In one embodiment, this invention relates to compounds of above referenced Formulas and any of the above applicable embodiments, wherein $R^1$ and $R^2$ together with the nitrogen and carbon to which they are attached form a 5-membered heterocyclic saturated ring, which ring optionally contains one additional heteroatom ring member selected from N, O and C(O), and $R^3$ is H, and pharmaceutically acceptable salts thereof.

In one embodiment, this invention relates to compounds of above referenced Formulas and any of the above applicable embodiments, wherein $R^1$ and $R^2$ together with the nitrogen and carbon to which they are attached form a 6-membered heterocyclic saturated ring, which ring optionally contains one additional heteroatom ring member selected from N, O and C(O), and $R^3$ is H, and pharmaceutically acceptable salts thereof.

In one embodiment, this invention relates to compounds of above referenced Formulas and any of the above applicable embodiments, wherein $R^1$ and $R^2$ together with the nitrogen and carbon to which they are attached form a 6-membered heterocyclic saturated ring, which ring contains one additional heteroatom ring member selected from N, O and C(O), and $R^3$ is H, and pharmaceutically acceptable salts thereof.

In the other embodiment, this invention relates to compounds of above referenced Formulas and any of the above applicable embodiments, wherein $R^1$ and $R^2$ together with the nitrogen and carbon to which they are attached form a 5 or 6-membered heterocyclic saturated ring, which ring optionally contains one additional heteroatom ring member selected from N or O, and $R^3$ is H, and pharmaceutically acceptable salts thereof.

In the other embodiment, this invention relates to compounds of above referenced Formulas and any of the above applicable embodiments, wherein $R^1$ and $R^2$ together with the nitrogen and carbon to which they are attached form a 5-membered heterocyclic saturated ring, which ring optionally contains one additional heteroatom ring member selected from N or O, and $R^3$ is H, and pharmaceutically acceptable salts thereof.

In the other embodiment, this invention relates to compounds of above referenced Formulas and any of the above applicable embodiments, wherein $R^1$ and $R^2$ together with the nitrogen and carbon to which they are attached form a 6-membered heterocyclic saturated ring, which ring optionally contains one additional heteroatom ring member selected from N or O, and $R^3$ is H, and pharmaceutically acceptable salts thereof.

In the other embodiment, this invention relates to compounds of above referenced Formulas and any of the above applicable embodiments, wherein $R^1$ and $R^2$ together with the nitrogen and carbon to which they are attached form a 6-membered heterocyclic saturated ring, which ring contains one additional heteroatom ring member selected from N or O, and $R^3$ is H, and pharmaceutically acceptable salts thereof.

In a further embodiment, this invention relates to compounds of above referenced Formulas and any of the above applicable embodiments, wherein $R^1$ and $R^2$ together with the nitrogen and carbon to which they are attached form a 5 membered, saturated heterocycle, which contain no additional heteroatom ring member, which ring is optionally substituted with one substituent of —Y—$R_c$, wherein Y is absent or C(O) and $R^c$ is selected from the group consisting of $C_{1-3}$haloalkyl, unsubstituted $C_{3-6}$ cycloalkyl, and unsubstituted 5 or 6 membered heterocyclyl, and $R^3$ is H, and pharmaceutically acceptable salts thereof.

In a further embodiment, this invention relates to compounds of above referenced Formulas and any of the above applicable embodiments, wherein $R^1$ and $R^2$ together with the nitrogen and carbon to which they are attached form a 5 membered unsubstituted, saturated heterocycle, which contains no additional heteroatom ring member, and $R^3$ is H, and pharmaceutically acceptable salts thereof.

In one embodiment, this invention relates to compounds of above referenced Formulas and any of the above applicable embodiments, wherein $R^4$ is H and pharmaceutically acceptable salts thereof.

In one embodiment, this invention relates to compounds of above referenced Formulas and any of the above applicable embodiments, wherein X is O and pharmaceutically acceptable salts thereof.

In one embodiment, this invention relates to compounds of above referenced Formulas and any of the above applicable embodiments, wherein n is 1 and pharmaceutically acceptable salts thereof.

In one embodiment, this invention relates to compounds of above referenced Formulas and any of the above applicable embodiments and pharmaceutically acceptable salts thereof, wherein A is

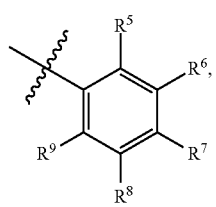

wherein
$R^5$ and $R^9$ are independently H or F;
$R^6$ and $R^8$ are independently selected from the group consisting of H, CN, and F; and
$R^7$ is selected from the group consisting of H, F, CN, $C_{1-3}$ alkyl, and $C_{1-3}$haloalkyl, or $R^7$ is -Q-(CH$_2$)$_m$—W, wherein
Q is 0,
m is 0 or 1, and
W is 5 or 6 membered heteroaryl or phenyl, wherein said heteroaryl or phenyl is optionally substituted with one or more substituents independently selected from the group consisting of $C_{1-3}$haloalkyl, CN, halo and $C_{1-5}$alkyl.

Further, in one embodiment, this invention relates to compounds of above referenced Formulas and any of the above applicable embodiments and pharmaceutically acceptable salts thereof, wherein A is

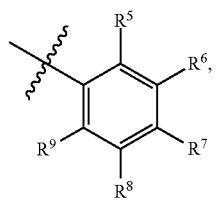

wherein
$R^5$ and $R^9$ are independently H or F;
$R^6$ and $R^8$ are independently selected from the group consisting of H, CN, and F; and
$R^7$ is selected from the group consisting of H, F, CN, $C_{1-3}$ alkyl, and $C_{1-3}$haloalkyl.

Yet, in another embodiment, this invention relates to compounds of above referenced Formulas and any of the above applicable embodiments and pharmaceutically acceptable salts thereof, wherein A is

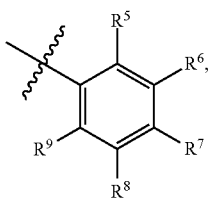

wherein
- $R^5$ and $R^9$ are independently H or F; and
- $R^6$ and $R^8$ are independently selected from the group consisting of H, CN, and F; and
- $R^7$ is —O—W, wherein W is 5 or 6 membered heteroaryl or phenyl, wherein said heteroaryl or phenyl is optionally substituted with one or more (e.g., one, or one or two) substituents independently selected from the group consisting of $C_{1-3}$haloalkyl, CN, halo and $C_{1-5}$alkyl.

In one embodiment, this invention relates to compounds of above referenced Formulas and any of the above applicable embodiments and pharmaceutically acceptable salts thereof, wherein A is

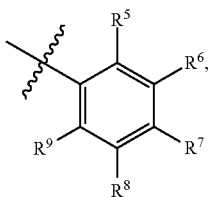

wherein
- $R^5$ and $R^9$ are independently H or F;
- $R^6$ and $R^8$ are independently selected from the group consisting of H, CN, and F; and
- $R^7$ is selected from the group consisting of H, F, CN, $C_{1-3}$alkyl, and $C_{1-3}$haloalkyl, or $R^7$ is —O—W, wherein W is selected from the group consisting of pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $C_{1-3}$haloalkyl and $C_{1-5}$alkyl.

In one embodiment, this invention relates to compounds of above referenced Formulas and any of the above applicable embodiments and pharmaceutically acceptable salts thereof, wherein A is

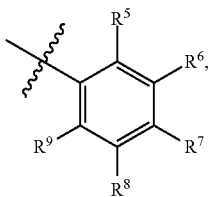

wherein
- $R^5$ and $R^9$ are independently H or F;
- $R^6$ and $R^8$ are independently selected from the group consisting of H, CN, and F; and
- $R^7$ is —O—W, wherein W is pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $CF_3$ and $CH_3$.

In one embodiment, the compound for Formula (I) is a compound of Formula (A-1)

Formula (A-1)

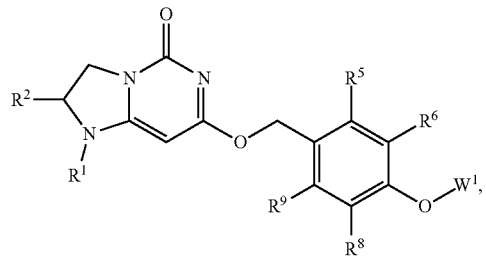

wherein
- $R^1$ and $R^2$ together with the nitrogen and carbon to which they are attached form a 5 or 6-membered heterocyclic saturated ring, which ring optionally contains one additional heteroatom ring member selected from the group consisting of N, O, and C(O), and which ring has no further substitution;
- $R^5$ and $R^9$ are independently H or F;
- $R^6$ and $R^8$ are independently selected from the group consisting of H or F; and
- $W^1$ is selected from the group consisting of pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $CF_3$ and $CH_3$, or a pharmaceutically acceptable salt thereof.

In one embodiment, the compound for Formula (I) is a compound of Formula (A-2)

Formula (A-2)

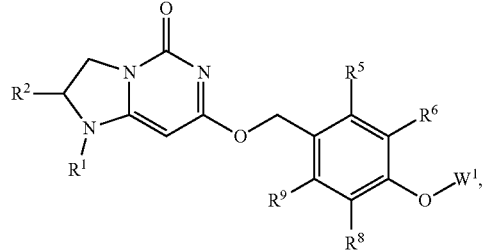

wherein
- $R^1$ and $R^2$ together with the nitrogen and carbon to which they are attached form a 5-membered heterocyclic saturated ring, which ring optionally contains one additional heteroatom ring member selected from the group consisting of N, O, and C(O), and which ring has no further substitution;
- $R^5$ and $R^9$ are independently H or F;
- $R^6$ and $R^8$ are independently selected from the group consisting of H or F; and $W^1$ is selected from the group consisting of pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $CF_3$ and $CH_3$, or a pharmaceutically acceptable salt thereof.

In one embodiment, the compound for Formula (I) is a compound of Formula (A-3)

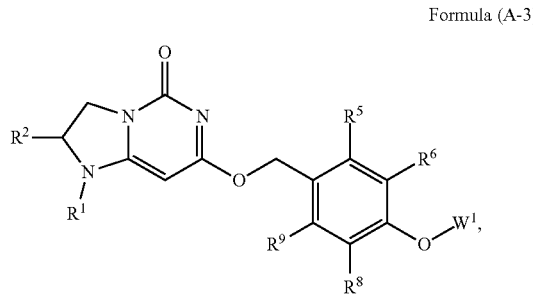

Formula (A-3)

wherein
- $R^1$ and $R^2$ together with the nitrogen and carbon to which they are attached form a 6-membered heterocyclic saturated ring, which ring optionally contains one additional heteroatom ring member selected from the group consisting of N, O, and C(O), and which ring has no further substitution;
- $R^5$ and $R^9$ are independently H or F;
- $R^6$ and $R^8$ are independently selected from the group consisting of H or F; and
- $W^1$ is selected from the group consisting of pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $CF_3$ and $CH_3$, or a pharmaceutically acceptable salt thereof.

In one embodiment, the compound for Formula (I) is a compound of Formula (A-4)

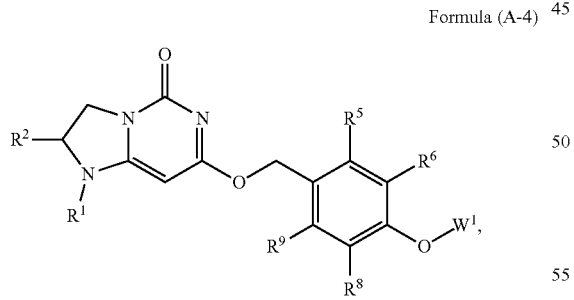

Formula (A-4)

wherein
- $R^1$ and $R^2$ together with the nitrogen and carbon to which they are attached form a 6-membered heterocyclic saturated ring, which ring contains one additional heteroatom ring member selected from the group consisting of N, O, and C(O), and which ring has no further substitution;
- $R^5$ and $R^9$ are independently H or F;
- $R^6$ and $R^8$ are independently selected from the group consisting of H or F; and $W^1$ is selected from the group consisting of pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $CF_3$ and $CH_3$, or a pharmaceutically acceptable salt thereof.

In one embodiment, the compound for Formula (I) is a compound of Formula (A-5)

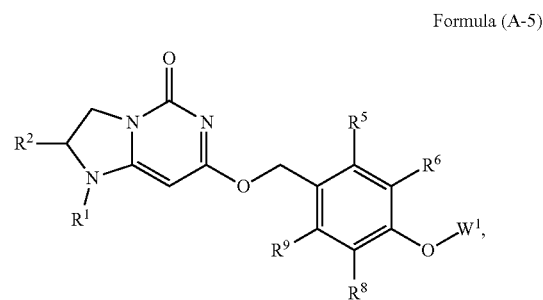

Formula (A-5)

wherein
- $R^1$ and $R^2$ together with the nitrogen and carbon to which they are attached form a 6-membered heterocyclic saturated ring, which ring contains one additional heteroatom ring member selected from the group consisting of O and which ring has no further substitution;
- $R^5$ and $R^9$ are independently H or F;
- $R^6$ and $R^8$ are independently selected from the group consisting of H or F; and
- $W^1$ is selected from the group consisting of pyridinyl, pyrimidinyl, pyrazolyl and phenyl, wherein said pyridinyl, pyrimidinyl, pyrazolyl or phenyl is optionally substituted with one or more (e.g., one, or one or two) substituents independently selected from the group consisting of $CF_3$ and $CH_3$, or a pharmaceutically acceptable salt thereof.

In one embodiment, the compound is

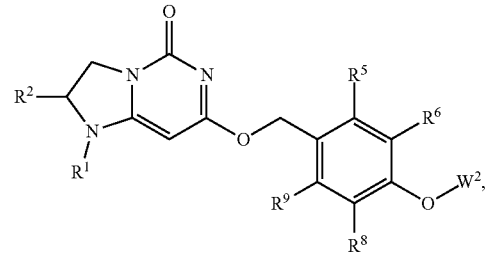

Formula (B)

wherein
- $R^1$ and $R^2$ together with the nitrogen and carbon to which they are attached form a 5 or 6-membered heterocyclic saturated ring, which ring optionally contains one additional heteroatom ring member selected from the group consisting of N, O, and C(O), and which ring has no further substitution;
- $R^5$ and $R^9$ are independently H or F;
- $R^6$ and $R^8$ are independently selected from the group consisting of H or F;
- $W^2$ is selected from the group consisting of H, halo, CN, $C_{1-3}$alkyl, $C_{1-3}$ alkyl and $C_{1-3}$haloalkyl;

or a pharmaceutically acceptable salt thereof.
In one embodiment, the compound is

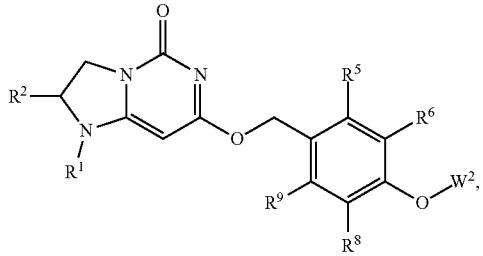

Formula (B)

wherein
R¹ and R² together with the nitrogen and carbon to which they are attached form a 5 or 6-membered heterocyclic saturated ring, which ring optionally contains one additional heteroatom ring member of 0, and which ring has no further substitution;
R⁵ and R⁹ are independently H or F;
R⁶ and R⁸ are independently selected from the group consisting of H or F;
W² is selected from the group consisting of H, halo, $C_{1-3}$ alkyl and $C_{1-3}$haloalkyl;
or a pharmaceutically acceptable salt thereof.

In one embodiment, the compound of Formula (I) is a compound of any one of Examples 1 to 66, 68-70, 72-265, 267-317, 319-354, 356-375, 377, and 381-412, a free base, free acid, or a salt (e.g., a pharmaceutically acceptable salt) thereof.

In one embodiment, the compound of Formula (I) is a compound of any one of Examples 36, 44, 50-66, 68-70, 72-265, 267-317, 319-354, 356-375, 377, and 381-412, a free base, free acid, or a salt (e.g., a pharmaceutically acceptable salt) thereof.

In one embodiment, the compound of Formula (I) is a compound of any one of Examples 1-35, 37-43 and 45-49, a free base, free acid, or a salt (e.g., a pharmaceutically acceptable salt) thereof.

In one embodiment, the compound of Formula (I) is a compound of any one of below compounds:
3-((3,4-difluorobenzyl)oxy)-6,7,8,9,9a,10-hexahydro-1H-pyrido[1',2':3,4]imidazo[1,2-c]pyrimidin-1-one,
3-((3,4,5-trifluorobenzyl)oxy)-6,7,8,9,9a,10-hexahydro-1H-pyrido[1',2':3,4]imidazo[1,2-c]pyrimidin-1-one,
3-(((1-oxo-6,7,8,9,9a,10-hexahydro-1H-pyrido[1',2':3,4]imidazo[1,2-c]pyrimidin-3-yl) oxy)methyl)benzonitrile,
3-((4-fluorobenzyl)oxy)-6,7,8,9,9a,10-hexahydro-1H-pyrido[1',2':3,4]imidazo-[1,2-c]pyrimidin-1-one,
3-((3,5-difluorobenzyl)oxy)-6,7,8,9,9a,10-hexahydro-1H-pyrido[1',2':3,4]imidazo[1,2-c]pyrimidin-1-one,
3-(2-(thiophen-2-yl)ethoxy)-6,7,8,9,9a,10-hexahydro-1H-pyrido[1',2':3,4]imidazo[1,2-c]pyrimidin-1-one,
3-((3-fluoro-4-((2-(trifluoromethyl)pyridin-4-yl)oxy)benzyl)oxy)-6,7,8,9,9a,10-hexahydro-1H-pyrido[1',2':3,4] imidazo[1,2-c]pyrimidin-1-one,
3-((3-fluoro-4-((5-(trifluoromethyl)pyridin-3-yl)oxy)benzyl)oxy)-6,7,8,9,9a,10-hexahydro-1H-pyrido[1',2':3,4] imidazo[1,2-c]pyrimidin-1-one,
3-((3,5-difluoro-4-((1-methyl-1H-pyrazol-4-yl)oxy)benzyl)oxy)-6,7,8,9,9a,10-hexahydro-1H-pyrido[1',2':3,4]imidazo[1,2-c]pyrimidin-1-one,
3-((3-fluoro-4-((1-methyl-1H-pyrazol-4-yl)oxy)benzyl)oxy)-6,7,8,9,9a,10-hexahydro-1H-pyrido[1',2':3,4]imidazo[1,2-c]pyrimidin-1-one,
3-((3-fluorobenzyl)oxy)-6,7,8,9,9a,10-hexahydro-1H-pyrido[1',2':3,4]imidazo[1,2-c] pyrimidin-1-one,
3-((3,5-difluorobenzyl)oxy)-6,7,8,9,9a,10-hexahydro-1H-pyrido[1',2':3,4]imidazo[1,2-c]pyrimidin-1-one,
3-((2,4-difluorobenzyl)oxy)-6,7,8,9,9a,10-hexahydro-1H-pyrido[1',2':3,4]imidazo[1,2-c] pyrimidin-1-one,
3-((2,3-difluorobenzyl)oxy)-6,7,8,9,9a,10-hexahydro-1H-pyrido[1',2':3,4]imidazo[1,2-c] pyrimidin-1-one,
3-((2,4,5-trifluorobenzyl)oxy)-6,7,8,9,9a,10-hexahydro-1H-pyrido[1',2':3,4]imidazo[1,2-c]pyrimidin-1-one,
3-((2,4-difluorobenzyl)(methyl)amino)-6,7,8,9,9a,10-hexahydro-1H-pyrido[1',2':3,4] imidazo[1,2-c]pyrimidin-1-one,
3-((3,5-difluoro-4-(1-(2-fluoroethyl)cyclopropoxy)benzyl)oxy)-6,7,8,9,9a,10-hexahydro-1H-pyrido[1',2':3,4]imidazo[1,2-c]pyrimidin-1-one,
3-((3, 5-difluoro-4-((1-methyl-1H-pyrazol-4-yl) oxy) benzyl) oxy)-7, 8, 8a, 9-tetrahydro pyrrolo[1',2':3,4]imidazo [1,2-c]pyrimidin-1(6H)-one,
3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one,
3-((3-fluoro-4-((1-methyl-1H-pyrazol-4-yl) oxy) benzyl) oxy)-7, 8, 8a, 9-tetrahydro pyrrolo[1',2':3,4]imidazo[1,2-c]pyrimidin-1(6H)-one,
3-((3-fluoro-4-((2-(trifluoromethyl) pyrimidin-5-yl) oxy) benzyl) oxy)-7, 8, 8a, 9-tetra hydropyrrolo[1',2':3,4]imidazo[1,2-c]pyrimidin-1(6H)-one,
3-((3,4,5-trifluorobenzyl)oxy)-7,8,8a,9-tetrahydropyrrolo[1',2':3,4]imidazo[1,2-c] pyrimidin-1(6H)-one,
3-((4-(3,4-difluorophenoxy)-3,5-difluorobenzyl)oxy)-7,8, 8a,9-tetrahydropyrrolo[1',2':3,4]imidazo[1,2-c]pyrimidin-1(6H)-one,
3-((3,5-difluoro-4-((6-(trifluoromethyl)pyridin-3-yl)oxy)benzyl)oxy)-7,8,8a,9-tetrahydro pyrrolo[1',2':3,4]imidazo [1,2-c]pyrimidin-1(6H)-one,
3-((3,5-difluoro-4-(3-(trifluoromethyl)phenoxy)benzyl)oxy)-7,8,8a,9-tetrahydropyrrolo[1',2':3, 4]imidazo[1,2-c]pyrimidin-1(6H)-one,
3-((6-(4-fluoro-3-(trifluoromethylphenoxy)pyridin-3-yl)methoxy)-7,8,8a,9-tetrahydro pyrrolo[1',2':3,4]imidazo [1,2-c]pyrimidin-1(6H)-one,
2-(3-fluorophenoxy)-5-(((1-oxo-1,6,7,8,8a,9-hexahydropyrrolo[1',2':3,4]imidazo[1,2-c] pyrimidin-3-yl)oxy)methyl)benzonitrile,
2-(3,5-difluorophenoxy)-5-(((1-oxo-1,6,7,8,8a,9-hexahydropyrrolo[1',2':3,4]imidazo[1,2-c] pyrimidin-3-yl)oxy)methyl)benzonitrile,
3-((3,5-difluoro-4-((2-(trifluoromethyl)pyrimidin-5-yl)oxy)benzyl)oxy)-7,8,8a,9-tetra hydropyrrolo[1',2':3,4]imidazo [1,2-c]pyrimidin-1(6H)-one,
3-((4-((3,3-difluorocyclohexyl)oxy)-3,5-difluorobenzyl)oxy)-7,8,8a,9-tetrahydropyrrolo[1',2':3,4]imidazo[1,2-c] pyrimidin-1(6H)-one,
3-((4-((3,3-difluorocyclopentyl)oxy)-3,5-difluorobenzyl)oxy)-7,8,8a,9-tetrahydropyrrolo[1',2':3,4]imidazo[1,2-c] pyrimidin-1(6H)-one,
3-((3,5-difluoro-4-((1-(3,3,3-trifluoropropyl)azetidin-3-yl)oxy)benzyl)oxy)-7,8,8a,9-tetra hydropyrrolo[1',2':3,4] imidazo[1,2-c]pyrimidin-1(6H)-one,
3-((2,4-difluorobenzyl)oxy)-7,8,8a,9-tetrahydropyrrolo[1', 2':3,4]imidazo[1,2-c] pyrimidin-1(6H)-one,
3-((2, 3-difluorobenzyl) oxy)-7, 8, 8a, 9-tetrahydropyrrolo[1',2':3, 4]imidazo[1,2-c] pyrimidin-1(6H)-one, 3-((3-fluorobenzyl)oxy)-7,8,8a,9-tetrahydropyrrolo[1',2':3, 4]imidazo[1,2-c]pyrimidin-1(6H)-one, 3-((3,5-difluorobenzyl)oxy)-7,8,8a,9-tetrahydropyrrolo[1', 2':3,4]imidazo[1,2-c] pyrimidin-1(6H)-one, 3-((3-fluorobenzyl)amino)-7,8,8a,9-tetrahydropyrrolo[1',2': 3,4]imidazo[1,2-c]pyrimidin-1(6H)-one, 3-((3,5-difluoro-4-(1-(2-fluoroethyl)cyclopropoxy)benzyl) oxy)-7,8,8a,9-tetrahydro pyrrolo[1',2':3,4]imidazo[1,2-c] pyrimidin-1(6H)-one, 3-((3,5-difluoro-4-((2-methylpyridin-4-yl)oxy)benzyl)oxy)-7, 8, 8a,9-tetrahydro pyrrolo[1',2':3,4]imidazo[1,2-c]pyrimidin-1(6H)-one, 7-((3,5-difluoro-4-((1-propyl-1H-pyrazol-4-yl)oxy)benzyl) oxy)-3,4,11,11atetrahydropyrimido[6',1':2,3]imidazo[5,1-c][1,4]oxazin-9(1H)-one, 7-(3, 5-difluoro-4-((2-(trifluoromethyl) pyridin-4-yl) oxy) benzyl) oxy)-3,4,11,11a tetrahydropyrimido[6',1':2,3]imidazo[5,1-c][1,4]oxazin-9(1H)-one, 7-((3,5-difluoro-4-((1-methyl-1H-pyrazol-4-yl)oxy)benzyl) oxy)-3,4,11,11a-tetrahydropyrimido[6',1':2,3]imidazo[5, 1-c][1,4]oxazin-9(1H)-one, 7-((4-((1-ethyl-1H-pyrazol-4-yl)oxy)-3,5-difluorobenzyl) oxy)-3,4,11,11a-tetrahydro pyrimido[6',1':2,3]imidazo[5, 1-c][1,4]oxazin-9(1H)-one, 7-((3,4,5-trifluorobenzyl)oxy)-3,4,11,11atetrahydropyrimido[6',1':2,3]imidazo[5,1-c][1,4] oxazin-9(1H)-one, 7-((3,5-difluoro-4-((2-methylpyridin-4-yl)oxy)benzyl)oxy)-3,4,11,11atetrahydropyrimido[6',1':2,3]imidazo[5,1-c][1, 4]oxazin-9(1H)-one, 7-((3,5-difluoro-4-((6-methylpyridin-3-yl)oxy)benzyl)oxy)-3,4,11,11atetrahydropyrimido[6',1':2,3]imidazo[5,1-c][1, 4]oxazin-9(1H)-one, 7-(3, 5-difluoro-4-((2-(trifluoromethyl) pyridin-4-yl)oxy) benzyl)oxy)-3, 4, 11,11a-tetra hydropyrimido[6',1':2,3] imidazo[5,1-c][1,4]oxazin-9(1H)-one, 7-((2,4-difluorobenzyl)oxy)-3,4,11,11a-tetrahydropyrimido [6',1':2,3]imidazo[5,1-c][1,4] oxazin-9(1H)-one, 7-((2,3-difluorobenzyl)oxy)-3,4,11,11a-tetrahydropyrimido [6',1':2,3]imidazo[5,1-c][1,4] oxazin-9(1H)-one, 7-(3-fluorobenzyl)oxy)-3,4,11,11a-tetrahydropyrimido[6', 1':2,3]imidazo[5,1-c][1,4] oxazin-9(1H)-one, 7-((3,5-difluorobenzyl)oxy)-3,4,11,11a-tetrahydropyrimido [6',1':2,3]imidazo[5,1-c][1,4] oxazin-9(1H)-one, 3-((3,5-difluoro-4-((2-(trifluoromethyl)pyridin-4-yl)oxy) benzyl)oxy)-8,9,9a,10-tetrahydropyrimido[6',1':2,3]imidazo[1,5-c][1,3]oxazin-1(6H)-one, 3-((3,5-difluoro-4-((2-(trifluoromethyl)pyridin-4-yl)oxy) benzyl)oxy)-8,9,9a,10-tetrahydropyrimido[6',1':2,3]imidazo[1,5-c][1,3]oxazin-1(6H)-one, 3-((3,5-difluoro-4-((1-methyl-1H-pyrazol-4-yl)oxy)benzyl) oxy)-8,9,9a,10-tetrahydropyrimdo[6',1':2,3]imidazo[1,5-c][1,3]oxazin-1(6H)-one, 3-((3,5-difluoro-4-((1-methyl-1H-pyrazol-4-yl)oxy)benzyl) oxy)-8,9,9a,10-tetrahydropyrimido[6',1':2,3]imidazo[1,5-c][1,3]oxazin-1(6H)-one, 3-((3-fluorobenzyl)oxy)-8,9,9a,10-tetrahydropyrimido[6',1': 2,3]imidazo[1,5-c][1,3] oxazin-1(6H)-one, 3-((3,4,5-trifluorobenzyl)oxy)-8,9,9a,10-tetrahydropyrimido[6',1':2,3]imidazo[1,5-c][1,3]oxazin-1(6H)-one, 3-((3,5-difluoro-4-(1-(2-fluoroethyl)cyclopropoxy)benzyl) oxy)-8,9,9a,10-tetrahydro pyrimido[6',1':2,3]imidazo[1, 5-c][1,3]oxazin-1(6H)-one, 6-((3,5-difluoro-4-((2-(trifluoromethyl)pyridin-4-yl)oxy) benzyl)oxy)-10,10a-dihydro-1H-oxazolo[3',4':3,4]imidazo[1,2-c]pyrimidin-8(3H)-one, 6-((3,5-difluoro-4-((1-methyl-1H-pyrazol-4-yl)oxy)benzyl) oxy)-10,10a-dihydro-1H-oxazolo[3',4':3,4]imidazo[1,2-c]pyrimidin-8(3H)-one, 6-((4-chloro-3-fluorobenzyl)oxy)-10,10a-dihydro-1H-oxazolo[3',4':3,4]imidazo[1,2c]pyrimidin-8(3H)-one, 6-((3,4,5-trifluorobenzyl)oxy)-10,10a-dihydro-1H-oxazolo [3',4':3,4]imidazo[1,2-c] pyrimidin-8(3H)-one, 6-((3,5-difluorobenzyl)oxy)-10,10a-dihydro-1H-oxazolo[3', 4':3,4]imidazo[1,2-c] pyrimidin-8(3H)-one, 6-((3-fluorobenzyl)oxy)-10,10a-dihydro-1H-oxazolo[3',4': 3,4]imidazo[1,2-c]pyrimidin-8(3H)-one, 6-((3,5-difluoro-4-((6-methylpyridin-3-yl)oxy)benzyl)oxy)-10,10a-dihydro-1H-oxazolo[3',4':3,4]imidazo[1,2-c]pyrimidin-8(3H)-one, 6-((3,5-difluoro-4-((1-propyl-1H-pyrazol-4-yl)oxy)benzyl) oxy)-10,10a-dihydro-1H-oxazolo[3',4':3,4]imidazo[1,2-c]pyrimidin-8(3H)-one, 6-((3,5-difluoro-4-((1-(trifluoromethyl)-1H-pyrazol-4-yl) oxy)benzyl)oxy)-10,10a-dihydro-1H-oxazolo[3',4':3,4] imidazo[1,2-c]pyrimidin-8(3H)-one, 6-((3,5-difluoro-4-((2-methylpyrimidin-5-yl)oxy)benzyl) oxy)-10,10a-dihydro-1H-oxazolo[3',4':3,4]imidazo[1,2-c]pyrimidin-8(3H)-one, 6-((3,5-difluoro-4-((2-methylpyridin-4-yl)oxy)benzyl)oxy)-10,10a-dihydro-1H-oxazolo[3',4':3,4]imidazo[1,2-c]pyrimidin-8(3H)-one, 6-((4-((1-ethyl-1H-pyrazol-4-yl)oxy)-3,5-difluorobenzyl) oxy)-10,10a-dihydro-1H-oxazolo[3',4':3,4]imidazo[1,2-c]pyrimidin-8(3H)-one, 6-((3,5-difluoro-4-((2-methylpyridin-4-yl)oxy)benzyl)oxy)-10,10a-dihydro-1H-oxazolo[3',4':3,4]imidazo[1,2-c]pyrimidin-8(3H)-one, 7-((3,5-difluoro-4-((2-(trifluoromethyl)pyridin-4-yl)oxy) benzyl)oxy)-3,4,11,11a-tetrahydropyrimido[6',1':2,3]imidazo[5,1-b][1,3]oxazin-9(2H)-one, 6-((3,5-difluoro-4-((2-(trifluoromethyl)pyridin-4-yl)oxy) benzyl)oxy)-10,10a-dihydro-2H-oxazolo[3',2':3,4]imidazo[1,2-c]pyrimidin-8(3H)-one, 6-((2,4-difluorobenzyl)oxy)-10,10a-dihydro-1H-oxazolo[3', 4':3,4]imidazo[1,2-c] pyrimidin-8(3H)-one, 6-((2,3-difluorobenzyl)oxy)-10,10a-dihydro-1H-oxazolo[3', 4':3,4]imidazo[1,2-c]pyrimidin-8(3H)-one, 6-((3,5-difluorobenzyl)oxy)-10,10a-dihydro-1H-oxazolo[3', 4':3,4]imidazo[1,2-c] pyrimidin-8(3H)-one, 6-((2,4,5-trifluorobenzyl)oxy)-10,10a-dihydro-1H-oxazolo [3',4':3,4]imidazo[1,2-c] pyrimidin-8(3H)-one, 6-((2,4-difluorobenzyl)oxy)-10,10a-dihydro-1H-oxazolo[3', 4':3,4]imidazo[1,2-c]pyrimidin-8(3H)-one, 3-((2,4-difluorobenzyl)oxy)-8,9,9a, 10-tetrahydropyrimido [6',1':2,3]imidazo[1,5-c] [1,3] oxazin-1(6H)-one, 6-((3-(((2-(trifluoromethyl)pyridin-4-yl)oxy)methyl)bicyclo [1.1.1]pentan-1-yl)methoxy)-10,10a-dihydro-1H-oxazolo [3',4':3,4]imidazo[1,2-c]pyrimidin-8(3H)-one, 3-((2,4-difluorobenzyl)oxy)-8,9,9a, 10-tetrahydropyrimido [6',1':2,3]imidazo[1,5-c][1,3]oxazin-1(6H)-one, 3-((2,4,5-trifluorobenzyl)oxy)-8,9,9a, 10-tetrahydropyrimido[6',1':2,3]imidazo[1,5-c][1,3]oxazin-1(6H)-one, 3-((3,5-difluorobenzyl)oxy)-8,9,9a,10-tetrahydropyrimido [6',1':2,3]imidazo[1,5-c] [1,3] oxazin-1(6H)-one, 3-((2,3-difluorobenzyl)oxy)-8,9,9a, 10-tetrahydropyrimido [6',1':2,3]imidazo[1,5-c] [1,3] oxazin-1(6H)-one, 6-(3-fluorophenethoxy)-10,10a-dihydro-1H-oxazolo[3',4':3, 4]imidazo[1,2-c]pyrimidin-8(3H)-one, 6-((3,5-difluoro-4-((1-methyl-1H-pyrazol-4-yl)oxy)benzyl) oxy)-10,10a-dihydro-2H-oxazolo[3',2':3,4]imidazo[1,2-c]pyrimidin-8(3H)-one, 4-(2-((8-oxo-3,8, 10,10a-tetrahydro-1H-oxazolo[3',4': 3,4]imidazo[1,2-c]pyrimidin-6-yl)oxy)ethyl)benzonitrile, 3-(3-fluorophenethyl)-8,9,9a,10-tetrahydropyrimido[6',1':2,3]imidazo[1,5-c][1,3]oxazin-1(6H)-one, 6-((3,5-difluoro-4-(1-(2-fluoroethyl)cyclopropoxy)benzyl)oxy)-10,10a-dihydro-1H-oxazolo[3',4':3,4]imidazo[1,2-c]pyrimidin-8(3H)-one, 6-((9-fluoro-3,4-dihydrospiro[benzo[b][1,4]dioxepine-2,1'-cyclopropan]-7-yl)methoxy)-10,10a-dihydro-1H-oxazolo[3',4':3,4]imidazo[1,2-c]pyrimidin-8(3H)-one, 3-((9-fluoro-3,4-dihydrospiro[benzo[b][1,4]dioxepine-2,1'-cyclopropan]-7-yl)methoxy)-8,9,9a,10-tetrahydropyrimido[6',1':2,3]imidazo[1,5-c][1,3]oxazin-1(6H)-one, 6-(3-fluorophenethyl)-10,10a-dihydro-1H-oxazolo[3',4':3,4]imidazo[1,2-c]pyrimidin-8(3H)-one, 6-(2,4-difluorophenethyl)-10,10a-dihydro-1H-oxazolo[3',4':3,4]imidazo[1,2-c]pyrimidin-8(3H)-one, 3-((4-((3,3-difluoropiperidin-1-yl)methyl)-3-fluorobenzyl)oxy)-6,7,8,9,9a,10-hexahydro-1H-pyrido[1',2':3,4]imidazo[1,2-c]pyrimidin-1-one, 3-((4-((4,4-difluorocyclohexyl)oxy)-3,5-difluorobenzyl)oxy)-7,8,8a,9-tetrahydro pyrrolo[1',2':3,4]imidazo[1,2-c]pyrimidin-1(6H)-one, 3-((4-((1-butylazetidin-3-yl)oxy)-3,5-difluorobenzyl)oxy)-7,8,8a,9-tetrahydropyrrolo[1',2':3,4]imidazo[1,2-c]pyrimidin-1(6H)-one, 3-((3,5-difluoro-4-(3-fluoropropyl)benzyl)oxy)-7,8,8a,9-tetrahydropyrrolo[1',2':3,4] imidazo[1,2-c]pyrimidin-1(6H)-one, 3-((3,5-difluoro-4-(2-fluoroethoxy)benzyl)oxy)-7,8,8a,9-tetrahydropyrrolo[1',2':3,4] imidazo[1,2-c]pyrimidin-1(6H)-one, 3-((2,3-difluorobenzyl)oxy)-7,8,8a,9-tetrahydropyrrolo[1',2':3,4]imidazo[1,2-c]pyrimidin-1(6H)-one, 3-((2,4,5-trifluorobenzyl)oxy)-7,8,8a,9-tetrahydropyrrolo[1',2':3,4]imidazo[1,2-c] pyrimidin-1(6H)-one, 3-((3,5-difluorobenzyl)oxy)-7,8,8a,9-tetrahydropyrrolo[1',2':3,4]imidazo[1,2-c]pyrimidin-1(6H)-one, 3-((2,4-difluorobenzyl)amino)-7,8,8a,9-tetrahydropyrrolo[1',2':3,4]imidazo[1,2-c] pyrimidin-1(6H)-one, 3-((3,5-difluorobenzyl)amino)-7,8,8a,9-tetrahydropyrrolo[1',2':3,4]imidazo[1,2-c] pyrimidin-1(6H)-one, 3-((2,4,5-trifluorobenzyl)oxy)-7,8,8a,9-tetrahydropyrrolo[1',2':3,4]imidazo[1,2-c]pyrimidin-1(6H)-one, 7-((2,4,5-trifluorobenzyl)oxy)-3,4,11,11a-tetrahydropyrimido[6',1':2,3]imidazo[5,1-c][1,4]oxazin-9(1H)-one, 7-((2,4,5-trifluorobenzyl)oxy)-3,4,11,11a-tetrahydropyrimido[6',1':2,3]imidazo[5,1-c][1,4]oxazin-9(1H)-one, 7-((2,3-difluorobenzyl)oxy)-3,4,11,11a-tetrahydropyrimido[6',1':2,3]imidazo[5,1-c][1,4]oxazin-9(1H)-one, 3-((3,5-difluorobenzyl)(methyl)amino)-7,8,8a,9-tetrahydropyrrolo[1',2':3,4]imidazo[1,2-c]pyrimidin-1(6H)-one, 3-((2,4-difluorobenzyl)(methyl)amino)-7,8,8a,9-tetrahydropyrrolo[1',2':3,4]imidazo[1,2-c]pyrimidin-1(6H)-one, 3-(3-fluorophenethyl)-7,8,8a,9-tetrahydropyrrolo[1',2':3,4]imidazo[1,2-c]pyrimidin-1(6H)-one, 3-((2,4,5-trifluorobenzyl)amino)-7,8,8a,9-tetrahydropyrrolo[1',2':3,4]imidazo[1,2-c]pyrimidin-1(6H)-one, 3-((3,5-difluorobenzyl)amino)-7,8,8a,9-tetrahydropyrrolo[1',2':3,4]imidazo[1,2-c]pyrimidin-1(6H)-one, 3-((2,3-difluorobenzyl)amino)-7,8,8a,9-tetrahydropyrrolo[1',2':3,4]imidazo[1,2-c]pyrimidin-1(6H)-one, 3-((3,4,5-trifluorobenzyl)amino)-7,8,8a,9-tetrahydropyrrolo[1',2':3,4]imidazo[1,2-c] pyrimidin-1(6H)-one, 3-((2,4-difluorobenzyl)amino)-6,7,8,9,9a,10-hexahydro-1H-pyrido[1',2':3,4]imidazo[1,2-c]pyrimidin-1-one, 3-((3-fluorobenzyl)amino)-6,7,8,9,9a,10-hexahydro-1H-pyrido[1',2':3,4]imidazo[1,2-c] pyrimidin-1-one, 3-((3,5-difluorobenzyl)amino)-6,7,8,9,9a,10-hexahydro-1H-pyrido[1',2':3,4]imidazo[1,2-c]pyrimidin-1-one, 3-((2,4,5-trifluorobenzyl)amino)-7,8,8a,9-tetrahydropyrrolo[1',2':3,4]imidazo[1,2-c] pyrimidin-1(6H)-one, 3-((3,4,5-trifluorobenzyl)amino)-7,8,8a,9-tetrahydropyrrolo[1',2':3,4]imidazo[1,2-c]pyrimidin-1(6H)-one, 3-((2,3-difluorobenzyl)amino)-7,8,8a,9-tetrahydropyrrolo[1',2':3,4]imidazo[1,2-c] pyrimidin-1(6H)-one, 3-((3-fluorobenzyl)(methyl)amino)-6,7,8,9,9a,10-hexahydro-1H-pyrido[1',2':3,4]imidazo[1,2-c]pyrimidin-1-one, 7-((2,4,5-trifluorobenzyl)amino)-3,4,11,11a-tetrahydropyrimido[6',1':2,3]imidazo[5,1-c][1,4]oxazin-9(1H)-one, 7-((2,3-difluorobenzyl)amino)-3,4,11,11a-tetrahydropyrimido[6',1':2,3]imidazo[5,1c]-[1,4]oxazin-9(1H)-one, 3-((2,4,5-trifluorobenzyl)amino)-6,7,8,9,9a,10-hexahydro-1H-pyrido[1',2':3,4]imidazo[1,2-c]pyrimidin-1-one, 3-((2,3-difluorobenzyl)amino)-6,7,8,9,9a,10-hexahydro-1H-pyrido[1',2':3,4]imidazo[1,2-c]pyrimidin-1-one, 7-(3-fluorophenethoxy)-3,4,11,11a-tetrahydropyrimido[6',1':2,3]imidazo[5,1-c][1,4] oxazin-9(1H)-one, 3-(3-fluorophenethoxy)-7,8,8a,9-tetrahydropyrrolo[1',2':3,4]imidazo[1,2-c]pyrimidin-1(6H)-one, 3-(methyl(2,4,5-trifluorobenzyl)amino)-7,8,8a,9-tetrahydropyrrolo[1',2':3,4]imidazo[1,2-c]pyrimidin-1(6H)-one, 3-(methyl(3,4,5-trifluorobenzyl)amino)-7,8,8a,9-tetrahydropyrrolo[1',2':3,4]imidazo[1,2-c]pyrimidin-1(6H)-one, 3-((3-fluorobenzyl)(methyl)amino)-7,8,8a,9-tetrahydropyrrolo[1',2':3,4]imidazo[1,2-c]pyrimidin-1(6H)-one, 3-((2,4-difluorobenzyl)(methyl)amino)-7,8,8a,9-tetrahydropyrrolo[1',2':3,4]imidazo[1,2-c]pyrimidin-1(6H)-one, 4-(2-((1-oxo-1,6,7,8,8a,9-hexahydropyrrolo[1',2':3,4]imidazo[1,2-c]pyrimidin-3-yl)oxy) ethyl)benzonitrile, 4-(2-((9-oxo-1, 3,4,9,11,11a-hexahydropyrimido[6',1':2,3]imidazo[5,1-c][1,4]oxazin-7-yl)oxy)ethyl)benzonitrile, 7-(3-fluorophenethyl)-3,4,11,11a-tetrahydropyrimido[6',1':2,3]imidazo[5,1-c][1,4]oxazin-9(1H)-one, 7-(3-fluorophenethyl)-3,4,11,11a-tetrahydropyrimido[6',1':2,3]imidazo[5,1-c][1,4] oxazin-9(1H)-one, 7-((3,5-difluoro-4-(1-(2-fluoroethyl)cyclopropoxy)benzyl)oxy)-3,4,11,11a-tetrahydropyrimido[6',1':2,3]imidazo[5,1-c][1,4]oxazin-9(1H)-one 7-((9-fluoro-3,4-dihydrospiro[benzo[b][1,4]dioxepine-2,1'-cyclopropan]-7-yl)methoxy)-3,4,11,11a-tetrahydropyrimido[6',1':2,3]imidazo[5,1-c][1,4]oxazin-9(1H)-one, 3-((9-fluoro-3,4-dihydrospiro[benzo[b][1,4]dioxepine-2,1'-cyclopropan]-7-yl)methoxy)-7,8,8a,9-tetrahydropyrrolo[1',2':3,4]imidazo[1,2-c]pyrimidin-1(6H)-one, 3-((9-fluoro-3,4-dihydrospiro[benzo[b][1,4]dioxepine-2,1'-cyclopropan]-7-yl)methoxy)-6,7,8,9,9a,10-hexahydro-1H-pyrido[1',2':3,4]imidazo[1,2-c]pyrimidin-1-one, 7-(2,4-difluorophenethyl)-3,4,11,11a-tetrahydropyrimido[6',1':2,3]imidazo[5,1-c][1,4] oxazin-9(1H)-one, 2-(azetidine-2-carbonyl)-7-((3,4-difluorobenzyl)oxy)-3,4,11,11a-tetrahydro-1H-pyrazino[1',2':3,4]imidazo[1,2-c]pyrimidin-9(2H)-one, 2-fluoro-5-(((((7,8a)-7-hydroxy-1-oxo-1,6,7,8,8a,9-hexahydropyrrolo[1',2':3,4]imidazo[1,2-c]pyrimidin-3-yl)oxy)methyl)benzonitrile, (7,8a)-3-((3,5-difluoro-4-((2-(trifluoromethyl)pyridin-4-yl)oxy)benzyl)oxy)-7-hydroxy-7,8,8a,9-tetrahydropyrrolo[1',2':3,4]imidazo[1,2-c]pyrimidin-1(6H)-one, (7,8a)-3-((3,5-difluoro-4-((2-(trifluoromethyl)pyridin-4-yl)oxy)benzyl)oxy)-7-hydroxy-7,8,8a,9-tetrahydropyrrolo[1',2':3,4]imidazo[1,2-c]pyrimidin-1(6H)-one, 5-((((7,8a)-7-Amino-1-oxo-1,6,7,8,8a,9-hexahydropyrrolo [1',2':3,4]imidazo[1,2-c] pyrimidin-3-yl)oxy)methyl)-2-fluorobenzonitrile, (7,8a)-7-amino-3-((3,5-difluoro-4-((2-(trifluoromethyl) pyridin-4-yl)oxy)benzyl)oxy)-7,8,8a,9-tetrahydropyrrolo [1',2':3,4]imidazo[1,2-c]pyrimidin-1(6H)-one, 5-((((7,8a)-7-amino-1-oxo-1,6,7,8,8a,9-hexahydropyrrolo [1',2':3,4]imidazo[1,2-c]pyrimidin-3-yl)oxy)methyl)-2-fluorobenzonitrile, (7,8a)-7-amino-3-((3,5-difluoro-4-((2-(trifluoromethyl) pyridin-4-yl)oxy)benzyl)oxy)-7,8,8a,9-tetrahydropyrrolo [1',2':3,4]imidazo[1,2-c]pyrimidin-1(6H)-one, 7-((3,5-difluoro-4-((6-methylpyridin-3-yl)oxy)benzyl)oxy)-1-methyl-1H-spiro[imidazo[1,2-c]pyrimidine-2,3'-oxetan]-5(3H)-one, a free base, free acid, or a salt (e.g., a pharmaceutically acceptable salt) thereof.

The compounds of the above referenced formulas, salts (e.g., pharmaceutically acceptable salts) thereof may exist in stereoisomeric forms (e.g., it contains one or more asymmetric carbon atoms). The individual stereoisomers (enantiomers and diastereomers) and mixtures of these are included within the scope of the present invention. The invention also covers the individual isomers of the compounds of the above referenced formulas, salts (e.g., pharmaceutically acceptable salts) thereof as mixtures with isomers thereof in which one or more chiral centers are inverted. Likewise, it is understood that the compounds of the above referenced formulas, salts (e.g., pharmaceutically acceptable salts) thereof may exist in tautomeric forms other than that shown in the formula and these are also included within the scope of the present invention. It is to be understood that the present invention includes all combinations and subsets of the particular groups defined hereinabove. The scope of the present invention includes mixtures of stereoisomers as well as purified enantiomers or enantiomerically/diastereomerically enriched mixtures. Also included within the scope of the invention are individual isomers of the compounds of the above referenced formulas, salts (e.g., pharmaceutically acceptable salts) thereof, as well as any wholly or partially equilibrated mixtures thereof. The present invention also includes the individual isomers of the compounds of the above referenced formulas, salts (e.g., pharmaceutically acceptable salts) thereof as well as mixtures with isomers thereof in which one or more chiral centers are inverted. It is to be understood that the present invention includes all combinations and subsets of the particular groups defined hereinabove. The different isomeric forms may be separated or resolved one from the other by conventional methods (e.g. chiral HPLC), or any given isomer may be obtained by conventional synthetic methods e.g. stereospecific or asymmetric syntheses.

The invention also includes various deuterated forms of compounds of the above referenced formulas, salts (e.g., pharmaceutically acceptable salts) thereof. Each available hydrogen atom attached to a carbon atom may be independently replaced with a deuterium atom. A person of ordinary skill in the art will know how to synthesize deuterated forms of compounds of the above referenced formulas, salts (e.g., pharmaceutically acceptable salts) thereof. Commercially available deuterated starting materials may be employed in the preparation of deuterated forms of compounds of the above referenced formulas, salts (e.g., pharmaceutically acceptable salts) thereof, or they may be synthesized using conventional techniques employing deuterated reagents (e.g. lithium aluminum deuteride).

In addition to the free base or free acid form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free acid or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

In certain embodiments, compounds of the present invention may contain an acidic functional group, which is acidic enough to form salts. Representative salts include pharmaceutically-acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically-acceptable organic primary, secondary, and tertiary amines including aliphatic amines, aromatic amines, aliphatic diamines, and hydroxy alkylamines such as methylamine, ethylamine, diethylamine, triethylamine, ethylenediamine, ethanolamine, diethanolamine, and cyclohexylamine.

In certain embodiments, compounds of the present invention may contain a basic group and are therefore capable of forming pharmaceutically acceptable acid addition salts by treatment with a suitable acid. Suitable acids include pharmaceutically-acceptable inorganic acids and pharmaceutically acceptable organic acids. These salts may be crystalline or amophorus. Exemplary pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, di nitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. Some of these salts form solvates, some are crystalline.

The compounds described herein, their salts (e.g., pharmaceutically acceptable salts), deuterated form, solvates or hydrates thereof, may exist in one or more polymorphic form. Therefore, in a further aspect, the invention provides a polymorph of a compound defined herein, their salts (e.g., pharmaceutically acceptable salts), or a polymorph of a solvate or hydrate of a compound described herein or a salt (e.g., pharmaceutically acceptable salt) thereof.

The compounds of the above referenced formulas and salts (including pharmaceutically acceptable salts) thereof may be in the form of a solvate. For solvates of the compounds of the above referenced formulas, including solvates of salts of the compounds of the above referenced formulas, that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, dimethylsulfoxide, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Solvates include stoichiometric solvates as well as compositions containing variable amounts of the incorporated solvent(s), e.g. a hydrate includes stoichiometic hydrates and compositions containing variable amounts of water.

The invention also includes isotopically labeled compounds and salts, which are identical to compounds of the above referenced formulas or salts thereof, but for the fact that one or more atoms are replaced by an atom having an atomic mass or mass number different from the atomic mass or mass number most commonly found in nature. Examples of isotopes that can be incorporated into compounds of the above referenced formulas or salts thereof isotopes of hydrogen, carbon, nitrogen, fluorine, such as $^3H$, $^{11}C$, $^{14}C$ and $^{18}F$. Such isotopically-labeled compound of the above referenced formulas or salts thereof are useful in drug and/or substrate tissue distribution assays. For example, $^{11}C$ and $^{18}F$ isotopes are useful in PET (positron emission tomography). PET is useful in brain imaging. Isotopically-labeled compounds of the above referenced formulas and salts thereof can generally be prepared by carrying out the procedures disclosed below, by substituting a readily available isotopically-labeled reagent for a non-isotopically labeled reagent. In one embodiment, compounds of the above referenced formulas or salts thereof are not isotopically labeled.

As used herein, the terms "compound(s) of the invention" or "compound(s) of the present invention" mean a compound of the above referenced formulas, as defined herein, in any form, i.e., any salt or non-salt form (e.g., as a free acid or base form, or as a salt, for example, a pharmaceutically acceptable salt thereof), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms. In the context of pharmaceutical composition and methods of treatment discussed herein, the terms of "compounds of the invention" mean a compound of the above referenced formulas, as defined herein, in the form of any pharmaceutically acceptable salt thereof or non-salt form (e.g., as a free acid or base form), deuterated form and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, a compound of the invention includes a compound of the above referenced formulas, or a salt thereof, for example a pharmaceutically acceptable salt thereof. Representative compounds of this invention include the specific compounds described.

C. Synthesis of Compounds

The process to be utilized in the preparation of the compounds described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

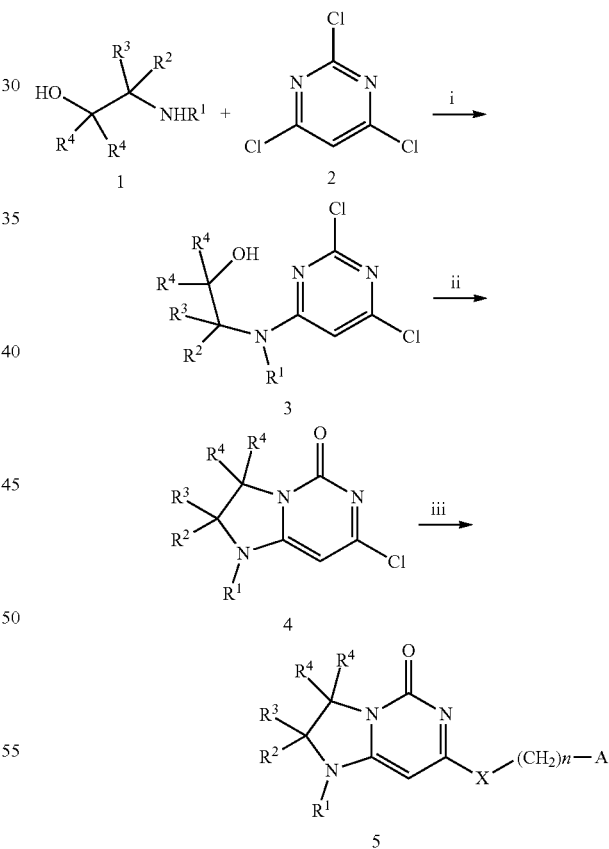

General reaction scheme

General Reaction Scheme provides an exemplary synthesis for compound 5. $R^1$, $R^2$, $R^3$, $R^4$, X, n and A are as defined in Formula (I).

Step (i) may be carried out as $S_N2Ar$ reaction by starting from compound 1 as nucleophile to react with compound 2 using appropriate base such as triethylamine (TEA) in an aprotic polar solvent (e.g., DMF) to provide compound 3.

Step (ii) provides synthesis of compound 4 through cyclization of 3 under Mitsunobu condition (e.g., DIAD, DEAD). Step (iii) may be carried out by reacting compound 4 with H—X—(CH$_2$)$_n$-A in the presence of a suitable base such as NaH or diisopropyl ethylamine in a suitable solvent such as dimethylformamide (DMF) or dioxane to provide final compound 5.

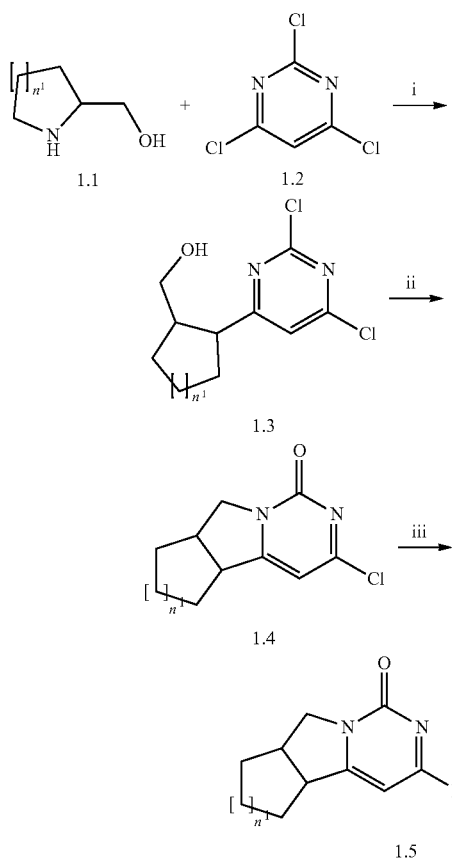

Scheme 1

$n^1$ is 0, 1, or 2

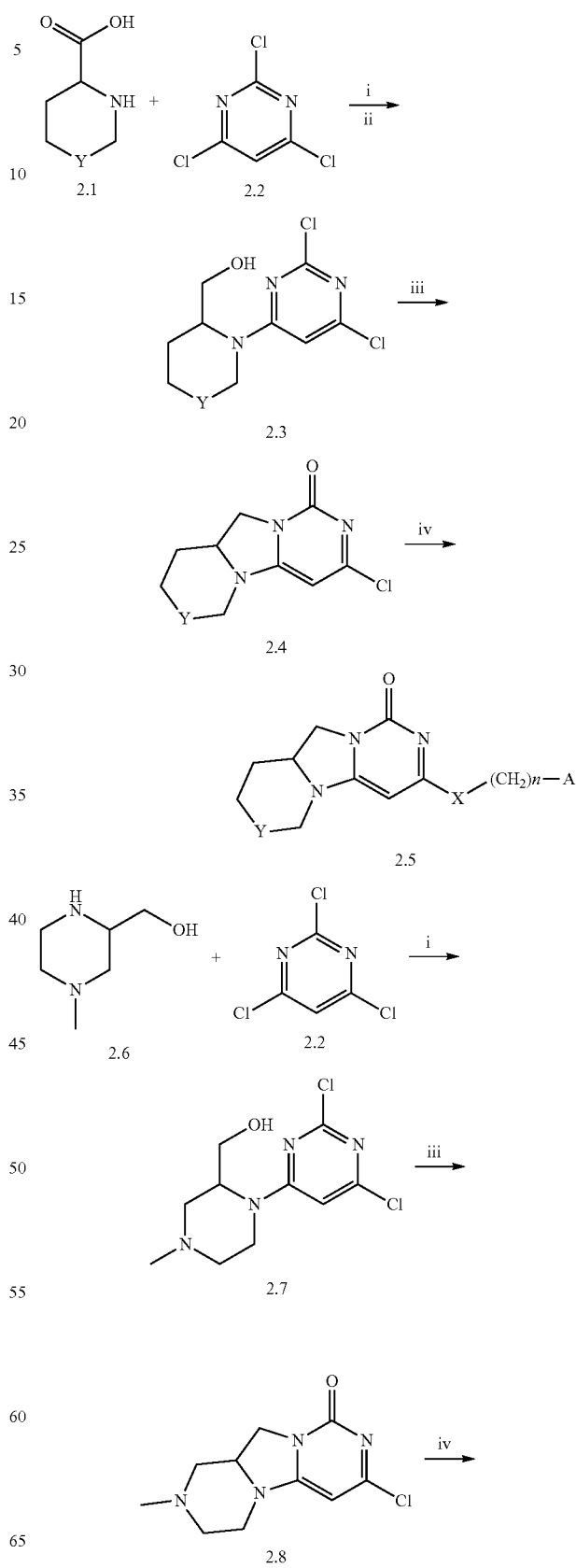

Scheme 2

Scheme 1 provides an exemplary synthesis for compound 1.5. n and A are as defined in Formula (I). X is as defined in Formula (I) except X is absent. Step (i) may be carried out by reacting compound 1.1 with compound 1.2 using appropriate reagents such as triethylamine (TEA) in an appropriate solvent such as acetonitrile under a suitable temperature such as room temperature to provide compound 1.3. Step (ii) may be taken place by reacting compound 1.3 with a suitable reagent such as triethylamine (TEA) and methanesulfonyl chloride (MsCl) at appropriate temperature such as 0° C. to obtain compound 1.4. Step (iii) may be carried out by reacting compound 1.4 with H—X—(CH$_2$)$_n$-A, in the presence of a suitable base such as NaH or diisopropyl ethylamine in a suitable solvent such as DMF or dioxane to provide O- or NH-linked final compound 1.5. Sonogashira coupling of compound 1.4 and HC≡C—W, followed by hydrogenation afforded carbon-linked compound 1.5. W is as define in Formula (I). Variation of reaction conditions and reagents, which is obvious to one skilled in the art, may be applied for different —X—(CH$_2$)$_n$-A groups.

-continued

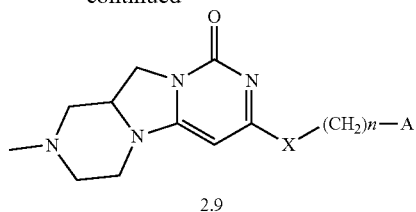

2.9

X: O or absent
Y: O or CH$_2$

-continued

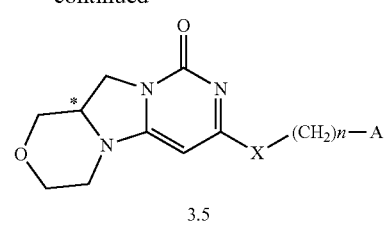

3.5

X = O, NH or absent

General Experimental Scheme 2 provides an exemplary synthesis for compounds 2.5 and 2.9. n and A are as defined in Formula (I). Step (i) may be carried out by reacting compound 2.1 with compound 2.2 using appropriate reagents such as triethylamine (TEA) in an appropriate solvent such as acetonitrile under a suitable temperature such as room temperature followed by reduction with BH$_3$ in step (ii) to provide compound 2.3. Step (iii) may be taken place by reacting compound 2.3 with a suitable reagent such as triethylamine (TEA) or K$_2$CO$_3$ and methanesulfonyl chloride (MsCl) in an appropriate solvent such as THF or dioxane at an appropriate temperature such as 95° C. to provide compound 2.4. Step (iv) may be proceeded by reacting compound 2.4 with H—X—(CH$_2$)$_n$-A in the presence of a suitable base such as NaH in a suitable solvent such as DMF at suitable temperature such as 0° C. or Sonogashira coupling of compound 2.4 and HC≡C—W followed by hydrogenation to afford compound 2.5. W is as defined in Formula (I). Similarly to the synthesis of O-linked compound 2.5, compound 2.9 was prepared starting from alcohol 2.6 and trichloropyrimidine 2.2. Variation of reaction conditions and reagents, which is obvious to one skilled in the art, may be applied for different —X—(CH$_2$)$_n$-A groups.

Scheme 3 provides an exemplary synthesis for compounds 3.5. n and A are as defined in Formula (I). X is as defined in Formula (I) except X is absent. Step (i) may be taken place by reacting compound 3.1 with a suitable reagent such as HCl in an appropriate solvent such as methanol at appropriate temperature such as room temperature to provide compound 3.2. Similarly to the step (ii) of Scheme 1, compound 3.4 may be obtained in step (ii) by reacting compound 3.3 with a suitable reagent such as triethylamine (TEA) and methanesulfonyl chloride (MsCl) at appropriate temperature such as 0° C. to provide compound 3.4. Then final compound 3.5 may be provided by carrying out step (iii) by reacting compound 3.4 with H—X—(CH$_2$)$_n$-A in the presence of a suitable base such as NaH or diisopropyl ethylamine in a suitable solvent such as DMF or dioxane to provide compound 3.5. Sonogashira coupling of 3.4 and HC≡C—W followed by hydrogenation can provide carbon-linked compound 3.5. Variation of reaction conditions and reagents, which is obvious to one skilled in the art, may be applied for different —X—(CH$_2$)$_n$-A groups.

Scheme 3

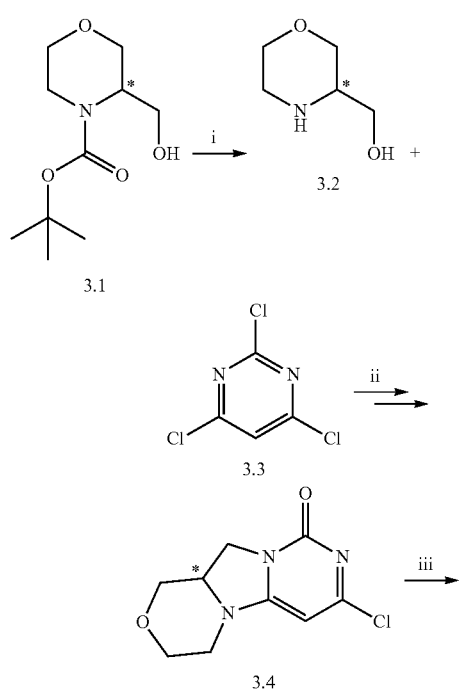

Scheme 4

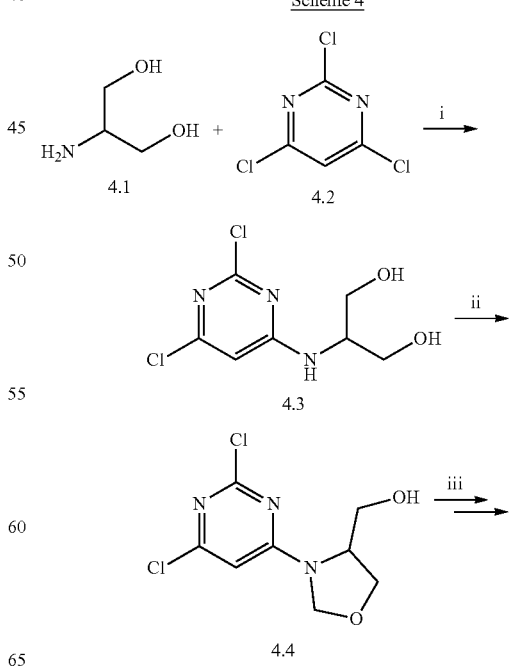

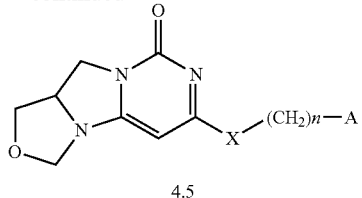

4.5

General Experimental Scheme 4 provides an exemplary synthesis for compound 4.5. A and n are as defined in Formula (I). X is as defined as Formula (I) except that X is NH, or N—C$_{1-3}$ alkyl. Step (i) may be carried out by reacting compound 4.1 with compound 4.2 using appropriate reagents such as triethylamine (TEA) in an appropriate solvent such as ethanol under a suitable temperature such as room temperature to provide compound 4.3. Step (ii) may be taken place by reacting compound 4.3 with a suitable reagent such as paraformaldehyde and para-toluene sulfonic acid (PTSA) in an appropriate solvent such as toluene under reflux to obtain compound 4.4. Final compound 4.5 may be prepared by starting from compound 4.4 by carrying out similar reactions described from 1.3 to 1.5 in Scheme 1. Variation of reaction conditions and reagents, which is obvious to one skilled in the art, may be applied for different —X—(CH$_2$)$_n$-A groups.

pound 5.1 with compound 5.2 using appropriate reagents such as DIAD and Ph$_3$P in an appropriate solvent such as THF under a suitable temperature such as room temperature, and then followed by desilylation in step (ii) to provide compound 5.3. Step (iii) may be carried out by oxidation with a Dess-Martin reagent followed by cyclization in step (iv) with 2-aminoethanol or 3-aminopropan-1-ol in an appropriate solvent such as dioxane to obtain compound 5.4. Step (v) may be proceeded by reacting compound 5.4 with H—X—(CH$_2$)$_n$-A, in the presence of a suitable base such as NaH in a suitable solvent such as DMF to afford compound 5.5. Variation of reaction conditions and reagents, which is obvious to one skilled in the art, may be applied for different —X—(CH$_2$)$_n$-A groups.

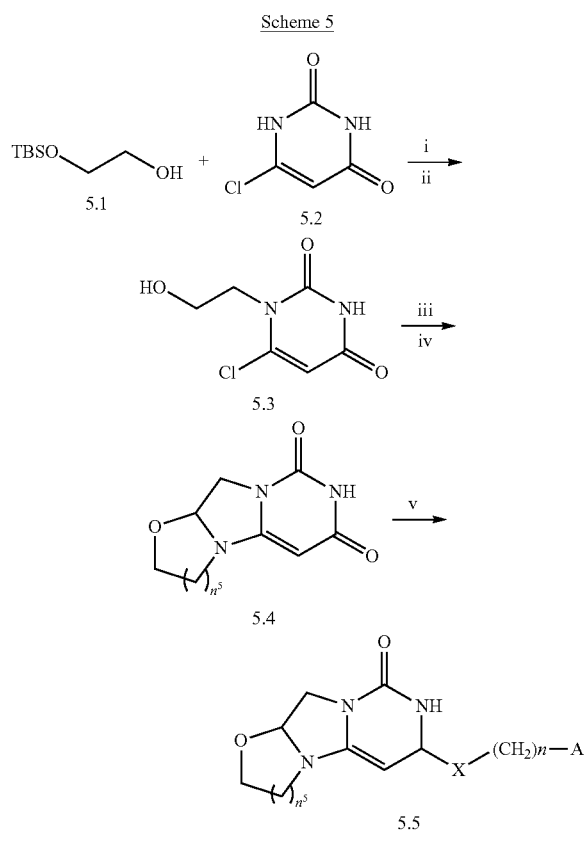

n$^5$ = 1 or 2

General Experimental Scheme 5 provides an exemplary synthesis for compounds 5.5. A, X and n are as defined in Formula (I). Step (i) may be carried out by reacting com-

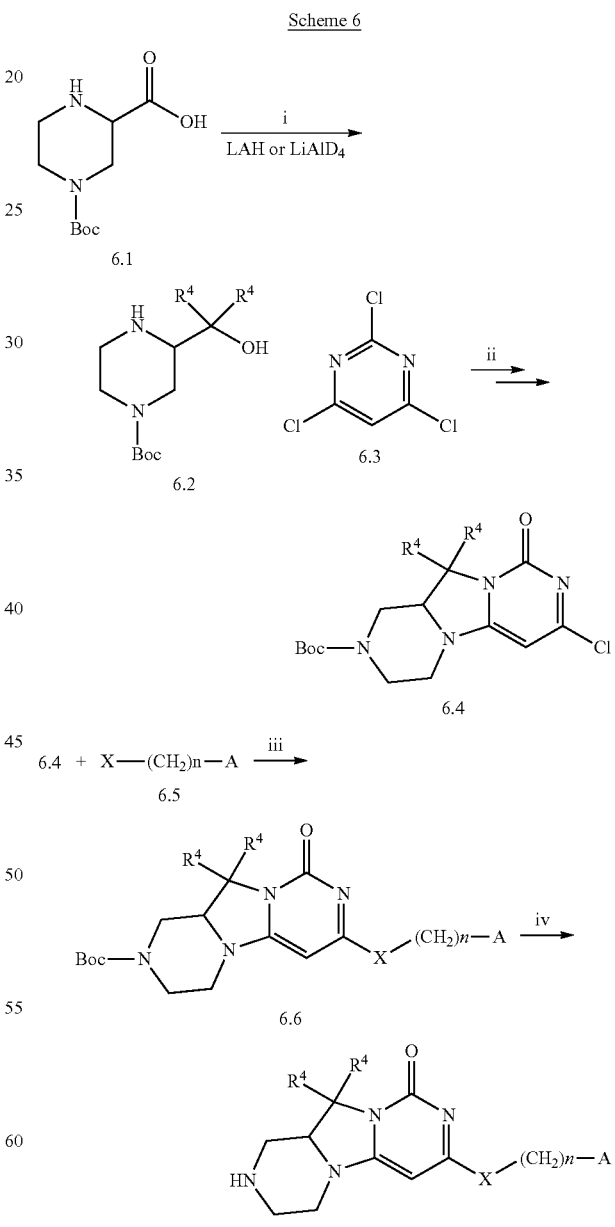

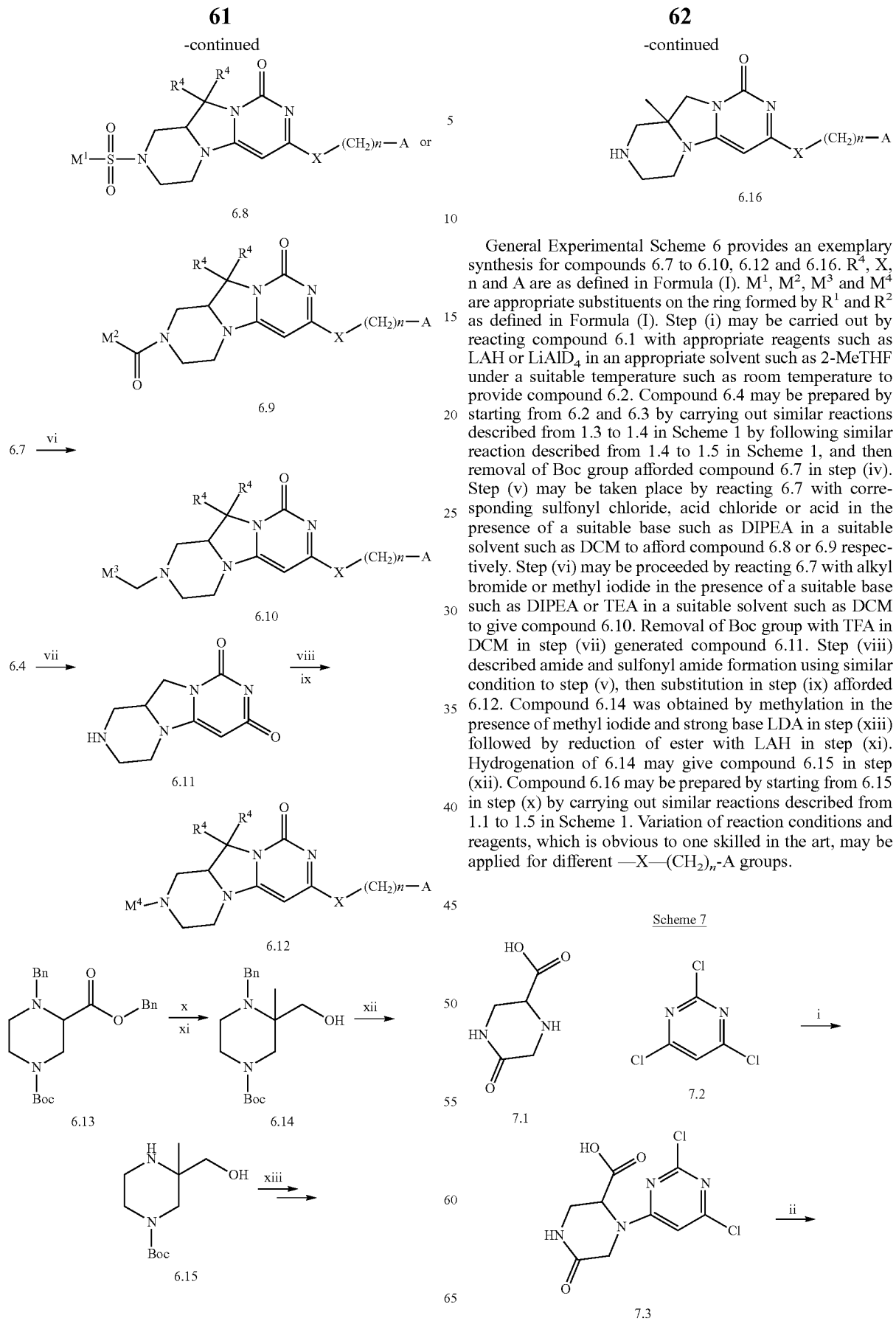

General Experimental Scheme 6 provides an exemplary synthesis for compounds 6.7 to 6.10, 6.12 and 6.16. $R^4$, X, n and A are as defined in Formula (I). $M^1$, $M^2$, $M^3$ and $M^4$ are appropriate substituents on the ring formed by $R^1$ and $R^2$ as defined in Formula (I). Step (i) may be carried out by reacting compound 6.1 with appropriate reagents such as LAH or $LiAlD_4$ in an appropriate solvent such as 2-MeTHF under a suitable temperature such as room temperature to provide compound 6.2. Compound 6.4 may be prepared by starting from 6.2 and 6.3 by carrying out similar reactions described from 1.3 to 1.4 in Scheme 1 by following similar reaction described from 1.4 to 1.5 in Scheme 1, and then removal of Boc group afforded compound 6.7 in step (iv). Step (v) may be taken place by reacting 6.7 with corresponding sulfonyl chloride, acid chloride or acid in the presence of a suitable base such as DIPEA in a suitable solvent such as DCM to afford compound 6.8 or 6.9 respectively. Step (vi) may be proceeded by reacting 6.7 with alkyl bromide or methyl iodide in the presence of a suitable base such as DIPEA or TEA in a suitable solvent such as DCM to give compound 6.10. Removal of Boc group with TFA in DCM in step (vii) generated compound 6.11. Step (viii) described amide and sulfonyl amide formation using similar condition to step (v), then substitution in step (ix) afforded 6.12. Compound 6.14 was obtained by methylation in the presence of methyl iodide and strong base LDA in step (xiii) followed by reduction of ester with LAH in step (xi). Hydrogenation of 6.14 may give compound 6.15 in step (xii). Compound 6.16 may be prepared by starting from 6.15 in step (x) by carrying out similar reactions described from 1.1 to 1.5 in Scheme 1. Variation of reaction conditions and reagents, which is obvious to one skilled in the art, may be applied for different —X—$(CH_2)_n$-A groups.

Scheme 7

-continued

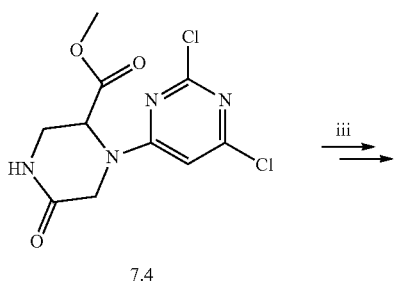
7.4

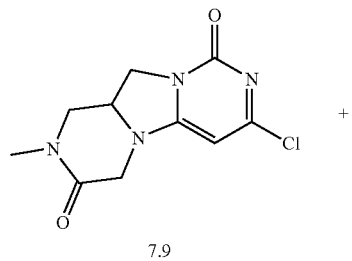
7.9

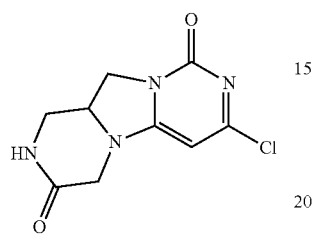
7.5

X—(CH₂)n—A  →ⁿⁱⁱ
7.6

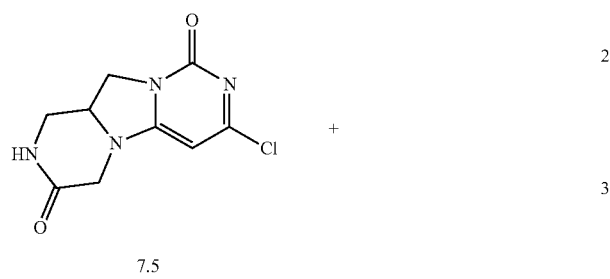
7.5

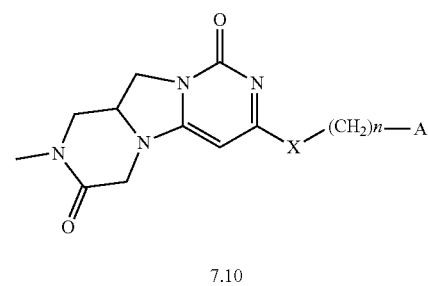
7.10

General Experimental Scheme 7 provides an exemplary synthesis for compounds 7.7, 7.8 and 7.11. n and A are as defined in Formula (I). X is as defined in Formula (I) except X is absent. Step (i) may be carried out by reacting compound 7.1 with compound 7.2 using appropriate reagents such as $K_2CO_3$ in an appropriate solvent such as ethanol under a suitable temperature such as 50° C. to provide compound 7.3. Step (ii) may be taken place by reacting compound 7.3 with iodomethane in the presence of $K_2CO_3$ in DMF to give compound 7.4. Reduction following by cyclization in step (iii) may afford compound 7.5. Step (iv) may be proceeded by reacting compound 7.3 with 7.6, in the presence of a suitable base such as NaH or TEA in a suitable solvent such as DMF, to provide compound 7.7. N-alkylation in step (v) may provide compound 7.8. N-methylation in step (vi) following by substitution in step (vii) provided compound 7.10. Variation of reaction conditions and reagents, which is obvious to one skilled in the art, may be applied for different —X—(CH₂)ₙ-A groups.

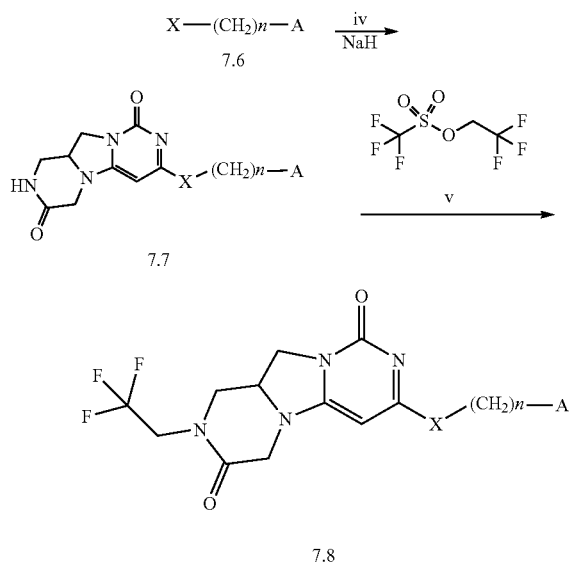

Scheme 8

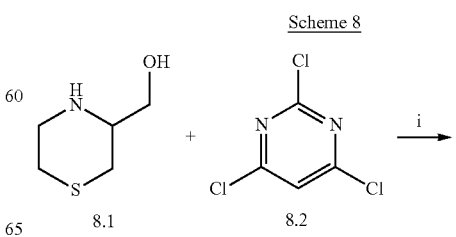
8.1   8.2

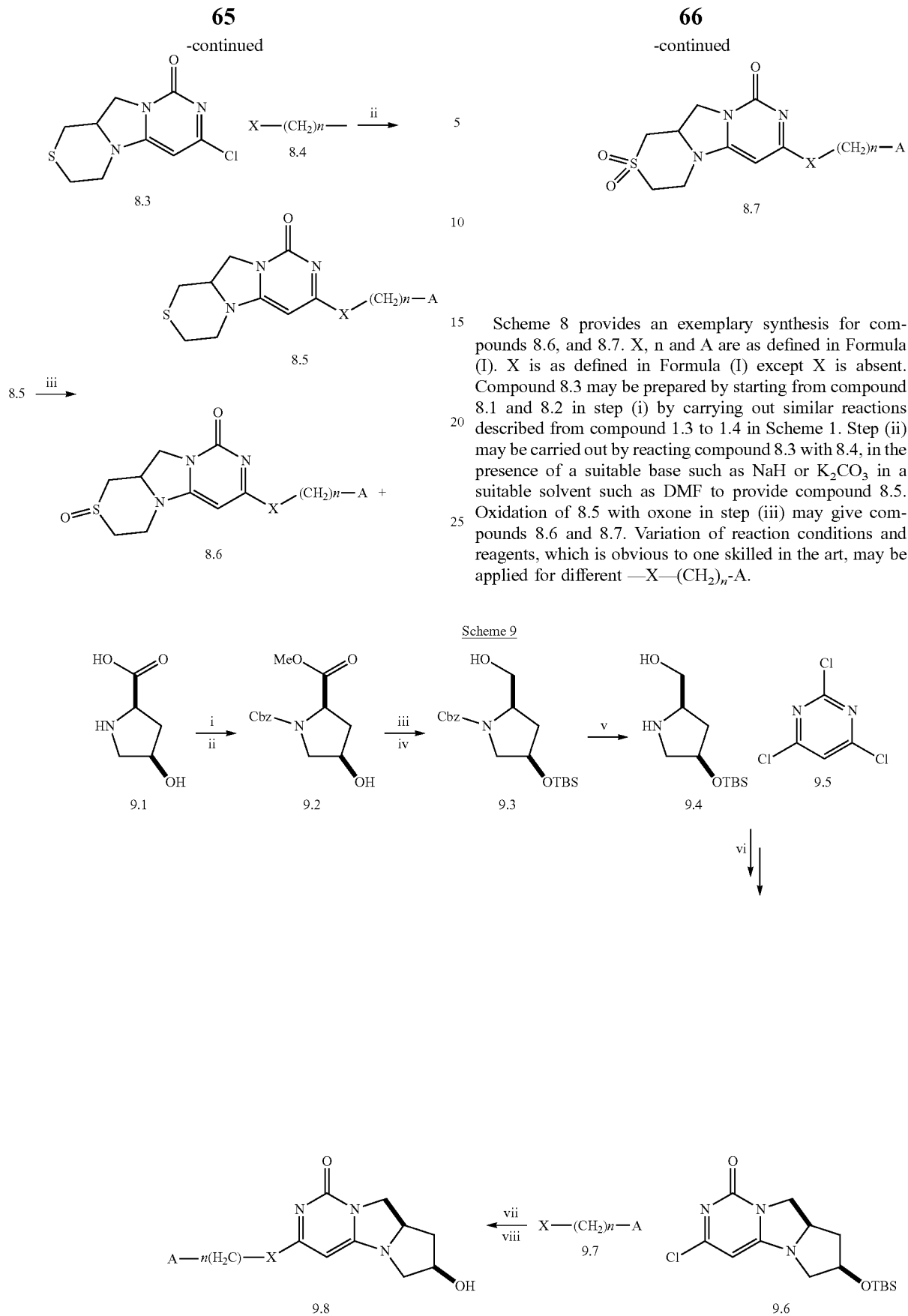

Scheme 8 provides an exemplary synthesis for compounds 8.6, and 8.7. X, n and A are as defined in Formula (I). X is as defined in Formula (I) except X is absent. Compound 8.3 may be prepared by starting from compound 8.1 and 8.2 in step (i) by carrying out similar reactions described from compound 1.3 to 1.4 in Scheme 1. Step (ii) may be carried out by reacting compound 8.3 with 8.4, in the presence of a suitable base such as NaH or $K_2CO_3$ in a suitable solvent such as DMF to provide compound 8.5. Oxidation of 8.5 with oxone in step (iii) may give compounds 8.6 and 8.7. Variation of reaction conditions and reagents, which is obvious to one skilled in the art, may be applied for different —X—$(CH_2)_n$-A.

Scheme 9

General Experimental Scheme 9 provides an exemplary synthesis for compound 9.8. X, n and A are as defined in Formula (I). Protection of NH followed by ester formation may afford compound 9.2 in step (i) and (ii). Protection of secondary hydroxyl group by TBS in step (iii) following reduction with DIBAL-H in step (iv) may give compound 9.3. Deprotection of carboxybenzy (Cbz) under hydrogenation condition in step (v) may provide compound 9.4. Compound 9.6 may be prepared by starting from compound 9.4 and 9.5 in step (vi) by carrying out similar reactions described from 1.3 to 1.4 in Scheme 1. Substitution in step (vii) following removal of TVS group in step (viii) may provide compound 9.8.

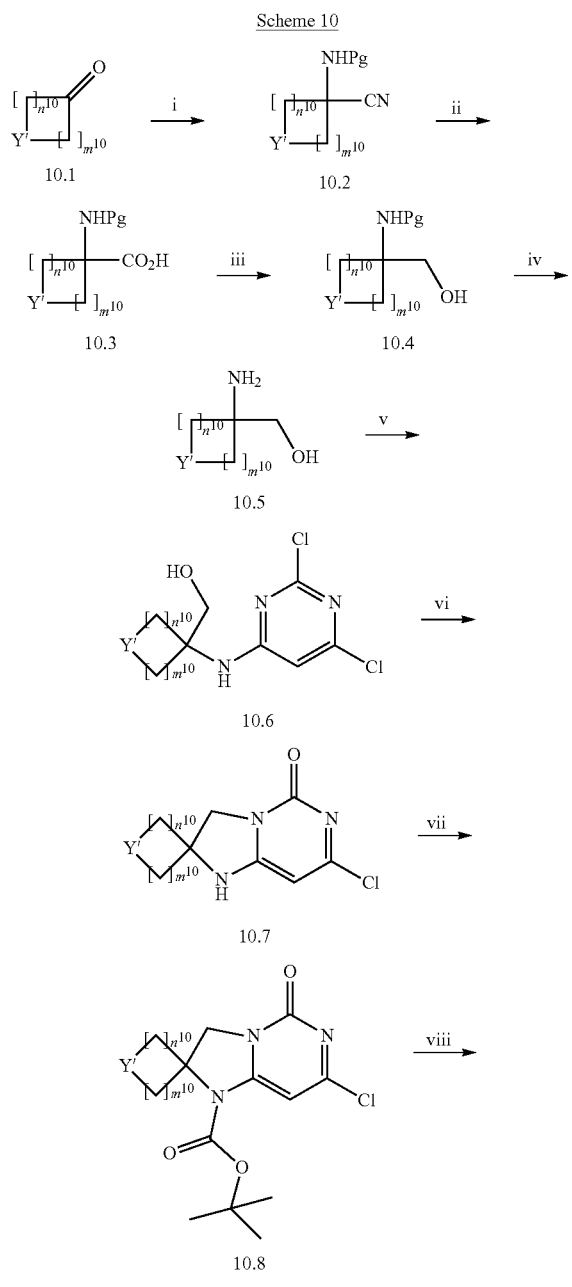

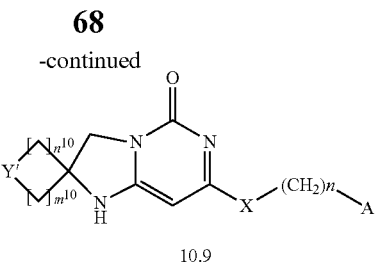

Y' = O or N
$n^{10}$ and $m^{10}$ are independently 1 or 2
Pg is protecting group Scheme 10 provides an exemplary synthesis for spiro-compounds 10.9. X, A and n are as defined in Formula (I). Step (i) may be carried out by reacting carbonyl compound 10.1 with a suitably protected amine and trimethylsilyl cyanide (TMSCN) to get compound 10.2. Hydrolysis with hydroxide in a protic solvent such as methanol can provide compound 10.3. Reduction of 10.3 to 10.4 can be accomplished with a hydride reducing agent such as LAH in a polar solvent like THF or 2-MeTHF. Deprotection of the nitrogen protecting group on the amine can be accomplished using standard conditions to provide compound 10.5. Coupling of the amino-alcohol 10.5 with trichloropyrmidine in a polar solvent in the presence of an amine base such as triethylamine (TEA) or diisopropylethylamine (DIPEA) provides alcohol 10.6. Cyclization to the fused choloropyrimidinone 10.7 can be accomplished by reaction with a suitable reagent such as TEA and methanesulfonyl chloride (MsCl) at appropriate temperature such as 0° C. followed by warming in the presence of carbonate in acetonitrile. Boc protection of the amine can be accomplished under standard conditions to provide key intermediate 10.8. The final steps (viii) may be carried out by reacting compound 10.8 with substituted benzyl alcohols or benzyl amines in the presence of a suitable base such as NaH or diisopropyl ethylamine in a suitable solvent such as DMF or dioxane to provide O- or NH-linked final compound 10.9 after Boc-deprotection. Variation of reaction conditions and reagents, which is obvious to one skilled in the art, may be applied for different —X—$(CH_2)_n$-A.

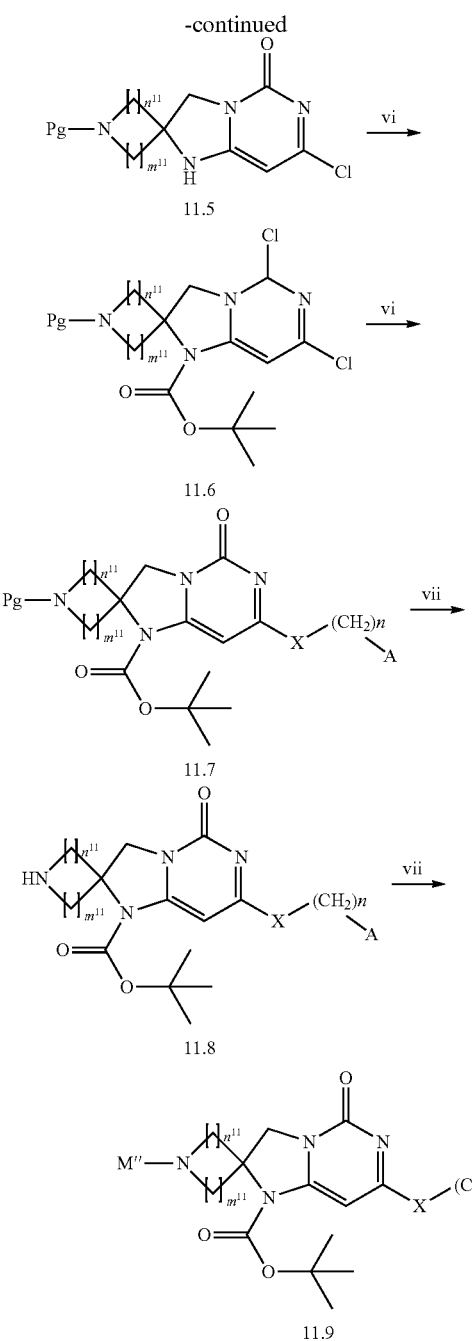

$n^{11}$ and $m^{11}$ are indepndently 1 or 2
Pg is protecting group
M" is appropriate substituent on spiro-ring Scheme 11 provides an exemplary synthesis for spiro compounds 11.9. X, A and n are as defined in Formula (I). A variation on the Strecker amino acid synthesis during step (i) may be carried out to get compound 11.2 from a suitably protected amine containing ketone. Reduction of compound 11.1 to primary alcohol 11.3 can be accomplished with a hydride reducing agent such as LAH in a polar solvent like THF or 2-MeTHF. Coupling of the amino-alcohol 11.3 with trichloropyrmidine in a polar solvent in the presence of an amine base such as TEA (triethylamine) or DIPEA (diisopropylethylamine) provides alcohol 11.4. Cyclization to the fused choloropyrimidinone 11.5 can be accomplished by reaction with a suitable reagent such as triethylamine (TEA) and methanesulfonyl chloride (MsCl) at appropriate temperature such as 0° C. followed by warming in the presence of carbonate in acetonitrile. Boc protection of the amine can be accomplished under standard conditions to provide key intermediate 11.6. Steps vi and vii may be carried out by reacting compound 11.6 with substituted benzyl alcohols or benzyl amines in the presence of a suitable base such as NaH or diisopropyl ethylamine in a suitable solvent such as dimethylformamide (DMF) or dioxane to provide O- or NH-linked compounds 11.8 after protecting group removal. The resulting amine 11.8 can be coupled with acids, acid chlorides, sulfonyl chlorides, isocyanates, chloroformates and alkyl halides under standard conditions, and the boc-removed to provide final compound amides, ureas, sulfonamides, carbamates, and alkyl amines 11.9. Variation of reaction conditions and reagents, which is obvious to one skilled in the art, may be applied for different —X—(CH$_2$)$_n$-A.

Scheme 12

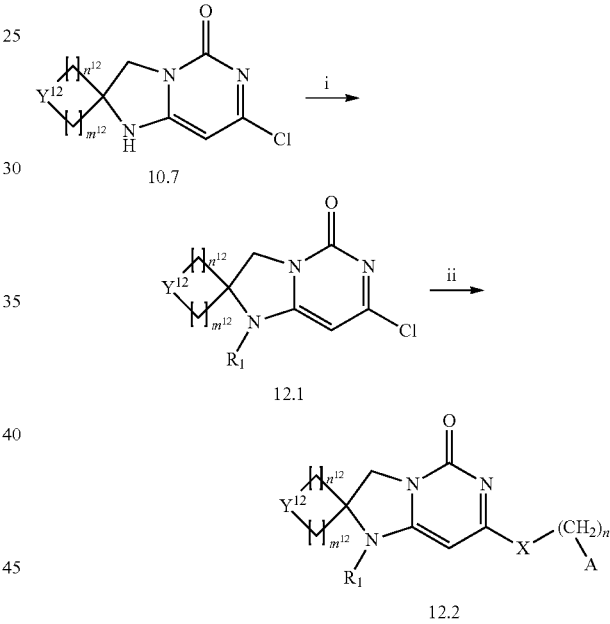

$n^{12}$, $m^{12}$ are independentl 1, 2, or 3,
$R^1$ is as defined in Formula (I) except H,
$Y^{12}$ = O, S, SO, or SO$_2$,
X = O, NH Scheme 12 provides an exemplary synthesis for spiro compounds 12.2. A and n are as defined in Formula (I). N-alkylation of 10.7 may be accomplished with a variety of alkylating agents such dialkyl sulfates and alkyl ($R^1$) halides with an appropriate base such as NaH or diisopropyl ethylamine in a suitable solvent such as dimethylformamide (DMF) or dioxane to provide chloropyrimidinone 12.1. The final step (ii) may be carried out by reacting compound 12.1 with substituted benzyl alcohols or benzyl amines in the presence of a suitable base such as NaH or diisopropyl ethylamine in a suitable solvent such as dimethylformamide (DMF) or dioxane to provide 0 or NH-linked final compound 12.2. Variation of reaction conditions and reagents, which is obvious to one skilled in the art, may be applied for different —X—(CH$_2$)$_n$-A.

Scheme 13

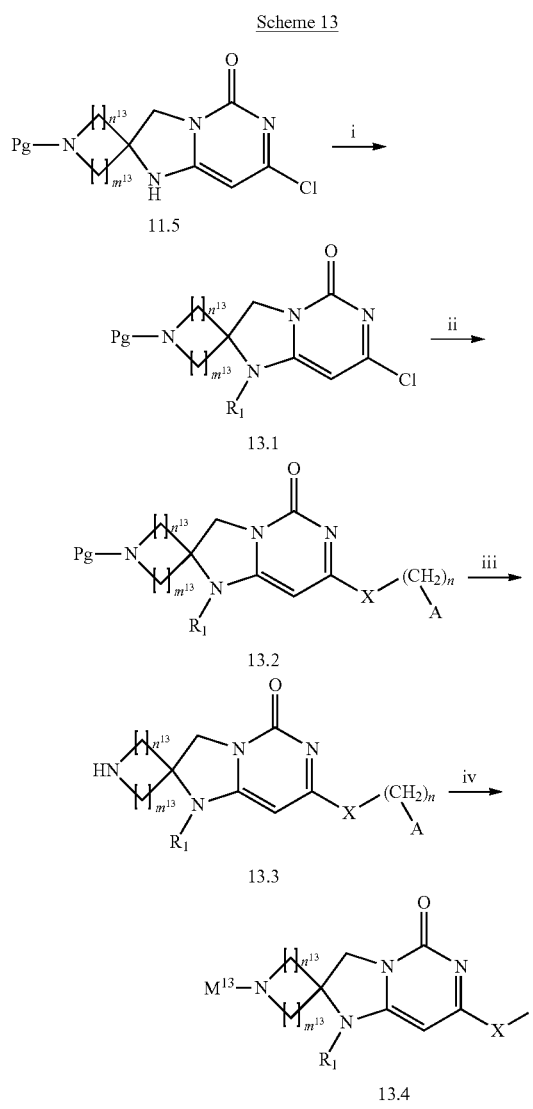

Y = O, NH
X = CO, SO$_2$, CO$_2$, CONH, CH$_2$
pg is protecting group
R$^1$ is as defined in Formula (I) but not H Scheme 13 provides an exemplary synthesis for spiro compounds 13.4 where n$^{13}$ and m$^{13}$ are independently 1 or 2. A and n are as defined in Formula (I). M$^{13}$ is an appropriate substituent on the spiro-ring system. N-alkylation of compound 11.5 may be accomplished with a variety of alkylating agents such dialkyl sulfates and R$^1$ alkyl halides with an appropriate base such as NaH or diisopropyl ethylamine in a suitable solvent such as dimethylformamide (DMF) or dioxane to provide chloropyrimidinone 13.1. Coupling of compound 13.1 (step ii) with substituted benzyl alcohols or benzyl amines in the presence of a suitable base such as NaH or diisopropyl ethylamine in a suitable solvent such as dimethylformamide (DMF) or dioxane, provide O- or NH-linked compounds 13.2. Variation of reaction conditions and reagents, which is obvious to one one skilled in the art, may be applied for different —X—(CH$_2$)$_n$-A. After protecting group removal (step iii), the resulting amine 13.3 may be coupled with acids, acid chlorides, sulfonyl chlorides, isocyanates, chloroformates and alkyl halides under standard conditions to provide final compound amides, ureas, sulfonamides, carbamates, and alkyl amines 13.4.

The chemical names of compounds described in the present application follows the principle of IUPAC nomenclature.

All temperatures are reported in degrees Celsius. All other abbreviations are as described in the ACS Style Guide (American Chemical Society, Washington, D.C., 1986) unless the abbreviations are specifically defined below.

LCMS Conditions:
1) Acidic Conditions:
Mobile phase: water containing 0.05% TFA/0.05% acetonitrile
Column: Agilent SB-C18 4.6×30 mm-1.8 microns
Detection: MS and photodiode array detector (PDA)
2) Basic Conditions:
Mobile phase: water containing 10 mmol NH$_4$HCO$_3$/acetonitrile
Column: XBridge™ C18 4.6×50 mm-3.5 microns
Detection: MS and photodiode array detector (PDA)
Mass Directed Autoprep Purification (MDAP) Conditions:
1) Acidic Conditions:
Instrument: Waters instrument
Column: Sunfire Prep C18 column (5 um, 19×50 mm)
Mobile phase: water containing 0.05% TFA/acetonitrile.
2) Basic Conditions:
Instrument: Waters instrument
Column: Xbridge Prep C18 column (5 um, 19×50 mm)
Mobile phase: water containing 0.04% ammonia/acetonitrile.
Chiral HPLC Conditions
Instrument: Gilson JX281
Column: Chiralpak IA 5 um 4.6*350 mm
Phase: MeOH:EtOH=50:50
Prep-HPCL Conditions:
Instrument: HPLC: Agilent 1200, MS: Agilent 6120
Column: Ultimate_XB_C18; column size: 4.6*50 mm
Mobile phase: water containing 0.02% NH$_4$AC/acetonitrile Abbreviations and Resource Sources The following abbreviations and resources are used herein below:
ISCO system—Teledyne ISCO (http://www.isco.com/html/seFlashChromatography.html)
r.t/rt/RT—room temperature
ACN—acetonitrile
AIBN—azobisisobutylonitrile
Aq.—aqueous
9-BBN—9-borabicyclo(3.3.1)nonane
Brine—saturated NaCl aqueous solution
CDI—1,1'-carbonyldiimidazole
CV—column volumes
DAST—diethylaminosulfur trifluoride
DIAD—diethyl azodicarboxylate
DIBAL-H—diisobutylaluminium hydride
DIEA—1,3-diisopropylcarbodiimide
DCM—dichloromethane
DIAD—diisopropyl azodicarboxylate
DIPEA—N,N-diisopropylethylamine
DMAP—4-dimethylaminopyridine
DMF—N,N-dimethylformamide
DMP—Dess-Martin periodinane
DMSO—dimethyl sulfoxide
EtOH—ethanol
EA/EtOAc—ethyl acetate HATU—O-(7-azabenzotriazole-1-yl)-1,1,3,3-tetramethyl-uroniumhexafluorophosphate
KOAc—potassium acetate
LAH—lithium aluminium hydride
LDA—lithium diisopropylamide
FC—flash chromatography (usually conducted on silica gel column)
PTSA—P-toluenesulfonic Acid
MsCl—methanesulfonyl chloride
MTBE—methyl tertiary butyl ether
NaHMDS—sodiobis(trimethylsilyl)amine.
NBS—N-bromosuccinimide
NMP—N-methylpyrrolidone
sat.—saturated
T3P—propylphosphonic anhydride
TBAF—tetra-n-butylammonium fluoride
TBME—tert-butyl methyl ether
TBSCl—tert-butyldimethylsilyl chloride
TMSCN—trimethylsilyl cyanide
TEA or $Et_3N$—triethylamine
TFA—trifluoro acetic acid
THF—tetrahydrofuran
PE—petroleum ether

EXAMPLES

The following synthetic processes and examples are provided to more specifically illustrate the invention. These examples are not intended to limit the scope of the invention, but rather to provide guidance to the skilled artisan to prepare and use the compounds, compositions, and methods of the invention. While particular embodiments of the invention are described, the skilled artisan will appreciate that various changes and modifications can be made without departing from the spirit and scope of the invention.

In general, the compounds of the present invention may be prepared by standard techniques known in the art and by known processes analogous thereto. General methods for preparing compounds of the present invention are set forth below. All starting material and reagents described in the below general experimental schemes are commercially available.

In the procedures that follow, after each starting material, reference to an intermediate is sometimes provided. This is provided merely for assistance to the skilled chemist. The starting material may not necessarily have been prepared from the batch referred to.

D1

(1-(2,6-Dichloropyrimidin-4-yl)piperidin-2-yl)methanol

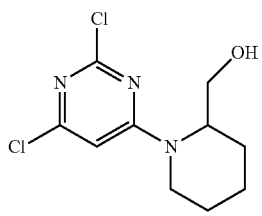 [SMILES: OCC1CCCCN1c1cc(Cl)nc(Cl)n1]

To a solution of 2,4,6-trichloropyrimidine (7.96 g, 43.4 mmol) in acetonitrile (50 mL) was added TEA (18.2 mL, 130 mmol) at 0° C. After 5 min at room temperature, a solution of piperidin-2-ylmethanol (5.00 g, 43.4 mmol) in DMF (5 mL) was added. The reaction was stirred at room temperature for 1 h and the mixture was then filtered and concentrated. The crude was purified via chromatography on silica gel (200-300 mesh, petroleum ether/ethyl acetate: 8/1 to 3/1) to give the title product as a white solid.

LC-MS (ESI): m/z 262[M+H]$^+$; 1.59 min (ret time)

D2

4-Chloro-6-(2-(hydroxymethyl)piperidin-1-yl)pyrimidin-2(1H)-one

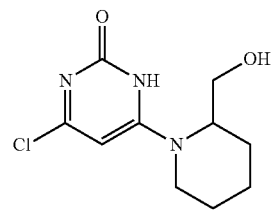 [SMILES: O=c1nc(Cl)cc(N2CCCCC2CO)[nH]1]

A mixture of (1-(2,6-dichloropyrimidin-4-yl)piperidin-2-yl)methanol (3.00 g, 11.4 mmol), LiOH (0.822 g, 34.3 mmol) and $H_2O_2$ (2.338 mL, 22.89 mmol) in water (10 mL) was stirred overnight at 45° C. After cooled to room temperature, the mixture was concentrated and the crude was purified via Biotage system with inverse phase to give the title product.

LC-MS (ESI): m/z 244 [M+H]$^+$; 1.15 min (ret time)

D3

3-Chloro-6,7,8,9,9a,10-hexahydro-1H-pyrido[1',2':3,4]imidazo[1,2-c]pyrimidin-1-one

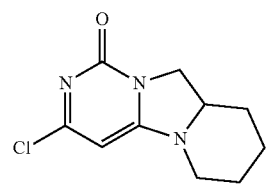 [SMILES: O=c1nc(Cl)cc2n1CC1CCCCN21]

To a mixture of 4-chloro-6-(2-(hydroxymethyl)piperidin-1-yl)pyrimidin-2(1H)-one D2 (1.00 g, 4.10 mmol) and $Et_3N$ (1.716 mL, 12.31 mmol) in THF (20 mL) was added dropwise MsCl (0.640 mL, 8.21 mmol). The reaction mixture was stirred for 2 hrs. The mixture was then concentrated and the crude was purified by HPLC to give the title product.

LC-MS (ESI): m/z 226 [M+H]$^+$; 0.94 min (ret time)

$^1$H NMR (400 MHz, DMSO-$d_6$): δ 5.96 (s, 1H), 4.18-4.03 (m, 1H), 3.93 (d, J=7.3 Hz, 1H), 3.79 (d, J=12.3 Hz, 1H), 3.56 (dd, J=11.5, 7.4 Hz, 1H), 3.01 (dd, J=17.3, 7.8 Hz, 1H), 1.92-1.73 (m, 2H), 1.66 (d, J=11.3 Hz, 1H), 1.53-1.30 (m, 3H).

D4

(S)-1-(2,6-dichloropyrimidin-4-yl)piperidine-2-carboxylic acid

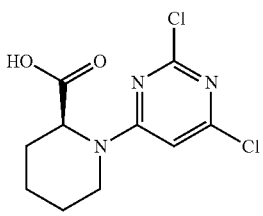 [SMILES: O=C(O)[C@@H]1CCCCN1c1cc(Cl)nc(Cl)n1]

To a solution of 2,4,6-trichloropyrimidine (14.20 g, 77.00 mmol) in acetonitrile (60 mL) was added (S)-piperidine-2-carboxylic acid (10 g, 77 mmol), followed by K$_2$CO$_3$ (21.40 g, 155.0 mmol). The reaction was stirred overnight at room temperature and then acidified with 2 M HCl solution to pH=4. The mixture was extracted with ethyl acetate twice and combined organic parts were dried over Na$_2$SO$_4$, filtered and concentrated to give the residue as yellow oil. The crude was used into next step without purification.

D5

(S)-(1-(2,6-dichloropyrimidin-4-yl)piperidin-2-yl)methanol

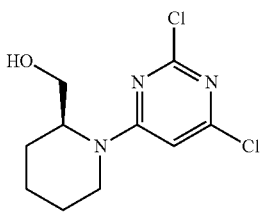 [SMILES: OC[C@@H]1CCCCN1c1cc(Cl)nc(Cl)n1]

To a solution of (S)-1-(2,6-dichloropyrimidin-4-yl)piperidine-2-carboxylic acid (16.0 g, 57.9 mmol) in dry tetrahydrofuran (THF) (160 mL) at 0° C. under N$_2$ was added slowly LiAlH$_4$ (8.80 g, 232 mmol). The reaction was stirred at room temperature for 3 hrs. The mixture was then quenched with water, filtered and the filtrate was concentrated to give the crude as brown oil, which was used into next step without purification.

LCMS (ESI): m/z 262, 264 [M+H]$^+$; 2.72 min (ret time)

D6

(S)-6-chloro-4-(2-(hydroxymethyl)piperidin-1-yl)pyrimidin-2(1H)-one

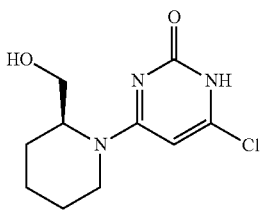 [SMILES: O=c1nc(N2CCCC[C@H]2CO)cc(Cl)[nH]1]

To a mixture of (S)-(1-(2,6-dichloropyrimidin-4-yl)piperidin-2-yl)methanol (14.0 g, 53.4 mmol) and lithium hydroxide one hydrate (6.72 g, 160 mmol) in water (96 mL) was added at room temperature to H$_2$O$_2$ (33% w/w aqueous solution, 10.9 mL, 106 mmol). The reaction mixture was stirred at 45° C. for 3 hrs and then quenched with Na$_2$S$_2$O$_3$ solution. Purification via reverse phase chromatography (water/acetonitrile, 0.05% TFA in water) afforded the title product as yellow oil.

LCMS (ESI): m/z 244 [M+H]$^+$; 1.89 min (ret time)

D7

(S)-3-chloro-6,7,8,9,9a,10-hexahydro-1H-pyrido[1',2':3,4]imidazo[1,2-c]pyrimidin-1-one

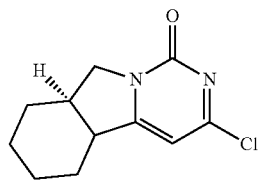 [SMILES: O=c1nc(Cl)cc2n1C[C@@H]1CCCCC21]

To a solution of (S)-6-chloro-4-(2-(hydroxymethyl)piperidin-1-yl)pyrimidin-2(1H)-one (1.10 g, 4.51 mmol) in dry tetrahydrofuran (THF) (20 mL) at room temperature was added Et$_3$N (1.89 mL, 13.5 mmol), followed by dropwise MsCl (0.704 mL, 9.03 mmol). The reaction mixture was stirred at room temperature for 2 hrs. Purification via reverse phase chromatography (water/acetonitrile, 0.05% TFA in water) then MDAP afforded the title product as a brown solid.

LCMS (ESI): m/z 226 [M+H]$^+$; 1.34 min (ret time)

D8

(R)-1-(2,6-dichloropyrimidin-4-yl)piperidine-2-carboxylic acid

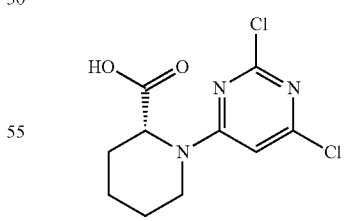

The title compound was prepared by a procedure similar to that described for D4 starting from 2,4,6-trichloropyrimidine, (R)-piperidine-2-carboxylic acid and K$_2$CO$_3$.

LCMS (ESI): m/z 276 [M+H]$^+$; 2.74 min (ret time)

D9

(R)-(1-(2,6-dichloropyrimidin-4-yl)piperidin-2-yl)methanol

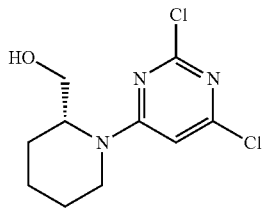

The title compound was prepared by a procedure similar to that described for D5 starting from (R)-1-(2,6-dichloropyrimidin-4-yl)piperidine-2-carboxylic acid and LiAlH$_4$.
LCMS (ESI): m/z 262 [M+H]$^+$; 2.71 min (ret time)

D10

(R)-6-chloro-4-(2-(hydroxymethyl)piperidin-1-yl)pyrimidin-2(1H)-one

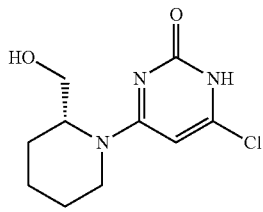 [SMILES: O=c1nc(N2CCCC[C@@H]2CO)cc(Cl)[nH]1]

The title compound was prepared by a procedure similar to that described for D6 starting from (R)-(1-(2,6-dichloropyrimidin-4-yl)piperidin-2-yl)methanol, lithium hydroxide one hydrate and H$_2$O$_2$.
LCMS (ESI): m/z 244 [M+H]$^+$; 1.44 min (ret time)

D11

(R)-3-chloro-6,7,8,9,9a,10-hexahydro-1H-pyrido[1',2':3,4]imidazo[1,2-c]pyrimidin-1-one

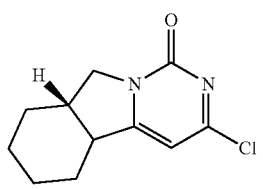 [SMILES: O=c1nc(Cl)cc2n1C[C@H]1CCCCC21]

The title compound was prepared by a procedure similar to that described for D7 starting from (R)-6-chloro-4-(2-(hydroxymethyl)piperidin-1-yl)pyrimidin-2(1H)-one, Et$_3$N and MsCl.
LCMS (ESI): m/z 226 [M+H]$^+$; 1.39 min (ret time)

D12

(1-(2,6-Dichloropyrimidin-4-yl)pyrrolidin-2-yl)methanol

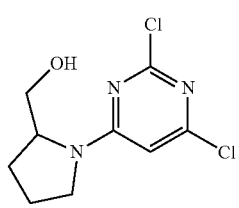 [SMILES: OCC1CCCN1c1cc(Cl)nc(Cl)n1]

To the solution of 2, 4, 6-trichloropyrimidine (2.176 g, 11.86 mmol) and triethylamine (2.76 mL, 19.77 mmol) in acetonitrile (25 mL) was added dropwise pyrrolidin-2-yl-methanol (1.0 g, 9.89 mmol) in acetonitrile (5 mL) at 0° C. The mixture was stirred for 2 hrs at room temperature and collected the solution by filtration, concentrated in vacuum and the residue was purified via silica flash column. After removing solvent, a pale solid of (1-(2, 6-dichloropyrimidin-4-yl) pyrrolidin-2-yl) methanol (1.4 g, 5.64 mmol, 57.1% yield) was afforded.
LC-MS (ESI): m/z 248 [M+H]$^+$; 2.42 min (ret time).

D13

3-Chloro-7,8,8a,9-tetrahydropyrrolo[1,2':3,4]imidazo[1,2-c]pyrimidin-1(6H)-one

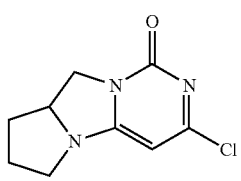 [SMILES: O=c1nc(Cl)cc2n1CC1CCCN21]

To the solution of (1-(2,6-dichloropyrimidin-4-yl)pyrrolidin-2-yl)methanol (300 mg, 1.209 mmol) and triethylamine (0.506 mL, 3.63 mmol) in tetrahydrofuran (15 mL) was added dropwise methanesulfonyl chloride (0.141 mL, 1.814 mmol) in tetrahydrofuran (5 mL) at 0° C. and the mixture was stirred further 10 min at 0° C. The result mixture was concentrated in vacuum and the residue was added acetonitrile (20.00 mL) and potassium carbonate (836 mg, 6.05 mmol). The suspension was refluxed for 4 hrs and filtrated in vacuum, the filtrate was concentrated in vacuum afforded crude product of 3-chloro-7,8,8a,9-tetrahydropyrrolo[1',2':3,4]imidazo[1,2-c]pyrimidin-1(6H)-one (256 mg, 1.209 mmol, 100% yield).
LC-MS (ESI): m/z 212 [M+H]$^+$; 1.33 min (ret time).

D14

(R)-(1-(2, 6-dichloropyrimidin-4-yl) pyrrolidin-2-yl) methanol

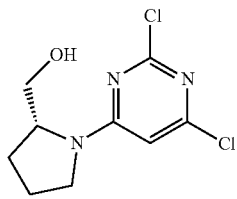 [SMILES: OC[C@H]1CCCN1c1cc(Cl)nc(Cl)n1]

The title compound was prepared by a procedure similar to that described for D12 starting from D-prolinol and 2, 4, 6-trichloropyrimidine.

LC-MS (ESI): m/z 248 [M+H]$^+$; 2.43 min (ret time).

An exemplary synthesis is provided below: To the solution of 2, 4, 6-trichloropyrimidine (3.26 g, 17.80 mmol) and triethylamine (4.13 mL, 29.7 mmol) in acetonitrile (25 mL) was added dropwise D-prolinol (1.456 mL, 14.83 mmol) in acetonitrile (5 mL) at 0° C. The mixture was stirred for 2 hours at room temperature and collected the solution by filtration, concentrated in vacuum and the residue was purified via silica flash column. After removing solvent, a pale solid of (R)-(1-(2, 6-dichloropyrimidin-4-yl) pyrrolidin-2-yl) methanol (2.5 g, 10.08 mmol, 67.9% yield) was afforded.

LC-MS (ESI): m/z 248 [M+H]$^+$; 2.43 min (ret time).

D16

(S)-(1-(2, 6-dichloropyrimidin-4-yl) pyrrolidin-2-yl) methanol

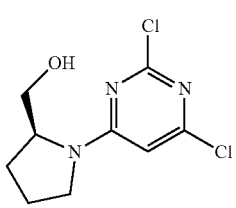

The title compound was prepared by a procedure similar to that described for (1-(2,6-dichloropyrimidin-4-yl)pyrrolidin-2-yl)methanol starting from L-prolinol and 2, 4, 6-trichloropyrimidine.

LC-MS (ESI): m/z 248 [M+H]$^+$; 2.42 min (ret time).

An exemplary process is provided: To the solution of 2, 4, 6-trichloropyrimidine (3.26 g, 17.80 mmol) and triethylamine (4.13 mL, 29.7 mmol) in acetonitrile (25 mL) was added dropwise L-prolinol (1.456 mL, 14.83 mmol) in acetonitrile (5 mL) at 0° C. The mixture was stirred for 2 hrs at room temperature and collected the solution by filtration, concentrated in vacuum and the residue was purified via silica flash column. The title compound was afforded (2.5 g, 10.08 mmol, 67.9% yield) as a pale solid.

LC-MS (ESI): m/z 248 [M+H]$^+$; 2.43 min (ret time).

D15

(R)-3-chloro-7,8,8a,9-tetrahydropyrrolo[1,2':3,4] imidazo[1,2-c]pyrimidin-1(6H)-one

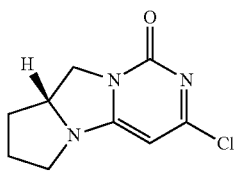 [SMILES: O=c1nc(Cl)cc2n1C[C@H]1CCCN21]

The title compound was prepared by a procedure similar to that described for D13 starting from (R)-(1-(2, 6-dichloropyrimidin-4-yl) pyrrolidin-2-yl) methanol.

An exemplary synthesis is provided below: to the solution of (R)-(1-(2, 6-dichloropyrimidin-4-yl) pyrrolidin-2-yl) methanol (1.95 g, 7.86 mmol) and triethylamine (3.29 mL, 23.58 mmol) in tetrahydrofuran (15 mL) was added dropwise methanesulfonyl chloride (0.919 mL, 11.79 mmol) in tetrahydrofuran (5 mL) at 0° C. and the mixture was stirred for 10 min at 0° C. The result mixture was concentrated in vacuum and acetonitrile (20.00 mL) and potassium carbonate (3.26 g, 23.58 mmol) was added to the residue. The suspension was refluxed for 4 h and filtrated in vacuum. The filtrate was concentrated in vacuum to afford the title compound (1.663 mg, 7.86 mmol, 100% yield).

LC-MS (ESI): m/z 212 [M+H]$^+$; 1.33 min (ret time).

D17

(S)-3-chloro-7,8,8a,9-tetrahydropyrrolo[1',2':3,4] imidazo[1,2-c]pyrimidin-1(6H)-one

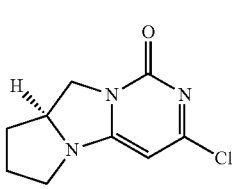 [SMILES: O=c1nc(Cl)cc2n1C[C@@H]1CCCN21]

The title compound was prepared by a procedure similar to that described for D13 starting from (S)-(1-(2, 6-dichloropyrimidin-4-yl) pyrrolidin-2-yl) methanol.

An exemplary process is provided: To the solution of (S)-(1-(2, 6-dichloropyrimidin-4-yl) pyrrolidin-2-yl) methanol (400 mg, 1.612 mmol) and triethylamine (0.674 mL, 4.84 mmol) in tetrahydrofuran (15 mL) was added dropwise methanesulfonyl chloride (0.188 mL, 2.418 mmol) in tetrahydrofuran (5 mL) at 0° C. and the mixture was stirred for 10 min at 0° C. The resulting mixture was concentrated in vacuum and the residue was added acetonitrile (20.00 mL) and potassium carbonate (668 mg, 4.84 mmol). The suspension was refluxed for 4 h and filtrated in vacuum. The filtrate was concentrated in vacuum to afford the title compound (341 mg, 1.612 mmol, 100% yield).

D18

(4-(2,6-Dichloropyrimidin-4-yl)morpholin-3-yl)methanol

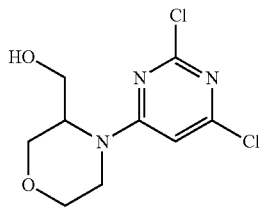 [SMILES: OCC1COCCN1c1cc(Cl)nc(Cl)n1]

The title compound was prepared by a procedure similar to that described for D12 starting from morpholin-3-yl-methanol and 2, 4, 6-trichloropyrimidine.

LC-MS (ESI): m/z 265 [M+H]$^+$; 2.13 min (ret time).

D19

7-chloro-3,4,11,11a-tetrahydropyrimido[6',1':2,3]imidazo[5,1-c][1,4]oxazin-9(1H)-one

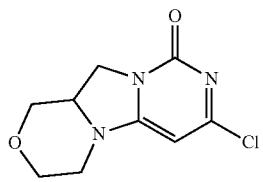 [SMILES: O=c1nc(Cl)cc2n1CC1COCCN21]

The title compound was prepared by a procedure similar to that described for D13 starting from (4-(2, 6-dichloropyrimidin-4-yl) morpholin-3-yl) methanol.

D20

(S)-morpholin-3-ylmethanol hydrochloride

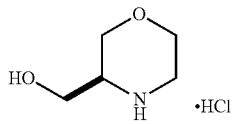

To a solution of (S)-tert-butyl 3-(hydroxymethyl)morpholine-4-carboxylate (10.20 g, 47.0 mmol) in MeOH (60 mL) was added dropwise HCl/MeOH (4M, 35.4 mL, 141 mmol) at 0° C. The reaction mixture was stirred at room temperature overnight. Then the mixture was concentrated under reduced pressure to give the title compound (8.50 g, 100%) as a white solid.

$^1$H NMR (300 MHz, DMSO-d$_6$): δ 9.74 (br s, 1H), 9.34 (br s, 1H), 4.95 (s, 2H), 3.88-3.84 (m, 2H), 3.69-3.56 (m, 3H), 3.23-2.98 (m, 3H).

D21

(S)-(4-(2, 6-dichloropyrimidin-4-yl) morpholin-3-yl) methanol

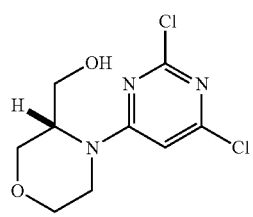 [SMILES: OC[C@H]1COCCN1c1cc(Cl)nc(Cl)n1]

The title compound was prepared by a procedure similar to that described for D12 starting from morpholin-3-yl-methanol and (S)-morpholin-3-ylmethanol hydrochloride.

$^1$H NMR (300 MHz, CDCl$_3$): δ 6.47 (s, 1H), 4.11-3.92 (m, 6H), 3.68-3.53 (m, 2H), 3.39-3.32 (m, 1H), 1.79 (t, J=5.7 Hz, 1H).

D22 (S)-7-chloro-3,4,11,11a-tetrahydropyrimido[6',1':2,3]imidazo[5,1-c][1,4]oxazin-9(1H)-one

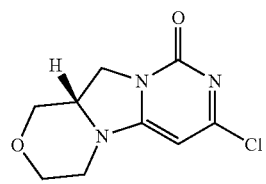 [SMILES: O=c1nc(Cl)cc2n1C[C@H]1COCCN21]

The title compound was prepared by a procedure similar to that described for D13 starting from (S)-(4-(2,6-dichloropyrimidin-4-yl)morpholin-3-yl)methanol.

LC-MS (ESI): m/z 228 [M+H]$^+$; 2.26 min (ret time).

D23

(R)-morpholin-3-ylmethanol hydrochloride

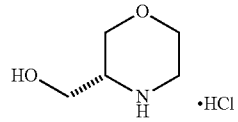

The title compound was prepared by a procedure similar to that described for D20 starting from (R)-tert-butyl 3-(hydroxymethyl)morpholine-4-carboxylate.

$^1$H NMR (300 MHz, DMSO-d$_6$): δ 9.42 (br s, 2H), 5.42 (t, 1H), 2.71-3.934 (m, 2H), 3.51-3.71 (m, 4H), 3.01-3.24 (m, 3H).

D24

(R)-(4-(2,6-dichloropyrimidin-4-yl)morpholin-3-yl)methanol

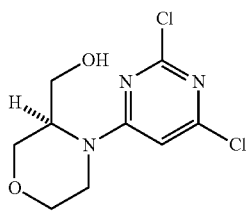 [SMILES: OC[C@@H]1COCCN1c1cc(Cl)nc(Cl)n1]

The title compound was prepared by a procedure similar to that described for D12 starting from morpholin-3-yl-methanol and (R)-morpholin-3-ylmethanol hydrochloride.

$^1$H NMR (300 MHz, CDCl$_3$): δ 6.47 (s, 1H), 3.91-4.35 (m, 6H), 3.53-3.68 (m, 2H), 3.32-3.39 (m, 1H), 1.86 (t, 1H).

D25

(R)-7-chloro-3,4,11,11a-tetrahydropyrimido[6',1':2,3]imidazo[5,1-c][1,4]oxazin-9(1H)-one

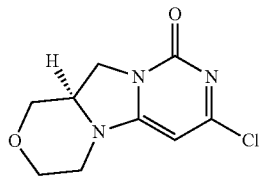 [SMILES: O=c1nc(Cl)cc2n1C[C@@H]1COCCN21]

The title compound was prepared by a procedure similar to that described for D13 starting from (R)-(4-(2,6-dichloropyrimidin-4-yl)morpholin-3-yl)methanol.

LC-MS (ESI): m/z 228 [M+H]$^-$; 2.53 min (ret time).

D26

(S)-1,3-oxazinane-4-carboxylic acid

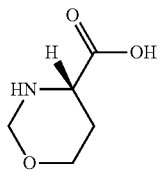

A solution of (S)-2-amino-4-hydroxybutanoic acid (15 g, 126 mmol) and 37% formalin (11 mL, 149 mmol) in 2N NaOH (63 mL) was stirred at 2-10° C. overnight. 3N HCl was added to the reaction mixture to adjust the pH to 2-3. The solvent was removed by lyophilization to give the title compound (20 g, 100%) as a white solid.

$^1$H NMR (300 MHz, DMSO-d$_6$): δ 10.18-9.65 (br s, 1H), 4.87 (d, J=9.3 Hz, 1H), 4.44 (d, J=9.3 Hz, 1H), 4.29-4.24 (m, 1H), 4.03-3.98 (m, 1H), 3.78-3.69 (m, 1H), 2.09-2.04 (m, 1H), 1.93-1.81 (m, 1H).

D27

(S)-3-(2,6-dichloropyrimidin-4-yl)-1,3-oxazinane-4-carboxylic acid

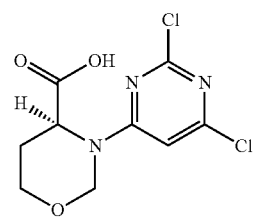 [SMILES: O=C(O)[C@@H]1CCOCN1c1cc(Cl)nc(Cl)n1]

To a mixture of crude (S)-1,3-oxazinane-4-carboxylic acid (7.5 g, 45 mmol) in EtOH (100 mL) was added TEA (11.4 g, 113 mmol) and 2,4,6-trichloropyrimidine (7.0 g, 38 mmol), the reaction mixture was stirred overnight at room temperature. Then the reaction mixture was filtered and the filtrate was concentrated and the residue was purified by chromatography on gel silica (DCM/MeOH=15/1) to give the title compound (4 g, 33%) as a yellow oil. The crude compound was used in the next step without further purification.

D28

(S)-(3-(2,6-dichloropyrimidin-4-yl)-1,3-oxazinan-4-yl)methanol

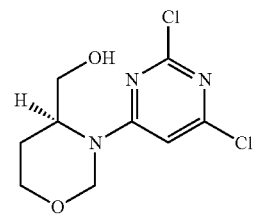 [SMILES: OC[C@@H]1CCOCN1c1cc(Cl)nc(Cl)n1]

To a solution of crude (S)-3-(2,6-dichloropyrimidin-4-yl)-1,3-oxazinane-4-carboxylic acid (D27) (4.0 g, 14 mmol) in THF (50 mL) was added BH$_3$.THF (1M in hexane, 28 mL, 28 mmol) dropwise under ice bath. After the addition, the reaction mixture was stirred at room temperature for 5 hrs. The reaction was quenched with MeOH (5 mL) and concentrated. The residue was purified by column chromatography on gel silica (PE/EA=2/1) to give the title compound (620 mg, 17%) as a white solid.

$^1$H NMR (300 MHz, CDCl$_3$): δ 5.78 (s, 1H), 4.97 (d, J=9.3 Hz, 1H), 4.64 (d, J=9.3 Hz, 1H), 4.51-4.20 (m, 3H), 4.06-3.97 (m, 1H), 3.78-3.69 (m, 1H), 2.06-2.01 (m, 1H), 1.86-1.71 (m, 1H).

D29

(S)-(3-(2,6-dichloropyrimidin-4-yl)-1,3-oxazinan-4-yl)methyl methanesulfonate

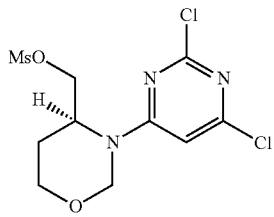 [SMILES: CS(=O)(=O)OC[C@@H]1CCOCN1c1cc(Cl)nc(Cl)n1]

To a solution of (S)-(3-(2,6-dichloropyrimidin-4-yl)-1,3-oxazinan-4-yl)methanol (600 mg, 2.28 mmol) in DCM (10 mL) was added MsCl (273 mg, 2.40 mmol) and TEA (460 mg, 4.56 mmol) at 0° C. After stirring at 0° C. for 20 min, H₂O (10 mL) was added and the mixture was extracted with DCM. The organic layer was washed with brine and dried over Na₂SO₄, filtered and concentrated to give the title compound (700 mg, 90%) which was used the in next step without further purification.

D30

(S)-3-chloro-8,9,9a,10-tetrahydropyrimido[6',1':2,3]imidazo[1,5-c][1,3]oxazin-1(6H)-one

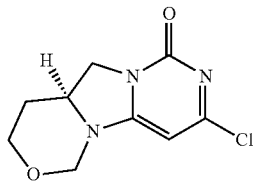 [SMILES: O=c1nc(Cl)cc2n1C[C@@H]1CCOCN21]

To a solution of (S)-(3-(2,6-dichloropyrimidin-4-yl)-1,3-oxazinan-4-yl)methyl methanesulfonate (700 mg, 2.05 mmol) in dioxane (4 mL) and H₂O (2 mL) was added K₂CO₃ (700 mg, 5.13 mmol). The reaction mixture was stirred at 95° C. for 2 hrs. After cooled to room temperature, H₂O (10 mL) was added and the reaction mixture extracted with DCM. The organic layer was washed with brine and dried over Na₂SO₄, filtered and concentrated. The residue was purified by column chromatography on gel silica (DCM/MeOH=50/1) to give the title compound (250 mg, 54%) as a white solid.

$^1$H NMR (300 MHz, CDCl₃): δ 5.73 (s, 1H), 5.04 (d, J=11.4 Hz, 1H), 4.65 (d, J=11.1 Hz, 1H), 4.25-4.09 (m, 3H), 3.99-3.94 (m, 1H), 3.83-3.74 (m, 1H), 2.02-1.97 (m, 1H), 1.75-1.70 (m, 1H).

D31

(R)-1,3-oxazinane-4-carboxylic acid

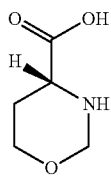

A solution of (R)-2-amino-4-hydroxybutanoic acid (15 g, 126 mmol) and 37% formaldehyde (11 mL, 149 mmol) in 2N NaOH (63 mL) was stirred at 2-10° C. overnight. 3N HCl was added to the reaction mixture to adjust the pH=2-3. The solvent was removed under lyophilization to give the title compound (16 g, 92%) as a white solid. The residue was used the in next step without further purification.

$^1$H NMR (300 MHz, DMSO-d₆): δ 10.18-9.65 (br s, 1H), 4.86 (d, J=9.0 Hz, 1H), 4.44 (d, J=9.0 Hz, 1H), 4.28-4.23 (m, 1H), 4.02-3.97 (m, 1H), 3.78-3.70 (m, 1H), 2.09-2.04 (m, 1H), 1.93-1.83 (m, 1H).

D32

(R)-3-(2,6-dichloropyrimidin-4-yl)-1,3-oxazinane-4-carboxylic acid

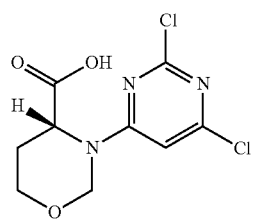 [SMILES: O=C(O)[C@H]1CCOCN1c1cc(Cl)nc(Cl)n1]

To a mixture of crude (R)-1,3-oxazinane-4-carboxylic acid (8.4 g, 50 mmol) in EtOH (120 mL) was added TEA (12.6 g, 125 mmol) and 2,4,6-trichloropyrimidine (10 g, 54 mmol). The reaction mixture was stirred overnight at room temperature. Then the reaction mixture was filtered and the filtrate was concentrated. The residue was purified by column chromatography on gel silica (DCM/MeOH=15/1) to give the title compound (6.0 g, 40%) as yellow oil. The crude compound was used in the next step without further purification.

D33

(R)-(3-(2,6-dichloropyrimidin-4-yl)-1,3-oxazinan-4-yl)methanol

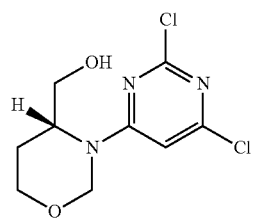 [SMILES: OC[C@H]1CCOCN1c1cc(Cl)nc(Cl)n1]

To a solution of crude (R)-3-(2,6-dichloropyrimidin-4-yl)-1,3-oxazinane-4-carboxylic acid (4.5 g, 16 mmol) in THF (50 mL) was added BH₃.THF (1M in hexane, 32 mL, 32 mmol) dropwise under ice bath. After the addition, the reaction mixture was stirred at room temperature for 5 hrs. The reaction was quenched with MeOH (5 mL) and concentrated. The residue was purified by column chromatography on gel silica (PE/EA=2/1) to give the title compound (800 mg, 19%) as a white solid.

¹H NMR (300 MHz, CDCl₃): δ 5.78 (s, 1H), 4.97 (d, J=9.3 Hz, 1H), 4.64 (d, J=9.3 Hz, 1H), 4.51-4.20 (m, 3H), 4.06-3.97 (m, 1H), 3.78-3.69 (m, 1H), 2.06-2.01 (m, 1H), 1.86-1.71 (m, 1H).

D34

(R)-(3-(2,6-dichloropyrimidin-4-yl)-1,3-oxazinan-4-yl)methyl methanesulfonate

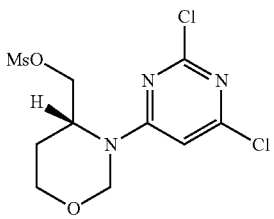 [SMILES: CS(=O)(=O)OC[C@H]1CCOCN1c1cc(Cl)nc(Cl)n1]

To a solution of (R)-(3-(2,6-dichloropyrimidin-4-yl)-1,3-oxazinan-4-yl)methanol (800 mg, 3.04 mmol) in DCM (10 mL) was added MsCl (362 mg, 3.20 mmol) and TEA (614 mg, 6.08 mmol) at 0° C. After stirring at 0° C. for 20 min, H₂O (10 mL) was added and the reaction mixture was extracted with DCM. The organic layer was washed with brine and dried over Na₂SO₄, filtered and concentrated to give the title compound (600 mg, 75%) which was used in the next step without further purification.

D35

(R)-3-chloro-8,9,9a,10-tetrahydropyrimido[6',1':2,3]imidazo[1,5-c][1,3]oxazin-1(6H)-one

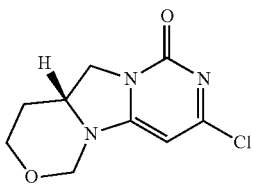 [SMILES: O=c1nc(Cl)cc2n1C[C@H]1CCOCN21]

To a solution of (R)-(3-(2,6-dichloropyrimidin-4-yl)-1,3-oxazinan-4-yl)methyl methanesulfonate (600 mg, 1.76 mmol) in dioxane (4 mL) and H₂O (2 mL) was added K₂CO₃ (728 mg, 5.28 mmol), the reaction mixture was stirred at 95° C. for 2 hrs. After cooled to room temperature, H₂O (10 mL) was added and the reaction mixture was extracted with DCM. The organic layer was washed with brine and dried over Na₂SO₄, filtered and concentrated. The residue was purified by column chromatography on gel silica (DCM/MeOH=50/1) to give the title compound (200 mg, 46%) as a white solid.

¹H NMR (300 MHz, CDCl₃): δ 5.73 (s, 1H), 5.04 (d, J=11.4 Hz, 1H), 4.65 (d, J=11.1 Hz, 1H), 4.25-4.09 (m, 3H), 3.99-3.94 (m, 1H), 3.83-3.74 (m, 1H), 2.02-1.97 (m, 1H), 1.75-1.70 (m, 1H).

D36

2-((2,6-Dichloropyrimidin-4-yl)amino)propane-1,3-diol

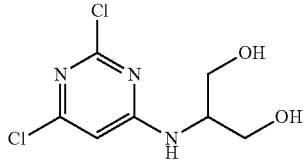 [SMILES: OCC(CO)Nc1cc(Cl)nc(Cl)n1]

To a solution of 2,4,6-trichloropyrimidine (12.49 g, 68.0 mmol) in THF (120 mL) was added Et₃N (10.30 g, 102.0 mmol) and 2-aminopropane-1,3-diol (6.20 g, 68.0 mmol) in EtOH (30 mL) was added dropwise at 0° C., then stirred at room temperature overnight. The reaction mixture was concentrated and the residue was purified by column chromatography on silica gel eluting with DCM/MeOH (5:1) to give the title compound (7.53 g, 47%) as a white solid.

¹H NMR (300 MHz, CD₃OD): δ6.50 (s, 1H), 4.20-4.23 (m, 1H), 3.72-3.62 (m, 4H).

D37

(3-(2,6-Dichloropyrimidin-4-yl)oxazolidin-4-yl)methanol

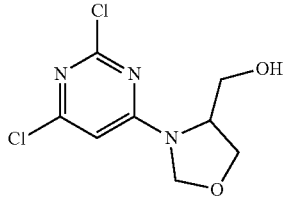 [SMILES: OCC1COCN1c1cc(Cl)nc(Cl)n1]

A mixture of 2-((2,6-dichloropyrimidin-4-yl)amino)propane-1,3-diol (7.51 g, 31.6 mmol), paraformaldehyde (947 mg, 31.6 mmol) and PTSA (300 mg, 1.6 mmol) in toluene (150 mL) was heated to reflux for 2 hours. The reaction mixture was cooled to room temperature and concentrated, the residue was purified by column chromatography on silica gel eluting with DCM/MeOH (100:1) to give the title compound (2.86 g, 36%) as a white solid.

¹H NMR (300 MHz, CDCl₃): δ 6.29 (s, 1H), 5.04-4.99 (m, 2H), 4.13-4.11 (m, 3H), 3.81-3.78 (m, 2H).

D38

(3-(2,6-Dichloropyrimidin-4-yl)oxazolidin-4-yl)methyl methanesulfonate

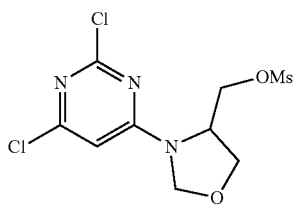 [SMILES: CS(=O)(=O)OCC1COCN1c1cc(Cl)nc(Cl)n1]

To a solution of (3-(2,6-dichloropyrimidin-4-yl)oxazolidin-4-yl)methanol (2.86 g, 11.4 mmol) and Et₃N (2.31 g, 22.9 mmol) in DCM (50 mL) was added dropwise methanesulfonyl chloride (1.38 g, 12.0 mmol) at 0° C. and the reaction mixture was stirred at room temperature for 0.5 h. The reaction was quenched with water (100 mL) and extracted with DCM (2×50 mL). The organic layer was combined, washed with brine (50 mL), dried over Na₂SO₄, filtered and concentrated to give the title compound (3.46 g, 92%) as a yellow power which was used directly for next step.

D39

6-Chloro-10,10a-dihydro-1H-oxazolo[3',4':3,4]imidazo[1,2-c]pyrimidin-8(3H)-one

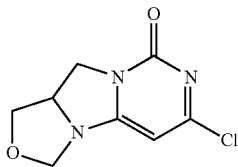 [SMILES: O=c1nc(Cl)cc2n1CC1COCN21]

To a solution of (3-(2,6-dichloropyrimidin-4-yl)oxazolidin-4-yl)methyl methanesulfonate (3.46, 10.5 mmol) in dioxane/H₂O (1:1, 40 mL) was added K₂CO₃ (4.37 g, 31.5 mmol) at room temperature. The reaction mixture was stirred at 95° C. for 7 hours. After cooled to room temperature, the mixture was diluted with water (20 mL), and extracted with DCM (2×100 mL). The combined organic layers were dried over Na₂SO₄, filtered and concentrated under reduced pressure. The residue was purified by column chromatography on silica gel eluting with DCM/MeOH (50:1) to give the title compound (908 mg, 36%) as a white solid.

¹H NMR (300 MHz, CDCl₃): δ 5.85 (s, 1H), 5.00-4.99 (m, 1H), 4.63-4.61 (m, 1H), 4.37-4.12 (m, 4H), 3.59-3.53 (m, 1H).

D40

(R)-6-chloro-10,10a-dihydro-1H-oxazolo[3',4':3,4]imidazo[1,2-c]pyrimidin-8(3H)-one

D41

(S)-6-chloro-10,10a-dihydro-1H-oxazolo[3',4':3,4]imidazo[1,2-c]pyrimidin-8(3H)-one

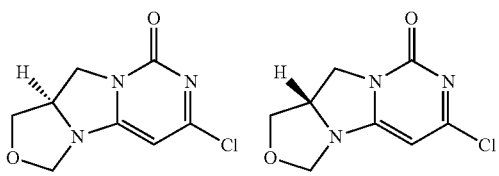

The racemic 6-chloro-10,10a-dihydro-1H-oxazolo[3',4':3,4]imidazo[1,2-c]pyrimidin-8(3H)-one (5.03 g, 23.6 mmol) was separated by chiral HPLC to give R-isomer (1.75 g, 35%) as a white solid and S-isomer (2.07 g, 41%) as a white solid. (Chiral Analysis Method: Column: chiralpak AYH (0.46 cm I.D×15 cm L); Wavelength: 230 nm; Mobile phase: hexane/methanol/DEA=70/30/0.2 (V/V/V); T=40° C.; Flow rate: 0.899 mL/min; Injection volume: 8 µL; Run time: 10 min.)

D40: Rt=5.85 min (identical with LT111530-168, chiral synthesis), Optical purity 99.5% (230 nm)

¹H NMR (300 MHz, CDCl₃): δ 5.86 (s, 1H), 5.01-4.99 (m, 1H), 4.63-4.61 (m, 1H), 4.34-4.12 (m, 4H), 3.59-3.54 (m, 1H).

D41: Rt=7.18 min, Optical purity 99.3% (230 nm)

¹H NMR (300 MHz, CDCl₃): δ 5.86 (s, 1H), 5.01-4.99 (m, 1H), 4.63-4.61 (m, 1H), 4.35-4.12 (m, 4H), 3.59-3.56 (m, 1H).

D42

1-(2-((Tert-butyldimethylsilyl)oxy)ethyl)-6-chloropyrimidine-2,4(1H,3H)-dione

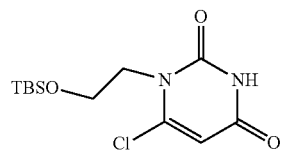 [SMILES: CC(C)(C)[Si](C)(C)OCCn1c(Cl)cc(=O)[nH]c1=O]

To a solution of 6-chloropyrimidine-2,4(1H,3H)-dione (100.0 g, 0.680 mol), 2-((tert-butyldimethylsilyl)oxy)ethanol (143.6 g, 0.816 mol) and Ph₃P (267.2 g, 1.02 mol) in dry THF (2000 mL) was added DIAD (206.0 g, 1.02 mol) in dry THF (500 mL) dropwise under N₂ at room temperature and the mixture was stirred overnight. The mixture was concentrated in vacuo. The residue was triturated with PE/EA (1:1, 500 mL), filtered and concentrated. The residue was purified by column chromatography on silica gel (PE/EA=5/1) to give the title compound (125.0 g, 60%) as a white solid.

¹H NMR (300 MHz, CDCl₃): δ 9.93 (br s, 1H), 5.87 (s, 1H), 4.19 (t, J=5.7 Hz 2H), 3.83 (t, J=5.7 Hz 2H), 0.84 (s, 9H), 0.02 (s, 6H).

D43

6-Chloro-1-(2-hydroxyethyl)pyrimidine-2,4(1H,3H)-dione

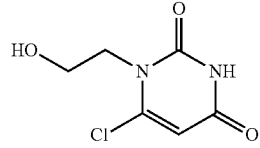 [SMILES: O=c1cc(Cl)n(CCO)c(=O)[nH]1]

To a solution of 1-(2-((tert-butyldimethylsilyl)oxy)ethyl)-6-chloropyrimidine-2,4(1H,3H)-dione (125.0 g, 0.410 mol) in dry MeOH (1200 mL) was added concentrated. HCl (12 N, 3.0 mL) at room temperature and the reaction mixture was stirred for 2 hrs, concentrated to remove MeOH. The residue was triturated with hexane (800 mL) to give the title compound (75.0 g, 96%) as a white solid.

$^1$H NMR (300 MHz, DMSO-$d_6$): δ 11.57 (s, 1H), 5.90 (s, 1H), 4.96 (t, J=6.3 Hz 1H), 3.98 (t, J=6.0 Hz 2H), 3.56 (t, J=5.7 Hz 2H).

D44

2-(6-Chloro-2,4-dioxo-3,4-dihydropyrimidin-1(2H)-yl)acetaldehyde

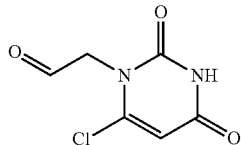 [SMILES: O=CCn1c(Cl)cc(=O)[nH]c1=O]

To a solution of 6-chloro-1-(2-hydroxyethyl)pyrimidine-2,4(1H,3H)-dione (75.0 g, 0.395 mol) in dry DCM (2000 mL) was added Dess-Martin periodinane (249 g, 0.593 mol) in one portion at room temperature. Then the mixture was stirred at 35° C. for 2 hrs and concentrated in vacuo at 35° C. The residue was purified by column chromatography on silica gel (PE/EA=5/1 to 2/1) to give the title compound (35.0 g, 47%) as a white solid.

$^1$H NMR (300 MHz, DMSO-$d_6$): δ11.56 (s, 1H), 9.58 (s, 1H), 6.00 s 1H), 4.93 (s, 2H).

D45

10,10a-Dihydro-2H-oxazolo[3',2':3,4]imidazo[1,2-c]pyrimidine-6,8(3H,7H)-dione

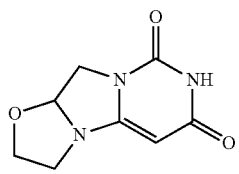 [SMILES: O=c1cc2n(c(=O)[nH]1)CC1OCCN21]

To a solution of 2-aminoethanol (2.64 g, 42.6 mmol) in dioxane (100 mL) was added 2-(6-chloro-2,4-dioxo-3,4-dihydropyrimidin-1(2H)-yl)acetaldehyde (8.00 g, 42.6 mmol) in dioxane (100 mL) dropwise at 80° C. After stirred for 1 h, the mixture was concentrated in vacuo. The residue was purified by column chromatography on silica gel (DCM/MeOH=40/1) to give the title compound (3.0 g, 36%) as a white solid.

$^1$H NMR (300 MHz, DMSO-$d_6$): δ 10.75 (br s, 1H), 5.12 (d, J=4.2 Hz 1H), 5.03 (s, 1H), 4.07-3.79 (m, 4H), 3.64-3.41 (m, 2H).

D46

3,4,11,11a-Tetrahydropyrimido[6',1':2,3]imidazo[5,1-b][1,3]oxazine-7,9(2H,8H)-dione

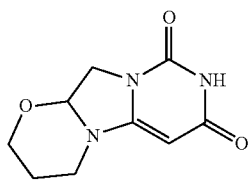 [SMILES: O=c1cc2n(c(=O)[nH]1)CC1OCCCN21]

To a solution of 3-aminopropan-1-ol (2.0 g, 26.6 mmol) in dioxane (200 mL) was added 2-(6-chloro-2,4-dioxo-3,4-dihydropyrimidin-1(2H)-yl)acetaldehyde (5.0 g, 26.6 mmol) in dioxane (100 mL) dropwise at 80° C. and the mixture was then stirred for further 1 h. The mixture was concentrated in vacuo. The residue was purified by column chromatography on silica gel eluted with DCM/MeOH (40:1) to give the title compound (2.1 g, 38%) as a white solid.

$^1$H NMR (300 MHz, DMSO-$d_6$): δ10.52 (br s, 1H), 5.26 (d, J=5.1 Hz 1H), 4.90 (s, 1H), 3.98-3.62 (m, 6H), 3.49-3.34 (m, 2H).

D47

(4-Methylpiperazin-2-yl)methanol

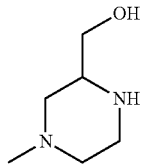

To a mixture of tert-butyl 3-(hydroxymethyl)piperazine-1-carboxylate (1.0 g, 4.6 mmol) in THF (20 mL) was added LiAH$_4$ (440 mg, 11.6 mmol) at room temperature. The mixture was heated to reflux for 2 hours, then cooled to 0° C. and quenched with MeOH (10 mL) and saturated potassium sodium tartrate (10 mL). The mixture was filtrated and the filtrate was evaporated to afford the title compound (600 mg, yield 100%) as yellow oil.

$^1$H NMR (300 MHz, CDCl$_3$): δ 3.62-3.57 (m, 1H), 3.50-3.45 (m, 1H), 3.04-2.99 (m, 1H), 2.95-2.85 (m, 2H), 2.73-2.60 (m, 2H), 2.29 (s, 3H), 2.07-1.99 (m, 1H), 1.86-1.79 (m, 1H).

D48

(1-(2,6-Dichloropyrimidin-4-yl)-4-methylpiperazin-2-yl)methanol

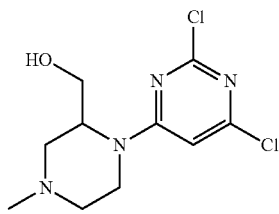 [SMILES: CN1CCN(c2cc(Cl)nc(Cl)n2)C(CO)C1]

A solution of 2,4,6-trichloropyrimidine (847 mg, 4.6 mmol), (4-methylpiperazin-2-yl)methanol (600 mg, 4.6 mmol) and TEA (1.40 g, 13.8 mmol) in EtOH (15 mL) was stirred at room temperature for 6 hours, concentrated and purified by flash chromatography on silica gel (DCM/MeOH=50/1) to give the title compounds (460 mg, yield 37%) as a white solid.

$^1$H NMR (300 MHz, CDCl$_3$): δ 6.56 (s, 0.22H), 6.44 (s, 0.71H), 4.72-4.71 (m, 0.39H), 4.57-4.50 (m, 0.38H), 4.05-3.99 (m, 1H), 3.95-3.88 (m, 1H), 3.65-3.54 (m, 1H), 3.12-3.07 (m, 1H), 2.97-2.88 (m, 1H), 2.84-2.71 (m, 1H), 2.37-2.35 (m, 1H), 2.32-2.31 (m, 3H), 2.19-2.08 (m, 1H).

D49

7-Chloro-2-methyl-3,4,11,11a-tetrahydro-1H-pyrazino[1',2':3,4]imidazo[1,2-c]pyrimidin-9(2H)-one

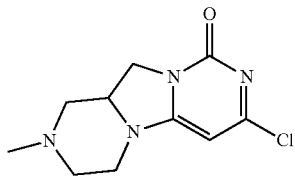 [SMILES: CN1CCN2c3cc(Cl)nc(=O)n3CC2C1]

To a solution of (1-(2,6-dichloropyrimidin-4-yl)-4-methylpiperazin-2-yl)methanol (460 mg, 1.67 mmol) and TEA (337 mg, 3.33 mmol) in DCM (10 mL) was added MsCl (229 mg, 2.00 mmol) at 0° C. The mixture was stirred at room temperature for 1 hour and concentrated. The residue was treated with $K_2CO_3$ (460 mg, 3.33 mmol), dioxane (20 mL) and $H_2O$ (4 mL) and the resulting mixture was heated to 70° C. for 3 hours, and then concentrated and purified by prep-TLC (DCM/MeOH=10/1) to give the title compound (100 mg) as a yellow solid.

$^1$H NMR (300 MHz, DMSO-$d_6$): δ 6.01 (s, 1H), 4.10-4.02 (m, 2H), 3.81-3.76 (m, 1H), 3.66-3.55 (m, 1H), 3.21-3.11 (m, 1H), 2.91-2.87 (m, 1H, 2.76-2.71 (m, 1H), 2.21 (m, 3H), 1.99-1.90 (m, 2H).

D50

3-Benzyl 1-tert-butyl 4-benzyl-3-methylpiperazine-1,3-dicarboxylate

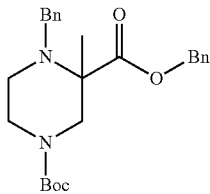 [SMILES: CC(C)(C)OC(=O)N1CCN(Cc2ccccc2)C(C)(C(=O)OCc2ccccc2)C1]

3-Benzyl 1-tert-butyl 4-benzylpiperazine-1,3-dicarboxylate (2 g, 4.87 mmol) was dried in a 250 mL round bottom flask under high vacuum prior to use. THF (50 mL) was added under argon, and the vessel cooled to 0° C. LDA (~1.5 M in THF) (3.4 mL, 5.10 mmol) was added dropwise. The reaction was stirred for 30 min at 0° C. and then quenched by addition of MeI (0.76 mL, 12.15 mmol). After stirring 15 min, the reaction was concentrated under reduced pressure. The crude was purified on a Combiflash silica cartridge (12 g) (0%-30% EtOAc/hexanes) to give the title compound (832 mg, 1.96 mmol, 40.2% yield) as tan yellow oil.

LC/MS: m/z 425.2 (M+H)$^+$, 1.23 min (ret. time);

$^1$H NMR (400 MHz, CD$_2$Cl$_2$): δ 7.17-7.46 (m, 10H), 5.02-5.30 (m, 2H), 4.22 (d, J=11.54 Hz, 1H), 3.98 (d, J=14.56 Hz, 1H), 3.69 (d, J=12.55 Hz, 1H), 3.62 (d, J=14.56 Hz, 1H), 2.93-3.15 (m, 2H), 2.68-2.87 (m, 1H), 2.47 (m, 1H), 1.42 (m, 12H).

D51 tert-Butyl 4-benzyl-3-(hydroxymethyl)-3-methylpiperazine-1-carboxylate

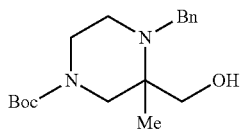 [SMILES: CC(C)(C)OC(=O)N1CCN(Cc2ccccc2)C(C)(CO)C1]

A solution of 3-benzyl 1-tert-butyl 4-benzyl-3-methylpiperazine-1,3-dicarboxylate (890 mg, 2.096 mmol) in 2-MeTHF (15 mL) was cooled to 0° C. under argon. LAH (2.3 M, in 2-MeTHF) (1 mL, 2.3 mmol) was added slowly. The reaction was quenched by addition of saturated $Na_2SO_4$ (0.38 mL, [4.4 mL per gram LAH]) after 1 h stirring, filtered and the filter cake was extracted with EtOAc. The combined organic layer was concentrated to give the title compound (714 mg, 2.23 mmol, 106% yield) as viscous yellow oil that was used without further purification.

LC/MS: m/z 321.1 (M+H)$^+$, 0.64 min (ret. time)

D52 tert-Butyl 4-(2,6-dichloropyrimidin-4-yl)-3-(hydroxymethyl)-3-methylpiperazine-1-carboxylate

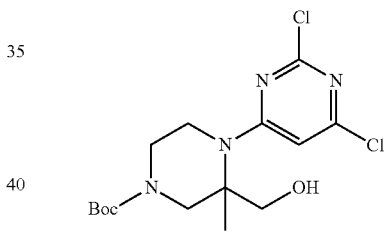

tert-Butyl 4-benzyl-3-(hydroxymethyl)-3-methylpiperazine-1-carboxylate (714 mg, 2.23 mmol) was dissolved in methanol (53 mL, in portions) and added to a 100 mL graduated cylinder. The solution was hydrogenated on an H-Cube through a 20% Pd(OH)$_2$/C cartridge at 60° C., using additional MeOH (20 mL) to ensure all of the starting material transferred through the H-Cube. The solution was concentrated under reduced pressure, then transferred to a 20 mL vial using EtOH, and concentrated under a stream of nitrogen at 50° C. A stirbar was added, then ethanol (12 mL), $Na_2CO_3$ (260 mg, 2.451 mmol), and 2,4,6-trichloropyrimidine (0.282 mL, 2.451 mmol) and the reaction was stirred over the weekend (66 h). ~80% of the starting material remained after stirring over the weekend. The reaction was concentrated under a stream of nitrogen at 50° C. then dissolved in DMF (10 mL). The reaction was stirred at room temperature overnight (20 h) then filtered through a 0.2 μm acrodisc. The filtrate was concentrated, then applied to isolate using DCM and concentrated under a stream of nitrogen at 50° C. The crude product was purified on a Combiflash silica cartridge (24 g) (0%-60% EtOAc/hexanes) to give the title compound (329 mg, 0.87 mmol, 39% yield) as a clear oil.

LC/MS: m/z 377.1 (M+H)$^+$, 1.05 min (ret. time)

D53 tert-Butyl 7-chloro-11a-methyl-9-oxo-3,4,11,11a-tetrahydro-1H-pyrazino[1',2':3,4]imidazo[1,2-c]pyrimidine-2(9H)-carboxylate

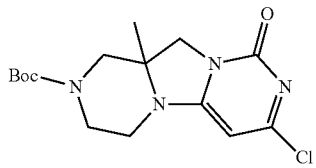 [SMILES: CC(C)(C)OC(=O)N1CCN2c3cc(Cl)nc(=O)n3CC2(C)C1]

A solution of tert-butyl 4-(2,6-dichloropyrimidin-4-yl)-3-(hydroxymethyl)-3-methylpiperazine-1-carboxylate (35 mg, 0.093 mmol) in THF (1.2 mL) was cooled to 0° C. and TEA (0.03 mL, 0.215 mmol) then MsCl (0.01 mL, 0.128 mmol) as a solution in THF (0.1 mL) were added dropwise and stirred for 15 min at 0° C. The reaction was then concentrated under a stream of nitrogen at 50° C., resulting in a white solid. The resulting material was taken up in acetonitrile (1.2 mL). $K_2CO_3$ (39 mg, 0.282 mmol) was added, and the resulting suspension was heated to 80° C. for 40 min. After cooling to room temperature, the reaction mixture was filtered, concentrated. The residue was partitioned between $H_2O$ (1 mL) and $CH_2Cl_2$ (3 mL). The layers were separated and the aqeuous phase was further extracted with $CH_2Cl_2$ (2×1 mL). The combined organic phases were concentrated under a stream of nitrogen at 50° C. to give the title compound (29 mg, 0.085 mmol, 92% yield) as a mustard yellow solid. The crude material was used without further purification.

LC/MS: m/z 341.1 $(M+H)^+$, 0.71 min (ret. time);

$^1$H NMR (400 MHz, $CD_2Cl_2$): δ 3.78-4.13 (m, 2H), 3.71 (s, 2H), 3.11-3.21 (m, 2H), 2.68-2.99 (m, 2H), 1.28 (s, 12H).

D54 tert-Butyl 3-(dideuterio(hydroxy)methyl)piperazine-1-carboxylate

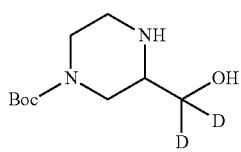

A suspension of 4-(tert-butoxycarbonyl)piperazine-2-carboxylic acid (4.5 g, 19.54 mmol) in 2-methyltetrahydrofuran (2-MeTHF) (60 ml) was sonicated for 20 min, cooled to 0° C., then a solution of Lithium aluminum deuteride (1M in THF) (24.5 ml, 24.50 mmol) was added in portions. The reaction mixture was stirred for 15 min at 0° C., then stirred at room temperature for 20 h. The reaction was quenched with saturated $Na_2SO_4$ (2.6 mL) dropwise, and stirred for an additional 15 min, filtered and the filter cake was further extracted with EtOAc (6×50 mL). The filtrate was dried over anhydrous $Na_2SO_4$, filtered and concentrated to give the title compound (3.47 g, 15.90 mmol, 81% yield) as a red sticky solid, which was used without further purification.

LC/MS: m/z 219.0 $(M+H)^+$, 0.34 min (ret. time)

D55 tert-Butyl 4-(2,6-dichloropyrimidin-4-yl)-3-(dideuterio(hydroxy)methyl)piperazine-1-carboxylate

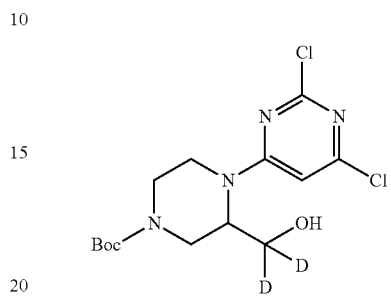

The title compound was prepared by a procedure similar to that described for D52 starting from tert-butyl 3-(hydroxymethyl)piperazine-1-carboxylate.

LC/MS: m/z 365.0 $(M+H)^+$, 0.98 min (ret. time)

$^1$H NMR (400 MHz, $CDCl_3$): δ 4.16-4.47 (m, 2H), 3.99 (dd, J=11.04, 3.51 Hz, 1H), 3.68 (s, 1H), 3.47 (br. s., 1H), 3.25 (d, J=2.76 Hz, 1H), 2.74-2.98 (m, 2H), 1.50 (s, 9H).

D56 tert-Butyl 7-chloro-11,11-dideuterio-9-oxo-3,4,11,11a-tetrahydro-1H-pyrazino[1,2':3,4]imidazo[1,2-c]pyrimidine-2(9H)-carboxylate

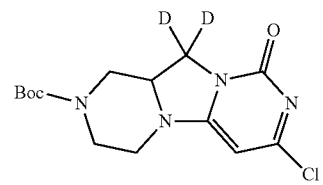 [SMILES: [2H]C1([2H])C2CN(C(=O)OC(C)(C)C)CCN2c2cc(Cl)nc(=O)n21]

The title compound was prepared by a procedure similar to that described for D53 starting from tert-butyl 4-(2,6-dichloropyrimidin-4-yl)-3-(dideuterio(hydroxy)methyl)piperazine-1-carboxylate LC/MS: m/z 329.0 $(M+H)^+$, 0.67 min (ret. time)

D57 tert-Butyl 4-(2,6-dichloropyrimidin-4-yl)-3-(hydroxymethyl)piperazine-1-carboxylate

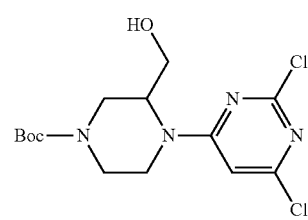 [SMILES: CC(C)(C)OC(=O)N1CCN(c2cc(Cl)nc(Cl)n2)C(CO)C1]

To a mixture of tert-butyl 3-(hydroxymethyl)piperazine-1-carboxylate (14.05 g, 65.0 mmol) and Na$_2$CO$_3$ (8.2 g, 77 mmol) was added ethanol (316 ml) followed by addition of 2,4,6-trichloropyrimidine (9 ml, 78 mmol). The reaction mixture was stirred for 3 d at rt, filtered through a cinter funnel, concentrated, and taken up in DCM. Then Isolute was added, and the heterogeneous mixture was concentrated. The residue was purified on a Combiflash silica cartridge (330 g) (0%-70% EtOAc/hexanes) to give the title compound (7.1 g, 19.55 mmol, 30.1% yield) as an orange-white amorphous solid.

LC/MS: m/z 363.2 (M+H)$^+$, 0.92 min (ret. time)

D58 tert-Butyl 7-chloro-9-oxo-3,4,11,11a-tetrahydro-1H-pyrazino[1',2':3,4]imidazo[1,2-c] pyrimidine-2(9H)-carboxylate

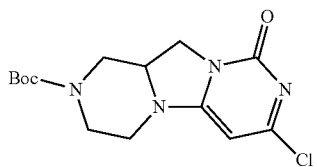 [SMILES: CC(C)(C)OC(=O)N1CCN2c3cc(Cl)nc(=O)n3CC2C1]

A solution of tert-butyl 4-(2,6-dichloropyrimidin-4-yl)-3-(hydroxymethyl)piperazine-1-carboxylate (7.1 g, 19.55 mmol) in THF (225 ml) was cooled to 0° C. and TEA (5.45 ml, 39.1 mmol) then MsCl (1.675 ml, 21.50 mmol) as a solution in THF (25 ml) were added dropwise, stirred for 15 min at 0° C. The reaction mixture was then concentrated, and the residue was taken up in acetonitrile (250 ml). K$_2$CO$_3$ (8.10 g, 58.6 mmol) was added, and the resulted suspension was heated to 80° C. for 38 min. After cooling to rt, the reaction mixture was filtered and the filtrate was concentrated. The residue was partitioned between H$_2$O (100 mL) and CHCl$_3$ (100 mL). The layers were separated and the aqeuous phase was further extracted with CHCl$_3$ (3×50 mL). The organic phases were combined and concentrated under reduced pressure to give the title compound (6.23 g, 19.06 mmol, 98% yield) as an amorphous brown/red solid. The crude material was used without further purification.

LC/MS: m/z 327.0 (M+H)$^+$, 0.68 min (ret. time);
$^1$H NMR (400 MHz, CDCl$_3$): δ 5.49 (s, 1H), 3.95-4.42 (m, 4H), 3.69 (dd, J=12.05, 7.53 Hz, 1H), 3.48 (d, J=11.29 Hz, 1H), 3.22 (td, J=12.42, 2.76 Hz, 1H), 3.08-2.78 (m, 2H), 1.45 (s, 9H).

D59

7-Chloro-3,4,11,11a-tetrahydro-1H-pyrazino[1',2':3,4]imidazo[1,2-c]pyrimidin-9(2H)-one

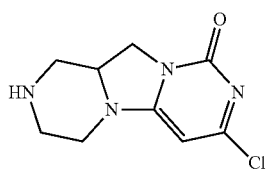 [SMILES: O=c1nc(Cl)cc2n1CC1CNCCN21]

To a solution of tert-butyl 7-chloro-9-oxo-3,4,11,11a-tetrahydro-1H-pyrazino[1',2':3,4]imidazo[1,2-c] pyrimidine-2(9H)-carboxylate (1.84 g, 5.63 mmol) in dry dichloromethane (DCM) (6.5 mL was added TFA (6.5 mL, 84 mmol). The reaction mixture was stirred at rt for 1.75 h, concentrated under a stream of nitrogen at 50° C., taken up in DCM/MeOH and concentrated under a stream of nitrogen at 50° C., then placed under high vacuum to give the title compound (2.01 g, 6.47 mmol, 115% yield) as a brown solid that was used without purification.

LC/MS: m/z 226.9 (M+H)$^+$, 0.1 min (ret. time)

D60

1-(2,6-Dichloropyrimidin-4-yl)-5-oxopiperazine-2-carboxylic acid

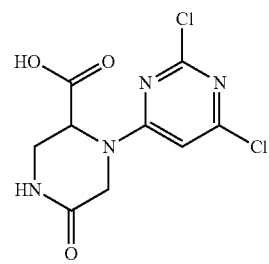 [SMILES: O=C1CN(c2cc(Cl)nc(Cl)n2)C(C(=O)O)CN1]

To a suspension of 5-oxopiperazine-2-carboxylic acid (2000 mg, 13.88 mmol) and sodium carbonate (2941 mg, 27.8 mmol) in ethanol (50 mL) was added 2,4,6-trichloropyrimidine (1.596 mL, 13.88 mmol). The reaction mixture was heated to 50° C. overnight, concentrated. Then 20 mL water was added, filtered and got 2.9 g 1-(2,6-dichloropyrimidin-4-yl)-5-oxopiperazine-2-carboxylic acid as a white solid (with some minor isomer).

LC/MS: m/z 290.8 (M+H)$^+$, 0.55 min(ret. time)

D61

Methyl 1-(2,6-dichloropyrimidin-4-yl)-5-oxopiperazine-2-carboxylate

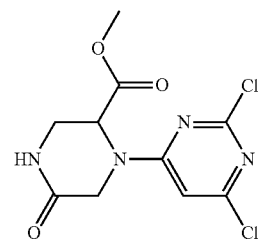 [SMILES: COC(=O)C1CNC(=O)CN1c1cc(Cl)nc(Cl)n1]

To a suspension of 1-(2,6-dichloropyrimidin-4-yl)-5-oxopiperazine-2-carboxylic acid (2900 mg, 9.96 mmol) and potassium carbonate (4131 mg, 29.9 mmol) in DMF (20 mL) was added iodomethane (1.246 mL, 19.93 mmol). The reaction mixture was stirred at rt for 30 min, and concentrated. Then water and EA were added, filtered to get 866 mg crude solid product. The filtrate was separated and extracted the aqueous layer twice with EA, concentrated. The crude product was purified via CombiFlash Rf 200 with a gradient of 100% DCM to 10% MeOH in DCM to afford the title compound (940 mg) as a white solid.

LC/MS: m/z 304.8 (M+H)$^+$, 0.63 min(ret. time)

D62

4-(2,6-Dichloropyrimidin-4-yl)-5-(hydroxymethyl) piperazin-2-one

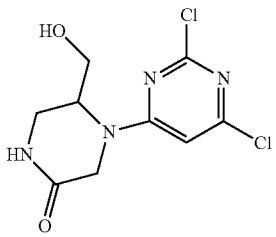 [SMILES: O=C1CN(c2cc(Cl)nc(Cl)n2)C(CO)CN1]

To a solution of methyl 1-(2,6-dichloropyrimidin-4-yl)-5-oxopiperazine-2-carboxylate (1800 mg, 5.90 mmol) in ethanol (50 mL) was added sodium tetrahydroborate (670 mg, 17.70 mmol). The reaction mixture was stirred at rt overnight. Then acetic acid (2.362 mL, 41.3 mmol) was added and stirred for 10 min, concentrated, and then EA and water were added. The water layer was extracted twice with EA. The combined organic layers were concentrated and purification via CombiFlash Rf 200 afforded the title compound (807 mg) as a white solid.

LC/MS: m/z 276.9 (M+H)$^+$, 0.46 min(ret. time)

D63

7-Chloro-11,11a-dihydro-1H-pyrazino[1',2':3,4]imidazo[1,2-c]pyrimidine-3,9(2H,4H)-dione

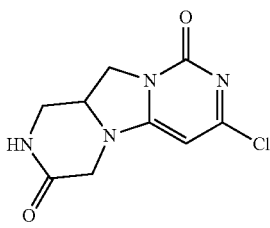 [SMILES: O=C1CN2c3cc(Cl)nc(=O)n3CC2CN1]

To a solution of 4-(2,6-dichloropyrimidin-4-yl)-5-(hydroxymethyl)piperazin-2-one (807 mg, 2.91 mmol) in THF (30 mL) at 0° C. was added methanesulfonyl chloride (0.295 mL, 3.79 mmol) and triethylamine (0.807 mL, 5.82 mmol). The reaction mixture was stirred at 0° C. for 30 min, concentrated. The residue was taken up in acetonitrile (30.0 mL), and then potassium carbonate (1207 mg, 8.74 mmol) was added. The resulted suspension was heated to 82° C. for 1 h, filtered and concentrated. The residue was purified using CombiFlash Rf 200 to afford the title compound (450 mg) as a white solid.

LC/MS: m/z 241.0 (M+H)$^+$, 0.20 min(ret. time)

D64

7-Chloro-2-methyl-11,11a-dihydro-1H-pyrazino[1', 2':3,4]imidazo[1,2-c]pyrimidine-3,9(2H,4H)-dione

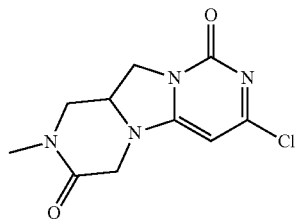 [SMILES: CN1CC2Cn3c(cc(Cl)nc3=O)N2CC1=O]

A suspension of 7-chloro-11,11a-dihydro-1H-pyrazino[1', 2':3,4]imidazo[1,2-c]pyrimidine-3,9(2H,4H)-dione (200 mg, 0.831 mmol) and 18-crown-6 (10.39 mg, 0.042 mmol) in THF (14 mL) and DMSO (2 mL) at 0° C., was added sodium hydride (49.9 mg, 1.247 mmol). The reaction mixture was stirred for 20 min at rt, then, iodomethane (0.083 mL, 1.330 mmol) was added at 0° C. The reaction mixture was stirred at rt overnight, quenched by addition of water, and concentrated. The residue was purified using CombiFlash Rf 200 to afford the title compound (200 mg) as a yellow solid.

LC/MS: m/z 254.9 (M+H)$^+$, 0.16 min(ret. time)

D65

4-(2,6-Dichloropyrimidin-4-yl)thiomorpholin-3yl) methanol

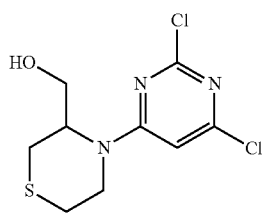 [SMILES: OCC1CSCCN1c1cc(Cl)nc(Cl)n1]

To a mixture of the thiomorpholin-3-ylmethanol (1.23 g, 9.20 mmol, 1.0 equiv) and 2,4,6-trichloropyrimidine (1.86 g, 10.12 mmol, 1.1 equiv) in EtOH (25 mL) at 0° C. was added Et$_3$N (1.54 mL, 1.2 equiv) dropwise. The reaction mixture was stirred overnight, concentrated. The residue was partitioned between 5% MeOH in DCM (100 and 50 mL) and water (30 mL) and saturated NaHCO$_3$ solution (10 mL). The combined organic was dried over Na$_2$SO$_4$, filtered and concentrated to afford 3 g of the crude as a clear thick oil. This crude material was combined with the crudes from two scout runs starting from a total of 1.00 g of thiomorpholin-3-ylmethanol. These crude materials were adsorbed onto Isolute. Purification was performed on a Teledyne-Isco Combiflash Rf system using a Redi-Sep 80 g silica gel cartridge with gradient elution of 0% EtOAc in hexane to 70% EtOAc in hexane over a 40 min period (the first 5 min was holding time for 0% EtOAc in hexane, flow rate at 60 mL/min, UV at 254 nm). There were three peaks eluting out. The third peak was the desired product. The appropriate fractions were combined and concentrated to give the title compound as a white foamy residue (2.87 g).

LC/MS: m/z 280/282 (M/M+2)⁺, 0.76 min (ret. time).
¹H NMR (400 MHz, DMSO-d₆): δ7.05 (s, 1H), 4.90 (t, J=5.65 Hz, 1H), 3.80 (br. s., 2H), 2.89 (br. s., 1H), 2.71 (s, 1H), 2.74 (s, 2H), 2.62 (br. s., 1H).

D66

7-Chloro-3,4,11,11a-tetrahydropyrimido[6',1':2,3] imidazo[5,1-c][1,4]thiazin-9(1H)-one

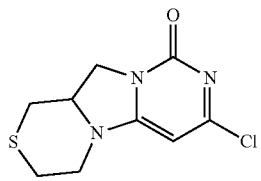 [SMILES: O=c1nc(Cl)cc2n1CC1CSCCN21]

To a chilled (ice bath) solution of (4-(2, 6-dichloropyrimidin-4-yl)thiomorpholin-3-yl)methanol (2.70 g, 9.64 mmol, 1.0 equiv) in THF (70 mL) was added Et₃N (4.0 mL, 28.90 mmol, 3.0 equiv) and then a solution of MsCl (1.66 g, 14.46 mmol, 1.5 equiv) in THF (15 mL) portion wise. The reaction mixture was stirred at 0° C. for 30 min, and then concentrated. The residue was taken up in 80 ml of ACN, followed by addition of K₂CO₃ (4.00 g, 28.90 mmol, 3.0 equiv). The mixture was heated at 85° C. for 1.5 h. The mixture was cooled to rt, and filtered. The filtrate was concentrated to give a light brownish residue. This residue was partitioned between 5% MeOH in DCM (100 mL, 50 mL, 2×30 mL) and brine (15 mL) and 5 mL of saturated NaHCO₃. The middle emulsion was filtered through celite to give a clear phase separation. The combined organic was dried over Na₂SO₄, filtered, and concentrated to give a brownish residue (3.15 g). This residue was redissolved in 5% MeOH in DCM and adsorbed onto Isolute. Purification was performed on a Teledyne-Isco Combiflash Rf purification system using a Redi-Sep 80 g silica gel cartridge with gradient elution of 0% A in DCM to 100% A in DCM over a 40 min period (the first 5 min was holding time for 0% A in DCM, A was a 10/1 mixture of DCM/MeOH, flow rate at 60 mL/min, UV at 254 nm). The appropriate fractions were combined and concentrated to give the title compound (2.23 g) as a light pinkish solid.

LC/MS: m/z 243.8 (M+H)⁺, 0.47 min (ret. time).
¹HNMR (400 MHz, DMSO-d₆): δ6.02 (s, 1H), 4.22-4.05 (m, 3H), 3.69-3.56 (m, 1H), 3.29-3.16 (m, 1H), 2.94-2.81 (m, 1H), 2.81-2.67 (m, 2H), 2.66-2.55 (m, 1H).

D67

(2R,4R)-1-((Benzyloxy)carbonyl)-4-hydroxypyrrolidine-2-carboxylic acid

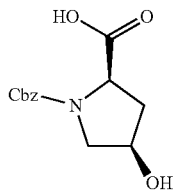

(2R,4R)-4-hydroxypyrrolidine-2-carboxylic acid (1.00 g, 7.63 mmol) was added to water (15.10 ml) followed by adding sodium bicarbonate (1.60 g, 19.07 mmol). To this mixture was added a solution of benzyl chloroformate (1.198 ml, 8.39 mmol) in toluene (3.77 mL) dropwise and the reaction was allowed to stir at RT. After 12 h, reaction contents were added to separatory funnel and separated the layers. Excess benzyl chloroformate was removed by washing the aqueous layer with 5×6 mL Et₂O. Acidified the aqueous layer to pH=2 with the dropwise addition of concentrated HCl (37%), affording a white precipitate. Diluted with 30 mL EtOAc and separated the resulting layers. The aqueous layer was extracted with 6×10 mL EtOAc, and the combined organics were dried over Na₂SO₄, filtered and concentrated in vacuo to give (2R,4R)-1-((benzyloxy)carbonyl)-4-hydroxypyrrolidine-2-carboxylic acid as a white solid.

LC/MS: m/z 265.9 (M+H)⁺, 0.60 min (ret. time).

D68

(2R,4R)-1-Benzyl 2-methyl 4-hydroxypyrrolidine-1,2-dicarboxylate

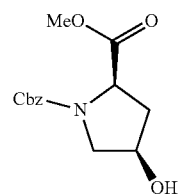 [SMILES: COC(=O)[C@H]1C[C@@H](O)CN1C(=O)OCc1ccccc1]

(2R,4R)-1-((benzyloxy)carbonyl)-4-hydroxypyrrolidine-2-carboxylic acid (1.68 g, 6.33 mmol) was added to N,N-dimethylformamide (DMF) (10 ml) followed by the addition of sodium bicarbonate (1.064 g, 12.67 mmol). Added methyl iodide (1.980 ml, 31.7 mmol) dropwise and placed in a 50° C. bath. After 3 h, cooled to RT and partitioned between 150 mL EtOAc and 50 mL H₂O. The resulting layers were separated. The organic layers were washed with 5×30 mL H₂O and 1×20 mL brine. The organics were dried over Na₂SO₄, filtered and concentrated in vacuo to give (2R, 4R)-1-benzyl 2-methyl 4-hydroxypyrrolidine-1,2-dicarboxylate a white solid.

LC/MS: m/z 279.9 (M+H)⁺, 0.71 min (ret. time).

D69

(2R,4R)-1-Benzyl 2-methyl 4-((tert-butyldimethylsilyl)oxy)pyrrolidine-1,2-dicarboxylate

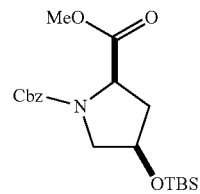 [SMILES: COC(=O)[C@H]1C[C@@H](O[Si](C)(C)C(C)(C)C)CN1C(=O)OCc1ccccc1]

(2R,4R)-1-benzyl 2-methyl 4-hydroxypyrrolidine-1,2-dicarboxylate (1.04 g, 3.72 mmol) was added to DCM (18.62 ml) following by adding imidazole (0.507 g, 7.45 mmol) and TBSCl (0.730 g, 4.84 mmol). A white suspension formed. After 12 h at RT, LCMS showed complete consumption of starting material. Partitioned between 30 mL EtOAc and 20 mL H₂O and separated the resulting layers. The aqueous layer was back-extracted with 3×10 mL EtOAc. The combined organics were dried over Na₂SO₄, filtered and concentrated in vacuo to give a pale yellow oil. Purification by normal-phase HPLC (80 g CombiFlash column, 0-30% EtOAc:Hex) gave (2R,4R)-1-benzyl 2-methyl 4-((tert-butyldimethylsilyl)oxy)pyrrolidine-1,2-dicarboxylate as thick, colorless oil.

LC/MS: m/z 394.0 (M+H)⁺, 1.36 min (ret. time).

D70

(2R,4R)-Benzyl 4-((tert-butyldimethylsilyl)oxy)-2-(hydroxymethyl)pyrrolidine-1-carboxylate

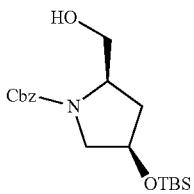 [SMILES: CC(C)(C)[Si](C)(C)O[C@@H]1C[C@H](CO)N(C(=O)OCc2ccccc2)C1]

Dissolved (2R,4R)-1-benzyl 2-methyl 4-((tert-butyldimethylsilyl)oxy)pyrrolidine-1,2-dicarboxylate (1.33 g, 3.38 mmol) in THF (16.90 ml) and cooled to 0° C. Added DIBAL-H (1.5M in toluene) (1.923 g, 13.52 mmol) dropwise. The reaction was carried out for 1.5 hours. The reaction mixture was quenched by adding to 100 mL saturated Rochelle salts at RT, stirred for 16 h. The reaction mixture was partitioned with 20 mL EtOAc, separated layers, and back-extracted aqueous with 3×5 mL EtOAc. The combined organics was dried over Na₂SO₄, filtered and concentrated in vacuo to give a clear, colorless oil. The crude material was dissolved in 2 mL DCM and purified by normal-phase HPLC (40 g CombiFlash column, 0-50% EtOAc:Hex) to give (2R,4R)-benzyl 4-((tert-butyldimethylsilyl)oxy)-2-(hydroxymethyl)pyrrolidine-1-carboxylate as a thick, colorless oil.

LC/MS: m/z 366.1 (M+H)⁺, 1.27 min (ret. time).

D71

((2R,4R)-4-((tert-Butyldimethylsilyl)oxy)pyrrolidin-2-yl)methanol

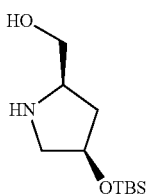 [SMILES: CC(C)(C)[Si](C)(C)O[C@H]1CN[C@@H](CO)C1]

Palladium on carbon (167 mg, 0.157 mmol) was added to (2R,4R)-Benzyl 4-((tert-butyldimethylsilyl)oxy)-2-(hydroxymethyl)pyrrolidine-1-carboxylate (574.3 mg, 1.571 mmol) under N₂. Anhydrous methanol (7856 µl) was added, evacuated under vacuum and back-filled with H₂ (balloon, atmospheric pressure) for three times. The reaction mixture was allowed to stir under H₂ at RT. After 3 h, the mixture was filtered through Celite, and washed with MeOH and concentrated to give the title compound as orange oil.

LC/MS: m/z 232.0 (M+H)⁺, 0.71 min (ret. time).

D72

((2R,4R)-4-((tert-Butyldimethylsilyl)oxy)-1-(2,6-dichloropyrimidin-4-yl)pyrrolidin-2-yl)methanol

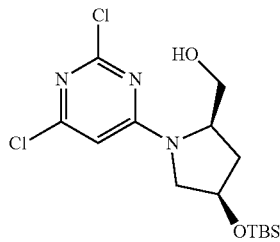 [SMILES: CC(C)(C)[Si](C)(C)O[C@@H]1C[C@H](CO)N(c2cc(Cl)nc(Cl)n2)C1]

A solution of ((2R,4R)-4-((tert-Butyldimethylsilyl)oxy)pyrrolidin-2-yl)methanol (364 mg, 1.573 mmol) and TEA (658 µl, 4.72 mmol) in tetrahydrofuran (THF) (3513 µl) was added dropwise via cannula to a solution of 2,4,6-trichloropyrimidine (181 µl, 1.573 mmol) in THF (3513 µl) at −78° C. The reaction was allowed to gradually warm to RT. After 14 h, the mixture was partitioned between 20 mL EtOAc and 10 mL saturated NaHCO₃. The aqueous layer was back-extracted with 3×5 mL EtOAc. The combined organics were dried over Na₂SO₄, filtered and concentrated. The crude was purified by normal-phase HPLC (24 g CombiFlash column, 0-30% EtOAc:Hex) to give the title compound as an off-white solid.

LC/MS: m/z 380.0 (M+H)⁺, 1.29 min (ret. time).

D73

(7R,8aR)-7-((tert-Butyldimethylsilyl)oxy)-3-chloro-7,8,8a,9 tetrahydropyrrolo[1,2':3,4]imidazo[1,2-c]pyrimidin-1(6H)-one

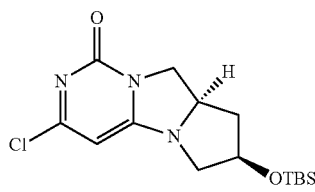 [SMILES: CC(C)(C)[Si](C)(C)O[C@@H]1C[C@@H]2Cn3c(cc(Cl)nc3=O)N2C1]

A solution of ((2R,4R)-4-((tert-Butyldimethylsilyl)oxy)-1-(2,6-dichloropyrimidin-4-yl)pyrrolidin-2-yl)methanol (458.7 mg, 1.212 mmol) in DCM (5497 µl) was treated with TEA (845 µl, 6.06 mmol) at RT. MsCl (283 µl, 3.64 mmol) was subsequently added dropwise. After 20 min at RT, the mixture was concentrated in vacuo and the resulting solid was suspended in acetonitrile (5497 µl). K₂CO₃ (503 mg, 3.64 mmol) was added and the resulting suspension was heated to 80° C. The mixture was then partitioned the reaction mixture between 20 mL EtOAc and 15 mL saturated NaHCO₃. The aqueous layer was back-extracted with 3×8 mL EtOAc. The combined organics were dried over Na₂SO₄, filtered and concentrated. The crude was purified by CombiFlash (2.4 g, 0-100% EtOAc:Hex) to give the title compound as a white solid.

LC/MS: m/z 342.0 (M+H)⁺, 0.97 min (ret. time).

D74 tert-Butyl ((3S,5R)-1-(2,6-dichloropyrimidin-4-yl)-5-(hydroxymethyl)pyrrolidin-3-yl)carbamate

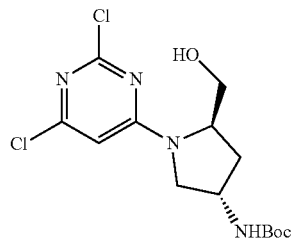 [SMILES: CC(C)(C)OC(=O)N[C@H]1C[C@H](CO)N(c2cc(Cl)nc(Cl)n2)C1]

A solution of tert-butyl ((3S,5R)-5-(hydroxymethyl)pyrrolidin-3-yl)carbamate hydrochloride (250 mg, 0.989 mmol) and TEA (1103 µl, 7.91 mmol) in THF (1847 µl) was added dropwise via syringe to a solution of 2,4,6-trichloropyrimidine (148 µl, 1.286 mmol) in THF (1847 µl) at −78° C. The reaction was allowed to gradually warm to RT and stirred for 30 min. The mixture was partitioned with 10 mL EtOAc and 5 mL saturated NaHCO₃ and the resulting layers were separated. The aqueous layer was back-extracted with 3×5 mL EtOAc. The combined organics were dried Na₂SO₄, filtered and concentrated. The crude was purification by normal-phase HPLC (24 g CombiFlash column, 0-50% EtOAc:Hex) to give the title compound as a white solid.

LC/MS: m/z 362.9 (M+H)⁺, 0.88 min (ret. time).

D75 tert-Butyl ((7S,8aR)-3-chloro-1-oxo-1,6,7,8,8a,9-hexahydropyrrolo[1,2':3,4]imidazo[1,2-c]pyrimidin-7-yl)carbamate

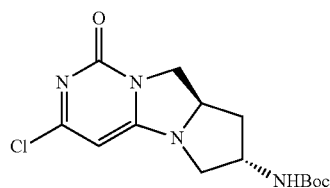 [SMILES: CC(C)(C)OC(=O)N[C@H]1C[C@@H]2Cn3c(cc(Cl)nc3=O)N2C1]

A solution of tert-Butyl ((3S,5R)-1-(2,6-dichloropyrimidin-4-yl)-5-(hydroxymethyl)pyrrolidin-3-yl)carbamate (195.9 mg, 0.539 mmol) in DCM (2446 µl) was treated with TEA (376 µl, 2.70 mmol). The resulting reaction mixture was subsequently cooled to 0° C. and MsCl (126 µl, 1.618 mmol) was added dropwise. The reaction was allowed to gradually warm to RT and stirred for 20 min. The mixture was concentrated and suspended in acetonitrile (2446 µl). The resulting suspension was treated with K₂CO₃ (224 mg, 1.618 mmol) and heated to 80° C. After 14 hrs, the reaction contents were partitioned between 15 mL EtOAc and 10 mL saturated NaHCO₃. The aqueous layer was back-extracted with 3×5 mL EtOAc. The combined organics were dried over Na₂SO₄, filtered and concentrated. The crude was purification by normal-phase HPLC (12 g CombiFlash column, 0-5% MeOH: DCM) to give the title compound as a white solid.

LC/MS: m/z 327.0 (M+H)⁺, 0.67 min (ret. time).

D76

3-(Benzyloxy)-5-(trifluoromethyl)pyridine

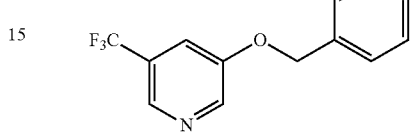

To a mixture of NaH (159 mg, 6.61 mmol) in DMF (5 mL) was added phenylmethanol (477 mg, 4.41 mmol). The solution was stirred at room temperature for 15 min and then 3-chloro-5-(trifluoromethyl)pyridine (800 mg, 4.41 mmol) was added in portion. The mixture was stirred at room temperature for another 3 hrs. After added 20 mL water, the mixture was extracted by EA (15 mL×3), washed with brine (20 mL×2) and dried to give the title compound (600 mg, 0.867 mmol, 19.67% yield).

LC-MS (ESI): m/z 254[M+H]⁺; 1.48 min (ret time).

D77

5-(Trifluoromethyl)pyridin-3-ol

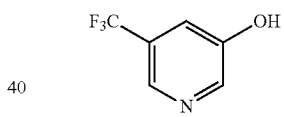

A mixture of 3-(benzyloxy)-5-(trifluoromethyl)pyridine (600 mg, 2.369 mmol) and Pd/C (252 mg, 0.2369 mmol, 10% wt) in methanol (5 mL) was stirred under hydrogen for 3 hrs. After filtration, the title compound (300 mg, 0.727 mmol, 30.7% yield) was obtained without further purification.

LC-MS (ESI): m/z 162[M−H]⁺; 1.30 min (ret time).

D78

5-Formyl-2-((5-(trifluoromethyl)pyridin-3-yl)oxy)benzonitrile

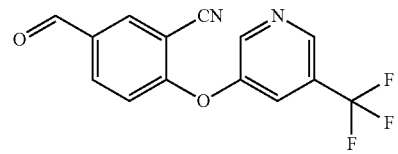 [SMILES: N#Cc1cc(C=O)ccc1Oc1cncc(C(F)(F)F)c1]

A mixture of 5-(trifluoromethyl)pyridin-3-ol (300 mg, 1.839 mmol), 2-fluoro-5 formylbenzonitrile (274 mg, 1.839 mmol) and K₂CO₃ (508 mg, 3.68 mmol) in NMP (2 mL) was put in a vessel. The reaction vessel was sealed and heated in CEM Discover (microwave) to 120° C. for 1 hr. After cooling the reaction, the mixture was filtered off. After removing the solvent under vacuo, the product gained without further purification was used for nest step directly.

LC-MS (ESI): m/z 293[M+H]$^+$; 1.64 min (ret time).

D79

5-(Hydroxymethyl)-2-((5-(trifluoromethyl)pyridin-3-yl)oxy)benzonitrile

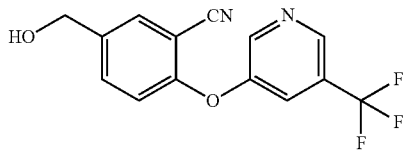 [SMILES: N#Cc1cc(CO)ccc1Oc1cncc(C(F)(F)F)c1]

To a stirring solution of 5-formyl-2-((5-(trifluoromethyl)pyridin-3-yl)oxy)benzonitrile (220 mg, 0.753 mmol) in methanol (15 mL) was added NaBH$_4$ (57.0 mg, 1.506 mmol) in a portion. The reaction mixture was kept stirring at room temperature for 3 hrs. Then acetone (5 mL) was added to quench this reaction. After removing all the solvent under vacuo, silica gel chromatography was set up for purification using EA/PE=1:1 as elute to give the title compound (120 mg, 0.328 mmol, 43.5% yield) as yellow oil.

LC-MS (ESI): m/z 293[M−H]$^+$; 1.23 min (ret time).

D80

2-Chloro-5-(2-fluoro-4-formylphenoxy)benzonitrile

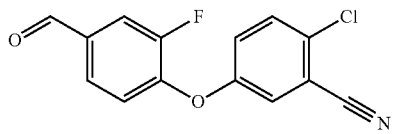 [SMILES: N#Cc1cc(Oc2ccc(C=O)cc2F)ccc1Cl]

To a solution of 2-chloro-5-hydroxybenzonitrile (2 g, 13.02 mmol) in DMF (30 mL) was added 3,4-difluorobenzaldehyde (1.851 g, 13.02 mmol) and K$_2$CO$_3$ (3.60 g, 26.0 mmol). The mixture was then stirred at 100° C. for 16 hrs. After cooled to room temperature, the mixture was concentrated and the crude was purified by pre-TLC eluting with 25% EtOAc in petroleum ether to give the title compound (130 mg, 0.472 mmol, 3.62% yield).

LC-MS (ESI): m/z 276[M+H]$^+$; 1.22 min (ret time).

D81

2-Chloro-5-(2-fluoro-4-(hydroxymethyl)phenoxy)benzonitrile

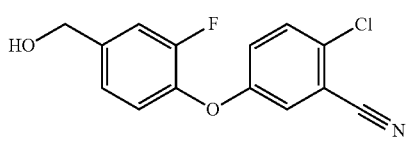 [SMILES: N#Cc1cc(Oc2ccc(CO)cc2F)ccc1Cl]

The title compound was prepared by a procedure similar to that described for D79 starting from 2-chloro-5-(2-fluoro-4-formylphenoxy)benzonitrile (5.9 g, 21.40 mmol).

LC-MS (ESI): m/z 278[M+H]$^+$; 1.65 min (ret time).

D82

5-Formyl-2-{[3-(trifluoromethyl)phenyl]oxy}benzonitrile

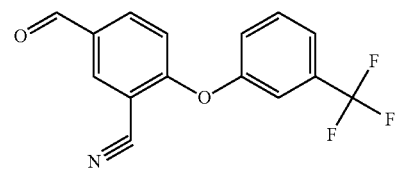 [SMILES: N#Cc1cc(C=O)ccc1Oc1cccc(C(F)(F)F)c1]

To a solution of 2-fluoro-5-formyl-benzonitrile (2.0 g, 13.41 mmol) and 3-trifluoromethyl-phenol (1.63 mL, 13.41 mmol) in DMF (10 mL) was added potassium carbonate (1.85 g, 13.41 mmol). The reaction mixture was stirred at 60° C. for 2 hrs under microwave. The resultant mixture was filtrated, concentrated and the crude was purification via FC to give the title compound (3 g, 73% yield) as a white solid.

LC-MS (ESI): m/z 292[M+H]$^+$; 3.38 min (ret time).

D83

5-(Hydroxymethyl)-2-{[3-(trifluoromethyl)phenyl]oxy}benzonitrile

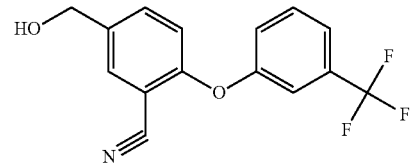 [SMILES: N#Cc1cc(CO)ccc1Oc1cccc(C(F)(F)F)c1]

To a solution of 5-formyl-2-{[3-(trifluoromethyl)phenyl]oxy}benzonitrile (5 g, 17.17 mmol) in methanol (30 mL) at 0° C. was added NaBH$_4$ (0.39 g, 10.30 mmol). The mixture was then stirred at room temperature for 30 min. The reaction mixture was quenched with acetone and concentrated. The crude was purification via ISCO system (DCM/MeOH: 20/1) to give the title compound (5.5 g) as clear oil.

LC-MS (ESI): m/z 294[M+H]$^+$; 3.09 min (ret time).

$^1$H NMR (400 MHz, CDCl$_3$): δ 7.72 (s, 1H), 7.5 (m, 3H), 7.32 (s, 1H), 7.25 (s, 1H), 6.92 (d, J=8.8 Hz, 1H), 4.72 (s, 2H).

D84

(3,4-Difluoro-5-methylphenyl)methanol

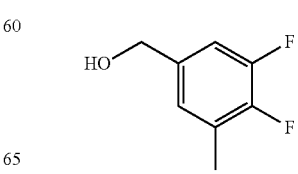

To the solution of 3,4-difluoro-5-methylbenzaldehyde (70 mg, 0.448 mmol) in methanol (2 mL) was added NaBH$_4$ (25.4 mg, 0.673 mmol). The solution was stirred at room temperature for 30 min. The reaction mixture was diluted with water and extracted with EA. The organic phase was washed with brine, driver over Na$_2$SO$_4$, filtrated and evaporated in vacuo to give the title compound (35 mg, 0.221 mmol, 49.4% yield) as white solid.

D85

3-Fluoro-5-(hydroxymethyl)benzonitrile

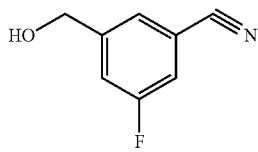 [SMILES: N#Cc1cc(F)cc(CO)c1]

To a solution of 3-cyano-5-fluorobenzoic acid (3 g, 18.17 mmol) in tetrahydrofuran (THF) (60 mL) was added CDI (4.42 g, 27.3 mmol) at 0° C., after added, the mixture was stirred at 23° C. for 30 min, the cooled to 0° C. again, was added sodium borohydride (1.375 g, 36.3 mmol) drop wise, then which was stirred at 23° C. for 16 hrs, quenched with saturated NH$_4$Cl aqueous, filtered, dried over Na$_2$SO$_4$, concentrated to give crude, which was purified by flash column (PE:EA=10:1) to give the target.

LC-MS (ESI): m/z 152 [M+H]$^+$; 0.97 min (ret time).

$^1$H NMR (400 MHz, MeOD): δ 7.53 (m, 1H), 7.41 (m, 2H), 4.64 (d, 2H).

D86

(3-Chloro-4,5-difluorophenyl)methanol

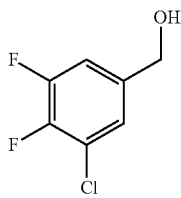 [SMILES: OCc1cc(F)c(F)c(Cl)c1]

A mixture of 3-chloro-4,5-difluorobenzoic acid (0.750 g, 3.90 mmol) and CDI (0.695 g, 4.28 mmol) in THF (10 mL) was stirred under nitrogen at room temp for 1 h. Then a solution of NaBH$_4$ (0.221 g, 5.84 mmol) in water (2.0 mL) was added drop wise. The reaction mixture was stirred at 10° C. for 16 hrs, adjusted to pH=1 with 1 M HCl solution, concentrated to remove THF, and extracted with ethyl acetate. The organic part was washed with a solution of NaHCO$_3$ and concentrated. Purification via preparative TLC afforded the title product.

LC-MS (ESI): m/z 179 [M+H]$^+$; 1.10 min (ret time).

$^1$H NMR (400 MHz, CDCl$_3$): δ 7.15-7.13 (m, 1H), 7.11-7.04 (m, 2H), 4.63-4.56 (t, 2H), 2.57 (s, 1H).

D87

3-Fluoro-4-((2-(trifluoromethyl)pyridin-4-yl)oxy)benzaldehyde

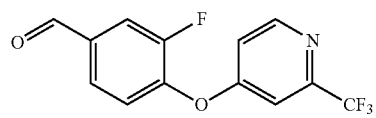

The title compound was prepared by a procedure similar to that described for D80 starting from 3,4-difluorobenzaldehyde and 2-(trifluoromethyl)pyridin-4-ol.

LC-MS (ESI): m/z 286 [M+H]$^+$; 0.81 min (ret time).

D88

3-Fluoro-4-((2-(trifluoromethyl)pyridin-4-yl)oxy)phenyl)methanol

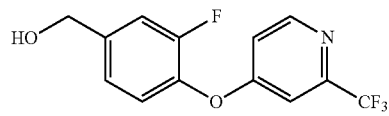

The title compound was prepared by a procedure similar to that described for D79 starting from 3-fluoro-4-((2-(trifluoromethyl)pyridin-4-yl)oxy)benzaldehyde.

LC-MS (ESI): m/z 288 [M+H]$^+$; 0.76 min (ret time).

D89

4-(3,4-Difluorophenoxy)-3-fluorobenzaldehyde

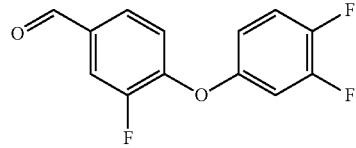 [SMILES: O=Cc1ccc(Oc2ccc(F)c(F)c2)c(F)c1]

A mixture of 3,4-difluorobenzaldehyde (400 mg, 2.81 mmol), 3,4-difluorophenol (366 mg, 2.81 mmol) and K$_2$CO$_3$ (778 mg, 5.63 mmol) was put in a vessel. The reaction vessel was sealed and heated in CEM Discover using initial normal to 120° C. for 1 hr. After cooling the reaction, the mixture was filtered off. After removing the solvent under vacuo, the product gained without further purification was used for nest step directly.

LC-MS (ESI): m/z 252 [M+H]$^+$; 1.72 min (ret time).

D90

(4-(3,4-Difluorophenoxy)-3-fluorophenyl)methanol

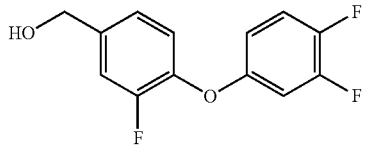 [SMILES: OCc1ccc(Oc2ccc(F)c(F)c2)c(F)c1]

To a stirring solution of 4-(3,4-difluorophenoxy)-3-fluorobenzaldehyde (220 mg, 0.872 mmol) in methanol (15 mL) was added NaBH$_4$ (33.0 mg, 0.872 mmol) in a portion. The reaction mixture was kept stirring at r.t. for 3 hrs. Then acetone (5 mL) was added to quench this reaction. After removing all the solvent under vacuo, silica gel chromatography was set up for purification using EA/PE=1:1 as elute to get (4-(3,4-difluorophenoxy)-3-fluorophenyl)methanol (100 mg, 0.263 mmol, 30.1% yield) as yellow oil.

LC-MS (ESI): m/z 253 [M−H]$^+$; 1.68 min (ret time).

D91

2-(3,4-Difluorophenoxy)-5-formylbenzonitrile

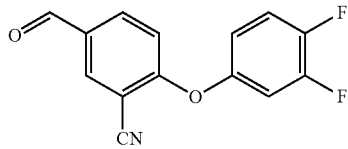 [SMILES: N#Cc1cc(C=O)ccc1Oc1ccc(F)c(F)c1]

A mixture of 2-fluoro-5-formylbenzonitrile (300 mg, 2.012 mmol), 3,4-difluorophenol (288 mg, 2.213 mmol) and potassium carbonate (556 mg, 4.02 mmol) was put in a vessel. The reaction vessel was sealed and heated in CEM Discover using initial normal to 120° C. for 1 hr. After cooling the reaction, the mixture was filtered off. After removing the solvent under vacuo, the product gained without further purification was used for nest step directly.

LC-MS (ESI): m/z 260 [M+H]$^+$; 1.47 min (ret time).

D92

2-(3,4-Difluorophenoxy)-5-(hydroxymethyl)benzonitrile

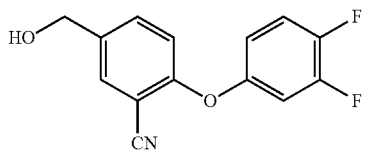 [SMILES: N#Cc1cc(CO)ccc1Oc1ccc(F)c(F)c1]

To a stirring solution of 2-(3,4-difluorophenoxy)-5-formylbenzonitrile (400 mg, 1.543 mmol) in methanol (12 mL) was added NaBH$_4$ (58.4 mg, 1.543 mmol) in a portion. The reaction mixture was kept stirring at r.t. for 3 h. Then acetone (5 mL) was added to quench this reaction. After removing all the solvent under vacuo, silica gel chromatography was set up for purification using EA/PE=1:1 as elute to get 2-(3,4-difluorophenoxy)-5-(hydroxymethyl)benzonitrile (300 mg, 1.100 mmol, 71.3% yield) as yellow oil.

LC-MS (ESI): m/z 260 [M−H]$^+$; 1.62 min (ret time).

D93

2-Chloro-4-(2-cyano-4-formylphenoxy)benzonitrile

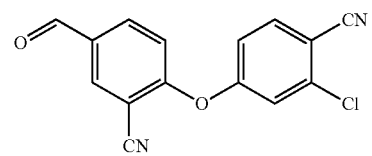 [SMILES: N#Cc1ccc(Oc2ccc(C=O)cc2C#N)cc1Cl]

The title compound was prepared by a procedure similar to that described for D80 starting from 2-fluoro-5-formylbenzonitrile and 2-chloro-4-hydroxybenzonitrile.

LC-MS (ESI): m/z 283 [M+H]$^+$; 3.07 min (ret time)

D94

2-Chloro-4-(2-cyano-4-(hydroxymethyl)phenoxy)benzonitrile

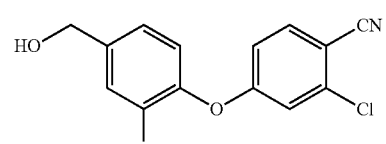

The title compound was prepared by a procedure similar to that described for D79 starting from 2-chloro-4-(2-cyano-4-formylphenoxy)benzonitrile.

LC-MS (ESI): m/z 285 [M+H]$^+$; 2.79 min (ret time)

D95

7-((3,5-Difluoro-4-((5-(trifluoromethyl)pyridin-3-yl)oxy)benzyl)oxy)-1-methyl-2,3-dihydroimidazo[1,2-c]pyrimidin-5(1H)-one

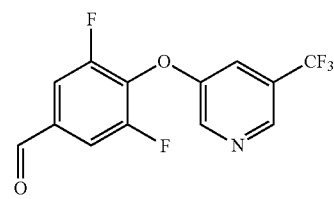 [SMILES: O=Cc1cc(F)c(Oc2cncc(C(F)(F)F)c2)c(F)c1]

The title compound was prepared by a procedure similar to that described for D80 starting from 5-(trifluoromethyl)pyridin-3-ol and 3,4,5-trifluorobenzaldehyde.

LC-MS (ESI): m/z 303 [M+H]$^+$; 1.22 (ret time).

D96

(3,5-Difluoro-4-((5-(trifluoromethyl)pyridin-3-yl)oxy)phenyl)methanol

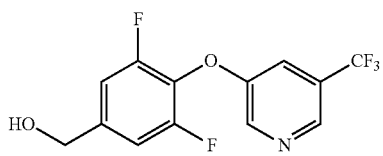 [SMILES: OCc1cc(F)c(Oc2cncc(C(F)(F)F)c2)c(F)c1]

The title compound was prepared by a procedure similar to that described for D79 starting from 3,5-difluoro-4-((5-(trifluoromethyl)pyridin-3-yl)oxy)benzaldehyde.

LC-MS (ESI): m/z 306 [M+H]$^+$; 0.93 (ret time).

D97

3-Fluoro-4-((6-(trifluoromethyl)pyridin-3-yl)oxy)benzaldehyde

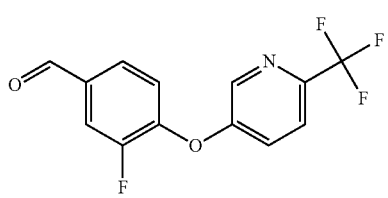 [SMILES: O=Cc1ccc(Oc2ccc(C(F)(F)F)nc2)c(F)c1]

To the solution of 3,4-difluorobenzaldehyde (500 mg, 3.52 mmol) and 6-(trifluoromethyl)pyridin-3-ol (574 mg, 3.52 mmol) in acetonitrile (10 ml), was added K$_2$CO$_3$ (729 mg, 5.28 mmol). The reaction mixture was sealed and heated in Biotage Initiator using initial normal to 130° C. for 4 h. After cooling the reaction, the reaction mixture was filtrated and evaporated in vacuo to give 3-fluoro-4-((6-(trifluoromethyl)pyridin-3-yl)oxy)benzaldehyde (903 mg, 3.17 mmol, 90% yield) as brown solid.

D98

(3-Fluoro-4-((6-(trifluoromethyl)pyridin-3-yl)oxy)phenyl)methanol

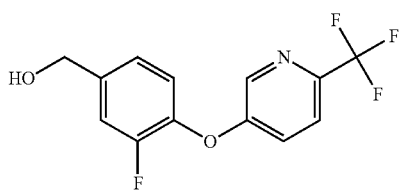 [SMILES: OCc1ccc(Oc2ccc(C(F)(F)F)nc2)c(F)c1]

To the solution of 3-fluoro-4-((6-(trifluoromethyl)pyridin-3-yl)oxy)benzaldehyde (900 mg, 3.16 mmol) in methanol (12 ml), was added NaBH$_4$ (179 mg, 4.73 mmol). The solution was stirred at rt for 10 min. The reaction mixture was partition between water and EA. The organic phase was washed with brine, dried over Na$_2$SO$_4$ and evaporated in vacuo to give crude product (3-fluoro-4-((6-(trifluoromethyl)pyridin-3-yl)oxy)phenyl)methanol (480 mg, 1.671 mmol, 53.0% yield) as black oil.

LC-MS (ESI): m/z 288 [M+H]$^+$; 2.88 min (ret time).

D99

5-Formyl-2-(4-(trifluoromethyl)phenoxy)benzonitrile

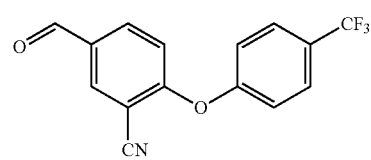 [SMILES: N#Cc1cc(C=O)ccc1Oc1ccc(C(F)(F)F)cc1]

The title compound was prepared by a procedure similar to that described for D80 starting from 2-fluoro-5-formylbenzonitrile and 4-(trifluoromethyl)phenol.

LC-MS (ESI): m/z 292 [M+H]$^+$; 3.41 min (ret time).

D100

5-(Hydroxymethyl)-2-(4-(trifluoromethyl)phenoxy)benzonitrile

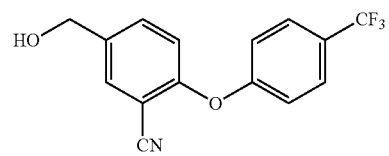 [SMILES: N#Cc1cc(CO)ccc1Oc1ccc(C(F)(F)F)cc1]

The title compound was prepared by a procedure similar to that described for D79 starting from 5-(hydroxymethyl)-2-(4-(trifluoromethyl)phenoxy)benzonitrile.

LC-MS (ESI): m/z 294 [M+H]$^+$; 3.13 min (ret time).

D101

2-(4-Chloro-3-fluorophenoxy)-5-formylbenzonitrile

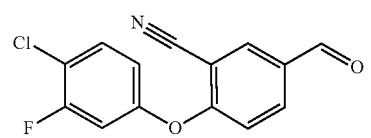 [SMILES: N#Cc1cc(C=O)ccc1Oc1ccc(Cl)c(F)c1]

The title compound was prepared by a procedure similar to that described for D80 starting from 2-fluoro-5-formylbenzonitrile and 4-chloro-3-fluorophenol.

LC-MS (ESI): m/z 276 [M+H]$^+$; 3.33 min (ret time)

D102

2-(4-Chloro-3-fluorophenoxy)-5-(hydroxymethyl)benzonitrile

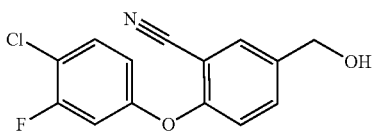 [SMILES: N#Cc1cc(CO)ccc1Oc1ccc(Cl)c(F)c1]

The title compound was prepared by a procedure similar to that described for D79 starting from 2-(3-chloro-4-fluorophenoxy)-5-formylbenzonitrile.

LC-MS (ESI): m/z 278 [M+H]$^+$; 3.02 min (ret time)

D103

3,5-Difluoro-4-((6-(trifluoromethyl)pyridin-3-yl)oxy)benzaldehyde

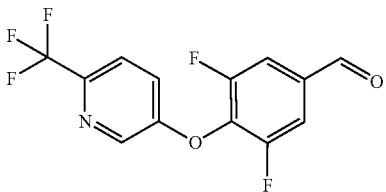 [SMILES: O=Cc1cc(F)c(Oc2ccc(C(F)(F)F)nc2)c(F)c1]

The title compound was prepared by a procedure similar to that described for D80 starting from 2,4,5-trifluorobenzaldehyde and 6-(trifluoromethyl) pyridin-3-ol.

LC-MS (ESI): m/z 304 [M+H]$^+$; 3.29 min (ret time).

D104

(3,5-Difluoro-4-((6-(trifluoromethyl)pyridin-3-yl)oxy)phenyl)methanol

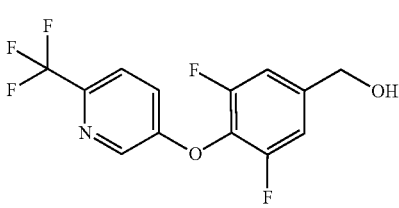 [SMILES: OCc1cc(F)c(Oc2ccc(C(F)(F)F)nc2)c(F)c1]

The title compound was prepared by a procedure similar to that described for D79 starting 3,5-difluoro-4-((6-(trifluoromethyl)pyridin-3-yl)oxy)benzaldehyde.

LC-MS (ESI): m/z 306 [M+H]$^+$; 3.03 min (ret time)

D105

4-((2-Chloropyridin-4-yl)oxy)-3,5-difluorobenzaldehyde

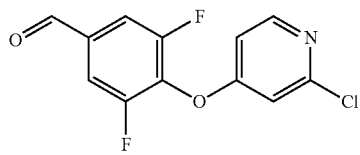 [SMILES: O=Cc1cc(F)c(Oc2ccnc(Cl)c2)c(F)c1]

A mixture of 3,4,5-trifluorobenzaldehyde (500 mg, 3.12 mmol), 2-chloropyridin-4-ol (405 mg, 3.12 mmol) and K$_2$CO$_3$ (647 mg, 4.68 mmol) in acetonitrile (10 mL) was sealed in a microwave vial and irradiated with a microwave using initial normal to 130° C. for 1 h, then filtered and concentrated to give the crude as brown oil.

LCMS (ESI): m/z 270 [M+H]$^+$; 3.02 min (ret time)

D106

(4-((2-Chloropyridin-4-yl)oxyl-3,5-difluorophenyl)methanol

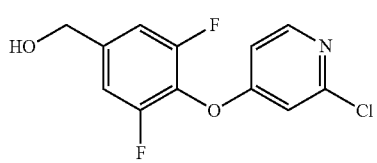 [SMILES: OCc1cc(F)c(Oc2ccnc(Cl)c2)c(F)c1]

To a solution of 4-((2-chloropyridin-4-yl)oxy)-3,5-difluorobenzaldehyde (746 mg, 2.77 mmol) in methanol (8 mL) was added NaBH$_4$ (157 mg, 4.15 mmol). The reaction mixture was stirred at rt for 10 min., and partitioned between water and ethyl acetate. Organic part was washed with brine, dried over anhydrous Na$_2$SO$_4$ and evaporated in vacuo to give the crude as brown oil.

LCMS (ESI): m/z 272 [M+H]$^+$; 2.69 min (ret time)

D107

3-(2-Fluoro-4-formylphenoxy)-5-(trifluoromethyl)benzonitrile

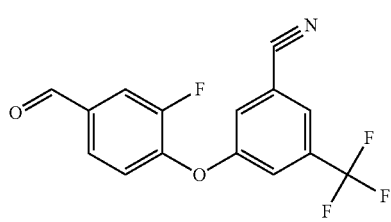 [SMILES: N#Cc1cc(Oc2ccc(C=O)cc2F)cc(C(F)(F)F)c1]

To the solution of 3,4-difluorobenzaldehyde (150 mg, 1.056 mmol) and 3-hydroxy-5-(trifluoromethyl)benzonitrile (198 mg, 1.056 mmol) in acetonitrile (3 ml) was added K$_2$CO$_3$ (219 mg, 1.583 mmol). The reaction mixture was sealed and heated in Biotage Initiator using under 130° C. for 1 h. After cooling the reaction, the reaction mixture was filtrated and evaporated in vacuo to give 3-(2-fluoro-4-formylphenoxy)-5-(trifluoromethyl)benzonitrile (294 mg, 0.950 mmol, 90% yield) as brown oil.

D108

3-(2-Fluoro-4-(hydroxymethyl)phenoxy)-5-(trifluoromethyl)benzonitrile

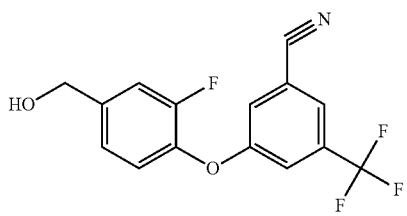 [SMILES: N#Cc1cc(Oc2ccc(CO)cc2F)cc(C(F)(F)F)c1]

To the solution of 3-(2-fluoro-4-formylphenoxy)-5-(trifluoromethyl)benzonitrile (290 mg, 0.938 mmol) in methanol (4 ml), was added NaBH$_4$ (53.2 mg, 1.407 mmol). The solution was stirred at rt for 10 min. The reaction mixture was partition between water and EA. The organic phase was washed with brine, dried over Na$_2$SO$_4$ and evaporated in vacuo to give crude product 3-(2-fluoro-4-(hydroxymethyl)phenoxy)-5-(trifluoromethyl)benzonitrile (280 mg, 0.900 mmol, 96% yield) as brown oil.

D109

3,5-Difluoro-4-((2-(trifluoromethyl)pyridin-4-yl)oxy)benzaldehyde

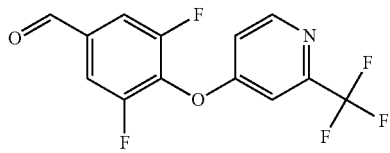 [SMILES: O=Cc1cc(F)c(Oc2ccnc(C(F)(F)F)c2)c(F)c1]

To a solution of 2-(trifluoromethyl)pyridin-4-ol (1.019 g, 6.25 mmol) and K$_2$CO$_3$ (1.727 g, 12.49 mmol) in acetonitrile (250 mL) stirred under nitrogen at 20° C. was added a solution of 3,4,5-trifluorobenzaldehyde (1 g, 6.25 mmol) in acetonitrile (50 mL) dropwise during 5 min. The reaction mixture was stirred at 70° C. for 18 hrs. The reaction mixture was diluted with ethyl acetate (20 mL) and the organic phase was washed with water (2×20 mL), saturated brine (20 mL), dried over sodium sulphate and evaporated in vacuo to give the title compound (2.0 g, 6.02 mmol, 96% yield) as a brown gum.

LC-MS (ESI): m/z 304 [M+H]$^+$; 3.64 min (ret time).

An alternative process of preparing the compound is provided: To a solution of 3,4,5-trifluorobenzaldehyde (2356 mg, 14.72 mmol) and 2-(trifluoromethyl)pyridin-4-ol (2000 mg, 12.26 mmol) in N,N-dimethylformamide (6 mL), K$_2$CO$_3$ (3390 mg, 24.53 mmol) was added. The mixture was irradiated with a microwave at 110° C. and stirred for 3 h, and concentrated. The crude product was washed with EtOAc, and then filtered. The organic phase was concentrated to afford the title compound (4 g, 6.86 mmol, 55.9% yield) as a oil.

LC-MS (ESI): m/z 304 [M+H]$^+$; 1.06 min (ret time).

D110

(3,5-Difluoro-4-((2-(trifluoromethyl)pyridin-4-yl)oxy)phenyl)methanol

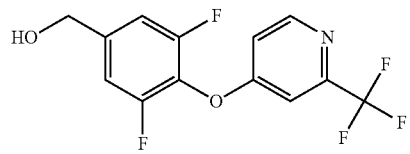 [SMILES: OCc1cc(F)c(Oc2ccnc(C(F)(F)F)c2)c(F)c1]

To a solution of 3,5-difluoro-4-((2-(trifluoromethyl)pyridin-4-yl)oxy)benzaldehyde (50 g, 165 mmol) in methanol (400 mL) was added NaBH$_4$ (3.12 g, 82 mmol) at 0° C. for 10 min. The reaction progress was monitored by TLC and mobile phase was 30% EtOAc in PE. The reaction mixture was quenched with ice water (200 mL) and evaporated under reduced pressure to remove methanol and crude was diluted with ethyl acetate (200 mL) and water (200 mL), organic layer was separated and washed with brine solution (100 mL), dried over Na$_2$SO$_4$ and evaporated completely afforded crude product 50 g, washed with PE and dried to afford the title compound (45 g, 144 mmol, 88% yield) as a white solid.

LC-MS (ESI): m/z 306 [M+H]$^+$; 2.13 min (ret time).

Another exemplary process is provided as: to a solution of 3,5-difluoro-4-((2-(trifluoromethyl)pyridin-4-yl)oxy)benzaldehyde (4000 mg, 13.19 mmol) in methanol (30 mL) was added NaBH$_4$ (250 mg, 6.60 mmol) at 0° C. for 10 min in portion. The reaction mixture was stirred at 5° C. for 0.5 h, concentrated, and dissolved in water, then extracted with EtOAc. The combined organic phase was washed with brine, dried over anhydrous Na$_2$SO$_4$, filtered, and concentrated. The crude product was purified by silica gel column (PE/EtOAc 5:1 to 1:1) to afford the title compound (3900 mg, 12.61 mmol, 96% yield) as a white solid.

LC-MS (ESI): m/z 306 [M+H]$^+$; 1.65 min (ret time).

D111

3-Fluoro-4-((5-(trifluoromethyl)pyridin-3-yl)oxy)benzaldehyde

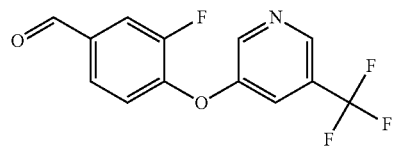 [SMILES: O=Cc1ccc(Oc2cncc(C(F)(F)F)c2)c(F)c1]

To a solution of 3,4-difluorobenzaldehyde (436 mg, 3.07 mmol) in DMF (30 mL) was added 5-(trifluoromethyl)pyridin-3-ol (500 mg, 3.07 mmol), K$_2$CO$_3$ (847 mg, 6.13 mmol) was added to the mixture, then the mixture was stirred at 100° C. for 16 hrs, concentrated to give the crude, purified by pre-TLC eluting with 25% EtOAc in petroleum ether to give the 3-fluoro-4-((5-(trifluoromethyl)pyridin-3-yl)oxy)benzaldehyde (298 mg, 1.045 mmol, 34.1% yield).

LC-MS (ESI): m/z 286 [M+H]$^+$; 1.50 min (ret time).

D112

(3-Fluoro-4-((5-(trifluoromethyl)pyridin-3-yl)oxy)phenyl)methanol

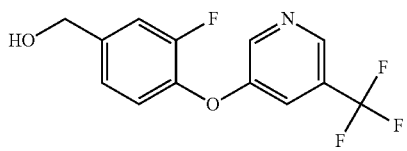 [SMILES: OCc1ccc(Oc2cncc(C(F)(F)F)c2)c(F)c1]

To a solution of 3-fluoro-4-((5-(trifluoromethyl)pyridin-3-yl)oxy)benzaldehyde (298 mg, 1.045 mmol) in methanol (5 mL) stirred under nitrogen was added solid NaBH$_4$ (44.4 mg, 1.174 mmol) portionwise at 0° C. The reaction mixture was stirred at 23° C. for 16 hrs, quenched with saturated NH$_4$Cl solution, the solution was extracted by EtOAc (3×20 mL), and the organic was dried with anhydrous Na$_2$SO$_4$, concentrated to give the target compound (3-fluoro-4-((5 (trifluoromethyl)pyridin-3-yl)oxy)phenyl)methanol (126 mg, 0.439 mmol, 42.0% yield) which was used in the next reaction without further purification.

LC-MS (ESI): m/z 288 [M+H]$^+$; 1.24 min (ret time).

D113

2-Fluoro-4-(hydroxymethyl)phenol

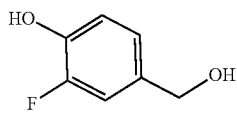

The title compound was prepared by a procedure similar to that described for D79 starting from 3-fluoro-4-hydroxybenzaldehyde.

D114

(3-Fluoro-4-((2-(trifluoromethyl) pyrimidin-5-yl)oxy) phenyl) methanol

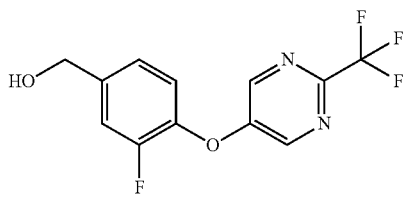 [SMILES: OCc1ccc(Oc2cnc(C(F)(F)F)nc2)c(F)c1]

The title compound was prepared by a procedure similar to that described for D80 starting from 5-bromo-2-(trifluoromethyl)pyrimidine and 2-fluoro-4-(hydroxymethyl)phenol.

LC-MS (ESI): m/z 289[M+H]$^+$; 0.99 min (ret time).

$^1$H NMR (400 MHz, CDCl$_3$): δ 8.52 (s, 2H), 7.32 (d, 1H), 7.25-7.20 (m, 2H), 4.76 (s, 2H).

D115

1-Methyl-1H-pyrazol-4-ol

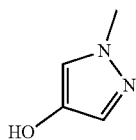

To a solution of 1-methyl-4-(4,4,5,5-tetramethyl-1,3,2-dioxaborolan-2-yl)-1H-pyrazole (100 mg, 0.481 mmol) in THF (20 mL) was added hydrogen peroxide (32.7 mg, 0.961 mmol) and sodium hydroxide (38.4 mg, 0.961 mmol) at 0° C. and stirred at this temperature for 3 min then warmed to room temperature (5° C.) for further 50 min. The reaction was diluted with water acidified with HCl (2N) and extracted four times with DCM and four times with DCM/isopropanol (4:1). The combined organic layers were dried over Na$_2$SO$_4$, filtered and concentrated to give the title compound (30 mg, 38.2% yield) as yellow oil.

$^1$H NMR (400 MHz, CDCl$_3$): δ 7.13 (s, 1H), 7.03 (s, 1H), 3.77 (s, 3H).

D116

3,5-Difluoro-4-((1-methyl-1H-pyrazol-4-yl)oxy)benzaldehyde

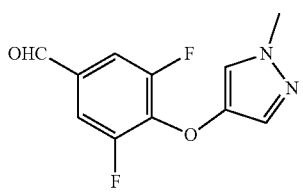 [SMILES: Cn1cc(Oc2c(F)cc(C=O)cc2F)cn1]

The mixture of 3,4,5-trifluorobenzaldehyde (1958 mg, 12.23 mmol), K$_2$CO$_3$ (2818 mg, 20.39 mmol) and 1-methyl-1H-pyrazol-4-ol (1000 mg, 10.19 mmol) in DMF (6 mL) was sealed in a tube and heated to 110° C. by microwave for 3 hrs. The reaction mixture was concentrated to get the crude product which was treated with EtOAc, the solid was filtered off and the organic phase was concentrated to give the title compound (800 mg, 26.4% yield) as oil.

LC-MS (ESI): m/z 239 [M+H]$^+$; 0.9 min (ret time).

D117

(3,5-Difluoro-4-((1-methyl-1H-pyrazol-4-yl)oxy)phenyl)methanol

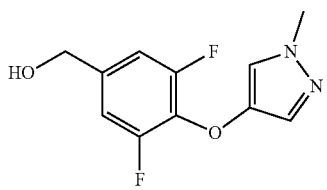 [SMILES: Cn1cc(Oc2c(F)cc(CO)cc2F)cn1]

To a solution of 3,5-difluoro-4-((1-methyl-1H-pyrazol-4-yl)oxy)benzaldehyde (800 mg, 3.36 mmol) in methanol (30 mL) was added portion wise sodium tetrahydroborate (127 mg, 3.36 mmol) at 0° C. then warm to 5° C. for 0.5 h. The solvent was removed and treated with water then extracted with ethyl acetate. Combined organic parts were washed with brine, dried over anhydrous Na$_2$SO$_4$, filtered and concentrated to get the crude product which was purified by silica gel column eluting with petroleum ether/EtOAc (5:1-1:1) to give the title compound (495 mg, 97% yield) as a white solid.

LC-MS (ESI): m/z 241 [M+H]$^+$; 1.23 min (ret time).

D118

3-Fluoro-4-((1-methyl-1Hpyrazol-4-yl) oxy) benzaldehyde

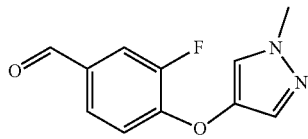 [SMILES: Cn1cc(Oc2ccc(C=O)cc2F)cn1]

The title compound was prepared by a procedure similar to that described for D116 starting from 3, 4-difluorobenzaldehyde and 1-methyl-1H-pyrazol-4-ol.

LC-MS (ESI): m/z 221 [M+H]$^+$; 1.21 min (ret time).

D119

(3-Fluoro-4-((1-methyl-1Hpyrazol-4-yl) oxy) phenyl) methanol

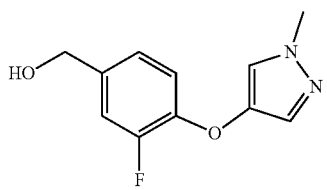 [SMILES: Cn1cc(Oc2ccc(CO)cc2F)cn1]

The title compound was prepared by a procedure similar to that described for D117 starting from 3-fluoro-4-((1-methyl-1Hpyrazol-4-yl) oxy) benzaldehyde.

LC-MS (ESI): m/z 223[M+H]$^+$; 1.17 min (ret time).

D120

1-(4-Bromo-2,6-difluorophenoxy)cyclopropanecarbaldehyde

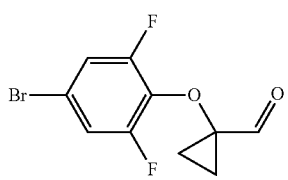 [SMILES: O=CC1(Oc2c(F)cc(Br)cc2F)CC1]

To a solution of (1-(4-bromo-2,6-difluorophenoxy)cyclopropyl)methanol (5.0 g, 18.0 mmol) in DCM (100 mL) was added Dess-Martin periodinane (11.4 g, 27.0 mmol) portionwise at 0° C. The mixture was stirred at room temperature overnight, and then diluted with DCM (100 mL). The organic phase was separated, washed with sat. NaHCO$_3$ (100 mL), sat. Na$_2$SO$_3$ (100 mL) and brine, dried over Na$_2$SO$_4$, concentrated and purified by flash chromatography column (PE/EA=40/1) to give title compound (6.8 g, 90.2%) as colorless oil.

$^1$H NMR (300 MHz, CDCl$_3$): δ 9.92 (s, 1H), 7.12 (m, 2H), 1.46 (m, 4H).

D121

5-Bromo-1,3-difluoro-2-(1-vinylcyclopropoxy)benzene

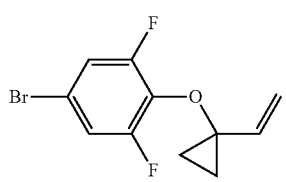

To a solution of bromo(methyl)triphenylphosphorane (2.58 g, 7.20 mmol) in THF (20 mL) was added LiN[Si(CH$_3$)$_3$]$_2$ (1 M in THF, 7.90 mL, 7.90 mmol) dropwise at −78° C. and the solution was stirred at the same temperature for 30 min. Then 1-(4-bromo-2,6-difluorophenoxy)cyclopropanecarbaldehyde (1.0 g, 3.6 mmol) in THF (2.0 mL) was added into above solution at −78° C. dropwise. The mixture was stirred at room temperature for 2 hours, quenched with water (20 mL) and the solution was separated. The aqueous was extracted with EtOAc (20 mL×2). The combined organic phases were washed with brine, dried over Na$_2$SO$_4$, filtered, concentrated and subjected to flash chromatography column (PE/EA=50/1) to give title compound (500 mg, 51%) as colorless oil.

$^1$H NMR (300 MHz, CDCl$_3$): δ 7.06 (m, 2H), 6.02 (dd, J=17.4, 10.8 Hz, 1H), 5.09 (m, 2H), 1.27 (m, 2H), 0.92 (m, 2H).

D122

2-(1-(4-Bromo-2,6-difluorophenoxy)cyclopropyl) ethanol

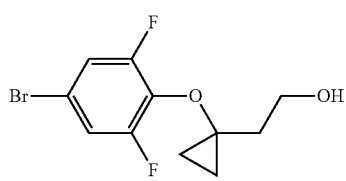 [SMILES: OCCC1(Oc2c(F)cc(Br)cc2F)CC1]

To a solution of 5-bromo-1,3-difluoro-2-(1-vinylcyclopropoxy)benzene (500 mg, 1.82 mmol) in THF (5 mL) was added 9-BBN (0.5 M in THF, 7.30 mL, 3.65 mmol) at room temperature and the solution was stirred at the same temperature for 2 hours until no starting material was detected by TLC. Aqueous NaOH solution (3.0 M, 0.91 mL, 2.73 mmol) was added into above solution, followed by H₂O₂ (30% in water, 1.1 mL, 9.1 mmol) at 0° C. The mixture was then stirred at room temperature for 1 hour, diluted with brine (20 mL) and then extracted with EtOAc (30 ml×3). The organic phase was dried over Na₂SO₄, filtered, concentrated and subjected to flash chromatography column (PE/EA=20/1 and 3/1) to give title compound (400 mg, 75%) as colorless oil.

¹H NMR (300 MHz, CDCl₃): δ 7.08 (m, 2H), 3.98 (t, J=5.7 Hz, 2H), 2.00 (t, J=5.7 Hz, 2H), 1.01 (m, 2H), 0.65 (m, 2H).

D123

2-(1-(4-Bromo-2,6-difluorophenoxy)cyclopropyl) ethyl 4-methyl benzenesulfonate

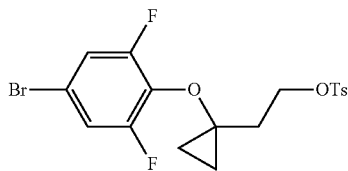 [SMILES: Cc1ccc(S(=O)(=O)OCCC2(Oc3c(F)cc(Br)cc3F)CC2)cc1]

To a solution of 2-(1-(4-bromo-2,6-difluorophenoxy)cyclopropyl)ethanol (290 mg, 1.00 mmol), Et₃N (300 mg, 3.00 mmol) and DMAP (20 mg) in DCM (5 mL) was added chloro(4-methylphenyl)sulfone (285 mg, 1.50 mmol) at 0° C. The mixture was stirred at room temperature for 2 hours. The reaction solution was diluted with DCM (30 mL) and then washed with water (30 mL), 1N HCl (30 mL) and brine, successively. The organic phase was dried over Na₂SO₄, filtered, concentrated and subjected to flash chromatography column (PE/EA=20/1) to give title compound (220 mg, 49%) as colorless oil.

¹H NMR (300 MHz, CDCl₃): δ 7.81 (d, J=8.1 Hz, 2H), 7.34 (d, J=8.1 Hz, 2H), 7.04 (m, 2H), 4.37 (d, J=7.2 Hz, 2H), 2.45 (s, 3H), 2.07 (t, J=7.2 Hz, 2H), 1.00 (m, 2H), 0.61 (m, 2H).

D124

5-Bromo-1,3-difluoro-2-(1-(2-fluoroethyl)cyclopropoxy)benzene

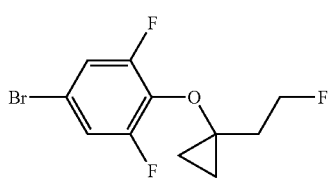 [SMILES: FCCC1(Oc2c(F)cc(Br)cc2F)CC1]

A solution of 2-(1-(4-bromo-2,6-difluorophenoxy)cyclopropyl)ethyl 4-methylbenzenesulfonate (220 mg, 0.49 mmol) and TBAF (1 M in THF, 2.5 mL, 2.5 mmol) in THF (5.0 mL) was stirred at 110° C. in a sealed vial for 3 hours. The reaction solution was diluted with EtOAc (30 mL) and then washed with 1N HCl (30 mL), brine successively. The organic layer was dried over Na₂SO₄, filtered, concentrated and purified by Prep-TLC (PE/EA=20/1) to give title compound (70 mg, 49%) as colorless oil.

¹H NMR (300 MHz, CDCl₃): δ 7.08 (m, 2H), 4.76 (dt, J=47.1, 6.3 Hz, 2H), 2.14 (dt, J=22.5, 6.3 Hz, 2H), 1.07 (m, 2H), 0.67 (m, 2H).

D125

Ethyl 3,5-difluoro-4-(1-(2-fluoroethyl)cyclopropoxy)benzoate

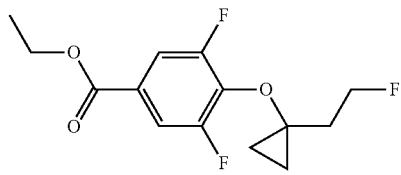 [SMILES: CCOC(=O)c1cc(F)c(OC2(CCF)CC2)c(F)c1]

A mixture of 5-bromo-1,3-difluoro-2-(1-(2-fluoroethyl)cyclopropoxy)benzene (400 mg, 1.36 mmol), KOAc (267 mg, 2.72 mmol) and Pd(dppf)Cl₂ (99 mg, 0.14 mmol) in EtOH (5 mL) was stirred at 80° C. under CO (1 atm) for 2 hours. The reaction solution was filtered. The filtrate was concentrated and subjected to flash chromatography column (PE/EA=30/1) to give the title compound (300 mg, 79.3%) as colorless oil.

¹H NMR (300 MHz, CDCl₃): δ 7.59 (m, 2H), 4.75 (dt, J=46.8, 6.0 Hz, 2H), 4.36 (q, J=6.9 Hz, 2H), 2.18 (dt, J=22.8, 6.0 Hz, 2H), 1.38 (t, J=6.9 Hz, 3H), 1.09 (m. 2H), 0.74 (m, 2H).

D126

(3,5-Difluoro-4-(1-(2-fluoroethyl)cyclopropoxy)phenyl)methanol

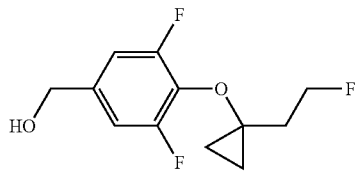 [SMILES: OCc1cc(F)c(OC2(CCF)CC2)c(F)c1]

To a solution of ethyl 3, 5-difluoro-4-(1-(2-fluoroethyl)cyclopropoxy)benzoate (310 mg, 1.10 mmol), in THF (20 mL) was added LiAlH₄ (61.0 mg, 1.64 mmol) portionwise at 0° C. The reaction mixture was stirred at 0° C. for another 1 hour. The reaction was then quenched with sat. Na₂SO₄ (10 mL) and the suspension was filtered. The filtrate was diluted with EtOAc (30 mL) and then washed with brine. The organic phase was dried over Na₂SO₄, filtered and concentrated to give the crude title compound (210 mg, 79%) as colorless oil, which was used for the next reaction without purification.

¹H NMR (300 MHz, CDCl₃): δ 6.92 (m, 2H), 4.79 (dt, J=46.8, 6.6 Hz, 2H), 2.14 (dt, J=22.5, 6.6 Hz, 2H), 1.09 (m, 2H), 0.66 (m, 2H).

D127

1-Ethyl-1H-pyrazol-4-ol

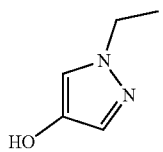

To the suspension of NaH (1.855 g, 77 mmol) in tetrahydrofuran (THF) (100 mL), a solution of 4-(4,4,5,5-tetramethyl-1,3,2-dioxaborolan-2-yl)-1H-pyrazole (10 g, 51.5 mmol) in THF (15 mL) was added dropwise at 0° C. under $N_2$ atmosphere. The result mixture was stirred for 30 minutes and then iodoethane (16.08 g, 103 mmol) was added. The result solution was stirred and left warm to room temperature overnight, filtered and the filtrate was added 15% NaOH aqueous (30 mL), then $H_2O_2$ (12 mL, 30%, 105 mmol, 2.1 eq) after the reaction mixture was cooled to 0° C. under ice-salt bath. The reaction mixture was stirred for another 1 hour then extracted with EtOAc (200 mL×2), and the water phase was acidified with concentrated HCl aqueous to pH=1-2, extracted with EtOAc (200 ml×5), the combined organic phase was washed with water 20 mL, dried over $MgSO_4$, concentrated to give the title compound (4.2 g, 72.7% yield) as yellow oil.

LC-MS (ESI): m/z 113 [M+H]$^+$; 0.45 min (ret time).

D128

4-(1-Ethyl-1H-pyrazol-4-yloxy)-3,5-difluorobenzaldehyde

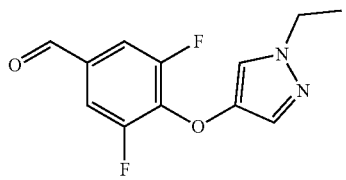 [SMILES: CCn1cc(Oc2c(F)cc(C=O)cc2F)cn1]

The reaction tube containing 3,4,5-trifluorobenzaldehyde (2.86 g, 17.84 mmol), $K_2CO_3$ (2.465 g, 17.84 mmol), 1-ethyl-1H-pyrazol-4-ol (2.0 g, 17.84 mmol) and DMF (20 mL) was sealed and heated to 110° C. for 3 hours under microwave. The reaction mixture was cooled and diluted by EtOAc (500 mL), washed with brine (25 mL×6), dried over $MgSO_4$, concentrated to get the crude product which was purified with silica gel column, eluting with PE/EtOAc=10 to give the title compound (3.7 g, 41.1%) as yellow oil.

LC-MS (ESI): m/z 253 [M+H]$^+$; 1.54 min (ret time).

D129

(4-(1-Ethyl-1H-pyrazol-4-yloxy)-3,5-difluorophenyl)methanol

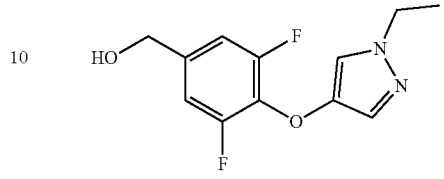

To the solution of 4-((1-ethyl-1H-pyrazol-4-yl)oxy)-3,5-difluorobenzaldehyde (3.5 g, 13.88 mmol) in methanol (50 mL) was added $NaBH_4$ (0.263 g, 6.94 mmol) at 0° C. After 20 minutes, the reaction was quenched with water 100 mL. Methanol was removed and the residue was extracted with EtOAc (25 mL×2), the organic phase was dried over $MgSO_4$, concentrated to get the crude product which was purified by silica gel column, eluting with PE/EtOAc=5/1 to give impurity product which was washed by Petroleum ether (30 mL) to give the title compound (2.1 g, 8.26 mmol, 59.5% yield) as a light yellow solid.

LC-MS (ESI): m/z 255 [M+H]$^+$; 1.43 min (ret time).

D130

1-Isopropyl-1H-pyrazol-4-ol

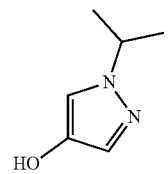

To the suspension of NaH (0.309 g, 7.73 mmol) in THF (20 mL) was added a solution of 4-(4,4,5,5-tetramethyl-1,3,2-dioxaborolan-2-yl)-1H-pyrazole (1 g, 5.15 mmol) in THF (1.5 mL) at 0° C. under $N_2$ atmosphere. The resulting mixture was stirred for 30 min and then 2-iodopropane (1.752 g, 10.31 mmol) was added. The result solution was stirred and left warm to room temperature for 8 hrs. The reaction mixture was diluted with EtOAc (100 mL), filtered and the filtrate was concentrated. The crude product was dissolved in THF (20 mL) and cooled to 0° C. under ice-brine bath. Then $H_2O_2$ (1 mL, 30 wt %) was added dropwise, followed by dropwise addition of 2N NaOH aqueous. After stirred for 2 hours, the reaction was quenched with 20 mL of water, acidified to pH=6-7, extracted with DCM (100 mL×2). The combined organic phase was dried over $MgSO_4$ and concentrated to give the title compound (850 mg, 4.01 mmol, 78% yield) as yellow oil.

LC-MS (ESI): m/z 127 [M+H]$^+$; 0.65 min (ret time).

D131

3,5-Difluoro-4-((1-isopropyl-1H-pyrazol-4-yl)oxy)benzaldehyde

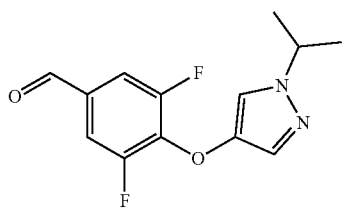 [SMILES: CC(C)n1cc(Oc2c(F)cc(C=O)cc2F)cn1]

A mixture of 3,4,5-trifluorobenzaldehyde (800 mg, 5.00 mmol) and 1-isopropyl-1H-pyrazol-4-ol (850 mg, 4.04 mmol) and K₂CO₃ (690 mg, 5 mmol) was dissolved in DMF (20 mL) and sealed with a tube. The resulting mixture was stirred and heated to 110° C. for 3 hours in microwave. The reaction mixture was cooled and diluted with EtOAc (300 mL) and saturated NH₄Cl aqueous (30 mL), the organic phase was washed with brine (25 mL×6), dried over MgSO₄, concentrated. The crude product was purified with silica gel column, eluenting with petrolium ether/EtOAc=3/1.

LC-MS (ESI): m/z 267 [M+H]$^+$; 1.61 min (ret time).

D132

(3,5-Difluoro-4-((1-isopropyl-1H-pyrazol-4-yl)oxy)phenyl)methanol

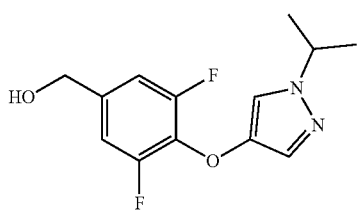 [SMILES: CC(C)n1cc(Oc2c(F)cc(CO)cc2F)cn1]

To the solution of 3, 5-difluoro-4-((1-isopropyl-1H-pyrazol-4-yl)oxy)benzaldehyde in methanol (5 mL) cooled to 0° C. in ice-brine bathe, NaBH₄ (95 mg, 2.5 mmol) was added portions. The result was stirred for 20 minutes and quenched with 10 mL of water. After the solvent was removed, the residue was extracted with EtOAc (30 mL×3). The combined organic phase was dried over MgSO₄, and concentrated to get the crude product.

LC-MS (ESI): m/z 269 [M+H]$^+$; 1.49 min (ret time).

D133

4-(3,4-Difluorophenoxy)-3,5-difluorobenzaldehyde

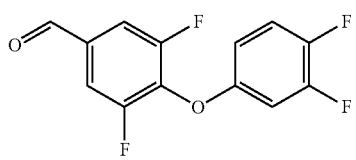 [SMILES: O=Cc1cc(F)c(Oc2ccc(F)c(F)c2)c(F)c1]

The title compound was prepared by a procedure similar to that described for D80 starting from 3,4,5-trifluorobenzaldehyde and 3,4-difluorophenol.

LC-MS (ESI): m/z 271 [M+H]$^+$; 1.76 min (ret time).

D134

(4-(3,4-Difluorophenoxy)-3,5-difluorophenyl)methanol

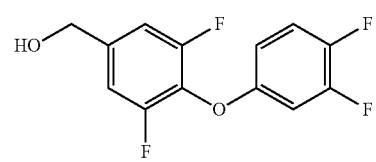 [SMILES: OCc1cc(F)c(Oc2ccc(F)c(F)c2)c(F)c1]

The title compound was prepared by a procedure similar to that described for D79 starting from 4-(3,4-difluorophenoxy)-3,5-difluorobenzaldehyde LC-MS (ESI): m/z 273[M+H]$^+$; 1.66 min (ret time).

D135

2-Chloro-5-(dibromomethyl)-3-fluoropyridine

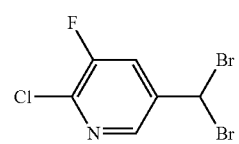 [SMILES: Fc1cc(C(Br)Br)cnc1Cl]

A suspension of 2-chloro-3-fluoro-5-methylpyridine (5.0 g, 34.3 mmol), dibenzoyl peroxide (1.109 g, 3.43 mmol) and NBS (18.34 g, 103 mmol) in CCl₄ (100 mL) was refluxed for overnight, then cooled to rt and washed with water and brine, dried over sodium sulfate, and concentrated. Purification via ISCO system afforded the title product (8.2 g) as a brown solid.

LC-MS (ESI): m/z 300 [M+H]$^+$; 3.25 min (ret time).

D136

6-Chloro-5-fluoro-3-pyridinecarbaldehyde

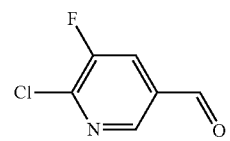

A suspension 2-chloro-5-(dibromomethyl)-3-fluoropyridine (2.3 g, 7.58 mmol), silver nitrate (5.15 g, 30.3 mmol) in a mixed solvents of ethanol (10 mL) and water (10 mL) was stirred for 1 h at 100° C., then filtrated, and concentrated. The residue was dissolved in ethyl acetate, washed with water and brine, dried over sodium sulfate, and concentrated. Purification via ISCO system afforded the title product (1.0 g) as a pale solid.

LC-MS (ESI): m/z 159 [M+H]+; 2.01 min (ret time).

D137

6-{[4-Chloro-3-(trifluoromethyl)phenyl]oxy}-5-fluoro-3-pyridinecarbaldehyde

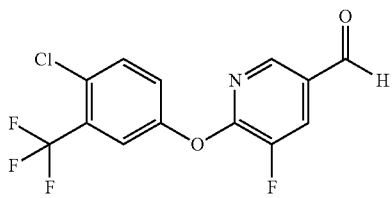 [SMILES: O=Cc1cnc(Oc2ccc(Cl)c(C(F)(F)F)c2)c(F)c1]

The title compound was prepared by a procedure similar to that described for D80 starting from 6-chloro-5-fluoro-3-pyridinecarbaldehyde and 4-chloro-3-(trifluoromethyl)phenol.

LC-MS (ESI): m/z 320 [M+H]+; 3.62 min (ret time).

D138

(6-{[4-Chloro-3-(trifluoromethyl)phenyl]oxy}-5-fluoro-3-pyridinyl)methanol

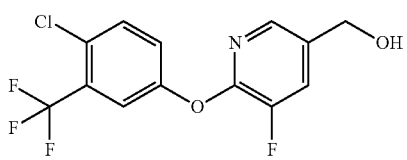 [SMILES: OCc1cnc(Oc2ccc(Cl)c(C(F)(F)F)c2)c(F)c1]

The title compound was prepared by a procedure similar to that described for D79 starting from 6-{[4-chloro-3-(trifluoromethyl)phenyl]oxy}-5-fluoro-3-pyridinecarbaldehyde.

LC-MS (ESI): m/z 322 [M+H]+; 3.52 min (ret time).

D139

2-(4-Chloro-3-(trifluoromethyl)phenoxy)-5-formylbenzonitrile

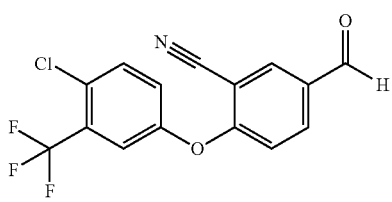 [SMILES: N#Cc1cc(C=O)ccc1Oc1ccc(Cl)c(C(F)(F)F)c1]

The title compound was prepared by a procedure similar to that described for D80 starting from 2-fluoro-5-formylbenzonitrile and 4-chloro-3-(trifluoromethyl)phenol.

LC-MS (ESI): m/z 326 [M+H]+; 1.84 min (ret time).

D140

2-(4-Chloro-3-(trifluoromethyl)phenoxy)-5-(hydroxymethyl)benzonitrile

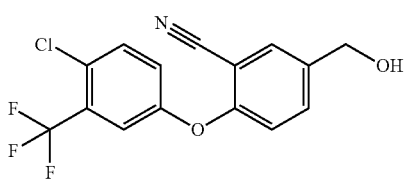 [SMILES: N#Cc1cc(CO)ccc1Oc1ccc(Cl)c(C(F)(F)F)c1]

The title compound was prepared by a procedure similar to that described for D79 starting from 2-(4-chloro-3-(trifluoromethyl)phenoxy)-5-formylbenzonitrile.

LC-MS (ESI): m/z 328 [M+H]+; 1.68 min (ret time).

D141

3,5-Difluoro-4-(3-(trifluoromethyl)phenoxy)benzaldehyde

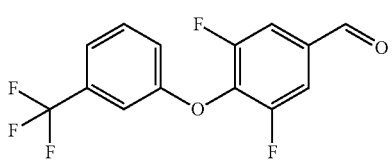 [SMILES: O=Cc1cc(F)c(Oc2cccc(C(F)(F)F)c2)c(F)c1]

The title compound was prepared by a procedure similar to that described for D80 starting from 3,4,5-trifluorobenzaldehyde and 3-(trifluoromethyl)phenol.

LC-MS (ESI): m/z 305 [M+H]+; 3.36 min (ret time).

D142

(3,5-Difluoro-4-(3-(trifluoromethyl)phenoxy)phenyl)methanol

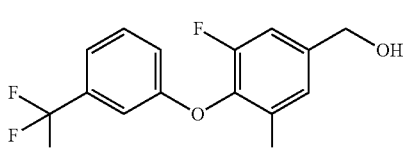

The title compound was prepared by a procedure similar to that described for D79 starting from 3,5-difluoro-4-(3-(trifluoromethyl)phenoxy)benzaldehyde.

LC-MS (ESI): m/z 305 [M+H]+; 3.36 min (ret time).

D143

6-(4-Chloro-3-(trifluoromethyl)phenoxy)nicotinaldehyde

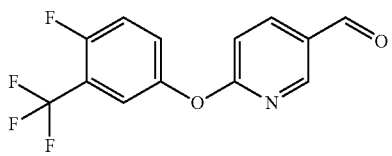 [SMILES: O=Cc1ccc(Oc2ccc(F)c(C(F)(F)F)c2)nc1]

The title compound was prepared by a procedure similar to that described for D80 starting from 6-chloronicotinaldehyde and 4-fluoro-3-(trifluoromethyl)phenol.

LC-MS (ESI): m/z 286 [M+H]$^+$; 3.34 min (ret time)

D144

(6-(4-Fluoro-3-(trifluoromethyl)phenoxy)pyridin-3-yl)methanol

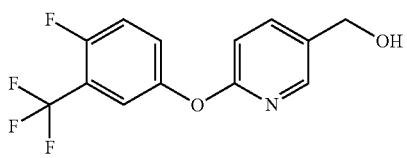 [SMILES: OCc1ccc(Oc2ccc(F)c(C(F)(F)F)c2)nc1]

The title compound was prepared by a procedure similar to that described for D79 starting from 6-(4-fluoro-3-(trifluoromethyl)phenoxy)nicotinaldehyde.

LC-MS (ESI): m/z 288 [M+H]$^+$; 2.90 min (ret time)

D145

2-(3-Fluorophenoxy)-5-formylbenzonitrile

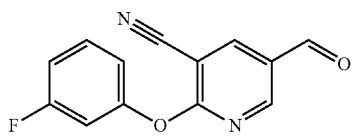 [SMILES: N#Cc1cc(C=O)cnc1Oc1cccc(F)c1]

The title compound was prepared by a procedure similar to that described for D80 starting from 2-fluoro-5-formylbenzonitrile and 3-fluorophenol.

LC-MS (ESI): m/z 242 [M+H]$^+$; 3.09 min (ret time)

D146

2-(3-Fluorophenoxy)-5-(hydroxymethyl)benzonitrile

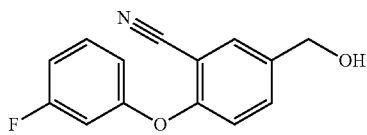 [SMILES: N#Cc1cc(CO)ccc1Oc1cccc(F)c1]

The title compound was prepared by a procedure similar to that described for D79 starting from 2-(3-fluorophenoxy)-5-formylbenzonitrile.

LC-MS (ESI): m/z 244 [M+H]$^+$; 2.78 min (ret time)

D147

2-(3,5-Difluorophenoxy)-5-formylbenzonitrile

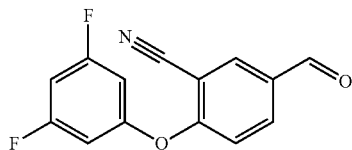 [SMILES: N#Cc1cc(C=O)ccc1Oc1cc(F)cc(F)c1]

The title compound was prepared by a procedure similar to that described for D80 starting from 2-fluoro-5-formylbenzonitrile and 3-fluorophenol.

LC-MS (ESI): m/z 260 [M+H]$^+$; 3.13 min (ret time)

D148

2-(3,5-Difluorophenoxy)-5-(hydroxymethyl)benzonitrile

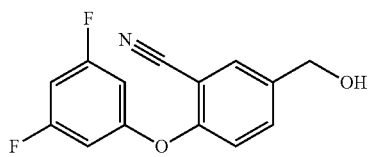 [SMILES: N#Cc1cc(CO)ccc1Oc1cc(F)cc(F)c1]

The title compound was prepared by a procedure similar to that described for D79 starting from 2-(3,5-difluorophenoxy)-5-formylbenzonitrile.

LC-MS (ESI): m/z 262 [M+H]$^+$; 2.83 min (ret time)

D149

2-(Trifluoromethyl)pyrimidin-5-ol

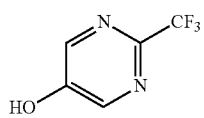

To a solution of 1,3-diaminopropan-2-ol (3.60 g, 40.0 mmol) in xylene (30 mL) was added ethyl 2,2,2-trifluoroacetate (5.70 g, 40.8 mmol) and stirred at 130° C. overnight, then the mixture was cooled to room temperature and concentrated. The residue was dissolved in nitrobenzene (60 mL), and then MeONa (8.50 g, 157.0 mmol) was added. The reaction mixture was stirred at 120° C. for 1 h. Then the mixture was cooled to room temperature and poured into water (200 mL), extracted with EA (200 mL). The aqueous phase adjust to pH=4 with 6M HCl and extracted with EA (200 mL), dried over Na$_2$SO$_4$, filtered and concentrated to give a crude product. The residue was purified by column chromatography on silica gel eluting with DCM/MeOH (30:1) to give the title compound (1.80 g, 28% yield) as a yellow solid.

¹H NMR (300 MHz, DMSO-d₆): δ 11.48 (br s, 1H), 8.52 (s, 2H).

D150

3,5-Difluoro-4-((2-(trifluoromethyl)pyrimidin-5-yl)oxy)benzaldehyde

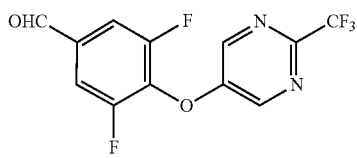 [SMILES: O=Cc1cc(F)c(Oc2cnc(C(F)(F)F)nc2)c(F)c1]

To a solution of 2-(trifluoromethyl)pyrimidin-5-ol (1.61 g, 10.0 mmol) in DMF (30 mL) was added 3,4,5-trifluorobenzaldehyde (1.60 g, 10.0 mmol) and K₂CO₃ (4.14 g, 30.0 mmol). The reaction mixture was stirred at 80° C. overnight. Then the mixture was cooled to room temperature and poured into water (150 mL), extracted with EA (2×100 mL), dried over Na₂SO₄, filtered and concentrated to give a crude product. The residue was purified by column chromatography on silica gel eluting with PE/EA (10:1) to give the title compound (2.10 g, 69% yield) as yellow oil.

¹H NMR (300 MHz, CDCl₃): δ 9.97 (s, 1H), 8.59 (s, 2H), 7.65 (d, J=7.2 Hz, 2H).

D151

(3,5-Difluoro-4-((2-(trifluoromethyl)pyrimidin-5-yl)oxy)phenyl)methanol

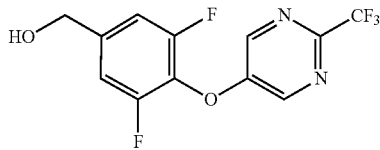 [SMILES: OCc1cc(F)c(Oc2cnc(C(F)(F)F)nc2)c(F)c1]

To a solution of 3,5-difluoro-4-((2-(trifluoromethyl)pyrimidin-5-yl)oxy)benzaldehyde (2.10 g, 6.9 mmol) in MeOH (20 mL) was added in portions NaBH₄ (262 mg, 6.9 mmol) at 0° C. Then the reaction mixture was stirred at room temperature for 0.5 h and poured into water (50 mL), extracted with EA (2×30 mL), dried over Na₂SO₄, filtered and concentrated to give a crude product. The residue was purified by column chromatography on silica gel eluting with PE/EA (10:1) to give the title compound (957 mg, 45% yield) as a yellow solid.

¹H NMR (300 MHz, CDCl₃): δ 8.55 (s, 2H), 7.13 (d, J=8.1 Hz, 2H), 4.76 (d, J=5.7 Hz, 2H).

D152

Methyl 3,5-difluoro-4-((3-hydroxycyclohexyl)oxy)benzoate

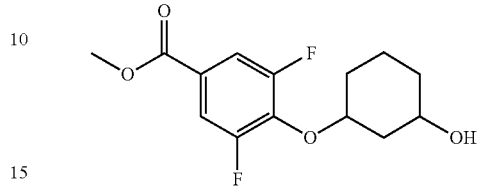

To a solution of methyl 3,5-difluoro-4-hydroxybenzoate (376 mg, 2 mmol), cyclohexane-1,3-diol (464 mg, 4 mmol) and PPh₃ (1.05 g, 4 mmol) in THF (15 mL) was added DIAD (808 mg, 4 mmol) dropwise at 0° C. under N₂. The reaction was slowly warmed up to room temperature and stirred for 30 min. The mixture was concentrated, and the residue was triturated with TBME, and filtered. The filtrate was concentrated and purified with silica gel column (TBME/EA=3/1~1/1) to give the title compound (500 mg, yield 87%) as yellow oil.

¹H NMR (300 MHz, CDCl₃): δ 7.62-7.54 (m, 2H), 4.32-4.22 (m, 1H), 3.91 (s, 3H), 3.75-3.69 (m, 1H), 1.97-1.46 (m, 8H).

D153

Methyl 3,5-difluoro-4-((3-oxocyclohexyl)oxy)benzoate

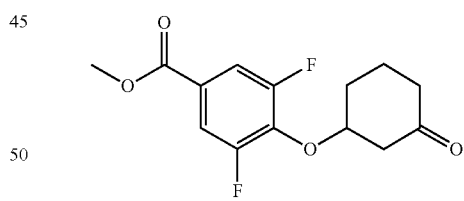

To a solution of methyl 3,5-difluoro-4-((3-hydroxycyclohexyl)oxy)benzoate (500 mg, 1.75 mmol) in DCM (10 mL) was added DMP (964 mg, 2.27 mmol) at room temperature and the reaction was stirred at room temperature overnight. The reaction was diluted with TBME/PE (1:1, 30 mL), then filtered. The filtrate was washed with water and brine, dried, concentrated and purified with silica gel column (PE/EA=10/1) to give the title compound (300 mg, yield 60%) as colorless oil.

¹H NMR (300 MHz, CDCl₃): δ 7.62-7.55 (m, 2H), 4.78-4.71 (m, 1H), 3.90 (s, 3H), 2.71 (d, J=5.1 Hz, 2H), 2.46-2.36 (m, 2H), 2.25-2.13 (m, 1H), 2.09-2.03 (m, 2H), 1.82-1.72 (m, 1H).

D154

Methyl 4-((3,3-difluorocyclohexyl)oxy)-3,5-difluorobenzoate

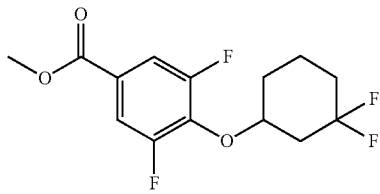 [SMILES: COC(=O)c1cc(F)c(OC2CCCC(F)(F)C2)c(F)c1]

To a solution of methyl 3,5-difluoro-4-((3-oxocyclohexyl)oxy)benzoate (800 mg, 2.8 mmol), in DCM (10 mL) was added DAST (1.36 g, 8.4 mmol) at room temperature and the reaction was stirred at room temperature overnight. The reaction was poured into sat. NaHCO$_3$ (80 mL) with stirring at RT, then extracted with DCM (40 mL×2). The combined organic layer was dried, concentrated and purified with silica gel column (PE/EA=20/1) to give the title compound (820 mg, yield 95%) as colorless oil.
$^1$H NMR (300 MHz, CDCl$_3$): δ 7.64~7.55 (m, 2H), 4.43-4.37 (m, 1H), 3.91 (s, 3H), 2.60-2.49 (m, 1H), 3.13-1.49 (m, 7H).

D155 (4-((3,3-Difluorocyclohexyl)oxy)-3,5-difluorophenyl)methanol

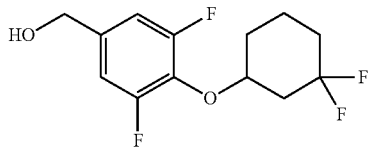 [SMILES: OCc1cc(F)c(OC2CCCC(F)(F)C2)c(F)c1]

To a solution of methyl 4-((3,3-difluorocyclohexyl)oxy)-3,5-difluorobenzoate (1.73 g, 5.7 mmol) in THF (40 mL) was added LiAlH$_4$ (215 mg, 5.7 mmol) at 0° C. The mixture was stirred at room temperature for 1 hour. MeOH (10 mL) was added to quench the reaction. Potassium sodium tartrated (sat. 10 mL) was added, the mixture was stirred at room temperature for 20 min. The mixture was filtered and the filtrate was evaporated. The residue was purified by flash chromatography on silica gel (PE/EA=40/1-10/1) to give the title compound (722 mg, yield 46%) as yellow oil.
$^1$H NMR (300 MHz, CDCl$_3$): 6.94-6.91 (m, 2H), 4.63 (s, 2H), 4.22-4.20 (m, 1H), 2.56-2.52 (m, 1H), 2.11-1.51 (m, 8H).

D156

Methyl 4-((3-(benzyloxy)cyclopentyl)oxy)-3,5-difluorobenzoate

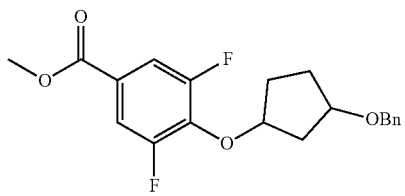 [SMILES: COC(=O)c1cc(F)c(OC2CCC(OCc3ccccc3)C2)c(F)c1]

To a solution of methyl 3,5-difluoro-4-hydroxybenzoate (376 mg, 2 mmol), 3-(benzyloxy)cyclopentanol (420 mg, 2.2 mmol) and PPh$_3$ (1.05 g, 4 mmol) in THF (15 mL) was added DIAD (808 mg, 4 mmol) dropwise at 0° C. under N$_2$. The reaction was stirred at RT for 2 hours. The mixture was concentrated and the residue was triturated with TBME/PE (1:3, 30 mL), filtered. The filtrate was concentrated and purified with silica gel column (PE/EA=30/1~20/1) to give the title compound (600 mg, yield 83%) as yellow oil.
$^1$H NMR (300 MHz, CDCl$_3$): δ 7.62-7.53 (m, 2H), 7.37-7.25 (m, 5H), 4.94-4.90 (m, 1H), 4.52 (s, 2H), 4.05-4.01 (m, 1H), 3.90 (s, 3H), 2.33-2.23 (m, 1H), 2.12-1.80 (m, 5H).

D157

Methyl 3,5-difluoro-4-((3-hydroxycyclopentyl)oxy)benzoate

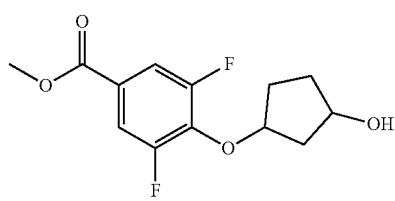 [SMILES: COC(=O)c1cc(F)c(OC2CCC(O)C2)c(F)c1]

A mixture of methyl 4-((3-(benzyloxy)cyclopentyl)oxy)-3,5-difluorobenzoate (3.9 g, 10.8 mmol) and 10% Pd/C (wet, 1.3 g) in MeOH (30 mL) was stirred at 50° C. under H$_2$ (50 psi) for 2 days. The mixture was filtered, concentrated and purified with silica gel column (PE/EA=50/1~10/1) to give the title compound (1.51 g, yield 52%) as colorless oil.
$^1$H NMR (300 MHz, CDCl$_3$): δ 7.65-7.57 (m, 2H), 5.10-5.07 (m, 1H), 4.61-4.38 (m, 1H), 3.91 (s, 3H), 2.24-1.80 (m, 6H).

D158

Methyl 3,5-difluoro-4-((3-oxocyclopentyl)oxy)benzoate

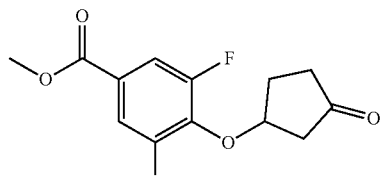

To a solution of methyl 3,5-difluoro-4-((3-hydroxycyclopentyl)oxy)benzoate (1.51 g, 5.6 mmol) in DCM (30 mL) was added DMP (3.06 g, 7.2 mmol) at RT and the reaction was then stirred at RT for 4 hours. The reaction was diluted with water (50 mL) and filtered. The filtrate was extracted with DCM (50 mL×2), dried over Na$_2$SO$_4$, filtered, concentrated and purified by silica gel column (PE/EA=5/1) to give the title compound (1.48 g, yield 99%) as yellow oil.
$^1$H NMR (300 MHz, CDCl$_3$): δ 7.62-7.59 (m, 2H), 5.22-5.21 (m, 1H), 3.91 (s, 3H), 2.62-2.49 (m, 3H), 2.35-2.30 (m, 2H), 2.18-2.09 (m, 1H).

D159

Methyl 4-((3,3-difluorocyclopentyl)oxy)-3,5-difluorobenzoate

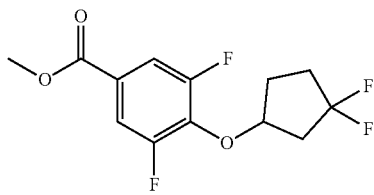 [SMILES: COC(=O)c1cc(F)c(OC2CCC(F)(F)C2)c(F)c1]

To a solution of methyl 3,5-difluoro-4-((3-oxocyclopentyl)oxy)benzoate (2.24 g, 8.3 mmol), in DCM (40 mL) was added DAST (4.00 g, 24.9 mmol) at RT, the reaction was stirred at RT overnight. The reaction was poured into sat. NaHCO$_3$ (320 mL) with stirring at RT, then extracted with DCM (50 mL×2). The combined DCM was dried over Na$_2$SO$_4$, concentrated and purified with silica gel column (PE/EA=20/1) to give the title compound (1.02 g, yield 42%) as yellow oil.

$^1$H NMR (300 MHz, CDCl$_3$): δ 7.61-7.59 (m, 2H), 4.96 (br s, 1H), 3.91 (s, 3H), 2.57-2.43 (m, 3H), 2.18-2.03 (m, 3H).

D160

(4-((3,3-Difluorocyclopentyl)oxy)-3,5-difluorophenyl)methanol

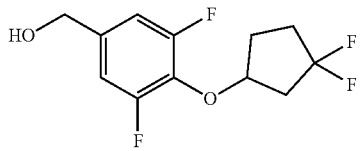 [SMILES: OCc1cc(F)c(OC2CCC(F)(F)C2)c(F)c1]

To a solution of methyl 4-((3,3-difluorocyclopentyl)oxy)-3,5-difluorobenzoate (1.02 g, 3.5 mmol) in dry THF (30 mL) was added LiAlH$_4$ (133 mg, 3.5 mmol) in portions at 0° C. under N$_2$. The reaction mixture was stirred at RT for 0.5 hours, then added drop wise MeOH (5 mL) at room temperature and stirred for 10 min, added sat. Potassium sodium tartrate tetrahydrate (aq, 15 mL) were stirred for 1 h, added Na$_2$SO$_4$ and stirred for 1 hour. The reaction mixture was filtered and concentrated under reduced pressure to give the residue. The residue was purified by silica gel column (PE/EA=5:1) to give the title compound (808 mg, yield 88%) as yellow oil.

$^1$H NMR (300 MHz, CDCl$_3$): 6.96-6.89 (m, 2H), 4.83-4.82 (m, 1H), 4.64-4.62 (m, 2H), 2.51-2.41 (m, 3H), 2.16-2.00 (m, 3H), 1.81-1.77 (m, 1H).

D161

4-((1-Benzhydrylazetidin-3-yl)oxy)-3,5-difluorobenzoic acid

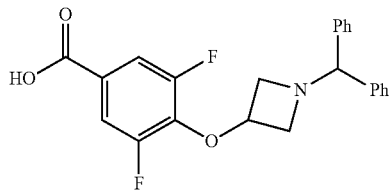 [SMILES: O=C(O)c1cc(F)c(OC2CN(C(c3ccccc3)c3ccccc3)C2)c(F)c1]

To a solution of 3,4,5-trifluorobenzoic acid (50 g, 284 mmol) and 1-benzhydrylazetidin-3-ol (68 g, 284 mmol) in DMF (1 L) was added NaH (60% in mineral oil, 34 g, 852 mmol) at 0° C. The mixture was stirred at room temperature for 16 hrs and then stirred at 50° C. for 3 hrs. The mixture was poured into ice-water. The mixture was acidified with conc. HCl to pH=3, then filtered to give a solid. The solid was triturated with PE (300 mL) and filtered to give the title compound (88 g, yield 79%) as a white solid.

$^1$H NMR (300 MHz, DMSO-d$_6$): δ7.66-7.26 (m, 12H), 5.21-4.99 (m, 1H), 3.81-3.31 (m, 4H).

D162

Methyl 4-((1-benzhydrylazetidin-3-yl)oxy)-3,5-difluorobenzoate

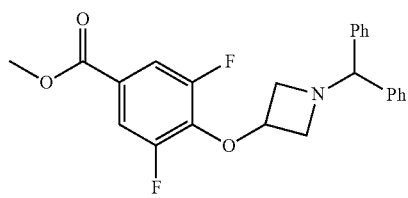 [SMILES: COC(=O)c1cc(F)c(OC2CN(C(c3ccccc3)c3ccccc3)C2)c(F)c1]

A mixture of 4-((1-benzhydrylazetidin-3-yl)oxy)-3,5-difluorobenzoic acid (10 g, 25.3 mmol) and conc H$_2$SO$_4$ (1 mL) in MeOH (100 mL) was stirred at 80° C. overnight. The mixture was concentrated and poured into ice-water (50 mL). The aqueous solution was extracted with DCM (100 mL×2), dried over Na$_2$SO$_4$, concentrated to give the crude title compound (11 g, yield 100%) as a yellow solid.

D163

Methyl 4-(azetidin-3-yloxy)-3,5-difluorobenzoate

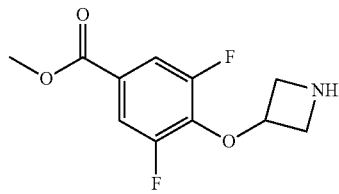 [SMILES: COC(=O)c1cc(F)c(OC2CNC2)c(F)c1]

A mixture of methyl 4-((1-benzhydrylazetidin-3-yl)oxy)-3,5-difluorobenzoate (35 g, 85 mmol), 20% Pd(OH)$_2$/C (6 g) and AcOH (6 mL) in MeOH (1.0 L) was stirred at 70° C. under H$_2$ (50 Psi) overnight. The mixture was filtered, concentrated and the residue was purified by flash chromatograph on silica gel (DCM/MeOH=30/1 to 10/1) to give the title compound (38 g, yield 91%) as a yellow solid.

$^1$H NMR (300 MHz, DMSO-d$_6$): δ7.64-7.55 (m, 2H), 5.14-5.10 (m, 1H), 4.18-4.06 (m, 4H), 3.92 (s, 3H).

D164

Methyl 3,5-difluoro-4-((1-(3,3,3-trifluoropropyl)azetidin-3-yl)oxy)benzoate

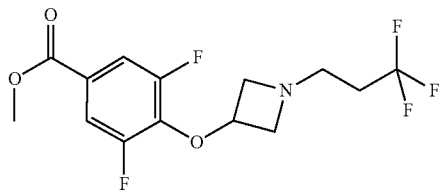 [SMILES: COC(=O)c1cc(F)c(OC2CN(CCC(F)(F)F)C2)c(F)c1]

A solution of methyl 4-(azetidin-3-yloxy)-3,5-difluorobenzoate (1.0 g, 4.1 mmol), 1,1,1-trifluoro-3-iodopropane (922 mg, 4.1 mmol) and DIEA (1.06 g, 8.2 mmol) in acetonitrile (20 mL) was heated to reflux and stirred for 4 hours. The solution was evaporated and purified by flash chromatograph on silica gel (PE/EA=20/1) to give the title compound (620 mg, yield 45%) as yellow oil.

$^1$H NMR (300 MHz, CDCl$_3$): δ 7.62-7.55 (m, 2H), 4.91-4.87 (m, 1H), 3.91 (s, 3H), 3.80-3.75 (m, 2H), 3.27-3.22 (m, 2H), 2.78-2.73 (m, 2H), 2.26-2.13 (m, 2H).

D165

(3,5-Difluoro-4-((1-(3,3,3-trifluoropropyl)azetidin-3-yl)oxy)phenyl)methanol

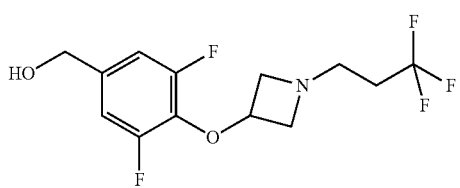 [SMILES: OCc1cc(F)c(OC2CN(CCC(F)(F)F)C2)c(F)c1]

To a solution of methyl 3,5-difluoro-4-((1-(3,3,3-trifluoropropyl)azetidin-3-yl)oxy)benzoate (620 mg, 1.8 mmol) in THF (30 mL) was added LiAlH$_4$ (70 mg, 1.8 mmol) at 0° C. Then the mixture was stirred at 0° C. for 30 min. The mixture was quenched with Na$_2$SO$_4$.10H$_2$O (2.0 g). The mixture was filtered and evaporated to give the title compound (480 mg, yield 81%) as yellow oil.

LC-MS (ESI): m/z 312 [M+H]$^+$; 3.65 min (ret time).

$^1$H NMR (300 MHz, CDCl$_3$): δ 6.94-6.91 (m, 2H), 4.75-4.71 (m, 1H), 4.62 (s, 2H), 3.76-3.71 (m, 2H), 3.2-3.19 (m, 2H), 2.77-2.72 (m, 2H), 2.22-2.12 (m, 2H).

D166

Methyl 4-((1-butylazetidin-3-yl)oxy)-3,5-difluorobenzoate

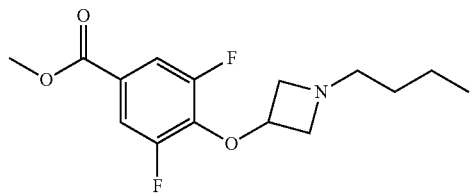 [SMILES: CCCCN1CC(Oc2c(F)cc(C(=O)OC)cc2F)C1]

A mixture of methyl 4-(azetidin-3-yloxy)-3,5-difluorobenzoate (2.0 g, 8.2 mmol), 1-bromobutane (1.4 g, 9.8 mmol) and DIEA (1.6 g, 12.3 mmol) in CH$_3$CN (20 mL) was stirred at 95° C. overnight. The reaction mixture was concentrated and purified by flash chromatography on silica gel (PE: EA=10:1) to give the title compound (850 mg, 34%) as a yellow oil.

LC-MS (ESI): m/z 300 [M+H]$^+$; 2.88 min (ret time).

D167 (4-((1-Butylazetidin-3-yl)oxy)-3,5-difluorophenyl)methanol

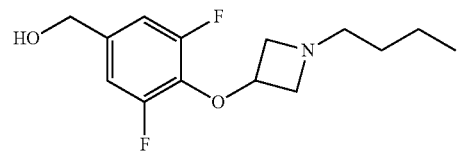 [SMILES: CCCCN1CC(Oc2c(F)cc(CO)cc2F)C1]

To a solution of methyl 4-((1-butylazetidin-3-yl)oxy)-3,5-difluorobenzoate (1.1 g, 3.7 mmol) in THF (20 mL) was added LiAlH$_4$ (141 mg, 3.7 mmol) at 0° C. The mixture was stirred at 0° C. for 30 min. The mixture was quenched with MeOH (5 mL) and sat potassium sodium tartrate (10 mL). The mixture was stirred at room temperature for 30 min. Na$_2$SO$_4$ (15 g) was added, filtered and concentrated to give title compound (630 mg, 63%) as yellow oil.

LC-MS (ESI): m/z 272 [M+H]$^+$; 2.43 min (ret time).

$^1$H NMR (300 MHz, CDCl$_3$): δ 6.96-6.90 (m, 2H), 4.60 (s, 2H), 4.50-4.46 (m, 1H), 3.67-3.62 (m, 2H), 3.15-3.10 (m, 2H), 2.52-2.47 (m, 2H), 1.39-1.29 (m, 4H), 0.94-0.90 (m, 2H

D168

Ethyl 3-(4-bromo-2,6-difluorophenyl)acrylate

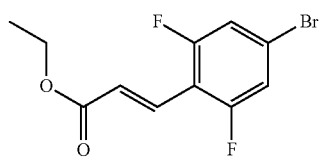 [SMILES: CCOC(=O)/C=C/c1c(F)cc(Br)cc1F]

To a solution of 4-bromo-2,6-difluorobenzaldehyde (25.0 g, 113.1 mmol) in EA (113 mL) was added PPh$_3$ (41.49 g, 158.4 mmol), sat. NaHCO$_3$ (226 mL) and ethyl 2-bromoacetate (28.34 g, 169.7 mmol). The reaction mixture was stirred vigorously at room temperature for 3 hours. The reaction mixture was diluted with water (150 mL) and extracted with EA (300 mL), the organic layers was washed with water (250 mL) and brine (250 mL), dried over anhydrous $Na_2SO_4$, filtered and concentrated under reduced pressure to give the residue. The residue was purified by silica gel column (PE/EA=40:1) to give the title compound (33.25 g, yield 100%) as a white solid.

$^1$H NMR (300 MHz, $CDCl_3$): δ 7.67 (d, J=16.5 Hz, 1H), 7.14 (d, J=7.8 Hz, 2H), 6.71 (d, J=16.5 Hz, 1H), 4.27 (q, J=7.2 Hz, 2H), 1.33 (t, J=7.2 HZ, 3H).

D169

3-(4-Bromo-2,6-difluorophenyl)propan-1-ol

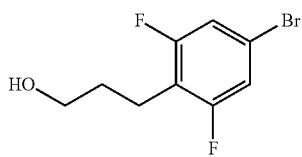 [SMILES: OCCCc1c(F)cc(Br)cc1F]

To a solution of ethyl 3-(4-bromo-2,6-difluorophenyl) acrylate (17.46 g, 60.0 mmol) in dry THF (500 mL) was added $LiBH_4$ (6.06 g, 300.0 mmol) at 0° C. under $N_2$. The reaction mixture was stirred at RT overnight, then added drop wise sat.$NH_4Cl$ (aq, 200 mL) at room temperature, added water (200 mL) and extracted with EA (400 mL), washed with brine (200 mL), dried over $Na_2SO_4$, filtered and concentrated under reduced pressure to give the residue. The residue was purified by silica gel column (PE/EA=10:1) to give the title compound (8.10 g, yield 54%) as colorless oil.

$^1$H NMR (300 MHz, $CDCl_3$): δ 7.06-7.02 (m, 2H), 3.68-3.63 (m, 2H), 2.75-2.60 (m, 2H), 1.87-1.80 (m, 2H).

D170

Methyl 3,5-difluoro-4-(3-hydroxypropyl)benzoate

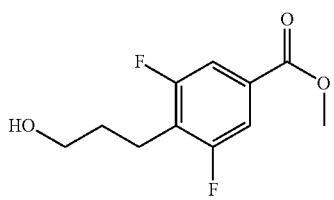 [SMILES: COC(=O)c1cc(F)c(CCCO)c(F)c1]

A mixture of 3-(4-bromo-2,6-difluorophenyl)propan-1-ol (8.10 g, 32.3 mmol), $Pd(dppf)Cl_2$ (2.63 g, 3.2 mmol) and TEA (6.52 g, 64.5 mmol) in MeOH (100 mL) was stirred at 100° C. under CO (2 MPa) for 24 hours. The reaction mixture was cooled to room temperature, filtered and concentrated. The residue dissolved in EA (400 mL), washed with water (200 mL) and brine (200 mL), dried over $Na_2SO_4$, filtered and concentrated under reduced pressure to give the residue. The residue was purified by silica gel column (PE/EA=5:1) to give the title compound (2.83 g, yield 38%) as red oil.

$^1$H NMR (300 MHz, $CDCl_3$): δ 7.53 (d, J=8.1 Hz, 2H), 3.92 (s, 3H), 3.67 (t, J=6.6 Hz, 2H), 2.81 (t, J=7.5 Hz, 2H), 1.91-1.84 (m, 2H), 1.51 (br s, 1H)

D171

Methyl 3,5-difluoro-4-(3-fluoropropyl)benzoate

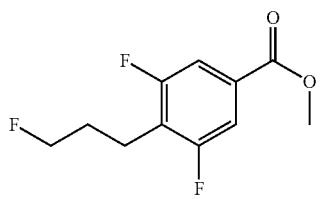 [SMILES: COC(=O)c1cc(F)c(CCCF)c(F)c1]

To a solution of methyl 3,5-difluoro-4-(3-hydroxypropyl) benzoate (1.04 g, 4.5 mmol) in DCM (20 mL) was added dropwise DAST (1.09 g, 6.8 mmol) at 0° C. The reaction mixture was stirred at RT for 1.5 hours. The reaction mixture was quenched with sat. $NaHCO_3$ (aq, 40 mL), extracted with DCM (40 mL) and dried over $Na_2SO_4$. Filtered and concentrated to give the residue. The residue was purified by silica gel column (PE/EA=25:1) to give the title compound (470 mg, yield 45%) as yellow oil.

$^1$H NMR (300 MHz, $CDCl_3$): δ 7.53 (d, J=8.1 Hz, 2H), 4.55 (t, J=6.0 Hz, 1H), 4.39 (t, J=6.0 Hz, 1H), 3.91 (s, 3H), 2.85 (t, J=7.5 Hz, 2H), 2.06-1.93 (m, 2H).

D172

(3,5-Difluoro-4-(3-fluoropropyl)phenyl)methanol

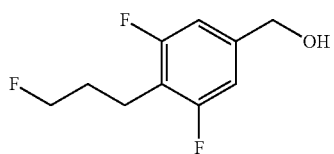 [SMILES: OCc1cc(F)c(CCCF)c(F)c1]

To a solution of methyl 3,5-difluoro-4-(3-fluoropropyl) benzoate (470 mg, 2.0 mmol) in dry THF (20 mL) was added $LiAlH_4$ (77 mg, 2.0 mmol) in portions at 0° C. under $N_2$. The reaction mixture was stirred at RT for 0.5 hours, then added drop wise MeOH (10 mL) at room temperature and stirred for 10 min, added sat. Potassium sodium tartrate (aq, 15 mL) stirred 0.5 hours, added $Na_2SO_4$ and stirred 0.5 hours, filtered and concentrated under reduced pressure to give the residue. The residue was purified by silica gel column (PE/EA=10:1) to give the title compound (356 mg, yield 86%) as a yellow solid.

$^1$H NMR (300 MHz, $CDCl_3$): δ 6.88 (d, J=7.8 Hz, 2H), 4.65 (s, 2H), 4.54 (t, J=6.0 Hz, 1H), 4.38 (t, J=6.0 Hz, 1H), 2.79 (t, J=7.5 Hz, 2H), 2.04-1.91 (m, 2H), 1.74 (br s, 1H).

D173

3,5-Difluoro-4-((2-methylpyridin-4-yl)oxy)benzaldehyde

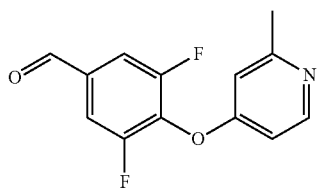 [SMILES: Cc1cc(Oc2c(F)cc(C=O)cc2F)ccn1]

To a solution of 3,4,5-trifluorobenzaldehyde (2.9 g, 18 mmol) 2-methylpyridin-4-ol (2.0 g, 18 mmol) in dry DMF (50 mL) was added $K_2CO_3$ (7.6 g, 55 mmol) at 80° C. The reaction mixture was stirred at 80° C. overnight. The reaction mixture was concentrated and the residue was dissolved with water (100 mL), extracted with EA (100 mL×3). The combined organic layers were dried over anhydrous $Na_2SO_4$, concentrated under reduced pressure. The residue was purified by column chromatography on silica gel eluting with PE/EA (4:1) to give the title compound (1.5 g, 34% yield) as colorless oil.

$^1$H NMR (300 MHz, $CDCl_3$): δ 9.95 (t, J=1.8 Hz, 1H), 8.40 (d, J=5.7 Hz, 1H), 7.63-7.57 (m, 2H), 6.70-6.67 (m, 2H), 2.53 (s, 3H).

D174

(3,5-Difluoro-4-((2-methylpyridin-4-yl)oxy)phenyl)methanol

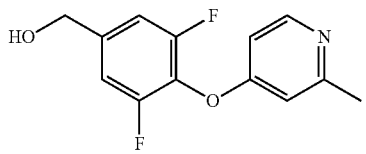 [SMILES: Cc1cc(Oc2c(F)cc(CO)cc2F)ccn1]

To a solution of 3,5-difluoro-4-((2-methylpyridin-4-yl)oxy)benzaldehyde (1.5 g, 6.0 mmol) in MeOH (50 mL) was added $NaBH_4$ (228 mg, 6.0 mmol) at 0° C. The reaction mixture was stirred at RT for 2 h. The reaction mixture was concentrated and the residue was dissolved with water (100 mL), extracted with EA (100 mL×3). The combined organic layers were dried over anhydrous $Na_2SO_4$, and concentrated under reduced pressure. The residue was purified by prep-HPLC to give the title compound (1.45 g, 97% yield) as a white solid.

$^1$H NMR (300 MHz, $CDCl_3$): δ 8.31 (d, J=5.7 Hz, 1H), 7.10-7.05 (m, 2H), 4.73 (d, J=5.7 Hz, 2H), 2.50 (s, 3H), 2.17 (t, J=0.9 Hz, 1H). LCMS: rt=3.260 min, $[M+H]^+$=252.

D175

2-(4-Fluoro-3-(trifluoromethyl)phenoxy)-5-formylbenzonitrile

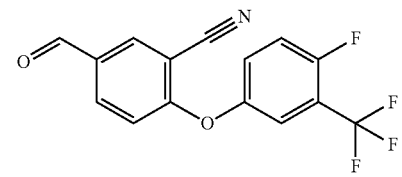 [SMILES: N#Cc1cc(C=O)ccc1Oc1ccc(F)c(C(F)(F)F)c1]

To the solution of 2-fluoro-5-formylbenzonitrile (1.5 g, 10.06 mmol) and 4-fluoro-3-(trifluoromethyl)phenol (1.812 g, 10.06 mmol) in acetonitrile (18 ml), was added $K_2CO_3$ (1.807 g, 13.08 mmol). The reaction mixture was sealed and heated in Biotage Initiator using initial normal to 130° C. for 1 h. After cooling the reaction, the reaction mixture was filtrated and evaporated in vacuo to give crude product 2-(4-fluoro-3-(trifluoromethyl)phenoxy)-5-formylbenzonitrile (3 g, 9.70 mmol, 96% yield) as a white solid.

LCMS: Rt=3.38 min, $[M-H]^+$=310.

D176

2-(4-Fluoro-3-(trifluoromethyl)phenoxy)-5-(hydroxymethyl)benzonitrile

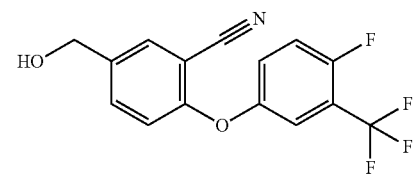 [SMILES: N#Cc1cc(CO)ccc1Oc1ccc(F)c(C(F)(F)F)c1]

To the solution of 2-(4-fluoro-3-(trifluoromethyl)phenoxy)-5-formylbenzonitrile (3 g, 9.70 mmol) in methanol (30 ml), was added $NaBH_4$ (0.551 g, 14.55 mmol). The reaction mixture was stirred at rt for 30 min, then quenched by water and extracted with EA twice. The organic phase was washed with brine, dried over $Na_2SO_4$ and evaporated in vacuo to give crude product 2-(4-fluoro-3-(trifluoromethyl)phenoxy)-5-(hydroxymethyl)benzonitrile (2.3 g, 7.39 mmol, 76% yield) as white solid LCMS: Rt=1.70 min, $[M-H]^+$=310.

D177

4-Bromo-1-(1-ethoxyethyl)-1H-pyrazole

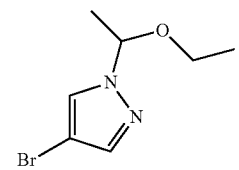

To a solution of 4-bromo-1H-pyrazole (6.0 g, 41 mmol), ethoxyethene (3.5 g, 49 mmol) in THF (60 mL) was added HCl in dioxane (sat. 1 mL). The mixture was stirred at room temperature for 3 hrs. NaHCO$_3$ (sat. 5 mL) was added to quench the reaction. The mixture was extracted DCM (100 mL×3), washed with water (100 mL×3), brine, dried over anhydrous Na$_2$SO$_4$ and concentrated under reduced pressure to give the title compound (10 g, 100% yield) as grey oil.

$^1$H NMR (300 MHz, CDCl$_3$): δ 7.59 (d, J=0.6 Hz, 1H), 7.44 (d, J=0.6 Hz, 1H), 5.45 (q, J=6.0 Hz, 1H), 3.47-3.29 (m, 2H), 1.62 (d, J=6.0 Hz, 3H), 1.13 (t, J=6.9 Hz, 3H).

D178

1-(1-Ethoxyethyl)-4-(4,4,5,5-tetramethyl-1,3,2-dioxaborolan-2-yl)-1H-pyrazole

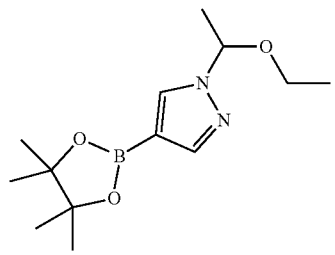 [SMILES: CCOC(C)n1cc(B2OC(C)(C)C(C)(C)O2)cn1]

To a solution of 4-bromo-1-(1-ethoxyethyl)-1H-pyrazole (6.2 g, 28 mmol) in THF (100 mL) was added i-PrMgCl (2 mmol/L, 25 mL) at room temperature for 3 hrs. 2-isopropoxy-4,4,5,5-tetramethyl-1,3,2-dioxaborolane (12.6 g, 67.9 mmol) was added at room temperature for 3 h. NH$_4$Cl (sat. 20 mL) was added to quench the reaction. The mixture was extracted PE:EtOAc=(200 mL:200 mL×3), washed with water (300 mL×3), brine, dried over anhydrous Na$_2$SO$_4$ and concentrated under reduced pressure to give the title compound (7 g, 100% yield) as yellow oil.

$^1$H NMR (300 MHz, CDCl$_3$): δ 7.89 (s, 1H), 7.78 (s, 1H), 5.54-5.52 (m, 1H), 3.46-3.31 (m, 3H), 1.70-1.64 (m, 3H), 1.36 (s, 9H), 1.21-1.10 (m, 3H).

D179

1-(1-Ethoxyethyl)-1H-pyrazol-4-ol

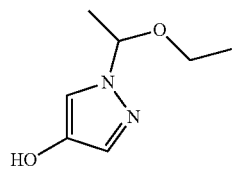

To a solution of 1-(1-ethoxyethyl)-4-(4,4,5,5-tetramethyl-1,3,2-dioxaborolan-2-yl)-1H-pyrazole (7.0 g, 27 mmol) in THF (100 mL) was added NaOH (2 mmol/L, 16 mL), H$_2$O$_2$ (30%, 2.5 mL, 32 mL) at room temperature for 2 hrs. HCl (2 mol/L, 20 mL) was added to adjust pH=6-7. The mixture was extracted DCM (200 mL×3), washed with water (100 mL×3), brine, dried over anhydrous Na$_2$SO$_4$ and concentrated under pressure concentrated and purified by column chromatography on silica gel eluting with PE/EA (4:1-2:1) to give the title compound (4.2 g, 100% yield) as yellow oil.

$^1$H NMR (300 MHz, CDCl$_3$): δ 7.23 (d, J=0.9 Hz, 1H), 7.17 (d, J=0.9 Hz, 1H), 5.34 (q, J=6.0 Hz, 1H), 3.44-3.27 (m, 2H), 1.58 (d, J=6.0 Hz, 3H), 1.11 (t, J=7.2 Hz, 3H).

D180

4-((1-(1-Ethoxyethyl)-1H-pyrazol-4-yl)oxy)-3,5-difluorobenzaldehyde

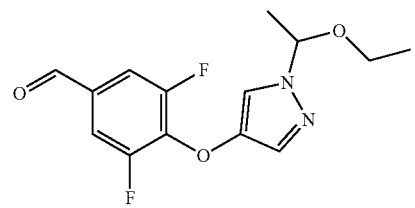 [SMILES: CCOC(C)n1cc(Oc2c(F)cc(C=O)cc2F)cn1]

A mixture of 1-(1-ethoxyethyl)-1H-pyrazol-4-ol (3.0 g, 19 mmol), 3,4,5-trifluorobenzaldehyde (3.0 g, 19 mmol), K$_2$CO$_3$ (8.0 g, 58 mmol) in DMF (20 mL) was stirred at 60° C. for 2 hrs. The mixture was washed with water (200 mL×3), brine, extracted DCM (200 mL×3), dried over anhydrous Na$_2$SO$_4$ and concentrated under pressure concentrated and purified by column chromatography on silica gel eluting with PE/EA (4:1-2:1) to give the title compound (2.1 g, 37% yield) as yellow oil.

$^1$H NMR (300 MHz, CDCl$_3$): δ 9.89 (t, J=1.8 Hz, 1H), 7.55-7.53 (m, 2H), 7.44 (s, 1H), 7.32 (s, 1H), 5.40 (q, J=6.0 Hz, 1H), 3.47-3.33 (m, 2H), 1.61 (d, J=6.0 Hz, 3H), 1.13 (t, J=7.2 Hz, 3H).

D181

4-((1H-Pyrazol-4-yl)oxy)-3,5-difluorobenzaldehyde

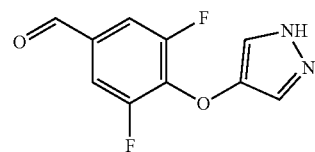 [SMILES: O=Cc1cc(F)c(Oc2cn[nH]c2)c(F)c1]

A mixture of 4-((1-(1-ethoxyethyl)-1H-pyrazol-4-yl) oxy)-3,5-difluorobenzaldehyde (2.1 g, 7.1 mmol) in HCl (2 mol/L): HCl in dioxane (sat.)=15 mL: 15 mL was stirred at room temperature for 1 h. NaOH (2 mol/L, 50 mL) was added to adjust pH=6-7. The mixture was extracted EtOAc (200 mL×3), washed with water (200 mL×3), brine, dried over anhydrous Na$_2$SO$_4$ and concentrated under pressure concentrated and purified by column chromatography on silica gel eluting with PE/EA (1:1) to give the title compound (1.5 g, 94% yield) as yellow oil.

$^1$H NMR (300 MHz, CDCl$_3$): δ 9.89 (t, J=1.8 Hz, 1H), 7.53-7.45 (m, 4H).

D182

3,5-Difluoro-4-((1-propyl-1H-pyrazol-4-yl)oxy)benzaldehyde

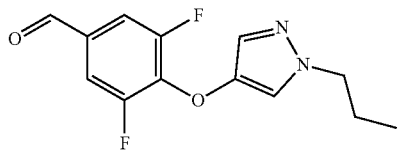 [SMILES: CCCn1cc(Oc2c(F)cc(C=O)cc2F)cn1]

A mixture of 4-((1H-pyrazol-4-yl)oxy)-3,5-difluorobenzaldehyde (1.5 g, 6.7 mmol), 1-bromopropane (1.65 g, 13.4 mmol), K₂CO₃ (2.78 g, 20.1 mmol) in DMF (25 mL) was stirred at 30° C. overnight. The mixture was washed with water (100 mL×3), brine, extracted EtOAc (100 mL×3), dried over anhydrous Na₂SO₄ and concentrated under pressure concentrated and purified by column chromatography on silica gel eluting with PE/EA (4:1) to give the title compound (1.2 g, 80% yield) as yellow oil.

¹H NMR (300 MHz, CDCl₃): δ 9.89-9.88 (m, 1H), 7.54-7.47 (m, 2H), 7.30-7.27 (m, 2H), 3.99 (t, J=6.9 Hz, 2H), 1.91-1.76 (m, 2H), 0.91 (t, J=4.2 Hz, 3H).

D183

(3,5-Difluoro-4-((1-propyl-1H-pyrazol-4-yl)oxy)phenyl)methanol

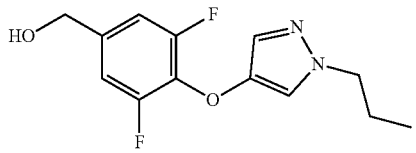 [SMILES: CCCn1cc(Oc2c(F)cc(CO)cc2F)cn1]

To a solution of 3,5-difluoro-4-((1-propyl-1H-pyrazol-4-yl)oxy)benzaldehyde (1.2 g, 4.51 mmol) in methanol (20 mL) was added NaBH₄ (171 mg, 45.1 mmol) at RT for 1 h. NaOH (sat. 1 mL) was added to quench the reaction. The mixture was concentrated with silica gel and purified by column chromatography on silica gel eluting with PE/EA (4:1) to give the title compound (1.2 g, 99% yield) as a white solid.

LCMS: Rt=3.505 min, [M+H]⁺=269.

¹H NMR (300 MHz, CDCl₃) δ 7.25-7.20 (m, 2H), 6.98 (d, J=3.6 Hz, 2H), 4.66 (d, J=3.6 Hz, 2H), 3.96 (t, J=3.6 Hz, 2H), 2.10 (t, J=6.0 Hz, 1H), 1.86-1.79 (m, 2H), 0.89 (t, J=7.2 Hz, 3H).

D184

3,5-Difluoro-4-((6-methylpyridin-3-yl)oxy)benzaldehyde

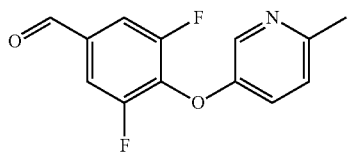 [SMILES: Cc1ccc(Oc2c(F)cc(C=O)cc2F)cn1]

To a solution of 3,4,5-trifluorobenzaldehyde (2.9 g, 18 mmol), 6-methylpyridin-3-ol (2.0 g, 18 mmol) in dry DMF (50 mL) was added K₂CO₃ (7.6 g, 55 mmol) at 50° C. The reaction mixture was stirred at 50° C. overnight, and then concentrated. The residue was dissolved with water (100 mL), extracted with EA (100 mL×3). The combined organic layers was dried over anhydrous Na₂SO₄, concentrated under reduced pressure and purified by column chromatography on silica gel eluting with PE/EA (4:1) to give the title compound (4.0 g, 89% yield) as colorless oil.

¹H NMR (300 MHz, CDCl₃): δ 9.91 (t, J=1.8 Hz, 1H), 8.27 (d, J=3.0 Hz, 1H), 7.59-7.51 (m, 2H), 7.19-7.09 (m, 2H), 2.53 (s, 3H).

D185

(3,5-Difluoro-4-((6-methylpyridin-3-yl)oxy)phenyl)methanol

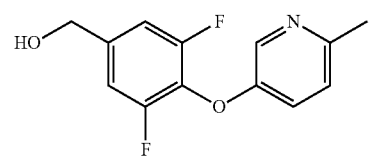 [SMILES: Cc1ccc(Oc2c(F)cc(CO)cc2F)cn1]

To a solution of 3,5-difluoro-4-((6-methylpyridin-3-yl)oxy)benzaldehyde (4.0 g, 16 mmol) in MeOH (50 mL) was added NaBH₄ (610 mg, 16.1 mmol) at 0° C. The reaction mixture was stirred at RT for 2 h. The reaction mixture was concentrated and the residue was dissolved with water (100 mL), extracted with EA (100 mL×3). The combined organic layers was dried over anhydrous Na₂SO₄, concentrated under reduced pressure and purified by prep-HPLC to give the title compound (3.76 g, 94% yield) as a white solid.

¹H NMR (300 MHz, CDCl₃): δ 8.23 (d, J=2.7 Hz, 1H), 7.26-7.01 (m, 4H), 4.71 (d, J=5.7 Hz, 2H), 2.51 (s, 3H), 2.33 (t, J=6.0 Hz, 1H).

D186

4-((1-(Bromodifluoromethyl)-1H-pyrazol-4-yl)oxy)-3,5-difluorobenzaldehyde

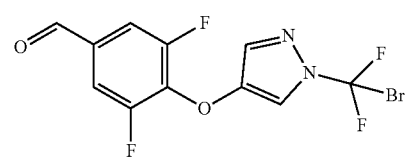 [SMILES: O=Cc1cc(F)c(Oc2cnn(C(F)(F)Br)c2)c(F)c1]

A mixture of 4-((1H-pyrazol-4-yl)oxy)-3,5-difluorobenzaldehyde, CF₂Br₂ (3 ml), K₂CO₃ (4.25 g, 30.9 mmol) in DMF (35 mL) was stirred at room temperature overnight. The mixture was filtrated, concentrated and purified by column chromatography on silica gel eluting with PE/EA (9:1) to give the title compound (600 mg, 17% yield) as yellow oil.

¹H NMR (300 MHz, CDCl₃): δ 9.91 (t, J=1.8 Hz, 1H), 7.67-7.54 (m, 4H).

D187

3,5-Difluoro-4-((1-(trifluoromethyl)-1H-pyrazol-4-yl)oxy)benzaldehyde

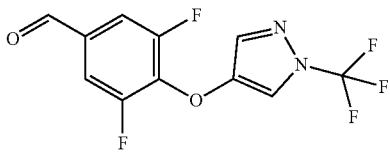 [SMILES: O=Cc1cc(F)c(Oc2cnn(C(F)(F)F)c2)c(F)c1]

To a solution of 4-((1-(bromodifluoromethyl)-1H-pyrazol-4-yl)oxy)-3,5-difluorobenzaldehyde (600 mg, 1.61 mmol), HgO (1.1 g, 5.07 mol) in isopropyl ether (20 mL) was added HF-Pyridine solution (2 mL) at room temperature overnight. Sat. KF solution (1 mL) was added to quench the reaction. The reaction mixture was concentrated and the residue was dissolved with water (40 mL), and extracted with EA (20 mL×3). The combined organic layers was dried over anhydrous Na$_2$SO$_4$, concentrated and purified by column chromatography on silica gel eluting with PE/EA (4:1) to give the title compound (450 mg, 75% yield) as yellow oil.

$^1$H NMR (300 MHz, CDCl$_3$): δ 9.92-9.90 (m, 1H), 7.68-7.52 (m, 4H).

D188

(3,5-Difluoro-4-((1-(trifluoromethyl)-1H-pyrazol-4-yl)oxy)phenyl)methanol

To a solution of 3,5-difluoro-4-((1-(trifluoromethyl)-1H-pyrazol-4-yl)oxy)benzaldehyde (420 mg, 1.44 mmol) in methanol (20 mL) was added NaBH$_4$ (55 mg, 1.44 mmol) at room temperature for 1 hour. NaOH (sat. 1 mL) was added to quench the reaction. The mixture was concentrated with silica gel and purified by column chromatography on silica gel eluting with PE/EA (4:1) to give the title compound (160 mg, 40% yield) as yellow oil.

$^1$H NMR (300 MHz, CDCl$_3$): δ 7.59-7.47 (m, 2H), 7.07-6.96 (m, 2H), 4.70 (t, J=4.8 Hz, 2H), 2.50 (s, 1H). LCMS: Rt=3.822 min, [M+H]$^+$=295.

D189

3,5-Difluoro-4-((2-methylpyrimidin-5-yl)oxy)benzaldehyde

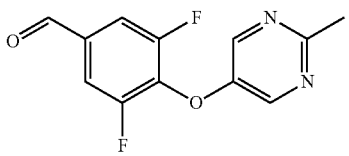 [SMILES: Cc1ncc(Oc2c(F)cc(C=O)cc2F)cn1]

To a solution of 2-methylpyrimidin-5-ol (4.5 g, 41 mmol) and 3,4,5-trifluorobenzaldehyde (6.6 g, 41 mmol) in DMF (150 mL) was added NaH (60% in mineral oil, 3.3 g, 82 mmol) at 0° C. The reaction mixture was stirred at RT for 2 hrs. The reaction mixture was concentrated and the residue was dissolved with water (100 mL), extracted with EA (200 mL×3). The combined organic layers were washed with brine and dried over anhydrous Na$_2$SO$_4$, then filtered and concentrated under reduced pressure. The residue was purified by column chromatography on silica gel eluting with (PE/EA=50/1) to give the title compound (5.6 g, 55% yield) as a white solid.

$^1$H NMR (300 MHz, CDCl$_3$): δ 9.93 (t, J=1.8 Hz, 1H), 8.39 (s, 2H), 7.61-7.58 (m, 2H), 2.73 (s, 3H).

D190

(3,5-Difluoro-4-((2-methylpyrimidin-5-yl)oxy)phenyl)methanol

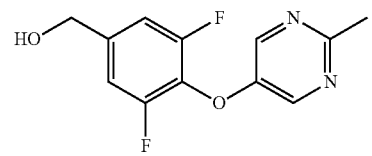 [SMILES: Cc1ncc(Oc2c(F)cc(CO)cc2F)cn1]

To a solution of 3,5-difluoro-4-((5-methylpyrimidin-2-yl)oxy)benzaldehyde (4.0 g, 16 mmol) in methanol (100 mL) was added NaBH$_4$ (1.2 g, 32 mmol) in portions at 0° C. The reaction mixture was stirred at RT for 2 hrs. Then H$_2$O (5 mL) was added to quench the reaction and the solution was concentrated. The residue was purified by column chromatography on silica gel eluting with PE/EA=5/1 to give the title compound (2.6 g, 66%) as a white solid.

$^1$H NMR (300 MHz, CDCl$_3$): δ 8.34 (s, 2H), 7.06 (d, J=8.4 Hz, 2H), 4.72 (d, J=5.7 Hz, 2H), 2.71 (s, 3H), 1.97 (t, J=5.7 Hz, 1H).

D191

3-Hydroxy-3-phenylcyclobutanecarboxylic acid

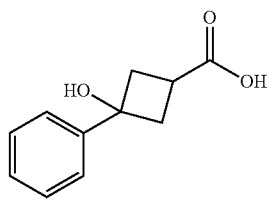 [SMILES: O=C(O)C1CC(O)(c2ccccc2)C1]

To a solution of 3-oxocyclobutanecarboxylic acid (100 g, 0.876 mol) in dry THF (1200 mL) was added PhMgBr (2.9 M, 604 mL, 1.752 mol) drop wise over 6 hrs at room temperature under N$_2$. Then saturated aq. NH$_4$Cl (1200 mL) was added and the mixture was acidified with 12M conc. HCl to pH=3. The mixture was filtered and the solution was extracted with ether (2000 mL×2). The combined organic layers were washed with brine (1000 mL×1), dried over Na$_2$SO$_4$, filtered and concentrated to give the title compound (168 g, 100%) as a white solid.

¹H NMR (300 MHz, DMSO-d₆): δ 12.18 (s, 1H), 7.53-7.25 (m, 5H), 5.67 (s, 1H), 2.70-2.46 (m, 5H).

D192

3-Chloro-3-phenylcyclobutanecarboxylic acid

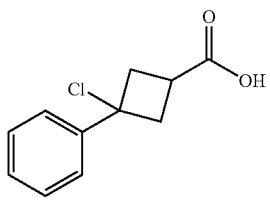 [SMILES: O=C(O)C1CC(Cl)(c2ccccc2)C1]

To a solution of 3-hydroxy-3-phenylcyclobutanecarboxylic acid (168.0 g, 0.87 mol) in toluene (1500 mL) was added conc. HCl (1000 mL). The mixture was stirred at room temperature for 4 hrs. The organic phase was separated, washed with water (1000 mL, brine (1000 mL) and concentrated to give the title compound (152 g, 83%) as a white solid.

¹H NMR (300 MHz, DMSO-d₆): δ 7.41-7.33 (m, 5H), 2.97-2.94 (m, 5H).

D193

Methyl 3-chloro-3-phenylcyclobutanecarboxylate

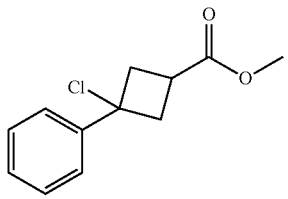

To a solution of 3-chloro-3-phenylcyclobutanecarboxylic acid (152 g, 0.72 mol) and K₂CO₃ (219 g, 1.58 mol) in DMF (1500 mL) was added CH₃I (205 g, 1.44 mol). The mixture was stirred at room temperature for overnight. The result mixture was filtered and diluted with water (1500 mL), extracted with EA (2500 mL). The organic phase was separated, washed with brine (2000 mL), dried over Na₂SO₄, filtered and concentrated. The residue was purified by column chromatography on silica gel eluting with PE/EtOAc (50:1~30:1) to give the title compound (130 g, 80%) as a white solid.

¹H NMR (300 MHz, CDCl₃): δ 7.48-7.30 (m, 5H), 3.70 (s, 3H), 3.30-2.90 (m, 5H).

D194

Methyl 3-phenylbicyclo[1.1.0]butane-1-carboxylate

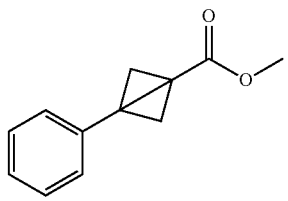

To a solution of NaHMDS (2.0 M, 350 mL, 0.70 mol) in THF (1000 mL) was added a solution of methyl 3-chloro-3-phenylcyclobutanecarboxylate (130.0 g, 0.58 mol) in THF (500 mL). The mixture was stirred at 70° C. for 5 hours. The mixture was cooled to room temperature. Then saturated NH₄Cl (500 mL) was added and the mixture was filtered. The filtrate was extracted with ether (2000 mL). The organic phase was washed with brine (2000 mL), dried over Na₂SO₄, filtered and concentrated. The residue was purified by column chromatography on silica gel eluting with PE/EtOAc (50:1) to give a yellow solid and then recrystallization from hexane (500 mL) to give the title compound (67.4 g, 62%) as a white solid.

¹H NMR (300 MHz, CDCl₃): δ 7.31-7.29 (m, 5H), 3.48 (s, 3H), 3.93-2.92 (m, 2H), 1.61-1.60 (m, 2H).

D195

2,2-Dichloro-3-phenylbicyclo[1.1.1]pentane-1-carboxylic acid

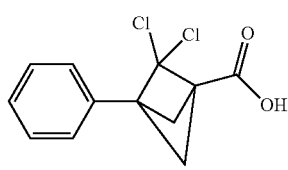 [SMILES: O=C(O)C12CC(c3ccccc3)(C1)C2(Cl)Cl]

A mixture of methyl 3-phenylbicyclo[1.1.0]butane-1-carboxylate (67.4 g, 0.358 mol) and diglyme (270 mL) in 02014 (2700 mL) was heated to 120° C. Then, CCl₃COONa (249.0 g, 1.343 mol) was added in one portion. The mixture was heated to 140° C. for 3 hours and then cooled to room temperature, filtered through Celite and the filter cake was washed with DCM (300 mL×3). The filtrate was concentrated and purified by column chromatography on silica gel eluting with PE/DCM (50:1-20:1) to give the crude product which was recrystallized from hexane to give the title compound (44.8 g, 46%) as a white solid.

¹H NMR (300 MHz, DMSO-d₆): δ 7.38-7.25 (m, 5H), 3.83 (s, 3H), 3.56-3.03 (m, 2H), 1.95-1.80 (m, 2H).

D196

3-Phenylbicyclo[1.1.1]pentane-1-carboxylic acid

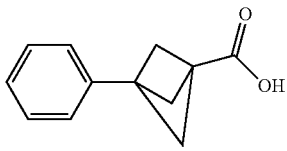 [SMILES: O=C(O)C12CC(c3ccccc3)(C1)C2]

A mixture of 2,2-dichloro-3-phenylbicyclo[1.1.1]pentane-1-carboxylic acid (10.0 g, 36.9 mmol), Bu₃SnH (48.3 g, 166 mmol) and AIBN (200 mg) was stirred under N₂ at 130° C. for 16 hours. After cooled to room temperature, AIBN (200 mg) was added and the mixture was stirred under N₂ at 130° C. for 20 hours. The mixture was cooled to room temperature, Bu₃SnH (5.68 g) and AIBN (200 mg) were added and stirred under N₂ at 130° C. for 20 hours. The mixture was cooled to room temperature; AIBN (200 mg) was added and stirred under N₂ at 130° C. for 20 hours. After cooling, 10% NaOH (200 mL) was added. The mixture was heated at 100° C. for 2 hours. The mixture was cooled to room temperature, extracted with ether (100 mL). The aqueous solution was acidified with conc. HCl to pH=4, extracted with ether (200 mL×3). The organic layer was washed with brine, dried over Na₂SO₄, filtered and concentrated to give the title compound (2.7 g, 30%) as a yellow solid.

¹H NMR (300 MHz, CDCl₃): δ 7.33-7.22 (m, 5H), 2.37 (s, 6H).

D197

Methyl 3-phenylbicyclo[1.1.1]pentane-1-carboxylate

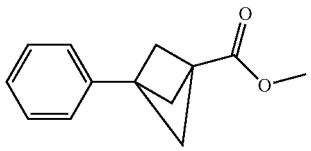

To a mixture of 50% KOH (40 mL) in ether (40 mL) was added amino-N-methyl-N-nitrosoamide (13.8 g) dropwise at 0° C. Ten minutes later, the organic phase was separated, dried over KOH to give a solution of CH₂N₂ in ether (130 mL). To a solution of 3-phenylbicyclo[1.1.1]pentane-1-carboxylic acid (2.70 g, 14.3 mol) in ether (130 mL) was added the above solution of CH₂N₂ in ether (130 mL). The mixture was stirred at room temperature for 1 hour. 1 N HCl (100 mL) was added and stirred 10 min. The organic phase was separated, washed with saturated NaHCO₃ (100 mL), brine (100 mL), dried over Na₂SO₄, filtered and concentrated to give the title compound (1.57 g, 54%) as brown oil.

¹H NMR (300 MHz, CDCl₃): δ 7.45-7.21 (m, 5H), 3.73 (s, 3H), 2.33 (s, 6H).

D198

3-(Methoxycarbonyl)bicyclo[1.1.1]pentane-1-carboxylic acid

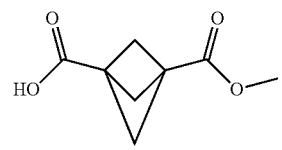

To a solution of methyl 3-phenylbicyclo[1.1.1]pentane-1-carboxylate (2.26 g, 11.2 mmol) in CCl₄ (68 mL), MeCN (68 mL) and H₂O (100 mL) was added NaIO₄ (43.1 g, 201.6 mmol) and RuCl₃·nH₂O (90 mg). The mixture was stirred at room temperature for 1 day, extracted with DCM (100 mL×3). The organic phase was separated, washed with brine (200 mL), dried over Na₂SO₄, filtered and concentrated. The residue was purified by column chromatography on silica gel eluting with DCM/MeOH (20:1) to give black oil. The black oil was further purified by prep-TLC to give the title compound (220 mg, 11%) as a black solid.

¹H NMR (300 MHz, CDCl₃): δ 3.69 (s, 3H), 2.34 (s, 6H).

D199

Bicyclo[1.1.1]pentane-1,3-diyldimethanol

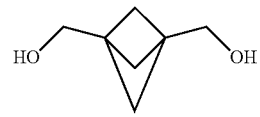

To a solution of 3-(methoxycarbonyl)bicyclo[1.1.1]pentane-1-carboxylic acid (220 mg, 1.29 mmol) in THF (5 mL) was added BH₃·THF (1.0 M, 2.6 mL, 2.58 mmol) dropwise at 0° C. The mixture was stirred at room temperature for 2 hours and followed by addition of MeOH (5 mL). The mixture was concentrated to give the title compound (180 mg, 100%) as a black solid.

¹H NMR (300 MHz, CDCl₃): δ 3.62 (s, 4H), 1.64 (s, 6H).

D200

(3-(((2-(Trifluoromethyl)pyridin-4-yl)oxy)methyl)bicyclo[1.1.1]pentan-1-yl)methanol

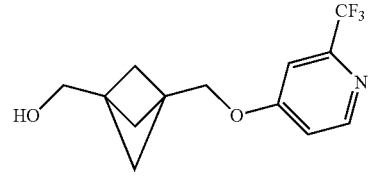 [SMILES: OCC12CC(COc3ccnc(C(F)(F)F)c3)(C1)C2]

To a solution of bicyclo[1.1.1]pentane-1,3-diyldimethanol (90 mg, 0.63 mmol) in DMF (2 mL) was added NaH (60% in mineral oil, 25 mg, 0.63 mmol) at 5° C. and stirred for 10 min, followed by addition of 4-chloro-2-(trifluoromethyl)pyridine (102 mg, 0.56 mmol). The mixture was stirred at 5° C. for overnight, diluted with water (5 mL) and extracted with EA (10 mL×3). The organic phases was washed with brine (20 mL), dried over Na₂SO₄, filtered and concentrated. The residue was purified by prep-TLC (DCM/MeOH=20:1) to give the title compound (32 mg, 24%) as a white solid.

¹H NMR (300 MHz, CDCl₃): δ 8.51 (d, J=5.7 Hz, 1H), 7.26 (s, 1H), 7.18 (d, J=2.4 Hz, 1H), 6.95-6.92 (m, 1H), 4.01 (s, 2H), 3.64 (s, 2H), 1.78 (s, 6H).

D201

(4-Fluoro-3-(methylsulfonyl)phenyl)methanol

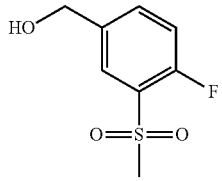

To a solution of 4-fluoro-3-(methylsulfonyl)benzaldehyde (150 mg, 0.742 mmol) in methanol (2 mL) was added NaBH₄ (42.1 mg, 1.113 mmol). The solution was stirred at room temperature for 30 min. The mixture was diluted with water and extracted with EA. The organic phase was washed with brine, driver over Na₂SO₄, filtrated and concentrated in vacuo to give the title compound (120 mg, 0.588 mmol, 79% yield) as brown oil.

LC-MS (ESI): m/z 205 [M+H]⁺; 1.36 min (ret time).

D202

Methyl 4-(bromomethyl)-3-fluorobenzoate

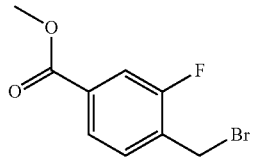

To a mixture of 1-bromopyrrolidine-2,5-dione (3.18 g, 17.84 mmol) in perchloromethane (20 mL) was added methyl 3-fluoro-4-methylbenzoate (2.5 g, 14.87 mmol) and (E)-2,2'-(diazene-1,2-diyl)bis(2-methylpropanenitrile) (0.244 g, 1.487 mmol). The resulting mixture was stirred at 70° C. for 2 hours. The mixture was concentrated in vacuo and the crude was purified by column chromatography on silica gel eluting with petroleum ether/EtOAc (100% to 20/1) to give the title compound (2.44 g, 8.62 mmol, 58.0% yield) as yellow oil.

LC-MS (ESI): m/z 247 [M−H]⁺; 1.76 min (ret time).

D203

Methyl 4-((3,3-difluoropiperidin-1-yl)methyl)-3-fluorobenzoate

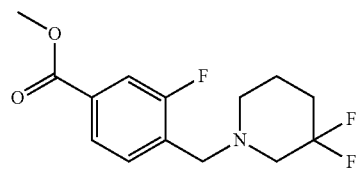 [SMILES: COC(=O)c1ccc(CN2CCCC(F)(F)C2)c(F)c1]

A mixture of methyl 4-(bromomethyl)-3-fluorobenzoate (200 mg, 0.810 mmol), 3,3-difluoropiperidine (98 mg, 0.810 mmol) and potassium carbonate (336 mg, 2.429 mmol) in acetonitrile (20 mL) was stirred at 80° C. for 2 hours. The mixture was then diluted with CH₂Cl₂ and washed with water (30 mL×2). The organic phase was dried over Na₂SO₄, filtered and concentrated in vacuo to give the title compound (270 mg, 0.459 mmol, 56.7% yield) as light yellow oil.

LC-MS (ESI): m/z 288 [M+H]⁺; 1.53 min (ret time).

D204

(4-((3,3-Difluoropiperidin-1-yl)methyl)-3-fluorophenyl)methanol

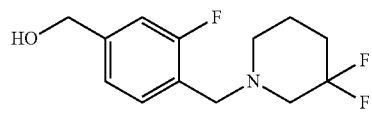 [SMILES: OCc1ccc(CN2CCCC(F)(F)C2)c(F)c1]

To a solution of methyl 4-((3,3-difluoropiperidin-1-yl)methyl)-3-fluorobenzoate (270 mg, 0.940 mmol) in THF (10 mL) was added LiAlH₄ (71.3 mg, 1.880 mmol) at 0° C. The mixture was stirred at room temperature for 1 hour. The mixture was quenched with water (0.1 mL), 15% NaOH solution (0.1 mL) and water (0.1 mL). The mixture was filtered and washed with EtOAc (20 mL). The filtrate was concentrated in vacuo to give the title compound (223 mg, 0.826 mmol, 88% yield) as colorless oil.

LC-MS (ESI): m/z 260 [M+H]⁺; 1.20 min (ret time).

D205

4-((4,4-Difluorocyclohexyl)oxy)-3,5-difluorobenzoic acid

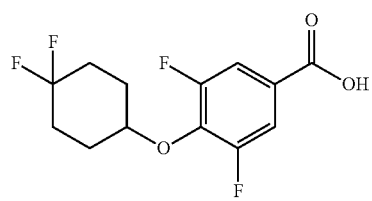 [SMILES: O=C(O)c1cc(F)c(OC2CCC(F)(F)CC2)c(F)c1]

To a solution of 3,4,5-trifluorobenzoic acid (1.14 g, 6.5 mmol) and 4,4-difluorocyclohexanol (800 mg, 6.5 mmol) in DMF (50 mL) was added NaH (60% in mineral oil, 1.04 g, 25.9 mmol) at 0° C. The mixture was stirred at room temperature for 6 hours. The mixture was poured into ice-water (100 mL). The mixture was acidified with conc. HCl to pH<7, extracted with EA (50 mL×3), brine, dried over $Na_2SO_4$, filtered and evaporated to give the title compound (1.9 g, yield 100%) as a yellow solid.

D206

(4-((4,4-Difluorocyclohexyl)oxy)-3,5-difluorophenyl)methanol

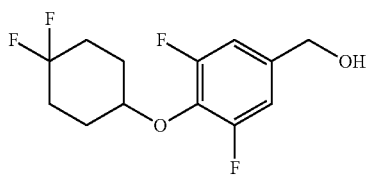 [SMILES: OCc1cc(F)c(OC2CCC(F)(F)CC2)c(F)c1]

To a solution of $BH_3$-THF (1 M in THF, 14.4 mL, 14.4 mmol) was added 4-((4,4-difluorocyclohexyl)oxy)-3,5-difluorobenzoic acid (2.1 g, 7.2 mmol) in THF (20 mL) at 0° C. The mixture was heated to reflux and stirred for 3 hours. The mixture was cooled to room temperature and quenched with MeOH (10 mL). The solution was then concentrated and purified by prep-TLC (DCM/MeOH=30/1) to give the title compound (1.4 g, yield 70%) as a white solid.

$^1$H NMR (300 MHz, $CDCl_3$): δ 6.97-6.90 (m, 2H), 4.63 (s, 2H), 4.37-4.36 (m, 1H), 2.34-1.36 (m, 8H).

D207

4-(Benzyloxy)-3,5-difluorobenzoic acid

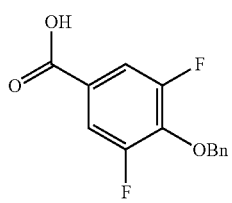 [SMILES: O=C(O)c1cc(F)c(OCc2ccccc2)c(F)c1]

To a solution of 3,4,5-trifluorobenzoic acid (3.52 g, 20 mmol) and phenylmethanol (2.16 g, 20 mmol) in DMF (50 mL) was added NaH (60% in mineral oil, 3.2 g, 80 mmol) at 0° C. The mixture was stirred at room temperature overnight. The mixture was quenched with ice water (100 mL). The mixture was acidified with conc. HCl to pH<7, extracted with EA (50 mL×3). The organic layer was washed with brine, dried over $Na_2SO_4$, filtered, evaporated and purified by flash chromatograph on silica gel (PE/EA=4/1) to give the title compound (5.0 g, yield 88%) as a yellow solid.

$^1$H NMR (300 MHz, $CDCl_3$): δ 7.64-7.61 (m, 2H), 7.46-7.33 (m, 5H), 5.31 (s, 2H).

D208

Methyl 4-(benzyloxy)-3,5-difluorobenzoate

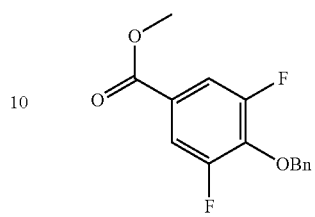

A solution of 4-(benzyloxy)-3,5-difluorobenzoic acid (5.0 g, 18.9 mmol) and conc $H_2SO_4$ (1 mL) in MeOH (50 mL) was heated to reflux and stirred overnight. The solution was evaporated and treated with water (30 mL). The mixture was extracted with EA (50 mL×3). The organic layer was washed with brine, dried over $Na_2SO_4$ and concentrated. The residue was purified by flash chromatograph on silica gel (PE/EA=20/1) to give the title compound (4.6 g, yield 88%) as yellow oil.

$^1$H NMR (300 MHz, $CDCl_3$): δ 7.58-7.53 (m, 2H), 7.45-7.32 (m, 5H), 5.28 (s, 2H), 3.89 (s, 3H).

D209

Methyl-3,5-difluoro-4-hydroxybenzoate

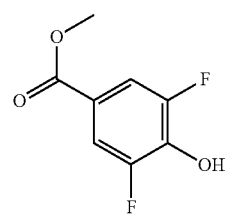

A mixture of methyl 4-(benzyloxy)-3,5-difluorobenzoate (4.6 g, 16.5 mmol) and Pd/C (10% wet, 200 mg) in MeOH (30 mL) was stirred at room temperature under $H_2$ (1 atm) for 4 hours. The mixture was filtered and evaporated to give the title compound (2.3 g, yield 74%) as a yellow solid.

$^1$H NMR (300 MHz, $CDCl_3$): δ 7.64-7.61 (m, 2H), 3.91 (s, 3H).

D210

Methyl 3,5-difluoro-4-(2-fluoroethoxy)benzoate

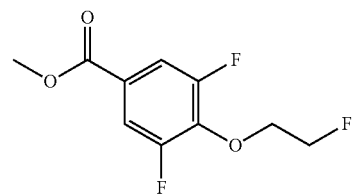 [SMILES: COC(=O)c1cc(F)c(OCCF)c(F)c1]

A mixture of methyl 3,5-difluoro-4-hydroxybenzoate (1.4 g, 7.45 mmol), 1-bromo-2-fluoroethane (946 mg, 7.45 mmol), Cs₂CO₃ (2.9 g, 8.9 mmol) in acetonitrile (30 mL) was stirred at 70° C. for 4 hours. The reaction mixture was washed with water, extracted with EA (50 mL×2), dried over Na₂SO₄, filtrated, concentrated. The crude was purified by flash chromatography on silica gel (PE/EA=4:1) to give the title compound (1.5 g, yield 87%) as colorless oil.

¹H NMR (300 MHz, CDCl₃): δ 7.57-7.54 (m, 2H), 4.77 (t, J=3.9 Hz, 1H), 4.61 (t, J=3.9 Hz, 1H), 4.51-4.48 (m, 1H), 4.41-4.39 (m, 1H), 3.88 (s, 3H).

D211

(3,5-Difluoro-4-(2-fluoroethoxy)phenyl)methanol

To a mixture of methyl 3,5-difluoro-4-(2-fluoroethoxy) benzoate (1.5 g, 6.4 mmol) in THF (20 mL) was added LiAlH₄ (243 mg, 6.4 mmol) at 0° C. The mixture was stirred at 0° C. for 1 hour. MeOH was added to quench the reaction. Potassium sodium tartrate (sat. 10 mL) was added and the mixture was stirred at room temperature 1 hour. The mixture was filtered and the filtrate was evaporated and purified by flash chromatography on silica gel (PE/EA=4/1 to 1/1) to give the title compound (1.16 g, yield 89%) as colorless oil.

¹H NMR (300 MHz, CDCl₃): δ 6.96-6.87 (m, 2H), 4.80-4.77 (m, 1H), 4.64-4.60 (m, 3H), 4.42-4.39 (m, 1H), 4.31-4.29 (m, 1H), 2.09 (t, J=6.0 Hz, 1H).

D212

5-(Hydroxymethyl)-2-methylbenzonitrile

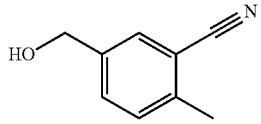

To an ice-cold solution of 5-formyl-2-methylbenzonitrile (0.5 g, 3.44 mmol) in 1:1 MeOH/2-MeTHF (9 mL) was added NaBH₄ (0.145 g, 3.83 mmol), and the reaction mixture was stirred for 3 h. The reaction mixture was diluted with saturated NH₄Cl which resulted in a grayish white precipitate. The aqueous layer was extracted with EtOAc (3×100 mL). The combined organics were washed with brine, dried on Na₂SO₄, filtered, and concentrated under reduced pressure to provide 5-(hydroxymethyl)-2-methylbenzonitrile (460 mg, 3.13 mmol, 91% yield) as a moderately viscous light-yellow liquid.

LC-MS (ESI): m/z 148[M+H]⁺; 0.56 min (ret time).

D213

(S)-6-(4-bromophenethoxy)-10,10a-dihydro-1H-oxazolo[3',4':3,4]imidazo[1,2-c]pyrimidin-8(3H)-one

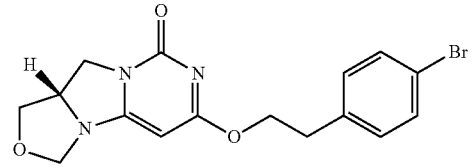 [SMILES: O=c1nc(OCCc2ccc(Br)cc2)cc2n1C[C@H]1COCN21]

To a solution of (S)-6-chloro-10,10a-dihydro-1H-oxazolo[3',4':3,4]imidazo[1,2-c]pyrimidin-8(3H)-one and 2-(4-bromophenyl)ethanol (103 mg, 0.51 mmol) in DMF (5 mL) was added NaH (60% in mineral oil, 38 mg, 0.94 mmol) at 0° C. The reaction mixture was stirred at room temperature for 2 h. The reaction mixture was concentrated and the residue was quenched with water (40 mL), extracted with EtOAc (40 mL×3). The combined organic layers were dried over anhydrous Na₂SO₄, filtered, concentrated under reduced pressure and purified by prep-HPLC to give the title compound (40 mg, yield 23%) as a white solid.

LC-MS (ESI): m/z 380[M+H]⁺; 2.26 min (ret time).

D214

(R)-3-((3-fluorophenyl)ethynyl)-8,9,9a,10 tetrahydropyrimido[6',1':2,3]imidazo[1,5-c][1,3] oxazin-1(6H)-one

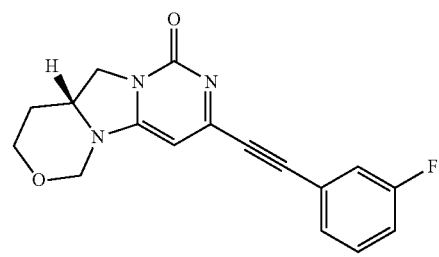 [SMILES: O=c1nc(C#Cc2cccc(F)c2)cc2n1C[C@H]1CCOCN21]

A mixture of (R)-3-chloro-8,9,9a,10-tetrahydropyrimido[6',1':2,3]imidazo[1,5-c][1,3]oxazin-1(6H)-one (90 mg, 0.40 mmol), 1-ethynyl-3-fluorobenzene (96 mg, 0.80 mmol), Pd(PPh₃)₄ (23 mg, 0.02 mmol) and CuI (8 mg, 0.04 mmol) in TEA/MeCN (2 mL/2 mL) was stirred overnight at room temperature under N₂. The mixture was evaporated and purified by TLC (DCM/MeOH=20/1) to give the title compound (25 mg, yield 20%) as a yellow solid.

LC-MS (ESI): m/z 312[M+H]⁺; 1.89 min (ret time).

D215

(S)-6-((3-fluorophenyl)ethynyl)-10,10a-dihydro-1H-oxazolo[3',4':3,4]imidazo[1,2-c] pyrimidin-8(3H)-one

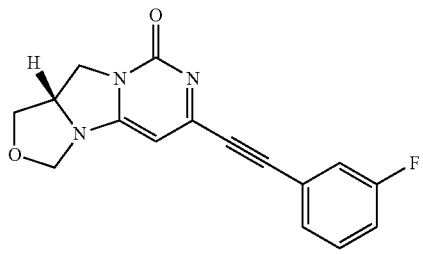 [SMILES: O=c1nc(C#Cc2cccc(F)c2)cc2n1C[C@H]1COCN21]

A mixture of (S)-6-chloro-10,10a-dihydro-1H-oxazolo[3',4':3,4]imidazo[1,2-c]pyrimidin-8(3H)-one (90 mg, 0.42 mmol), 1-ethynyl-3-fluorobenzene (101 mg, 0.84 mmol), Pd(PPh$_3$)$_4$ (24 mg, 0.021 mmol) and CuI (8 mg, 0.042 mmol) in TEA/MeCN (1 mL/1 mL) was stirred at RT under N$_2$ overnight. The reaction mixture was filtered and concentrated, the residue was purified by prep TLC (DCM/MeOH=20:1) to give the target compound (30 mg, yield 24%) as a yellow solid.

LC-MS (ESI): m/z 298[M+H]$^+$; 1.85 min (ret time).

D216

(S)-6-((2,4-difluorophenyl)ethynyl)-10,10a-dihydro-1H-oxazolo[3',4':3,4]imidazo[1,2-c] pyrimidin-8(3H)-one

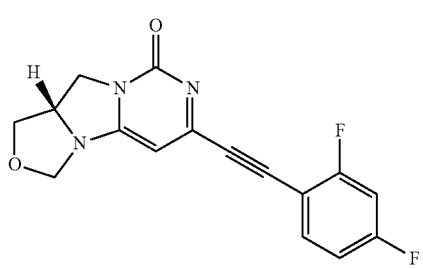 [SMILES: O=c1nc(C#Cc2ccc(F)cc2F)cc2n1C[C@H]1COCN21]

A mixture of (S)-6-chloro-10,10a-dihydro-1H-oxazolo[3',4':3,4]imidazo[1,2-c]pyrimidin-8(3H)-one (100 mg, 0.47 mmol), 1-ethynyl-2,4-difluorobenzene (97 mg, 0.70 mmol), Pd(PPh$_3$)$_4$ (27 mg, 0.024 mmol) and CuI (9 mg, 0.047 mmol) in TEA/MeCN (2 mL/2 mL) was stirred at RT under N$_2$ overnight. The reaction mixture was concentrated, the residue was purified by prep HPLC (Column: XB C18, 4.6×33 mm; Mobile phase: A: H2O, B: MeCN, 20-95% B) to give the title compound (50 mg, yield 34%) as a light yellow solid.

LC-MS (ESI): m/z 316 [M+H]$^+$; 1.89 min (ret time).

D217

(S)-3-((3-fluorophenyl)ethynyl)-7,8,8a,9-tetrahydropyrrolo[1',2':3,4]imidazo[1,2 c]-pyrimidin-1(6H)-one

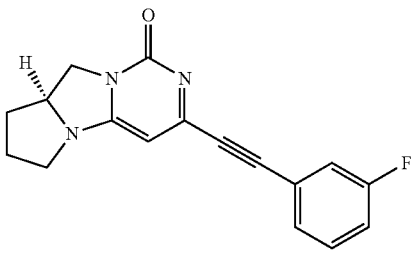 [SMILES: O=c1nc(C#Cc2cccc(F)c2)cc2n1C[C@@H]1CCCN21]

A mixture of (S)-3-chloro-7,8,8a,9-tetrahydropyrrolo[1',2':3,4]imidazo[1,2-c]pyrimidin-1(6H)-one (90 mg, 0.43 mmol), 1-ethynyl-3-fluorobenzene (102 mg, 0.86 mmol), Pd(PPh$_3$)$_2$Cl$_2$ (15 mg, 0.02 mmol), DBU (13 mg, 0.09 mmol), P(n-Bu)$_3$ (8 mg, 0.04 mmol) and Cs$_2$CO$_3$ (168 mg, 0.52 mmol) in DMF (2 mL) was purged with N$_2$. The reaction mixture was heated under microwave condition at 150° C. for 10 min. Then the reaction was evaporated under reduced pressure. The residue was purified by silica gel chromatography (MeOH/DCM=1/30) to give the title compound (30 mg, 24%) as a yellow solid.

LC-MS (ESI): m/z 296 [M+H]$^+$; 1.98 min (ret time).

D218

(R)-3-(4-bromophenethoxy)-7,8,8a,9-tetrahydropyrrolo[1',2':3,4]imidazo[1,2-c]pyrimidin-1(6H)-one

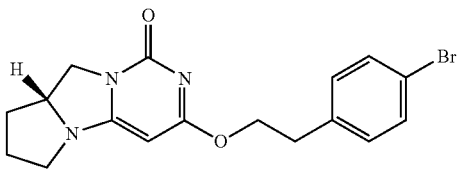 [SMILES: O=c1nc(OCCc2ccc(Br)cc2)cc2n1C[C@H]1CCCN21]

To a solution of (R)-3-chloro-7,8,8a,9-tetrahydropyrrolo[1',2':3,4]imidazo[1,2-c]pyrimidin-1(6H)-one (100 mg, 0.47 mmol) and 2-(4-bromophenyl)ethanol (105 mg, 0.52 mmol) in DMF (5 mL) was added NaH (60% in mineral oil, 38 mg, 0.94 mmol) at 0° C. The reaction mixture was stirred at room temperature for 2 h. The reaction mixture was concentrated. The residue was dissolved with water (40 mL), extracted with EtOAc (40 mL×3). The combined organic layers were dried over anhydrous Na$_2$SO$_4$, concentrated under reduced pressure and purified by prep-HPLC to give the title compound (75 mg, yield 42%) as a white solid.

LC-MS (ESI): m/z 376 [M+H]$^+$; 2.36 min (ret time).

D219

(S)-7-(4-bromophenethoxy)-3,4,11,11a-tetrahydropyrimido[6',1':2,3]imidazo[5,1-c][1,4] oxazin-9(1H)-one

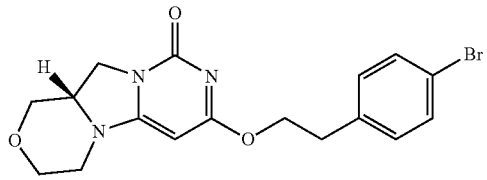 [SMILES: O=c1nc(OCCc2ccc(Br)cc2)cc2n1C[C@H]1COCCN21]

To a solution of (S)-7-chloro-3,4,11,11a-tetrahydropyrimido[6',1':2,3]imidazo[5,1-c][1,4]oxazin-9(1H)-one (100 mg, 0.44 mmol) and 2-(4-bromophenyl)ethanol (96 mg, 0.48 mmol) in DMF (5 mL) was added NaH (60% in mineral oil, 35 mg, 0.88 mmol) at 0° C. The reaction mixture was stirred at room temperature for 2 h. The reaction mixture was concentrated. The residue was dissolved with water (40 mL), extracted with EA (40 mL×3). The combined organic layers were dried over anhydrous $Na_2SO_4$, concentrated under reduced pressure and purified by prep-HPLC to give the title compound (90 mg, yield 52%) as a white solid.

LC-MS (ESI): m/z 394 $[M+H]^+$; 2.21 min (ret time).

D220

(R)-7-((3-fluorophenyl)ethynyl)-3,4,11,11a-tetrahydropyrimido[6',1':2,3]imidazo[5,1-c][1,4] oxazin-9(1H)-one

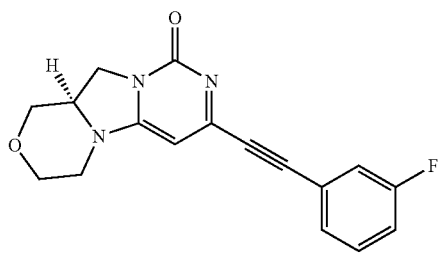 [SMILES: O=c1nc(C#Cc2cccc(F)c2)cc2n1C[C@@H]1COCCN21]

A mixture of (R)-7-chloro-3,4,11,11a-tetrahydropyrimido[6',1':2,3]imidazo[5,1-c][1,4]oxazin-9(1H)-one (80 mg, 0.35 mmol), 1-ethynyl-3-fluorobenzene (85 mg, 0.70 mmol), $Pd(PPh_3)_4$ (20 mg, 0.0175 mmol) and CuI (7 mg, 0.035 mmol) in TEA (2 mL) was degassed with $N_2$. The reaction was stirred at 120° C. for 10 min under microwave irradiation. The mixture was evaporated and purified by TLC (DCM/MeOH=30/1) to give title compound (20 mg, yield 15%) as a yellow solid.

LC-MS (ESI): m/z 312 $[M+H]^+$; 1.65 min (ret time).

D221

(S)-7-((3-fluorophenyl)ethynyl)-3,4,11,11a-tetrahydropyrimido[6',1':2,3]imidazo[5,1-c]-[1,4] oxazin-9(1H)-one

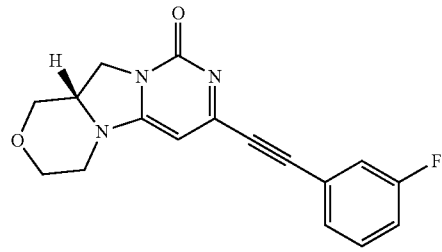 [SMILES: O=c1nc(C#Cc2cccc(F)c2)cc2n1C[C@H]1COCCN21]

A mixture of (S)-7-chloro-3,4,11,11a-tetrahydropyrimido[6',1':2,3]imidazo[5,1-c][1,4]oxazin-9(1H)-one (100 mg, 0.44 mmol), 1-ethynyl-3-fluorobenzene (106 mg, 0.88 mmol), $Pd(PPh_3)_4$ (25 mg, 0.022 mmol) and CuI (8 mg, 0.044 mmol) in TEA/MeCN (2 mL/2 mL) was stirred overnight at room temperature under $N_2$. The mixture was evaporated and purified by TLC (DCM/MeOH=20/1) to give the title compound (30 mg, yield 22%) as a yellow solid. LCMS: Rt=1.926 min, $[M+H]^+$=312.

LC-MS (ESI): m/z 312 $[M+H]^+$; 1.93 min (ret time).

D222

(S)-7-((2,4-difluorophenyl)ethynyl)-3,4,11,11a-tetrahydropyrimido[6',1':2,3]imidazo[5,1-c] [1,4]oxazin-9(1H)-one

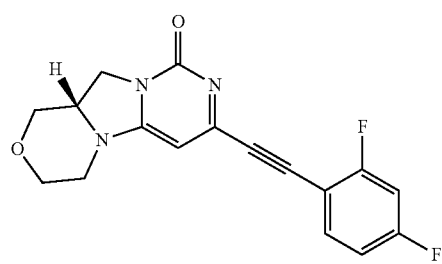 [SMILES: O=c1nc(C#Cc2ccc(F)cc2F)cc2n1C[C@H]1COCCN21]

A mixture of (S)-7-chloro-3,4,11,11a-tetrahydropyrimido[6',1':2,3]imidazo[5,1-c][1,4]oxazin-9(1H)-one (100 mg, 0.44 mmol), 1-ethynyl-2,4-difluorobenzene (91 mg, 0.66 mmol), $Pd(PPh_3)_4$ (25 mg, 0.022 mmol) and CuI (8 mg, 0.044 mmol) in TEA/MeCN (2 mL/2 mL) was stirred at RT under $N_2$ overnight. The reaction mixture was concentrated, the residue was purified by prep TLC (DCM/MeOH=30:1) to give the title compound (50 mg, yield 33%) as a light yellow solid.

LC-MS (ESI): m/z 329 $[M+H]^+$; 1.93 min (ret time).

D223

2-Cyclobutoxy-5-formylbenzonitrile

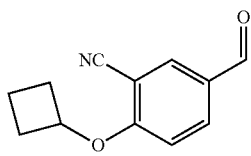 [SMILES: N#Cc1cc(C=O)ccc1OC1CCC1]

A suspension of 2-fluoro-5-formylbenzonitrile (300 mg, 2.012 mmol) and cesium carbonate (730 mg, 2.241 mmol) in acetonitrile (2 mL) was stirred at ambient temperature for 18 hrs, and then heated at 60° C. for 30 min. The reaction mixture was poured into water (2 mL) and extracted with EtOAc (3×1 mL). The combined organic layer was washed with brine, dried (anhydrous $Na_2SO_4$), filtered, and concentrated. The crude was purified on a Combiflash silica cartridge (12 g) (0-80% EtOAc/hexanes) then by reverse phase prep HPLC [10-90% $CH_3CN/H_2O$ (0.1% $NH_4OH$)] to give the title compound (60 mg, 0.298 mmol, 14.82% yield) as a white solid.

LC/MS: m/z 202.4 $(M+H)^+$, 0.85 min (ret. time)

D224

2-(Cyclopentyloxy)-5-formylbenzonitrile

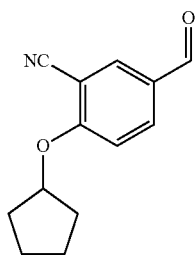 [SMILES: N#Cc1cc(C=O)ccc1OC1CCCC1]

A suspension of 2-fluoro-5-formylbenzonitrile (300 mg, 2.012 mmol) and potassium carbonate (700 mg, 5.06 mmol) in DMSO (2 mL) was sealed and heated in Biotage Initiator using initial high to 120° C. for 1 h. The reaction mixture was poured into water (6 mL) and extracted with EtOAc (5×2 mL). The combined organic layer was washed with brine, dried (anhydrous $Na_2SO_4$), filtered, and concentrated. The crude was purified on a Combiflash silica cartridge (12 g) (0-80% EtOAc/hexanes) then further purified by prep reverse phase HPLC [10-90% $CH_3CN/H_2O$ (0.1% $NH_4OH$)] to give the title compound (23 mg, 0.107 mmol, 5.31% yield) as a hazy gummy solid.

LC/MS: m/z 216.6 $(M+H)^+$, 0.94 min (ret. time)

D225 tert-Butyl 7-((2,3-difluorophenyl)ethynyl)-9-oxo-3,4,11,11a-tetrahydro-1H-pyrazino[1',2':3,4]imidazo[1,2-c]pyrimidine-2(9H)-carboxylate

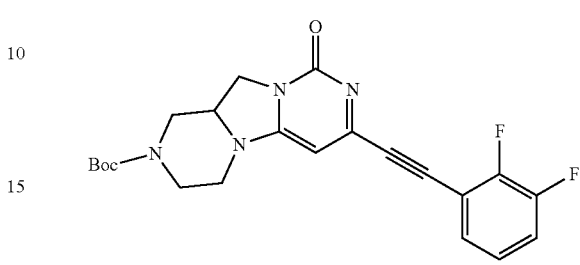

A solution of bis(triphenylphosphine)palladium(II) chloride (4 mg, 5.70 µmol), triphenylphosphine (3 mg, 0.011 mmol), copper(I) iodide (3 mg, 0.016 mmol), TEA (0.68 mL, 4.88 mmol), 1-ethynyl-2,3-difluorobenzene (0.11 mL, 0.796 mmol) and tert-butyl 7-chloro-9-oxo-3,4,11,11a-tetrahydro-1H-pyrazino[1',2':3,4]imidazo[1,2-c]pyrimidine-2(9H)-carboxylate (0.204 g, 0.624 mmol) in THF (2.5 mL) was heated at 65° C. overnight. After cooling to room temperature, the reaction was concentrated. The crude was purified on a Combiflash silica cartridge (12 g) (0-20% MeOH/DCM) to give the title compound (171 mg, 0.399 mmol, 63.9% yield) as an amorphous white solid.

LC/MS: m/z 429.2 $(M+H)^+$, 0.79 min (ret. time)

D226

7-((2,3-Difluorophenyl)ethynyl)-3,4,11,11a-tetrahydropyrimido[6',1':2,3]imidazo[5,1-c][1,4]thiazin-9(1H)-one

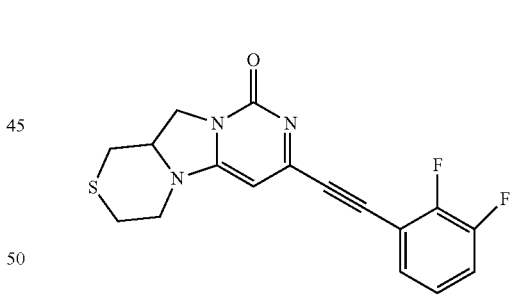

A mixture of 7-chloro-3,4,11,11a-tetrahydropyrimido[6',1':2,3]imidazo[5,1-c][1,4]thiazin-9(1H)-one (400 mg, 1.64 mmol, 1.0 equiv), 1-ethynyl-2,3-difluorobenzene (272 mg, 1.97 mmol, 1.2 equiv), and $Et_3N$ (1.2 mL, 5.0 equiv) in 8 mL of THF was bubbled with $N_2$ at rt for 10 min, followed by addition of $PdCl_2(PPh_3)_2$ (115 mg, 0.1 equiv) and CuI (31 mg, 0.1 equiv). The resulting mixture was capped and heated at 90° C. for 12 hrs. The cooled mixture was filtered through celite and the filtrate was concentrated. The residue was dissolved in 10% MeOH in DCM (20 mL) and washed with water (3 mL), diluted with saturated $NaHCO_3$ (2 mL). The aqueous was back extracted with 10% MeOH in DCM (2×5 mL). The combined organic was dried over $Na_2SO_4$, filtered, and concentrated. The crude material was purified by Teledyne-Isco Combiflash (40 g silica gel cartridge) to give the title compound (293 mg) as a light tan-colored solid.

LC/MS: m/z 346 (M+H)$^+$, 0.634 min (ret. time).

$^1$H NMR (400 MHz, 1:1 CD$_2$Cl$_2$: CD$_3$OD): δ 7.29 (t, J=6.27 Hz, 1H), 7.26-7.17 (m, 1H), 7.13-7.02 (m, 1H), 5.92 (s, 1H), 4.31-4.22 (m, 1H), 4.22-4.11 (m, 1H), 4.00-3.92 (m, 1H), 3.74-3.67 (m, 1H), 3.40-3.29 (m, 1H), 2.84-2.73 (m, 2H), 2.54-2.50 (m, 1H).

D227 tert-Butyl 7-((3,4-difluorobenzyl)oxy)-9-oxo-3,4,11,11a-tetrahydro-1H-pyrazino[1',2':3,4] imidazo[1,2-c]pyrimidine-2(9H)-carboxylate

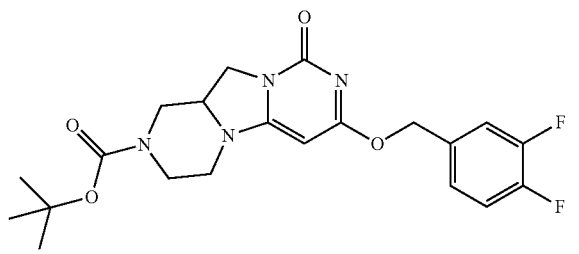 [SMILES: CC(C)(C)OC(=O)N1CCN2c3cc(OCc4ccc(F)c(F)c4)nc(=O)n3CC2C1]

To a solution of tert-butyl 7-chloro-9-oxo-3,4,11,11a-tetrahydro-1H-pyrazino[1',2':3,4]imidazo[1,2-c] pyrimidine-2(9H)-carboxylate (2.832 g, 8.67 mmol) and (3,4-difluorophenyl)methanol (1.249 g, 8.67 mmol) in anhydrous 2-Me-THF (65 mL) was added NaH (0.867 g, 21.67 mmol) and the reaction was stirred at room temperature. Saturated NH$_4$Cl (50 mL) was added and the aqueous layer was extracted with EtOAc (2×25 mL). The combined organic layer was concentrated and purified by flash chromatography to give 3.303 g (88%) of the title compound as a sticky pale brown solid.

LC/MS: m/z 435.0 (M+H)$^+$, 0.86 min (ret. time)

$^1$H NMR (400 MHz, CD$_2$Cl$_2$): δ 7.31-7.22 (m, 1H), 7.20-7.06 (m, 2H), 5.31 (br. s., 2H), 5.02 (s, 1H), 4.13 (dd, J=8.9, 11.7 Hz, 3H), 3.94-3.79 (m, 1H), 3.66 (s, 1H), 3.48-3.37 (m, 1H), 3.21-3.08 (m, 1H), 2.95-2.63 (m, 2H), 1.46 (s, 9H)

D228

7-((3,4-Difluorobenzyl)oxy)-3,4,11,11a-tetrahydro-1H-pyrazino[1',2':3,4]imidazo[1,2-c] pyrimidin-9(2H)-one

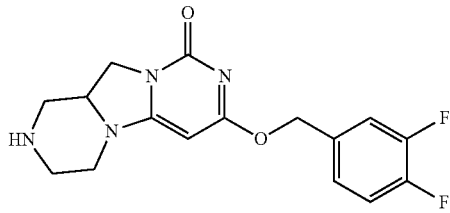 [SMILES: O=c1nc(OCc2ccc(F)c(F)c2)cc2n1CC1CNCCN21]

A mixture of tert-butyl 7-((3,4-difluorobenzyl)oxy)-9-oxo-3,4,11,11a-tetrahydro-1H-pyrazino[1',2':3,4] imidazo [1,2-c]pyrimidine-2(9H)-carboxylate (3 g, 6.91 mmol) in TFA (20 mL, 260 mmol) was stirred at room temperature for 30 min. The mixture was then concentrated. This solid was taken up in MeOH (30 mL), and BIO RAD AG 4-X4 resin (16 g) was added. The mixture was filtered, and the filtercake was rinsed with MeOH (2×30 mL). The filtrate was concentrated under reduced pressure and dried under high vacuum to give 1.604 g (70%) of the title compound as a sticky brown solid.

LC/MS: m/z 335.0 (M+H)$^+$, 0.47 min (ret. time)

$^1$H NMR (400 MHz, METHANOL-d$_4$): δ 7.40-7.31 (m, 1H), 7.29-7.17 (m, 2H), 5.34-5.20 (m, 2H), 4.21-4.06 (m, 1H), 4.02-3.83 (m, 1H), 3.70-3.50 (m, 2H), 3.17 (d, J=12.8 Hz, 2H), 3.05-2.89 (m, 1H), 2.79-2.59 (m, 2H).

D229 tert-Butyl (1-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)cyclopropyl)carbamate

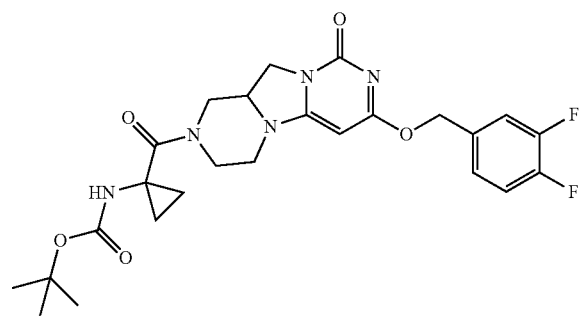 [SMILES: CC(C)(C)OC(=O)NC1(C(=O)N2CCN3c4cc(OCc5ccc(F)c(F)c5)nc(=O)n4CC3C2)CC1]

A solution of 50 wt % T3P in EtOAc (0.11 mL, 0.185 mmol) was added dropwise over 1 min, 45 sec to a solution of 7-((3,4-difluorobenzyl)oxy)-3,4,11,11a-tetrahydro-1H-pyrazino[1',2':3,4]imidazo[1,2-c] pyrimidin-9(2H)-one (50 mg, 0.150 mmol), 1-((tertbutoxycarbonyl) amino)-cyclopropanecarboxylic acid (31 mg, 0.154 mmol), and anhydrous TEA (0.09 mL, 0.649 mmol) in anhydrous DCM (1 mL) in a 2 dram vial. The vial was capped, and the reaction was stirred at room temperature. After 25 min at room temperature, the reaction was washed with 10% citric acid (1 mL) and saturated NaHCO$_3$ (1 mL). The mixture was concentrated and the crude product was then purified by flash chromatography to give 35.9 mg (46%) of the title compound.

LC/MS: m/z 518.1 (M+H)$^+$0.82 min (ret. time)

The following intermediates D230-D237 listed in Table 1 were prepared by a procedure similar to that described for D229:

TABLE 1

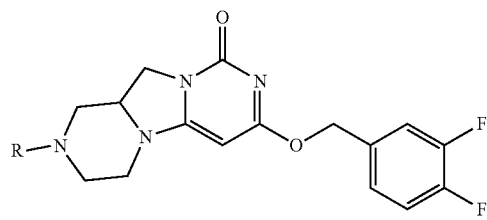

| NO# | R | Yield | LC/MS | Name |
|---|---|---|---|---|
| D230 | tert-butyl carbamate with gem-dimethyl ketone linker | 47% | m/z 534.1 (M + H)+ 0.91 min (ret. time) | tert-butyl (4-(7-((3,4-difluorobenzyl)oxy)-9-oxo-3,4,11,11a-tetrahydro 1H-pyrazino[1',2':3,4]imidazo[1,2-c]pyrimidin-2(9H)-yl)-2-methyl-4-oxobutan-2-yl)carbamate |
| D231 | tert-butyl carbamate with gem-dimethyl ketone | 22% | m/z 520.1 (M + H)+ 0.83 min (ret. time) | tert-butyl (1-(7-((3,4-difluorobenzyl)oxy)-9-oxo-3,4,11,11a-tetrahydro 1Hpyrazino[1',2':3,4]imidazo[1,2-c]pyrimidin-2(9H)-yl)-2-methyl-1-oxopropan-2-yl)carbamate |
| D232 | Boc-azetidine-2-carbonyl (2S) | 55% | m/z 518.2 (M + H)+ 0.81 min (ret. time) | (2S)-tert-butyl 2-(7-((3,4-difluorobenzyl)oxy)-9-oxo 2,3,4,9,11,11a-hexahydro-1H-pyrazino[1',2':3,4]imidazo[1,2-c]pyrimidine-2-carbonyl)azetidine-1-carboxylate |
| D233 | Boc-pyrrolidine-2-carbonyl (2S) | 46% | m/z 532.2 (M + H)+ 083 min (ret. time) | (2S)-tert-butyl 2-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)pyrrolidine-1-carboxylate |
| D234 | Boc-4-fluoropyrrolidine-2-carbonyl (2S,4S) | 35% | m/z 550.2 (M + H)+ 0.81 min (ret. time) | (2S,4S)-tert-butyl 2-(7-((3,4-difluorobenzyl)oxy)-9-oxo-2,3,4,9,11,11ahexahydro-1Hpyrazino[1',2':3,4]imidazo[1,2-c]pyrimidine-2-carbonyl)-4-fluoropyrrolidine-1-carboxylate |
| D235 | Boc-4,4-difluoropyrrolidine-2-carbonyl (2S) | 49% | m/z 568.2 (M + H)+ 0.89 min (ret. time) | (2S)-tert-butyl 2-(7-((3,4-difluorobenzyl)oxy)-9-oxo-2,3,4,9,11,11ahexahydro-1Hpyrazino[1',2':3,4]imidazo[1,2-c]pyrimidine-2-carbonyl)-4,4-difluoropyrrolidine-1-carboxylate |
| D236 | Boc-pyrrolidine-2-carbonyl (2R) | 45% | m/z 532.1 (M + H)+ 0.85 min (ret. time) | (2R)-tert-butyl 2-(7-((3,4-difluorobenzyl)oxy)-9-oxo-2,3,4,9,11,11ahexahydro-1H-pyrazino[1',2':3,4]imidazo[1,2-c]pyrimidine-2-carbonyl)pyrrolidine-1-carboxylate |

TABLE 1-continued

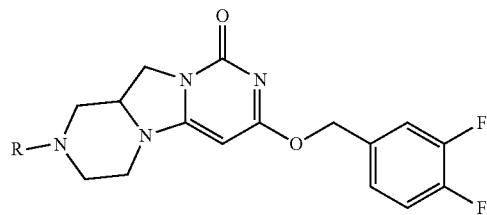

| NO# | R | Yield | LC/MS | Name |
|---|---|---|---|---|
| D237 | 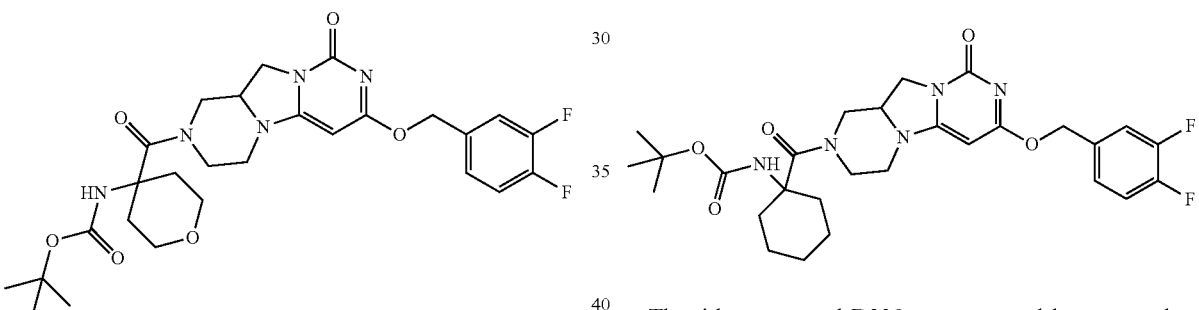 | 41% | m/z 532.1 (M + H)+ 0.83 min (ret. time) | tert-butyl (1-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)cyclobutyl)carbamate |

D238 tert-Butyl (4-(7-((3,4-difluorobenzyl)oxy)-9-oxo-2,3,4,9,11,11a-hexahydro-1H-pyrazino[1',2':3,4] imidazo[1,2-c]pyrimidine-2-carbonyl)tetrahydro-2H-pyran-4-yl)carbamate A solution of HATU (57 mg, 0.150 mmol), 4-((tertbutoxycarbonyl)amino)tetrahydro-2H-pyran-4 carboxylic acid (37 mg, 0.151 mmol) and anhydrous TEA (0.05 mL, 0.361 mmol) in anhydrous DMF (1 mL) was stirred at room temperature for 30 min. 7-((3,4-difluorobenzyl)oxy)-3,4,11,11a-tetrahydro-1H-pyrazino[1',2':3,4]imidazo[1,2-c]pyrimidin-9(2H)-one (50 mg, 0.150 mmol) was then added, and stirring was continued at room temperature. After 1.5 h, DCM (2 mL) was added, and the mixture was washed with 10% citric acid (1×1 mL) and saturated NaHCO$_3$ (1×1 mL). The mixture was concentrated and purified by flash chromatography to give 30.2 mg (36%) of the title compound as a clear, colorless film.

LC/MS: m/z 562.1 (M+H)+, 0.82 min (ret. time)

D239 tert-Butyl (1-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)cyclohexyl)carbamate The title compound D239 was prepared by a procedure similar to that described for D238 starting from 1-((tertbutoxycarbonyl)amino)cyclohexanecarboxylic acid.

LC/MS: m/z 560.2 (M+H)+, 0.92 min (ret. time)

D240

3-(Benzylamino)oxetane-3-carbonitrile

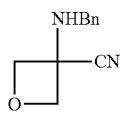

A solution of oxetan-3-one (14.0 g, 194 mmol, 1 equiv) in 50 mL of EtOH was added gradually to a stirred and chilled (ice bath) solution of N-benzylamine (22.9 g, 214 mmol, 1.1 equiv) in 50 mL of EtOH in a 500 mL flask, followed by gradual addition of TMSCN (23.1 g, 233 mmol, 1.2 equiv) in 50 mL of EtOH, and the final addition of NH$_4$Cl (3.1 g, 58 mmol, 0.3 equiv) in one portion. The resulting mixture was heated in an oil bath at 80° C. for 18 h. The mixture was cooled to room temperature and filtered. The filtrate was concentrated. The residue was partitioned between EtOAc (50 and 25 mL) and saturated aqueous NaHCO$_3$ (40 mL).

The organic was dried over Na$_2$SO$_4$, filtered, and concentrated to give a brownish residue (41.2 g). This material was re-dissolved in DCM, absorbed onto isolute, and divided into 3 equal portions. Purification (each portion) was performed on a Teledyne-Isco Combiflash Rf purification system using a Redi-Sep 120 g silica gel cartridge with gradient elution of 0% EtOAc in hexane to 100% EtOAc over a 40 min period (the first 5 min was holding time for 0% EtOAc in hexane, flow rate at 85 mL/min, UV at 254 nm). The desired product began eluting at 17 min. Appropriate fractions were combined and concentrated to give the title compound (32.1 g) as a clear light yellow-colored thick oil which solidified upon ageing.

LC/MS: m/z 188.9 (M+H)$^+$, 0.70 min (ret. time). $^1$H NMR (400 MHz, CDCl$_3$) δ ppm 1.98 (br. s., 1H) 3.88 (d, J=6.53 Hz, 2H) 4.48 (d, J=6.53 Hz, 2H) 4.86 (d, J=6.78 Hz, 2H) 7.29-7.46 (m, 5H).

D241

3-(Benzylamino)oxetane-3-carboxylic acid

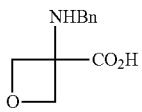

A mixture of 3-(benzylamino)oxetane-3-carbonitrile (34.5 g, 183 mmol, 1 equiv) and 61 mL of 6N NaOH (366 mmol, 2 equiv) in a 500 mL RB flask was heated in an oil bath at 110° C. for 20 min. The mixture was cooled to rt, and then chilled in an ice bath.

To the cold mixture was added 6 N HCl to adjust pH to 7. A thick suspension resulted, and was let settled at room temperature for 30 min, followed by filtration. The cake was washed with water (40 mL) and aspirated under vacuum at room temperature for 2 days. The solids were further dried under high vacuum over P$_2$O$_5$ at room temperature for 8 h to give the title compound (27.1 g) as light beige powdery solids.

LC/MS: m/z 207.9 (M+H)$^+$, 0.09-0.28 min (ret. time). $^1$H NMR (400 MHz, DMSO-d$_6$) δ ppm 3.72 (s, 2H) 4.45 (d, J=6.27 Hz, 2H) 4.69 (d, J=6.02 Hz, 2H) 7.22-7.30 (m, 1H) 7.30-7.43 (m, 4H).

D242

(3-(Benzylamino)oxetan-3-yl)methanol

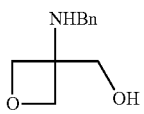

3-(Benzylamino)oxetane-3-carboxylic acid (8.0 g, 38.6 mmol, 1 equiv) was added as solids portionwise (in small portions) to a stirred chilled (ice bath) solution of LAH (2M in THF, 50 mL, 100 mmol, 2.6 equiv) in 150 mL of THF in a 1 L flask fitted with a large magnetic stirring bar, a thermometer, and under N$_2$. The addition temperature (internal) was around 4-6° C. Addition took 1 h to complete. The mixture was stirred in the ice bath for another 30 min. The mixture was diluted with another 125 mL of THF, followed by careful addition of 16.7 mL of saturated Na$_2$SO$_4$ solution. The internal temperature stayed around 15° C. and never exceeded 20° C. After completion of Na$_2$SO$_4$ solution addition, the ice bath was removed. The resulting whitish mixture was stirred at room temperature for 20 min. The whitish suspension was filtered through celite. The cake was washed repeatedly with EtOAc (total 400 mL). The filtrate was dried over Na$_2$SO$_4$, filtered, and concentrated. The residue was re-dissolved in DCM, and absorbed onto Isolute. Purification was performed on a Teledyne-Isco Combiflash Rf purification system using a Redi-Sep 120 g silica gel cartridge with gradient elution of 0% A in DCM to 50% A in DCM over a 40 min period (the first 2 min was holding time for 0% A in DCM, A was a mixture of 80/800/3200 NH$_4$OH/MeOH/DCM, flow rate at 85 mL/min, UV at 254 nm). The desired product eluted at 17-22 min. Appropriate fractions were combined and concentrated to provide the title compound (5.41 g) as a brownish thick oil, which solidified upon ageing.

LC/MS: m/z 193.9 (M+H)$^+$, 0.09-0.36 min (ret. time). $^1$H NMR (400 MHz, DMSO-d$_6$) δ ppm 3.62 (d, J=5.52 Hz, 2H) 3.77 (br. s., 2H) 4.27 (d, J=6.02 Hz, 2H) 4.45 (d, J=6.02 Hz, 2H) 4.86 (t, J=5.65 Hz, 1H) 7.17-7.26 (m, 1H) 7.30 (t, J=7.40 Hz, 2H) 7.34-7.43 (m, 2H).

D243

(3-Aminooxetan-3-yl)methanol

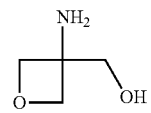

A mixture of (3-(benzylamino)oxetan-3-yl)methanol (6.50 g, 33.6 mmol) and Pd(OH)$_2$ (20% on carbon, 618 mg) in 65 mL of MeOH in a 500 mL Parr bottle was hydrogenated under 50-55 psi at room temperature for a total of 12 h. Additional Pd(OH)$_2$ (200 mg) were added as a slurry in 4 mL of MeOH. Hydrogenation at 50-55 psi was continued for another 4 h. The mixture was filtered through celite and rinsed with MeOH (15 mL). The filtrate was concentrated to provide the title compound (3.73 g) as a light greenish thick oil.

$^1$H NMR (400 MHz, CHLOROFORM-d) δ ppm 3.83 (s, 2H) 4.45 (d, J=6.53 Hz, 2H) 4.51 (d, J=6.78 Hz, 2H).

D244

(3-((2,6-Dichloropyrimidin-4-yl)amino)oxetan-3-yl)methanol

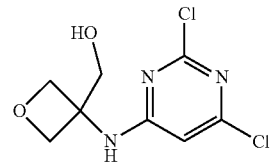 [SMILES: OCC1(Nc2cc(Cl)nc(Cl)n2)COC1]

(3-Aminooxetan-3-yl)methanol (3.46 g, 33.6 mmol, 1 equiv) was stirred with DIPEA (5.6 mL, 32.1 mmol, 3 equiv)

in 12 mL of THF cooled in a water bath (no ice). To this stirred mixture was added 2,4,6-trichloropyrimidine (1.35 mL, 11.8 mmol, 1.1 equiv) over a 3 min period. The mixture was stirred at room temperature for 48 h. The mixture was concentrated. The residue was partitioned between water (15 mL), and saturated NaHCO$_3$ (10 mL) and EtOAc (100, 50 and 30 mL). The organic was dried over Na$_2$SO$_4$, and filtered. The filtrate was directly absorbed onto Isolute and concentrated. The resulting adsorbed Isolute material was splitted into two equal halves. Purification (each portion) was performed on a Teledyne-Isco Combiflash Rf purification system using a Redi-Sep 120 g silica gel cartridge with gradient elution of 0% A in hexane to 100% A in hexane over a 35 min period (A was a mixture of 2.5% MeOH in EtOAc, flow rate at 85 mL/min, UV at 254 nm). Three large peaks eluted out. The last peak was the desired product (eluting at 25 min). Appropriate fractions were combined and concentrated to provide the title compound (4.03 g) as a white solid residue.

LC/MS: m/z 249.8 (M+H)$^+$, 0.61 min (ret. time). $^1$H NMR (400 MHz, DMSO-d$_6$) δ ppm 3.79 (d, J=5.52 Hz, 2H) 4.41-4.61 (m, 4H) 5.19 (t, J=5.52 Hz, 1H) 6.54 (s, 1H) 8.77 (br. s., 1H).

D245

7-Chloro-1H-spiro[imidazo[1,2-c]pyrimidine-2,3'-oxetan]-5(3H)-one

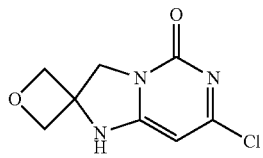 [SMILES: O=c1nc(Cl)cc2n1CC1(COC1)N2]

A suspension of (3-((2,6-dichloropyrimidin-4-yl)amino)oxetan-3-yl)methanol (1.67 g, 6.7 mmol, 1 equiv) and DIPEA (5.8 mL, 33.4 mmol, 5 equiv) in 20 mL of THF in a 200 mL flask was sonicated at room temperature until most solid particles dissolved and turned into a cloudy mixture. This mixture was chilled in an ice bath, and followed with addition of methanesulfonic anhydride (2.91 g, 16.69 mmol, 2.5 equiv) portionwise as solids. The mixture was stirred naturally (ice not renewed). After 1 h, the reaction was complete. The mixture was concentrated. The brownish oily residue was taken up in 2.9 mL of DIEPA (2.5 equiv), 4 mL of propionitrile and 10 mL of water. The resulting mixture was heated at 100° C. for 90 min, cooled to room temperature, and aged overnight. The resulting suspension was stored in the refrigerator (4° C.) for 3 h, followed by filtration. The solids collected were washed with water (4 mL) and TBME (3 mL), and dried under high vacuum to provide the title compound (621 mg) as beige solid.

LC/MS: m/z 213.9 (M+H)$^+$, 0.11-0.26 min (ret. time), eluting at the solvent front. $^1$H NMR (400 MHz, DMSO-d$_6$) δ ppm 4.31 (s, 2H) 4.69 (q, J=7.28 Hz, 4H) 5.68 (s, 1H) 9.72 (s, 1H).

D246 tert-Butyl 7-chloro-5-oxo-3,5-dihydro-1H-spiro[imidazo[1,2-c]pyrimidine-2,3'-oxetane]-1-carboxylate

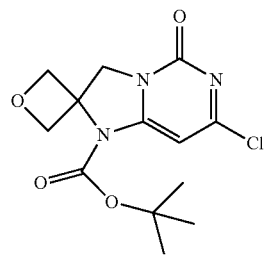 [SMILES: CC(C)(C)OC(=O)N1c2cc(Cl)nc(=O)n2CC12COC2]

A mixture of 7-chloro-1H-spiro[imidazo[1,2-c]pyrimidine-2,3'-oxetan]-5(3H)-one (207 mg, 1.1 mmol, 1 equiv), Boc-anhydride (278 mg, 1.3 mmol, 1.2 equiv), DMAP (6.5 mg, 0.05 mmol, 0.05 equiv) and DIPEA (464 uL, 2.7 mmol, 2.5 equiv) in 5 mL of THF in a 20 mL vial was stirred at room temperature for 4 h. The suspension was filtered. The cake was washed with TBME (3 mL) and dried under vacuum to give the title compound (258 mg) as an off-white powdery solid.

LC/MS: m/z 314.0 (M+H)$^+$, 0.72 min (ret. time).
$^1$H NMR (400 MHz, DMSO-d$_6$) δ ppm 1.60 (s, 9H) 4.44 (s, 2H) 4.63 (d, J=7.28 Hz, 2H) 5.15 (d, J=7.53 Hz, 2H) 6.61 (s, 1H).

D247

7-Chloro-1-methyl-1H-spiro[imidazo[1,2-c]pyrimidine-2,3'-oxetan]-5(3H)-one

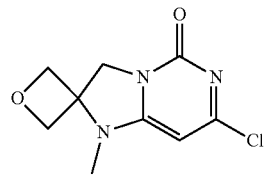

To a mixture of 7-chloro-1H-spiro[imidazo[1,2-c]pyrimidine-2,3'-oxetan]-5(3H)-one (533 mg, 2.5 mmol, 1 equiv) and Cs$_2$CO$_3$ (1.63 g, 5.0 mmol, 2 equiv) in 20 mL of propionitrile in a 40 mL vial was added dimethyl sulfate (191 uL, 2.0 mmol, 0.8 equiv). The mixture was heated at 90° C. for 40 min. The hot mixture was filtered through celite. The cake was washed with hot ACN (4×10 mL) and 10% ACN in DCM (20 mL). The filtrate was concentrated to give a brownish solid residue (518 mg), which was redissolved in 10% ACN in DCM and adsorbed onto Isolute. Purification was performed on a Teledyne-Isco Combiflash Rf purification system using a Redi-Sep 80 g silica gel cartridge with gradient elution of 0% A in DCM to 100% A in DCM over a 35 min period (A was a mixture of 80/800/3200 NH$_4$OH/MeOH/DCM, flow rate at 60 mL/min, UV at 254 nm). The desired product eluted at 16.5 min. Appropriate fractions were combined and concentrated to give the title compound (193 mg) as a beige powdery solid.

LC/MS: m/z 227.9 (M+H)$^+$, 0.36 min (ret. time).

¹H NMR (400 MHz, DMSO-d₆) δ ppm 3.17 (s, 3H) 4.32 (s, 2H) 4.66 (d, J=8.03 Hz, 2H) 4.91 (d, J=8.03 Hz, 2H) 5.96 (s, 1H).

D248

(4-Aminotetrahydro-2H-pyran-4-yl)methanol

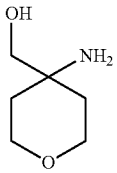

To a 100 mL round bottomed flask, 4-aminotetrahydro-2H-pyran-4-carboxylic acid (5 g, 34.4 mmol) was added to methanol (50 mL) and solution was cooled in ice. To this was added thionyl chloride (5.03 mL, 68.9 mmol) dropwise and solution was stirred at 0° C. for 1 h then heated to 50° C. and stirred overnight. Solvent was evaporated to a white solid, which was taken up in sat. Na₂CO₃, extracted with DCM, washed with brine, and dried (MgSO4) and evaporated to yield methyl 4-aminotetrahydro-2H-pyran-4-carboxylate (2.86 g, 17.9 mmol, 52.1% yield) as a pale yellow liquid.

¹H NMR (400 MHz, CDCl₃) δ ppm 1.15-1.27 (m, 2H) 1.43 (s, 2H) 1.82 (ddd, J=13.36, 9.22, 4.02 Hz, 2H) 3.32-3.41 (m, 2H) 3.48 (s, 3H) 3.54-3.64 (m, 2H).

To a 200 mL round bottom flask in an ice bath was added lithium aluminum hydride (1.34 g, 35.2 mmol) with steady stirring at 0° C. A solution of methyl 4-aminotetrahydro-2H-pyran-4-carboxylate (2.8 g, 17.59 mmol) in tetrahydrofuran (THF) (10 ml) was added dropwise via addition funnel. Upon addition of the substrate, the reaction was allowed to stir, and warmed naturally to room temperature for 2 h. The reaction was then quenched by dropwise addition of 5.9 mL of saturated Na₂SO₄ (quenching formula: 4.4 mL/g of LAH). White precipitate formed was filtered and the solution was evaporated to yield (4-aminotetrahydro-2H-pyran-4-yl)methanol (1.35 g, 10.29 mmol, 58.5% yield) as an oil.

¹H NMR (400 MHz, CD₃OD) δ ppm 1.43 (d, J=13.80 Hz, 2H) 1.69 (ddd, J=13.30, 9.16, 4.14 Hz, 2H) 3.42 (s, 2H) 3.65-3.86 (m, 4H); LCMS: (MH+)=132 rt=0.08 min.

D249

(4-((2,6-Dichloropyrimidin-4-yl)amino)tetrahydro-2H-pyran-4-yl)methanol

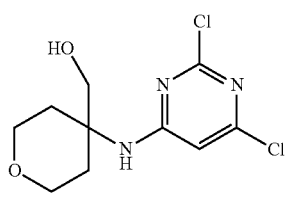

To a 100 ml round bottomed flask was added (4-aminotetrahydro-2H-pyran-4-yl)methanol (0.68 g, 5.18 mmol in 10 mL of THF at 0° C. To this was added sodium hydride (0.622 g, 15.55 mmol) and solution was stirred for 30 min. 2,4,6-trichloropyrimidine (0.594 mL, 5.18 mmol) dissolved in tetrahydrofuran (THF) (15 mL) was added dropwise and then reaction was allowed to warm to RT and stirred for 4 h. The solution was diluted with ethyl acetate and water and the layers were separated, and the aqueous layer was extracted with EtOAc (3×10 mL). The combined organic layers were washed with saturated NaCl (1×10 mL), dried (MgSO₄), and concentrated under reduced pressure. The crude material was purified on a Teledyne-Isco Combiflash Rf purification system. The residue was dissolved in 5 mL of DCM and injected on a Teledyne-Isco RediSep Rf silica gel column (12 g) and was eluted with a gradient of DCM to 10% meoh/DCM over 10 minutes. The appropriate fractions were collected and evaporated to yield a mixture of the two products. The fractions were dried down and re-purified on 4 g combiflash column eluting with a gradient of 50% hexanes/ethyl acetate to 100% EtOAc yielding (4-((2,6-dichloropyrimidin-4-yl)amino)tetrahydro-2H-pyran-4-yl)methanol (330 mg, 1.186 mmol, 22.89% yield) as a solid.

¹H NMR (400 MHz, CDCl₃) δ ppm 1.41 (d, J=13.30 Hz, 2H) 1.66-1.81 (m, 2H) 3.72-3.84 (m, 4H) 4.16-4.24 (m, 2H) 6.73 (s, 1H); LCMS: (MH+)=279 rt=0.49 min.

D250

7-Chloro-2',3',5',6'-tetrahydro-1H-spiro[imidazo[1,2-c]pyrimidine-2,4'-pyran]-5(3H)-one

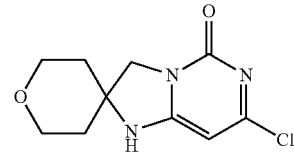 [SMILES: O=c1nc(Cl)cc2n1CC1(CCOCC1)N2]

To a 25 ml round bottomed flask was added (4-((2,6-dichloropyrimidin-4-yl)amino)tetrahydro-2H-pyran-4-yl)methanol (200 mg, 0.719 mmol) and DIEA (0.377 mL, 2.157 mmol in THF (3 mL). Solution was cooled to 0° C. and stirred for 30 min. methanesulfonyl chloride (0.067 mL, 0.863 mmol was added and then reaction was allowed to warm to RT and stirred 1 h. LCMS shows mesylate is formed and solution was heated to 70° C. overnight. A white precipitate formed and was filtered to yield 7-chloro-2',3',5',6'-tetrahydro-1H-spiro[imidazo[1,2-c]pyrimidine-2,4'-pyran]-5(3H)-one (107 mg, 0.443 mmol, 61.6% yield as a white powder.

¹H NMR (400 MHz, DMSO-d6) δ ppm 1.69-1.92 (m, 4H) 3.46-3.65 (m, 2H) 3.70-3.83 (m, 2H) 3.95 (s, 2H) 6.13 (s, 1H).

D251

7-Chloro-5-oxo-2',3,3',5,5',6'-hexahydro-1H-spiro[imidazo[1,2-c]pyrimidine-2,4'-pyran]-1-carboxylate

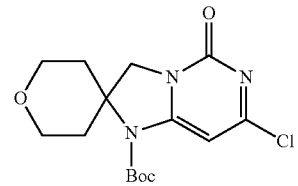 [SMILES: CC(C)(C)OC(=O)N1c2cc(Cl)nc(=O)n2CC12CCOCC2]

To a 100 mL round bottomed flask was added 7-chloro-2',3',5',6'-tetrahydro-1H-spiro[imidazo[1,2-c]pyrimidine-2,4'-pyran]-5(3H)-one (900 mg, 3.73 mmol) and DMF (20 mL). To this was added 60% NaH (746 mg, 18.65 mmol) and solution was stirred for 1 h. Boc$_2$O (0.94 mL, 5.6 mmol) was added and solution was stirred for 1 h. After 2 h, the reaction has apparently stalled, and more 60% NaH (750 mg) was added followed by Boc$_2$O (0.94 mL, 5.6 mmol) and reaction stirred an additional hour at RT. Solution was treated with dropwise addition of water, until quenched, then 20 mL added followed by DCM; organics separated and aqueous washed with DCM (2×), organics combined, washed with water (2×), brine, dried over magnesium sulfate and evaporated to a white solid. The solid was triturated with hexanes and filtered to yield 7-chloro-5-oxo-2',3,3',5,5',6'-hexahydro-1H-spiro[imidazo[1,2-c]pyrimidine-2,4'-pyran]-1-carboxylate (687 mg, 54%).

$^1$H NMR (400 MHz, CDCl$_3$) δ ppm 0.80-0.96 (m, 2H) 1.60-1.72 (m, 11H) 2.79-2.93 (m, 2H) 3.45 (t, J=12.30 Hz, 2H) 4.06-4.18 (m, 4H) 6.77 (s, 1H); LCMS: (MH+)=342 rt=0.83 min.

D252

(4-((2,6-Dichloropyrimidin-4-yl)(methyl)amino) tetrahydro-2H-pyran-4-yl)methanol

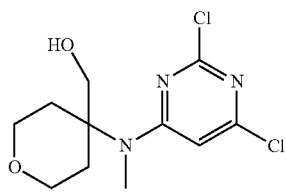 [SMILES: CN(c1cc(Cl)nc(Cl)n1)C1(CO)CCOCC1]

To a 20 ml round microwave vial was added (4-(methylamino)tetrahydro-2H-pyran-4-yl)methanol (900 mg, 6.20 mmol in tetrahydrofuran (15 mL) at rt. To this was added DIEA (3.25 mL, 18.60 mmol) and 2,4,6-trichloropyrimidine (0.711 mL, 6.20 mmol) and solution was stirred for 10 min. The reaction vessel was sealed and irradiated in a Biotage Initiator microwave using normal power setting to 100° C. for 2 hours. Solution was evaporated and the residue was dissolved in DMSO (1 mL), filtered through a 0.45 m acrodisc, and purified on a Gilson HPLC (Sunfire 5 m C18 OBD 30×100 mm preparatory column), eluting at 30 mL/min with a linear gradient running from 10% CH$_3$CN/H$_2$O (0.1% TFA) to 90% CH$_3$CN/H$_2$O (0.1% TFA) over 10 min. The desired fractions were concentrated by rotovap to yield (4-((2,6-dichloropyrimidin-4-yl)(methyl)amino)tetrahydro-2H-pyran-4-yl)methanol (233 mg, 0.798 mmol, 12.87% yield).

$^1$H NMR (400 MHz, CDCl$_3$) δ ppm 2.15-2.26 (m, 4H) 3.08 (s, 3H) 3.68-3.87 (m, 4H) 4.06 (s, 2H) 6.53 (s, 1H); LCMS: (MH+)=293 rt=0.71 min.

D253

7-Chloro-1-methyl-2',3',5',6'-tetrahydro-1H-spiro [imidazo[1,2-c]pyrimidine-2,4'-pyran]-5(3H)-one

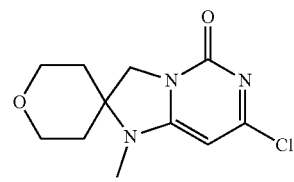 [SMILES: CN1c2cc(Cl)nc(=O)n2CC12CCOCC2]

To a 20 ml scintillation vial was added (4-((2,6-dichloropyrimidin-4-yl)(methyl)amino)tetrahydro-2H-pyran-4-yl) methanol (245 mg, 0.839 mmol) and DIEA (0.879 mL, 5.03 mmol) in THF (4 mL). Solution was cooled to 0° C. and stirred for 30 min. Mesyl chloride (0.196 mL, 2.52 mmol was added (turned tan cloudy) and then reaction was allowed to warm to RT and stirred 1 h, the reaction mixture was yellow cloudy. After the reaction was complete, the solution was transferred to a 5 mL microwave vial and the reaction vessel was sealed and irradiated in a Biotage Initiator microwave using normal power setting to 100° C. for 1 hour. Solution was evaporated over a stream of nitrogen. The mixture was filtered and rinsed with ether to yield an off white precipitate which was expected product 7-chloro-1-methyl-2',3',5',6'-tetrahydro-1H-spiro[imidazo [1,2-c]pyrimidine-2,4'-pyran]-5(3H)-one (152 mg, 0.594 mmol, 70.9% yield.

$^1$H NMR (400 MHz, DMSO-d$_6$) δ ppm 1.61 (d, J=12.55 Hz, 2H) 1.89-2.03 (m, 2H) 2.87 (s, 3H) 3.41 (t, J=11.92 Hz, 2H) 3.89 (d, J=7.28 Hz, 2H) 4.00 (s, 2H) 5.91 (s, 1H); LCMS: (MH+)=256 RT=0.42 min.

D254 tert-Butyl 4-amino-4-(hydroxymethyl)piperidine-1-carboxylate

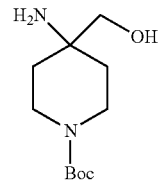

To a 500 mL round bottom flask in an ice bath was added LAH (3.11 g, 82 mmol) to THF (200 ml) with steady stirring at 0° C. The solution was stirred 30 min and then 4-amino-1-(tert-butoxycarbonyl)piperidine-4-carboxylic acid (10 g, 40.9 mmol) was added portionwise to the LAH suspension over the course of 20 minutes and the reaction was allowed to stir, warming naturally to room temperature 4 h. An additional 50 mL of THF was added to facitlitate stirring. The reaction was then quenched by dropwise addition of 13.7 mL of saturated Na$_2$SO$_4$ (recipe=4.4 mL solution/g LAH). The resulting white precipitate was filtered and solution evaporated to yield tert-butyl 4-amino-4-(hydroxymethyl)piperidine-1-carboxylate (6.32 g, 27.4 mmol, 67.0% yield) as a colorless oil.

$^1$H NMR (400 MHz, CDCl$_3$) δ ppm 1.35-1.45 (m, 2H) 1.47 (s, 9H) 1.54 (dd, J=9.91, 4.14 Hz, 2H) 3.22-3.33 (m, 2H) 3.37 (s, 2H) 3.59-3.73 (m, 2H): LCMS: (MH+)=231 rt=0.52 min.

D255

Butyl 4-((2,6-dichloropyrimidin-4-yl)amino)-4-(hydroxymethyl)piperidine-1-carboxylate

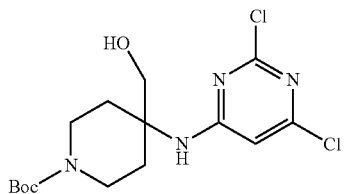 [SMILES: CC(C)(C)OC(=O)N1CCC(CO)(Nc2cc(Cl)nc(Cl)n2)CC1]

To a 200 ml round bottomed flask was added tert-butyl 4-amino-4-(hydroxymethyl)piperidine-1-carboxylate (6.32 g, 27.4 mmol) in tetrahydrofuran (THF) (25.00 mL) at 0° C. To this was added 60% sodium hydride (3.29 g, 82 mmol) and solution was stirred for 30 min at 0° C. 2,4,6-trichloropyrimidine (3.15 mL, 27.4 mmol) dissolved in tetrahydrofuran (THF) (75 mL) was added to a 500 mL flask and cooled to 0° C. The alkoxide solution was added dropwise via pipette to the pyrimidine solution and the reaction was stirred at 0° C. for 1 h then allowed to warm to RT and stirred 1 h. Water was slowly added (approx 20 mL) and the solution was diluted with ethyl acetate and water and the layers were separated, and the aqueous layer was extracted with EtOAc (3×10 mL). The combined organic layers were washed with saturated NaCl (1×10 mL), dried by using MgSO$_4$, and concentrated under reduced pressure. The crude material was purified on a Teledyne-Isco Combiflash Rf purification system. The residue was dissolved in 5 mL of DCM and injected on a Teledyne-Isco RediSep Rf silica gel column (80 g) and was eluted with a gradient of ethyl acetate and hexanes (50-100%) over 30 minutes. The desired fractions were concentrated by rotovap giving tert-butyl 4-((2,6-dichloropyrimidin-4-yl)amino)-4-(hydroxymethyl)piperidine-1-carboxylate (3.15 g, 6.10 mmol, 22.21% yield) as a yellow oil. NMR data indicates a ratio of 73:27 of desired to not desired isomers. Mixture separated in subsequent step.

$^1$H NMR (400 MHz, CDCl$_3$) δ ppm 1.22-1.41 (m, 11H) 1.47-1.64 (m, 2H) 3.09-3.26 (m, 2H) 3.66 (br. s., 2H) 4.06-4.16 (m, 2H) 6.67 (s, 1H) 6.98 (s, 1H); LCMS: (MH+) =378 rt=0.75 min.

D256 tert-Butyl 7-chloro-5-oxo-3,5-dihydro-1H-spiro[imidazo[1,2-c]pyrimidine-2,4'-piperidine]-1'-carboxylate

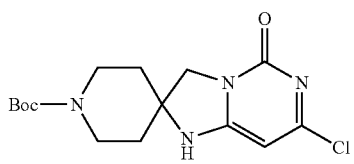 [SMILES: CC(C)(C)OC(=O)N1CCC2(CC1)Cn1c(cc(Cl)nc1=O)N2]

To a 100 ml round bottomed flask was added tert-butyl 4-((2,6-dichloropyrimidin-4-yl)amino)-4-(hydroxymethyl)piperidine-1-carboxylate (3.15 g, 8.35 mmol) and DIEA (8.75 mL, 50.1 mmol) in THF (40 mL). Solution was cooled to 0° C. and stirred for 30 min. Mesyl chloride (1.952 mL, 25.05 mmol) was added (turned cloudy) and then reaction was allowed to stir in ice for 1 h. The solution was evaporated and the residue was taken up in DCM (5 mL) and purified on combiflash. The crude material was injected on a Teledyne-Isco RediSep Rf silica gel column (40 g) and was eluted with a gradient of ethyl acetate and hexanes (0-100%) over 25 minutes. The appropriate fractions were collected and evaporated to yield 3.4 g of a mixture of the two isomers by nmr.

$^1$H NMR (400 MHz, CDCl$_3$) δ ppm 1.39-1.47 (m, 9H) 1.55-1.70 (m, 2H) 2.22-2.40 (m, 2H) 2.94 (s, 3H) 3.01-3.10 (m, 2H) 3.83 (d, J=12.30 Hz, 2H) 4.55 (d, J=8.03 Hz, 2H) 6.50 (s, 1H); LCMS: (MH+)=456 rt=1.09 min.

To a 200 mL round bottomed flask was added tert-butyl 4-((2,6-dichloropyrimidin-4-yl)amino)-4-(((methylsulfonyl)oxy)methyl)piperidine-1-carboxylate (2 g, 4.40 mmol) and potassium carbonate (2.43 g, 17.6 mmol) in acetonitrile (80 mL) and water (10 mL). Reaction was stirred at 50° C. 6 h. The solution was diluted with water and ethyl acetate, organics separated and then washed with brine, dried over magnesium sulfate and evaporated. The residue was dissolved in 10% MeOH/DCM and purified by Combiflash (24 g silica gel column-0-10% MeOH/DCM, 30 min). Fractions were evaporated to yield tert-butyl 7-chloro-5-oxo-3,5-dihydro-1H-spiro[imidazo[1,2-c]pyrimidine-2,4'-piperidine]-1'-carboxylate (344 mg, 23%) as a pale yellow powder.

$^1$H NMR (400 MHz, CDCl$_3$) δ ppm 1.43-1.54 (m, 9H) 1.84 (d, J=6.78 Hz, 2H) 1.93-2.02 (m, 2H) 3.29-3.42 (m, 2H) 3.73-3.85 (m, 2H) 3.96 (s, 2H) 6.00 (s, 1H); LCMS: (MH+) =341 rt=0.66 min.

D257 di-tert-Butyl 7-chloro-5-oxo-1H-spiro[imidazo[1,2-c]pyrimidine-2,4'-piperidine]-1,1'(3H,5H)-dicarboxylate

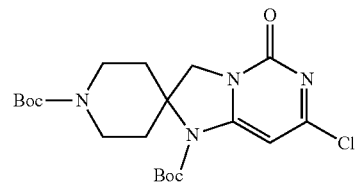 [SMILES: CC(C)(C)OC(=O)N1CCC2(CC1)Cn1c(cc(Cl)nc1=O)N2C(=O)OC(C)(C)C]

To a 100 mL round bottomed flask was added tert-butyl 7-chloro-5-oxo-3,5-dihydro-1H-spiro[imidazo[1,2-c]pyrimidine-2,4'-piperidine]-1'-carboxylate (344 mg, 1.01 mmol) in THF (20 mL) and this was cooled in ice and stirred for 15 min. To this was added 60% sodium hydride (202 mg, 5.05 mmol) and solution was stirred in ice for 15 min. Boc anhydride (440 mg, 2.02 mmol) was added via pipette then stirred for 30 min in ice, then allowed to warm to RT and stirred 1 h. The mixture was treated with water and then ethyl acetate and the organics were washed with brine and then evaporated to a white powder. The powder was triturated with hexanes to yield a white powder (263 mg, 60%).

$^1$H NMR (400 MHz, CDCl$_3$) δ ppm 1.42-1.52 (m, 9H) 1.57-1.65 (m, 9H) 1.67-1.78 (m, 2H) 2.60-2.85 (m, 4H) 4.11 (s, 2H) 6.77 (s, 1H) LCMS: (MH+)=441 rt=1.04 min.

D258 tert-Butyl 7-((3,4-difluorobenzyl)oxy)-5-oxo-3,5-dihydro-1H-spiro[imidazo[1,2-c]pyrimidine-2,4'-piperidine]-1'-carboxylate

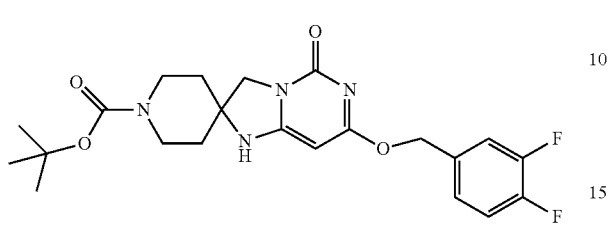

To a 25 mL round bottomed flask was added (3,4-difluorophenyl)methanol (102 □mL, 0.895 mmol) in THF (5 mL) and this was cooled in ice and stirred for 15 min. To this was added 60% sodium hydride (120 mg, 2.99 mmol) and solution was stirred in ice for 15 min. Solid di-tert-butyl 7-chloro-5-oxo-1H-spiro[imidazo[1,2-c]pyrimidine-2,4'-piperidine]-1,1'(3H,5H)-dicarboxylate (263 mg, 0.598 mmol) was added, and then stirred for 30 min in ice; the solution was allowed to warm to RT and stirred 1 h. The mixture was treated with water and then ethyl acetate, aqueous extracted with ethyl acetate, organics combined, washed with brine, dried over magnesium sulfate and evaporated to an oil. The residue was dissolved in 2 mL of DMSO and purified by Gilson HPLC (Sunfire C18 column-gradient 10-90% water/acetonitrile over 12 minutes) to yield tert-butyl 7-((3,4-difluorobenzyl)oxy)-5-oxo-3,5-dihydro-1H-spiro[imidazo[1,2-c]pyrimidine-2,4'-piperidine]-1'-carboxylate (93 mg, 35%).

$^1$H NMR (400 MHz, DMSO-$d_6$) δ ppm 1.42 (s, 9H) 1.67 (br. s., 2H) 1.78 (br. s., 2H) 3.30 (br. s., 2H) 3.52 (br. s., 2H) 3.89 (br. s., 2H) 5.28-5.45 (m, 3H) 7.33 (br. s., 1H) 7.44-7.64 (m, 2H) 9.51-9.82 (m, 1H); LCMS: (MH+)=449 rt=0.81 min.

D259

4-Amino-1-benzylpiperidine-4-carboxylic acid

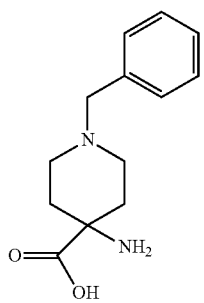 [SMILES: NC1(C(=O)O)CCN(Cc2ccccc2)CC1]

The title compound was synthesized in 2 steps from 1-benzylpiperidin-4-one to yield a yellow solid (10.25 g, 81%) (See procedures described in WO2006052722).

$^1$H NMR (400 MHz, DMSO-$d_6$) δ ppm 1.25 (d, J=12.80 Hz, 2H) 1.91-2.03 (m, 2H) 2.25 (t, J=10.29 Hz, 2H) 2.43-2.50 (m, 2H) 7.19-7.34 (m, 5H); LCMS MH+=235; rt=0.17 min.

D260

(4-Amino-1-benzylpiperidin-4-yl)methanol

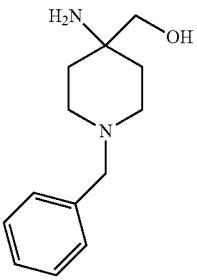 [SMILES: NC1(CO)CCN(Cc2ccccc2)CC1]

To a 200 mL round bottomed flask, 4-amino-1-benzylpiperidine-4-carboxylic acid (10.25 g, 43.7 mmol) was added to methanol (100 mL) and solution was cooled in ice. To this was added thionyl chloride (6.39 mL, 87 mmol) dropwise and solution was stirred at 0° C. for 1 h then allowed to warm to RT, then heated to 50° C. and stirred over weekend. Solution was filtered and solvent was evaporated to an oily liquid, which was taken up in sat. Na$_2$CO$_3$, extracted with DCM, washed with brine and dried by using MgSO$_4$ and evaporated to yield methyl 4-amino-1-benzylpiperidine-4-carboxylate (4.21 g, 16.95 mmol, 38.8% yield) as a pale yellow liquid.

$^1$H NMR (400 MHz, CDCl$_3$) δ ppm 1.52-1.63 (m, 2H) 2.15 (dt, J=13.36, 6.74 Hz, 2H) 2.52 (d, J=4.27 Hz, 4H) 3.54 (s, 2H) 3.74 (s, 3H) 7.18-7.42 (m, 5H); LCMS: (MH+)=249 rt=0.26 min.

To a 200 mL round bottom flask was added Lithium aluminum hydride (1.287 g, 33.9 mmol) to tetrahydrofuran (45 ml) with steady stirring at 0° C. The addition funnel was charged with a solution of methyl 4-amino-1-benzylpiperidine-4-carboxylate (4.21 g, 16.95 mmol) in tetrahydrofuran (10 ml) and added, dropwise, to the LAH suspension over the course of 10 minutes and the reaction was allowed to stir, warming naturally to room temperature 2 h. The reaction was then quenched by dropwise addition of 5.7 mL of saturated Na$_2$SO$_4$ (recipe=4.4 mL solution/g LAH). The resulting white precipitate was filtered and solution evaporated to yield (4-amino-1-benzylpiperidin-4-yl)methanol (2.5 g, 11.35 mmol, 66.9% yield) as an oil.

$^1$H NMR (400 MHz, CDCl$_3$) δ ppm 1.39 (d, J=13.55 Hz, 2H) 1.53-1.64 (m, 2H) 2.22-2.35 (m, 2H) 2.45-2.56 (m, 2H) 3.29 (s, 2H) 3.47 (s, 2H) 7.14-7.32 (m, 5H); LCMS: (MH+)=221 rt=0.16 min.

D261

(1-Benzyl-4-((2,6-dichloropyrimidin-4-yl)amino)piperidin-4-yl)methanol

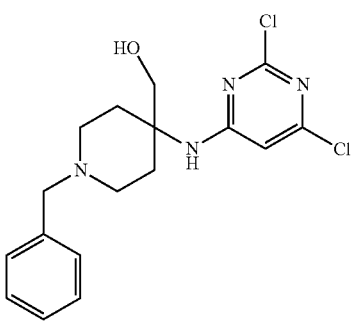 [SMILES: OCC1(Nc2cc(Cl)nc(Cl)n2)CCN(Cc2ccccc2)CC1]

To a 250 ml round bottomed flask was added (4-amino-1-benzylpiperidin-4-yl)methanol (2.5 g, 11.35 mmol) in 25 mL of THF at 0° C. To this was added sodium hydride (1.362 g, 34.0 mmol) and solution was stirred for 30 min. 2,4,6-trichloropyrimidine (1.301 mL, 11.35 mmol) dissolved in THF (25 mL) was added dropwise and then reaction was allowed to warm to RT and stirred overnight. The solution was diluted with ethyl acetate and water and the layers were separated, and the aqueous layer was extracted with EtOAc. The combined organic layers were washed with saturated NaCl, dried (MgSO$_4$), and concentrated under reduced pressure. The crude material was purified on a Teledyne-Isco Combiflash Rf purification system. The residue was dissolved in 10 mL of DCM and injected on a Teledyne-Isco RediSep Rf silica gel column (40 g) and was eluted with a gradient of ethyl acetate and hexanes (50-100%) over 30 minutes. The appropriate fractions were collected and evaporated to yield (1-benzyl-4-((2,6-dichloropyrimidin-4-yl)amino)piperidin-4-yl)methanol (732 mg, 1.993 mmol, 17.56% yield) as a white powder.

1H NMR (400 MHz, CD$_3$OD) δ ppm 1.75 (t, J=10.92 Hz, 2H) 2.32 (d, J=11.04 Hz, 4H) 2.71 (d, J=11.80 Hz, 2H) 3.55 (s, 2H) 3.83 (s, 2H) 6.59 (s, 1H) 7.24-7.39 (m, 5H); LCMS: (MH+)=368 rt=0.67 min.

D262

1'-Benzyl-7-chloro-1H-spiro[imidazo[1,2-c]pyrimidine-2,4'-piperidin]-5(3H)-one

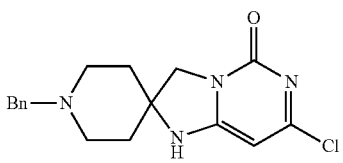 [SMILES: O=c1nc(Cl)cc2n1CC1(CCN(Cc3ccccc3)CC1)N2]

To a 25 ml round bottomed flask was added (1-benzyl-4-((2,6-dichloropyrimidin-4-yl)amino)piperidin-4-yl)methanol (732 mg, 1.993 mmol) and DIEA (1.044 mL, 5.98 mmol) in THF (10 mL). Solution was cooled to 0° C. and stirred for 30 min. Methanesulfonyl chloride (0.186 mL, 2.392 mmol) was added and then reaction was allowed to warm to RT and stirred 3 h, reaction was still not complete, so additional mesyl chloride (0.186 mL, 2.392 mmol) was added and solution was heated to 70° C. overnight. Additional DIEA (2 mL, 12 mmol) was added and heated at 70° C. for 2 h. Solution was then diluted with ethyl acetate and water, resulting in a brown precipitate which was filtered to yield 1'-benzyl-7-chloro-1H-spiro[imidazo[1,2-c]pyrimidine-2,4'-piperidin]-5(3H)-one (409 mg, 1.236 mmol, 62.0% yield)

$^1$H NMR (400 MHz, DMSO-d$_6$) δ ppm 1.78 (d, J=16.31 Hz, 4H) 2.29 (br. s., 2H) 2.52 (br. s., 2H) 3.80 (br. s., 2H) 5.62 (br. s., 1H) 7.21-7.44 (m, 5H) 9.05 (br. s., 1H); LCMS (MH+)=331 rt=0.46 min.

D263 tert-Butyl 1'-benzyl-7-chloro-5-oxo-3,5-dihydro-1H-spiro[imidazo[1,2-c]pyrimidine-2,4'-piperidine]-1-carboxylate

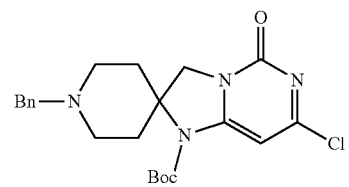 [SMILES: CC(C)(C)OC(=O)N1c2cc(Cl)nc(=O)n2CC12CCN(Cc1ccccc1)CC2]

To a 25 mL round bottomed flask was added t-benzyl-7-chloro-1H-spiro[imidazo[1,2-c]pyrimidine-2,4'-piperidin]-5(3H)-one (408 mg, 1.233 mmol) and DIEA (0.646 mL, 3.70 mmol) in THF (10 mL). To this was added DMAP (75 mg, 0.617 mmol) and solution was stirred for 10 min. Boc$_2$O (0.430 mL, 1.850 mmol) was added and solution was stirred for 1 h. The solution was diluted with ethyl acetate and water and the layers were separated, and the aqueous layer was extracted with EtOAc. The combined organic layers were washed with saturated NaCl, dried by using MgSO$_4$, and concentrated under reduced pressure to yield tert-butyl 1'-benzyl-7-chloro-5-oxo-3,5-dihydro-1H-spiro[imidazo[1,2-c]pyrimidine-2,4'-piperidine]-1-carboxylate (525 mg, 1.218 mmol, 99% yield) as a tan solid.

$^1$H NMR (400 MHz, CDCl$_3$) δ ppm 1.52-1.69 (m, 11H) 1.98 (t, J=11.54 Hz, 2H) 2.75 (t, J=12.17 Hz, 2H) 2.84-2.94 (m, 2H) 3.45 (br. s., 2H) 3.95 (s, 2H) 6.66 (s, 1H) 7.18-7.28 (m, 5H); LCMS: (MH+)=431, RT=0.73 min.

EXAMPLES

E1

3-((4-Fluorobenzyl)oxy)-6,7,8,9,9a,10-hexahydro-1H-pyrido[1,2':3,4]imidazo[1,2-c] pyrimidin-1-one trifluoroacetate salt

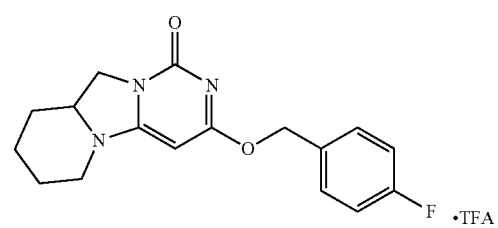 [SMILES: O=c1nc(OCc2ccc(F)cc2)cc2n1CC1CCCCN21]

To a solution of 3-chloro-6,7,8,9,9a,10-hexahydro-1H-pyrido[1',2':3,4]imidazo[1,2-c]pyrimidin-1-one (30 mg, 0.13 mmol) and (4-fluorophenyl)methanol (16.8 mg, 0.13 mmol) in DMF (1 mL) was added sodium hydride (10.6 mg, 0.27 mmol). The reaction mixture was stirred at rt for 30 min., then quenched with water. Direct purification via MDAP afforded the title product of TFA salt (25 mg, 43.8%) as a white solid.

$^1$H NMR (400 MHz, CDCl$_3$): δ 7.38 (m, 2H), 7.04 (m, 2H), 5.30 (s, 2H), 5.27 (s, 1H), 4.27 (t, 1H), 3.97-3.88 (m, 2H), 3.69 (m, 2H), 3.08 (m, 1H), 2.01 (m, 2H), 1.82 (m, 1H), 1.57-1.49 (m, 3H).

E2

3-((3,4,5-Trifluorobenzyl)oxy)-6,7,8,9,9a,10-hexahydro-1H-pyrido[1',2':3,4]imidazo[1,2-c] pyrimidin-1-one

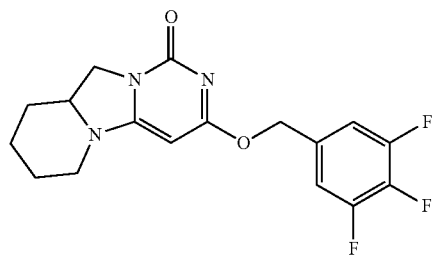 [SMILES: O=c1nc(OCc2cc(F)c(F)c(F)c2)cc2n1CC1CCCCN21]

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and (3,4,5-trifluorophenyl)methanol.

LCMS (ESI): m/z 352 [M+H]$^+$; 2.33 min (ret time).

E3

3-((3,5-Difluorobenzyl)oxy)-6,7,8,9,9a,10-hexahydro-1H-pyrido[1',2':3,4]imidazo-[1,2-c] pyrimidin-1-one

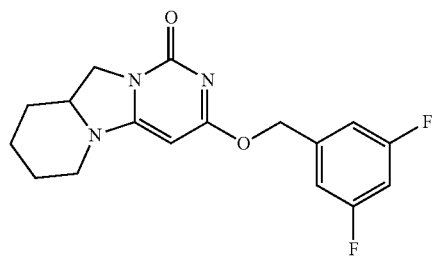 [SMILES: O=c1nc(OCc2cc(F)cc(F)c2)cc2n1CC1CCCCN21]

The title compound was prepared by a procedure similar to that described for E1 starting from (3,5-difluorophenyl)methanol and 3-chloro-6,7,8,9,9a,10-hexahydro-1H-pyrido-[1',2':3,4]imidazo[1,2-c]pyrimidin-1-one.

LC-MS (ESI): m/z 334 [M+H]$^+$; 1.37 min (ret time)

E4

4-(((1-Oxo-6,7,8,9,9a,10-Hexahydro-1H-pyrido[1',2':3,4]imidazo[1,2-c]pyrimidin-3-yl)oxy) methyl) benzonitrile

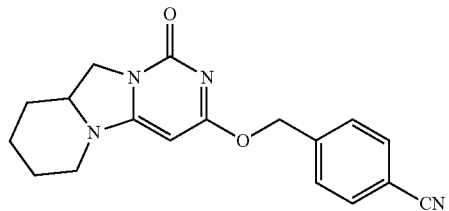 [SMILES: N#Cc1ccc(COc2cc3n(c(=O)n2)CC2CCCCN32)cc1]

The title compound was prepared by a procedure similar to that described for E1 starting from 4-(hydroxymethyl) benzonitrile and 3-chloro-6,7,8,9,9a,10-hexahydro-1H-pyrido-[1',2':3,4]imidazo[1,2-c]pyrimidin-1-one.

LC-MS (ESI): m/z 323 [M+H]$^+$; 1.30 min (ret time)

E5

3-((3,4-Difluorobenzyl)oxy)-6,7,8,9,9a,10-hexahydro-1H-pyrido[1',2':3,4]imidazo[1,2-c] pyrimidin-1-one

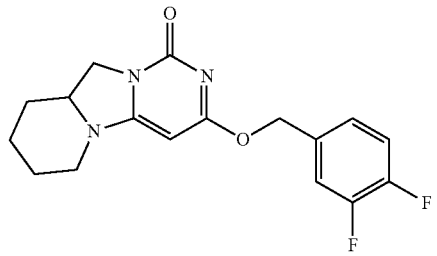 [SMILES: O=c1nc(OCc2ccc(F)c(F)c2)cc2n1CC1CCCCN21]

The title compound was prepared by a procedure similar to that described for E1 starting from (3,4-difluorophenyl)methanol and 3-chloro-6,7,8,9,9a,10-hexahydro-1H-pyrido-[1',2':3,4]imidazo[1,2-c]pyrimidin-1-one.

LC-MS (ESI): m/z 334 [M+H]$^+$; 1.21 min (ret time).

E6

3-(((1-Oxo-6,7,8,9,9a,10-hexahydro-1H-pyrido[1',2':3,4]imidazo[1,2-c]pyrimidin-3-yl)oxy) methyl)benzonitrile

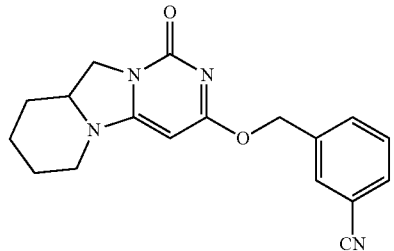

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and 3-(hydr-oxymethyl)benzonitrile.

LC-MS (ESI): m/z 323 [M+H]$^+$; 1.30 min (ret time)

E7

3-((3-Chloro-4-(trifluoromethyl)benzyl)oxy)-6,7,8,9,9a,10-hexahydro-1H-pyrido[1',2':3,4] imidazo[1,2-c] pyrimidin-1-one

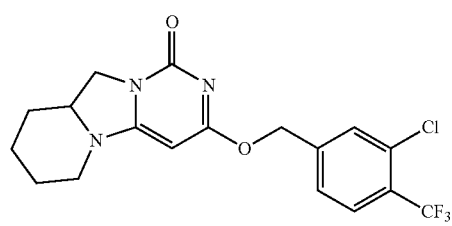 [SMILES: O=c1nc(OCc2ccc(C(F)(F)F)c(Cl)c2)cc2n1CC1CCCCN21]

The title compound was prepared by a procedure similar to that described for E1 starting from 3-chloro-6,7,8,9,9a,10-hexahydro-1H-pyrido-[1',2':3,4]imidazo[1,2-c]pyrimidin-1-one and (3-chloro-4-(trifluoromethyl)phenyl)methanol LC-MS (ESI): m/z 400 [M+H]$^+$; 1.49 min (ret time)

E8

3-((2,4-Difluorobenzyl)oxy)-6,7,8,9,9a,10-hexahydro-1H-pyrido[1',2':3,4]imidazo[1,2-c] pyrimidin-1-one

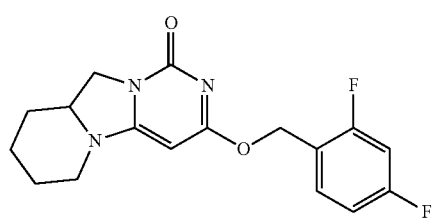 [SMILES: O=c1nc(OCc2ccc(F)cc2F)cc2n1CC1CCCCN21]

The title compound was prepared by a procedure similar to that described for E1 starting from 3-chloro-6,7,8,9,9a,10-hexahydro-1H-pyrido-[1',2':3,4]imidazo[1,2-c]pyrimidin-1-one and (2,4-difluorophenyl)methanol.

LC-MS (ESI): m/z 334[M+H]$^+$; 2.14 min (ret time).

E9

3-((4-Methylbenzyl)oxy)-6,7,8,9,9a,10-hexahydro-1H-pyrido[1,2':3,4]imidazo[1,2-c] pyrimidin-1-one

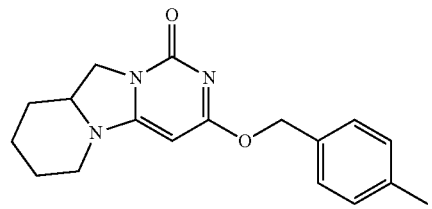 [SMILES: Cc1ccc(COc2cc3n(c(=O)n2)CC2CCCCN32)cc1]

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and p-tolyl-methanol.

LCMS (ESI): m/z 312 [M+H]$^+$; 2.28 min (ret time)

E10

5-(((1-Oxo-6,7,8,9,9a,10-hexahydro-1H-pyrido[1',2':3,4]imidazo[1,2-c]pyrimidin-3-yl)oxy) methyl)-2-((5-(trifluoromethyl)pyridin-3-yl)oxy)benzonitrile

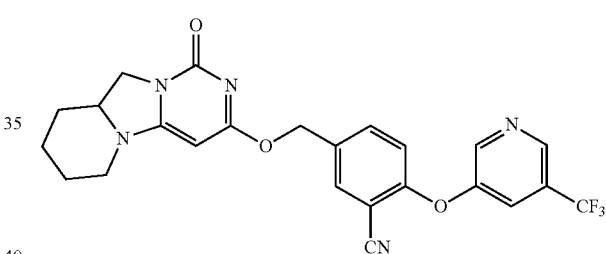

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and 5-(hydroxymethyl)-2-((5-(trifluoromethyl)pyridin-3-yl)oxy)benzonitrile.

LCMS (ESI): m/z 484 [M+H]$^+$; 2.63 min (ret time).

E11

2-Chloro-5-(2-fluoro-4-(((1-oxo-6,7,8,9,9a,10-hexahydro-1H-pyrido[1',2':3,4]imidazo[1,2-c]pyrimidin-3-yl)oxy)methyl)phenoxy)benzonitrile

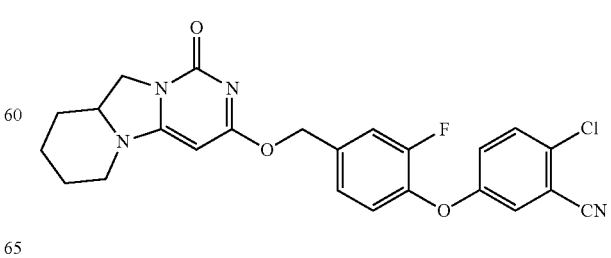

The title compound was prepared by a procedure similar to that described for E1 starting from 2-chloro-5-(2-fluoro- 4-(hydroxymethyl) phenoxy)benzonitrile and 3-chloro-6,7,8,9,9a,10-hexahydro-1H-pyrido[1',2':3,4]imidazo[1,2-c]pyrimidin-1-one.

LCMS (ESI): m/z 467 [M+H]$^+$; 2.80 min (ret time).

E12

5-(((1-Oxo-6,7,8,9,9a,10-hexahydro-1H-pyrido[1',2':3,4]imidazo[1,2-c]pyrimidin-3-yl)oxy) methyl)-2-(3-(trifluoromethyl)phenoxy)benzonitrile

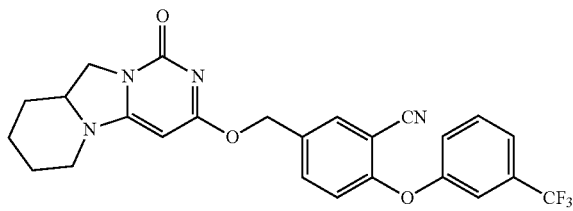 [SMILES: N#Cc1cc(COc2cc3n(c(=O)n2)CC2CCCCN32)ccc1Oc1cccc(C(F)(F)F)c1]

The title compound was prepared by a procedure similar to that described for E1 starting from 5-(hydroxymethyl)-2-(3-(trifluoromethyl)phenoxy)benzonitrile and 3-chloro-6,7,8,9,9a,10-hexahydro-1H-pyrido[1',2':3,4]imidazo[1,2-c]pyrimidin-1-one.

LCMS (ESI): m/z 483 [M+H]$^+$; 2.95 min (ret time)

E13

3-((4-Fluoro-3-(trifluoromethyl)benzyl)oxy)-6,7,8,9,9a,10-hexahydro-1H-pyrido-[1',2':3,4] imidazo[1,2-c]pyrimidin-1-one

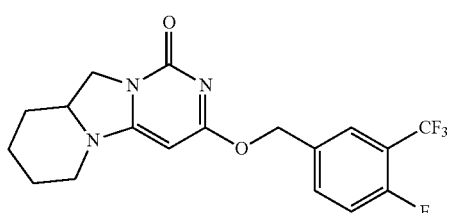

The title compound was prepared by a procedure similar to that described for E1 starting from (4-fluoro-3-(trifluoromethyl)phenyl)methanol and 3-chloro-6,7,8,9,9a,10-hexahydro-1H-pyrido-[1',2':3,4]imidazo[1,2-c]pyrimidin-1-one.

LCMS (ESI): m/z 384 [M+H]$^+$; 2.52 min (ret time).

E14

3-((3,4-Difluoro-5-methylbenzyl)oxy)-6,7,8,9,9a,10-hexahydro-1H pyrido[1',2':3,4]imidazo-[1,2-c]pyrimidin-1-one

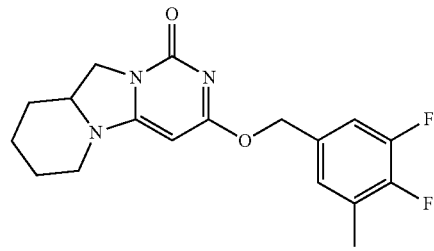 [SMILES: Cc1cc(COc2cc3n(c(=O)n2)CC2CCCCN32)cc(F)c1F]

The title compound was prepared by a procedure similar to that described for E1 starting from (3,4-difluoro-5-methylphenyl)methanol and 3-chloro-6,7,8,9,9a,10-hexahydro-1H-pyrido-[1',2':3,4]imidazo[1,2-c]pyrimidin-1-one.

LCMS (ESI): m/z 348 [M+H]$^+$; 2.40 min (ret time)

E15

3-Fluoro-5-(((1-oxo-6,7,8,9,9a,10-hexahydro-1H-pyrido[1',2':3,4]imidazo[1,2-c]pyrimidin-3-yl)oxy) methyl)benzonitrile

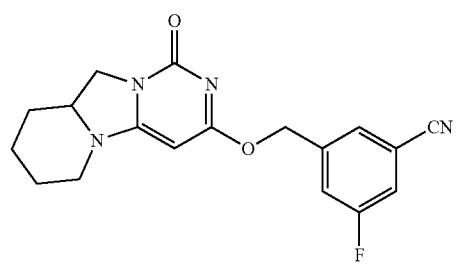 [SMILES: N#Cc1cc(F)cc(COc2cc3n(c(=O)n2)CC2CCCCN32)c1]

The title compound was prepared by a procedure similar to that described for E1 starting from 3-fluoro-5-(hydroxymethyl)benzonitrile and 3-chloro-6,7,8,9,9a,10-hexahydro-1H-pyrido[1',2':3,4]-imidazo[1,2-c]pyrimidin-1-one.

LCMS (ESI): m/z 341[M+H]$^+$; 2.09 min (ret time).

E16

3-((3-Chloro-4,5-difluorobenzyl)oxy)-6,7,8,9,9a,10-hexahydro-1H-pyrido[1',2':3,4] imidazo[1,2-c]pyrimidin-1-one

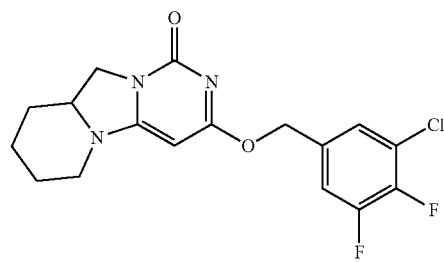 [SMILES: O=c1nc(OCc2cc(F)c(F)c(Cl)c2)cc2n1CC1CCCCN21]

The title compound was prepared by a procedure similar to that described for E1 starting from (3-chloro-4,5-difluorophenyl)methanol and 3-chloro-6,7,8,9,9a,10-hexahydro-1H-pyrido[1',2':3,4]imidazo[1,2-c]pyrimidin-1-one.

LCMS (ESI): m/z 368 [M+H]+; 2.52 min (ret time)

E17

3-((3-Fluoro-4-((2-(trifluoromethyl)pyridin-4-yl)oxy)benzyl)oxy)-6,7,8,9,9a,10-hexahydro-1H-pyrido[1',2':3,4]imidazo[1,2-c]pyrimidin-1-one

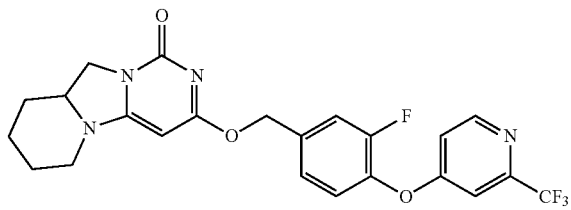 [SMILES: O=c1nc(OCc2ccc(Oc3ccnc(C(F)(F)F)c3)c(F)c2)cc2n1CC1CCCCN21]

The title compound was prepared by a procedure similar to that described for E1 starting from (3-fluoro-4-((2-(trifluoromethyl)pyridin-4-yl)oxy)phenyl)methanol and 3-chloro-6,7,8,9,9a,10-hexahydro-1H-pyrido[1',2':3,4] imidazo[1,2-c]pyrimidin-1-one.

LC-MS (ESI): m/z 477 [M+H]+; 1.99 min (ret time).

E18

3-((4-(3,4-Difluorophenoxy)-3-fluorobenzyl)oxy)-6,7,8,9,9a,10-hexahydro-1H-pyrido[1',2':3,4]imidazo[1,2-c]pyrimidin-1-one

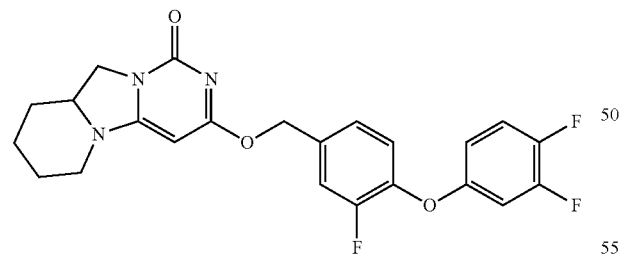

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and (4-(3,4-difluorophenoxy)-3-fluorophenyl)methanol.

LCMS (ESI): m/z 444 [M+H]+; 2.88 min (ret time).

E19

2-(3,4-Difluorophenoxy)-5-(((1-oxo-6,7,8,9,9a,10-hexahydro-1H-pyrido[1',2':3,4]imidazo-[1,2-c]pyrimidin-3-yl)oxy)methyl)benzonitrile

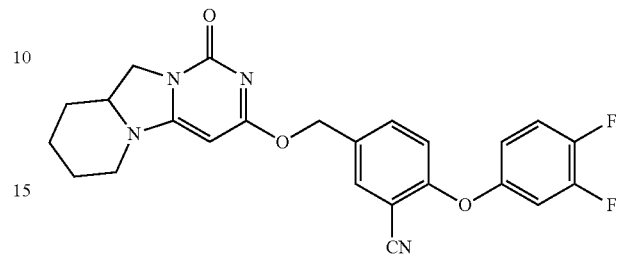

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and 2-(3,4-difluorophenoxy)-5-(hydroxymethyl)benzonitrile.

LCMS (ESI): m/z 451 [M+H]+; 2.73 min (ret time).

E20

2-Chloro-4-(2-cyano-4-(((1-oxo-6,7,8,9,9a,10-hexahydro-1H-pyrido[1',2':3,4]imidazo[1,2-c] pyrimidin-3-yl)oxy)methyl)phenoxy)benzonitrile

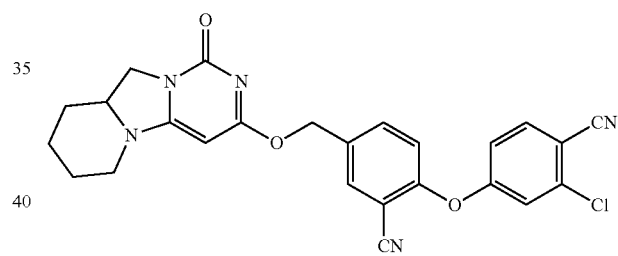

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and 2-chloro-4-(2-cyano-4-(hydroxymethyl)phenoxy)benzonitrile.

LCMS (ESI): m/z 474 [M+H]+; 2.70 min (ret time)

E210

3-((3,5-Difluoro-4-((5-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

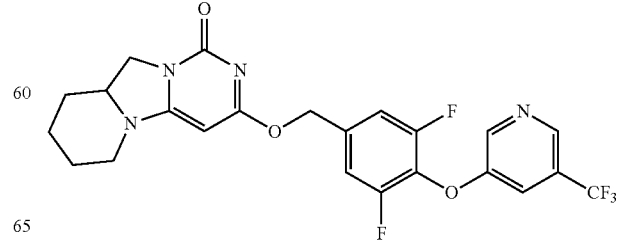

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and (3,5-difluoro-4-((5-(trifluoromethyl)pyridin-3-yl)oxy)phenyl)methanol.

LCMS (ESI): m/z 495 [M+H]⁺; 2.78 min (ret time)

E22

3-((3-Fluoro-4-((6-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

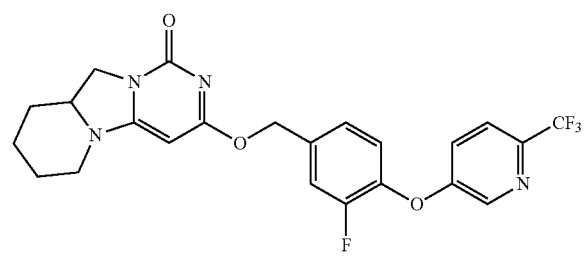 [SMILES: O=c1nc(OCc2ccc(Oc3ccc(C(F)(F)F)nc3)c(F)c2)cc2n1CC1CCCCN21]

The title compound was prepared by a procedure similar to that described for E1 starting from (3-fluoro-4-((6-(trifluoromethyl)pyridin-3-yl)oxy)phenyl)methanol and 3-chloro-6,7,8,9,9a,10-hexa-hydro-1H-pyrido[1',2':3,4]imidazo[1,2-c]pyrimidin-1-one.

LC-MS (ESI): m/z 477 [M+H]⁺; 1.04 min (ret time).

E23

5-(((1-Oxo-6,7,8,9,9a,10-hexahydro-1H-pyrido[1',2':3,4]imidazo[1,2-c]pyrimidin-3-yl)oxy)methyl)-2-(4-(trifluoromethyl)phenoxy)benzonitrile

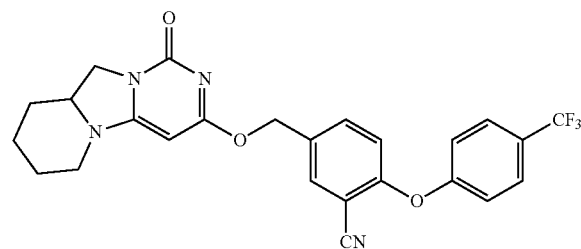 [SMILES: N#Cc1cc(COc2cc3n(c(=O)n2)CC2CCCCN32)ccc1Oc1ccc(C(F)(F)F)cc1]

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and 5-(hydr-oxymethyl)-2-(4-(trifluoromethyl)phenoxy)benzonitrile.

LCMS (ESI): m/z 483 [M+H]⁺; 2.90 min (ret time).

E24

2-(4-Chloro-3-fluorophenoxy)-5-(((1-oxo-6,7,8,9,9a,10-hexahydro-1H pyrido-[1',2':3,4]imidazo[1,2-c]pyrimidin-3-yl)oxy)methyl)benzonitrile

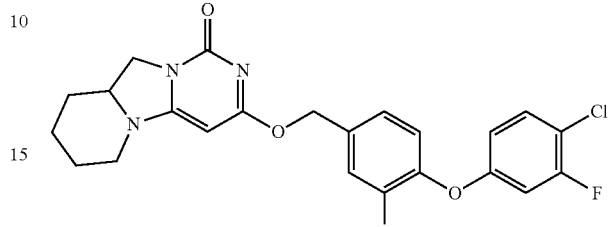

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and 2-(4-chloro-3-fluorophenoxy)-5-(hydroxymethyl)benzonitrile.

LCMS (ESI): m/z 467 [M+H]⁺; 2.85 min (ret time).

E25

3-((3,5-Difluoro-4-((6-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

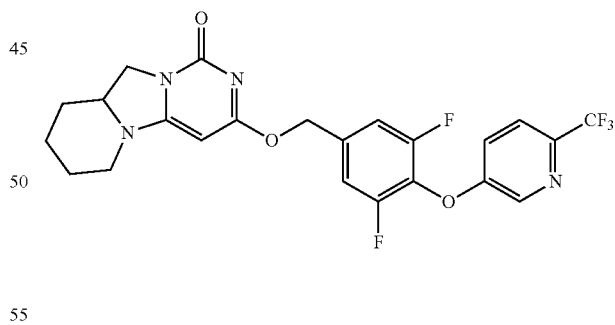

The title compound was prepared by a procedure similar to that described for E1 starting from (3,5-difluoro-4-((6-(trifluoromethyl)pyridin-3-yl)oxy)phenyl)methanol and 3-chloro-6,7,8,9,9a,10-hexahydro-1H-pyrido[1',2':3,4] imidazo[1,2-c] pyrimidin-1-one.

LC-MS (ESI): m/z 495 [M+H]⁺; 1.07 min (ret time).

E26

3-((4-((2-Chloropyridin-4-yl)oxy)-3,5-difluorobenzyl)oxy)-6,7,8,9,9a,10-hexahydro-1H-pyrido[1,2':3,4]imidazo[1,2-c]pyrimidin-1-one

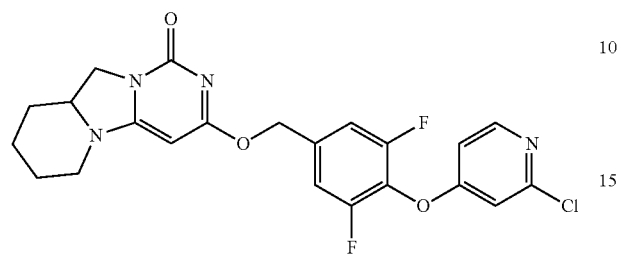

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and (4-((2-chloropyridin-4-yl)oxy)-3,5-difluorophenyl)methanol.

LCMS (ESI): m/z 461 [M+H]$^+$; 2.58 min (ret time).

E27

3-((3-Chloro-4-fluorobenzyl)oxy)-6,7,8,9,9a,10-hexahydro-1H-pyrido[1',2':3,4]imidazo[1,2 c]pyrimidin-1-one

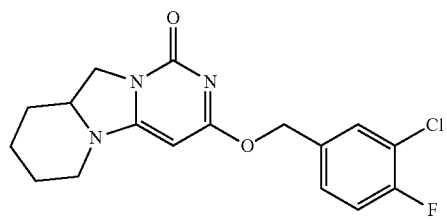 [SMILES: O=c1nc(OCc2ccc(F)c(Cl)c2)cc2n1CC1CCCCN21]

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and (3-chloro-4-fluorophenyl)methanol.

LCMS (ESI): m/z 350 [M+H]$^+$; 2.36 min (ret time).

E28

3-(2-Fluoro-4-(((1-oxo-6,7,8,9,9a,10-hexahydro-1H-pyrido[1',2':3,4]imidazo[1,2-c]pyrimidin-3-yl)oxy)methyl)phenoxy)-5-(trifluoromethyl)benzonitrile

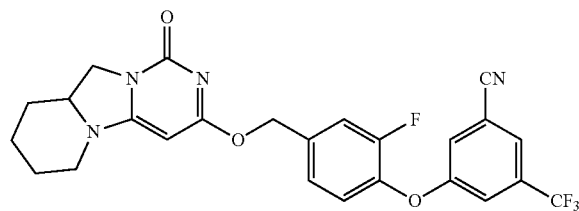 [SMILES: N#Cc1cc(Oc2ccc(COc3cc4n(c(=O)n3)CC3CCCCN43)cc2F)cc(C(F)(F)F)c1]

The title compound was prepared by a procedure similar to that described for E1 starting from 3-(2-fluoro-4-(hydroxymethyl)phenoxy)-5-(trifluoromethyl)benzonitrile and 3-chloro-6,7,8,9,9a,10-hexahydro-1H-pyrido[1',2':3,4]imidazo[1,2-c]pyrimidin-1-one.

LCMS (ESI): m/z 501 [M+H]$^+$; 2.91 min (ret time).

E29

3-((3-Chloro-5-fluorobenzyl)oxy)-6,7,8,9,9a,10-hexahydro-1H-pyrido[1',2':3,4]imidazo[1,2-c]pyrimidin-1-one

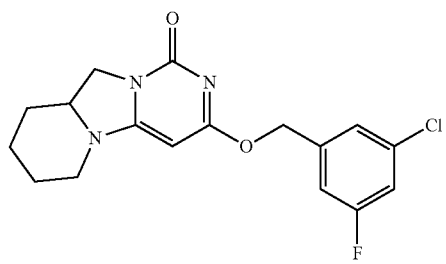 [SMILES: O=c1nc(OCc2cc(F)cc(Cl)c2)cc2n1CC1CCCCN21]

The title compound was prepared by a procedure similar to that described for E1 starting from 3-chloro-6,7,8,9,9a,10-hexahydro-1H-pyrido[1',2':3,4]imidazo[1,2-c]pyrimidin-1-one and (3-chloro-5-fluorophenyl)methanol.

LCMS (ESI): m/z 350 [M+H]$^+$; 2.42 min (ret time).

E30

(R)-3-((3,4-Difluorobenzyl)oxy)-6,7,8,9,9a,10-hexahydro-1H-pyrido[1',2':3,4]imidazo[1,2-c]pyrimidin-1-one

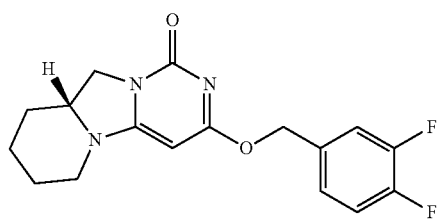 [SMILES: O=c1nc(OCc2ccc(F)c(F)c2)cc2n1C[C@H]1CCCCN21]

The title compound was prepared by a procedure similar to that described for E1 starting from (R)-3-chloro-6,7,8,9,9a,10-hexahydro-1H-pyrido[1',2':3,4]imidazo[1,2-c]pyrimidin-1-one and (3,4-difluorophenyl)methanol.

LCMS (ESI): m/z 334 [M+H]$^+$; 2.29 min (ret time).

199

E31

(S)-3-((3,4-Difluorobenzyl)oxy)-6,7,8,9,9a,10-hexahydro-1H-pyrido[1',2':3,4]imidazo[1,2-c]pyrimidin-1-one

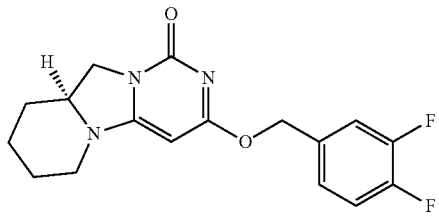 [SMILES: O=c1nc(OCc2ccc(F)c(F)c2)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (3,4-difluorophenyl)methanol.
LCMS (ESI): m/z 334 [M+H]$^+$; 2.23 min (ret time)

E32

(S)-3-((3,4,5-Trifluorobenzyl)oxy)-6,7,8,9,9a,10-hexahydro-1H-pyrido[1',2':3,4]imidazo[1,2-c]pyrimidin-1-one

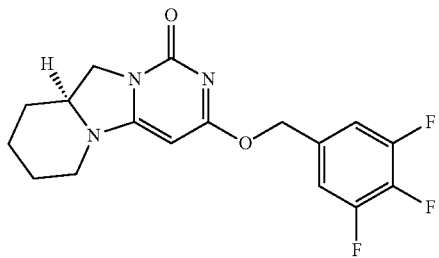 [SMILES: O=c1nc(OCc2cc(F)c(F)c(F)c2)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (3,4,5-trifluorophenyl)methanol.
LCMS (ESI): m/z 352 [M+H]$^+$; 2.37 min (ret time)

E33

(S)-3-(((1-Oxo-6,7,8,9,9a,10-hexahydro-1H-pyrido[1',2':3,4]imidazo[1,2-c]pyrimidin-3-yl) oxy)methyl)benzonitrile

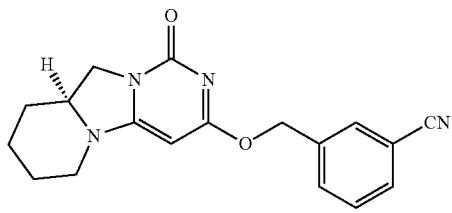 [SMILES: N#Cc1cccc(COc2cc3n(c(=O)n2)C[C@@H]2CCCCN32)c1]

200

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and 3-(hydroxymethyl)benzonitrile.
LCMS (ESI): m/z 323 [M+H]$^+$; 2.40 min (ret time).

E34

(S)-3-((4-Fluorobenzyl)oxy)-6,7,8,9,9a,10-hexahydro-1H-pyrido[1',2':3,4]imidazo-[1,2-c] pyrimidin-1-one

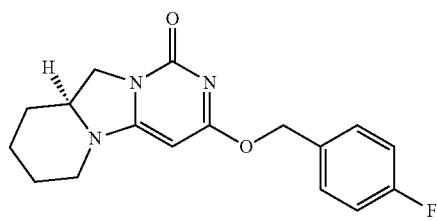 [SMILES: O=c1nc(OCc2ccc(F)cc2)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (4-fluorophenyl)methanol.
LCMS (ESI): m/z 316 [M+H]$^+$; 2.31 min (ret time).

E35

(S)-3-((3,5-Difluorobenzyl)oxy)-6,7,8,9,9a,10-hexahydro-1H-pyrido[1',2':3,4]imidazo[1,2-c]pyrimidin-1-one

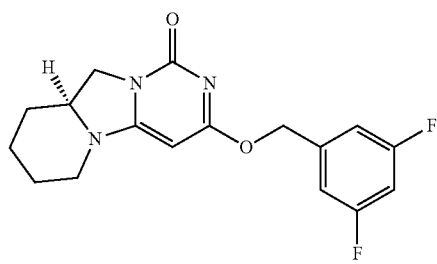 [SMILES: O=c1nc(OCc2cc(F)cc(F)c2)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (3,5-difluorophenyl)methanol.
LCMS (ESI): m/z 334 [M+H]$^+$; 2.76 min (ret time).

E36

(S)-3-(2-(Thiophen-2-yl)ethoxy)-6,7,8,9,9a,10-hexahydro-1H-pyrido[1',2':3,4]imidazo[1,2-c]pyrimidin-1-one

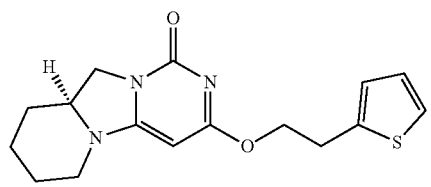 [SMILES: O=c1nc(OCCc2cccs2)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and 2-(thiophen-2-yl)ethanol.
LCMS (ESI): m/z 318 [M+H]$^+$; 2.69 min (ret time).

E37

3-((3,5-difluoro-4-((2-(trifluoromethyl)pyridin-4-yl)oxy)benzyl)oxy)-6,7,8,9,9a,10-hexahydro-1H-pyrido[1',2':3,4]imidazo[1,2-c]pyrimidin-1-one

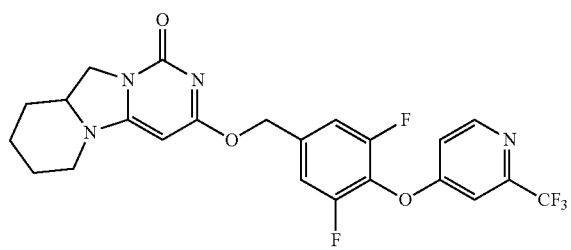 [SMILES: O=c1nc(OCc2cc(F)c(Oc3ccnc(C(F)(F)F)c3)c(F)c2)cc2n1CC1CCCCN21]

The title compound was prepared by a procedure similar to that described for E1 starting from (3,5-difluoro-4-((2-(trifluoromethyl)pyridin-4-yl)oxy)phenyl)methanol and 3-chloro-6,7,8,9,9a,10-hexahydro-1H-pyrido[1',2':3,4]imidazo[1,2-c]pyrimidin-1-one.
LC-MS (ESI): m/z 495 [M+H]$^+$; 2.04 min (ret time).

E38

3-((3-Fluoro-4-((6-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

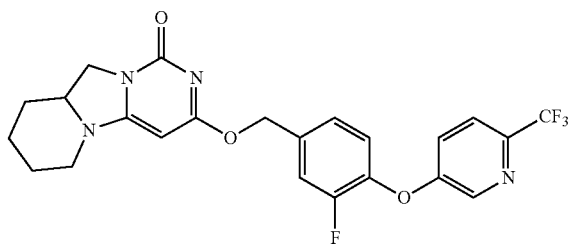 [SMILES: O=c1nc(OCc2ccc(Oc3ccc(C(F)(F)F)nc3)c(F)c2)cc2n1CC1CCCCN21]

The title compound was prepared by a procedure similar to that described for E1 starting from (3-fluoro-4-((6-(trifluoromethyl)pyridin-3-yl)oxy)phenyl)methanol and 3-chloro-6,7,8,9,9a,10-hexa-hydro-1H-pyrido[1',2':3,4]imidazo[1,2-c]pyrimidin-1-one.
LC-MS (ESI): m/z 477 [M+H]$^+$; 1.04 min (ret time).

E39

3-((3,5-Difluoro-4-((6-(trifluoromethyl)pyridin-3-yl)oxy)benzyl)oxy)-6,7,8,9,9a,10-hexahydro 1H-pyrido[1',2':3,4]imidazo[1,2-c]pyrimidin-1-one

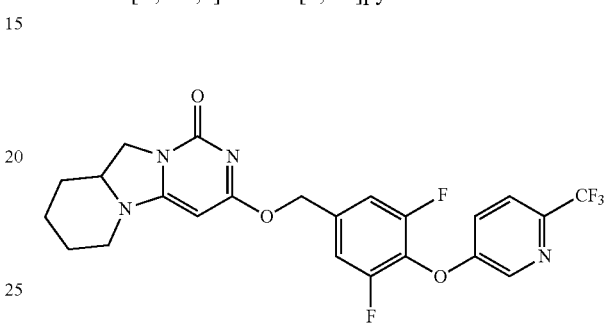

The title compound was prepared by a procedure similar to that described for E1 starting from (3,5-difluoro-4-((6-(trifluoromethyl)pyridin-3-yl)oxy)phenyl)methanol and 3-chloro-6,7,8,9,9a,10-hexahydro-1H-pyrido[1',2':3,4]imidazo[1,2-c]pyrimidin-1-one.
LC-MS (ESI): m/z 495 [M+H]$^+$; 1.07 min (ret time).

E40

(S)-3-((3-Fluoro-4-((2-(trifluoromethyl)pyridin-4-yl)oxy)benzyl)oxy)-6,7,8,9,9a,10-hexahydro-1H-pyrido[1',2':3,4]imidazo[1,2-c]pyrimidin-1-one

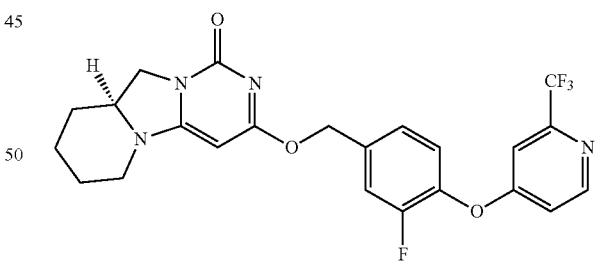

The title compound was prepared by a procedure similar to that described for E1 starting from (3-fluoro-4-((2-(trifluoromethyl)pyridin-4-yl)oxy)phenyl)methanol and (S)-3-chloro-6,7,8,9,9a,10-hexahydro-1H-pyrido[1',2': 3,4] imidazo[1,2-c]pyrimidin-1-one.
LC-MS (ESI): m/z 477 [M+H]$^+$; 1.03 min(ret time).

E41

3-((4-Fluorobenzyl)oxy)-6,7,8,9,9a,10-hexahydro-1H-pyrido[1',2':3,4]imidazo[1,2-c]pyrimidin-1-one

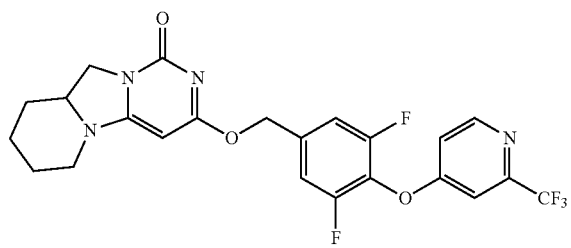 [SMILES: O=c1nc(OCc2cc(F)c(Oc3ccnc(C(F)(F)F)c3)c(F)c2)cc2n1CC1CCCCN21]

The title compound was prepared by a procedure similar to that described for E1 starting from (3,5-difluoro-4-((2-(trifluoromethyl)pyridin-4-yl)oxy)phenyl)methanol and 3-chloro-6,7,8,9,9a,10-hexahydro-1H-pyrido[1',2':3,4] imidazo[1,2-c]pyrimidin-1-one.

LC-MS (ESI): m/z 495 [M+H]$^+$; 1.05 min (ret time).

E42

(S)-3-((3-fluoro-4-((5-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

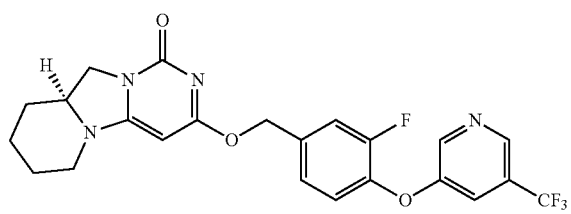 [SMILES: O=c1nc(OCc2ccc(Oc3cncc(C(F)(F)F)c3)c(F)c2)cc2n1C[C@@H]1CCCCN21]

The title compound was prepared by a procedure similar to that described for E1 starting from (3-fluoro-4-((5-(trifluoromethyl)pyridin-3-yl)oxy)phenyl)methanol and (S)-3-chloro-6,7,8,9,9a,10-hexahydro-1H-pyrido[1',2':3,4]imidazo[1,2-c]pyrimidin-1-one.

LC-MS (ESI): m/z 477[M+H]$^+$; 1.03 min (ret time).

E43

3-((3-fluoro-4-((2-(trifluoromethyl)pyrimidin-5-yl)oxy)benzyl)oxy)-6,7,8,9,9a,10-hexahydro-1H-pyrido[1',2':3,4]imidazo[1,2-c]pyrimidin-1-one

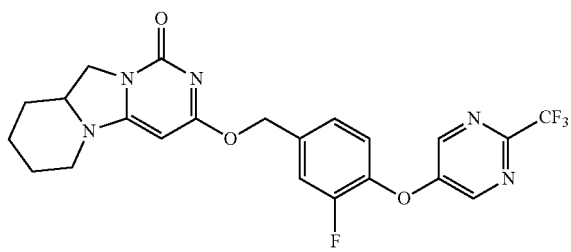 [SMILES: O=c1nc(OCc2ccc(Oc3cnc(C(F)(F)F)nc3)c(F)c2)cc2n1CC1CCCCN21]

The title compound was prepared by a procedure similar to that described for E1 starting from (3-fluoro-4-((2-(trifluoromethyl)pyrimidin-5-yl)oxy)phenyl)methanol and 3-chloro-6,7,8,9,9a,10-hexahydro-1H-pyrido[1',2':3,4] imidazo[1,2-c]pyrimidin-1-one.

LC-MS (ESI): m/z 478 [M+H]$^+$; 1.24 min (ret time).

E44

3-((3-Fluoro-4-((2-(trifluoromethyl)pyridin-4-yl)oxy)benzyl)oxy)-6,7,8,9,9a,10-hexahydro-1H-pyrido[1',2':3,4]imidazo[1,2-c]pyrimidin-1-one

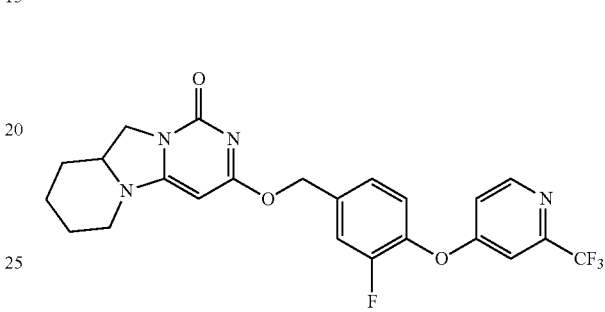

The title compound was prepared by a procedure similar to that described for E1 starting from 3-fluoro-4-((2-(trifluoromethyl)pyridin-4-yl)oxy)phenyl)methanol and 3-chloro-6,7,8,9,9a,10-hexahydro-1H-pyrido-[1',2': 3,4]imidazo[1,2-c]pyrimidin-1-one.

LC-MS (ESI): m/z 477 [M+H]$^+$; 1.99 min (ret time).

E45

3-((3,5-Difluoro-4-((2-(trifluoromethyl)pyridin-4-yl)oxy)benzyl)oxy)-6,7,8,9,9a,10-hexahydro-1H-pyrido[1',2':3,4]imidazo[1,2-c]pyrimidin-1-one

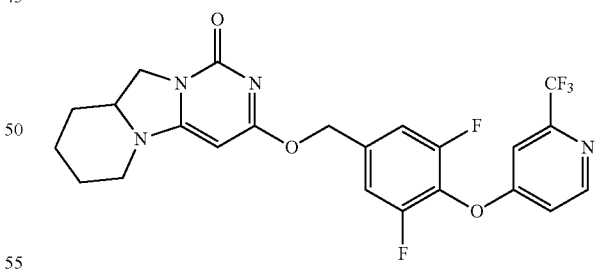

The title compound was prepared by a procedure similar to that described for E1 starting from (3,5-difluoro-4-((2-(trifluoromethyl)pyridin-4-yl)oxy)phenyl)methanol and 3-chloro-6,7,8,9,9a,10-hexahydro-1H-pyrido[1',2':3,4]imidazo[1,2-c]pyrimidin-1-one.

LC-MS (ESI): m/z 495 [M+H]$^+$; 1.06 min (ret time).

E46

3-((3-Fluoro-4-((2-(trifluoromethyl)pyrimidin-5-yl)oxy)benzyl)oxy)-6,7,8,9,9a,10-hexahydro-1H-pyrido[1',2':3,4]imidazo[1,2-c]pyrimidin-1-one

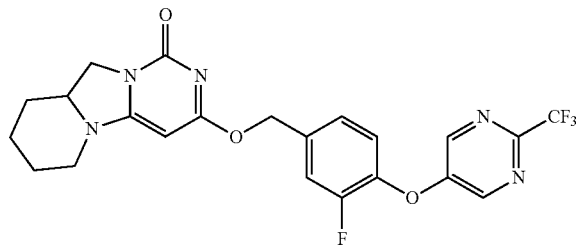 [SMILES: O=c1nc(OCc2ccc(Oc3cnc(C(F)(F)F)nc3)c(F)c2)cc2n1CC1CCCCN21]

The title compound was prepared by a procedure similar to that described for E1 starting from (3-fluoro-4-((2-(trifluoromethyl)pyrimidin-5-yl)oxy)phenyl)methanol and 3-chloro-6,7,8,9,9a,10-hexahydro-1H-pyrido[1',2':3,4]imidazo[1,2-c]pyrimidin-1-one.

LC-MS (ESI): m/z 478 [M+H]$^+$; 2.00 min (ret time).

E47

3-((3-Fluoro-4-((5-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

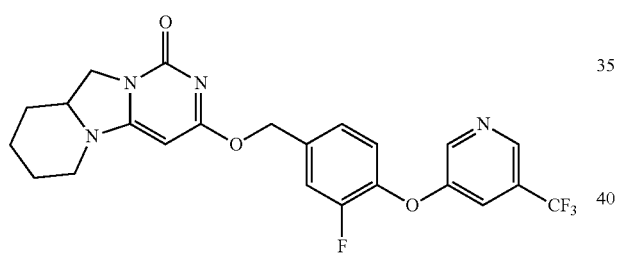

The title compound was prepared by a procedure similar to that described for E1 starting from (3-fluoro-4-((5-(trifluoromethyl)pyridin-3-yl)oxy)phenyl)methanol and 3-chloro-6,7,8,9,9a,10-hexahydro-1H-pyrido[1',2':3,4]imidazo[1,2-c]pyrimidin-1-one.

LC-MS (ESI): m/z 477 [M+H]$^+$; 1.99 min (ret time).

E48

3-((3-Fluoro-4-((6-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

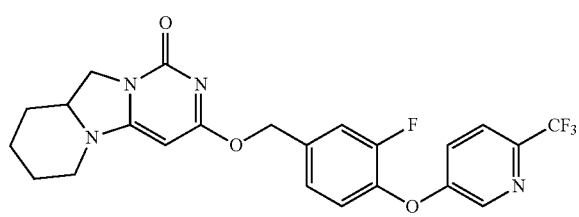 [SMILES: O=c1nc(OCc2ccc(Oc3ccc(C(F)(F)F)nc3)c(F)c2)cc2n1CC1CCCCN21]

The title compound was prepared by a procedure similar to that described for E1 starting from (3-fluoro-4-((6-(trifluoromethyl)pyridin-3-yl)oxy)phenyl)methanol and 3-chloro-6,7,8,9,9a,10-hexahydro-1H-pyrido[1',2':3,4]imidazo[1,2-c]pyrimidin-1-one.

LC-MS (ESI): m/z 477 [M+H]$^+$; 1.08 min (ret time).

E49

3-((3,5-difluoro-4-((6-(trifluoromethyl)pyridin-3-yl)oxy)benzyl)oxy)-6,7,8,9,9a,10-hexahydro-1H-pyrido[1',2':3,4]imidazo[1,2-c]pyrimidin-1-one

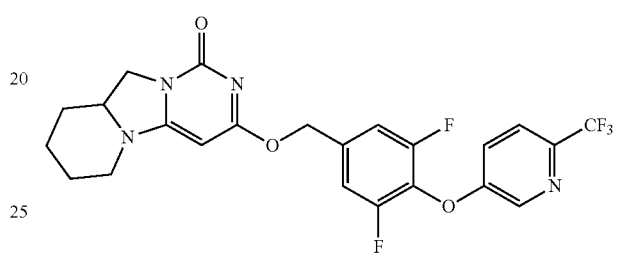

The title compound was prepared by a procedure similar to that described for E1 starting from (3,5-difluoro-4-((6-(trifluoromethyl)pyridin-3-yl)oxy)phenyl)methanol and 3-chloro-6,7,8,9,9a,10-hexahydro-1H-pyrido[1',2':3,4]imidazo[1,2-c]pyrimidin-1-one.

LCMS (ESI): m/z 495 [M+H]$^+$; 1.10 min (ret time).

E50

(S)-3-((3,5-difluoro-4-((1-methyl-1H-pyrazol-4-yl)oxy)benzyl)oxy)-6,7,8,9,9a,10-hexahydro-1H-pyrido[1',2':3,4]imidazo[1,2-c]pyrimidin-1-one

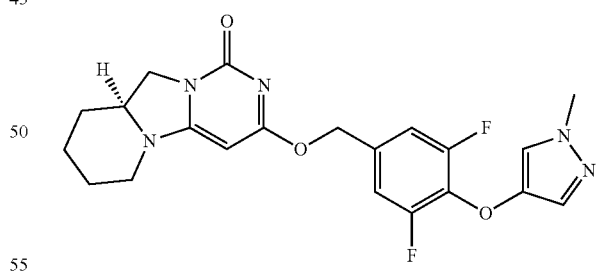

The title compound was prepared by a procedure similar to that described for E1 starting from (3,5-difluoro-4-((1-methyl-1H-pyrazol-4-yl)oxy)phenyl)methanol and (S)-3-chloro-6,7,8,9,9a,10-hexahydro-1H-pyrido[1',2':3,4]imidazo[1,2-c]pyrimidin-1-one LCMS (ESI): m/z 430 [M+H]$^+$; 1.34 min (ret time).

E51

(S)-3-((3-fluoro-4-((1-methyl-1H-pyrazol-4-yl)oxy)benzyl)oxy)-6,7,8,9,9a,10-hexahydro-1H-pyrido[1,2':3,4]imidazo[1,2-c]pyrimidin-1-one

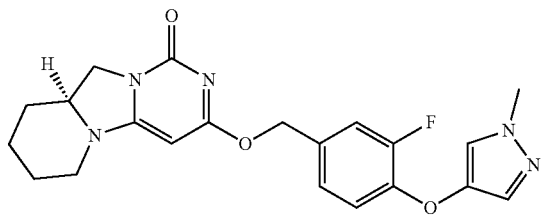 [SMILES: Cn1cc(Oc2ccc(COc3cc4n(c(=O)n3)C[C@@H]3CCCCN43)cc2F)cn1]

The title compound was prepared by a procedure similar to that described for E1 starting from (3-fluoro-4-((1-methyl-1H-pyrazol-4-yl)oxy)phenyl)methanol and (S)-3-chloro-6,7,8,9,9a,10-hexahydro-1H-pyrido[1',2':3,4]imidazo[1,2-c]pyrimidin-1-one LCMS (ESI): m/z 412 [M+H]$^+$; 1.15 min (ret time).

E52

(R)-3-((3-Fluorobenzyl)oxy)-6,7,8,9,9a,10-hexahydro-1H-pyrido[1',2':3,4]imidazo[1,2-c] pyrimidin-1-one

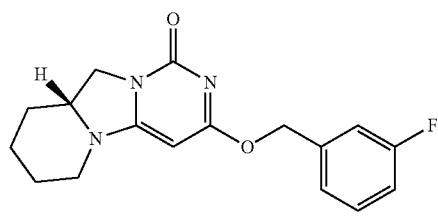 [SMILES: O=c1nc(OCc2cccc(F)c2)cc2n1C[C@H]1CCCCN21]

The title compound was prepared by a procedure similar to that described for E1 starting from (R)-3-chloro-6,7,8,9,9a,10-hexahydro-1H-pyrido[1',2':3,4]imidazo[1,2-c]pyrimidin-1-one and (3-fluorophenyl)methanol.

LCMS (ESI): m/z 316 [M+H]$^+$; 3.83 min (ret time).

$^1$H NMR (300 MHz, CDCl$_3$): δ 7.34-7.26 (m, 1H), 7.17-7.11 (m, 2H), 7.02-6.97 (m, 1H), 5.39 (s, 2H), 4.99 (s, 1H), 4.24-4.19 (m, 1H), 3.77-3.64 (m, 2H), 3.55-3.51 (m, 1H), 3.02-2.97 (m, 1H), 2.01-1.92 (m, 2H), 1.76 (d, J=5.7 Hz, 1H), 1.61-1.45 (m, 3H).

E53

(R)-3-((3,5-Difluorobenzyl)oxy)-6,7,8,9,9a,10-hexahydro-1H-pyrido[1',2':3,4]imidazo[1,2-c] pyrimidin-1-one

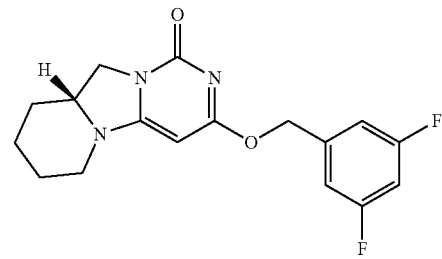 [SMILES: O=c1nc(OCc2cc(F)cc(F)c2)cc2n1C[C@H]1CCCCN21]

The title compound was prepared by a procedure similar to that described for E1 starting from (R)-3-chloro-6,7,8,9,9a,10-hexahydro-1H-pyrido[1',2':3,4]imidazo[1,2-c]pyrimidin-1-one and (3,5-difluorophenyl)methanol.

LCMS (ESI): m/z 334 [M+H]$^+$; 3.97 min (ret time).

$^1$H NMR (300 MHz, CDCl$_3$): δ 6.91 (d, J=4.5 Hz, 2H), 6.75-6.71 (m, 1H), 5.37 (s, 2H), 5.00 (s, 1H), 4.24-4.19 (m, 1H), 3.78-3.76 (m, 1H), 3.69-3.65 (m, 1H), 3.56-3.53 (m, 1H), 3.04-3.00.

E54

(R)-3-((3,4,5-Trifluorobenzyl)oxy)-6,7,8,9,9a,10-hexahydro-1H-pyrido[1',2':3,4]imidazo[1,2-c]pyrimidin-1-one

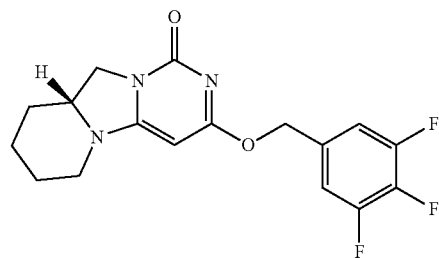 [SMILES: O=c1nc(OCc2cc(F)c(F)c(F)c2)cc2n1C[C@H]1CCCCN21]

The title compound was prepared by a procedure similar to that described for E1 starting from (R)-3-chloro-6,7,8,9,9a,10-hexahydro-1H-pyrido[1',2':3,4]imidazo[1,2-c]pyrimidin-1-one and (3,4,5-trifluorophenyl)methanol.

LCMS (ESI): m/z 352 [M+H]$^+$; 4.10 min (ret time).

$^1$H NMR (300 MHz, CDCl$_3$): δ 7.02 (t, J=5.4 Hz, 1H), 5.32 (s, 2H), 4.98 (s, 1H), 4.24-4.19 (m, 1H), 3.79-3.75 (m, 1H), 3.69-3.64 (m, 1H), 3.56-3.52 (m, 1H), 3.04-2.97 (m, 1H), 1.95 (d, J=8.1 Hz, 2H), 1.78-1.76 (m, 1H), 1.57-1.48 (m, 3H).

E55

(R)-3-((2,4-Difluorobenzyl)oxy)-6,7,8,9,9a,10-hexahydro-1H-pyrido[1',2':3,4]imidazo[1,2-c] pyrimidin-1-one

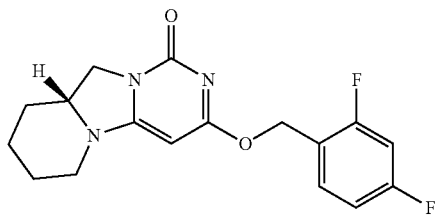 [SMILES: O=c1nc(OCc2ccc(F)cc2F)cc2n1C[C@H]1CCCCN21]

The title compound was prepared by a procedure similar to that described for E1 starting from (R)-3-chloro-6,7,8,9,9a,10-hexahydro-1H-pyrido[1',2':3,4]imidazo[1,2-c]pyrimidin-1-one and (2,4-difluorophenyl)methanol.

LCMS (ESI): m/z 334 [M+H]$^+$; 3.88 min (ret time).

$^1$H NMR (300 MHz, CDCl$_3$): δ 7.49-7.43 (m, 1H), 6.88-6.79 (m, 1H), 5.40 (s, 2H), 4.95 (s, 1H), 4.24-4.19 (m, 1H), 3.77-3.72 (m, 1H), 3.69-3.64 (m, 1H), 3.51 (t, J=7.2 Hz, 1H), 2.99 (t, J=7.5 Hz, 1H), 2.01-1.93 (m, 2H), 1.76-1.73 (m, 1H), 1.59-1.46 (m, 3H).

E56

(R)-3-((2,3-Difluorobenzyl)oxy)-6,7,8,9,9a,10-hexahydro-1H-pyrido[1',2':3,4]imidazo[1,2-c] pyrimidin-1-one

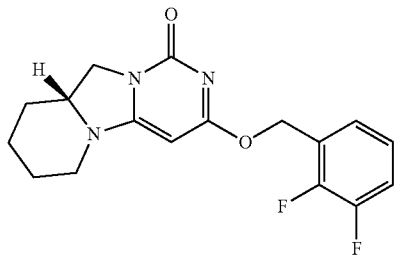 [SMILES: O=c1nc(OCc2cccc(F)c2F)cc2n1C[C@H]1CCCCN21]

The title compound was prepared by a procedure similar to that described for E1 starting from (R)-3-chloro-6,7,8,9,9a,10-hexahydro-1H-pyrido[1',2':3,4]imidazo[1,2-c]pyrimidin-1-one and (2,3-difluorophenyl)methanol.

LCMS (ESI): m/z 334 [M+H]$^+$; 3.88 min (ret time).

$^1$H NMR (300 MHz, CDCl$_3$): δ 7.26-7.21 (m, 1H), 7.14-7.05 (m, 2H), 5.47 (s, 2H), 4.97 (s, 1H), 4.24-4.19 (m, 1H), 3.77-3.53 (m, 2H), 3.51 (t, J=9.6 Hz, 1H), 3.03-2.96 (m, 1H), 1.96 (t, J=9.0 Hz, 2H), 1.75 (d, J=3.6 Hz, 1H), 1.60-1.43 (m, 3H).

E57

(S)-3-((2,4-Difluorobenzyl)oxy)-6,7,8,9,9a,10-hexahydro-1H-pyrido[1',2':3,4]imidazo[1,2-c] pyrimidin-1-one

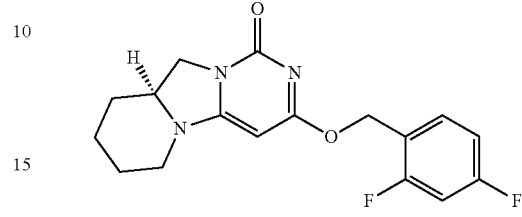

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (2,4-difluorophenyl)methanol.

LCMS (ESI): m/z 334 [M+H]$^+$; 3.30 min (ret time).

$^1$H NMR (300 MHz, CDCl$_3$): δ 7.46-7.43 (m, 1H), 6.87-6.77 (m, 2H), 5.38 (s, 2H), 4.94 (s, 1H), 4.23-4.16 (m, 1H), 3.76-3.61 (m, 2H), 3.51-3.46 (m, 1H), 2.98 (d, J=3.0 Hz, 1H), 2.02-1.44 (m, 6H).

E58

(S)-3-((2,3-Difluorobenzyl)oxy)-6,7,8,9,9a,10-hexahydro-1H-pyrido[1',2':3,4]imidazo[1,2-c] pyrimidin-1-one

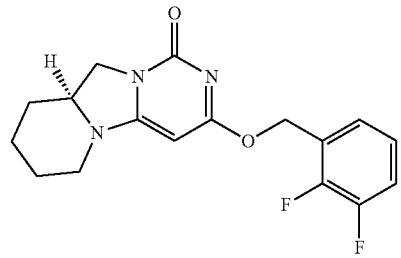 [SMILES: O=c1nc(OCc2cccc(F)c2F)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (2,3-difluorophenyl)methanol.

LCMS (ESI): m/z 334 [M+H]$^+$; 3.89 min (ret time).

$^1$H NMR (300 MHz, CDCl$_3$): δ 7.28-7.05 (m, 3H), 5.46 (s, 2H), 4.97 (s, 1H), 4.24-4.18 (m, 1H), 3.78-3.49 (m, 3H), 2.99 (d, J=2.7 Hz, 1H), 1.96-1.45 (m, 6H).

E59

(S)-3-((2,4,5-Trifluorobenzyl)oxy)-6,7,8,9,9a,10-hexahydro-1H-pyrido[1',2':3,4]imidazo[1,2-c]pyrimidin-1-one

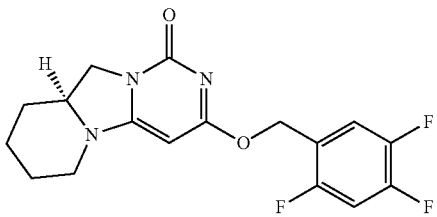 [SMILES: O=c1nc(OCc2cc(F)c(F)cc2F)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (2,4,5-trifluorophenyl)methanol.

LCMS (ESI): m/z 352 [M+H]⁺; 4.00 min (ret time).

¹H NMR (300 MHz, CDCl₃): δ 7.33-7.27 (m, 1H), 6.97-6.88 (m, 1H), 5.39 (s, 2H), 4.97 (m, 1H), 4.25-4.18 (m, 1H), 3.76-3.50 (m, 3H), 3.01-3.00 (m, 1H), 1.97-1.93 (m, 2H), 1.77-1.75 (m, 2H), 1.52-1.46 (m, 3H).

E60

(S)-3-((3-Fluorobenzyl)oxy)-6,7,8,9,9a,10-hexahydro-1H-pyrido[1',2':3,4]imidazo[1,2-c] pyrimidin-1-one

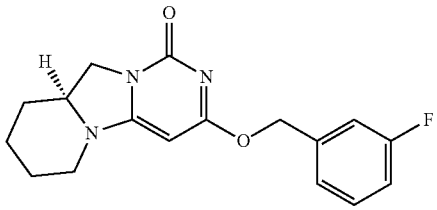 [SMILES: O=c1nc(OCc2cccc(F)c2)cc2n1C[C@@H]1CCCCN21]

The title compound was prepared by a procedure similar to that described for E1 starting from (S)-3-chloro-6,7,8,9,9a,10-hexahydro-1H-pyrido[1',2':3,4]imidazo[1,2-c]pyrimidin-1-one and (3-fluorophenyl)methanol.

LCMS (ESI): m/z 316 [M+H]⁺; 3.83 min (ret time).

¹H NMR (300 MHz, CDCl₃): δ 7.32-7.27 (m, 1H), 7.17-7.09 (m, 2H), 6.98 (d, J=1.8 Hz, 1H), 5.38 (s, 2H), 4.99 (s, 1H), 4.24-4.17 (m, 1H), 3.74-3.62 (m, 2H), 3.54-3.50 (m, 1H), 3.01-2.98 (m, 1H), 1.95-1.91 (m, 3H), 1.73 (s, 1H), 1.51-1.45 (m, 3H).

E61

(S)-3-((2,4-Difluorobenzyl)(methyl)amino)-6,7,8,9,9a,10-hexahydro-1H-pyrido[1',2':3,4] imidazo[1,2-c]pyrimidin-1-one

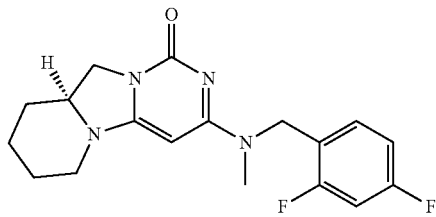 [SMILES: CN(Cc1ccc(F)cc1F)c1cc2n(c(=O)n1)C[C@@H]1CCCCN21]

To a solution of (S)-3-((2,4-difluorobenzyl)amino)-6,7,8,9,9a,10-hexahydro-1H-pyrido[1',2':3,4]imidazo[1,2-c]pyrimidin-1-one (64.0 mg, 0.193 mmol) and K₂CO₃ (133 mg, 0.965 mmol) in DMF (3 mL) was added CH₃I (137 mg, 0.965 mmol) at room temperature. The mixture was stirred at room temperature overnight. To the reaction mixture was added water (10 mL), extracted with EtOAc (30 mL×3), washed with brine (10 mL), dried over Na₂SO₄, filtered and concentrated under reduced pressure. The residue was purified with prep-HPLC to give the title compound (39 mg, 59%) as a pale yellow solid.

LCMS (ESI): m/z 347 [M+H]⁺; 3.11 min (ret time).

¹H NMR (300 MHz, CDCl₃): δ 7.61-7.58 (m, 1H), 6.88-6.73 (m, 2H), 4.63 (s, 1H), 4.36 (s, 2H), 4.12-4.04 (m, 1H), 3.56-3.45 (m, 3H), 3.41 (s, 3H), 2.92-2.88 (m, 1H), 1.97-1.90 (m, 2H), 1.76-1.60 (m, 1H), 1.56-1.36 (m, 3H).

E62

(R)-3-((3,5-Difluoro-4-(1-(2-fluoroethyl)cyclopropoxy)benzyl)oxy)-6,7,8,9,9a,10-hexahydro-1H-pyrido[1',2':3,4]imidazo[1,2-c]pyrimidin-1-one

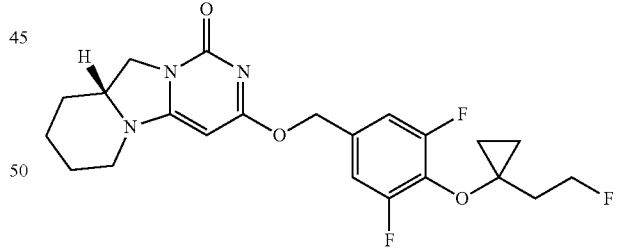

The title compound was prepared by a procedure similar to that described for E1 starting from (3,5-difluoro-4-(1-(2-fluoroethyl)cyclopropoxy)phenyl)methanol and (R)-3-chloro-6,7,8,9,9a,10-hexahydro-1H-pyrido[1',2':3,4]imidazo[1,2-c]pyrimidin-1-one.

LCMS (ESI): m/z 436 [M+H]⁺; 4.48 min (ret time).

¹H NMR (400 MHz, CDCl₃): δ 6.97-6.92 (m, 2H), 5.31 (s, 2H), 4.98 (s, 1H), 4.84 (t, J=6.0 Hz, 1H), 4.73 (t, J=6.0 Hz, 1H), 4.24-4.19 (m, 1H), 3.79-3.74 (m, 1H), 3.69-3.64 (m, 1H), 3.55-3.52 (m, 1H), 3.03-2.97 (m, 1H), 2.18-2.15 (m, 1H), 2.11 (t, J=6.4 Hz, 1H), 1.97-1.93 (m, 2H), 1.78-1.75 (m, 1H), 1.54-1.45 (m, 3H), 1.09 (t, J=6.8 Hz, 2H), 0.67-0.64 (m, 2H).

E63

3-((3, 5-Difluoro-4-((1-methyl-1H-pyrazol-4-yl)oxy)benzyl)oxy)-7,8,8a,9-tetrahydro pyrrolo[1',2':3, 4]imidazo[1, 2-c] pyrimidin-1(6H)-one

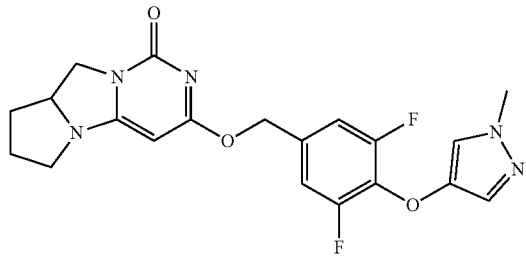 [SMILES: Cn1cc(Oc2c(F)cc(COc3cc4n(c(=O)n3)CC3CCCN43)cc2F)cn1]

To the solution of 3-chloro-7,8,8a,9-tetrahydropyrrolo[1',2':3,4]imidazo[1,2-c]pyrimidin-1(6H)-one (85 mg, 0.402 mmol) and (3,5-difluoro-4-((1-methyl-1H-pyrazol-4-yl)oxy)phenyl)methanol (96 mg, 0.402 mmol) in N,N-dimethylformamide (10 mL), sodium hydride (48.2 mg, 1.205 mmol) was added at 0° C. and stirred further 10 min. The result mixture was quenched and purified via C-18 flash column, removed the solvent afforded white solid of 3-((3, 5-difluoro-4-((1-methyl-1H-pyrazol-4-yl)oxy)benzyl)oxy)-7,8,8a,9-tetrahydropyrrolo[1',2':3,4]imidazo[1,2-c]pyrimidin-1 (6H)-one (55 mg, 0.126 mmol, 31.3% yield).

LC-MS (ESI): m/z 416 [M+H]$^+$; 3.55 min (ret time).

$^1$H NMR (400 MHz, DMSO-d$_6$): δ 7.61 (s, 1H), 7.32-7.27 (m, 3H), 5.34 (s, 1H), 5.30-5.23 (q, 2H), 4.10-4.01 (m, 2H), 3.89-3.85 (m, 1H), 3.73 (s, 3H), 3.40-3.28 (m, 2H), 2.03-1.87 (m, 3H), 1.49-1.42 (m, 1H).

E64

3-((4-((1-Ethyl-1H-pyrazol-4-yl) oxy)-3, 5-difluorobenzyl) oxy)-7, 8, 8a, 9-tetrahydropyrrolo[1',2':3, 4]imidazo[1,2-c]pyrimidin-1(6H)-one

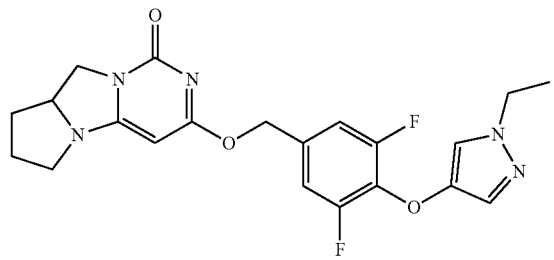 [SMILES: CCn1cc(Oc2c(F)cc(COc3cc4n(c(=O)n3)CC3CCCN43)cc2F)cn1]

The title compound was prepared by a procedure similar to that described for E63 starting from 3-chloro-7,8,8a,9-tetrahydropyrrolo[1',2':3,4]imidazo[1,2-c]pyrimidin-1(6H)-one and (4-((1-ethyl-1H-pyrazol-4-yl)oxy)-3,5-difluorophenyl)methanol.

LC-MS (ESI): m/z 430 [M+H]$^+$; 3.71 min (ret time).

$^1$H NMR (400 MHz, DMSO-d$_6$): δ7.66 (s, 1H), 7.38-7.28 (m, 3H), 5.34 (s, 1H), 5.30-5.23 (q, 2H), 4.07-3.99 (m, 4H), 3.88-3.85 (m, 1H), 3.35-3.28 (m, 2H), 2.08-1.89 (m, 3H), 1.49-1.39 (m, 1H), 1.33-1.23 (t, 3H).

E65

3-((3, 5-Difluoro-4-((1-isopropyl-1H-pyrazol-4-yl)oxy) benzyl) oxy)-7, 8, 8a, 9-tetrahydro pyrrolo[1', 2':3,4]imidazo[1,2-c]pyrimidin-1(6H)-one

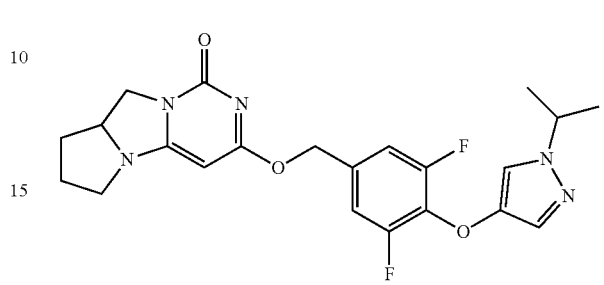

The title compound was prepared by a procedure similar to that described for E63 starting from 3-chloro-7,8,8a,9-tetrahydropyrrolo[1',2':3,4]imidazo[1,2-c]pyrimidin-1(6H)-one and (3,5-difluoro-4-((1-isopropyl-1H-pyrazol-4-yl)oxy)phenyl)methanol.

LC-MS (ESI): m/z 444 [M+H]$^+$; 2.56 min (ret time).

$^1$H NMR (400 MHz, DMSO-d$_6$): δ7.69 (s, 1H), 7.32-7.26 (m, 3H), 5.34 (s, 1H), 5.30-5.23 (q, 2H), 4.40-4.34 (m, 1H), 4.09-4.01 (m, 2H), 3.89-3.83 (m, 1H), 3.31-3.28 (m, 2H), 2.03-1.86 (m, 3H), 1.49-1.39 (m, 1H), 1.36-1.34 (d, 6H).

E66

(R)-3-((3, 5-difluoro-4-((1-methyl-1H-pyrazol-4-yl)oxy) benzyl) oxy)-7, 8, 8a, 9-tetrahydro pyrrolo[1', 2':3,4]imidazo[1,2-c]pyrimidin-1(6H)-one

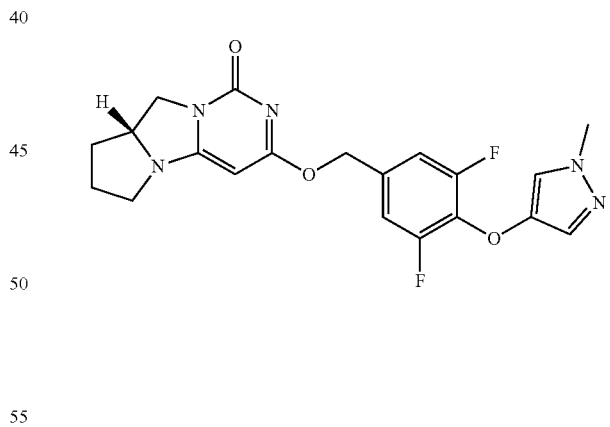

The title compound was prepared by a procedure similar to that described for E63 starting from (R)-3-chloro-7, 8, 8a, 9-tetrahydropyrrolo[1',2':3,4]imidazo[1,2-c]pyrimidin-1 (6H)-one and (3,5-difluoro-4-((1-methyl-1H-pyrazol-4-yl)oxy)phenyl)methanol.

LC-MS (ESI): m/z 416 [M+H]$^+$; 2.28 min (ret time).

$^1$H NMR (400 MHz, DMSO-d$_6$): δ7.61 (s, 1H), 7.32-7.27 (m, 3H), 5.34 (s, 1H), 5.30-5.23 (q, 2H), 4.10-4.01 (m, 2H), 3.89-3.85 (m, 1H), 3.73 (s, 3H), 3.40-3.28 (m, 2H), 2.03-1.87 (m, 3H), 1.49-1.42 (m, 1H).

E67

(R)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

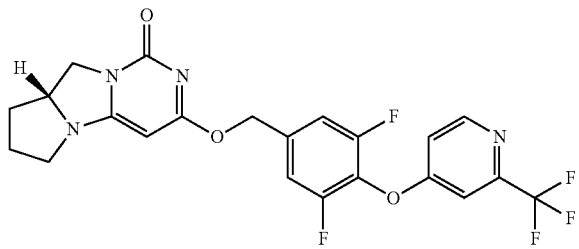 [SMILES: O=c1nc(OCc2cc(F)c(Oc3ccnc(C(F)(F)F)c3)c(F)c2)cc2n1C[C@H]1CCCN21]

To a solution of (R)-3-chloro-7,8,8a,9-tetrahydropyrrolo[1',2':3,4]imidazo[1,2-c]pyrimidin-1(6H)-one (85 mg, 0.402 mmol) and (3,5-difluoro-4-((2-(trifluoromethyl)pyridin-4-yl)oxy)phenyl)methanol (123 mg, 0.402 mmol) in DMF (10 mL) was added sodium hydride (48.2 mg, 1.205 mmol) at 0° C. and stirred for 10 min. The reaction mixture was quenched and purification via C-18 flash column afforded the title compound (50 mg, 0.099 mmol, 24.62% yield) as a white.

LC-MS (ESI): m/z 481 [M+H]$^+$; 2.83 min (ret time).

$^1$H NMR (400 MHz, DMSO-d$_6$): δ 8.70-8.68 (d, 1H), 7.67-7.66 (d, 1H), 7.47-7.45 (d, 2H), 7.33-7.31 (dd, 1H), 5.37 (s, 1H), 5.37-5.30 (q, 2H), 4.10-4.02 (m, 2H), 3.90-3.84 (m, 1H), 3.33-3.27 (m, 2H), 2.04-1.85 (m, 3H), 1.50-1.42 (m, 1H).

$^{19}$F NMR (376 MHz, DMSO-d$_6$): δ (ppm): −66.65, −126.83.

E68

(R)-3-((3-fluoro-4-((1-methyl-1H-pyrazol-4-yl) oxy) benzyl) oxy)-7, 8, 8a, 9-tetrahydro pyrrolo[1',2':3,4]imidazo[1,2-c]pyrimidin-1(6H)-one

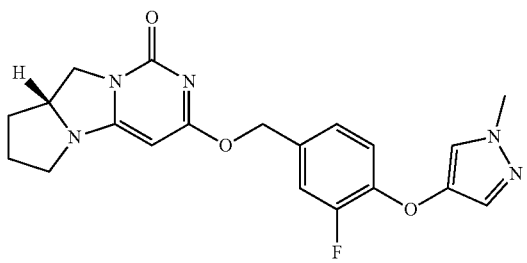 [SMILES: Cn1cc(Oc2ccc(COc3cc4n(c(=O)n3)C[C@H]3CCCN43)cc2F)cn1]

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (3-fluoro-4-((1-methyl-1H-pyrazol-4-yl)oxy)phenyl)methanol.

LC-MS (ESI): m/z 398 [M+H]$^+$; 2.28 min (ret time).

$^1$H NMR (400 MHz, DMSO-d$_6$): δ 7.76 (s, 1H), 7.40-7.36 (m, 2H), 7.19-7.17 (d, 1H), 7.09-7.05 (t, 1H), 5.29 (s, 1H), 5.25-5.18 (q, 2H), 4.08-4.00 (m, 2H), 3.89-3.82 (m, 1H), 3.80 (s, 3H), 3.30-3.25 (m, 2H), 2.03-1.83 (m, 3H), 1.48-1.41 (m, 1H).

E69

(R)-3-((3-fluoro-4-((2-(trifluoromethyl) pyrimidin-5-yl) oxy) benzyl) oxy)-7, 8, 8a, 9-tetra hydropyrrolo[1',2':3,4]imidazo[1,2-c]pyrimidin-1(6H)-one

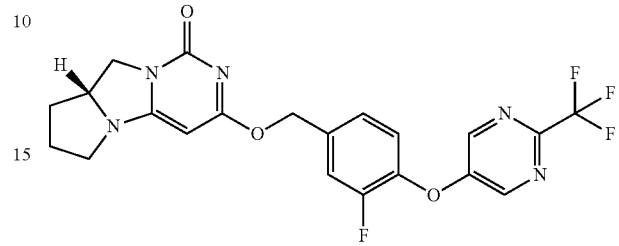

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (3-fluoro-4-((2-(trifluoromethyl)pyrimidin-5-yl)oxy)phenyl)methanol.

LC-MS (ESI): m/z 464 [M+H]$^+$; 2.71 min (ret time).

$^1$H NMR (400 MHz, DMSO-d$_6$): δ 8.89 (s, 2H), 7.56-7.47 (m, 2H), 7.36-7.34 (d, 1H), 5.34 (s, 1H), 5.35-5.28 (q, 2H), 4.07-4.01 (m, 2H), 3.90-3.84 (m, 1H), 3.33-3.27 (m, 2H), 2.08-1.84 (m, 3H), 1.49-1.39 (m, 1H).

E70

(R)-3-((3,4,5-trifluorobenzyl)oxy)-7,8,8a,9-tetrahydropyrrolo[1',2':3,4]imidazo[1,2-c] pyrimidin-1(6H)-one

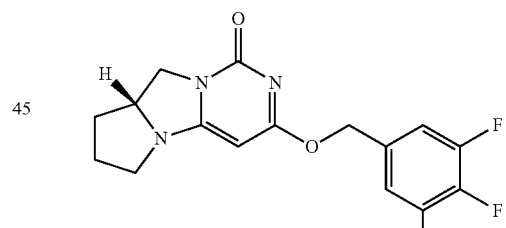

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (3,4,5-trifluorophenyl)methanol.

LC-MS (ESI): m/z 338 [M+H]$^+$; 2.37 min (ret time).

$^1$H NMR (400 MHz, DMSO-d$_6$): δ7.41-7.37 (m, 2H), 5.34 (s, 1H), 5.30-5.23 (s, 2H), 4.09-4.03 (m, 2H), 3.89-3.83 (m, 1H), 3.40-3.28 (m, 2H), 2.20-1.97 (m, 3H), 1.52-1.42 (m, 1H).

E71

(S)-3-((3, 5-difluoro-4-((2-(trifluoromethyl) pyridin-4-yl) oxy) benzyl) oxy)-7, 8, 8a, 9-tetra hydropyrrolo[1',2':3,4]imidazo[1,2-c]pyrimidin-1(6H)-one

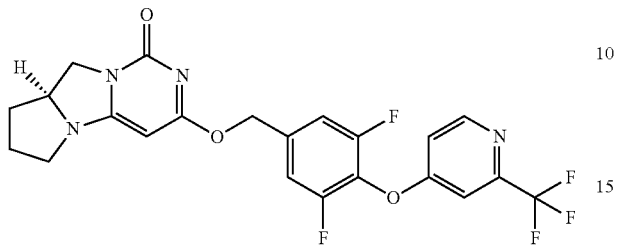

The title compound was prepared by a procedure similar to that described for 3-((3, 5-difluoro-4-((1-methyl-1H-pyrazol-4-yl)oxy)benzyl)oxy)-7,8, 8a, 9-tetrahydro pyrrolo[1',2':3,4] imidazo[1, 2-c] pyrimidin-1(6H)-one starting from (S)-3-chloro-7, 8, 8a, 9-tetrahydropyrrolo[1',2':3,4] imidazo[1,2-c]pyrimidin-1(6H)-one and (3,5-difluoro-4-((2-(trifluoromethyl)pyridin-4-yl)oxy)phenyl)methanol.

LC-MS (ESI): m/z 481 [M+H]$^+$; 3.04 min (ret time).
$^1$H NMR (400 MHz, DMSO-d$_6$): δ 8.70-8.68 (d, 1H), 7.68-7.67 (d, 1H), 7.47-7.45 (d, 2H), 7.33-7.31 (dd, 1H), 5.37 (s, 2H), 5.33 (s, 1H), 4.08-4.02 (m, 2H), 3.889-3.86 (m, 1H), 3.33-3.27 (m, 2H), 2.04-1.85 (m, 3H), 1.50-1.45 (m, 1H).

An exemplary process is provided: to a solution of (S)-3-chloro-7,8,8a,9-tetrahydropyrrolo[1',2':3,4]imidazo[1,2-c]pyrimidin-1(6H)-one (57 mg, 0.269 mmol) and (3,5-difluoro-4-((2-(trifluoromethyl)pyridin-4-yl)oxy)phenyl) methanol (82 mg, 0.269 mmol) in DMF (10 mL) was added sodium hydride (32.3 mg, 0.808 mmol) at 0° C. and stirred for 10 min. The reaction mixture was quenched and purification via C-18 flash column afforded the title compound (45.8 mg, 0.091 mmol, 33.6% yield) as a white solid.

LC-MS (ESI): m/z 481 [M+H]$^+$; 3.04 min (ret time).
$^1$H NMR (400 MHz, DMSO-d$_6$): δ 8.70-8.68 (d, 1H), 7.68-7.67 (d, 1H), 7.47-7.45 (d, 2H), 7.33-7.31 (dd, 1H), 5.37 (s, 2H), 5.33 (s, 1H), 4.08-4.02 (m, 2H), 3.88-3.86 (m, 1H), 3.31-3.29 (m, 2H), 2.04-1.85 (m, 3H), 1.50-1.45 (m, 1H).
$^{19}$F NMR (376 MHz, DMSO-d$_6$): δ (ppm): −66.62, −126.82.

E72

(S)-3-((3-fluoro-4-((2-(trifluoromethyl) pyrimidin-5-yl) oxy) benzyl) oxy)-7, 8, 8a, 9-tetra hydropyrrolo[1',2':3,4]imidazo[1,2-c]pyrimidin-1(6H)-one

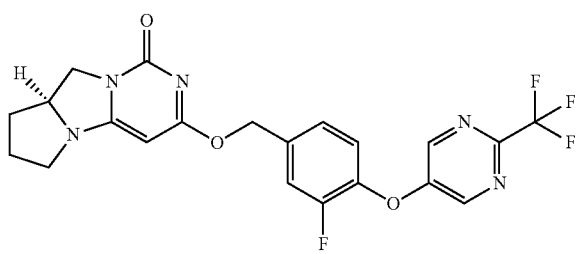 [SMILES: O=c1nc(OCc2ccc(Oc3cnc(C(F)(F)F)nc3)c(F)c2)cc2n1C[C@@H]1CCCN21]

The title compound was prepared by a procedure similar to that described for E63 starting from (R)-3-chloro-7, 8, 8a, 9-tetrahydropyrrolo[1',2':3,4]imidazo[1,2-c]pyrimidin-1 (6H)-one and (3-fluoro-4-((2-(trifluoromethyl)pyrimidin-5-yl)oxy)phenyl)methanol.

LC-MS (ESI): m/z 464 [M+H]$^+$; 2.89 min (ret time).
$^1$H NMR (400 MHz, DMSO-d$_6$): δ 8.89 (s, 2H), 7.55-7.47 (m, 2H), 7.36-7.34 (d, 1H), 5.34 (s, 1H), 5.35-5.28 (q, 2H), 4.07-4.01 (m, 2H), 3.90-3.84 (m, 1H), 3.33-3.28 (m, 2H), 2.04-1.87 (m, 3H), 1.47-1.42 (m, 1H).

E73

(S)-3-((3,4,5-trifluorobenzyl)oxy)-7,8,8a,9-tetrahydropyrrolo[1,2':3,4]imidazo[1,2-c] pyrimidin-1(6H)-one

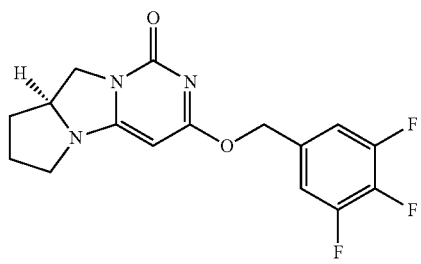 [SMILES: O=c1nc(OCc2cc(F)c(F)c(F)c2)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1 (6H)-one and (3,4,5-trifluorophenyl)methanol.

LC-MS (ESI): m/z 338 [M+H]$^+$; 2.37 min (ret time).
$^1$H NMR (400 MHz, DMSO-d$_6$): δ7.41-7.37 (m, 2H), 5.34 (s, 1H), 5.30-5.23 (s, 2H), 4.09-4.03 (m, 2H), 3.89-3.83 (m, 1H), 3.40-3.28 (m, 2H), 2.20-1.97 (m, 3H), 1.52-1.42 (m, 1H).

E74

(S)-3-((4-(3,4-difluorophenoxy)-3,5-difluorobenzyl) oxy)-7,8,8a,9-tetrahydropyrrolo[1',2':3,4]imidazo[1,2-c]pyrimidin-1(6H)-one

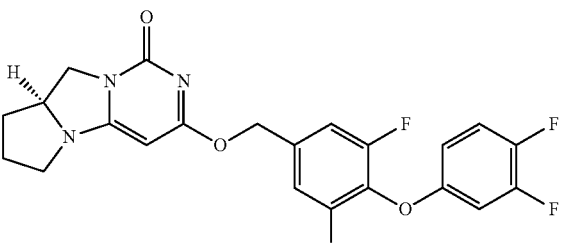

The title compound was prepared by a procedure similar to that described for E63 starting from (S)-3-chloro-7, 8, 8a, 9-tetrahydropyrrolo[1',2':3,4]imidazo[1,2-c]pyrimidin-1 (6H)-one and (4-(3,4-difluorophenoxy)-3,5-difluorophenyl) methanol.

LC-MS (ESI): m/z 448 [M+H]$^+$; 2.98 min (ret time).
$^1$H NMR (400 MHz, DMSO-d$_6$): δ7.58-7.41 (m, 3H), 7.28-7.23 (m, 1H), 6.82-6.80 (m, 1H), 5.36 (s, 1H), 5.31-

5.27 (q, 2H), 4.08-4.01 (m, 2H), 3.88-3.86 (m, 1H), 3.38-3.28 (m, 2H), 2.02-1.76 (m, 3H), 1.47-1.44 (m, 1H).

E75

3-((3, 5-difluoro-4-((2-(trifluoromethyl) pyridin-4-yl) oxy) benzyl) oxy)-7, 8, 8a, 9-tetrahydro pyrrolo[1', 2':3, 4]imidazo[1,2-c]pyrimidin-1(6H)-one

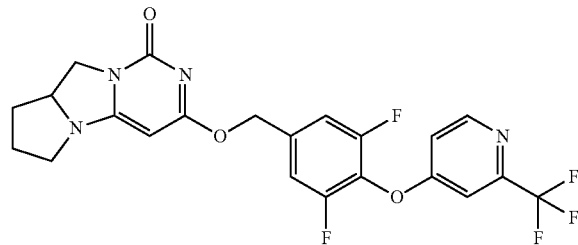 [SMILES: O=c1nc(OCc2cc(F)c(Oc3ccnc(C(F)(F)F)c3)c(F)c2)cc2n1CC1CCCN21]

The title compound was prepared by a procedure similar to that described for E63 starting from 3-chloro-7, 8, 8a, 9-tetrahydropyrrolo[1',2':3,4]imidazo[1,2-c]pyrimidin-1(6H)-one and (3,5-difluoro-4-((2-(trifluoromethyl)pyridin-4-yl)oxy)phenyl)methanol.

LC-MS (ESI): m/z 481 [M+H]$^+$; 2.83 min (ret time).

$^1$H NMR (400 MHz, DMSO-d$_6$): δ 8.70-8.68 (d, 1H), 7.68-7.66 (d, 1H), 7.47-7.45 (d, 2H), 7.33-7.31 (dd, 1H), 5.37 (s, 1H), 5.37-5.30 (q, 2H), 4.10-4.02 (m, 2H), 3.90-3.84 (m, 1H), 3.33-3.27 (m, 2H), 2.04-1.85 (m, 3H), 1.50-1.42 (m, 1H).

E76

3-((6-(4-Chloro-3-(trifluoromethyl)phenoxy)-5-fluoropyridin-3-yl)methoxy)-7,8,8a,9 tetra hydro pyrrolo[1',2':3,4]imidazo[1,2-c]pyrimidin-1(6H)-one

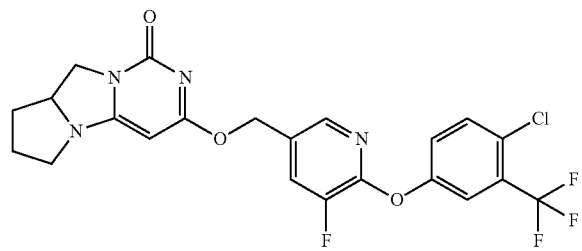 [SMILES: O=c1nc(OCc2cnc(Oc3ccc(Cl)c(C(F)(F)F)c3)c(F)c2)cc2n1CC1CCCN21]

The title compound was prepared by a procedure similar to that described for E63 starting from 3-chloro-7, 8, 8a, 9-tetrahydropyrrolo[1', 2':3, 4] imidazo[1, 2-c] pyrimidin-1(6H)-one and (6-(4-chloro-3-(trifluoromethyl)phenoxy)-5-fluoropyridin-3-yl)methanol.

LC-MS (ESI): m/z 498 [M+H]$^+$; 3.14 min (ret time).

$^1$H NMR (400 MHz, DMSO-d$_6$): δ 8.04-7.98 (m, 2H), 7.82-7.80 (m, 1H), 7.62-7.60 (q, 1H), 7.33-7.31 (dd, 1H), 5.28 (s, 1H), 5.31-5.23 (q, 2H), 4.06-4.00 (m, 2H), 3.89-3.86 (m, 1H), 3.26-3.26 (m, 2H), 2.02-1.86 (m, 3H), 1.45-1.40 (m, 1H).

E77

2-(4-Chloro-3-(trifluoromethyl)phenoxy)-5-(((1-oxo-1,6,7,8,8a,9-hexahydropyrrolo[1,2':3,4]imidazo[1,2-c]pyrimidin-3-yl)oxy)methyl)benzonitrile

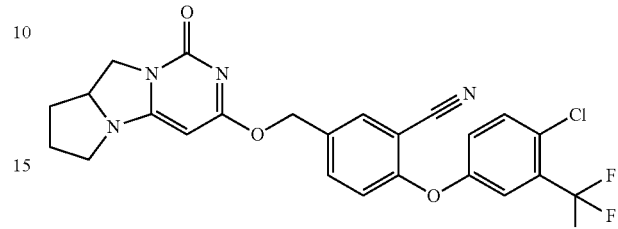

The title compound was prepared by a procedure similar to that described for E63 starting from 3-chloro-7, 8, 8a, 9-tetrahydropyrrolo[1', 2':3, 4] imidazo[1, 2-c] pyrimidin-1(6H)-one and 2-(4-chloro-3-(trifluoromethyl)phenoxy)-5-(hydroxymethyl)benzonitrile.

LC-MS (ESI): m/z 503 [M+H]$^+$; 3.34 min (ret time).

$^1$H NMR (400 MHz, DMSO-d$_6$): δ 8.03-8.02 (d, 1H), 7.84-7.82 (d, 1H), 7.77-7.74 (m, 2H), 7.54-7.51 (m, 1H), 7.20-7.18 (d, 1H), 5.64 (s, 1H), 5.37-5.30 (q, 2H), 4.21-4.09 (m, 2H), 3.92-3.88 (m, 1H), 3.40-3.36 (m, 2H), 2.08-1.96 (m, 3H), 1.57-1.47 (m, 1H).

E78

3-((3,5-Difluoro-4-((6-(trifluoromethyl)pyridin-3-yl)oxy)benzyl)oxy)-7,8,8a,9-tetrahydro pyrrolo[1',2':3,4]imidazo[1,2-c]pyrimidin-1(6H)-one

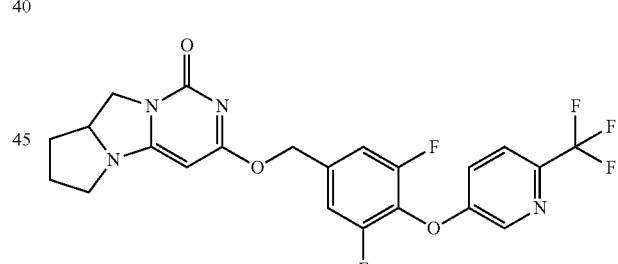

The title compound was prepared by a procedure similar to that described for E63 starting from 3-chloro-7, 8, 8a, 9-tetrahydropyrrolo[1', 2':3, 4] imidazo[1, 2-c] pyrimidin-1(6H)-one and (3,5-difluoro-4-((6-(trifluoromethyl)pyridin-3-yl)oxy)phenyl)methanol, LC-MS (ESI): m/z 481 [M+H]$^+$; 3.09 min (ret time).

$^1$H NMR (400 MHz, DMSO-d$_6$): δ 8.70-8.69 (d, 1H), 7.92-7.90 (d, 1H), 7.65-7.62 (dd, 1H), 7.46-7.44 (d, 2H), 5.37 (s, 1H), 5.37-5.29 (q, 2H), 4.08-3.90 (m, 2H), 3.88-3.86 (m, 1H), 3.32-3.29 (m, 2H), 2.06-1.85 (m, 3H), 1.47-1.42 (m, 1H).

E79

(R)-3-((3,5-difluoro-4-((6-(trifluoromethyl)pyridin-3-yl)oxy)benzyl)oxy)-7,8,8a,9-tetrahydro pyrrolo[1',2':3,4]imidazo[1,2-c]pyrimidin-1(6H)-one

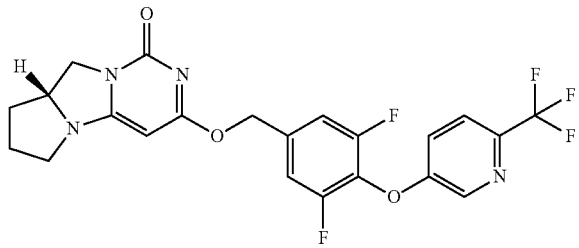 [SMILES: O=c1nc(OCc2cc(F)c(Oc3ccc(C(F)(F)F)nc3)c(F)c2)cc2n1C[C@H]1CCCN21]

The title compound was prepared by a procedure similar to that described for E63 starting from (R)-3-chloro-7, 8, 8a, 9-tetrahydropyrrolo[1', 2':3, 4] imidazo[1, 2-c] pyrimidin-1 (6H)-one and (3,5-difluoro-4-((6-(trifluoromethyl)pyridin-3-yl)oxy)phenyl)methanol.

LC-MS (ESI): m/z 481 [M+H]$^+$; 3.08 min (ret time).

$^1$H NMR (400 MHz, DMSO-d$_6$): δ 8.70-8.69 (d, 1H), 7.92-7.90 (d, 1H), 7.65-7.62 (dd, 1H), 7.46-7.44 (d, 2H), 5.37 (s, 1H), 5.37-5.29 (q, 2H), 4.08-3.90 (m, 2H), 3.88-3.86 (m, 1H), 3.32-3.29 (m, 2H), 2.05-1.85 (m, 3H), 1.49-1.42 (m, 1H).

E80

(S)-3-((3,5-difluoro-4-((6-(trifluoromethyl)pyridin-3-yl)oxy)benzyl)oxy)-7,8,8a,9-tetrahydro pyrrolo[1',2':3,4]imidazo[1,2-c]pyrimidin-1(6H)-one

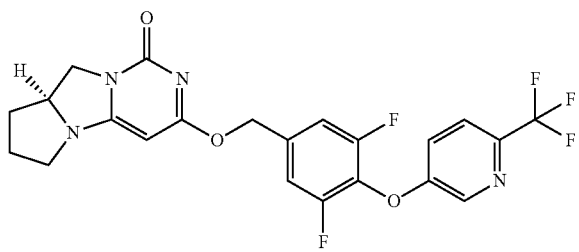 [SMILES: O=c1nc(OCc2cc(F)c(Oc3ccc(C(F)(F)F)nc3)c(F)c2)cc2n1C[C@@H]1CCCN21]

The title compound was prepared by a procedure similar to that described for E63 starting from (S)-3-chloro-7, 8, 8a, 9-tetrahydropyrrolo[1', 2':3, 4] imidazo[1, 2-c] pyrimidin-1 (6H)-one and (3,5-difluoro-4-((6-(trifluoromethyl)pyridin-3-yl)oxy)phenyl)methanol, LC-MS (ESI): m/z 481 [M+H]$^+$; 3.08 min (ret time).

$^1$H NMR (400 MHz, DMSO-d$_6$): δ 8.70-8.69 (d, 1H), 7.92-7.90 (d, 1H), 7.65-7.62 (dd, 1H), 7.46-7.44 (d, 2H), 5.37 (s, 1H), 5.37-5.29 (q, 2H), 4.08-3.90 (m, 2H), 3.88-3.86 (m, 1H), 3.32-3.29 (m, 2H), 2.05-1.85 (m, 3H), 1.49-1.42 (m, 1H).

E81

3-((3,5-difluoro-4-(3-(trifluoromethyl)phenoxy)benzyl)oxy)-7,8,8a,9-tetrahydropyrrolo[1',2':3, 4]imidazo[1,2-c]pyrimidin-1(6H)-one

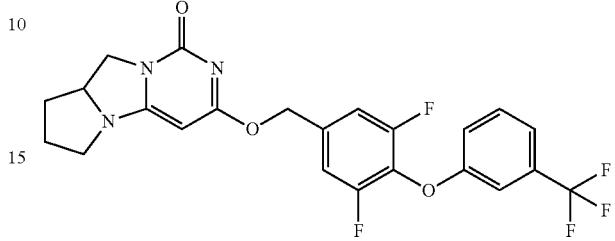

The title compound was prepared by a procedure similar to that described for E63 starting from 3-chloro-7, 8, 8a, 9-tetrahydropyrrolo[1', 2':3, 4] imidazo[1, 2-c] pyrimidin-1 (6H)-one and (3, 5-difluoro-4-(3-(trifluoromethyl)phenoxy)phenyl)methanol.

LC-MS (ESI): m/z 480 [M+H]$^+$; 3.43 min (ret time).

$^1$H NMR (400 MHz, DMSO-d$_6$): δ7.64-7.60 (t, 1H), 7.53-7.51 (d, 1H), 7.43-7.37 (m, 3H), 7.28-7.26 (m, 1H), 5.37 (s, 1H), 5.35-5.28 (q, 2H), 4.08-4.02 (m, 2H), 3.88-3.86 (m, 1H), 3.32-3.29 (m, 2H), 2.04-1.88 (m, 3H), 1.47-1.42 (m, 1H).

E82

3-((6-(4-fluoro-3-(trifluoromethyl)phenoxy)pyridin-3-yl)methoxy)-7,8,8a,9-tetrahydro pyrrolo[1',2':3,4]imidazo[1,2-c]pyrimidin-1(6H)-one

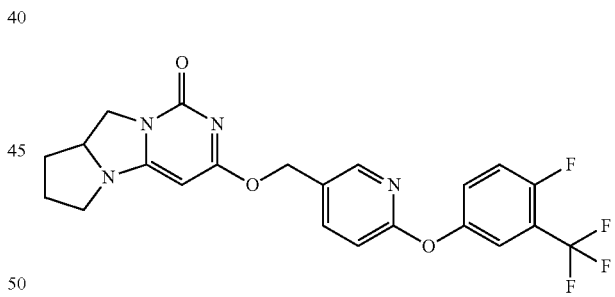

The title compound was prepared by a procedure similar to that described for E63 starting from 3-chloro-7, 8, 8a, 9-tetrahydropyrrolo[1', 2':3, 4] imidazo[1, 2-c] pyrimidin-1 (6H)-one and (6-(4-fluoro-3-(trifluoromethyl)phenoxy)pyridin-3-yl)methanol.

LC-MS (ESI): m/z 463 [M+H]$^+$; 2.86 min (ret time).

$^1$H NMR (400 MHz, DMSO-d$_6$): δ 8.20-8.20 (d, 1H), 7.97-7.96 (d, 1H), 7.95-7.56 (m, 3H), 7.16-7.14 (d, 1H), 5.27 (s, 1H), 5.29-5.21 (q, 2H), 4.06-4.00 (m, 2H), 3.87-3.85 (m, 1H), 3.32-3.26 (m, 2H), 2.01-1.86 (m, 3H), 1.45-1.42 (m, 1H).

E83

(S)-3-((3,5-difluoro-4-(3-(trifluoromethyl)phenoxy)benzyl)oxy)-7,8,8a,9-tetrahydropyrrolo[1',2':3,4]imidazo[1,2-c]pyrimidin-1(6H)-one

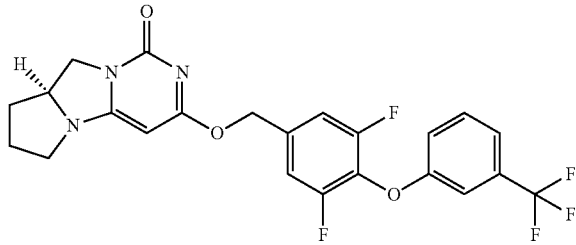 [SMILES: O=c1nc(OCc2cc(F)c(Oc3cccc(C(F)(F)F)c3)c(F)c2)cc2n1C[C@@H]1CCCN21]

The title compound was prepared by a procedure similar to that described for E63 starting from (S)-3-chloro-7, 8, 8a, 9-tetrahydropyrrolo[1', 2':3, 4] imidazo[1, 2-c] pyrimidin-1 (6H)-one and (3, 5-difluoro-4-(3-(trifluoromethyl)phenoxy)phenyl)methanol.

LC-MS (ESI): m/z 480 [M+H]$^+$; 3.17 min (ret time).

$^1$H NMR (400 MHz, DMSO-d$_6$): δ7.64-7.60 (t, 1H), 7.53-7.51 (d, 1H), 7.43-7.37 (m, 3H), 7.28-7.26 (m, 1H), 5.37 (s, 1H), 5.35-5.28 (q, 2H), 4.08-4.02 (m, 2H), 3.88-3.86 (m, 1H), 3.32-3.29 (m, 2H), 2.04-1.88 (m, 3H), 1.47-1.42 (m, 1H).

E84

(S)-3-((6-(4-fluoro-3-(trifluoromethyl)phenoxy)pyridin-3-yl)methoxy)-7,8,8a,9-tetrahydro pyrrolo[1',2':3,4]imidazo[1,2-c]pyrimidin-1(6H)-one

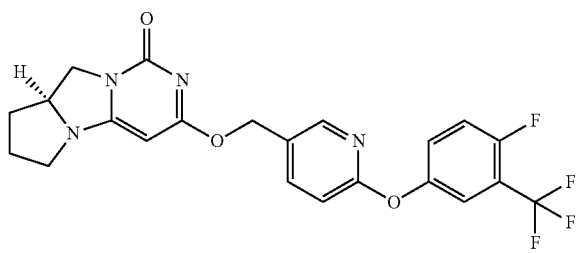 [SMILES: O=c1nc(OCc2ccc(Oc3ccc(F)c(C(F)(F)F)c3)nc2)cc2n1C[C@@H]1CCCN21]

The title compound was prepared by a procedure similar to that described for E63 starting from (S)-3-chloro-7, 8, 8a, 9-tetrahydropyrrolo[1', 2':3, 4] imidazo[1, 2-c] pyrimidin-1 (6H)-one and (6-(4-fluoro-3-(trifluoromethyl)phenoxy)pyridin-3-yl)methanol.

LC-MS (ESI): m/z 463 [M+H]$^+$; 2.86 min (ret time).

$^1$H NMR (400 MHz, DMSO-d$_6$): δ 8.20-8.20 (d, 1H), 7.97-7.96 (d, 1H), 7.95-7.56 (m, 3H), 7.16-7.14 (d, 1H), 5.27 (s, 1H), 5.29-5.21 (q, 2H), 4.06-4.00 (m, 2H), 3.87-3.85 (m, 1H), 3.32-3.26 (m, 2H), 2.01-1.86 (m, 3H), 1.45-1.42 (m, 1H).

E85

2-(3-fluorophenoxy)-5-(((1-oxo-1,6,7,8,8a,9-hexahydropyrrolo[1,2':3,4]imidazo[1,2-c] pyrimidin-3-yl)oxy)methyl)benzonitrile

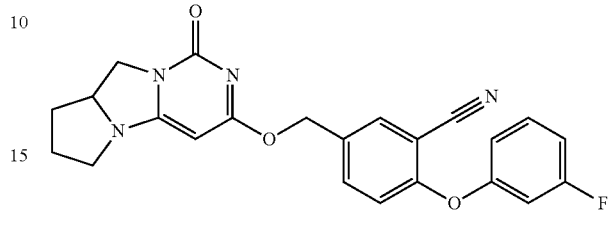

The title compound was prepared by a procedure similar to that described for E63 starting from 3-chloro-7, 8, 8a, 9-tetrahydropyrrolo[1', 2':3, 4] imidazo[1, 2-c] pyrimidin-1 (6H)-one and 2-(3-fluorophenoxy)-5-(hydroxymethyl)benzonitrile.

LC-MS (ESI): m/z 419 [M+H]$^+$; 2.89 min (ret time).

$^1$H NMR (400 MHz, DMSO-d$_6$): δ7.97-7.96 (d, 1H), 7.74-7.71 (m, 1H), 7.53-7.47 (q, 1H), 7.14-7.09 (m, 3H), 7.00-6.98 (m, 1H), 5.32 (s, 1H), 5.32-5.24 (q, 2H), 4.06-4.00 (m, 2H), 3.89-3.83 (m, 1H), 3.30-3.25 (m, 2H), 2.04-1.81 (m, 3H), 1.48-1.38 (m, 1H).

E86

(S)-2-(3-fluorophenoxy)-5-(((1-oxo-1,6,7,8,8a,9-hexahydropyrrolo[1',2':3,4]imidazo[1,2-c] pyrimidin-3-yl)oxy)methyl)benzonitrile

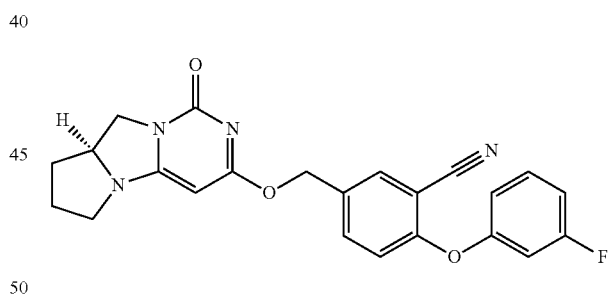

The title compound was prepared by a procedure similar to that described for E63 starting from (S)-3-chloro-7, 8, 8a, 9-tetrahydropyrrolo[1', 2':3, 4] imidazo[1, 2-c] pyrimidin-1 (6H)-one and 2-(3-fluorophenoxy)-5-(hydroxymethyl)benzonitrile.

LC-MS (ESI): m/z 419 [M+H]$^+$; 2.89 min (ret time).

$^1$H NMR (400 MHz, DMSO-d$_6$): δ7.97-7.96 (d, 1H), 7.74-7.72 (m, 1H), 7.53-7.48 (q, 1H), 7.15-7.09 (m, 3H), 7.00-6.98 (m, 1H), 5.32 (s, 1H), 5.32-5.24 (q, 2H), 4.09-4.01 (m, 2H), 3.89-3.83 (m, 1H), 3.31-3.25 (m, 2H), 2.04-1.82 (m, 3H), 1.48-1.38 (m, 1H).

E87

2-(3,5-Difluorophenoxy)-5-(((1-oxo-1,6,7,8,8a,9-hexahydropyrrolo[1,2':3,4]imidazo[1,2-c]pyrimidin-3-yl)oxy)methyl)benzonitrile

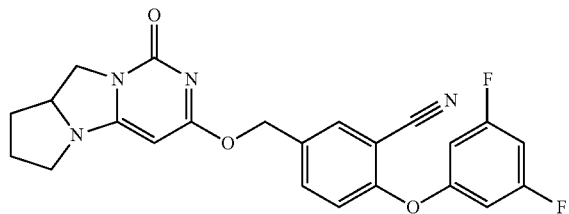 [SMILES: N#Cc1cc(COc2cc3n(c(=O)n2)CC2CCCN32)ccc1Oc1cc(F)cc(F)c1]

The title compound was prepared by a procedure similar to that described for E63 starting from 3-chloro-7, 8, 8a, 9-tetrahydropyrrolo[1', 2':3, 4] imidazo[1, 2-c] pyrimidin-1 (6H)-one and 2-(3,5-difluorophenoxy)-5-(hydroxymethyl)benzonitrile.

LC-MS (ESI): m/z 437 [M+H]$^+$; 2.96 min (ret time).

$^1$H NMR (400 MHz, DMSO-d$_6$): δ7.95-7.95 (d, 1H), 7.72-7.69 (dd, 1H), 7.59-7.47 (m, 2H), 7.09-7.04 (m, 2H), 5.31 (s, 1H), 5.31-5.23 (q, 2H), 4.09-4.00 (m, 2H), 3.89-3.83 (m, 1H), 3.31-3.25 (m, 2H), 2.05-1.81 (m, 3H), 1.48-1.38 (m, 1H).

E88

(S)-2-(3,5-difluorophenoxy)-5-(((1-oxo-1,6,7,8,8a,9-hexahydropyrrolo[1',2':3,4]imidazo[1,2-c] pyrimidin-3-yl)oxy)methyl)benzonitrile

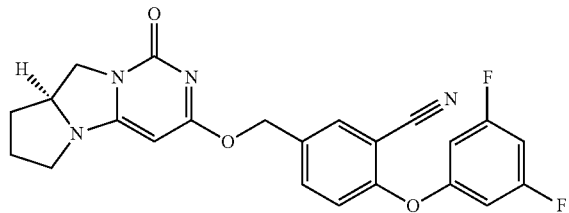 [SMILES: N#Cc1cc(COc2cc3n(c(=O)n2)C[C@@H]2CCCN32)ccc1Oc1cc(F)cc(F)c1]

The title compound was prepared by a procedure similar to that described for E63 starting from (S)-3-chloro-7, 8, 8a, 9-tetrahydropyrrolo[1', 2':3, 4] imidazo[1, 2-c] pyrimidin-1 (6H)-one and 2-(3,5-difluorophenoxy)-5-(hydroxymethyl)benzonitrile.

LC-MS (ESI): m/z 437 [M+H]$^+$; 2.96 min (ret time).

$^1$H NMR (400 MHz, DMSO-d$_6$): δ7.95-7.95 (d, 1H), 7.72-7.69 (dd, 1H), 7.59-7.47 (m, 2H), 7.09-7.04 (m, 2H), 5.31 (s, 1H), 5.31-5.23 (q, 2H), 4.09-4.00 (m, 2H), 3.89-3.83 (m, 1H), 3.31-3.25 (m, 2H), 2.04-1.81 (m, 3H), 1.48-1.38 (m, 1H).

E89

3-((3,4,5-Trifluorobenzyl)oxy)-7,8,8a,9-tetrahydropyrrolo[1',2':3,4]imidazo[1,2-c] pyrimidin-1(6H)-one

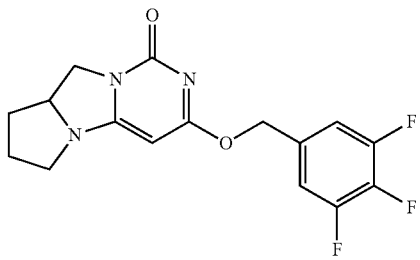 [SMILES: O=c1nc(OCc2cc(F)c(F)c(F)c2)cc2n1CC1CCCN21]

The title compound was prepared by a procedure similar to that described for E63 starting from 3-chloro-7, 8, 8a, 9-tetrahydropyrrolo[1',2':3,4]imidazo[1,2-c]pyrimidin-1 (6H)-one and (3,4,5-trifluorophenyl)methanol.

LC-MS (ESI): m/z 338 [M+H]$^+$; 2.53 min (ret time).

$^1$H NMR (400 MHz, DMSO-d$_6$): δ 7.40-7.36 (m, 2H), 5.33 (s, 1H), 5.33-5.20 (q, 2H), 4.04-4.00 (m, 2H), 3.89-3.85 (m, 1H), 3.31-3.27 (m, 2H), 2.01-1.87 (m, 3H), 1.48-1.41 (m, 1H).

E90

3-((3,5-Difluoro-4-((2-(trifluoromethyl)pyrimidin-5-yl)oxy)benzyl)oxy)-7,8,8a,9-tetrahydro pyrrolo[1',2':3,4]imidazo[1,2-c]pyrimidin-1(6H)-one

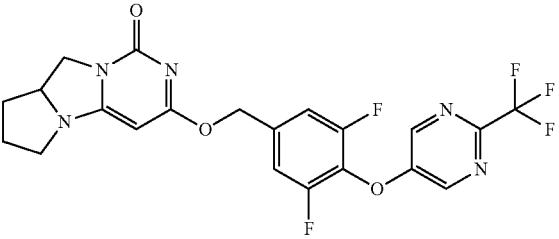 [SMILES: O=c1nc(OCc2cc(F)c(Oc3cnc(C(F)(F)F)nc3)c(F)c2)cc2n1CC1CCCN21]

The title compound was prepared by a procedure similar to that described for E63 starting from 3-chloro-7, 8, 8a, 9-tetrahydropyrrolo[1',2':3,4]imidazo[1,2-c]pyrimidin-1 (6H)-one and (3,5-difluoro-4-((2-(trifluoromethyl)pyrimidin-5-yl)oxy)phenyl)methanol.

LC-MS (ESI): m/z 482 [M+H]$^+$; 2.85 min (ret time).

$^1$H NMR (400 MHz, CD$_3$OD): δ 8.73 (s, 2H), 7.35-7.33 (m, 2H), 5.41 (s, 1H), 5.45-5.36 (q, 2H), 4.19-4.15 (m, 2H), 4.03-3.97 (m, 1H), 3.48-3.33 (m, 2H), 2.18-1.97 (m, 3H), 1.57-1.47 (m, 1H).

E91

(S)-3-((3,5-difluoro-4-((2-(trifluoromethyl)pyrimidin-5-yl)oxy)benzyl)oxy)-7,8,8a,9-tetra hydropyrrolo[1',2':3,4]imidazo[1,2-c]pyrimidin-1(6H)-one

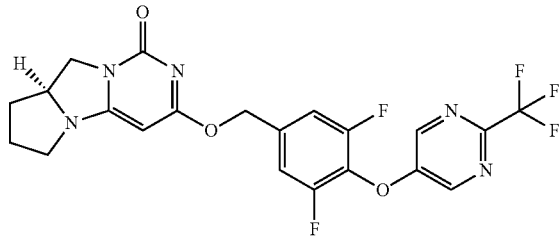 [SMILES: O=c1nc(OCc2cc(F)c(Oc3cnc(C(F)(F)F)nc3)c(F)c2)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1 (6H)-one and (3-fluoro-4-((2-(trifluoromethyl)pyrimidin-5-yl)oxy)phenyl)methanol.

LC-MS (ESI): m/z 482 [M+H]$^+$; 2.85 min (ret time).

$^1$H NMR (400 MHz, CD$_3$OD): δ 8.73 (s, 2H), 7.35-7.33 (m, 2H), 5.41 (s, 1H), 5.45-5.36 (q, 2H), 4.19-4.15 (m, 2H), 4.03-3.97 (m, 1H), 3.48-3.33 (m, 2H), 2.17-1.97 (m, 3H), 1.57-1.47 (m, 1H).

E92

3-((4-((3,3-difluorocyclohexyl)oxy)-3,5-difluorobenzyl)oxy)-7,8,8a,9-tetrahydropyrrolo[1',2':3,4]imidazo[1,2-c]pyrimidin-1(6H)-one

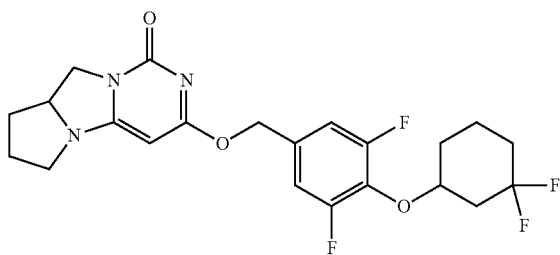 [SMILES: O=c1nc(OCc2cc(F)c(OC3CCCC(F)(F)C3)c(F)c2)cc2n1CC1CCCN21]

The title compound was prepared by a procedure similar to that described for E63 starting from 3-chloro-7, 8, 8a, 9-tetrahydropyrrolo[1',2':3,4]imidazo[1,2-c]pyrimidin-1 (6H)-one and (4-((3,3-difluorocyclohexyl)oxy)-3,5-difluorophenyl)methanol.

LC-MS (ESI): m/z 454 [M+H]$^+$; 3.13 min (ret time).

$^1$H NMR (400 MHz, DMSO-d$_6$): δ 7.23-7.21 (d, 2H), 5.33 (s, 1H), 5.28-5.18 (q, 2H), 4.22-3.85 (m, 4H), 3.33-3.27 (m, 3H), 2.19-1.75 (m, 8H), 1.59-1.43 (m, 3H).

E93

(S)-3-((4-((3,3-difluorocyclohexyl)oxy)-3,5-difluorobenzyl)oxy)-7,8,8a,9-tetrahydropyrrolo[1',2':3,4]imidazo[1,2-c]pyrimidin-1(6H)-one

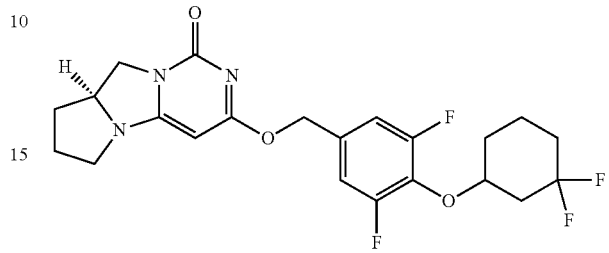

The title compound was prepared by a procedure similar to that described for E63 starting from 3-chloro-7, 8, 8a, 9-tetrahydropyrrolo[1',2':3,4]imidazo[1,2-c]pyrimidin-1 (6H)-one and (4-((3,3-difluorocyclohexyl)oxy)-3,5-difluorophenyl)methanol.

LC-MS (ESI): m/z 454 [M+H]$^+$; 3.14 min (ret time).

$^1$H NMR (400 MHz, DMSO-d$_6$): δ 7.23-7.21 (d, 2H), 5.33 (s, 1H), 5.28-5.18 (q, 2H), 4.22-3.85 (m, 4H), 3.33-3.27 (m, 3H), 2.19-1.75 (m, 8H), 1.59-1.43 (m, 3H).

E94

3-((4-((3,3-difluorocyclopentyl)oxy)-3,5-difluorobenzyl)oxy)-7,8,8a,9-tetrahydropyrrolo[1',2':3,4]imidazo[1,2-c]pyrimidin-1(6H)-one

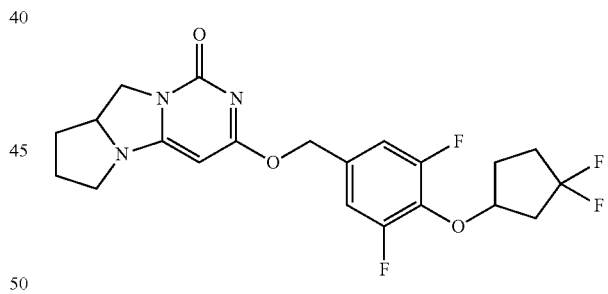

The title compound was prepared by a procedure similar to that described for E63 starting from 3-chloro-7, 8, 8a, 9-tetrahydropyrrolo[1',2':3,4]imidazo[1,2-c]pyrimidin-1 (6H)-one and (4-((3,3-difluorocyclopentyl)oxy)-3,5-difluorophenyl)methanol.

LC-MS (ESI): m/z 440 [M+H]$^+$; 2.81 min (ret time).

$^1$H NMR (400 MHz, DMSO-d$_6$): δ 7.24-7.24 (d, 2H), 5.33 (s, 1H), 5.26-5.18 (q, 2H), 4.85 (s, 1H), 4.10-4.00 (m, 2H), 3.89-3.80 (m, 1H), 3.33-3.27 (m, 3H), 2.40-1.87 (m, 8H), 1.46-1.41 (m, 1H).

E95

(S)-3-((4-((3,3-difluorocyclopentyl)oxy)-3,5-difluorobenzyl)oxy)-7,8,8a,9-tetrahydropyrrolo[1',2':3,4]imidazo[1,2-c]pyrimidin-1(6H)-one

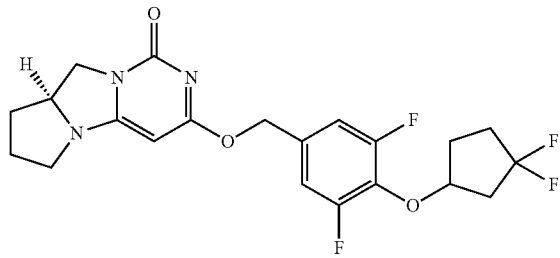 [SMILES: O=c1nc(OCc2cc(F)c(OC3CCC(F)(F)C3)c(F)c2)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1(6H)-one and (4-((3,3-difluorocyclohexyl)oxy)-3,5-difluorophenyl)methanol.

LC-MS (ESI): m/z 440 [M+H]$^+$; 2.81 min (ret time).

$^1$H NMR (400 MHz, DMSO-d$_6$): δ 7.24-7.24 (d, 2H), 5.33 (s, 1H), 5.26-5.18 (q, 2H), 4.85 (s, 1H), 4.10-4.00 (m, 2H), 3.89-3.80 (m, 1H), 3.33-3.27 (m, 3H), 2.40-1.87 (m, 8H), 1.46-1.41 (m, 1H).

E96

3-((3,5-Difluoro-4-((1-(3,3,3-trifluoropropyl)azetidin-3-yl)oxy)benzyl)oxy)-7,8,8a,9-tetrahydropyrrolo[1',2':3,4]imidazo[1,2-c]pyrimidin-1(6H)-one

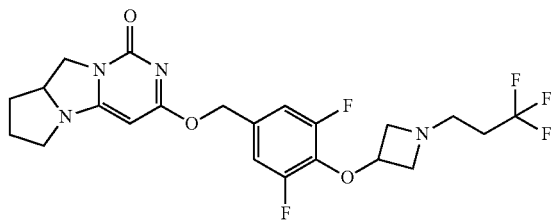 [SMILES: O=c1nc(OCc2cc(F)c(OC3CN(CCC(F)(F)F)C3)c(F)c2)cc2n1CC1CCCN21]

The title compound was prepared by a procedure similar to that described for E63 starting from 3-chloro-7, 8, 8a, 9-tetrahydropyrrolo[1',2':3,4]imidazo[1,2-c]pyrimidin-1(6H)-one and (3,5-difluoro-4-((1-(3,3,3-trifluoropropyl)azetidin-3-yl)oxy)phenyl)methanol.

LC-MS (ESI): m/z 487 [M+H]$^+$; 2.11 min (ret time).

$^1$H NMR (400 MHz, CD$_3$OD): δ8.03-8.01 (d, 2H), 6.13 (s, 1H), 6.05-5.98 (q, 2H), 5.56-5.54 (m, 1H), 4.85-4.81 (m, 2H), 4.70-4.66 (m, 1H), 4.44-4.41 (m, 2H), 4.12-4.08 (m, 2H), 3.94-3.91 (m, 2H), 3.47-3.43 (m, 2H), 3.18-3.06 (m, 2H), 2.86-2.68 (m, 3H), 2.28-2.22 (m, 1H).

E97

(S)-3-((3,5-difluoro-4-((1-(3,3,3-trifluoropropyl)azetidin-3-yl)oxy)benzyl)oxy)-7,8,8a,9-tetra hydropyrrolo[1',2':3,4]imidazo[1,2-c]pyrimidin-1(6H)-one

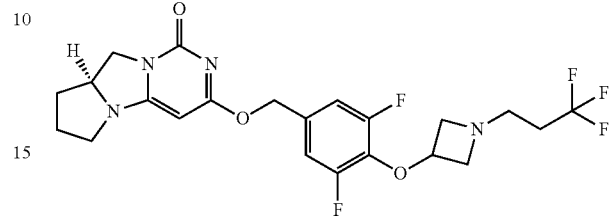

The title compound was prepared by a procedure similar to that described for E63 starting from (S)-3-chloro-7, 8, 8a, 9-tetrahydropyrrolo[1',2':3,4]imidazo[1,2-c]pyrimidin-1(6H)-one and (3,5-difluoro-4-((1-(3,3,3-trifluoropropyl)azetidin-3-yl)oxy)phenyl)methanol.

LC-MS (ESI): m/z 487 [M+H]$^+$; 2.10 min (ret time).

$^1$H NMR (400 MHz, DMSO-d$_6$): δ 8.03-8.01 (d, 2H), 6.13 (s, 1H), 6.05-5.98 (q, 2H), 5.56-5.54 (m, 1H), 4.85-4.81 (m, 2H), 4.70-4.66 (m, 1H), 4.44-4.41 (m, 2H), 4.12-4.08 (m, 2H), 3.94-3.91 (m, 2H), 3.47-3.43 (m, 2H), 3.18-3.06 (m, 2H), 2.86-2.68 (m, 3H), 2.28-2.22 (m, 1H).

E98

3-((4-((1-Butylazetidin-3-yl)oxy)-3,5-difluorobenzyl)oxy)-7,8,8a,9-tetrahydropyrrolo[1',2':3,4]imidazo[1,2-c]pyrimidin-1(6H)-one

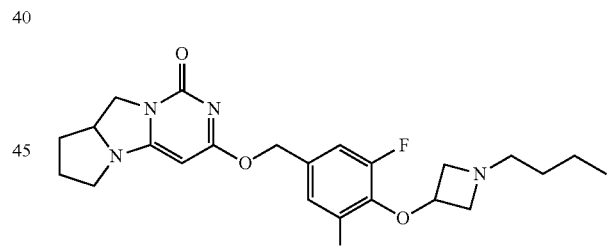

The title compound was prepared by a procedure similar to that described for E63 starting from 3-chloro-7, 8, 8a, 9-tetrahydropyrrolo[1',2':3,4]imidazo[1,2-c]pyrimidin-1(6H)-one and (4-((1-butylazetidin-3-yl)oxy)-3,5-difluorophenyl)methanol.

LC-MS (ESI): m/z 447 [M+H]$^+$; 2.06 min (ret time).

$^1$H NMR (400 MHz, DMSO-d$_6$): δ 7.21-7.18 (d, 2H), 5.32-5.16 (m, 3H), 4.71 (s, 1H), 4.04-3.78 (m, 2H), 3.58-3.55 (m, 2H), 3.31-3.27 (m, 1H), 3.01-2.98 (m, 2H), 2.83 (s, 1H), 2.41-2.34 (m, 2H), 2.01-1.87 (m, 2H), 1.46-1.41 (m, 1H), 1.30-1.20 (m, 6H), 0.87-0.84 (m, 3H).

E99

3-((3,5-Difluoro-4-(3-fluoropropyl)benzyl)oxy)-7,8,8a,9-tetrahydropyrrolo[1',2':3,4]imidazo[1,2-c]pyrimidin-1(6H)-one

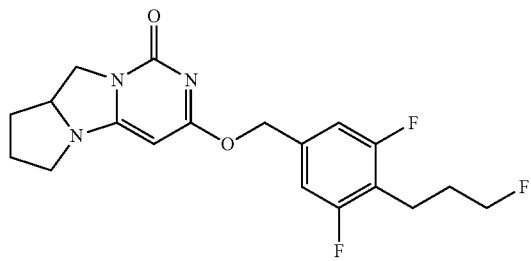 [SMILES: O=c1nc(OCc2cc(F)c(CCCF)c(F)c2)cc2n1CC1CCCN21]

The title compound was prepared by a procedure similar to that described for E63 starting from 3-chloro-7, 8, 8a, 9-tetrahydropyrrolo[1',2':3,4]imidazo[1,2-c]pyrimidin-1(6H)-one and (3,5-difluoro-4-(3-fluoropropyl)phenyl)methanol.

LC-MS (ESI): m/z 380 [M+H]$^+$; 2.61 min (ret time).

$^1$H NMR (400 MHz, DMSO-d$_6$): δ 7.13-7.11 (d, 2H), 5.34 (s, 1H), 5.26-5.21 (m, 2H), 4.54-4.39 (m, 2H), 4.04-4.00 (m, 2H), 3.87-3.85 (m, 1H), 3.30-3.28 (m, 2H), 2.74-2.68 (m, 2H), 2.05-1.80 (m, 5H), 1.48-1.38 (m, 1H).

E100

(R)-3-((2,4-difluorobenzyl)oxy)-7,8,8a,9-tetrahydropyrrolo[1,2':3,4]imidazo[1,2-c] pyrimidin-1(6H)-one

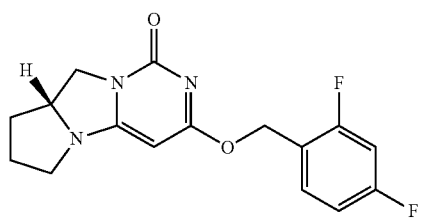 [SMILES: O=c1nc(OCc2ccc(F)cc2F)cc2n1C[C@H]1CCCN21]

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (2,4-difluoro-phenyl)methanol.

LC-MS (ESI): m/z 320 [M+H]$^+$; 3.65 min (ret time).

$^1$H NMR (400 MHz, CDCl$_3$): δ 7.46 (q, 1H), 6.89-6.80 (m, 2H), 5.46-5.35 (m, 2H), 5.09 (s, 1H), 4.21-4.01 (m, 3H), 3.43-3.36 (m, 1H), 3.29-3.20 (m, 1H), 2.19-1.95 (m, 3H), 1.51-1.40 (m, 1H).

E101

(R)-3-((2, 3-difluorobenzyl) oxy)-7, 8, 8a, 9-tetrahydropyrrolo[1', 2':3, 4]imidazo[1,2-c] pyrimidin-1 (6H)-one

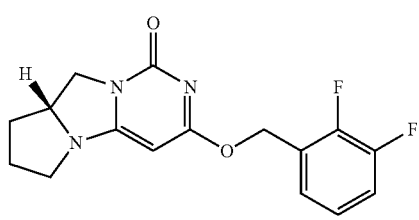 [SMILES: O=c1nc(OCc2cccc(F)c2F)cc2n1C[C@H]1CCCN21]

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (2,3-difluoro-phenyl)methanol.

LC-MS (ESI): m/z 320[M+H]$^+$; 3.65 min (ret time).

$^1$H NMR (300 MHz, CDCl$_3$): δ 7.25-7.02 (m, 3H), 5.51-5.41 (m, 2H), 5.10 (s, 1H), 4.21-4.02 (m, 3H), 3.44-3.36 (m, 1H), 3.30-3.21 (m, 1H), 2.20-1.93 (m, 3H), 1.52-1.38 (m, 1H).

E102

(R)-3-((3-fluorobenzyl)oxy)-7,8,8a,9-tetrahydropyrrolo[1',2':3,4]imidazo[1,2-c]pyrimidin-1(6H)-one

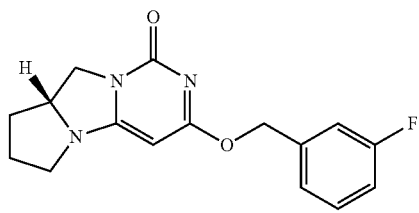 [SMILES: O=c1nc(OCc2cccc(F)c2)cc2n1C[C@H]1CCCN21]

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (3-fluorophenyl)methanol.

LC-MS (ESI): m/z 302 [M+H]$^+$; 3.60 min (ret time).

$^1$H NMR (300 MHz, CDCl$_3$): δ 7.35-7.28 (m, 1H), 7.17-7.10 (m, 2H), 7.02-6.96 (m, 1H), 5.44-5.33 (m, 2H), 5.12 (s, 1H), 4.21-4.00 (m, 3H), 3.45-3.37 (m, 1H), 3.30-3.21 (m, 1H), 2.19-1.93 (m, 3H), 1.52-1.38 (m, 1H).

E103

(R)-3-((3,5-difluorobenzyl)oxy)-7,8,8a,9-tetrahydro-pyrrolo[1,2':3,4]imidazo[1,2-c] pyrimidin-1(6H)-one

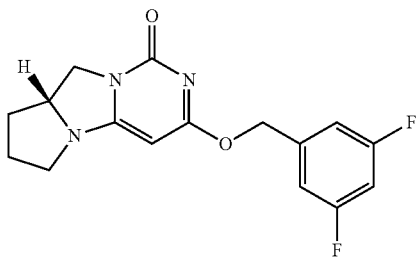 [SMILES: O=c1nc(OCc2cc(F)cc(F)c2)cc2n1C[C@H]1CCCN21]

The title compound was prepared by a procedure similar to that described for E63 starting from (R)-3-chloro-7, 8, 8a, 9-tetrahydropyrrolo[1',2':3,4]imidazo[1,2-c]pyrimidin-1 (6H)-one and (2,4-difluoro-phenyl)methanol.

1H NMR (300 MHz, CDCl$_3$): δ 6.91 (d, 2H), 6.77-6.71 (m, 1H), 5.43-4.32 (m, 2H), 5.14 (s, 1H), 4.22-4.03 (m, 3H), 3.46-3.39 (m, 1H), 3.32-3.23 (m, 1H), 2.20-1.95 (m, 3H), 1.53-1.39 (m, 1H).

LC-MS (ESI): m/z 320 [M+H]$^+$; 3.78 min (ret time).

E104

(R)-3-((3-fluorobenzyl)amino)-7,8,8a,9-tetrahydro-pyrrolo[1',2':3,4]imidazo[1,2-c]pyrimidin-1(6H)-one

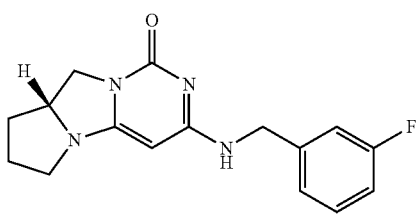 [SMILES: O=c1nc(NCc2cccc(F)c2)cc2n1C[C@H]1CCCN21]

To a solution of (R)-3-chloro-7,8,8a,9-tetrahydropyrrolo[1',2':3,4]imidazo[1,2-c]pyrimidin-1(6H)-one (100 mg, 0.473 mmol) and (3-fluorophenyl)methanamine (118 mg, 0.946 mmol) in 1,4-dioxane (4 mL) was added diisopropylethylamine (610 mg, 4.73 mmol) at room temperature. The reaction mixture was heated to 120° C. under microwave for 2 hours, concentrated under reduced pressure and purified with prep-HPLC to give the title compound (135 mg, 96%) as a pale yellow solid.

LC-MS (ESI): m/z 301 [M+H]$^+$; 2.87 min (ret time).

$^1$H NMR (300 MHz, CDCl$_3$): δ 7.29-7.22 (m, 1H), 7.09-7.00 (m, 2H), 6.94-6.88 (m, 1H), 4.74 (s, 1H), 4.57 (br s, 2H), 4.11-3.91 (m, 3H), 3.35-3.28 (m, 1H), 3.19-3.10 (m, 1H), 2.11-1.87 (m, 3H), 1.45-1.34 (m, 1H).

E105

(R)-3-((3,5-difluoro-4-(1-(2-fluoroethyl)cyclopropoxy)benzyl)oxy)-7,8,8a,9-tetrahydro pyrrolo[1', 2':3,4]imidazo[1,2-c]pyrimidin-1(6H)-one

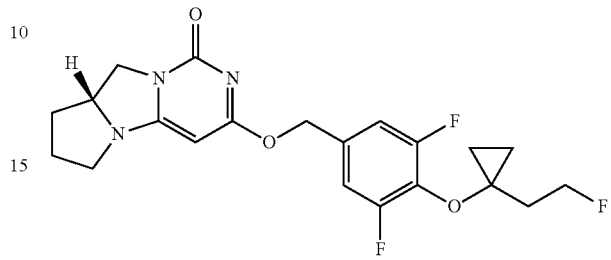

The title compound was prepared by a procedure similar to that described for E63 starting from (R)-3-chloro-7, 8, 8a, 9-tetrahydropyrrolo[1',2':3,4]imidazo[1,2-c]pyrimidin-1 (6H)-one and (3,5-difluoro-4-(1-(2-fluoroethyl)cyclopropoxy)phenyl) methanol.

LC-MS (ESI): m/z 422 [M+H]$^+$; 4.37 min (ret time).

$^1$H NMR (400 MHz, CDCl$_3$): δ 6.97-6.94 (m, 2H), 5.35-5.26 (m, 2H), 5.11 (s, 1H), 4.85-4.82 (m, 1H), 4.74-4.71 (m, 1H), 4.17-4.02 (m, 3H), 3.44-3.38 (m, 1H), 3.29-3.25 (m, 1H), 2.18-2.00 (m, 5H), 1.57-1.45 (m, 1H), 1.10-1.07 (m, 2H), 0.65 (t, 2H).

E106

(R)-3-((3,5-difluoro-4-((2-methylpyridin-4-yl)oxy)benzyl)oxy)-7,8,8a,9-tetrahydro pyrrolo[1',2':3,4]imidazo[1,2-c]pyrimidin-1(6H)-one

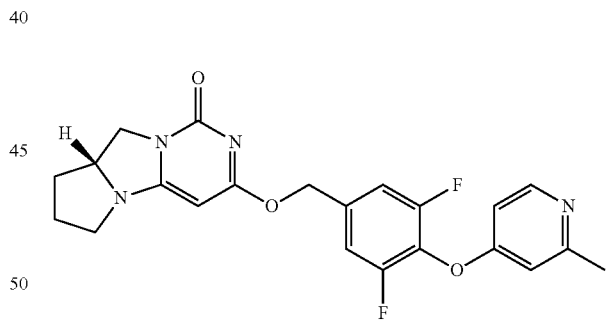

The title compound was prepared by a procedure similar to that described for E1 starting from (R)-3-chloro-7, 8, 8a, 9-tetrahydropyrrolo[1',2':3,4]imidazo[1,2-c]pyrimidin-1 (6H)-one and (3,5-difluoro-4-((2-methylpyridin-4-yl)oxy)phenyl)methanol.

LC-MS (ESI): m/z 427 [M+H]$^+$; 2.01 min (ret time).

$^1$H NMR (400 MHz, CD$_3$OD): δ8.33-8.31 (d, 1H), 7.31-7.29 (d, 2H), 6.87-6.81 (m, 2H), 5.44-5.35 (m, 3H), 4.18-4.15 (m, 2H), 4.03-3.97 (m, 1H), 3.48-3.37 (m, 2H), 3.12 (s, 3H), 2.18-1.98 (m, 3H), 1.58-1.50 (m, 1H).

E107

7-((3,5-Difluoro-4-((2-(trifluoromethyl) pyridin-4-yl) oxy) benzyl) oxy)-3, 4, 11, 11a-tetra hydropyrimido[6',1':2,3]imidazo[5,1-c][1,4]oxazin-9(1H)-one

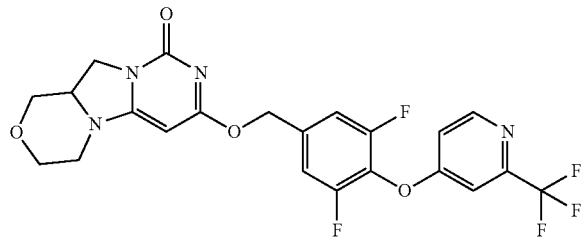 [SMILES: O=c1nc(OCc2cc(F)c(Oc3ccnc(C(F)(F)F)c3)c(F)c2)cc2n1CC1COCCN21]

The title compound was prepared by a procedure similar to that described for E63 starting from 7-chloro-3,4,11,11a-tetrahydropyrimido[6',1':2,3]imidazo[5,1-c][1,4]oxazin-9(1H)-one and (3,5-difluoro-4-((2-(trifluoromethyl)pyridin-4-yl)oxy)phenyl)methanol.

LC-MS (ESI): m/z 497 [M+H]$^+$; 2.64 min (ret time).

$^1$H NMR (400 MHz, DMSO-d$_6$): δ 8.70-8.68 (d, 1H), 7.68 (s, 1H), 7.46-6.44 (d, 2H), 7.33-7.31 (m, 1H), 5.42 (s, 1H), 5.34 (s, 2H), 4.11-4.3.79 (m, 4H), 3.68-3.33 (m, 5H).

E108

7-((3,5-Difluoro-4-((1-methyl-1H-pyrazol-4-yl)oxy) benzyl)oxy)-3,4,11,11a-tetrahydro pyrimido[6',1':2,3]imidazo[5,1-c][1,4]oxazin-9(1H)-one

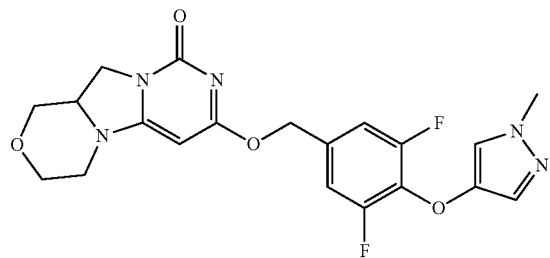 [SMILES: Cn1cc(Oc2c(F)cc(COc3cc4n(c(=O)n3)CC3COCCN43)cc2F)cn1]

The title compound was prepared by a procedure similar to that described for E63 starting from 7-chloro-3,4,11,11a-tetrahydropyrimido[6',1':2,3]imidazo[5,1-c][1,4]oxazin-9(1H)-one and (3,5-difluoro-4-((1-methyl-1H-pyrazol-4-yl)oxy)phenyl)methanol.

LC-MS (ESI): m/z 432 [M+H]$^+$; 2.11 min (ret time).

$^1$H NMR (400 MHz, MeOD-d$_4$): δ 7.61 (s, 1H), 7.31-7.27 (m, 3H), 5.39 (s, 1H), 5.26 (s, 2H), 4.04-3.80 (m, 4H), 3.73 (s, 3H), 3.66-3.33 (m, 5H).

E109

7-((4-((1-Ethyl-1H-pyrazol-4-yl)oxy)-3,5-difluorobenzyl)oxy)-3,4,11,11a-tetrahydropyrimido[6',1':2,3]imidazo[5,1-c][1,4]oxazin-9(1H)-one

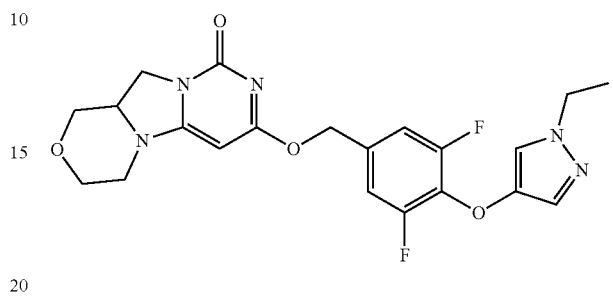

The title compound was prepared by a procedure similar to that described for E63 starting from 7-chloro-3,4,11,11a-tetrahydropyrimido[6',1':2,3]imidazo[5,1-c][1,4]oxazin-9 (1H)-one and (4-((1-ethyl-1H-pyrazol-4-yl)oxy)-3,5-difluorophenyl)methanol.

LC-MS (ESI): m/z 446 [M+H]$^+$; 3.45 min (ret time).

$^1$H NMR (400 MHz, DMSO-d$_6$): δ7.66 (s, 1H), 7.31-7.27 (m, 3H), 5.39 (s, 1H), 5.27 (s, 2H), 4.09-3.79 (m, 6H), 3.66-3.51 (s, 2H), 3.40-3.24 (m, 3H), 1.33-1.29 (t, 3H).

E110

7-((3,5-Difluoro-4-((2-(trifluoromethyl)pyrimidin-5-yl)oxy)benzyl)oxy)-3,4,11,11a-tetra hydropyrimido[6',1':2,3]imidazo[5,1-c][1,4]oxazin-9(1H)-one

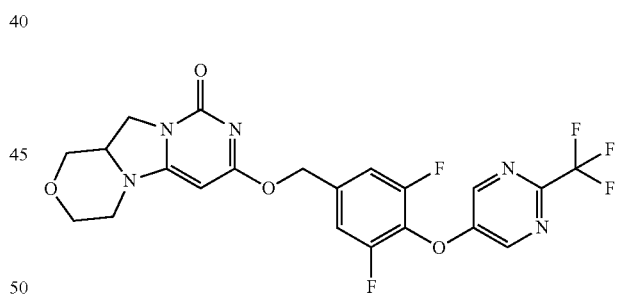

The title compound was prepared by a procedure similar to that described for E63 starting from 7-chloro-3,4,11,11a-tetrahydropyrimido[6',1':2,3]imidazo[5,1-c][1,4]oxazin-9 (1H)-one and (4-((1-ethyl-1H-pyrazol-4-yl)oxy)-3,5-difluorophenyl)methanol.

LC-MS (ESI): m/z 498 [M+H]$^+$; 2.65 min (ret time).

$^1$H NMR (400 MHz, CD$_3$OD): δ 8.70 (s, 2H), 7.32-7.30 (d, 2H), 5.38-5.35 (m, 3H), 4.14-3.87 (m, 4H), 3.66-3.50 (m, 3H), 3.44-3.33 (t, 2H).

E111

2-(4-Fluoro-3-(trifluoromethyl)phenoxy)-5-(((9-oxo-1,3,4,9,11,11a-hexahydropyrimido[6',1':2,3]imidazo[5,1-c][1,4]oxazin-7-yl)oxy)methyl)benzonitrile

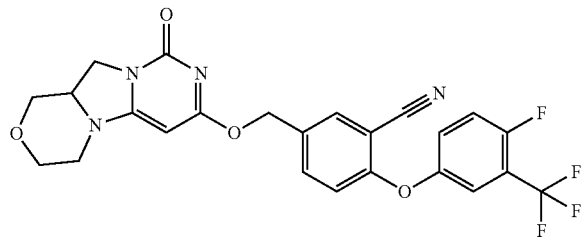 [SMILES: N#Cc1cc(COc2cc3n(c(=O)n2)CC2COCCN32)ccc1Oc1ccc(F)c(C(F)(F)F)c1]

The title compound was prepared by a procedure similar to that described for E63 starting from 7-chloro-3,4,11,11a-tetrahydropyrimido[6',1':2,3]imidazo[5,1-c][1,4]oxazin-9(1H)-one and 2-(4-fluoro-3-(trifluoromethyl)phenoxy)-5-(hydroxymethyl)benzonitrile.

LC-MS (ESI): m/z 503 [M+H]$^+$; 2.85 min (ret time).

$^1$H NMR (400 MHz, CD$_3$OD): δ7.95 (s, 1H), 7.71-7.62 (m, 4H), 7.08-7.05 (d, 1H), 5.36 (s, 1H), 5.27 (s, 2H), 3.99-3.80 (m, 4H), 3.65-3.51 (m, 2H), 3.44-3.33 (t, 3H).

E112

(S)-7-((3,5-difluoro-4-((1-propyl-1H-pyrazol-4-yl)oxy)benzyl)oxy)-3,4,11,11a tetrahydropyrimido[6',1':2,3]imidazo[5,1-c][1,4]oxazin-9(1H)-one

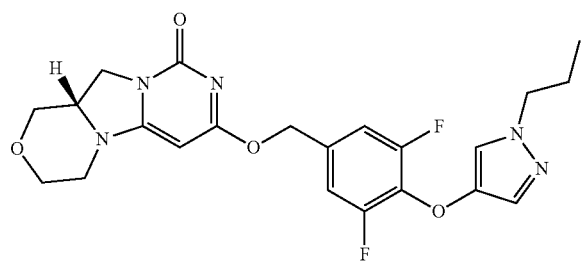 [SMILES: CCCn1cc(Oc2c(F)cc(COc3cc4n(c(=O)n3)C[C@H]3COCCN43)cc2F)cn1]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,5-difluoro-4-((1-propyl-1H-pyrazol-4-yl)oxy)phenyl)methanol.

LC-MS (ESI): m/z 460 [M+H]$^+$; 2.54 min (ret time).

$^1$H NMR (400 MHz, DMSO-d$_6$): δ7.65 (s, 1H), 7.31-7.28 (m, 3H), 5.39 (s, 1H), 5.26 (s, 2H), 4.09-3.79 (m, 6H), 3.66-3.51 (s, 2H), 3.40-3.24 (m, 3H), 1.77-1.68 (m, 2H), 0.80-0.76 (t, 3H).

E113

(S)-7-((3, 5-difluoro-4-((2-(trifluoromethyl) pyridin-4-yl) oxy) benzyl) oxy)-3, 4, 11, 11a tetrahydropyrimido[6',1':2,3]imidazo[5,1-c][1,4]oxazin-9(1H)-one

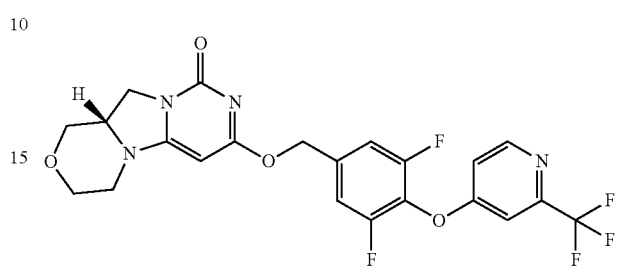

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,5-difluoro-4-((2-(trifluoromethyl)pyridin-4-yl)oxy)phenyl)methanol.

LC-MS (ESI): m/z 497 [M+H]$^+$; 2.66 min (ret time).

$^1$H NMR (400 MHz, DMSO-d$_6$): δ 8.70-8.68 (d, 1H), 7.67 (s, 1H), 7.46-7.44 (d, 2H), 7.32-7.31 (m, 1H), 5.42 (s, 1H), 5.34 (s, 2H), 4.11-3.79 (m, 4H), 3.68-3.26 (m, 5H).

E114

(S)-7-((3,5-difluoro-4-((1-methyl-1H-pyrazol-4-yl)oxy)benzyl)oxy)-3,4,11,11a-tetrahydropyrimido[6',1':2,3]imidazo[5,1-c][1,4]oxazin-9(1H)-one

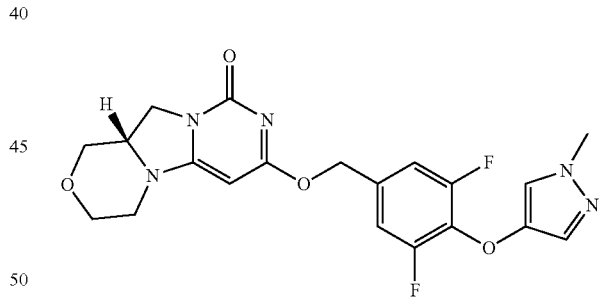

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,5-difluoro-4-((1-methyl-1H-pyrazol-4-yl)oxy)phenyl)methanol.

LC-MS (ESI): m/z 432 [M+H]$^+$; 2.19 min (ret time).

$^1$H NMR (400 MHz, CD$_3$OD): δ7.61 (s, 1H), 7.31-7.27 (m, 3H), 5.39 (s, 1H), 5.26 (s, 2H), 4.04-3.80 (m, 4H), 3.73 (s, 3H), 3.66-3.33 (m, 5H).

E115

(S)-7-((4-((1-ethyl-1H-pyrazol-4-yl)oxy)-3,5-difluorobenzyl)oxy)-3,4,11,11a-tetrahydropyrimido[6',1':2,3]imidazo[5,1-c][1,4]oxazin-9(1H)-one

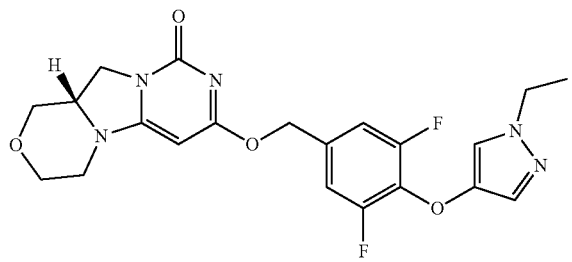 [SMILES: CCn1cc(Oc2c(F)cc(COc3cc4n(c(=O)n3)C[C@H]3COCCN43)cc2F)cn1]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (4-((1-ethyl-1H-pyrazol-4-yl)oxy)-3,5-difluorophenyl)methanol.

LC-MS (ESI): m/z 446 [M+H]$^+$; 2.34 min (ret time).

$^1$H NMR (400 MHz, DMSO-d$_6$): δ7.66 (s, 1H), 7.31-7.27 (m, 3H), 5.39 (s, 1H), 5.27 (s, 2H), 4.04-3.80 (m, 6H), 3.66-3.51 (s, 2H), 3.40-3.24 (m, 3H), 1.33-1.29 (t, 3H).

E116

(S)-7-((3,4,5-trifluorobenzyl)oxy)-3,4,11,11a tetrahydropyrimido[6',1':2,3]imidazo[5,1-c][1,4] oxazin-9(1H)-one

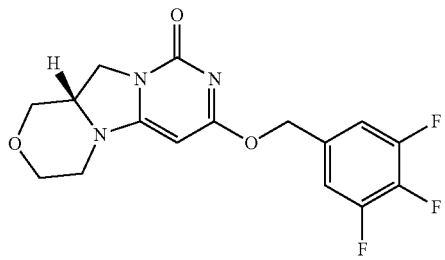 [SMILES: O=c1nc(OCc2cc(F)c(F)c(F)c2)cc2n1C[C@H]1COCCN21]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,4,5-trifluorophenyl)methanol.

LC-MS (ESI): m/z 354 [M+H]$^+$; 2.16 min (ret time).

$^1$H NMR (400 MHz, DMSO-d$_6$): δ 7.39-7.35 (m, 2H), 5.38 (s, 1H), 5.24 (s, 2H), 4.05-3.80 (m, 4H), 3.66-3.66 (m, 1H), 3.40-3.20 (m, 4H).

E117

(R)-7-((3,5-difluoro-4-((2-methylpyridin-4-yl)oxy)benzyl)oxy)-3,4,11,11atetrahydropyrimido[6',1':2,3]imidazo[5,1-c][1,4]oxazin-9(1H)-one

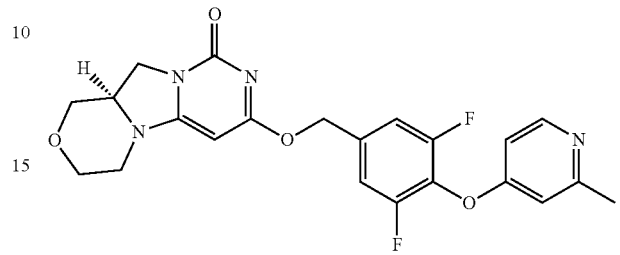

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3,5-difluoro-4-((2-methylpyridin-4-yl)oxy)phenyl)methanol.

LC-MS (ESI): m/z 443 [M+H]$^+$; 1.74 min (ret time).

$^1$H NMR (400 MHz, DMSO-d$_6$): δ 8.36-8.35 (d, 1H), 7.41-7.39 (d, 2H), 6.88-6.81 (m, 2H), 5.41 (s, 1H), 5.32 (s, 2H), 4.06-3.81 (m, 4H), 3.67-3.53 (m, 2H), 3.44-3.25 (m, 3H), 2.43 (s, 3H).

E118

(R)-7-((3,5-difluoro-4-((6-methylpyridin-3-yl)oxy)benzyl)oxy)-3,4,11,11atetrahydropyrimido[6',1':2,3]imidazo[5,1-c][1,4]oxazin-9(1H)-one

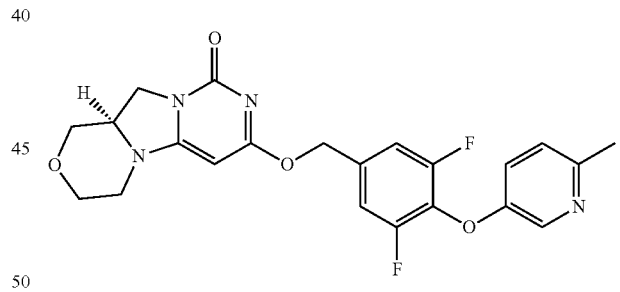

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3,5-difluoro-4-((6-methylpyridin-3-yl)oxy)phenyl)methanol.

LC-MS (ESI): m/z 443 [M+H]$^+$; 1.74 min (ret time).

$^1$H NMR (400 MHz, DMSO-d$_6$): δ 8.26-8.26 (d, 1H), 7.39-7.23 (d, 2H), 6.88-6.81 (m, 2H), 5.40 (s, 1H), 5.30 (s, 2H), 4.06-3.81 (m, 4H), 3.67-3.53 (m, 2H), 3.44-3.25 (m, 3H), 2.44 (s, 3H).

E119

(R)-7-((3, 5-difluoro-4-((2-(trifluoromethyl) pyridin-4-yl)oxy)benzyl)oxy)-3, 4, 11, 11a-tetra hydropyrimido[6',1':2,3]imidazo[5,1-c][1,4]oxazin-9(1H)-one

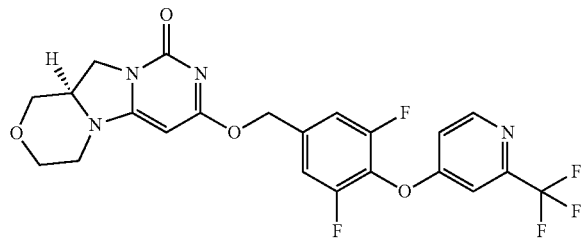 [SMILES: O=c1nc(OCc2cc(F)c(Oc3ccnc(C(F)(F)F)c3)c(F)c2)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3,5-difluoro-4-((2-(trifluoromethyl)pyridin-4-yl)oxy)phenyl)methanol.

LC-MS (ESI): m/z 497 [M+H]$^+$; 2.65 min (ret time).

$^1$H NMR (400 MHz, DMSO-d$_6$): δ 8.70-8.68 (d, 1H), 7.67 (s, 1H), 7.46-7.44 (d, 2H), 7.32-7.31 (m, 1H), 5.42 (s, 1H), 5.34 (s, 2H), 4.06-3.81 (m, 4H), 3.67-3.26 (m, 5H).

E120

(R)-7-((3,5-difluoro-4-((1-methyl-1H-pyrazol-4-yl)oxy)benzyl)oxy)-3,4,11,11a-tetrahydropyrimido[6',1':2,3]imidazo[5,1-c][1,4]oxazin-9(1H)-one

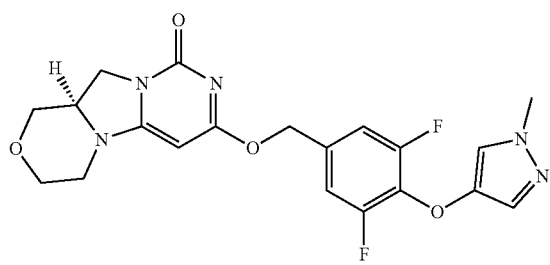 [SMILES: Cn1cc(Oc2c(F)cc(COc3cc4n(c(=O)n3)C[C@@H]3COCCN43)cc2F)cn1]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3,5-difluoro-4-((1-methyl-1H-pyrazol-4-yl)oxy)phenyl)methanol.

LC-MS (ESI): m/z 432 [M+H]$^+$; 2.12 min (ret time).

$^1$H NMR (400 MHz, MeOD-d$_4$): δ 7.61 (s, 1H), 7.28-7.27 (m, 3H), 5.38 (s, 1H), 5.27 (s, 2H), 4.05-3.80 (m, 4H), 3.73 (s, 3H), 3.66-3.27 (m, 5H).

E121

(R)-7-((4-((1-ethyl-1H-pyrazol-4-yl)oxy)-3,5-difluorobenzyl)oxy)-3,4,11,11a-tetrahydropyrimido[6',1':2,3]imidazo[5,1-c][1,4]oxazin-9(1H)-one

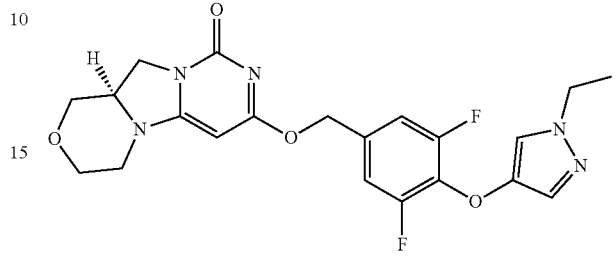

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (4-((1-ethyl-1H-pyrazol-4-yl)oxy)-3,5-difluorophenyl)methanol.

LC-MS (ESI): m/z 446 [M+H]$^+$; 2.36 min (ret time).

$^1$H NMR (400 MHz, DMSO-d$_6$): δ7.66 (s, 1H), 7.31-7.28 (m, 3H), 5.38 (s, 1H), 5.27 (s, 2H), 4.04-3.80 (m, 6H), 3.66-3.51 (s, 2H), 3.40-3.24 (m, 3H), 1.33-1.29 (t, 3H).

E122

(R)-7-((3,5-difluoro-4-((1-propyl-1H-pyrazol-4-yl)oxy)benzyl)oxy)-3,4,11,11a tetrahydropyrimido[6',1':2,3]imidazo[5,1-c][1,4]oxazin-9(1H)-one

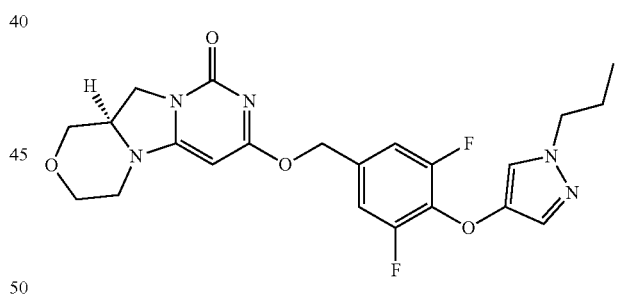

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3,5-difluoro-4-((1-propyl-1H-pyrazol-4-yl)oxy)phenyl)methanol.

LC-MS (ESI): m/z 460 [M+H]$^+$; 2.55 min (ret time).

$^1$H NMR (400 MHz, DMSO-d$_6$): δ7.65 (s, 1H), 7.31-7.28 (m, 3H), 5.39 (s, 1H), 5.26 (s, 2H), 4.09-3.79 (m, 6H), 3.66-3.51 (s, 2H), 3.40-3.24 (m, 3H), 1.77-1.68 (m, 2H), 0.80-0.76 (t, 3H).

E123

(R)-7-((3,4,5-trifluorobenzyl)oxy)-3,4,11,11atetrahydropyrimido[6',1':2,3]imidazo[5,1-c][1,4] oxazin-9(1H)-one

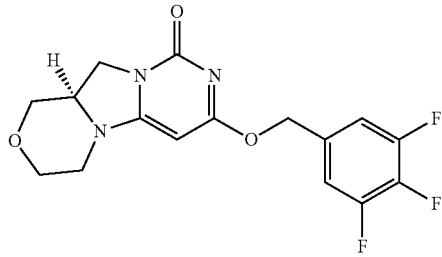 [SMILES: O=c1nc(OCc2cc(F)c(F)c(F)c2)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3,4,5-trifluorophenyl)methanol.

LC-MS (ESI): m/z 354 [M+H]$^+$; 2.17 min (ret time).

$^1$H NMR (400 MHz, DMSO-d$_6$): δ 7.39-7.35 (m, 2H), 5.38 (s, 1H), 5.24 (s, 2H), 4.05-3.80 (m, 4H), 3.66-3.66 (m, 1H), 3.40-3.20 (m, 4H).

E124

(S)-7-((3,5-difluoro-4-((2-methylpyridin-4-yl)oxy)benzyl)oxy)-3,4,11,11atetrahydropyrimido[6',1':2,3]imidazo[5,1-c][1,4]oxazin-9(1H)-one

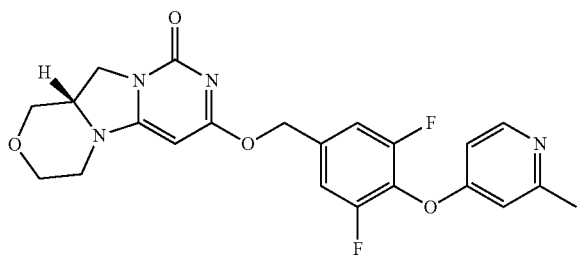 [SMILES: Cc1cc(Oc2c(F)cc(COc3cc4n(c(=O)n3)C[C@H]3COCCN43)cc2F)ccn1]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,5-difluoro-4-((2-methylpyridin-4-yl)oxy)phenyl)methanol.

LC-MS (ESI): m/z 443 [M+H]$^+$; 1.76 min (ret time).

$^1$H NMR (400 MHz, DMSO-d$_6$): δ 8.36-8.35 (d, 1H), 7.41-7.39 (d, 2H), 6.88-6.81 (m, 2H), 5.41 (s, 1H), 5.32 (s, 2H), 4.06-3.81 (m, 4H), 3.67-3.53 (m, 2H), 3.44-3.25 (m, 3H), 2.43 (s, 3H).

E125

(S)-7-((3,5-difluoro-4-((6-methylpyridin-3-yl)oxy)benzyl)oxy)-3,4,11,11atetrahydropyrimido[6',1':2,3]imidazo[5,1-c][1,4]oxazin-9(1H)-one

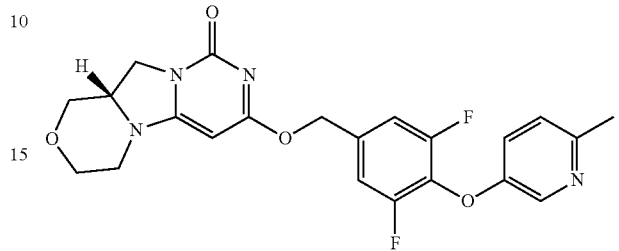

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,5-difluoro-4-((6-methylpyridin-3-yl)oxy)phenyl)methanol.

LC-MS (ESI): m/z 443 [M+H]$^+$; 1.82 min (ret time).

$^1$H NMR (400 MHz, DMSO-d$_6$): δ 8.26-8.26 (d, 1H), 7.39-7.23 (d, 2H), 6.88-6.81 (m, 2H), 5.40 (s, 1H), 5.30 (s, 2H), 4.06-3.81 (m, 4H), 3.67-3.53 (m, 2H), 3.44-3.25 (m, 3H), 2.44 (s, 3H).

E126

(S)-7-((2,4-difluorobenzyl)oxy)-3,4,11,11a-tetrahydropyrimido[6',1':2,3]imidazo[5,1-c][1,4] oxazin-9(1H)-one

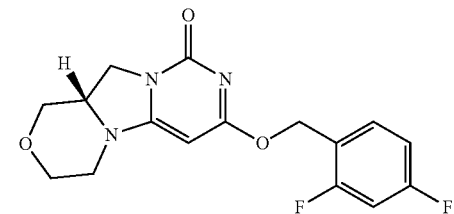 [SMILES: O=c1nc(OCc2ccc(F)cc2F)cc2n1C[C@H]1COCCN21]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (2,4-difluorophenyl)methanol.

LC-MS (ESI): m/z 336 [M+H]$^+$; 3.29 min (ret time).

$^1$H NMR (300 MHz, CDCl$_3$): δ 7.45 (q, 1H), 6.89-6.79 (m, 2H), 5.40 (t, 2H), 4.99 (s, 1H), 4.18-3.88 (m, 4H), 3.70-3.63 (m, 1H), 3.56-3.30 (m, 4H).

E127

(S)-7-((2,3-difluorobenzyl)oxy)-3,4,11,11a-tetrahydropyrimido[6',1':2,3]imidazo[5,1-c][1,4] oxazin-9(1H)-one

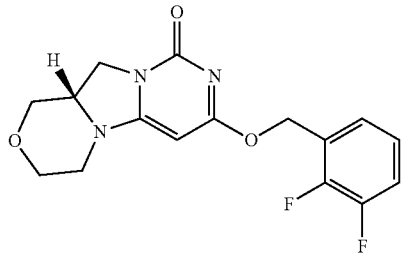 [SMILES: O=c1nc(OCc2cccc(F)c2F)cc2n1C[C@H]1COCCN21]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (2,3-difluorophenyl)methanol.

LC-MS (ESI): m/z 336 [M+H]$^+$; 3.29 min (ret time).

$^1$H NMR (300 MHz, CDCl$_3$): δ 7.24-7.02 (m, 3H), 5.47 (t, 2H), 5.01 (s, 1H), 4.19-3.88 (m, 4H), 3.70-3.64 (m, 1H), 3.57-3.34 (m, 4H).

E128

(S)-7-((3-fluorobenzyl)oxy)-3,4,11,11a-tetrahydropyrimido[6',1':2,3]imidazo[5,1-c][1,4] oxazin-9(1H)-one

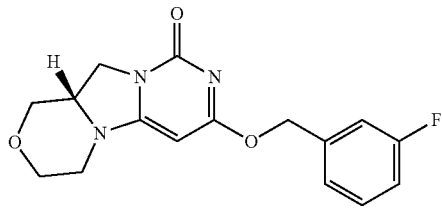 [SMILES: O=c1nc(OCc2cccc(F)c2)cc2n1C[C@H]1COCCN21]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3-fluorophenyl)methanol.

LC-MS (ESI): m/z 318 [M+H]$^+$; 3.26 min (ret time).

$^1$H NMR (300 MHz, CDCl$_3$): δ 7.35-7.28 (m, 1H), 7.17-7.10 (m, 2H), 7.03-6.96 (m, 1H), 5.43-5.34 (m, 2H), 5.03 (s, 1H), 4.19-3.90 (m, 4H), 3.70-3.64 (m, 1H), 3.58-3.35 (m, 4H).

E129

(S)-7-((3,5-difluorobenzyl)oxy)-3,4,11,11a-tetrahydropyrimido[6',1':2,3]imidazo[5,1-c][1,4] oxazin-9(1H)-one

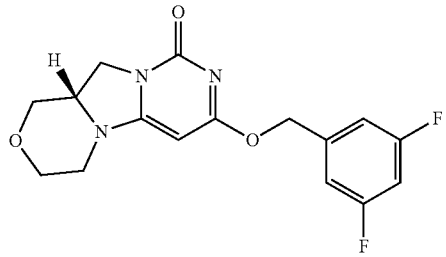 [SMILES: O=c1nc(OCc2cc(F)cc(F)c2)cc2n1C[C@H]1COCCN21]

The title compound was prepared by a procedure similar to that described for E63 starting from (S)-7-chloro-3,4,11,11a-tetrahydropyrimido[6',1':2,3]imidazo[5,1-c][1,4]oxazin-9(1H)-one and (3,5-difluorophenyl)methanol.

LC-MS (ESI): m/z 336[M+H]$^+$; 3.38 min (ret time).

$^1$H NMR (300 MHz, CDCl$_3$): δ 6.91 (d, 2H), 6.76-6.69 (m, 1H), 5.42-5.33 (m, 2H), 5.04 (s, 1H), 4.19-3.91 (m, 4H), 3.70-3.64 (m, 1H), 3.57-3.35 (m, 4H).

E130

(R)-7-((2,4-difluorobenzyl)oxy)-3,4,11,11a-tetrahydropyrimido[6',1':2,3]imidazo[5,1-c][1,4] oxazin-9(1H)-one

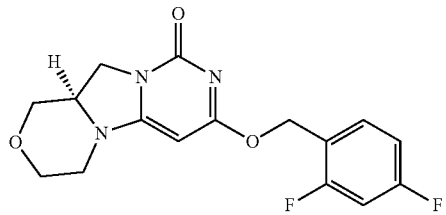 [SMILES: O=c1nc(OCc2ccc(F)cc2F)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (2,4-difluorophenyl)methanol.

LC-MS (ESI): m/z 336 [M+H]$^+$; 3.16 min (ret time).

$^1$H NMR (300 MHz, CDCl$_3$): δ 7.50-7.42 (m, 1H), 6.90-6.79 (m, 2H), 5.41 (s, 2H), 4.99 (s, 1H), 4.19-3.89 (m, 4H), 3.70-3.65 (m, 1H), 3.57-3.31 (m, 4H).

E131

(R)-7-((2,3-difluorobenzyl)oxy)-3,4,11,11a-tetrahydropyrimido[6',1':2,3]imidazo[5,1-c][1,4] oxazin-9(1H)-one

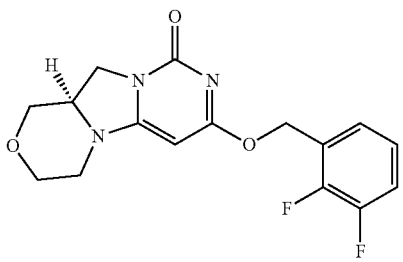 [SMILES: O=c1nc(OCc2cccc(F)c2F)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (2,3-difluorophenyl)methanol.

LC-MS (ESI): m/z 336 [M+H]$^+$; 3.32 min (ret time).

$^1$H NMR (300 MHz, CDCl$_3$): δ 7.25-7.03 (m, 3H), 5.47 (t, 2H), 5.01 (s, 1H), 4.19-3.89 (m, 4H), 3.70-3.64 (m, 1H), 3.58-3.32 (m, 4H).

E132

(R)-7-((3-fluorobenzyl)oxy)-3,4,11,11a-tetrahydropyrimido[6',1':2,3]imidazo[5,1-c][1,4] oxazin-9(1H)-one

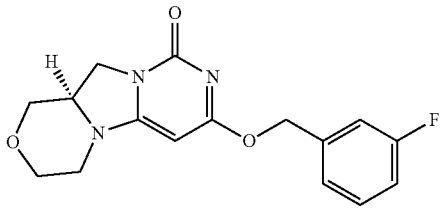 [SMILES: O=c1nc(OCc2cccc(F)c2)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3-fluorophenyl) methanol.

LC-MS (ESI): m/z 318 [M+H]$^+$; 3.26 min (ret time).

$^1$H NMR (300 MHz, CDCl$_3$): δ 7.36-7.27 (m, 1H), 7.18-7.10 (m, 2H), 7.04-6.97 (m, 1H), 5.44-5.35 (m, 2H), 5.04 (s, 1H), 4.19-3.91 (m, 4H), 3.70-3.65 (m, 1H), 3.58-3.35 (m, 4H).

E133

(R)-7-((3,5-difluorobenzyl)oxy)-3,4,11,11a-tetrahydropyrimido[6',1':2,3]imidazo[5,1-c][1,4] oxazin-9(1H)-one

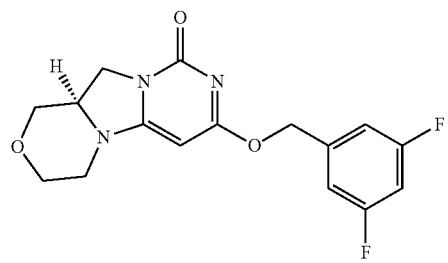 [SMILES: O=c1nc(OCc2cc(F)cc(F)c2)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4]oxazin-9(1H)-one and (3, 5-difluorophenyl) methanol.

LC-MS (ESI): m/z 336[M+H]$^+$; 3.39 min (ret time).

$^1$H NMR (300 MHz, CDCl$_3$): δ 6.94-6.88 (m, 2H), 6.78-6.70 (m, 1H), 5.43-5.33 (m, 2H), 5.04 (s, 1H), 4.20-3.92 (m, 4H), 3.70-3.65 (m, 1H), 3.59-3.36 (m, 4H).

E134

(S)-3-((3,5-difluoro-4-((2-(trifluoromethyl)pyridin-4-yl)oxy)benzyl)oxy)-8,9,9a,10-tetrahydropyrimido[6',1':2,3]imidazo[1,5-c][1,3]oxazin-1(6H)-one

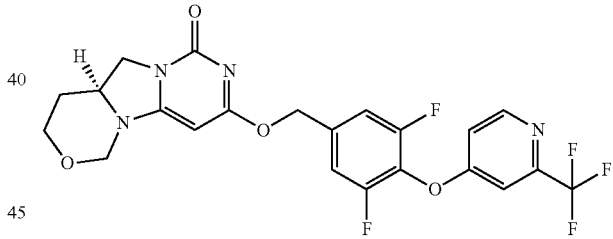

To a solution of (S)-3-chloro-8,9,9a,10-tetrahydropyrimido[6',1':2,3]imidazo[1,5-c][1,3]oxazin-1(6H)-one (60 mg, 0.26 mmol) and (3,5-difluoro-4-((2-(trifluoromethyl)pyridin-4-yl)oxy)phenyl)methanol (88 mg, 0.29 mmol) in DMF (4 mL) was added NaH (60% in mineral oil, 21 mg, 0.52 mmol) at 0° C. The reaction was stirred at room temperature for 2 hours. The mixture was then quenched with ice-water and extracted with EtOAc (40 mL×3). The extracts were combined and dried over Na$_2$SO$_4$, filtered, concentrated under reduced pressure. The crude was then purified with prep-HPLC (Column: XB C18, 4.6×33 mm; Mobile phase: A: H$_2$O, B: MeCN, 30-95% B) to give the title compound (40 mg, yield 31%) as a white solid.

LC-MS (ESI): m/z 497 [M+H]$^+$; 3.52 min (ret time).

$^1$H NMR (300 MHz, CDCl$_3$): δ 8.62 (d, J=5.7 Hz, 1H), 7.28 (s, 1H), 7.16-7.13 (m, 2H), 7.01-6.99 (m, 1H), 5.51-5.40 (m, 2H), 5.29 (d, J=3.3 Hz, 1H), 5.07 (d, J=11.7 Hz, 1H), 4.67 (d, J=11.1 Hz, 1H), 4.19-4.06 (m, 3H), 4.00-3.96 (m, 1H), 3.84-3.80 (m, 1H), 2.00-1.97 (m, 1H), 1.72-1.67 (m, 1H).

E135

(R)-3-((3,5-difluoro-4-((2-(trifluoromethyl)pyridin-4-yl)oxy)benzyl)oxy)-8,9,9a,10-tetrahydropyrimido[6',1':2,3]imidazo[1,5-c][1,3]oxazin-1(6H)-one

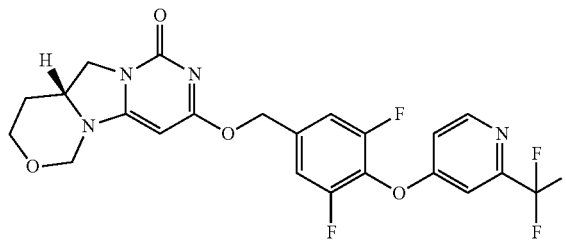

The title compound was prepared by a procedure similar to that described for E141 starting from (R)-3-chloro-8,9,9a,10-tetrahydropyrimido[6',1':2,3]imidazo[1,5-c][1,3]oxazin-1(6H)-one (60 mg, 0.26 mmol) and (3,5-difluoro-4-((2-(trifluoromethyl)pyridin-4-yl)oxy)phenyl)methanol (88 mg, 0.29 mmol) as a white solid.

LC-MS (ESI): m/z 497 [M+H]$^+$; 3.52 min (ret time).

$^1$H NMR (300 MHz, CDCl$_3$): δ 8.60 (d, J=5.7 Hz, 1H), 7.28 (s, 1H), 7.14-7.11 (m, 2H), 6.99-6.96 (m, 1H), 5.48-5.37 (m, 2H), 5.27 (s, 1H), 5.05 (d, J=11.7 Hz, 1H), 4.65 (d, J=11.1 Hz, 1H), 4.19-4.06 (m, 3H), 4.00-3.96 (m, 1H), 3.84-3.80 (m, 1H), 2.00-1.97 (m, 1H), 1.70-1.64 (m, 1H).

E136

(S)-3-((3,5-difluoro-4-((1-methyl-1H-pyrazol-4-yl)oxy)benzyl)oxy)-8,9,9a,10-tetrahydropyrimdo[6',1':2,3]imidazo[1,5-c][1,3]oxazin-1(6H)-one

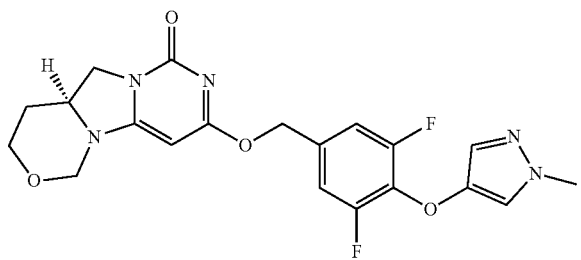 [SMILES: Cn1cc(Oc2c(F)cc(COc3cc4n(c(=O)n3)C[C@@H]3CCOCN43)cc2F)cn1]

The title compound was prepared by a procedure similar to that described for E141 starting from (3,5-difluoro-4-((1-methyl-1H-pyrazol-4-yl)oxy)phenyl)methanol (70 mg, 0.29 mmol) and (S)-3-chloro-8,9,9a,10-tetrahydropyrimido[6',1':2,3]imidazo[1,5-c][1,3]oxazin-1(6H)-one (60 mg, 0.26 mmol) as a white solid.

LC-MS (ESI): m/z 432 [M+H]$^+$; 3.29 min (ret time).

$^1$H NMR (300 MHz, CDCl$_3$): δ 7.29-7.24 (m, 1H), 7.18 (s, 1H), 7.02-6.99 (m, 2H), 5.41-5.30 (m. 2H), 5.24 (m, 1H), 5.03 (d, J=11.4 Hz, 1H), 4.64 (d, J=11.1 Hz, 1H), 4.16-4.15 (m, 2H), 4.15-4.12 (m, 1H), 4.10-4.03 (m, 1H), 3.93-3.77 (m, 3H), 3.77-3.73 (m, 1H), 2.00-1.95 (m, 1H), 1.68-1.58 (m, 1H).

E137

(R)-3-((3,5-difluoro-4-((1-methyl-1H-pyrazol-4-yl)oxy)benzyl)oxy)-8,9,9a,10-tetrahydropyrimido[6',1':2,3]imidazo[1,5-c][1,3]oxazin-1(6H)-one

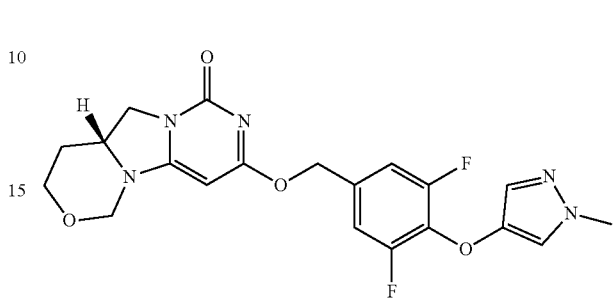

The title compound was prepared by a procedure similar to that described for E141 starting from (3,5-difluoro-4-((1-methyl-1H-pyrazol-4-yl)oxy)phenyl)methanol (70 mg, 0.29 mmol) and (R)-3-chloro-8,9,9a,10-tetrahydropyrimido[6',1':2,3]imidazo[1,5-c][1,3]oxazin-1(6H)-one (60 mg, 0.26 mmol) as a white solid.

LC-MS (ESI): m/z 432 [M+H]$^+$; 3.30 min (ret time).

$^1$H NMR (300 MHz, CDCl$_3$): δ 7.27-7.26 (m, 1H), 7.18 (s, 1H), 7.04-6.99 (m, 2H), 5.41-5.30 (m, 2H), 5.24 (s. 1H), 5.03 (d, J=11.4 Hz, 1H), 4.63 (d, J=11.1 Hz, 1H), 4.18-4.15 (m, 2H), 4.12-4.10 (m, 1H), 4.10-4.03 (m, 1H), 3.97-3.93 (m, 3H), 3.81-3.73 (m, 1H), 2.00-1.95 (m, 1H), 1.68-1.58 (m, 1H).

E138

(S)-3-((3-fluorobenzyl)oxy)-8,9,9a,10-tetrahydropyrimido[6',1':2,3]imidazo[1,5-c][1,3] oxazin-1(6H)-one

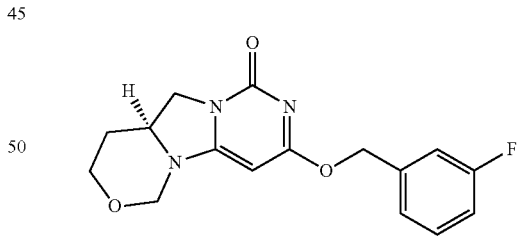

The title compound was prepared by a procedure similar to that described for E141 starting from (S)-3-chloro-8,9,9a,10-tetrahydropyrimido[6',1':2,3]imidazo[1,5-c][1,3]oxazin-1(6H)-one (50 mg, 0.20 mmol) and (3-fluorophenyl)methanol (28 mg, 0.22 mmol) as a white solid.

LC-MS (ESI): m/z 318 [M+H]$^+$; 3.40 min (ret time).

$^1$H NMR (300 MHz, CDCl$_3$): δ 7.35-7.24 (m, 1H), 7.17-7.10 (m, 2H), 7.03-6.96 (m, 1H), 5.44-5.35 (m, 1H), 5.24 (s, 1H), 5.02 (d, J=11.7 Hz, 1H), 4.62 (t, J=6.9 Hz, 1H), 4.18-4.02 (m, 3H), 3.99-3.93 (m, 1H), 3.80-3.72 (m, 1H), 2.04-1.93 (m, 1H), 1.69-1.56 (m, 1H).

E139

(S)-3-((3,4,5-trifluorobenzyl)oxy)-8,9,9a,10-tetrahydropyrimido[6',1':2,3]imidazo[1,5-c][1,3] oxazin-1(6H)-one

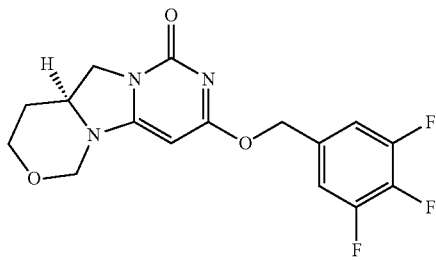 [SMILES: O=c1nc(OCc2cc(F)c(F)c(F)c2)cc2n1C[C@@H]1CCOCN21]

The title compound was prepared by a procedure similar to that described for E141 starting from (S)-3-chloro-8,9,9a,10-tetrahydropyrimido[6',1':2,3]imidazo[1,5-c][1,3]oxazin-1(6H)-one (50 mg, 0.20 mmol) and (3,4,5-trifluorophenyl)methanol (36 mg, 0.22 mmol) as a white solid.

LC-MS (ESI): m/z 354 [M+H]$^+$; 3.69 min (ret time).

$^1$H NMR (300 MHz, CDCl$_3$): δ 7.05-7.00 (m, 2H), 5.38-5.28 (m, 2H), 5.24 (s, 1H), 5.03 (d, J=11.1 Hz, 1H), 4.63 (d, J=11.1 Hz, 1H), 4.16-4.02 (m, 3H), 3.99-3.92 (m, 1H), 3.82-3.73 (m, 1H), 1.99-1.63 (m, 1H), 1.57-1.54 (m, 1H).

E140

(S)-3-((3,5-difluoro-4-(1-(2-fluoroethyl)cyclopropoxy)benzyl)oxy)-8,9,9a,10-tetrahydropyrimido[6',1':2,3]imidazo[1,5-c][1,3]oxazin-1(6H)-one

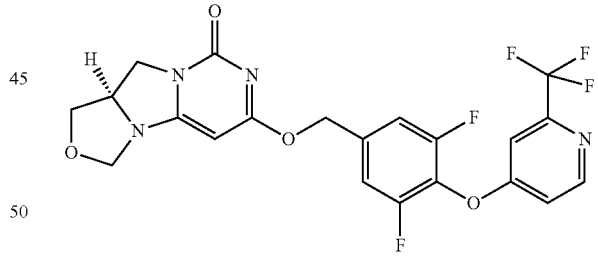

The title compound was prepared by a procedure similar to that described for E141 starting from (3,5-difluoro-4-(1-(2-fluoroethyl)cyclopropoxy)phenyl)methanol (40 mg, 0.16 mmol) and (S)-3-chloro-8,9,9a,10-tetrahydropyrimido[6',1': 2,3]imidazo[1,5-c][1,3]oxazin-1(6H)-one (35 mg, 0.16 mmol) as yellow oil.

LC-MS (ESI): m/z 438 [M+H]$^+$; 4.07 min (ret time).

$^1$H NMR (300 MHz, CDCl$_3$): δ 6.97-6.92 (m, 2H), 5.35-5.25 (m, 2H), 5.22 (s, 1H), 5.02 (d, J=12.3 Hz, 1H), 4.84 (t, J=6.3 Hz, 1H), 4.71-4.60 (m, 2H), 4.16-4.01 (m, 3H), 3.95-3.90 (m, 1H), 3.80-3.71 (m, 1H), 2.18-2.07 (m, 2H), 1.97-1.91 (m, 1H), 1.67-1.62 (m, 1H), 1.09-1.05 (m, 2H), 0.66-0.62 (m, 2H).

E141

(S)-6-((3,5-difluoro-4-((2-(trifluoromethyl)pyridin-4-yl)oxy)benzyl)oxy)-10,10a-dihydro-1H-oxazolo[3',4':3,4]imidazo[1,2-c]pyrimidin-8(3H)-one

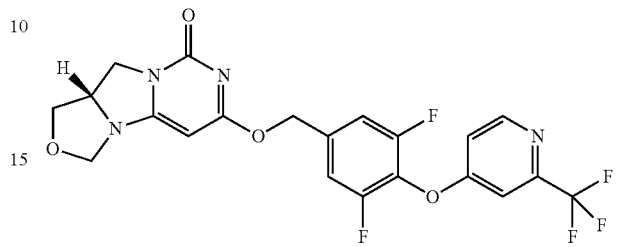

The title compound was prepared by a procedure similar to that described for E141 starting from ((S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((2-(trifluoromethyl)pyridin-4-yl)oxy)phenyl)methanol (63 mg, 0.21 mmol) as a white solid.

LC-MS (ESI): m/z 483 [M+H]$^+$; 4.04 min (ret time).

$^1$H NMR (300 MHz, CDCl$_3$): δ 8.60 (d, J=5.7 Hz, 1H), 7.26 (s, 1H), 7.15 (d, J=7.8 Hz, 2H), 5.43 (d, J=3.6 Hz, 2H), 5.39 (s, 1H), 4.99 (d, J=6.0 Hz, 1H), 4.60 (d, J=6.0 Hz, 1H), 4.29-4.11 (m, 4H), 3.55-3.50 (m, 1H).

E142

(R)-6-((3,5-difluoro-4-((2-(trifluoromethyl)pyridin-4-yl)oxy)benzyl)oxy)-10,10a-dihydro-1H-oxazolo[3',4':3,4]imidazo[1,2-c]pyrimidin-8(3H)-one The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((2-(trifluoromethyl)pyridin-4-yl)oxy)phenyl)methanol (58 mg, 0.19 mmol) as a red solid.

LC-MS (ESI): m/z 483 [M+H]$^+$; 3.54 min (ret time).

$^1$H NMR (300 MHz, CDCl$_3$): δ 8.60 (d, J=5.4 Hz, 1H), 7.26 (d, J=2.7 Hz, 1H), 7.13 (d, J=8.1 Hz, 2H), 6.99-6.97 (m, 1H), 5.48-5.37 (m, 3H), 5.10 (d, J=5.7 Hz, 1H), 4.60 (d, J=6.0 Hz, 1H), 4.32-4.09 (m, 4H), 3.55-3.50 (m, 1H).

E143

(S)-6-((3,5-difluoro-4-((1-methyl-1H-pyrazol-4-yl)oxy)benzyl)oxy)-10,10a-dihydro-1H-oxazolo[3',4':3,4]imidazo[1,2-c]pyrimidin-8(3H)-one

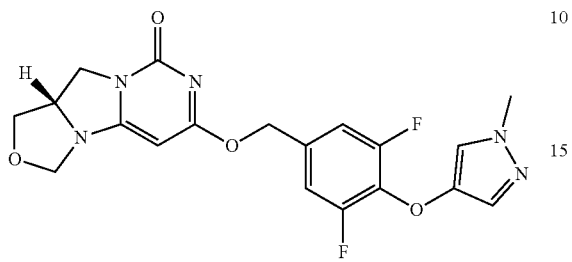

The title compound was prepared by a procedure similar to that described for E141 starting from (S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((1-methyl-1H-pyrazol-4-yl)oxy)phenyl)methanol (49 mg, 0.21 mmol) as a white solid.

LC-MS (ESI): m/z 418 [M+H]$^+$; 3.36 min (ret time).

$^1$H NMR (300 MHz, CDCl$_3$): δ 7.27 (d, J=2.1 Hz, 1H), 7.19 (s, 1H), 7.02 (d, J=6.3 Hz, 2H), 5.40-5.32 (m, 3H), 4.99 (d, J=4.5 Hz, 1H), 4.59 (d, J=4.2 Hz, 1H), 4.29-4.09 (m, 4H), 3.82 (s, 1H), 3.53-3.50 (m, 1H).

E144

(R)-6-((3,5-difluoro-4-((1-methyl-1H-pyrazol-4-yl)oxy)benzyl)oxy)-10,10a-dihydro-1H-oxazolo[3',4':3,4]imidazo[1,2-c]pyrimidin-8(3H)-one

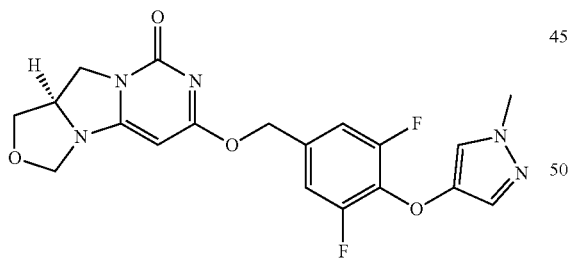

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((1-methyl-1H-pyrazol-4-yl)oxy)phenyl)methanol (47 mg, 0.19 mmol) as a yellow solid.

LC-MS (ESI): m/z 418 [M+H]$^+$; 3.36 min (ret time).

$^1$H NMR (300 MHz, CDCl$_3$): δ 7.25 (d, J=2.1 Hz, 1H), 7.01 (s, 1H), 6.99 (d, J=8.4 Hz, 2H), 5.34 (d, J=3.6 Hz, 3H), 4.96 (d, J=6.0 Hz, 1H), 4.57 (d, J=6.0 Hz, 1H), 4.26-4.06 (m, 4H), 3.79 (s, 3H), 3.52-3.47 (m, 1H).

E145

(S)-6-((4-chloro-3-fluorobenzyl)oxy)-10,10a-dihydro-1H-oxazolo[3',4':3,4]imidazo[1,2-c] pyrimidin-8(3H)-one

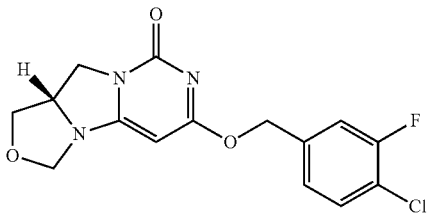 [SMILES: O=c1nc(OCc2ccc(Cl)c(F)c2)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (35 mg, 0.16 mmol) and (4-chloro-3-fluorophenyl)methanol (29 mg, 0.18 mmol) as a white solid.

LC-MS (ESI): m/z 338 [M+H]$^+$; 3.64 min (ret time).

$^1$H NMR (300 MHz, CDCl$_3$): δ 7.40-7.26 (m, 1H), 7.27-7.19 (m, 1H), 7.13-7.11 (m, 1H), 5.37-5.36 (m, 2H), 5.36-5.34 (m, 2H), 4.97 (d, J=5.7 Hz, 1H), 4.58 (d, J=6.0 Hz, 1H), 4.27-4.17 (m, 3H), 4.14-4.10 (m, 1H), 3.53-3.48 (m, 1H).

E146

(S)-6-((3,4,5-trifluorobenzyl)oxy)-10,10a-dihydro-1H-oxazolo[3',4':3,4]imidazo[1,2-c] pyrimidin-8(3H)-one

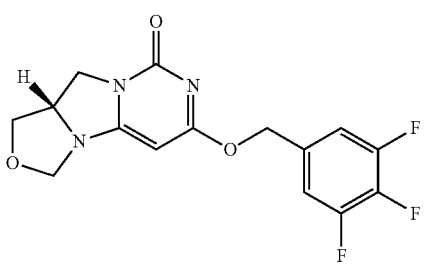 [SMILES: O=c1nc(OCc2cc(F)c(F)c(F)c2)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (35 mg, 0.16 mmol) and (3,4,5-trifluorophenyl)methanol (29 mg, 0.18 mmol) as a white solid.

LC-MS (ESI): m/z 340 [M+H]$^+$; 3.57 min (ret time).

$^1$H NMR (300 MHz, CDCl$_3$): δ 7.05-7.00 (m, 2H), 5.33 (d, J=5.7 Hz, 3H), 5.31 (s, 2H), 4.97 (d, J=6.0 Hz, 1H), 4.59 (d, J=5.7 Hz, 1H), 4.27-4.13 (m, 3H), 4.10-4.08 (m, 1H), 3.54-3.48 (m, 1H).

E147

(S)-6-((3,5-difluorobenzyl)oxy)-10,10a-dihydro-1H-oxazolo[3',4':3,4]imidazo[1,2-c]pyrimidin-8(3H)-one

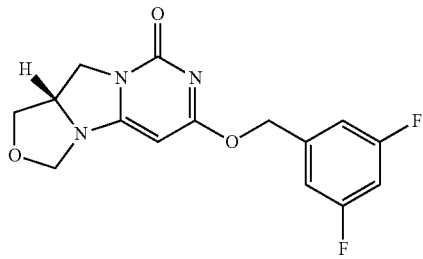 [SMILES: O=c1nc(OCc2cc(F)cc(F)c2)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (35 mg, 0.16 mmol) and (3,5-difluorophenyl)methanol (26 mg, 0.18 mmol) as a white solid.

LC-MS (ESI): m/z 322 [M+H]$^+$; 3.43 min (ret time).

$^1$H NMR (300 MHz, CDCl$_3$): δ 6.93-6.91 (m, 2H), 6.78-6.72 (m, 1H), 5.37 (t, J=4.2 Hz, 3H), 4.98 (d, J=6.0 Hz, 1H), 4.59 (d, J=5.7 Hz, 1H), 4.30-4.08 (m, 4H), 3.54-3.48 (m, 1H).

E148

(S)-6-((3-fluorobenzyl)oxy)-10,10a-dihydro-1H-oxazolo[3',4':3,4]imidazo[1,2-c]pyrimidin-8(3H)-one

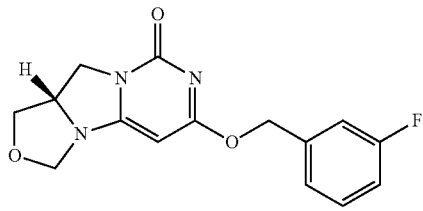 [SMILES: O=c1nc(OCc2cccc(F)c2)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (35 mg, 0.16 mmol) and (3-fluorophenyl)methanol (23 mg, 0.18 mmol) as a white solid.

LC-MS (ESI): m/z 304 [M+H]$^+$; 3.30 min (ret time).

$^1$H NMR (300 MHz, CDCl$_3$): δ 7.33-7.29 (m, 1H), 7.18-7.10 (m, 2H), 7.04-7.00 (m, 1H), 5.39 (d, J=3.0 Hz, 2H), 5.35 (s, 1H), 4.97 (d, J=5.7 Hz, 1H), 4.59 (d, J=5.7 Hz, 1H), 4.29-4.07 (m, 4H), 3.53-3.48 (m, 1H).

E149

(S)-6-((3,5-difluoro-4-((6-methylpyridin-3-yl)oxy)benzyl)oxy)-10,10a-dihydro-1H-oxazolo[3',4':3,4]imidazo[1,2-c]pyrimidin-8(3H)-one

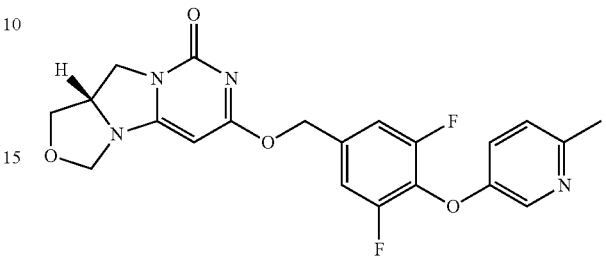

The title compound was prepared by a procedure similar to that described for E141 starting from ((S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((6-methylpyridin-3-yl)oxy)phenyl)methanol (52 mg, 0.21 mmol) as a white solid.

LC-MS (ESI): m/z 429 [M+H]$^+$; 3.55 min (ret time).

$^1$H NMR (300 MHz, CDCl$_3$): δ 8.28 (t, J=1.8 Hz, 1H), 7.10-7.05 (m, 4H), 5.38 (t, J=4.5 Hz, 3H), 4.98 (d, J=5.7 Hz, 1H), 4.60 (d, J=6.0 Hz, 1H), 4.29-4.11 (m, 4H), 3.55-3.49 (m, 1H), 2.52 (s, 3H).

E150

(S)-6-((3,5-difluoro-4-((1-propyl-1H-pyrazol-4-yl)oxy)benzyl)oxy)-10,10a-dihydro-1H-oxazolo[3',4':3,4]imidazo[1,2-c]pyrimidin-8(3H)-one

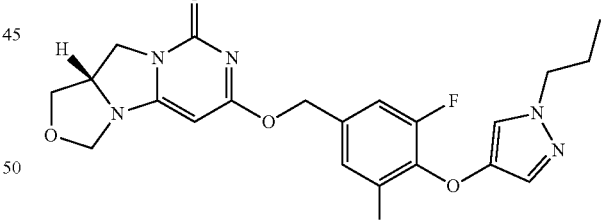

The title compound was prepared by a procedure similar to that described for E141 starting from (S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((1-propyl-1H-pyrazol-4-yl)oxy)phenyl)methanol (55 mg, 0.21 mmol) as a white solid.

LC-MS (ESI): m/z 446 [M+H]$^+$; 3.78 min (ret time).

$^1$H NMR (300 MHz, CDCl$_3$): δ 7.27-7.23 (m, 1H), 7.20-7.19 (m, 1H), 7.03-6.99 (m, 2H), 5.35 (s, 3H), 4.98 (t, J=4.2 Hz, 1H), 4.59 (t, J=4.2 Hz, 1H), 4.28-4.10 (m, 4H), 3.96 (t, J=7.8 Hz, 2H), 3.54-3.48 (m, 1H), 1.87-1.80 (m, 2H), 0.92-0.86 (m, 3H).

E151

(S)-6-((3,5-difluoro-4-((1-(trifluoromethyl)-1H-pyrazol-4-yl)oxy)benzyl)oxy)-10,10a-dihydro-1H-oxazolo[3',4':3,4]imidazo[1,2-c]pyrimidin-8(3H)-one

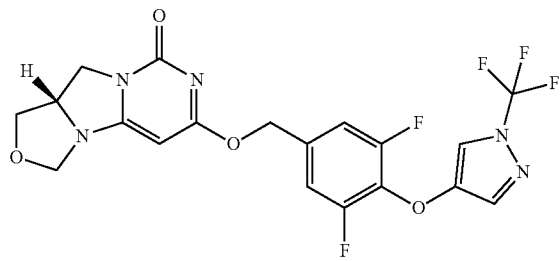 [SMILES: O=c1nc(OCc2cc(F)c(Oc3cnn(C(F)(F)F)c3)c(F)c2)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((1-(trifluoromethyl)-1H-pyrazol-4-yl)oxy)phenyl)methanol (61 mg, 0.21 mmol) as a white solid.

LC-MS (ESI): m/z 472 [M+H]$^+$; 4.11 min (ret time).

$^1$H NMR (300 MHz, CDCl$_3$): δ 7.63 (s, 1H), 7.51 (s, 1H), 7.07 (d, J=5.7 Hz, 2H), 5.38 (t, J=3.0 Hz, 3H), 4.99 (d, J=4.2 Hz, 1H), 4.60 (d, J=4.5 Hz, 1H), 4.29-4.10 (m, 4H), 3.54-3.50 (m, 1H).

E152

(S)-6-((3,5-difluoro-4-((2-methylpyrimidin-5-yl)oxy)benzyl)oxy)-10,10a-dihydro-1H-oxazolo[3',4':3,4]imidazo[1,2-c]pyrimidin-8(3H)-one

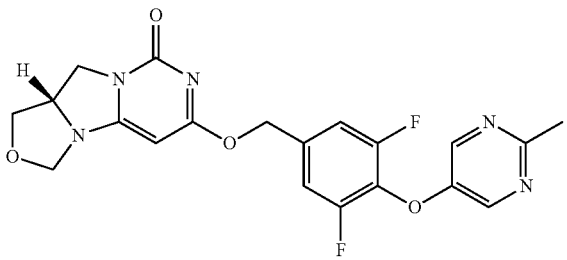 [SMILES: Cc1ncc(Oc2c(F)cc(COc3cc4n(c(=O)n3)C[C@H]3COCN43)cc2F)cn1]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((2-methylpyrimidin-5-yl)oxy)phenyl)methanol (52 mg, 0.21 mmol) as a white solid.

LC-MS (ESI): m/z 430 [M+H]$^+$; 3.35 min (ret time).

$^1$H NMR (300 MHz, CDCl$_3$): δ 8.37 (s, 2H), 7.12 (d, J=8.1 Hz, 2H), 5.41 (t, J=3.6 Hz, 3H), 5.01 (d, J=6.0 Hz, 1H), 4.62 (t, J=6.0 Hz, 1H), 4.30-4.11 (m, 4H), 3.56-3.51 (m, 1H), 2.73 (s, 3H).

E153

(R)-6-((3,4,5-trifluorobenzyl)oxy)-10,10a-dihydro-1H-oxazolo[3',4':3,4]imidazo[1,2-c] pyrimidin-8(3H)-one

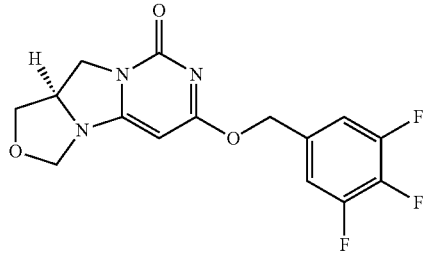 [SMILES: O=c1nc(OCc2cc(F)c(F)c(F)c2)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,4,5-trifluorophenyl)methanol (27 mg, 0.19 mmol) as a white solid.

LC-MS (ESI): m/z 340 [M+H]$^+$; 3.58 min (ret time).

$^1$H NMR (300 MHz, CDCl$_3$): δ 7.03 (t, J=6.6 Hz, 2H), 5.35-5.28 (m, 3H), 4.98 (d, J=5.7 Hz, 1H), 4.59 (d, J=6.0 Hz, 1H), 4.31-4.08 (m, 4H), 3.51 (t, J=7.2 Hz, 1H).

E154

(R)-6-((3,5-difluoro-4-((1-(trifluoromethyl)-1H-pyrazol-4-yl)oxy)benzyl)oxy)-10,10a-dihydro-1H-oxazolo[3',4':3,4]imidazo[1,2-c]pyrimidin-8(3H)-one

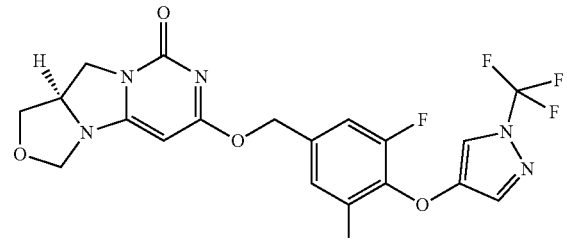

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((1-(trifluoromethyl)-1H-pyrazol-4-yl)oxy)phenyl)methanol (56 mg, 0.19 mmol) as a yellow solid.

LC-MS (ESI): m/z 472 [M+H]$^+$; 4.07 min (ret time).

$^1$H NMR (300 MHz, CDCl$_3$): δ 7.60 (s, 1H), 7.49 (s, 1H), 7.04 (d, J=8.7 Hz, 2H), 5.35 (d, J=5.1 Hz, 3H), 4.96 (d, J=6.0 Hz, 1H), 4.57 (d, J=6.0 Hz, 1H), 4.26-4.08 (m, 4H), 3.50-3.49 (m, 1H).

E155

(R)-6-((3,5-difluoro-4-((2-methylpyridin-4-yl)oxy)benzyl)oxy)-10,10a-dihydro-1H-oxazolo[3',4':3,4]imidazo[1,2-c]pyrimidin-8(3H)-one

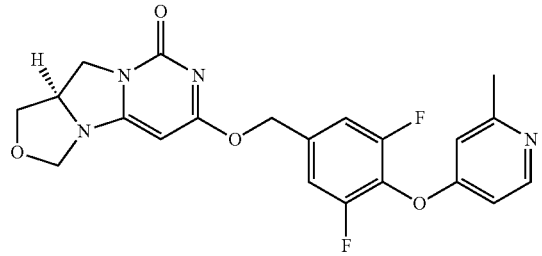 [SMILES: Cc1cc(Oc2c(F)cc(COc3cc4n(c(=O)n3)C[C@@H]3COCN43)cc2F)ccn1]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((2-methylpyridin-4-yl)oxy)phenyl)methanol (48 mg, 0.19 mmol) as a white solid.

LC-MS (ESI): m/z 429 [M+H]$^+$; 2.93 min (ret time).

$^1$H NMR (300 MHz, CDCl$_3$): δ 8.38 (d, J=5.4 Hz, 1H), 7.10 (d, J=8.1 Hz, 2H), 6.68 (d, J=8.1 Hz, 2H), 5.42 (t, J=6.9 Hz, 3H), 5.01 (d, J=6.0 Hz, 1H), 4.61 (d, J=6.0 Hz, 1H), 4.30-4.13 (m, 4H), 3.55-3.51 (m, 1H), 2.53 (m, 3H).

E156

(R)-6-((3,5-difluoro-4-((1-propyl-1H-pyrazol-4-yl)oxy)benzyl)oxy)-10,10a-dihydro-1H-oxazolo[3',4':3,4]imidazo[1,2-c]pyrimidin-8(3H)-one

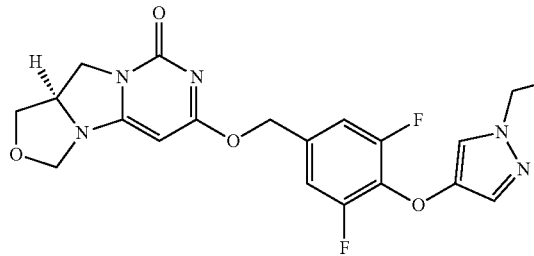

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((1-propyl-1H-pyrazol-4-yl)oxy)phenyl)methanol (51 mg, 0.19 mmol) as colorless oil.

LC-MS (ESI): m/z 446 [M+H]$^+$; 3.78 min (ret time).

$^1$H NMR (300 MHz, CDCl$_3$): δ 7.27 (s, 1H), 7.21 (s, 1H), 7.02 (d, J=8.4 Hz, 2H), 5.36 (t, J=1.2 Hz, 2H), 4.98 (d, J=5.7 Hz, 1H), 4.59 (d, J=6.0 Hz, 1H), 4.29-4.08 (m, 4H), 3.97 (t, J=6.9 Hz, 2H), 3.54-3.49 (m, 1H), 1.87-1.80 (m, 2H), 0.92-0.87 (m, 3H).

E157

(R)-6-((3,5-difluoro-4-((6-methylpyridin-3-yl)oxy)benzyl)oxy)-10,10a-dihydro-1H-oxazolo[3',4':3,4]imidazo[1,2-c]pyrimidin-8(3H)-one

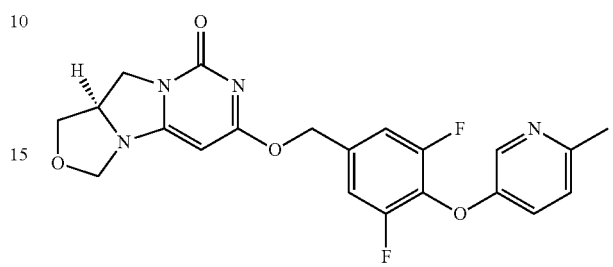

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((6-methylpyridin-3-yl)oxy)phenyl)methanol (48 mg, 0.19 mmol) as a yellow oil.

LC-MS (ESI): m/z 429 [M+H]$^+$; 3.62 min (ret time).

$^1$H NMR (300 MHz, CDCl$_3$): δ 8.26 (d, J=2.7 Hz, 1H), 7.10-7.04 (m, 4H) 5.37 (t, J=3.6 Hz, 3H), 4.98 (d, J=8.1 Hz, 1H), 5.42 (d, J=5.7 Hz, 1H), 4.27-4.17 (m, 4H), 3.54-3.49 (m, 1H), 2.50 (s, 3H).

E158

(R)-6-((4-((1-ethyl-1H-pyrazol-4-yl)oxy)-3,5-difluorobenzyl)oxy)-10,10a-dihydro-1H-oxazolo[3',4':3,4]imidazo[1,2-c]pyrimidin-8(3H)-one

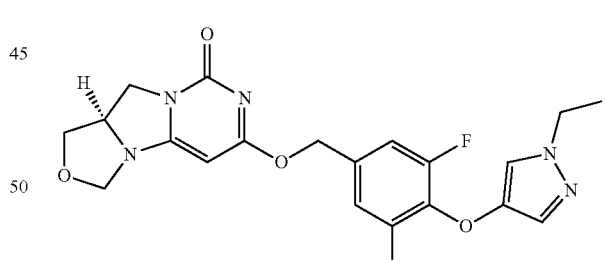

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (4-((1-ethyl-1H-pyrazol-4-yl)oxy)-3,5-difluorophenyl)methanol (48 mg, 0.19 mmol) as a colorless oil.

LC-MS (ESI): m/z 432 [M+H]$^+$; 3.03 min (ret time).

$^1$H NMR (300 MHz, CDCl$_3$): δ 7.26 (s, 1H), 7.21 (s, 1H), 7.03-6.99 (m, 2H), 5.38 (m, 3H), 4.97 (d, J=3.9 Hz, 1H), 4.58 (d, J=4.5 Hz, 1H), 4.29 (m, 7H), 3.52-3.48 (m, 1H), 1.43 (d, J=5.4 Hz, 3H).

E159

(R)-6-((3,5-difluoro-4-((2-methyl pyrimidin-5-yl)oxy)benzyl)oxy)-10,10a-dihydro-1H-oxazolo[3',4':3,4]imidazo[1,2-c]pyrimidin-8(3H)-one

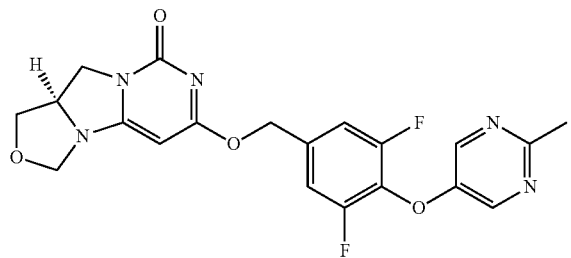 [SMILES: Cc1ncc(Oc2c(F)cc(COc3cc4n(c(=O)n3)C[C@@H]3COCN43)cc2F)cn1]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluoro-4-((2-methylpyrimidin-5-yl)oxy)phenyl)methanol (48 mg, 0.19 mmol) as a red solid.

LC-MS (ESI): m/z 430 [M+H]$^+$; 2.80 min (ret time).

$^1$H NMR (300 MHz, CDCl$_3$): δ 8.34 (s, 2H), 7.09 (d, J=6.0 Hz, 2H), 5.43-5.35 (m, 3H), 4.98 (d, J=4.2 Hz, 1H), 4.59 (d, J=4.5 Hz, 1H), 4.30-4.08 (m, 4H), 3.55-3.49 (m, 1H), 2.69 (s, 3H).

E160

(S)-6-((4-((1-ethyl-1H-pyrazol-4-yl)oxy)-3,5-difluorobenzyl)oxy)-10,10a-dihydro-1H-oxazolo[3',4':3,4]imidazo[1,2-c]pyrimidin-8(3H)-one

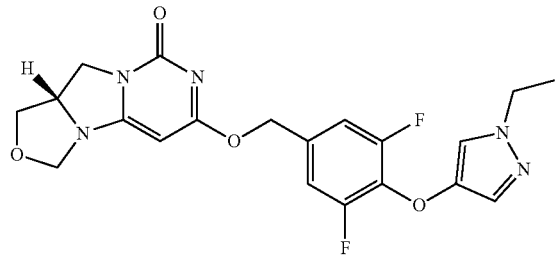 [SMILES: CCn1cc(Oc2c(F)cc(COc3cc4n(c(=O)n3)C[C@H]3COCN43)cc2F)cn1]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (40 mg, 0.19 mmol) and (4-((1-ethyl-1H-pyrazol-4-yl)oxy)-3,5-difluorophenyl)methanol (52 mg, 0.21 mmol) as a white solid.

LC-MS (ESI): m/z 432 [M+H]$^+$; 3.56 min (ret time).

$^1$H NMR (300 MHz, CDCl$_3$): δ 7.28 (s, 1H), 7.22 (s, 1H), 7.02 (d, J=3.3 Hz, 2H), 5.36 (t, J=3.0 Hz, 3H), 4.98 (d, J=4.5 Hz, 1H), 4.60 (d, J=1.2 Hz, 1H), 4.28-4.16 (m, 4H), 4.13-4.04 (m, 2H), 3.51 (t, J=6.0 Hz, 1H), 1.45 (t, J=5.4 Hz, 3H).

E161

(S)-6-((3,5-difluoro-4-((2-methylpyridin-4-yl)oxy)benzyl)oxy)-10,10a-dihydro-1H-oxazolo[3',4':3,4]imidazo[1,2-c]pyrimidin-8(3H)-one

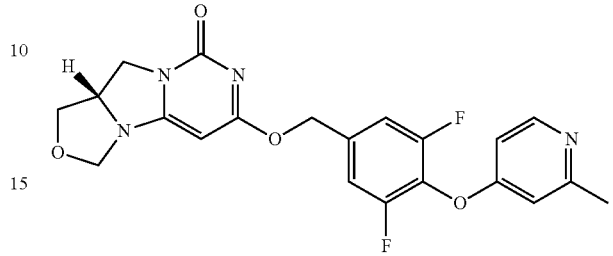

The title compound was prepared by a procedure similar to that described for E141 starting from (S)-6-chloro-10,10a-dihydro-1H-oxazolo[3',4':3,4]imidazo[1,2-c]pyrimidin-8(3H)-one (40 mg, 0.19 mmol) and (3,5-difluoro-4-((2-methylpyridin-4-yl)oxy)phenyl)methanol (52 mg, 0.21 mmol) as a white solid.

LC-MS (ESI): m/z 429 [M+H]$^+$; 3.51 min (ret time).

$^1$H NMR (300 MHz, CDCl$_3$): δ 8.36 (t, J=6.0 Hz, 1H), 7.09 (d, J=5.1 Hz, 2H), 6.69-6.65 (m, 2H), 5.41 (d, J=3.0 Hz, 2H), 5.38 (s, 1H), 4.99 (d, J=6.3 Hz, 1H), 4.59 (t, J=5.1 Hz, 1H), 4.29-4.11 (m, 4H), 3.55-3.50 (m, 2H), 2.50 (d, J=3.0 Hz, 3H).

E162 and E163

E162: Enantiomer 1: 7-((3,5-difluoro-4-((2-(trifluoromethyl)pyridin-4-yl)oxy)benzyl)oxy)-3,4,11,11a-tetrahydropyrimido[6',1':2,3]imidazo[5,1-b][1,3]oxazin-9(2H)-one E163: Enantiomer 2: 7-((3,5-difluoro-4-((2-(trifluoromethyl)pyridin-4-yl)oxy)benzyl)oxy)-3,4,11,11a-tetrahydropyrimido[6',1':2,3]imidazo[5,1-b][1,3]oxazin-9(2H)-one enantiomer 1

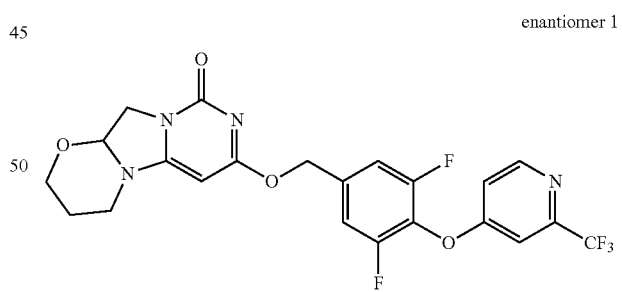

enantiomer 2

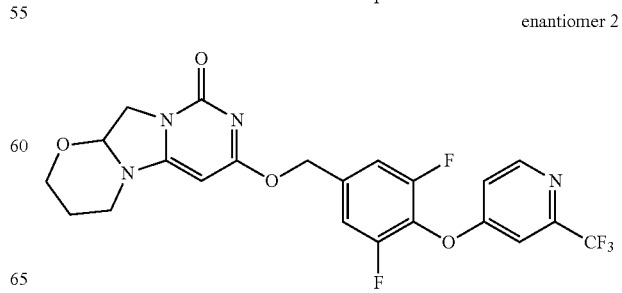

A mixture of 3,4,11,11a-tetrahydropyrimido[6',1':2,3]imidazo[5,1-b][1,3]oxazine-7,9(2H,8H)-dione (104 mg, 0.5 mmol) and Ag$_2$CO$_3$ (344 mg, 1.3 mmol) in toluene (5 mL) was heated to 70° C. Then, 4-(4-(bromomethyl)-2,6-difluorophenoxy)-2-(trifluoromethyl)pyridine (220 mg, 0.6 mmol) was added and the mixture was stirred at 110° C. for overnight. The mixture was cooled to room temperature, filtered. The filtrate was concentrated. The crude was purified by prep-TLC (DCM/MeOH=30/1) to give a white solid, which was further purified by chiral HPLC to give the title compounds enantiomer 1 (15 mg, yield 6%) and enantiomer 2 (12 mg, yield 5%) as white solids.

Enantiomer 1

LC-MS (ESI): m/z 497 [M+H]$^+$; 4.30 min (ret time).

$^1$H NMR (300 MHz, CD$_3$OD): δ8.51 (d, J=6.0 Hz, 1H), 7.33 (d, J=2.4 Hz, 1H), 7.24 (d, J=8.7 Hz, 2H), 7.08-7.05 (m, 1H), 5.45 (s, 1H), 5.31 (s, 2H), 5.28-5.26 (m, 1H), 4.00-3.84 (m, 2H), 3.84-3.74 (m, 3H), 3.53-3.22 (m, 1H), 1.86-1.82 (m, 1H), 1.47-1.44 (m, 1H).

Enantiomer 2

LC-MS (ESI): m/z 497 [M+H]$^+$; 3.71 min (ret time).

$^1$H NMR (300 MHz, CD$_3$OD): δ8.51 (d, J=5.7 Hz, 1H), 7.34 (d, J=2.4 Hz, 1H), 7.26 (d, J=5.1 Hz, 2H), 7.08-7.06 (m, 1H), 5.46 (s, 1H), 5.31 (s, 2H), 5.28-5.26 (m, 1H), 4.00-3.93 (m, 2H), 3.85-3.74 (m, 3H), 3.54-3.44 (m, 1H), 1.86-1.80 (m, 1H), 1.48-1.43 (m, 1H).

E164 and E165

E164: Enantiomer 1: 6-((3,5-difluoro-4-((2-(trifluoromethyl)pyridin-4-yl)oxy)benzyl)oxy)-10,10a-dihydro-2H-oxazolo[3',2':3,4]imidazo[1,2-c]pyrimidin-8(3H)-one E165: Enantiomer 2: 6-((3,5-difluoro-4-((2-(trifluoromethyl)pyridin-4-yl)oxy)benzyl)oxy)-10,10a-dihydro-2H-oxazolo[3',2':3,4]imidazo[1,2-c]pyrimidin-8(3H)-one enantiomer 1

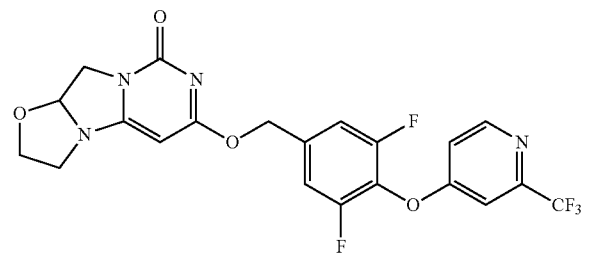

enantiomer 2

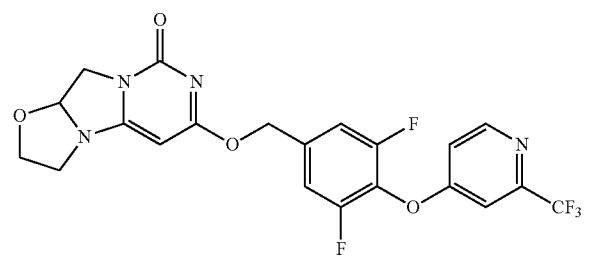

A mixture of 10,10a-dihydro-2H-oxazolo[3',2':3,4]imidazo[1,2-c]pyrimidine-6,8(3H,7H)-dione (80 mg, 0.410 mmol) and Ag$_2$CO$_3$ (282 mg, 1.03 mmol) in toluene (4 mL) was heated to 70° C. Then, 4-(4-(bromomethyl)-2,6-difluorophenoxy)-2-(trifluoromethyl)pyridine (166 mg, 0.451 mmol) was added and the reaction was then stirred at 100° C. for 2 days. The mixture was cooled to room temperature, filtered. The filtrate was concentrated. The residue was purified by prep-TLC (DCM/MeOH=25/1) to give a white solid, which was further purified by chiral HPLC to give the title compounds enantiomer 1 (6 mg, yield 3%) and enantiomer 2 (5 mg, yield 3%) as white solids.

Enantiomer 1

LC-MS (ESI): m/z 483 [M+H]$^+$; 3.65 min (ret time).

$^1$H NMR (300 MHz, CD$_3$OD): δ8.51 (d, J=5.7 Hz, 1H), 7.33 (d, J=2.1 Hz, 1H), 7.22 (d, J=2.7 Hz, 2H), 7.08-7.05 (m, 1H), 5.58 (s, 1H), 5.32 (s, 2H), 5.16-5.14 (m, 1H), 4.07 (s, 2H), 4.06-3.78 (m, 2H), 3.61-3.49 (m, 2H).

Enantiomer 2

LC-MS (ESI): m/z 483 [M+H]$^+$; 3.65 min (ret time).

$^1$H NMR (300 MHz, CD$_3$OD): δ8.51 (d, J=5.7 Hz, 1H), 7.33 (d, J=2.1 Hz, 1H), 7.22 (d, J=2.7 Hz, 2H), 7.08-7.05 (m, 1H), 5.58 (s, 1H), 5.32 (s, 2H), 5.16-5.14 (m, 1H), 4.07 (s, 2H), 4.06-3.78 (m, 2H), 3.61-3.49 (m, 2H).

E166

7-((3,5-Difluoro-4-((2-(trifluoromethyl)pyridin-4-yl)oxy)benzyl)oxy)-2-methyl-3,4,11,11a-tetrahydro-1H-pyrazino[1',2':3,4]imidazo[1,2-c]pyrimidin-9(2H)-one

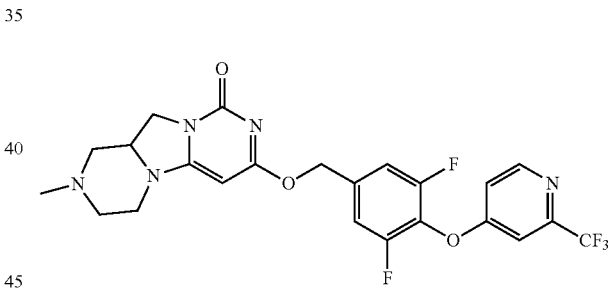

The title compound was prepared by a procedure similar to that described for E141 starting from 7-chloro-2-methyl-3,4,11,11a-tetrahydro-1H-pyrazino[1',2':3,4]imidazo[1,2-c]pyrimidin-9(2H)-one (50 mg, 0.21 mmol) and (3,5-difluoro-4-((2-(trifluoromethyl)pyridin-4-yl)oxy)phenyl)methanol (70 mg, 0.23 mmol) as an off-white solid.

LC-MS (ESI): m/z 510 [M+H]$^+$; 3.05 min (ret time).

$^1$H NMR (300 MHz, CDCl$_3$): δ 8.60 (d, J=5.7 Hz, 1H), 7.25-7.23 (m, 1H), 7.14-7.11 (m, 2H), 7.00-6.97 (m, 1H), 5.47-5.05 (m, 2H), 5.05 (s, 1H), 4.21-4.13 (m, 1H), 4.09-4.00 (m, 1H), 3.77-3.71 (m, 1H), 3.51-3.43 (m, 1H), 3.38-3.28 (m, 1H), 2.95-2.91 (m, 1H), 2.82-2.78 (m, 1H), 2.35 (s, 3H), 2.17-1.98 (m, 2H).

E167

7-((3,5-Difluoro-4-((1-methyl-1H-pyrazol-4-yl)oxy)benzyl)oxy)-2-methyl-3,4,11,11a-tetrahydro-1H-pyrazino[1',2':3,4]imidazo[1,2-c]pyrimidin-9(2H)-one

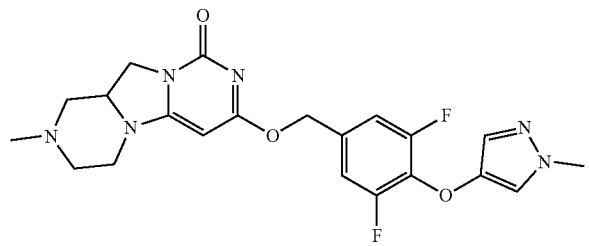

The title compound was prepared by a procedure similar to that described for E141 starting from 7-chloro-2-methyl-3,4,11,11a-tetrahydro-1H-pyrazino[1',2':3,4]imidazo[1,2-c]pyrimidin-9(2H)-one (50 mg, 0.21 mmol) and (3,5-difluoro-4-((1-methyl-1H-pyrazol-4-yl)oxy)phenyl)methanol (55 mg, 0.23 mmol) as a yellow solid.

LC-MS (ESI): m/z 445 [M+H]$^+$; 2.73 min (ret time).

$^1$H NMR (300 MHz, CDCl$_3$): δ 7.25-7.18 (m, 1H), 7.17-7.05 (m, 1H), 7.04-6.97 (m, 2H), 5.39-5.30 (m, 2H), 5.01 (s, 1H), 4.20-4.12 (m, 1H), 4.08-4.00 (m, 1H), 3.81 (s, 3H), 3.79-3.71 (m, 1H), 3.48-3.43 (m, 1H), 3.36-3.26 (m, 1H), 2.94-2.89 (m, 1H), 2.81-2.77 (m, 1H), 2.34 (s, 3H), 2.17-1.97 (m, 2H).

E168

(S)-6-((2,4-difluorobenzyl)oxy)-10,10a-dihydro-1H-oxazolo[3',4':3,4]imidazo[1,2-c] pyrimidin-8(3H)-one

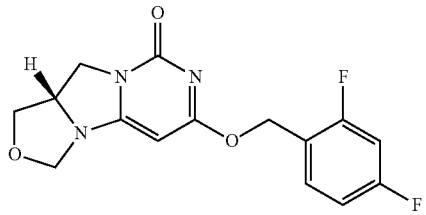 [SMILES: O=c1nc(OCc2ccc(F)cc2F)cc2n1C[C@H]1COCN21]

The title compound was prepared by a procedure similar to that described for E141 starting from (2,4-difluorophenyl)methanol (26 mg, 0.18 mmol) and (S)-6-chloro-10,10a-dihydro-1H-oxazolo[3',4':3,4]imidazo[1,2-c]pyrimidin-8(3H)-one (35 mg, 0.16 mmol) as a white solid.

LC-MS (ESI): m/z 322 [M+H]$^+$; 3.35 min (ret time).

$^1$H NMR (300 MHz, CDCl$_3$): δ 7.46 (d, J=6.6 Hz, 1H), 6.88-6.84 (m, 2H), 5.41 (d, J=3.9 Hz, 2H), 5.31 (s, 1H), 4.95 (d, J=5.7 Hz, 1H), 4.57 (d, J=5.7 Hz, 1H), 4.26-4.15 (m, 3H), 4.12-4.07 (m, 1H), 3.52-3.47 (m, 1H).

E169

(S)-6-((2,3-difluorobenzyl)oxy)-10,10a-dihydro-1H-oxazolo[3',4':3,4]imidazo[1,2-c]pyrimidin-8(3H)-one

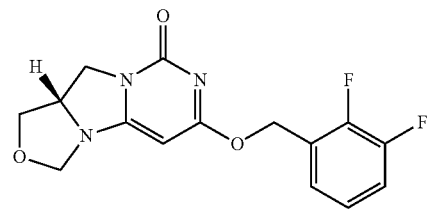 [SMILES: O=c1nc(OCc2cccc(F)c2F)cc2n1C[C@H]1COCN21]

The title compound was prepared by a procedure similar to that described for E141 starting from (2,3-difluorophenyl)methanol (26 mg, 0.18 mmol) and (S)-6-chloro-10,10a-dihydro-1H-oxazolo[3',4':3,4]imidazo[1,2-c]pyrimidin-8(3H)-one (35 mg, 0.16 mmol) as a white solid.

LC-MS (ESI): m/z 322 [M+H]$^+$; 3.36 min (ret time).

$^1$H NMR (300 MHz, CDCl$_3$): 7.26-7.09 (m, 3H), 5.48-5.47 (m, 2H), 5.33 (s, 1H), 4.96 (d, J=5.7 Hz, 1H) 4.57 (d, J=5.7 Hz, 1H), 4.27-4.18 (m, 3H), 4.14-4.07 (m, 1H), 3.52-3.47 (m, 1H).

E170

(R)-6-((4-chloro-3-fluorobenzyl)oxy)-10,10a-dihydro-1H-oxazolo[3',4':3,4]imidazo[1,2-c] pyrimidin-8(3H)-one

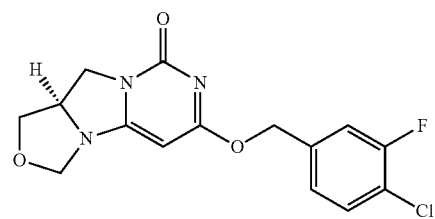 [SMILES: O=c1nc(OCc2ccc(Cl)c(F)c2)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (4-chloro-3-fluorophenyl)methanol (30 mg, 0.19 mmol) as a yellow solid.

LC-MS (ESI): m/z 338 [M+H]$^+$; 3.64 min (ret time).

$^1$H NMR (300 MHz, CDCl$_3$): δ 7.36 (t, J=8.1 Hz, 1H), 7.21-7.09 (m, 2H), 5.34 (t, J=6.3 Hz, 3H), 4.96 (d, J=6.0 Hz, 1H), 4.57 (d, J=6.3 Hz, 1H), 4.26-4.06 (m, 4H), 3.52-3.46 (m, 1H).

E171

(R)-6-((3-fluorobenzyl)oxy)-10,10a-dihydro-1H-oxazolo[3',4':3,4]imidazo[1,2-c]pyrimidin-8(3H)-one

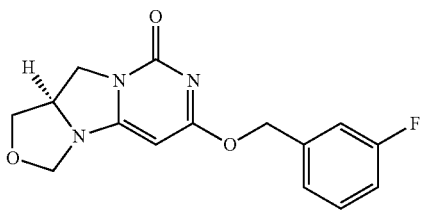 [SMILES: O=c1nc(OCc2cccc(F)c2)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3-fluorophenyl)methanol (24 mg, 0.19 mmol) as a yellow solid.

LC-MS (ESI): m/z 304 [M+H]$^+$; 3.29 min (ret time).

$^1$H NMR (300 MHz, CDCl$_3$): δ 7.33-7.26 (m, 2H), 7.15-7.07 (m, 2H), 7.01-6.95 (m, 1H), 5.41-5.33 (m, 3H), 4.95 (d, J=6.0 Hz, 1H), 4.55 (d, J=5.7 Hz, 1H), 4.27-4.04 (m, 4H), 3.50-3.45 (m, 1H).

E172

(R)-6-((2,3-difluorobenzyl)oxy)-10,10a-dihydro-1H-oxazolo[3',4':3,4]imidazo[1,2-c] pyrimidin-8(3H)-one

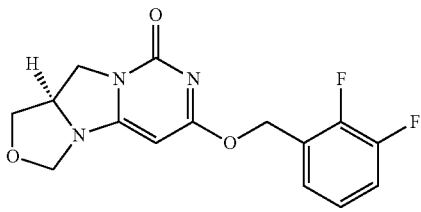 [SMILES: O=c1nc(OCc2cccc(F)c2F)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (2,3-difluorophenyl)methanol (27 mg, 0.19 mmol) as white oil.

LC-MS (ESI): m/z 322 [M+H]$^+$; 3.44 min (ret time).

$^1$H NMR (300 MHz, CDCl$_3$): δ 7.19-7.06 (m, 3H), 5.45 (t, J=1.8 Hz, 2H), 5.31 (s, 1H), 4.94 (d, J=6.3 Hz, 1H), 4.55 (d, J=6.0 Hz, 1H), 4.29-4.05 (m, 4H), 3.51-3.46 (m, 1H).

E173

(S)-6-((2,4,5-trifluorobenzyl)oxy)-10,10a-dihydro-1H-oxazolo[3',4':3,4]imidazo[1,2-c] pyrimidin-8(3H)-one

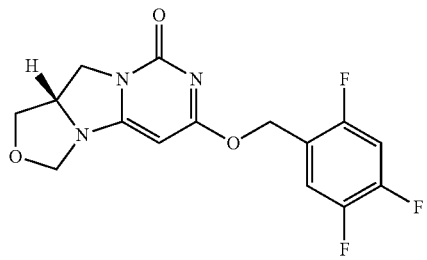 [SMILES: O=c1nc(OCc2cc(F)c(F)cc2F)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (35 mg, 0.16 mmol) and (2,4,5-trifluorophenyl)methanol (29 mg, 0.18 mmol) as a white solid.

LC-MS (ESI): m/z 340 [M+H]$^+$; 3.48 min (ret time).

$^1$H NMR (300 MHz, CDCl$_3$): δ 7.32-7.24 (m, 1H), 6.99-6.90 (m, 1H), 5.41 (s, 2H), 5.33 (s, 1H), 4.97 (d, J=6.0 Hz, 1H), 4.59 (d, J=6.0 Hz, 1H), 4.27-4.08 (m, 4H), 3.53-3.48 (m, 1H).

E174

(R)-6-((2,4-difluorobenzyl)oxy)-10,10a-dihydro-1H-oxazolo[3',4':3,4]imidazo[1,2-c]pyrimidin-8(3H)-one

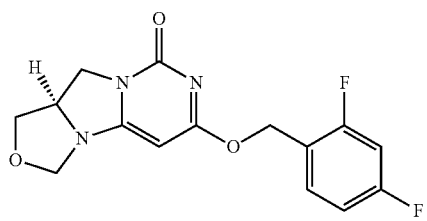 [SMILES: O=c1nc(OCc2ccc(F)cc2F)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (2,4-difluorophenyl)methanol (27 mg, 0.19 mmol) as a white solid.

LC-MS (ESI): m/z 322 [M+H]$^+$; 3.37 min (ret time).

$^1$H NMR (300 MHz, CDCl$_3$): δ 7.45-7.43 (m, 1H), 6.85-6.79 (m, 2H), 5.40 (d, J=2.7 Hz, 2H), 5.30 (s, 1H), 4.94 (d, J=5.7 Hz, 1H), 4.56 (d, J=6.0 Hz, 1H), 4.26-4.06 (m, 4H), 3.51-3.46 (m, 1H).

E175

(R)-6-((2,4,5-trifluorobenzyl)oxy)-10,10a-dihydro-1H-oxazolo[3',4':3,4]imidazo[1,2-c] pyrimidin-8(3H)-one

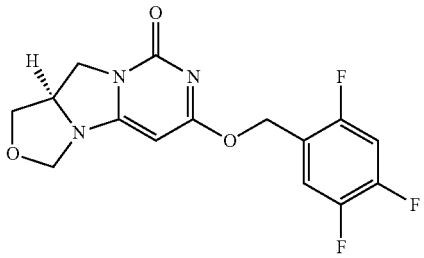 [SMILES: O=c1nc(OCc2cc(F)c(F)cc2F)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (2,4,5-trifluorophenyl)methanol (31 mg, 0.19 mmol) as a white solid.

LC-MS (ESI): m/z 340 [M+H]$^+$; 3.46 min (ret time).

$^1$H NMR (300 MHz, CDCl$_3$): δ 7.34-7.28 (m, 1H), 6.98-6.89 (m, 1H), 5.39 (d, J=1.5 Hz, 2H), 5.32 (s, 1H), 4.96 (d, J=4.8 Hz, 1H), 4.57 (d, J=6.0 Hz, 1H), 4.29-4.07 (m, 4H), 3.53-3.47 (m, 1H).

E176

(R)-6-((3,5-difluorobenzyl)oxy)-10,10a-dihydro-1H-oxazolo[3',4':3,4]imidazo[1,2-c] pyrimidin-8(3H)-one

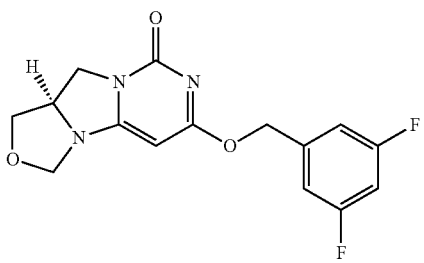 [SMILES: O=c1nc(OCc2cc(F)cc(F)c2)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (40 mg, 0.19 mmol) and (3,5-difluorophenyl)methanol (27 mg, 0.19 mmol) as yellow oil.

LC-MS (ESI): m/z 322 [M+H]$^+$; 3.43 min (ret time).

$^1$H NMR (300 MHz, CDCl$_3$): δ 6.90 (d, J=6.0 Hz, 2H), 6.77-6.70 (m, 1H), 5.41-5.32 (m, 3H), 4.97 (d, J=5.4 Hz, 12H), 4.58 (d, J=6.0 Hz, 1H), 4.31-4.07 (m, 4H), 3.52-3.47 (m, 1H).

E177

(R)-3-((2,4-difluorobenzyl)oxy)-8,9,9a,10-tetrahydropyrimido[6',1':2,3]imidazo[1,5-c][1,3] oxazin-1(6H)-one

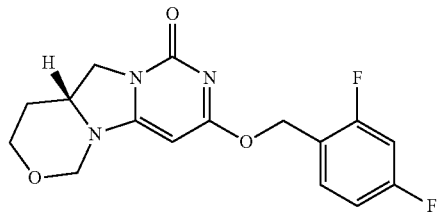 [SMILES: O=c1nc(OCc2ccc(F)cc2F)cc2n1C[C@H]1CCOCN21]

The title compound was prepared by a procedure similar to that described for E141 starting from (R)-3-chloro-8,9,9a,10-tetrahydropyrimido[6',1':2,3]imidazo[1,5-c][1,3] oxazin-1(6H)-one (45 mg, 0.20 mmol) and (2,4-difluorophenyl)methanol (32 mg, 0.22 mmol) as a white solid.

LC-MS (ESI): m/z 336 [M+H]$^+$; 3.40 min (ret time).

$^1$H NMR (300 MHz, CDCl$_3$): δ 7.50-7.42 (m, 1H), 6.90-6.79 (m, 2H), 5.47 (s, 2H), 5.47-5.41 (m, 1H), 5.20 (s, 1H), 4.99 (d, J=11.1 Hz, 1H), 4.61 (d, J=8.7 Hz, 1H), 4.15-4.02 (m, 3H), 4.95 (d, J=11.4 Hz, 1H), 3.80-3.71 (m, 1H), 2.04-1.90 (m, 1H), 1.67-1.53 (m, 1H).

E178

(R)-6-((3-(((2-(trifluoromethyl)pyridin-4-yl)oxy)methyl)bicyclo[1.1.1]pentan-1-yl)methoxy)-10,10a-dihydro-1H-oxazolo[3',4':3,4]imidazo[1,2-c]pyrimidin-8(3H)-one

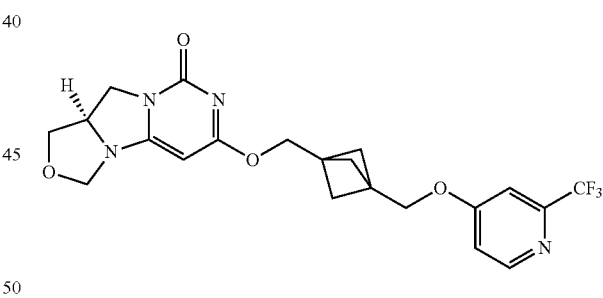

To a solution of (3-(((2-(trifluoromethyl)pyridin-4-yl)oxy)methyl)bicyclo[1.1.1]pentan-1-yl)methanol (15 mg, 0.055 mmol) in dry DMF (2 mL) was added NaH (60% in mineral oil, 5 mg, 0.110 mmol) at 10° C. and the mixture was stirred for 20 min. Then (R)-6-chloro-10,10a-dihydro-1H-oxazolo[3',4':3,4]imidazo[1,2-c]pyrimidin-8(3H)-one (12 mg, 0.055 mmol) was added and the reaction was stirred at room temperature for overnight. The mixture was diluted with ice-water (5 mL), extracted with EA (10 mL×2). The organic phases were dried over Na$_2$SO$_4$, filtered and concentrated. The residue was purified by prep-TLC (DCM/MeOH=20/1) to give the title compound (4 mg, yield 16%) as a white solid.

LC-MS (ESI): m/z 451 [M+H]$^+$; 3.81 min (ret time).

$^1$H NMR (300 MHz, CDCl$_3$): δ 8.52 (d, J=5.7 Hz, 1H), 7.18 (d, J=2.1 Hz, 1H), 6.95-6.92 (m, 1H), 5.31 (s, 1H), 4.98

(d, J=5.7 Hz, 1H), 4.58 (d, J=5.7 Hz, 1H), 4.40 (s, 2H), 4.26-4.17 (m, 3H), 4.09 (s, 3H), 3.52-3.49 (m, 1H), 1.85 (s, 6H).

E179

(S)-6-((3-(((2-(trifluoromethyl)pyridin-4-yl)oxy)methyl)bicyclo[1.1.1]pentan-1-yl)methoxy)-10,10a-dihydro-1H-oxazolo[3',4':3,4]imidazo[1,2-c]pyrimidin-8(3H)-one

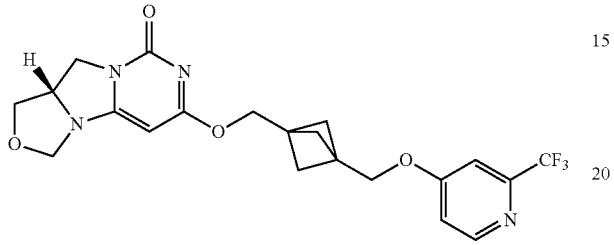

To a solution of (3-(((2-(trifluoromethyl)pyridin-4-yl)oxy)methyl)bicyclo[1.1.1]pentan-1-yl)methanol (15 mg, 0.055 mmol) in dry DMF (2 mL) was added NaH (60% in mineral oil, 5 mg, 0.110 mmol) at 10° C. and the mixture was stirred for 20 min. Then (S)-6-chloro-10,10a-dihydro-1H-oxazolo[3',4':3,4]imidazo[1,2-c]pyrimidin-8(3H)-one (12 mg, 0.055 mmol) was added and the mixture was stirred at room temperature for overnight. The mixture was diluted with ice-water (5 mL) and extracted with EA (10 mL×2). The organic phases were dried over Na$_2$SO$_4$, filtered and concentrated. The residue was purified by prep-TLC (DCM/MeOH=20/1) to give the title compound (7 mg, yield 16%) as a white solid.

LC-MS (ESI): m/z 451 [M+H]$^+$; 3.80 min (ret time).
$^1$H NMR (300 MHz, CDCl$_3$): δ 8.52 (d, J=5.1 Hz, 1H), 7.18 (d, J=2.1 Hz, 1H), 6.95-6.92 (m, 1H), 5.32 (s, 1H), 4.98 (d, J=5.7 Hz, 1H), 4.58 (d, J=5.7 Hz, 1H), 4.40 (s, 2H), 4.26-4.17 (m, 3H), 4.09 (s, 3H), 3.52-3.47 (m, 1H), 1.86 (s, 6H).

E180

(S)-3-((2,4-difluorobenzyl)oxy)-8,9,9a,10-tetrahydropyrimido[6',1':2,3]imidazo[1,5-c][1,3]oxazin-1(6H)-one

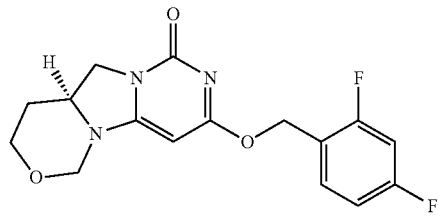 [SMILES: O=c1nc(OCc2ccc(F)cc2F)cc2n1C[C@@H]1CCOCN21]

The title compound was prepared by a procedure similar to that described for E141 starting from (S)-3-chloro-8,9,9a,10-tetrahydropyrimido[6',1':2,3]imidazo[1,5-c][1,3]oxazin-1(6H)-one (50 mg, 0.20 mmol) and (2,4-difluorophenyl)methanol (32 mg, 0.22 mmol) as a white solid.

LC-MS (ESI): m/z 336 [M+H]$^+$; 3.40 min (ret time).
$^1$H NMR (300 MHz, CDCl$_3$): δ 7.49-7.42 (m, 1H), 6.89-6.79 (m, 2H), 5.42 (t, J=3.0 Hz, 2H), 5.20 (s, 1H), 5.01 (d, J=11.1 Hz, 1H), 4.61 (d, J=10.8 Hz, 1H), 4.17-4.02 (m, 3H), 3.96 (t, J=9.9 Hz, 1H), 3.80-3.71 (m, 1H) 1.99-1.92 (m, 1H), 1.67-1.58 (m, 1H).

E181

(S)-3-((2,4,5-trifluorobenzyl)oxy)-8,9,9a,10-tetrahydropyrimido[6',1':2,3]imidazo[1,5-c][1,3]oxazin-1(6H)-one

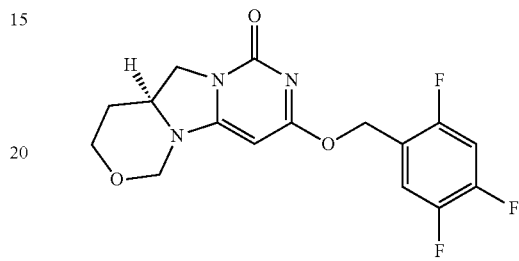

The title compound was prepared by a procedure similar to that described for E141 starting from (S)-3-chloro-8,9,9a,10-tetrahydropyrimido[6',1':2,3]imidazo[1,5-c][1,3]oxazin-1(6H)-one (50 mg, 0.20 mmol) and (2,4,5-trifluorophenyl)methanol (36 mg, 0.22 mmol) as a white solid.

LC-MS (ESI): m/z 354 [M+H]$^+$; 3.58 min (ret time).
$^1$H NMR (300 MHz, CDCl$_3$): δ 7.35-7.29 (m, 1H), 6.98-6.89 (m, 1H), 5.46-5.40 (m, 2H), 5.22 (s, 1H), 5.02 (d, J=11.4 Hz, 1H), 4.63 (d, J=11.4 Hz, 1H), 4.19-4.03 (m, 3H), 3.97-3.92 (m, 1H), 3.81-3.72 (m, 1H), 2.00-1.94 (m, 1H), 1.68-1.63 (m, 1H).

E182

(S)-3-((3,5-difluorobenzyl)oxy)-8,9,9a,10-tetrahydropyrimido[6',1':2,3]imidazo[1,5-c][1,3] oxazin-1(6H)-one

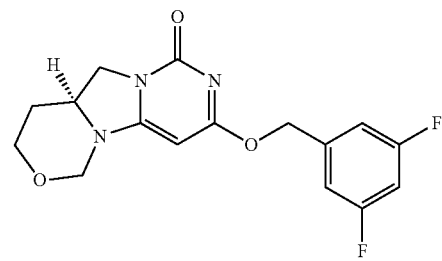 [SMILES: O=c1nc(OCc2cc(F)cc(F)c2)cc2n1C[C@@H]1CCOCN21]

The title compound was prepared by a procedure similar to that described for E141 starting from (S)-3-chloro-8,9,9a,10-tetrahydropyrimido[6',1':2,3]imidazo[1,5-c][1,3]oxazin-1(6H)-one (50 mg, 0.20 mmol) and (3,5-difluorophenyl)methanol (32 mg, 0.22 mmol) as a white solid.

LC-MS (ESI): m/z 336 [M+H]$^+$; 3.55 min (ret time).
$^1$H NMR (300 MHz, CDCl$_3$): δ 6.95-6.91 (m, 2H), 6.78-6.72 (m, 1H), 5.45-5.35 (m, 2H), 5.28 (s, 1H), 5.06 (d, J=11.1 Hz, 1H), 4.65 (d, J=11.7 Hz, 1H), 4.18-4.05 (m, 3H), 3.99-3.95 (m, 1H), 3.83-3.75 (m, 1H), 2.06-1.95 (m, 1H), 1.70-1.65 (m, 1H).

E183

(S)-3-((2,3-difluorobenzyl)oxy)-8,9,9a,10-tetrahydropyrimido[6',1':2,3]imidazo[1,5-c][1,3] oxazin-1(6H)-one

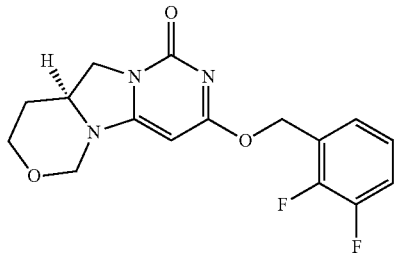 [SMILES: O=c1nc(OCc2cccc(F)c2F)cc2n1C[C@@H]1CCOCN21]

The title compound was prepared by a procedure similar to that described for E141 starting from (S)-3-chloro-8,9,9a,10-tetrahydropyrimido[6',1':2,3]imidazo[1,5-c][1,3]oxazin-1(6H)-one (50 mg, 0.20 mmol) and (2,3-difluorophenyl)methanol (32 mg, 0.22 mmol) as a white solid.

LC-MS (ESI): m/z 336 [M+H]$^+$; 3.46 min (ret time).

$^1$H NMR (300 MHz, CDCl$_3$): δ 7.25-7.19 (m, 1H), 7.15-7.04 (m, 2H), 5.48-5.47 (m, 2H), 5.22 (s, 1H), 5.01 (d, J=11.4 Hz, 1H), 4.61 (d, J=11.4 Hz, 1H), 4.17-4.02 (m, 4H), 3.80-3.72 (m, 1H), 1.98-1.92 (m, 1H), 1.67-1.62 (m, 1H).

E184

6-((3,5-Difluorobenzyl)oxy)-10,10a-dihydro-2H-oxazolo[3',2':3,4]imidazo[1,2-c]pyrimidin-8 (3H)-one

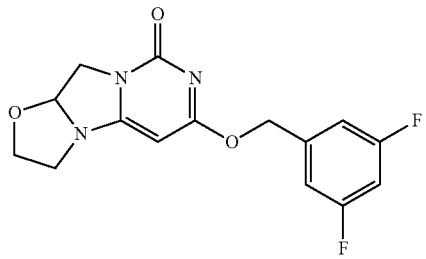 [SMILES: O=c1nc(OCc2cc(F)cc(F)c2)cc2n1CC1OCCN21]

A mixture of 10,10a-dihydro-2H-oxazolo[3',2':3,4]imidazo[1,2-c]pyrimidine-6,8(3H,7H)-dione (195 mg, 1.0 mmol) and Ag$_2$CO$_3$ (688 mg, 2.5 mmol) in toluene (5 mL) was heated to 70° C. 1-(bromomethyl)-3,5-difluorobenzene (288 mg, 1.1 mmol) was then added and the mixture was stirred at 100° C. for overnight. The mixture was cooled to room temperature and filtered. The filtrate was concentrated and purified by prep-TLC (DCM/MeOH=30/1) to give the title compound (80 mg, yield 25%) as a yellow solid.

LC-MS (ESI): m/z 322 [M+H]$^+$; 3.57 min (ret time).

$^1$H NMR (300 MHz, CDCl$_3$): δ 6.94-6.90 (m, 2H), 6.78-6.72 (m, 1H), 5.38 (d, J=3.0 Hz 1H), 5.18 (s, 2H), 5.17 (d, J=4.5 Hz 1H), 4.35-4.30 (s, 1H), 4.16-3.87 (s, 3H), 3.56 (t, J=6.9 Hz 2H).

E185

(R)-6-(3-fluorophenethoxy)-10,10a-dihydro-1H-oxazolo[3',4':3,4]imidazo[1,2-c]pyrimidin-8(3H)-one

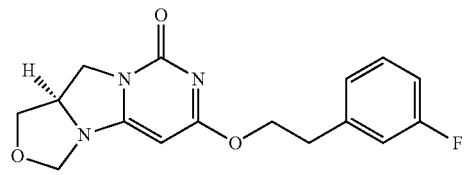 [SMILES: O=c1nc(OCCc2cccc(F)c2)cc2n1C[C@@H]1COCN21]

The title compound was prepared by a procedure similar to that described for E141 starting from (R)-6-chloro-10,10a-dihydro-1H-oxazolo[3',4':3,4]imidazo[1,2-c]pyrimidin-8(3H)-one (50 mg, 0.23 mmol) and 2-(3-fluorophenyl)ethanol (36 mg, 0.26 mmol) as a white solid.

LC-MS (ESI): m/z 318 [M+H]$^+$; 3.54 min (ret time).

$^1$H NMR (300 MHz, CDCl$_3$): δ 7.26-7.24 (m, 1H), 7.02-6.91 (m, 3H), 5.26 (s, 1H), 4.56 (d, J=6.3 Hz, 1H), 4.60-4.55 (m, 3H), 4.24-4.06 (m, 4H), 3.50-3.45 (m, 1H), 3.02 (t, J=6.6 Hz, 2H).

E186

(S)-6-(3-fluorophenethoxy)-10,10a-dihydro-1H-oxazolo[3',4':3,4]imidazo[1,2-c]pyrimidin-8(3H)-one

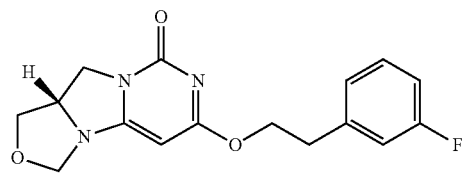 [SMILES: O=c1nc(OCCc2cccc(F)c2)cc2n1C[C@H]1COCN21]

The title compound was prepared by a procedure similar to that described for E141 starting from (S)-6-chloro-10,10a-dihydro-1H-oxazolo[3',4':3,4]imidazo[1,2-c]pyrimidin-8(3H)-one (50 mg, 0.23 mmol) and 2-(3-fluorophenyl)ethanol (36 mg, 0.26 mmol) as a white solid.

LC-MS (ESI): m/z 318 [M+H]$^+$; 3.54 min (ret time).

$^1$H NMR (300 MHz, CDCl$_3$): δ 7.29-7.24 (m, 1H), 7.02-6.91 (m, 3H), 5.26 (s, 1H), 4.95 (d, J=5.7 Hz, 1H), 4.59-4.55 (m, 3H), 4.24-4.08 (m, 4H), 3.50-3.45 (m, 1H), 3.02 (t, J=6.9 Hz, 2H).

E187

6-((2,3-Difluorobenzyl)oxy)-10,10a-dihydro-2H-oxazolo[3',2':3,4]imidazo[1,2-c]pyrimidin-8(3H)-one

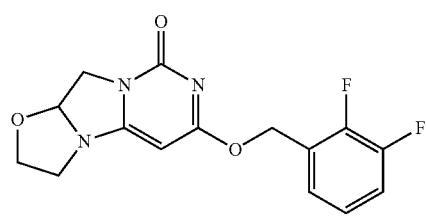 [SMILES: O=c1nc(OCc2cccc(F)c2F)cc2n1CC1OCCN21]

A mixture of 10,10a-dihydro-2H-oxazolo[3',2':3,4]imidazo[1,2-c]pyrimidine-6,8(3H,7H)-dione (195 mg, 1.0 mmol) and Ag₂CO₃ (828 mg, 3.0 mmol) in toluene (10 mL) was heated to 70° C. 1-(Bromomethyl)-2,3-difluorobenzene (621 mg, 3.0 mmol) was then added and the mixture was stirred at 110° C. for 2 days. The mixture was cooled to room temperature, filtered. The filtrate was concentrated and purified by prep-TLC (DCM/MeOH=30/1) to give a white solid, which was further purified by prep-HPLC to give the title compound (40 mg, yield 12%) as a yellow solid.

LC-MS (ESI): m/z 322 [M+H]⁺; 3.49 min (ret time).

¹H NMR (300 MHz, DMSO-d₆): δ7.92-7.23 (m, 3H), 7.68 (s, 1H), 5.42 (s, 2H), 5.19 (d, J=4.5 Hz, 1H), 4.14-3.38 (m, 6H).

E188

6-((3,4,5-Trifluorobenzyl)oxy)-10,10a-dihydro-2H-oxazolo[3',2':3,4]imidazo[1,2-c]pyrimidin-8(3H)-one

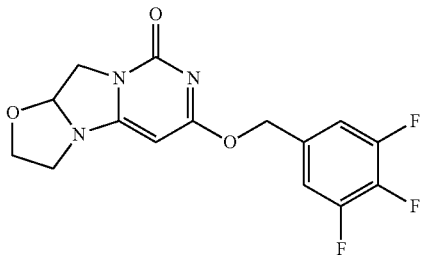 [SMILES: O=c1nc(OCc2cc(F)c(F)c(F)c2)cc2n1CC1OCCN21]

A mixture of 10,10a-dihydro-2H-oxazolo[3',2':3,4]imidazo[1,2-c]pyrimidine-6,8(3H,7H)-dione (195 mg, 1.0 mmol) and Ag₂CO₃ (828 mg, 3.0 mmol) in toluene (10 mL) was heated to 70° C. 5-(Bromomethyl)-1,2,3-trifluorobenzene (675 mg, 3.0 mmol) was added and the mixture was stirred at 110° C. for 2 days. The mixture was cooled to room temperature, and filtered. The filtrate was concentrated and purified by prep-TLC DCM/MeOH=30/1 to give a white solid, which was further purified by prep-HPLC to give the title compound (78 mg, yield 23%) as a white solid.

LC-MS (ESI): m/z 340 [M+H]⁺; 3.68 min (ret time).

¹H NMR (300 MHz, DMSO-d₆): δ7.43-7.39 (m, 2H), 5.70 (s, 1H), 5.27 (s, 2H), 5.19 (d, J=4.2 Hz 1H), 4.14-3.80 (m, 4H), 3.69-3.27 (m, 2H).

E189 and E190

E189: Enantiomer 1: 6-((3,5-difluoro-4-((1-methyl-1H-pyrazol-4-yl)oxy)benzyl)oxy)-10,10a-dihydro-2H-oxazolo[3',2':3,4]imidazo[1,2-c]pyrimidin-8(3H)-one (E189)

E190: Enantiomer 2: 6-((3,5-difluoro-4-((1-methyl-1H-pyrazol-4-yl)oxy)benzyl)oxy)-10,10a-dihydro-2H-oxazolo[3',2':3,4]imidazo[1,2-c]pyrimidin-8(3H)-one (E190)

enantiomer 1

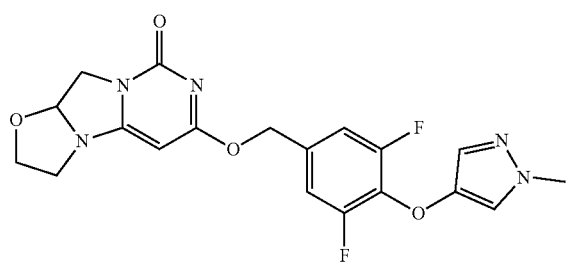

enantiomer 2

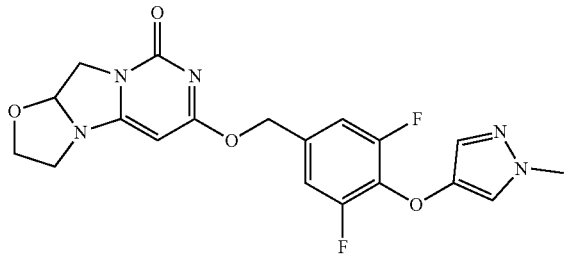

A mixture of 10,10a-dihydro-2H-oxazolo[3',2':3,4]imidazo[1,2-c]pyrimidine-6,8(3H,7H)-dione (120 mg, 0.615 mmol) and Ag₂CO₃ (423 mg, 1.538 mmol) in toluene (5 mL) was heated to 70° C. 4-(4-(Bromomethyl)-2,6-difluorophenoxy)-1-methyl-1H-pyrazole (224 mg, 0.738 mmol) was then added and the mixture was stirred at 110° C. for overnight. The mixture was cooled to room temperature, filtered. The filtrate was concentrated. The residue was purified by prep-HPLC to give a white solid, which was further purified by chiral HPLC to give the title compounds enantiomer 1 (21 mg, yield 8%) as yellow oil and enantiomer 2 (17 mg, yield 8%) as a yellow solid.

Enantiomer 1

LC-MS (ESI): m/z 418 [M+H]⁺; 3.42 min (ret time).

¹H NMR (300 MHz, CD₃OD): δ7.42 (s, 1H), 7.22-7.16 (m, 3H), 5.63 (s, 1H), 5.33 (s, 2H), 5.23-4.87 (m, 1H), 4.16 (s, 2H), 4.16-4.00 (m, 1H), 3.98-3.92 (m, 1H), 3.84 (s, 3H), 3.67-3.64 (m, 1H), 3.66-3.56 (m, 1H).

Enantiomer 2

LC-MS (ESI): m/z 418 [M+H]⁺; 3.42 min (ret time).

¹H NMR (300 MHz, CD₃OD): δ7.42 (s, 1H), 7.22-7.16 (m, 3H), 5.63 (s, 1H), 5.33 (s, 2H), 5.24-5.22 (m, 1H), 4.16 (s, 2H), 4.16-4.00 (m, 1H), 3.98-3.92 (m, 1H), 3.84 (s, 3H), 3.67-3.64 (m, 1H), 3.66-3.56 (m, 1H).

E191

(S)-4-(2-((8-oxo-3,8,10,10a-tetrahydro-1H-oxazolo[3',4':3,4]imidazo[1,2-c]pyrimidin-6-yl)oxy)ethyl)benzonitrile

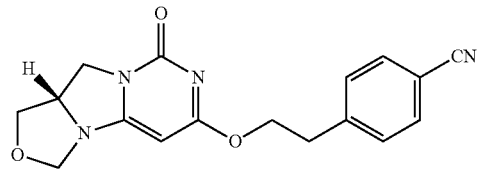 [SMILES: N#Cc1ccc(CCOc2cc3n(c(=O)n2)C[C@H]2COCN32)cc1]

To a solution of (S)-6-(4-bromophenethoxy)-10,10a-dihydro-1H-oxazolo[3',4':3,4]imidazo[1,2-c]pyrimidin-8(3H)-one (40 mg, 0.11 mmol) in DMF (4 mL) was added Zn(CN)₂ (26 mg, 0.22 mmol) and Pd(PPh₃)₄ (10 mg) under N₂. The reaction mixture was stirred at 150° C. in a microwave instrument for 20 min. The reaction mixture was concentrated and purified by prep-HPLC to give the title compound (20 mg, yield 56%) as a white solid.

LC-MS (ESI): m/z 325 [M+H]⁺; 3.24 min (ret time).

¹H NMR (300 MHz, CDCl₃): δ 7.59 (d, J=8.1 Hz, 2H), 7.36-7.26 (m, 2H), 5.23 (s, 1H), 4.95 (d, J=5.4 Hz, 1H), 4.62-4.55 (m, 3H), 4.25-4.06 (m, 4H), 3.51-3.46 (m, 1H), 3.11-3.07 (m, 2H).

E192

(R)-3-(3-fluorophenethyl)-8,9,9a,10-tetrahydropyrimido[6',1':2,3]imidazo[1,5-c][1,3]oxazin-1(6H)-one

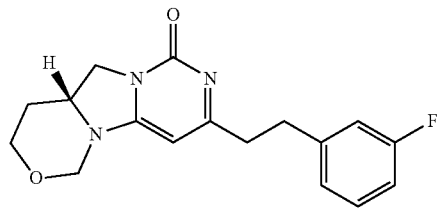 [SMILES: O=c1nc(CCc2cccc(F)c2)cc2n1C[C@H]1CCOCN21]

A solution of (R)-3-((3-fluorophenyl)ethynyl)-8,9,9a,10-tetrahydropyrimido[6',1':2,3]imidazo[1,5-c][1,3]oxazin-1(6H)-one (25 mg, 0.08 mmol) and 10% wet Pd/C (3 mg) in MeOH (3 mL) was stirred for 2 hours at room temperature under H₂ (1 atm). The mixture was filtered and the filtrate was evaporated. The residue was purified by TLC (DCM/MeOH=20/1) to give title compound (17 mg, yield 65%) as a light yellow solid.

LC-MS (ESI): m/z 316 [M+H]⁺; 2.58 min (ret time).
¹H NMR (300 MHz, CDCl₃): δ 7.26-7.19 (m, 1H), 7.00-6.88 (m, 3H), 5.53 (s, 1H), 5.05 (d, J=11.4 Hz, 1H), 4.63 (d, J=11.4 Hz, 1H), 4.18-4.08 (m, 3H), 4.01-3.98 (m, 1H), 3.82-3.73 (m, 1H), 3.07-3.01 (m, 2H), 2.82-2.77 (m, 2H), 1.99-1.89 (m, 2H), 1.70-1.65 (m, 1H).

E193

(R)-6-((3,5-difluoro-4-(1-(2-fluoroethyl)cyclopropoxy)benzyl)oxy)-10,10a-dihydro-1H-oxazolo[3',4':3,4]imidazo[1,2-c]pyrimidin-8(3H)-one

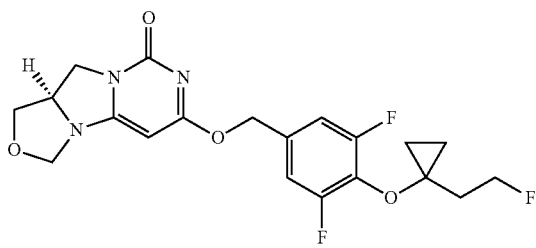 [SMILES: O=c1nc(OCc2cc(F)c(OC3(CCF)CC3)c(F)c2)cc2n1C[C@@H]1COCN21]

The title compound was prepared by a procedure similar to that described for E141 starting from (3,5-difluoro-4-(1-(2-fluoroethyl)cyclopropoxy)phenyl)methanol (40 mg, 0.16 mmol) and (R)-6-chloro-10,10a-dihydro-1H-oxazolo[3',4':3,4]imidazo[1,2-c]pyrimidin-8(3H)-one (34 mg, 0.16 mmol) as a white solid.

LC-MS (ESI): m/z 424 [M+H]⁺; 4.09 min (ret time).
¹H NMR (400 MHz, CDCl₃): δ 6.97-6.92 (m, 2H), 5.34-5.26 (m, 3H), 4.97 (d, J=6.0 Hz, 1H), 4.83 (t, J=6.4 Hz, 1H), 4.71 (t, J=6.4 Hz, 1H), 4.58 (d, J=5.6 Hz, 1H), 4.29-4.07 (m, 4H), 3.52-3.48 (m, 1H), 2.18-2.09 (m, 2H), 1.08 (t, J=6.8 Hz, 2H), 0.67-0.63 (m, 2H).

E194

(R)-6-((9-fluoro-3,4-dihydrospiro[benzo[b][1,4]dioxepine-2,1'-cyclopropan]-7-yl)methoxy)-10,10a-dihydro-1H-oxazolo[3',4':3,4]imidazo[1,2-c]pyrimidin-8(3H)-one

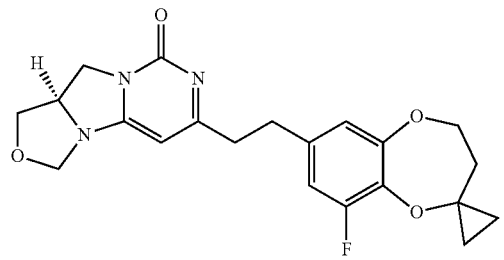 [SMILES: O=c1nc(CCc2cc(F)c3c(c2)OCCC2(CC2)O3)cc2n1C[C@@H]1COCN21]

The title compound was prepared by a procedure similar to that described for E141 starting from (3,5-difluoro-4-(1-(2-fluoroethyl)cyclopropoxy)phenyl)methanol (40 mg, 0.16 mmol) and (R)-6-chloro-10,10a-dihydro-1H-oxazolo[3',4': 3,4]imidazo[1,2-c]pyrimidin-8(3H)-one (34 mg, 0.16 mmol) as yellow oil.

LC-MS (ESI): m/z 402 [M+H]⁺; 3.56 min (ret time).
¹H NMR (300 MHz, CDCl₃): δ 6.84-6.80 (m, 2H), 5.34-5.23 (m, 3H), 4.97 (d, J=5.7 Hz, 1H), 4.59 (d, J=6.0 Hz, 1H), 4.30-4.07 (m, 6H), 3.53-3.48 (m, 1H), 2.21 (t, J=5.1 Hz, 2H), 1.08-1.04 (m, 2H), 0.63-0.53 (m, 2H).

E195

(R)-3-((3,5-difluoro-4-(1-(2-fluoroethyl)cyclopropoxy)benzyl)oxy)-8,9,9a,10-tetrahydropyrimido[6',1':2,3]imidazo[1,5-c][1,3]oxazin-1(6H)-one

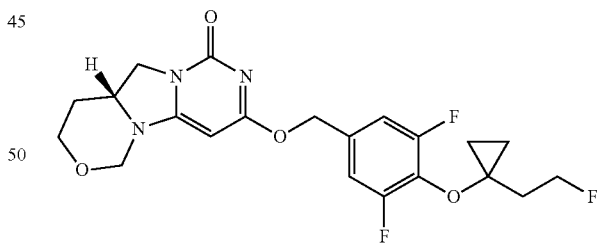

The title compound was prepared by a procedure similar to that described for E141 starting from (3,5-difluoro-4-(1-(2-fluoroethyl)cyclopropoxy)phenyl)methanol (40 mg, 0.16 mmol) and (R)-3-chloro-8,9,9a,10-tetrahydropyrimido[6',1':2,3]imidazo[1,5-c][1,3]oxazin-1(6H)-one (36 mg, 0.16 mmol) as colorless oil.

LC-MS (ESI): m/z 438 [M+H]⁺; 3.14 min (ret time).
¹H NMR (400 MHz, CDCl₃): δ 6.97-6.22 (m, 2H), 5.35-5.29 (m, 2H), 5.22 (s, 1H), 5.04-5.00 (m, 1H), 4.85 (d, J=6.3 Hz, 1H), 4.71-4.60 (m, 2H), 4.16-3.71 (m, 5H), 2.18-2.07 (m, 2H), 1.97-1.92 (m, 1H), 1.68-1.62 (m, 1H), 1.09-1.62 (t, J=6.6 Hz, 2H), 0.66-0.62 (t, J=6.0 Hz, 2H).

E196

(R)-3-((9-fluoro-3,4-dihydrospiro[benzo[b][1,4]dioxepine-2,1'-cyclopropan]-7-yl)methoxy)-8,9,9a,10-tetrahydropyrimido[6',1':2,3]imidazo[1,5-c][1,3]oxazin-1(6H)-one

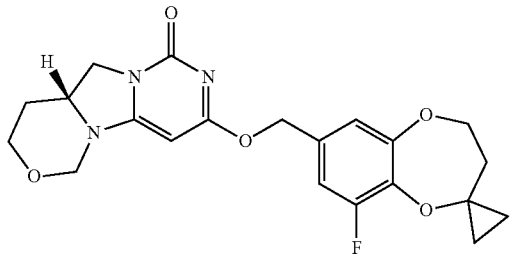 [SMILES: O=c1nc(OCc2cc(F)c3c(c2)OCCC2(CC2)O3)cc2n1C[C@H]1CCOCN21]

The title compound was prepared by a procedure similar to that described for E141 starting from (3,5-difluoro-4-(1-(2-fluoroethyl)cyclopropoxy)phenyl)methanol (40 mg, 0.16 mmol) and (R)-3-chloro-8,9,9a,10-tetrahydropyrimido[6',1':2,3]imidazo[1,5-c][1,3]oxazin-1(6H)-one (36 mg, 0.16 mmol) as colorless oil.

LC-MS (ESI): m/z 416 [M+H]$^+$; 3.03 min (ret time).

$^1$H NMR (400 MHz, CDCl$_3$): δ 6.84-6.79 (m, 2H), 5.32-5.22 (m, 3H), 5.01 (d, J=10.5 Hz, 1H), 4.02 (d, J=11.1 Hz, 1H), 4.26-4.22 (m, 2H), 4.15-3.72 (m, 5H), 2.20 (t, J=5.7 Hz, 2H), 1.98-1.92 (m, 1H), 1.66 (s, 1H), 1.07-1.03 (m, 2H), 0.62-0.57 (m, 2H).

E197

(S)-6-((3,5-difluoro-4-(1-(2-fluoroethyl)cyclopropoxy)benzyl)oxy)-10,10a-dihydro-1H-oxazolo[3',4':3,4]imidazo[1,2-c]pyrimidin-8(3H)-one

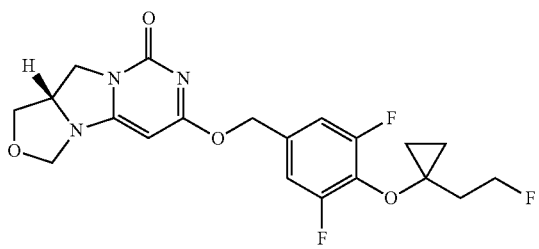 [SMILES: O=c1nc(OCc2cc(F)c(OC3(CCF)CC3)c(F)c2)cc2n1C[C@H]1COCN21]

The title compound was prepared by a procedure similar to that described for E141 starting from (3,5-difluoro-4-(1-(2-fluoroethyl)cyclopropoxy)phenyl)methanol (40 mg, 0.16 mmol) and (S)-6-chloro-10,10a-dihydro-1H-oxazolo[3',4':3,4]imidazo[1,2-c]pyrimidin-8(3H)-one (34 mg, 0.16 mmol) as a white solid.

LC-MS (ESI): m/z 424 [M+H]$^+$; 4.09 min (ret time).

$^1$H NMR (400 MHz, CDCl$_3$): δ 6.93 (d, J=8.4 Hz, 2H), 5.33-5.28 (m, 3H), 4.96 (d, J=5.7 Hz, 1H), 4.84 (t, J=6.3 Hz, 1H), 4.68 (t, J=6.0 Hz, 1H), 4.56 (t, J=5.7 Hz, 1H), 4.29-4.06 (m, 4H), 3.52-3.47 (m, 1H), 2.18-2.06 (m, 2H), 1.06 (t, J=6.6 Hz, 2H), 0.64 (t, J=6.6 Hz, 2H).

E198

(S)-6-((9-fluoro-3,4-dihydrospiro[benzo[b][1,4]dioxepine-2,1'-cyclopropan]-7-yl)methoxy)-10,10a-dihydro-1H-oxazolo[3',4':3,4]imidazo[1,2-c]pyrimidin-8(3H)-one

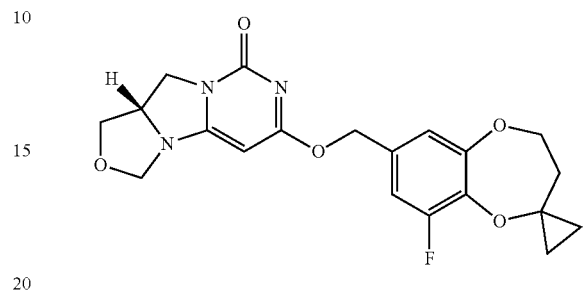

The title compound was prepared by a procedure similar to that described for E141 starting from (3,5-difluoro-4-(1-(2-fluoroethyl)cyclopropoxy)phenyl)methanol (40 mg, 0.16 mmol) and (S)-6-chloro-10,10a-dihydro-1H-oxazolo[3',4':3,4]imidazo[1,2-c]pyrimidin-8(3H)-one (36 mg, 0.16 mmol) as yellow oil.

LC-MS (ESI): m/z 402 [M+H]$^+$; 3.80 min (ret time).

$^1$H NMR (400 MHz, CDCl$_3$): δ 6.87-6.83 (m, 2H), 5.37-5.26 (m, 3H), 4.99 (d, J=5.4 Hz, 1H), 4.61 (d, J=5.7 Hz, 1H), 4.32-4.10 (m, 6H), 3.56-3.51 (m, 1H), 2.24 (t, J=6.0 Hz, 2H), 1.09 (t, J=6.0 Hz, 2H), 0.66-0.61 (m, 2H).

E199

7-((3,5-Difluoro-4-(1-(2-fluoroethyl)cyclopropoxy)benzyl)oxy)-2-methyl-3,4,11,11a-tetrahydro-1H-pyrazino[1',2':3,4]imidazo[1,2-c]pyrimidin-9(2H)-one

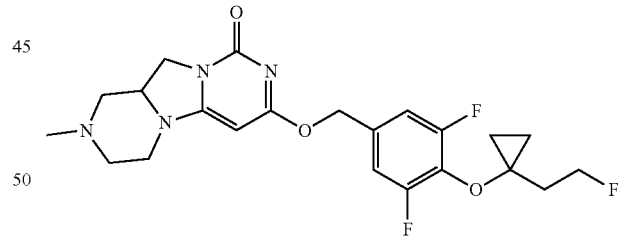

The title compound was prepared by a procedure similar to that described for E141 starting from (3,5-difluoro-4-(1-(2-fluoroethyl)cyclopropoxy)phenyl)methanol (47 mg, 0.19 mmol) and 7-chloro-2-methyl-3,4,11,11a-tetrahydro-1H-pyrazino[1',2':3,4]imidazo[1,2-c]pyrimidin-9(2H)-one (45 mg, 0.19 mmol) as yellow oil.

LC-MS (ESI): m/z 451 [M+H]$^+$; 3.97 min (ret time).

$^1$H NMR (300 MHz, CDCl$_3$): δ 6.93 (d, J=8.4 Hz, 2H), 5.28 (s, 2H), 5.00 (s, 1H), 4.84 (t, J=6.0 Hz, 1H), 4.69 (t, J=6.3 Hz, 1H), 4.17-4.11 (m, 1H), 4.02-4.01 (m, 1H), 3.74-3.68 (m, 1H), 3.46-3.29 (m, 2H), 2.92-2.88 (m, 1H), 2.78-2.74 (m, 1H), 2.32 (s, 3H), 2.18-1.90 (m, 4H), 1.06 (t, J=6.9 Hz, 2H), 0.63 (t, J=6.6 Hz, 2H).

E200

7-((3,5-Difluoro-4-((1-methyl-1H-pyrazol-4-yl)oxy)
benzyl)oxy)-3,4,11,11a tetrahydropyrimido[6',1':2,3]
imidazo[5,1-b][1,3]oxazin-9(2H)-one

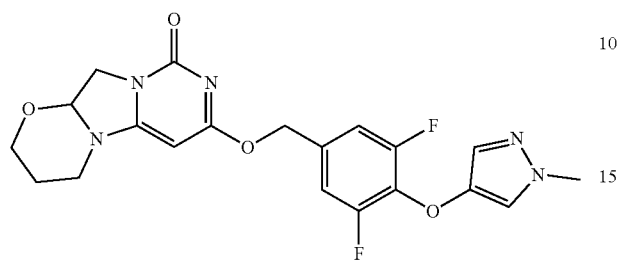

A mixture of 3,4,11,11a-tetrahydropyrimido[6',1':2,3]imidazo[5,1-b][1,3]oxazine-7,9(2H,8H)-dione (80 mg, 0.383 mmol) and Ag$_2$CO$_3$ (263 mg, 0.958 mmol) in toluene (5 mL) was stirred at 70° C. for 40 minutes. 4-(4-(Bromomethyl)-2,6-difluorophenoxy)-1-methyl-1H-pyrazole (128 mg, 0.421 mmol) was then added and the mixture was stirred at 110° C. for overnight. The mixture was filtered, concentrated in vacuo. The residue was purified by prep-TLC (DCM/MeOH=25/1) to give the title compound (56 mg, yield 34%) as a white solid.

LC-MS (ESI): m/z 432 [M+H]$^+$; 3.47 min (ret time).

$^1$H NMR (300 MHz, CD$_3$OD): δ7.33 (s, 1H), 7.13-7.05 (m, 3H), 5.40 (d, J=5.1 Hz, 1H) 5.26 (d, J=1.5 Hz, 3H) 3.99-3.91 (m, 2H), 3.83-3.79 (m, 3H), 3.75-3.66 (m, 3H), 3.52-3.42 (m, 1H), 1.47-1.41 (m, 1H), 1.19 (d, J=5.4 Hz, 1H).

E201

(S)-6-(3-fluorophenethyl)-10,10a-dihydro-1H-oxazolo[3',4':3,4]imidazo[1,2-c]pyrimidin-8(3H)-one

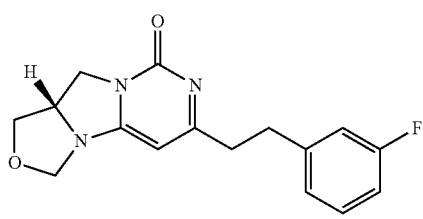 [SMILES: O=c1nc(CCc2cccc(F)c2)cc2n1C[C@H]1COCN21]

A solution of (S)-6-((3-fluorophenyl)ethynyl)-10,10a-dihydro-1H-oxazolo[3',4':3,4]imidazo[1,2-c]pyrimidin-8(3H)-one (30 mg, 0.10 mmol) and 10% wet Pd/C (3 mg) in MeOH (3 mL) was stirred for 2 hrs at room temperature under H$_2$ (1 atm). The mixture was filtered and the filtrate was evaporated. The residue was purified by prep TLC (DCM/MeOH=25/1) to give title compound (25 mg, yield 85%) as a white solid.

LC-MS (ESI): m/z 302 [M+H]$^+$; 2.58 min (ret time).

$^1$H NMR (300 MHz, CDCl$_3$): δ 7.26-7.19 (m, 1H), 7.00-6.86 (m, 3H), 5.59 (s, 1H), 4.93 (d, J=5.7 Hz, 1H), 4.57 (d, J=5.7 Hz, 1H), 4.30-4.20 (m, 3H), 4.13-4.08 (m, 1H), 3.53-3.48 (m, 1H), 3.08-3.02 (m, 2H), 2.86-2.81 (m, 2H).

E202

(S)-6-(2,4-difluorophenethyl)-10,10a-dihydro-1H-oxazolo[3',4':3,4]imidazo[1,2-c]pyrimidin-8(3H)-one

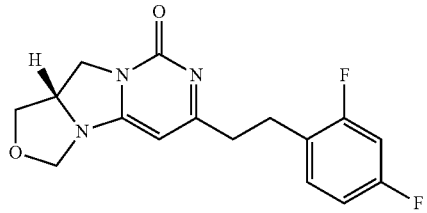 [SMILES: O=c1nc(CCc2ccc(F)cc2F)cc2n1C[C@H]1COCN21]

A solution of (S)-6-((2,4-difluorophenyl)ethynyl)-10,10a-dihydro-1H-oxazolo[3',4':3,4]imidazo[1,2-c]pyrimidin-8 (3H)-one (50 mg, 0.16 mmol) and 10% wet Pd/C (4 mg) in MeOH (5 mL) was stirred for 2 hrs at room temperature under H$_2$ (1 atm). The mixture was filtered and the filtrate was evaporated. The residue was purified by prep HPLC (Column: XB C18, 4.6×33 mm; Mobile phase: A: H$_2$O, B: MeCN, 20-95% B) to give the title compound (30 mg, yield 60%) as a white solid.

LC-MS (ESI): m/z 320 [M+H]$^+$; 3.29 min (ret time).

$^1$H NMR (300 MHz, CDCl$_3$): δ 7.17-7.12 (m, 1H), 6.81-6.74 (m, 2H), 5.62 (s, 1H), 4.95 (d, J=6.0 Hz, 1H), 4.57 (d, J=6.0 Hz, 1H), 4.30-4.23 (m, 3H), 4.13-4.08 (m, 1H), 3.53-3.48 (m, 1H), 3.06-3.01 (m, 2H), 2.84-2.79 (m, 2H).

E203

3-((4-(Methylsulfonyl)benzyl)oxy)-6,7,8,9,9a,10-hexahydro-1H-pyrido[1',2':3,4]imidazo[1,2-c]pyrimidin-1-one

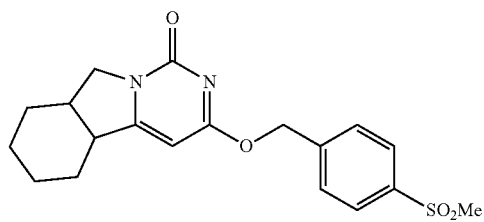 [SMILES: CS(=O)(=O)c1ccc(COc2cc3n(c(=O)n2)CC2CCCCC32)cc1]

The title compound was prepared by a procedure similar to that described for E1 starting from (4-(methylsulfonyl)phenyl)methanol and 3-chloro-6,7,8,9,9a,10-hexahydro-1H-pyrido[1',2':3,4]imidazo[1,2-c]pyrimidin-1-one.

LC-MS (ESI): m/z 376 [M+H]$^+$; 1.78 min (ret time).

E204

3-((4-Fluoro-3-(methylsulfonyl)benzyl)oxy)-6,7,8,9,9a,10-hexahydro-1H0pyrido[1,2':3,4]imidazo-[1,2-c]pyrimidin-1-one

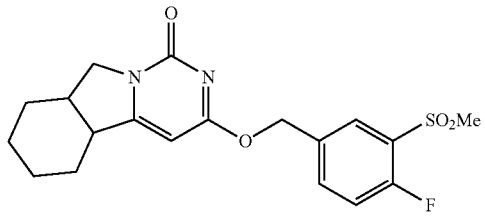 [SMILES: CS(=O)(=O)c1cc(COc2cc3n(c(=O)n2)CC2CCCCC32)ccc1F]

The title compound was prepared by a procedure similar to that described for E1 starting from (4-fluoro-3-(methylsulfonyl)phenyl)methanol and 3-chloro-6,7,8,9,9a,10-hexahydro-1H-pyrido[1',2':3,4]imidazo[1,2-c]pyrimidin-1-one.

LC-MS (ESI): m/z 394 [M+H]$^+$; 1.88 min (ret time).

E205

(S)-3-((4-((3,3-difluoropiperidin-1-yl)methyl)-3-fluorobenzyl)oxy)-6,7,8,9,9a,10-hexahydro-1H-pyrido[1',2':3,4]imidazo[1,2-c]pyrimidin-1-one

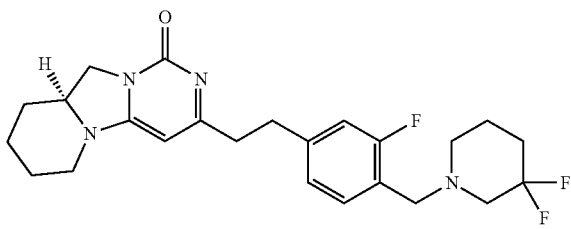 [SMILES: O=c1nc(CCc2ccc(CN3CCCC(F)(F)C3)c(F)c2)cc2n1C[C@@H]1CCCCN21]

The title compound was prepared by a procedure similar to that described for E1 starting from (4-((3,3-difluoropiperidin-1-yl)methyl)-3-fluorophenyl)methanol and (S)-3-chloro-6,7,8,9,9a,10-hexahydro-1H-pyrido[1',2':3,4]imidazo[1,2-c]pyrimidin-1-one.

LC-MS (ESI): m/z 449 [M+H]$^+$; 1.64 min (ret time).
$^1$HNMR (400 MHZ, CD$_3$OD): δ 7.43 (t, 1H), 7.21 (q, 2H), 5.34 (s, 2H), 5.29 (s, 1H), 4.20 (q, 1H), 3.94-3.85 (m, 1H), 3.73-3.69 (m, 1H), 3.69 (s, 2H), 3.62 (q, 1H), 3.06 (dt, 1H), 2.65 (t, 2H), 2.51 (t, 2H), 2.02-1.75 (m, 7H), 1.60-1.49 (m, 3H).

E206

(S)-3-((4-((4,4-difluorocyclohexyl)oxy)-3,5-difluorobenzyl)oxy)-7,8,8a,9-tetrahydropyrrolo[1',2':3,4]imidazo[1,2-c]pyrimidin-1(6H)-one

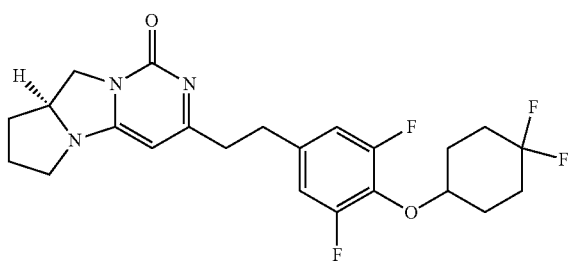 [SMILES: O=c1nc(CCc2cc(F)c(OC3CCC(F)(F)CC3)c(F)c2)cc2n1C[C@@H]1CCCN21]

The title compound was prepared by a procedure similar to that described for E63 starting from (S)-3-chloro-7,8,8a,9-tetrahydropyrrolo[1',2':3,4]imidazo[1,2-c]pyrimidin-1(6H)-one and (4-((4,4-difluorocyclohexyl)oxy)-3,5-difluorophenyl)methanol.

LC-MS (ESI): m/z 454 [M+H]$^+$; 2.92 min (ret time).
$^1$H NMR (400 MHz, DMSO-d$_6$): δ 7.23-7.21 (d, 1H), 5.32 (s, 1H), 5.23-5.18 (q, 2H), 4.38 (s, 1H), 3.4.09-4.00 (m, 2H), 3.87-3.83 (m, 1H), 3.50-3.27 (m, 2H), 2.16-1.76 (m, 11H), 1.48-1.39 (m, 1H).

E207

(S)-3-((4-((1-butylazetidin-3-yl)oxy)-3,5-difluorobenzyl)oxy)-7,8,8a,9-tetrahydropyrrolo[1',2':3,4]imidazo[1,2-c]pyrimidin-1(6H)-one

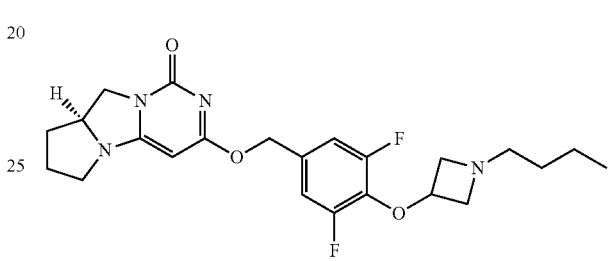

The title compound was prepared by a procedure similar to that described for E63 starting from (S)-3-chloro-7,8,8a,9-tetrahydropyrrolo[1',2':3,4]imidazo[1,2-c]pyrimidin-1(6H)-one and (4-((1-butylazetidin-3-yl)oxy)-3,5-difluorophenyl)methanol.

LC-MS (ESI): m/z 447 [M+H]$^+$; 2.06 min (ret time).
$^1$HNMR (400 MHZ, CD$_3$OD): δ 7.12-7.10 (d, 2H), 5.35-5.24 (m, 3H), 4.79-4.76 (s, 1H), 4.18-4.14 (m, 2H), 4.00-3.96 (m, 1H), 3.73-3.70 (m, 2H), 3.31-3.27 (m, 4H), 2.57-2.53 (s, 2H), 2.15-1.99 (m, 3H), 1.56-1.49 (m, 1H), 1.40-1.31 (m, 4H), 0.87-0.84 (m, 3H).

E208

(S)-3-((3,5-difluoro-4-(3-fluoropropyl)benzyl)oxy)-7,8,8a,9-tetrahydropyrrolo[1,2':3,4]imidazo[1,2-c]pyrimidin-1(6H)-one

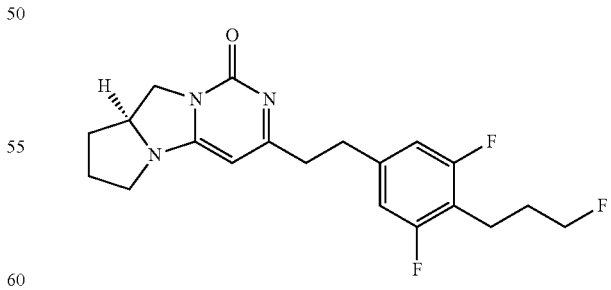

The title compound was prepared by a procedure similar to that described for E63 starting from (S)-3-chloro-7,8,8a,9-tetrahydropyrrolo[1',2':3,4]imidazo[1,2-c]pyrimidin-1(6H)-one and (3,5-difluoro-4-(3-fluoropropyl)phenyl)methanol.

LC-MS (ESI): m/z 380 [M+H]$^+$; 2.61 min (ret time).

¹H NMR (400 MHz, DMSO-d₆): δ 7.13-7.11 (d, 2H), 5.34 (s, 1H), 5.26-5.21 (m, 2H), 4.54-4.39 (m, 2H), 4.04-4.00 (m, 2H), 3.87-3.85 (m, 1H), 3.30-3.28 (m, 2H), 2.74-2.68 (m, 2H), 2.05-1.80 (m, 5H), 1.48-1.38 (m, 1H).

E209

3-((3,5-Difluoro-4-(2-fluoroethoxy)benzyl)oxy)-7,8,8a,9-tetrahydropyrrolo[1,2':3,4]imidazo[1,2-c]pyrimidin-1(6H)-one

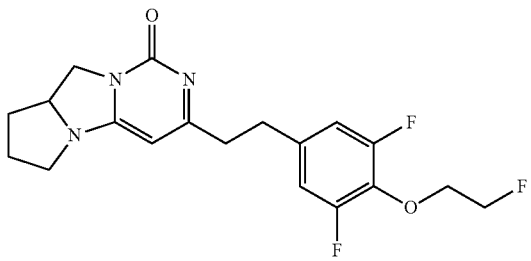

The title compound was prepared by a procedure similar to that described for E63 starting from 3-chloro-7, 8, 8a, 9-tetrahydropyrrolo[1',2':3,4]imidazo[1,2-c]pyrimidin-1(6H)-one and (3,5-difluoro-4-(2-fluoroethoxy)phenyl)methanol.

LC-MS (ESI): m/z 382 [M+H]; 2.48 min (ret time).

E210

(S)-3-((3,5-difluoro-4-(2-fluoroethoxy)benzyl)oxy)-7,8,8a,9-tetrahydropyrrolo[1,2':3,4]imidazo[1,2-c]pyrimidin-1(6H)-one

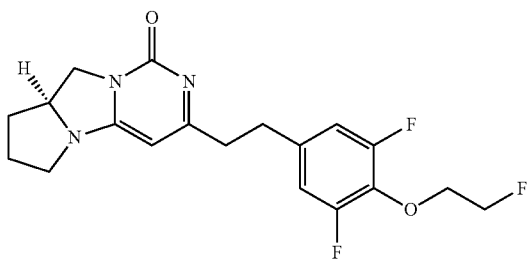 [SMILES: O=c1nc(CCc2cc(F)c(CCCF)c(F)c2)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1(6H)-one and (3,5-difluoro-4-(2-fluoroethoxy)phenyl)methanol.

LC-MS (ESI): m/z 382 [M+H]⁺; 2.48 min (ret time).

E211

(S)-(1-(2,6-dichloropyrimidin-4-yl)pyrrolidin-2-yl)methanol

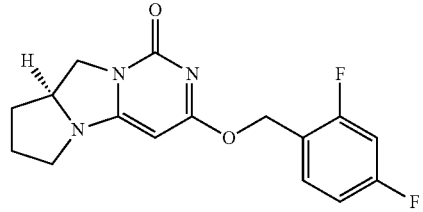 [SMILES: O=c1nc(OCc2ccc(F)cc2F)cc2n1C[C@@H]1CCCN21]

The title compound was prepared by a procedure similar to that described for E63 starting from (R)-3-chloro-7, 8, 8a, 9-tetrahydropyrrolo[1',2':3,4]imidazo[1,2-c]pyrimidin-1(6H)-one and (2,4-difluoro-phenyl)methanol.

LC-MS (ESI): m/z 320 [M+H]⁺; 3.65 min (ret time).

¹H NMR (300 MHz, CDCl₃): δ 7.46 (q, 1H), 6.89-6.78 (m, 2H), 5.40 (q, 2H), 5.08 (s, 1H), 4.21-4.00 (m, 3H), 3.43-3.35 (m, 1H), 3.28-3.20 (m, 1H), 2.18-1.93 (m, 3H), 1.51-1.37 (m, 1H).

E212

(S)-3-((2,3-difluorobenzyl)oxy)-7,8,8a,9-tetrahydropyrrolo[1',2':3,4]imidazo[1,2-c]pyrimidin-1(6H)-one

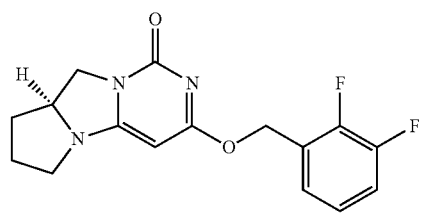 [SMILES: O=c1nc(OCc2cccc(F)c2F)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1(6H)-one and (2,3-difluoro-phenyl)methanol.

LC-MS (ESI): m/z 320 [M+H]⁺; 3.69 min (ret time).

¹H NMR (300 MHz, CDCl₃): δ 7.24-7.02 (m, 3H), 5.51-5.41 (m, 2H), 5.10 (s, 1H), 4.21-4.01 (m, 3H), 3.44-3.36 (m, 1H), 3.29-3.21 (m, 1H), 2.19-1.96 (m, 3H), 1.51-1.41 (m, 1H).

E213

(S)-3-((2,4,5-trifluorobenzyl)oxy)-7,8,8a,9-tetrahydropyrrolo[1,2':3,4]imidazo[1,2-c] pyrimidin-1(6H)-one

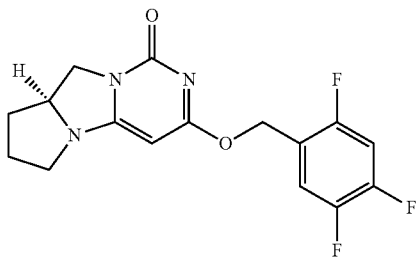 [SMILES: O=c1nc(OCc2cc(F)c(F)cc2F)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1 (6H)-one and (2,4,5-trifluoro-phenyl)methanol.

LC-MS (ESI): m/z 338 [M+H]$^+$; 3.81 min (ret time).

$^1$H NMR (300 MHz, CDCl$_3$): δ 7.35-7.29 (m, 1H), 6.97-6.86 (m, 1H), 5.44-5.30 (m, 2H), 5.10 (s, 1H), 4.21-3.98 (m, 3H), 3.45-3.34 (m, 1H), 3.30-3.20 (m, 1H), 2.19-1.95 (m, 3H), 1.52-1.38 (m, 1H).

E214

(S)-3-((3-fluorobenzyl)oxy)-7,8,8a,9-tetrahydropyrrolo[1,2':3,4]imidazo[1,2-c]pyrimidin-1(6H)-one

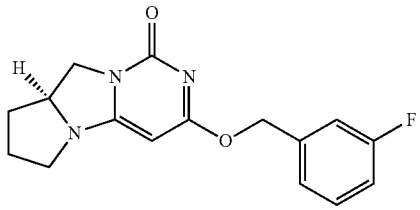 [SMILES: O=c1nc(OCc2cccc(F)c2)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1 (6H)-one and (3-fluorophenyl)methanol.

LC-MS (ESI): m/z 302 [M+H]$^+$; 3.63 min (ret time).

$^1$H NMR (300 MHz, CDCl$_3$): δ 7.35-7.30 (m, 1H), 7.17-7.10 (m, 2H), 7.03-6.96 (m, 1H), 5.44-5.33 (m, 2H), 5.12 (s, 1H), 4.21-4.01 (m, 3H), 3.45-3.37 (m, 1H), 3.30-3.21 (m, 1H), 2.19-1.94 (m, 3H), 1.52-1.38 (m, 1H).

E215

(S)-3-((3,5-difluorobenzyl)oxy)-7,8,8a,9-tetrahydropyrrolo[1',2':3,4]imidazo[1,2-c]pyrimidin-1(6H)-one

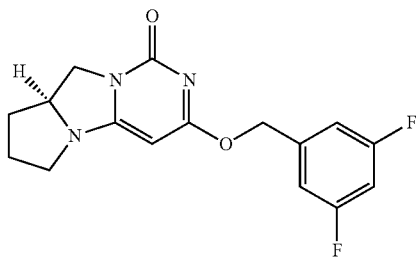 [SMILES: O=c1nc(OCc2cc(F)cc(F)c2)cc2n1C[C@@H]1CCCN21]

The title compound was prepared by a procedure similar to that described for E63 starting from (S)-3-chloro-7, 8, 8a, 9-tetrahydropyrrolo[1',2':3,4]imidazo[1,2-c]pyrimidin-1 (6H)-one and (3,5-difluorophenyl)methanol.

LC-MS (ESI): m/z 320 [M+H]$^+$; 3.78 min (ret time).

$^1$H NMR (300 MHz, CDCl$_3$): δ 6.94-6.89 (m, 2H), 6.77-6.69 (m, 1H), 5.43-5.31 (m, 2H), 5.14 (s, 1H), 4.21-4.02 (m, 3H), 3.46-3.38 (m, 1H), 3.32-3.23 (m, 1H), 2.20-1.95 (m, 3H), 1.53-1.39 (m, 1H).

E216

(R)-3-((2,4-difluorobenzyl)amino)-7,8,8a,9-tetrahydropyrrolo[1,2':3,4]imidazo[1,2-c] pyrimidin-1(6H)-one

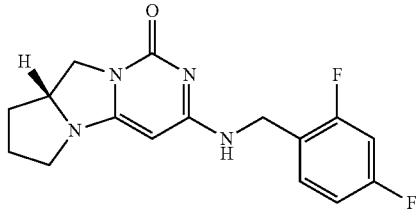 [SMILES: O=c1nc(NCc2ccc(F)cc2F)cc2n1C[C@H]1CCCN21]

The title compound was prepared by a procedure similar to that described for E104 starting from (R)-3-chloro-7, 8, 8a, 9-tetrahydropyrrolo[1',2':3,4]imidazo[1,2-c]pyrimidin-1 (6H)-one and (2,4-difluorophenyl)methanamine.

LC-MS (ESI): m/z 319[M+H]$^+$; 3.21 min (ret time).

$^1$H NMR (300 MHz, CD$_3$OD-d$_4$): δ 7.47-7.41 (m, 1H), 7.00-6.91 (m, 2H), 5.07-5.06 (m, 1H), 4.54-4.51 (m, 2H), 4.18-4.09 (m, 2H), 3.91-3.90 (m, 1H), 3.44-3.41 (m, 1H), 2.17-1.99 (m, 3H), 1.50-1.46 (m, 1H), 0.92-0.85 (m, 1H).

E217

(R)-3-((3,5-difluorobenzyl)amino)-7,8,8a,9-tetrahydropyrrolo[1,2':3,4]imidazo[1,2-c]pyrimidin-1(6H)-one

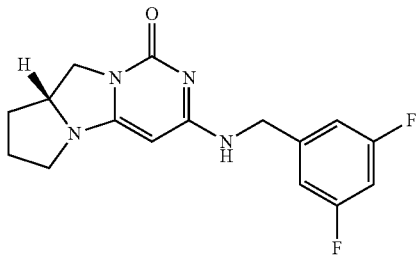 [SMILES: O=c1nc(NCc2cc(F)cc(F)c2)cc2n1C[C@H]1CCCN21]

The title compound was prepared by a procedure similar to that described for E104 starting from (R)-3-chloro-7,8,8a,9-tetrahydropyrrolo[1',2':3,4]imidazo[1,2-c]pyrimidin-1(6H)-one and (3,4-difluorophenyl)methanamine.

LC-MS (ESI): m/z 319 [M+H]$^+$; 3.22 min (ret time).

$^1$H NMR (300 MHz, CDCl$_3$): δ 6.85-6.81 (m, 2H), 6.70-6.64 (m, 1H), 4.73-4.58 (m, 3H), 4.14-4.07 (m, 1H), 4.01-3.96 (m, 2H), 3.39-3.31 (m, 1H), 3.19-3.16 (m, 1H), 2.15-1.94 (m, 3H), 1.45-1.38 (m, 1H).

E218

(R)-3-((2,4,5-trifluorobenzyl)oxy)-7,8,8a,9-tetrahydropyrrolo[1',2':3,4]imidazo[1,2-c]pyrimidin-1(6H)-one

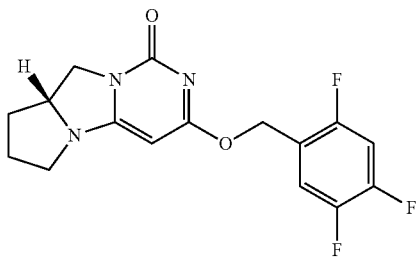 [SMILES: O=c1nc(OCc2cc(F)c(F)cc2F)cc2n1C[C@H]1CCCN21]

The title compound was prepared by a procedure similar to that described for E63 starting from (R)-3-chloro-7,8,8a,9-tetrahydropyrrolo[1',2':3,4]imidazo[1,2-c]pyrimidin-1(6H)-one and (2,4,5-trifluorophenyl)methanol.

LC-MS (ESI): m/z 338[M+H]$^+$; 3.75 min (ret time).

$^1$H NMR (300 MHz, CDCl$_3$): δ 7.35-7.28 (m, 1H), 6.97-6.89 (m, 1H), 5.44-5.33 (m, 2H), 5.10 (s, 1H), 4.21-4.02 (m, 3H), 3.45-3.37 (m, 1H), 3.30-3.21 (m, 1H), 2.18-1.98 (m, 3H), 1.52-1.41 (m, 1H).

E219

(R)-7-((2,4,5-trifluorobenzyl)oxy)-3,4,11,11a-tetrahydropyrimido[6',1':2,3]imidazo[5,1-c][1,4]oxazin-9(1H)-one

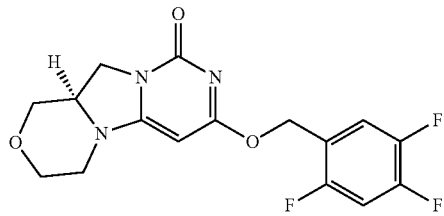 [SMILES: O=c1nc(OCc2cc(F)c(F)cc2F)cc2n1C[C@@H]1COCCN21]

The title compound was prepared by a procedure similar to that described for E63 starting from (R)-7-chloro-1-ethyl-2-(methoxymethyl)-2,3-dihydroimidazo[1,2-c]pyrimidin-5(1H)-one and (2,4,5-trifluorophenyl)methanol.

LC-MS (ESI): m/z 354 [M+H]$^+$; 3.41 min (ret time).

$^1$H NMR (300 MHz, CDCl$_3$): δ 7.35-7.28 (m, 1H), 6.98-6.90 (m, 1H), 5.40 (s, 2H), 5.01 (s, 1H), 4.20-3.91 (m, 4H), 3.71-3.65 (m, 1H), 3.58-3.34 (m, 4H).

E220

(S)-7-((2,4,5-trifluorobenzyl)oxy)-3,4,11,11a-tetrahydropyrimido[6',1':2,3]imidazo[5,1-c][1,4]oxazin-9(1H)-one

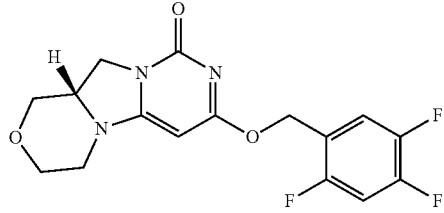 [SMILES: O=c1nc(OCc2cc(F)c(F)cc2F)cc2n1C[C@H]1COCCN21]

The title compound was prepared by a procedure similar to that described for E63 starting from (S)-7-chloro-1-ethyl-2-(methoxymethyl)-2,3-dihydroimidazo[1,2-c]pyrimidin-5(1H)-one and (2,4,5-trifluorophenyl)methanol.

LC-MS (ESI): m/z 354 [M+H]$^+$; 3.41 min (ret time).

$^1$H NMR (300 MHz, CDCl$_3$): δ 7.35-7.28 (m, 1H), 6.97-6.89 (m, 1H), 5.39 (t, J=13.2 Hz, 2H), 5.01 (s, 1H), 4.19-3.91 (m, 4H), 3.70-3.65 (m, 1H), 3.58-3.33 (m, 4H).

E221

(R)-7-((2,3-difluorobenzyl)oxy)-3,4,11,11a-tetrahydropyrimido[6',1':2,3]imidazo[5,1-c][1,4]oxazin-9(1H)-one

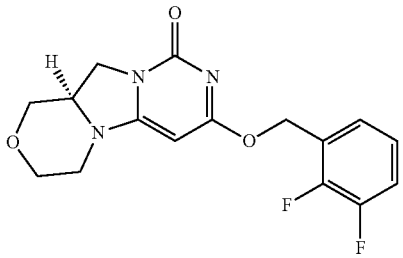 [SMILES: O=c1nc(OCc2cccc(F)c2F)cc2n1C[C@@H]1COCCN21]

The title compound was prepared by a procedure similar to that described for E63 starting from (R)-7-chloro-1-ethyl-2-(methoxymethyl)-2,3-dihydroimidazo[1,2-c]pyrimidin-5(1H)-one and (2,4, difluorophenyl)methanol.

LC-MS (ESI): m/z 336 [M+H]$^+$; 3.32 min (ret time).

$^1$H NMR (300 MHz, CDCl$_3$): δ 7.25-7.03 (m, 3H), 5.47 (t, J=12.6 Hz, 2H), 5.01 (s, 1H), 4.19-3.89 (m, 4H), 3.70-3.64 (m, 1H), 3.58-3.32 (m, 4H).

E222

(R)-3-((3,5-difluorobenzyl)(methyl)amino)-7,8,8a,9-tetrahydropyrrolo[1,2':3,4]imidazo[1,2-c]pyrimidin-1(6H)-one

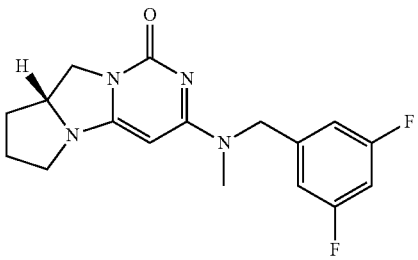 [SMILES: CN(Cc1cc(F)cc(F)c1)c1cc2n(c(=O)n1)C[C@H]1CCCN21]

To a solution of (R)-3-((3,5-difluorobenzyl)amino)-7,8,8a,9-tetrahydropyrrolo[1',2':3,4] imidazo[1,2-c] pyrimidin-1 (6H)-one (47 mg, 0.15 mmol) and potassium carbonate (61 mg, 0.44 mmol) in N, N-dimethylformamide (2 mL) was added iodomethane (42 mg, 0.30 mmol) at room temperature. The reaction mixture was stirred at room temperature for 2 days. The reaction mixture was poured into water (10 mL), extracted with EA (20 mL) twice. The combined organic layers was washed with water, brine and dried over anhydrous sodium sulfate, concentrated under reduced pressure and purified by prep-TLC (DCM/MeOH=15/1) to give the title compound (40 mg, yield 82%) as a white solid.

LC-MS (ESI): m/z 333 [M+H]$^+$; 2.96 min (ret time).

$^1$H NMR (300 MHz, CDCl$_3$): δ 7.02-7.00 (m, 2H), 6.72-6.66 (m, 1H), 4.88 (s, 1H), 4.73 (s, 2H), 4.30-4.19 (m, 2H), 3.99-3.96 (m, 1H), 3.80 (s, 3H), 3.51-3.44 (m, 1H), 3.28-3.24 (m, 1H), 2.28-2.08 (m, 3H), 1.57-1.51 (m, 1H).

E223

(R)-3-((2,4-difluorobenzyl)(methyl)amino)-7,8,8a,9-tetrahydropyrrolo[1,2':3,4]imidazo[1,2-c]pyrimidin-1(6H)-one

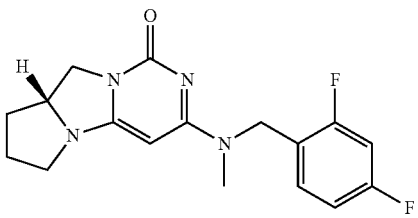 [SMILES: CN(Cc1ccc(F)cc1F)c1cc2n(c(=O)n1)C[C@H]1CCCN21]

The title compound was prepared by a procedure similar to that described for E222 starting from (R)-3-((2,4-difluorobenzyl)amino)-7,8,8a,9-tetrahydropyrrolo[1',2':3,4]imidazo[1,2-c]pyrimidin-1-(6H)-one and iodomethane.

LC-MS (ESI): m/z 333 [M+H]$^+$; 2.88 min (ret time).

$^1$H NMR (300 MHz, CDCl$_3$): δ 7.58-7.56 (m, 1H), 6.87-6.76 (m, 2H), 4.77 (s, 1H), 4.34 (s, 2H), 4.07-4.04 (m, 1H), 3.97-3.84 (m, 2H), 3.39-3.33 (m, 4H), 3.23-3.20 (m, 1H), 2.13-1.97 (m, 3H), 1.40-1.25 (m, 1H).

E224

(S)-3-(3-fluorophenethyl)-7,8,8a,9-tetrahydropyrrolo[1,2':3,4]imidazo[1,2-c]pyrimidin-1(6H)-one

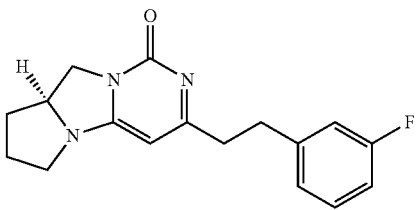 [SMILES: O=c1nc(CCc2cccc(F)c2)cc2n1C[C@@H]1CCCN21]

To a solution of (S)-3-((3-fluorophenyl)ethynyl)-7,8,8a, 9-tetrahydropyrrolo[1',2':3,4]imidazo[1,2-c]pyrimidin-1 (6H)-one (30 mg, 0.10 mmol) in methanol (5 mL) was added 10% Pd/C (3 mg). The reaction mixture was stirred at room temperature overnight under hydrogen and then filtered. The filtrate was evaporated under reduced pressure and purified by TLC (MeOH/DCM=1/30) to give the title compound (22 mg, 73%) as a yellow oil.

LC-MS (ESI): m/z 300 [M+H]$^+$; 3.32 min (ret time).

$^1$H NMR (300 MHz, CDCl$_3$): δ 7.23-7.18 (m, 1H), 7.00-6.84 (m, 3H), 5.40 (s, 1H), 4.22-4.06 (m, 3H), 3.41-3.36 (m, 1H), 3.29-3.23 (m, 1H), 3.07-3.01 (m, 2H), 2.81-2.76 (m, 2H), 2.19-1.99 (m, 2H), 1.51-1.47 (m, 1H).

E225

(R)-3-((2,4,5-trifluorobenzyl)oxy)-6,7,8,9,9a,10-hexahydro-1H-pyrido[1',2':3,4]imidazo[1,2-c]pyrimidin-1-one

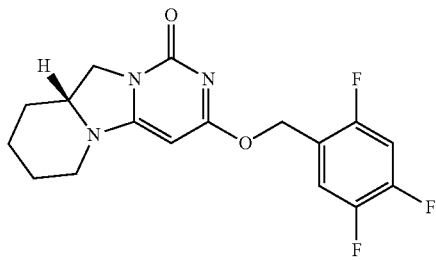 [SMILES: O=c1nc(OCc2cc(F)c(F)cc2F)cc2n1C[C@H]1CCCCN21]

The title compound was prepared by a procedure similar to that described for E1 starting from (2,4,5-trifluorophenyl)methanol and (R)-3-chloro-6,7,8,9,9a,10-hexahydro-1H-pyrido[1',2':3,4]imidazo[1,2-c]pyrimidin-1-one.

LC-MS (ESI): m/z 352 [M+H]$^+$; 4.00 min (ret time).

$^1$H NMR (300 MHz, CDCl$_3$): δ 7.34-7.28 (m, 1H), 6.96-6.90 (m, 1H), 5.39 (s, 2H), 4.97 (s, 1H), 4.24-4.19 (m, 1H), 3.79-3.76 (m, 1H), 3.69-3.65 (m, 1H), 3.55-3.51 (m, 1H), 3.00 (t, J=6.9 Hz, 1H), 1.96 (t, J=4.5 Hz, 2H), 1.76 (t, J=4.8 Hz, 1H), 1.59-1.47 (m, 3H).

E226

(S)-3-((2,4,5-trifluorobenzyl)amino)-7,8,8a,9-tetrahydropyrrolo[1',2':3,4]imidazo[1,2-c]pyrimidin-1(6H)-one

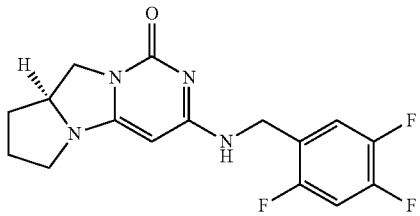 [SMILES: O=c1nc(NCc2cc(F)c(F)cc2F)cc2n1C[C@@H]1CCCN21]

The title compound was prepared by a procedure similar to that described for E104 starting from (S)-3-chloro-7,8,8a,9-tetrahydropyrrolo[1',2':3,4]imidazo[1,2-c]pyrimidin-1(6H)-one and (2,4,5-trifluorophenyl)methanamine.

LC-MS (ESI): m/z 337 [M+H]$^+$; 3.35 min (ret time).

$^1$H NMR (300 MHz, CD$_3$OD-d$_4$): δ 7.38-7.28 (m, 1H), 7.18-7.09 (m, 1H), 5.07 (s, 1H), 4.60-4.46 (m, 2H), 4.11-4.01 (m, 2H), 3.93-3.85 (m, 1H), 3.43-3.35 (m, 1H), 3.32-3.22 (m, 1H), 2.14-1.90 (m, 3H), 1.51-1.37 (m, 1H).

E227

(S)-3-((3,5-difluorobenzyl)amino)-7,8,8a,9-tetrahydropyrrolo[1',2':3,4]imidazo[1,2-c]pyrimidin-1(6H)-one

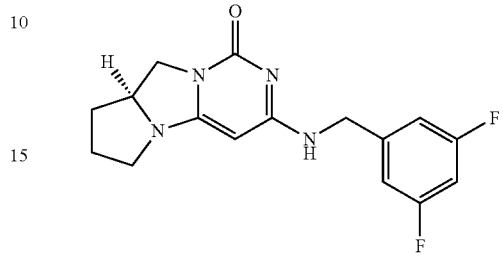

The title compound was prepared by a procedure similar to that described for E104 starting from (S)-3-chloro-7,8,8a,9-tetrahydropyrrolo[1',2':3,4]imidazo[1,2-c]pyrimidin-1(6H)-one and (3,5-difluorophenyl)methanamine.

LC-MS (ESI): m/z 319 [M+H]$^+$; 3.31 min (ret time).

$^1$H NMR (300 MHz, CDCl$_3$): δ 6.85 (d, 2H), 6.70-6.63 (m, 1H), 4.74-4.59 (m, 3H), 4.13-4.06 (m, 1H), 4.02-3.94 (m, 2H), 3.38-3.30 (m, 1H), 3.22-3.12 (m, 1H), 2.14-1.84 (m, 3H), 1.48-1.34 (m, 1H).

E228

(S)-3-((2,3-difluorobenzyl)amino)-7,8,8a,9-tetrahydropyrrolo[1',2':3,4]imidazo[1,2-c]pyrimidin-1(6H)-one

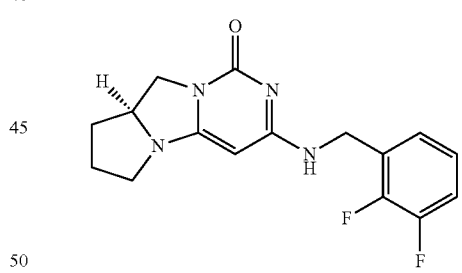

The title compound was prepared by a procedure similar to that described for E104 starting from (S)-3-chloro-7,8,8a,9-tetrahydropyrrolo[1',2':3,4]imidazo[1,2-c]pyrimidin-1(6H)-one and (2,3-difluorophenyl)methanamine.

LC-MS (ESI): m/z 319 [M+H]$^+$; 3.28 min (ret time).

$^1$H NMR (300 MHz, CDCl$_3$): δ 7.21-7.17 (m, 1H), 7.11-6.99 (m, 2H), 4.77-4.61 (m, 3H), 4.15-4.07 (m, 1H), 4.01-3.93 (m, 2H), 3.39-3.33 (m, 1H), 3.23-3.14 (m, 1H), 2.17-1.90 (m, 3H), 1.47-1.34 (m, 1H).

E229

(S)-3-((3,4,5-trifluorobenzyl)amino)-7,8,8a,9-tetrahydropyrrolo[1',2':3,4]imidazo[1,2-c] pyrimidin-1(6H)-one

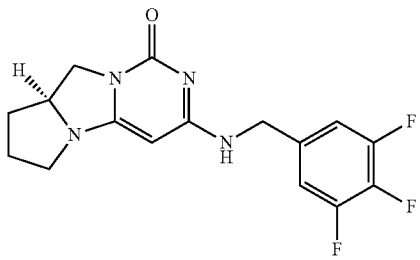 [SMILES: O=c1nc(NCc2cc(F)c(F)c(F)c2)cc2n1C[C@@H]1CCCN21]

The title compound was prepared by a procedure similar to that described for E104 starting from (S)-3-chloro-7, 8, 8a, 9-tetrahydropyrrolo[1', 2':3, 4]imidazo[1, 2-c]pyrimidin-1(6H)-one and (3,4,5-trifluorophenyl)methanamine.

LC-MS (ESI): m/z 337 [M+H]$^+$; 3.42 min (ret time).

$^1$H NMR (300 MHz, CD$_3$OD-d$_4$): 6.95 (t, J=7.5 Hz, 2H), 4.74-4.48 (m, 3H), 4.12-3.91 (m, 3H), 3.38-3.30 (m, 1H), 3.20-3.12 (m, 1H), 2.13-1.80 (m, 3H), 1.48-1.34 (m, 1H).

E230

(S)-3-((3-fluorobenzyl)amino)-7,8,8a,9-tetrahydropyrrolo[1,2':3,4]imidazo[1,2-c]pyrimidin-1(6H)-one

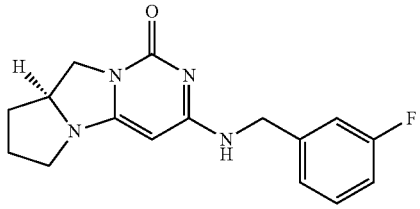

The title compound was prepared by a procedure similar to that described for E104 starting from (S)-3-chloro-7, 8, 8a, 9-tetrahydropyrrolo[1', 2':3, 4]imidazo[1, 2-c]pyrimidin-1(6H)-one and (3-fluorophenyl)methanamine.

LC-MS (ESI): m/z 301 [M+H]$^+$; 2.72 min (ret time).

$^1$H NMR (300 MHz, CDCl$_3$): δ 7.31-7.24 (m, 1H), 7.11-6.99 (m, 2H), 6.96-6.91 (m, 1H), 4.76-4.67 (m, 1H), 4.60-4.50 (m, 2H), 4.13-4.05 (m, 1H), 4.04-3.92 (m, 2H), 3.37-3.29 (m, 1H), 3.21-3.12 (m, 1H), 2.17-1.80 (m, 3H), 1.47-1.26 (m, 1H).

E231

(S)-3-((2,4-difluorobenzyl)amino)-7,8,8a,9-tetrahydropyrrolo[1',2':3,4]imidazo[1,2-c] pyrimidin-1(6H)-one

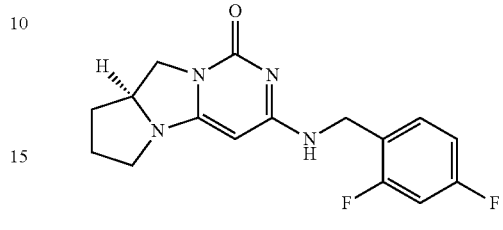

The title compound was prepared by a procedure similar to that described for E104 starting from (S)-3-chloro-7, 8, 8a, 9-tetrahydropyrrolo[1', 2':3, 4]imidazo[1, 2-c]pyrimidin-1(6H)-one and (2,4-difluorophenyl)methanamine.

LC-MS (ESI): m/z 319 [M+H]$^+$; 3.28 min (ret time).

$^1$H NMR (300 MHz, CDCl$_3$): δ 7.47-7.39 (m, 1H), 6.85-6.75 (m, 2H), 4.78 (s, 1H), 4.67-4.52 (m, 2H), 4.14-4.05 (m, 1H), 4.02-3.92 (m, 2H), 3.38-3.31 (m, 1H), 3.23-3.14 (m, 1H), 2.17-1.80 (m, 3H), 1.47-1.33 (m, 1H).

E232

(S)-3-((2,4-difluorobenzyl)amino)-6,7,8,9,9a,10-hexahydro-1H-pyrido[1',2':3,4]imidazo[1,2-c]pyrimidin-1-one

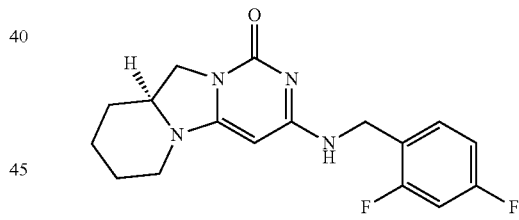

To a solution of (S)-3-chloro-6,7,8,9,9a,10-hexahydro-1H-pyrido[1',2':3,4]imidazo[1,2-c]pyrimidin-1-one (100 mg, 0.44 mmol) and (2,4-difluorophenyl)methanamine (95 mg, 0.66 mmol) in 1,4-dioxane (2 mL) was added DIEA (568 mg, 4.40 mmol) at room temperature. The reaction mixture was stirred at 100° C. overnight, concentrated under reduced pressure and purified with prep-HPLC to give the title compound (92 mg, 63%) as a yellow solid.

LC-MS (ESI): m/z 333 [M+H]$^+$; 2.94 min (ret time).

$^1$H NMR (300 MHz, CDCl$_3$): δ 7.45-7.38 (m, 1H), 6.86-6.75 (m, 2H), 4.63-4.51 (m, 3H), 4.18-4.12 (m, 1H), 3.70-3.55 (m, 2H), 3.49-3.45 (m, 1H), 2.97-2.88 (m, 1H), 2.03-1.63 (m, 3H), 1.57-1.35 (m, 3H).

E233

(S)-3-((3-fluorobenzyl)amino)-6,7,8,9,9a,10-hexahydro-1H pyrido[1',2':3,4]imidazo[1,2-c] pyrimidin-1-one

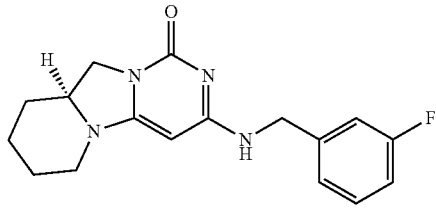 [SMILES: O=c1nc(NCc2cccc(F)c2)cc2n1C[C@@H]1CCCCN21]

The title compound was prepared by a procedure similar to that described for E232 starting from (3-fluorophenyl)methanamine and (S)-3-chloro-6,7,8,9,9a,10-hexahydro-1H-pyrido[1',2':3,4]imidazo[1,2-c]pyrimidin-1-one.

LC-MS (ESI): m/z 315 [M+H]+; 2.86 min (ret time).

1H NMR (300 MHz, CDCl3): δ 7.29-7.22 (m, 1H), 7.09-6.88 (m, 3H), 4.58 (d, J=10.8 Hz, 3H), 4.15-4.09 (m, 1H), 3.67-3.41 (m, 3H), 2.94-2.85 (m, 1H), 2.00-1.66 (m, 3H), 1.52-1.38 (m, 3H).

E234

(S)-3-((3,5-difluorobenzyl)amino)-6,7,8,9,9a,10-hexahydro-1H-pyrido[1',2':3,4]imidazo[1,2-c]pyrimidin-1-one

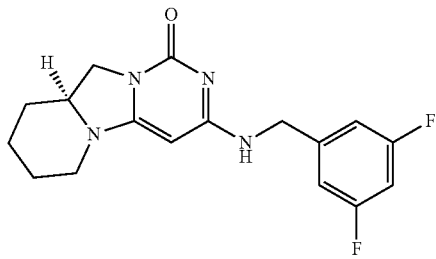 [SMILES: O=c1nc(NCc2cc(F)cc(F)c2)cc2n1C[C@@H]1CCCCN21]

The title compound was prepared by a procedure similar to that described for E232 starting from (3,5-difluorophenyl)methanamine and (S)-3-chloro-6,7,8,9,9a,10-hexahydro-1H-pyrido[1',2':3,4]imidazo[1,2-c]pyrimidin-1-one.

LC-MS (ESI): m/z 333 [M+H]+; 2.96 min (ret time).

1H NMR (300 MHz, CDCl3): δ 6.87-6.81 (m, 2H), 6.70-6.63 (m, 1H), 4.56 (d, J=13.2 Hz, 3H), 4.18-4.12 (m, 1H), 3.74-3.55 (m, 2H), 3.49-3.43 (m, 1H), 3.00-2.88 (m, 1H), 1.96-1.87 (m, 2H), 1.70-1.67 (m, 1H), 1.55-1.39 (m, 3H).

E235

(R)-3-((2,4,5-trifluorobenzyl)amino)-7,8,8a,9-tetrahydropyrrolo[1',2':3,4]imidazo[1,2-c] pyrimidin-1(6H)-one

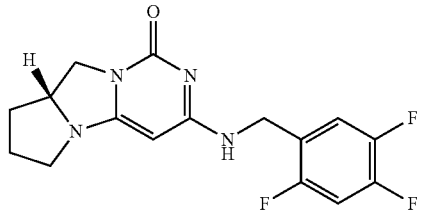 [SMILES: O=c1nc(NCc2cc(F)c(F)cc2F)cc2n1C[C@H]1CCCN21]

The title compound was prepared by a procedure similar to that described for E232 starting from (R)-3-chloro-7,8,8a,9-tetrahydropyrrolo[1',2':3,4]imidazo[1,2-c]pyrimidin-1(6H)-one and (2,4,5-trifluorophenyl)methanamine.

LC-MS (ESI): m/z 337 [M+H]+; 2.83 min (ret time).

1H NMR (300 MHz, CDCl3): δ 7.35-7.29 (m, 1H), 6.93-6.84 (m, 1H), 4.76 (s, 1H), 4.58 (br s, 2H), 4.14-4.07 (m, 1H), 4.03-3.95 (m, 2H), 3.39-3.31 (m, 1H), 3.22-3.14 (m, 1H), 2.14-1.94 (m, 3H), 1.48-1.39 (m, 1H).

E236

(R)-3-((3,4,5-trifluorobenzyl)amino)-7,8,8a,9-tetrahydropyrrolo[1',2':3,4]imidazo[1,2-c]pyrimidin-1(6H)-one The title compound was prepared by a procedure similar to that described for E104 starting from (R)-3-chloro-7,8,8a,9-tetrahydropyrrolo[1',2':3,4]imidazo[1,2-c]pyrimidin-1(6H)-one and (3,4,5-trifluorophenyl)methanamine.

LC-MS (ESI): m/z 337 [M+H]+; 3.46 min (ret time).

1H NMR (300 MHz, CDCl3): δ 7.01-6.93 (m, 2H), 4.70-4.54 (m, 3H), 4.11-3.91 (m, 3H), 3.37-3.30 (m, 1H), 3.20-3.11 (m, 1H), 2.13-1.86 (m, 3H), 1.47-1.34 (m, 1H).

E237

(R)-3-((2,3-difluorobenzyl)amino)-7,8,8a,9-tetrahydropyrrolo[1',2':3,4]imidazo[1,2-c] pyrimidin-1(6H)-one

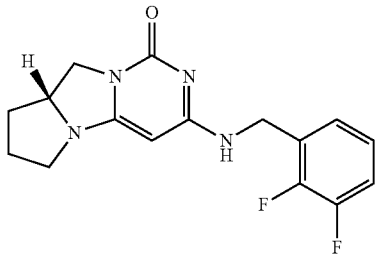 [SMILES: O=c1nc(NCc2cccc(F)c2F)cc2n1C[C@H]1CCCN21]

The title compound was prepared by a procedure similar to that described for E104 starting from (R)-3-chloro-7,8,8a,9-tetrahydropyrrolo[1',2':3,4]imidazo[1,2-c]pyrimidin-1(6H)-one and (2,3-difluorophenyl)methanamine.

LC-MS (ESI): m/z 319 [M+H]$^+$; 3.34 min (ret time).

$^1$H NMR (300 MHz, CDCl$_3$): δ 7.23-7.18 (m, 1H), 7.08-6.97 (m, 1H), 4.78 (s, 1H), 4.66 (br s, 2H), 4.12-4.04 (m, 1H), 4.02-3.91 (m, 2H), 3.37-3.30 (m, 1H), 3.22-3.13 (m, 1H), 2.12-1.85 (m, 3H), 1.46-1.32 (m, 1H).

E238

(S)-3-((3-fluorobenzyl)(methyl)amino)-6,7,8,9,9a,10-hexahydro-1H-pyrido[1',2':3,4]imidazo[1,2-c]pyrimidin-1-one

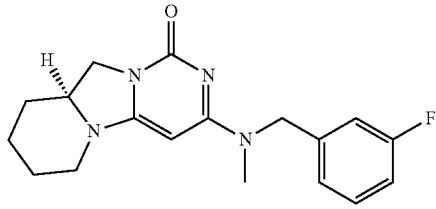 [SMILES: CN(Cc1cccc(F)c1)c1cc2n(c(=O)n1)C[C@@H]1CCCCN21]

The title compound was prepared by a procedure similar to that described for E222 starting from (S)-3-((3-fluorobenzyl)amino)-6,7,8,9,9a,10-hexahydro-1H-pyrido[1',2':3,4]imidazo[1,2 c]pyrimidin-1-one.

LC-MS (ESI): m/z 329 [M+H]$^+$; 3.82 min (ret time).

$^1$H NMR (300 MHz, CDCl$_3$): δ 7.29-7.22 (m, 1H), 7.11-7.13 (m, 2H), 6.91-6.85 (m, 1H), 4.59 (s, 1H), 4.37 (s, 2H), 4.12-4.07 (m, 1H), 3.57-3.44 (m, 3H), 3.42 (s, 3H), 2.92-2.82 (m, 1H), 1.96-1.85 (m, 2H), 1.75-1.71 (m, 1H), 1.56-1.35 (m, 3H).

E239

(S)-3-((3,5-difluorobenzyl)(methyl)amino)-7,8,8a,9-tetrahydropyrrolo[1',2':3,4]imidazo[1,2-c]pyrimidin-1(6H)-one

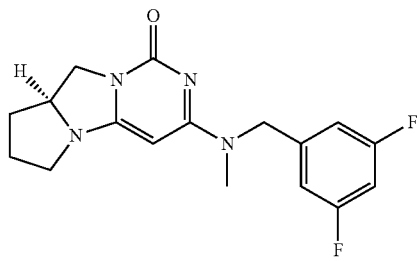 [SMILES: CN(Cc1cc(F)cc(F)c1)c1cc2n(c(=O)n1)C[C@@H]1CCCN21]

The title compound was prepared by a procedure similar to that described for E222 starting from (S)-3-((3,5-difluorobenzyl)amino)-7,8,8a,9-tetrahydropyrrolo[1',2':3,4]imidazo[1,2-c]pyrimidin-1(6H)-one and iodomethane.

LC-MS (ESI): m/z 333 [M+H]$^+$; 3.00 min (ret time).

$^1$H NMR (300 MHz, CDCl$_3$): δ 6.98-6.94 (m, 2H), 6.67-6.61 (m, 1H), 4.69 (s, 1H), 4.34 (s, 2H), 4.11-4.06 (m, 1H), 3.98-3.84 (m, 2H), 3.41 (s, 3H), 3.73-3.32 (m, 1H), 3.24-3.18 (m, 1H), 2.15-1.97 (m, 3H), 1.45-1.28 (m, 1H).

E240

(S)-3-((3,5-difluorobenzyl)(methyl)amino)-6,7,8,9,9a,10-hexahydro-1H-pyrido[1',2':3,4] imidazo[1,2-c]pyrimidin-1-one

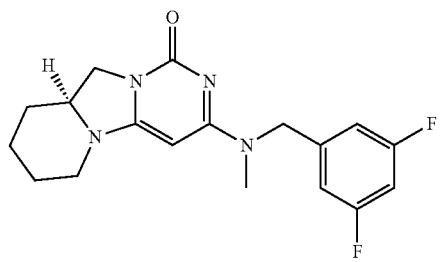 [SMILES: CN(Cc1cc(F)cc(F)c1)c1cc2n(c(=O)n1)C[C@@H]1CCCCN21]

The title compound was prepared by a procedure similar to that described for E222 starting from (S)-3-((3,5-difluorobenzyl)amino)-6,7,8,9,9a,10-hexahydro-1H-pyrido[1',2':3,4]imidazo[1,2-c]pyrimidin-1-one.

LC-MS (ESI): m/z 347 [M+H]$^+$; 3.17 min (ret time).

$^1$H NMR (300 MHz, CDCl$_3$): δ 6.98-6.94 (m, 2H), 6.66-6.60 (m, 1H), 4.54 (s, 1H), 4.36 (s, 2H), 4.13-4.08 (m, 1H), 3.56-3.42 (m, 3H), 3.41 (s, 3H), 2.91-2.84 (m, 1H), 1.96-1.89 (m, 2H), 1.76-1.72 (m, 1H), 1.59-1.37 (m, 3H).

301

E241

(R)-7-((2,4,5-trifluorobenzyl)amino)-3,4,11,11a-tetrahydropyrimido[6',1':2,3]imidazo[5,1-c][1,4]oxazin-9(1H)-one

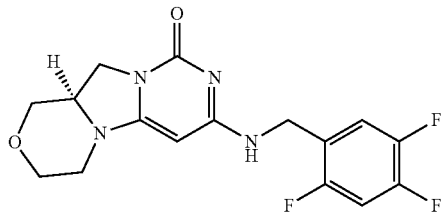 [SMILES: O=c1nc(NCc2cc(F)c(F)cc2F)cc2n1C[C@@H]1COCCN21]

The title compound was prepared by a procedure similar to that described for E104 starting from (R)-7-chloro-3,4,11,11a-tetrahydropyrimido[6',1':2,3] imidazo[5,1-c][1,4]oxazin-9(1H)-one and (2,4,5-trifluorophenyl)methanamine.

LC-MS (ESI): m/z 353 [M+H]$^+$; 3.07 min (ret time).

$^1$H NMR (300 MHz, CDCl$_3$): δ 7.37-7.28 (m, 1H), 7.18-7.10 (m, 1H), 5.03 (s, 1H), 4.49-4.48 (m, 2H), 4.08-3.94 (m, 3H), 3.88-3.83 (m, 1H), 3.60-3.48 (m, 3H), 3.41-3.31 (m, 2H).

E242

(R)-7-((2,3-difluorobenzyl)amino)-3,4,11,11a-tetrahydropyrimido[6',1':2,3]imidazo[5,1-c] [1,4]oxazin-9(1H)-one

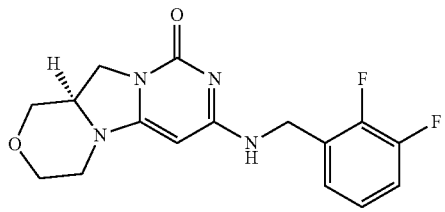 [SMILES: O=c1nc(NCc2cccc(F)c2F)cc2n1C[C@@H]1COCCN21]

The title compound was prepared by a procedure similar to that described for E104 starting from (R)-7-chloro-3,4,11,11a-tetrahydropyrimido[6',1':2,3] imidazo[5,1-c][1,4]oxazin-9(1H)-one and (2,3-difluorophenyl)methanamine.

LC-MS (ESI): m/z 335 [M+H]$^+$; 3.00 min (ret time).

$^1$H NMR (300 MHz, CDCl$_3$): δ 7.23-7.19 (m, 1H), 7.07-6.99 (m, 2H), 4.75 (s, 1H), 4.72-4.59 (m, 2H), 4.06-3.85 (m, 4H), 3.57-3.43 (m, 2H), 3.35-3.33 (m, 3H), 2.08-2.01 (m, 1H).

302

E243

(S)-3-((2,4,5-trifluorobenzyl)amino)-6,7,8,9,9a,10-hexahydro-1H-pyrido[1',2':3,4]imidazo[1,2-c]pyrimidin-1-one

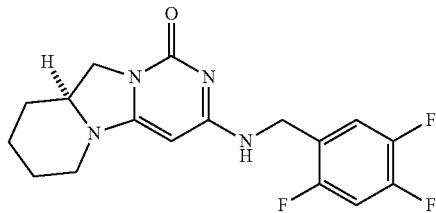 [SMILES: O=c1nc(NCc2cc(F)c(F)cc2F)cc2n1C[C@@H]1CCCCN21]

The title compound was prepared by a procedure similar to that described for E232 starting from (2,4,5-trifluorophenyl)methanamine and (S)-3-chloro-6,7,8,9,9a,10-hexahydro-1H-pyrido[1',2':3,4]imidazo[1,2-c]pyrimidin-1-one.

LC-MS (ESI): m/z 351 [M+H]$^+$; 3.54 min (ret time).

$^1$H NMR (300 MHz, CDCl$_3$): δ 7.31-7.28 (m, 1H), 6.93-6.84 (m, 1H), 4.63 (s, 1H), 4.61-4.54 (m, 2H), 4.19-4.12 (m, 1H), 3.69-3.55 (m, 2H), 3.50-3.44 (m, 1H), 2.97-2.90 (m, 1H), 1.97-1.88 (m, 2H), 1.71-1.65 (m, 1H), 1.54-1.39 (m, 3H).

E244

(S)-3-((2,3-difluorobenzyl)amino)-6,7,8,9,9a,10-hexahydro-1H-pyrido[1',2':3,4]imidazo[1,2-c]pyrimidin-1-one

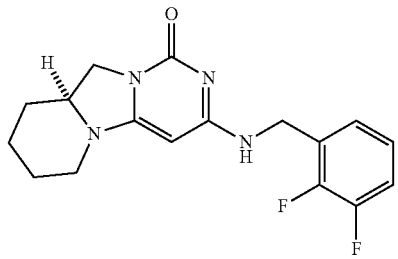 [SMILES: O=c1nc(NCc2cccc(F)c2F)cc2n1C[C@@H]1CCCCN21]

To a solution of (S)-3-chloro-6,7,8,9,9a,10-hexahydro-1H-pyrido[1',2':3,4]imidazo[1,2-c]pyrimidin-1-one (100 mg, 0.443 mmol) and (2,3-difluorophenyl)methanamine (95.0 mg, 0.665 mmol) in NMP (1.5 mL) was added DIEA (572 mg, 4.43 mmol) at room temperature. The reaction mixture was stirred at 100° C. for 12 hours. The reaction cooled to room temperature, purified with prep-HPLC to give the title compound (74 mg, 50%) as a off white solid.

LC-MS (ESI): m/z 333 [M+H]$^+$; 3.48 min (ret time).

$^1$H NMR (300 MHz, CDCl$_3$): δ 7.22-7.17 (m, 1H), 7.07-7.01 (m, 2H), 4.69-4.61 (m, 3H), 4.18-4.12 (m, 1H), 3.67-3.55 (m, 2H), 3.49-3.45 (m, 1H), 2.96-2.92 (m, 1H), 1.96-1.89 (m, 2H), 1.67-1.66 (m, 1H), 1.53-1.38 (m, 3H).

E245

(S)-3-((2,3-difluorobenzyl)(methyl)amino)-7,8,8a,9-tetrahydropyrrolo[1,2':3,4]imidazo[1,2-c]pyrimidin-1(6H)-one

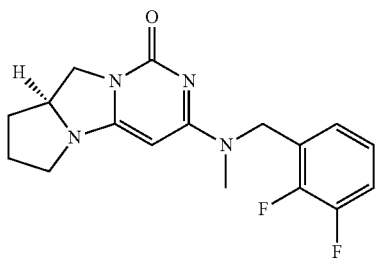 [SMILES: CN(Cc1cccc(F)c1F)c1cc2n(c(=O)n1)C[C@@H]1CCCN21]

The title compound was prepared by a procedure similar to that described for E222 starting from (S)-3-((2,3-difluorobenzyl)amino)-7,8,8a,9-tetrahydropyrrolo[1',2':3,4]imidazo[1,2-c]pyrimidin-1(6H)-one and idodomethane.

LC-MS (ESI): m/z 333 [M+H]$^+$; 3.01 min (ret time).
$^1$H NMR (300 MHz, CDCl$_3$): δ 7.39-7.35 (m, 1H), 7.06-7.00 (m, 2H), 4.79 (s, 1H), 4.43 (s, 2H), 4.12-4.06 (m, 1H), 4.00-3.84 (m, 2H), 3.41 (s, 3H), 3.38-3.34 (m, 1H), 3.27-3.18 (m, 1H), 2.15-2.08 (m, 2H), 2.06-1.96 (m, 1H), 1.47-1.28 (m, 1H).

E246

(R)-7-(3-fluorophenethoxy)-3,4,11,11a-tetrahydropyrimido[6',1':2,3]imidazo[5,1-c][1,4] oxazin-9(1H)-one

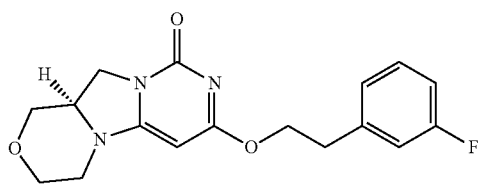 [SMILES: O=c1nc(OCCc2cccc(F)c2)cc2n1C[C@@H]1COCCN21]

The title compound was prepared by a procedure similar to that described for E63 starting from (R)-7-chloro-3,4,11,11a-tetrahydropyrimido[6',1':2,3]imidazo[5,1-c][1,4] oxazin-9(1H)-one and 2-(3-fluorophenyl)ethanol.

LC-MS (ESI): m/z 332 [M+H]$^+$; 3.48 min (ret time).
$^1$H NMR (300 MHz, CDCl$_3$): δ 7.28-7.21 (m, 1H), 7.02-6.91 (m, 3H), 4.93 (s, 1H), 4.56 (t, 2H), 4.16-3.89 (m, 4H), 3.67-3.62 (m, 1H), 3.54-3.48 (m, 1H), 3.40-3.33 (m, 2H), 3.01 (t, 2H).

E247

(S)-3-(3-fluorophenethoxy)-7,8,8a,9-tetrahydropyrrolo[1',2':3,4]imidazo[1,2-c]pyrimidin-1(6H)-one

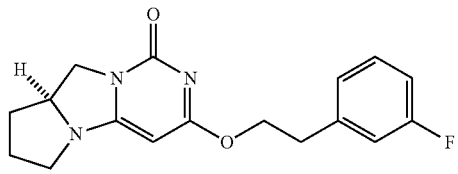 [SMILES: O=c1nc(OCCc2cccc(F)c2)cc2n1C[C@@H]1CCCN21]

The title compound was prepared by a procedure similar to that described for E63 starting from (S)-3-chloro-7,8,8a,9-tetrahydropyrrolo[1',2':3,4]imidazo[1,2-c]pyrimidin-1(6H)-one and 2-(3-fluorophenyl)ethanol.

LC-MS (ESI): m/z 316 [M+H]$^+$; 3.84 min (ret time).
$^1$H NMR (300 MHz, CDCl$_3$): δ 7.23-7.21 (m, 2H), 7.03-6.90 (m, 3H), 5.03 (s, 1H), 4.58-4.53 (m, 2H), 4.15-4.00 (m, 3H), 3.39-3.35 (m, 1H), 3.26-3.22 (m, 1H), 3.03-2.98 (m, 2H), 2.15-1.99 (m, 3H), 1.42 (t, 1H).

E248

(S)-7-(3-fluorophenethoxy)-3,4,11,11a-tetrahydropyrimido[6',1':2,3]imidazo[5,1-c][1,4] oxazin-9(1H)-one

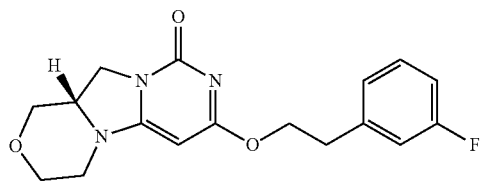 [SMILES: O=c1nc(OCCc2cccc(F)c2)cc2n1C[C@H]1COCCN21]

The title compound was prepared by a procedure similar to that described for E63 starting from (S)-7-chloro-3,4,11,11a-tetrahydropyrimido[6',1':2,3]imidazo[5,1-c][1,4] oxazin-9(1H)-one and 2-(3-fluorophenyl)ethanol.

LC-MS (ESI): m/z 332 [M+H]$^+$; 3.47 min (ret time).
$^1$H NMR (300 MHz, CDCl$_3$): δ 7.26-7.23 (m, 1H), 7.02-6.90 (m, 3H), 4.93 (s, 1H), 4.58 (t, 2H), 4.12-3.89 (m, 4H), 3.67-3.64 (m, 1H), 3.62-3.51 (m, 1H), 3.40-3.33 (m, 3H), 3.01 (t, 2H).

E249

(R)-3-(3-fluorophenethoxy)-7,8,8a,9-tetrahydropyrrolo[1',2':3,4]imidazo[1,2-c]pyrimidin-1(6H)-one

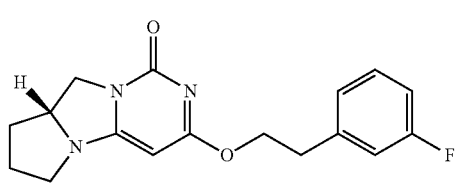 [SMILES: O=c1nc(OCCc2cccc(F)c2)cc2n1C[C@H]1CCCN21]

The title compound was prepared by a procedure similar to that described for E63 starting from (R)-3-chloro-7,8,8a,9-tetrahydropyrrolo[1',2':3,4]imidazo[1,2-c]pyrimidin-1(6H)-one and 2-(3-fluorophenyl)ethanol.

LC-MS (ESI): m/z 316 [M+H]$^+$; 3.84 min (ret time).

$^1$H NMR (300 MHz, CDCl$_3$): δ 7.28-7.21 (m, 1H), 7.02-6.90 (m, 3H), 5.02 (s, 1H), 4.55 (t, 2H), 4.15-4.00 (m, 3H), 3.39-3.34 (m, 1H), 3.28-3.22 (m, 1H), 3.01 (t, 2H), 2.45-2.04 (m, 3H), 1.58-1.42 (m, 1H).

E250

(S)-3-(methyl(2,4,5-trifluorobenzyl)amino)-7,8,8a,9-tetrahydropyrrolo[1',2':3,4]imidazo[1,2-c]pyrimidin-1(6H)-one

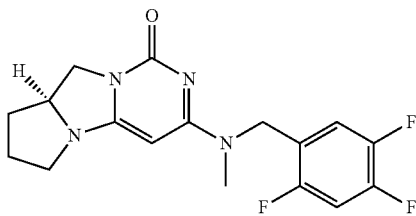 [SMILES: CN(Cc1cc(F)c(F)cc1F)c1cc2n(c(=O)n1)C[C@@H]1CCCN21]

The title compound was prepared by a procedure similar to that described for E222 starting from (S)-3-((2,4,5-trifluorobenzyl)amino)-7,8,8a,9-tetrahydropyrrolo[1',2':3,4]imidazo[1,2-c]pyrimidin-1(6H)-one and iodomethane.

LC-MS (ESI): m/z 351 [M+H]$^+$; 3.09 min (ret time).

$^1$H NMR (300 MHz, CDCl$_3$): δ 7.54-7.45 (m, 1H), 6.92-6.83 (m, 1H), 4.74 (s, 1H), 4.31 (s, 2H), 4.12-3.85 (m, 3H), 3.41 (s, 3H), 3.38-3.33 (m, 1H), 3.27-3.18 (m, 1H), 2.17-1.99 (m, 3H), 1.45-1.37 (m, 1H).

E251

(S)-3-(methyl(3,4,5-trifluorobenzyl)amino)-7,8,8a,9-tetrahydropyrrolo[1',2':3,4]imidazo[1,2-c]pyrimidin-1(6H)-one

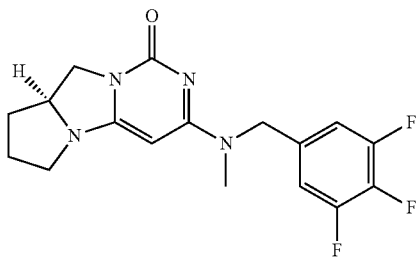 [SMILES: CN(Cc1cc(F)c(F)c(F)c1)c1cc2n(c(=O)n1)C[C@@H]1CCCN21]

The title compound was prepared by a procedure similar to that described for E222 starting from (S)-3-((3,4,5-trifluorobenzyl)amino)-7,8,8a,9-tetrahydropyrrolo[1',2':3,4]imidazo[1,2-c]pyrimidin-1(6H)-one and iodomethane.

LC-MS (ESI): m/z 351 [M+H]$^+$; 3.20 min (ret time).

$^1$H NMR (300 MHz, CDCl$_3$): δ 7.06 (t, 2H), 4.68 (s, 1H), 4.37 (s, 2H), 4.16-3.87 (m, 3H), 3.50 (s, 3H), 3.46-3.35 (m, 1H), 3.25-3.15 (m, 1H), 2.20-1.94 (m, 3H), 1.47-1.41 (m, 1H).

E252

(S)-3-((3-fluorobenzyl)(methyl)amino)-7,8,8a,9-tetrahydropyrrolo[1',2':3,4]imidazo[1,2-c]pyrimidin-1(6H)-one

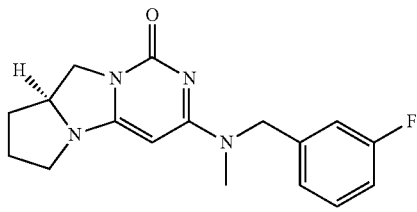 [SMILES: CN(Cc1cccc(F)c1)c1cc2n(c(=O)n1)C[C@@H]1CCCN21]

The title compound was prepared by a procedure similar to that described for E232 starting from (S)-3-((3-fluorobenzyl)amino)-7,8,8a,9-tetrahydropyrrolo[1',2':3,4]imidazo[1,2-c]pyrimidin-1(6H)-one and iodomethane.

LC-MS (ESI): m/z 315 [M+H]$^+$; 2.94 min (ret time).

$^1$H NMR (300 MHz, CDCl$_3$): δ 7.24-7.22 (m, 1H), 7.21-7.13 (m, 2H), 6.89-6.87 (m, 1H), 4.74 (s, 1H), 4.38 (s, 2H), 4.08-3.84 (m, 3H), 3.41 (s, 3H), 3.40-3.31 (m, 1H), 3.21-3.17 (m, 1H), 2.21-1.94 (m, 3H), 1.44-1.40 (m, 1H).

E253

(S)-3-((2,4-difluorobenzyl)(methyl)amino)-7,8,8a,9-tetrahydropyrrolo[1',2':3,4]imidazo[1,2-c]pyrimidin-1(6H)-one

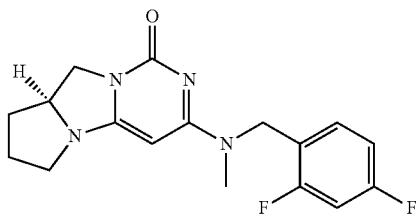 [SMILES: CN(Cc1ccc(F)cc1F)c1cc2n(c(=O)n1)C[C@@H]1CCCN21]

The title compound was prepared by a procedure similar to that described for E232 starting from (S)-3-((2,4-difluorobenzyl)amino)-7,8,8a,9-tetrahydropyrrolo[1',2':3,4]imidazo[1,2-c]pyrimidin-1 (6H)-one and iodomethane.

LC-MS (ESI): m/z 333 [M+H]$^+$; 3.00 min (ret time).

$^1$H NMR (300 MHz, CDCl$_3$): δ 7.62-7.53 (m, 1H), 6.88-6.73 (m, 2H), 4.78 (s, 1H), 4.35 (s, 2H), 4.11-4.05 (m, 1H), 3.98-3.90 (m, 1H), 3.88-3.85 (m, 1H), 3.40 (s, 3H), 3.37-3.33 (m, 1H), 3.26-3.17 (m, 1H), 2.16-1.93 (m, 3H), 1.44-1.37 (m, 1H).

E254

(R)-4-(2-((1-oxo-1,6,7,8,8a,9-hexahydropyrrolo[1',2':3,4]imidazo[1,2-c]pyrimidin-3-yl)oxy)ethyl)benzonitrile

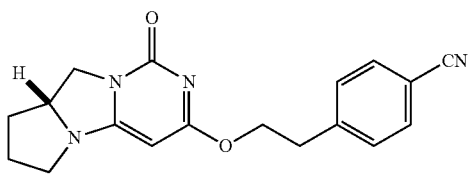 [SMILES: N#Cc1ccc(CCOc2cc3n(c(=O)n2)C[C@H]2CCCN32)cc1]

To a solution of (R)-3-(4-bromophenethoxy)-7,8,8a,9-tetrahydropyrrolo[1',2':3,4]imidazo[1,2-c]pyrimidin-1(6H)-one (75 mg, 0.20 mmol) in DMF (4 mL) was added Zn(CN)₂ (47 mg, 0.40 mmol) and Pd(PPh₃)₄ (20 mg) under nitrogen. The reaction mixture was stirred at 150° C. for 20 min. The reaction mixture was concentrated. The residue was dissolved with water (40 mL), extracted with EtOAc (40 mL×3). The combined organic layers were dried over anhydrous sodium sulfate, filtered, concentrated under reduced pressure and purified by prep-HPLC to give the title compound (30 mg, yield 47%) as a white solid.

LC-MS (ESI): m/z 323 [M+H]⁺; 3.54 min (ret time).

¹H NMR (300 MHz, CDCl₃): δ 7.60-7.57 (m, 2H), 7.35 (d, 2H), 4.99 (s, 1H), 4.60-4.55 (m, 2H), 4.15-4.00 (m, 3H), 3.39-3.35 (m, 1H), 3.28-3.21 (m, 1H), 3.07 (d, 2H), 2.16-2.04 (m, 3H), 1.55-1.42 (m, 1H).

E255

(S)-4-(2-((9-oxo-1,3,4,9,11,11a-hexahydropyrimido[6',1':2,3]imidazo[5,1-c][1,4]oxazin-7-yl)oxy)ethyl)benzonitrile

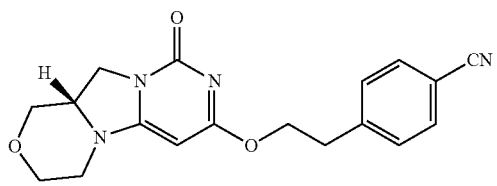 [SMILES: N#Cc1ccc(CCOc2cc3n(c(=O)n2)C[C@H]2COCCN32)cc1]

The title compound was prepared by a procedure similar to that described for E254 starting from (S)-7-(4-bromophenethoxy)-3,4,11,11a-tetrahydropyrimido[6',1':2,3]imidazo[5,1-c][1,4]oxazin-9(1H)-one.

LC-MS (ESI): m/z 339 [M+H]⁺; 3.19 min (ret time).

¹H NMR (300 MHz, CDCl₃): δ 7.58 (d, 2H), 7.35-7.26 (m, 2H), 4.90 (s, 1H), 4.58 (t, 2H), 4.13-3.89 (m, 4H), 3.67-3.62 (m, 1H), 3.52-3.47 (m, 1H), 3.41-3.32 (m, 3H), 3.09-3.05 (m, 2H).

E256

(R)-7-(3-fluorophenethyl)-3,4,11,11a-tetrahydropyrimido[6',1':2,3]imidazo[5,1-c][1,4]oxazin-9(1H)-one

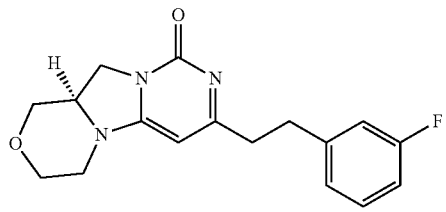 [SMILES: O=c1nc(CCc2cccc(F)c2)cc2n1C[C@@H]1COCCN21]

The title compound was prepared by a procedure similar to that described for E224 starting from (R)-7-((3-fluorophenyl)ethynyl)-3,4,11,11a-tetrahydropyrimido[6',1':2,3]imidazo[5,1-c][1,4] oxazin-9(1H)-one.

LC-MS (ESI): m/z 316 [M+H]⁺; 3.05 min (ret time).

¹H NMR (300 MHz, CDCl₃): δ 57.26-7.21 (m, 1H), 7.00-6.88 (m, 3H), 5.29 (s, 1H), 4.24-4.17 (m, 1H), 4.11-4.09 (m, 1H), 4.03-3.91 (m, 2H), 3.75-3.69 (m, 1H), 3.49-3.35 (m, 4H), 3.04 (t, 2H), 2.76 (t, 2H).

E257

(S)-7-(3-fluorophenethyl)-3,4,11,11a-tetrahydropyrimido[6',1':2,3]imidazo[5,1-c][1,4] oxazin-9(1H)-one

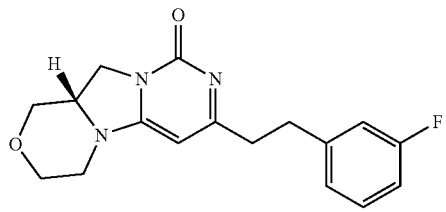 [SMILES: O=c1nc(CCc2cccc(F)c2)cc2n1C[C@H]1COCCN21]

The title compound was prepared by a procedure similar to that described for E224 starting from (R)-7-((3-fluorophenyl)ethynyl)-3,4,11,11a-tetrahydropyrimido[6',1':2,3] imidazo[5,1-c][1,4] oxazin-9(1H)-one.

LC-MS (ESI): m/z 316 [M+H]⁺; 3.06 min (ret time).

¹H NMR (300 MHz, CDCl₃): δ 7.26-7.21 (m, 1H), 7.00-6.88 (m, 3H), 5.29 (s, 1H), 4.24-4.17 (m, 1H), 4.14-4.09 (m, 1H), 4.04-3.92 (m, 2H), 3.76-3.72 (m, 1H), 3.53-3.36 (m, 4H), 3.04 (t, 2H), 2.77 (t, 2H).

E258

(R)-7-((3,5-difluoro-4-(1-(2-fluoroethyl)cyclo-propoxy)benzyl)oxy)-3,4,11,11a-tetrahydropyrimido[6',1':2,3]imidazo[5,1-c][1,4]oxazin-9(1H)-one

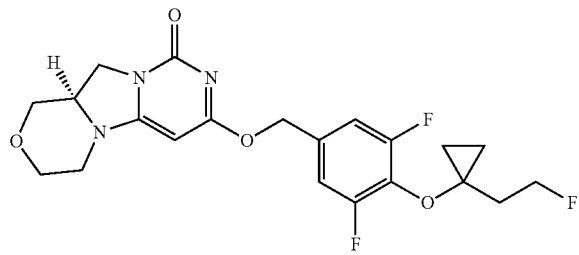 [SMILES: O=c1nc(OCc2cc(F)c(OC3(CCF)CC3)c(F)c2)cc2n1C[C@@H]1COCCN21]

The title compound was prepared by a procedure similar to that described for E63 starting from (3,5-difluoro-4-(1-(2-fluoroethyl)cyclopropoxy)phenyl)methanol and (R)-7-chloro-3,4,11,11a-tetrahydropyrimido[6',1':2,3]imidazo[5,1-c][1,4]oxazin-9(1H)-one.

LC-MS (ESI): m/z 438 [M+H]$^+$; 4.03 min (ret time).

$^1$H NMR (300 MHz, CDCl$_3$): δ 6.94-6.90 (m, 2H), 5.32-5.25 (m, 2H), 5.01 (s, 1H), 4.81 (t, 1H), 4.70 (t, 1H), 4.16-3.89 (m, 4H), 3.66-3.62 (m, 1H), 3.54-3.48 (m, 1H), 3.40-3.33 (m, 3H), 2.16-2.07 (m, 2H), 1.06 (t, 2H), 0.63 (t, 2H).

E259

(S)-3-((3,5-difluoro-4-(1-(2-fluoroethyl)cyclo-propoxy)benzyl)oxy)-7,8,8a,9-tetrahydro pyrrolo[1',2':3,4]imidazo[1,2-c]pyrimidin-1(6H)-one

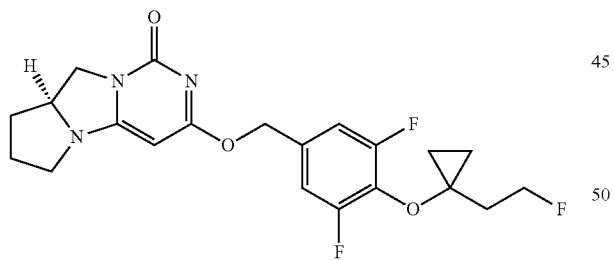

The title compound was prepared by a procedure similar to that described for E63 starting from (3,5-difluoro-4-(1-(2-fluoroethyl)cyclopropoxy)phenyl)methanol and (S)-3-chloro-7,8,8a,9-tetra hydropyrrolo[1',2':3,4]imidazo[1,2-c]pyrimidin-1(6H)-one.

LC-MS (ESI): m/z 422 [M+H]$^+$; 4.36 min (ret time).

$^1$H NMR (300 MHz, CDCl$_3$): δ 6.96-6.70 (m, 2H), 5.34-5.23 (m, 2H), 5.10 (s, 1H), 4.84 (t, 1H), 4.68 (t, 1H), 4.16-4.00 (m, 3H), 3.43-3.36 (m, 1H), 3.29-3.20 (m, 1H), 2.18-1.99 (m, 5H), 1.47-1.41 (m, 1H), 1.07 (t, 2H), 0.66-0.62 (m, 2H).

E260

(R)-7-((9-fluoro-3,4-dihydrospiro[benzo[b][1,4]dioxepine-2,1'-cyclopropan]-7-yl)methoxy)-3,4,11,11a-tetrahydropyrimido[6',1':2,3]imidazo[5,1-c][1,4]oxazin-9(1H)-one

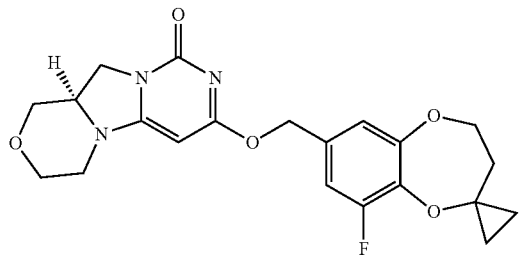 [SMILES: O=c1nc(OCc2cc(F)c3c(c2)OCCC2(CC2)O3)cc2n1C[C@@H]1COCCN21]

To a solution of (3,5-difluoro-4-(1-(2-fluoroethyl)cyclopropoxy)phenyl)methanol (40 mg, 0.16 mmol) and (R)-7-chloro-3,4,11,11a-tetrahydropyrimido[6',1':2,3]imidazo[5,1-c][1,4]oxazin-9(1H)-one (36 mg, 0.16 mmol) in DMF (4 mL) was added NaH (60% in mineral oil, 13 mg, 0.33 mmol) at 0° C. The reaction mixture was stirred at room temperature for 2 hours. The reaction was quenched with water (1 mL) and extracted with EtOAc (5 mL×3). The separate organic solution was successively washed with water (5 mL) and brine (5 mL). The extracts were combined and dried over Na$_2$SO$_4$, filtered, concentrated under reduced pressure and purified by prep-HPLC to give the title compound (9 mg, 10%) as yellow oil.

LC-MS (ESI): m/z 416 [M+H]$^+$; 2.89 min (ret time).

$^1$H NMR (300 MHz, CDCl$_3$): δ 6.82-6.79 (m, 2H), 5.26 (s, 2H), 5.05 (s, 1H), 4.26-4.18 (m, 2H), 4.11-3.89 (m, 4H), 3.69-3.63 (m, 1H), 3.53-3.34 (m, 4H), 2.20 (t, 2H), 1.06-1.03 (m, 2H), 0.61-0.57 (m, 2H).

E261

(S)-3-((9-fluoro-3,4-dihydrospiro[benzo[b][1,4]dioxepine-2,1'-cyclopropan]-7-yl)methoxy)-7,8,8a,9-tetrahydropyrrolo[1',2':3,4]imidazo[1,2-c]pyrimidin-1(6H)-one

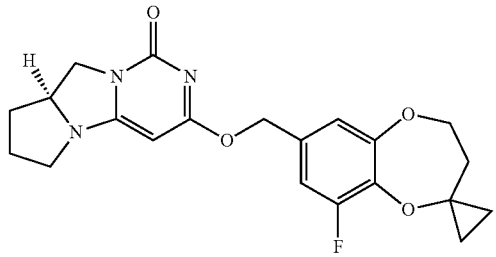 [SMILES: O=c1nc(OCc2cc(F)c3c(c2)OCCC2(CC2)O3)cc2n1C[C@@H]1CCCN21]

The title compound was prepared by a procedure similar to that described for E260 starting from (3,5-difluoro-4-(1-(2-fluoroethyl)cyclopropoxy)phenyl)methanol and (S)-3-chloro-7,8,8a,9-tetra hydropyrrolo[1',2':3,4]imidazo[1,2-c]pyrimidin-1(6H)-one.

LC-MS (ESI): m/z 400 [M+H]$^+$; 2.58 min (ret time).

$^1$H NMR (300 MHz, CDCl$_3$): δ 6.83-6.80 (m, 2H), 5.32-5.21 (m, 2H), 5.11 (s, 1H), 4.27-4.02 (m, 5H), 3.44-

3.37 (m, 1H), 3.30-3.23 (m, 1H), 2.26-1.98 (m, 5H), 1.47-1.42 (m, 1H), 1.08-1.04 (m, 2H), 0.62-0.58 (m, 2H).

E262

(S)-7-((3,5-difluoro-4-(1-(2-fluoroethyl)cyclopropoxy)benzyl)oxy)-3,4,11,11a-tetrahydropyrimido[6',1':2,3]imidazo[5,1-c][1,4]oxazin-9(1H)-one

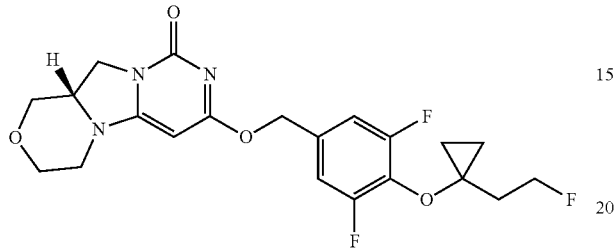

The title compound was prepared by a procedure similar to that described for E63 starting from (3,5-difluoro-4-(1-(2-fluoroethyl)cyclopropoxy)phenyl)methanol and (S)-7-chloro-3,4,11,11a-tetrahydropyrimido[6',1':2,3]imidazo[5,1-c][1,4]oxazin-9(1H)-one.

LC-MS (ESI): m/z 438 [M+H]$^+$; 4.03 min (ret time).

$^1$H NMR (300 MHz, CDCl$_3$): δ 7.07 (d, 2H), 5.38 (s, 1H), 5.26 (s, 1H), 4.80 (t, 1H), 4.64 (t, 1H), 4.15-4.12 9 (m, 2H), 4.02-3.96 (m, 1H), 3.91-3.86 (m, 1H), 3.64-3.30 (m, 6H), 2.20-2.06 (m, 2H), 1.00-0.98 (m, 2H), 0.70-0.65 (m, 2H).

E263

(S)-3-((3,5-difluoro-4-(1-(2-fluoroethyl)cyclopropoxy)benzyl)oxy)-6,7,8,9,9a,10-hexahydro-1H-pyrido[1',2':3,4]imidazo[1,2-c]pyrimidin-1-one

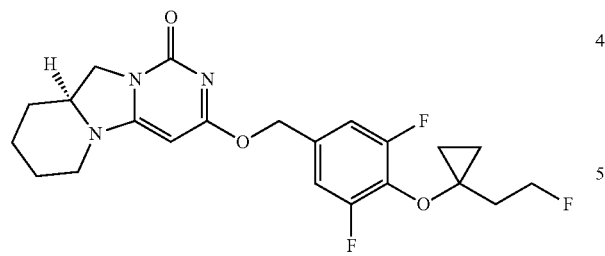

The title compound was prepared by a procedure similar to that described for E63 starting from (3,5-difluoro-4-(1-(2-fluoroethyl)cyclopropoxy)phenyl)methanol and (S)-3-chloro-6,7,8,9,9a,10-hexahydro-1H-pyrido[1',2':3,4]imidazo[1,2-c]pyrimidin-1-one.

LC-MS (ESI): m/z 436 [M+H]$^+$; 3.95 min (ret time).

$^1$H NMR (400 MHz, CDCl$_3$): δ 6.93 (d, J=8.4 Hz, 2H), 5.29 (s, 2H), 4.97 (s, 1H), 4.85 (t, J=6.3 Hz, 1H), 4.69 (t, J=6.0 Hz, 1H), 4.23-4.16 (m, 1H), 3.77-3.50 (m, 3H), 2.99-2.97 (m, 1H), 2.18-2.06 (m, 2H), 1.95-1.91 (m, 1H), 1.82-1.73 (m, 2H), 1.53-1.45 (m, 3H), 1.07 (t, J=6.6 Hz, 2H), 0.64 (t, J=6.6 Hz, 2H).

E264

(S)-3-((9-fluoro-3,4-dihydrospiro[benzo[b][1,4]dioxepine-2,1'-cyclopropan]-7-yl)methoxy)-6,7,8,9,9a,10-hexahydro-1H-pyrido[1',2':3,4]imidazo[1,2-c]pyrimidin-1-one

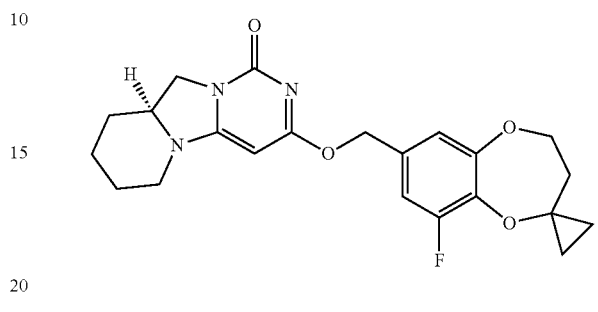

The title compound was prepared by a procedure similar to that described for E63 starting from (3,5-difluoro-4-(1-(2-fluoroethyl)cyclopropoxy)phenyl)methanol and (S)-3-chloro-6,7,8,9,9a,10-hexahydro-1H-pyrido[1',2':3,4]imidazo[1,2-c]pyrimidin-1-one.

LC-MS (ESI): m/z 414 [M+H]$^+$; 4.02 min (ret time).

$^1$H NMR (400 MHz, CDCl$_3$): δ 6.83-6.79 (m, 2H), 5.26 (s, 2H), 4.97 (s, 1H), 4.26-4.17 (m, 3H), 3.77-3.48 (m, 3H), 3.01-2.97 (m, 1H), 2.21-2.17 (m, 2H), 1.96-1.91 (m, 2H), 1.76-1.72 (m, 1H), 1.54-1.44 (m, 3H), 1.07-1.03 (m, 2H), 0.61-0.57 (m, 2H).

E265

(S)-7-(2,4-difluorophenethyl)-3,4,11,11a-tetrahydropyrimido[6',1':2,3]imidazo[5,1-c][1,4]oxazin-9(1H)-one

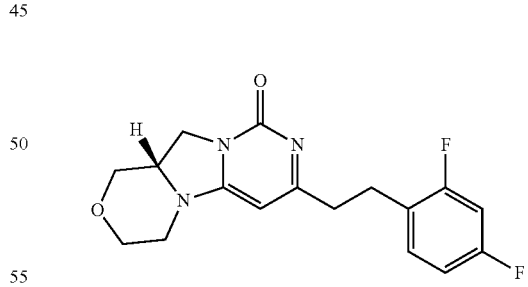

The title compound was prepared by a procedure similar to that described for E224 starting from (S)-7-((2,4-difluorophenyl)ethynyl)-3,4,11,11a-tetrahydropyrimido[6',1':2,3]imidazo[5,1-c][1,4]oxazin-9(1H)-one.

LC-MS (ESI): m/z 334 [M+H]$^+$; 2.60 min (ret time).

$^1$H NMR (300 MHz, CDCl$_3$): δ 7.20-7.14 (m, 1H), 6.79-6.73 (m, 2H), 5.31 (s, 1H), 4.26-4.17 (m, 1H), 4.11-4.03 (m, 1H), 4.00-3.92 (m, 2H), 3.74-3.68 (m, 1H), 3.52-3.46 (m, 1H), 3.44-3.34 (m, 3H), 3.05-3.00 (m, 2H), 2.77-2.71 (m, 2H).

E266

2-Fluoro-5-(((9-oxo-2,3,4,9,11,11a-hexahydro-1H-pyrazino[1',2':3,4]imidazo[1,2-c]pyrimidin-7-yl)oxy)methyl)benzonitrile

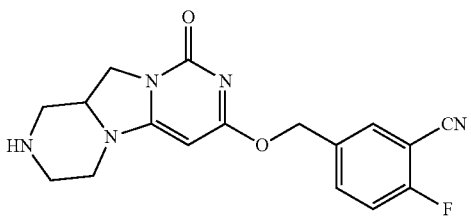 [SMILES: N#Cc1cc(COc2cc3n(c(=O)n2)CC2CNCCN32)ccc1F]

To a solution of tert-Butyl 7-chloro-9-oxo-3,4,11,11a-tetrahydro-1H-pyrazino[1',2':3,4]imidazo[1,2-c] pyrimidine-2(9H)-carboxylate (2.95 g, 9.03 mmol) and 2-fluoro-5-(hydroxymethyl)benzonitrile (1.364 g, 9.03 mmol) in 2-MeTHF (64 mL) was added NaH (0.910 g, 22.75 mmol) in small portions. The reaction was stirred at room temperature for 35 min then quenched with saturated NH₄Cl. The layers were separated, and the aqueous layer was extracted with EtOAc for 3 times. The combined organics were then washed with brine, dried (anhydrous Na₂SO₄), filtered and concentrated. The crude was purified on a Combiflash silica cartridge (80 g) (0-15% MeOH/DCM) to give the intermediate tert-butyl 7-((3-cyano-4-fluorobenzyl)oxy)-9-oxo-3,4,11,11a-tetrahydro-1H-pyrazino[1',2':3,4]imidazo[1,2-c]pyrimidine-2(9H)-carboxylate (3.44 g, 7.79 mmol, 86% yield) as a pale yellow brittle solid. (LC/MS: m/z 442.2 (M+H)⁺, 0.82 min (ret. time)). To this intermediate (3.44 g, 7.79 mmol) dissolved in DCM (18 mL) was added TFA (18 mL, 234 mmol). The reaction was stirred for 0.75 h at room temperature and the mixture was diluted with DCM (50 mL) and concentrated. The crude material was redissolved in MeOH/DCM and concentrated under reduced pressure (three times), then dissolved in THF and concentrated under reduced pressure (three times) resulting in the title compound (4.42 g, 7.76 mmol, 100% yield) as a tan brittle solid.

LC/MS: m/z 341.9 (M+H)⁺, 0.54 min (ret. time).

¹H NMR (300 MHz, CD₃OD): δ 7.82-7.68 (m, 2H), 7.30 (t, J=8.78 Hz, 1H), 5.44-5.30 (m, 2H), 5.20 (s, 1H), 4.16 (dd, J=11.42, 9.16 Hz, 1H), 4.05-3.89 (m, 1H), 3.71-3.48 (m, 2H), 3.29-3.10 (m, 2H), 3.01 (dd, J=12.55, 2.76 Hz, 1H), 2.83-2.57 (m, 2H).

The following compounds E267-E279 were prepared by a procedure similar to that described for E266 starting from the requisite chloropyrimidinone intermediate and the requisite benzyl alcohol:

TABLE 2

| Ex # | Name | Structure | Ret. time | m/z | ¹H NMR (400 MHz) |
|---|---|---|---|---|---|
| E267 | 7-((3-Fluoro-4-((2-(trifluoromethyl)pyridin-4-yl)oxy)benzyl)oxy)-3,4,11,11a-tetrahydro-1H-pyrazino[1',2':3,4]imidazo[1,2-c]pyrimidin-9(2H)-one | 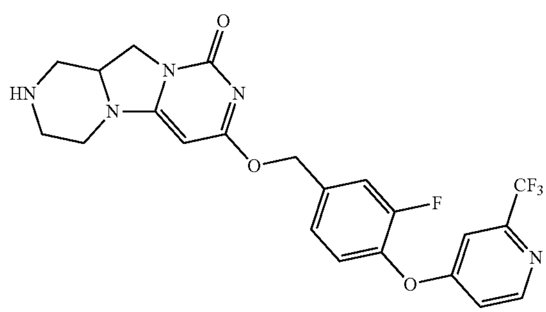 [SMILES: O=c1nc(OCc2ccc(Oc3ccnc(C(F)(F)F)c3)c(F)c2)cc2n1CC1CNCCN21] | 0.73 | 478.1 | (CHLOROFORM-d) δ ppm 1.84 (br. s., 1 H) 2.69 (t, J = 11.17 Hz, 1 H) 2.80 (td, J = 11.86, 3.14 Hz, 1 H) 3.04 (d, J = 10.54 Hz, 1 H) 3.15-3.29 (m, 2 H) 3.45 (d, J = 11.54 Hz, 1 H) 3.70 (dd, J = 11.54, 6.53 Hz, 1 H) 3.87-4.02 (m, 1 H) 4.19 (dd, J = 11.42, 9.16 Hz, 1 H) 5.03 (s, 1 H) 5.44 (s, 2 H) 6.96 (dd, J = 5.40, 1.63 Hz, 1 H) 7.15-7.37 (m, 4 H) 8.58 (d, J = 5.52 Hz, 1 H) |
| E268 | 7-((2,3-Difluorobenzyl)oxy)-3,4,11,11a-tetrahydro-1H-pyrazino[1',2':3,4]imidazo[1,2-c]pyrimidin-9(2H)-one | 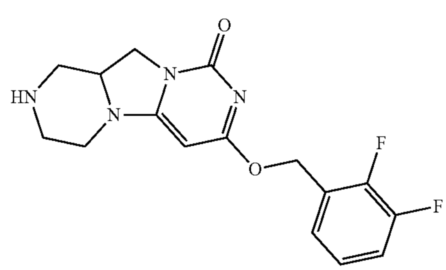 [SMILES: O=c1nc(OCc2cccc(F)c2F)cc2n1CC1CNCCN21] | 0.52 | 335.3 | (CHLOROFORM-d) δ ppm 1.79 (br. s., 1 H) 2.64-2.85 (m, 2 H) 3.03 (dd, J = 12.05, 2.51 Hz, 1 H) 3.13-3.29 (m, 2 H) 3.43 (dd, J = 13.05, 2.51 Hz, 1 H) 3.70 (dd, J = 11.54, 6.53 Hz, 1 H) 3.88-3.99 (m, 1 H) 4.19 (dd, J = 11.42, 8.91 Hz, 1 H) 5.00 (s, 1 H) 5.49 (s, 2 H) 7.03-7.20 (m, 2 H) 7.24 (t, J = 6.65 Hz, 1 H) |

TABLE 2-continued

| Ex # | Name | Structure | Ret. time | m/z | ¹H NMR (400 MHz) |
|---|---|---|---|---|---|
| E269 | 5-(((11,11-Dideutero-9-oxo-2,3,4,9,11,11a-hexahydro-1H-pyrazino[1',2':3,4]imidazo[1,2-c]pyrimidin-7-yl)oxy)methyl)-2-fluorobenzonitrile 2,2,2-trifluoroacetate | 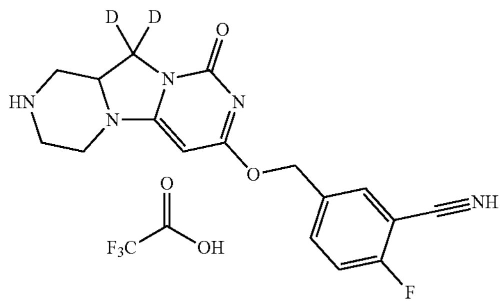 | 0.54 | 344.1 | (METHANOL-d₄) δ ppm 2.66 (s, 2 H) 3.21-3.36 (m, 2 H) 3.53-3.77 (m, 3 H) 4.25 (d, J = 12.05 Hz, 1 H) 4.56 (d, J = 9.03 Hz, 1 H) 5.41 (s, 2 H) 5.92 (s, 1 H) 7.44 (t, J = 8.91 Hz, 1 H) 7.80-7.87 (m, 1 H) 7.90 (d, J = 6.02 Hz, 1 H) |
| E270 | 7-((3,5-Difluoro-4-((2-(trifluoromethyl)pyridin-4-yl)oxy)benzyl)oxy)-3,4,11,11a-tetrahydro-1H-pyrazino[1',2':3,4]imidazo[1,2-c]pyrimidin-9(2H)-one | 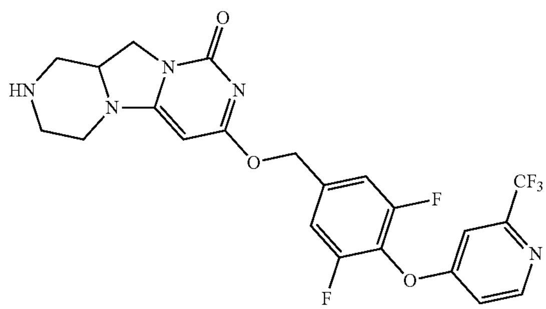 [SMILES: O=c1nc(OCc2cc(F)c(Oc3ccnc(C(F)(F)F)c3)c(F)c2)cc2n1CC1CNCCN21] | 0.76 | 496.1 | (CHLOROFORM-d) δ ppm 2.08 (br. s., 1 H) 2.62-2.88 (m, 2 H) 3.06 (d, J = 11.80 Hz, 1 H) 3.15-3.32 (m, 2 H) 3.46 (d, J = 12.80 Hz, 1 H) 3.70 (dd, J = 11.04, 6.53 Hz, 1 H) 3.97 (m, 1 H) 4.13-4.27 (m, 1 H) 5.05 (s, 1 H) 5.34-5.51 (m, 2 H) 6.95-7.03 (m, 1 H) 7.13 (d, J = 8.78 Hz, 2 H) 7.23-7.31 (m, 1 H) 8.60 (m, 1 H) |
| E271 | 2-Methyl-5-(((9-oxo-2,3,4,9,11,11a-hexahydro-1H-pyrazino[1',2':3,4]imidazo[1,2-c]pyrimidin-7-yl)oxy)methyl)benzonitrile | 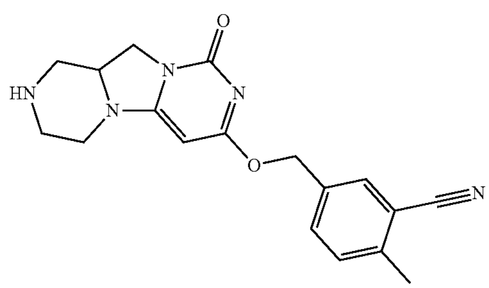 [SMILES: Cc1ccc(COc2cc3n(c(=O)n2)CC2CNCCN32)cc1C#N] | 0.53 | 338.0 | (CHLOROFORM-d) δ ppm 1.79 (br. s., 1 H) 2.56 (s, 3 H) 2.70 (t, J = 11.17 Hz, 1 H) 2.75-2.87 (m, 1 H) 3.05 (d, J = 11.80 Hz, 1 H) 3.13-3.32 (m, 2 H) 3.46 (d, J = 11 Hz, 1 H) 3.71 (dd, J = 11.54, 6.53 Hz, 1 H) 3.87-4.02 (m, 1 H) 4.19 (dd, J = 11.42, 9.16 Hz, 1 H) 5.02 (s, 1 H) 5.32-5.46 (m, 2 H) 7.25-7.37 (m, 1 H) 7.52 (d, J = 7.78 Hz, 1 H) 7.66 (s, 1 H) |
| E272 | 3-(((9-Oxo-2,3,4,9,11,11a-hexahydro-1H-pyrazino[1',2':3,4]imidazo[1,2-c]pyrimidin-7-yl)oxy)methyl)benzonitrile | 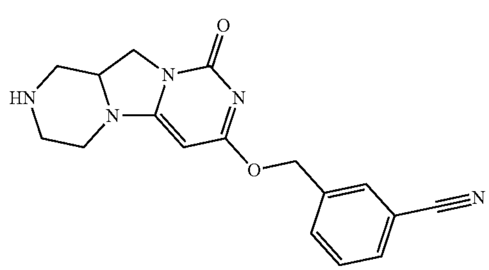 [SMILES: N#Cc1cccc(COc2cc3n(c(=O)n2)CC2CNCCN32)c1] | 0.52 | 324.4 | (CHLOROFORM-d) δ ppm 1.81 (br. s., 1 H) 2.58-2.86 (m, 2H) 2.98-3.32 (m, 3 H) 3.45 (d, J = 12.30 Hz, 1 H) 3.69 (dd, J = 11.54, 6.53 Hz, 1 H) 3.85-4.02 (m, 1 H) 4.18 (dd, J = 11.17, 9.16 Hz, 1 H) 5.03 (s, 1 H) 5.34-5.53 (m, 2 H) 7.39-7.74 (m, 4H) |

TABLE 2-continued

| Ex # | Name | Structure | Ret. time | m/z | ¹H NMR (400 MHz) |
|---|---|---|---|---|---|
| E273 | 7-((3,5-Difluoro-4-((5-(trifluoromethyl)pyridin-3-yl)oxy)benzyl)oxy)-3,4,11,11a-tetrahydro-1H-pyrazino[1',2':3,4]imidazo[1,2-c]pyrimidin-9(2H)-one | 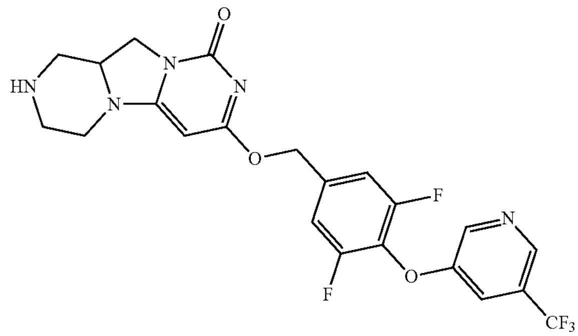 [SMILES: O=c1nc(OCc2cc(F)c(Oc3cncc(C(F)(F)F)c3)c(F)c2)cc2n1CC1CNCCN21] | 0.74 | 496.3 | (CHLOROFORM-d) δ ppm 1.79 (br. s., 1 H) 2.62-2.87 (m, 2 H) 3.04 (d, J = 11.29 Hz, 1 H) 3.11-3.30 (m, 2 H) 3.44 (d, J = 11.80 Hz, 1 H) 3.69 (dd, J = 11.54, 6.53 Hz, 1 H) 3.86-3.99 (m, 1 H) 4.18 (dd, J = 11.17, 9.41 Hz, 1 H) 5.03 (s, 1 H) 5.32-5.52 (m, 2 H) 7.11 (d, J = 8.53 Hz, 2 H) 7.40 (br. s., 1 H) 8.45-8.70 (m, 2 H) |
| E274 | 7-((3,4-Difluorobenzyl)oxy)-3,4,11,11a-tetrahydro-1H-pyrazino[1',2':3,4]imidazo[1,2-c]pyrimidin-9(2H)-one | 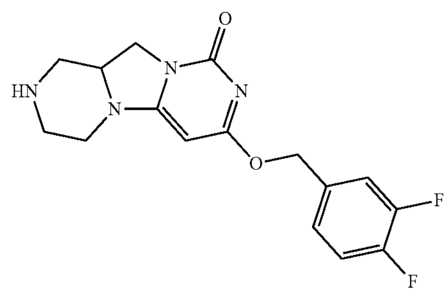 [SMILES: O=c1nc(OCc2ccc(F)c(F)c2)cc2n1CC1CNCCN21] | 0.52 | 334.9 | (METHANOL-d₄) δ ppm 2.62-2.85 (m, 2 H) 3.02 (d, J = 12.80 Hz, 1 H) 3.13-3.31 (m, 2 H) 3.59-3.75 (m, 2 H) 3.93-4.08 (m, 1 H) 4.13-4.28 (m, 1 H) 5.25-5.42 (m, 3 H) 7.21-7.33 (m, 2 H) 7.33-7.46 (m, 1 H) |
| E275 | 7-((3-Bromo-4-chlorobenzyl)oxy)-3,4,11,11a-tetrahydro-1H-pyrazino[1',2':3,4]imidazo[1,2-c]pyrimidin-9(2H)-one | 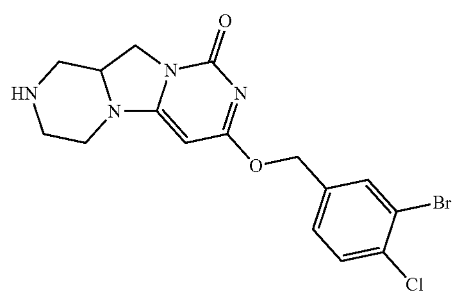 | 0.69 | 411.0 | (CHLOROFORM-d) δ ppm 2.05 (s, 1 H) 2.62-2.86 (m, 2 H) 3.04 (d, J = 11.04 Hz, 1 H) 3.13-3.30 (m, 2 H) 3.43 (d, J = 13.05 Hz, 1 H) 3.69 (dd, J = 11.54, 6.53 Hz, 1 H) 3.89-4.02 (m, 1 H) 4.18 (dd, J = 10.92, 9.41 Hz, 1 H) 5.00 (s, 1 H) 5.28-5.42 (m, 2 H) 7.29 (d, J = 8.03 Hz, 1 H) 7.42 (d, J = 8.28 Hz, 1 H) 7.67 (s, 1 H) |
| E276 | 7-((3-Bromo-4-fluorobenzyl)oxy)-3,4,11,11a-tetrahydro-1H-pyrazino[1',2':3,4]imidazo[1,2-c]pyrimidin-9(2H)-one | 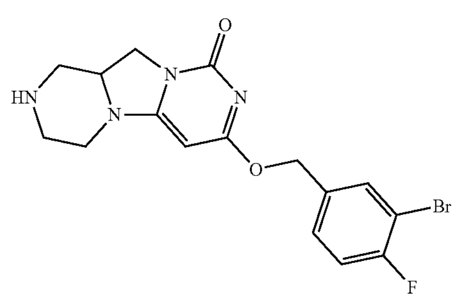 [SMILES: O=c1nc(OCc2ccc(F)c(Br)c2)cc2n1CC1CNCCN21] | 0.59 | 394.9 | (CHLOROFORM-d) δ ppm 1.83 (br. s., 1 H) 2.69 (t, J = 11.29 Hz, 1 H) 2.79 (td, J = 11.92, 3.01 Hz, 1 H) 3.04 (d, J = 11.80 Hz, 1 H) 3.11-3.31 (m, 2 H) 3.43 (d, J = 12.55 Hz, 1 H) 3.69 (dd, J = 11.67, 6.40 Hz, 1 H) 3.84-4.02 (m, 1 H) 4.18 (dd, J = 11.17, 9.16 Hz, 1 H) 4.99 (s, 1 H) 5.17-5.48 (m, 2H) 7.11 (t, J = 8.41 Hz, 1 H) 7.21-7.48 (m, 1 H) 7.62 (d, J = 6.27 Hz, 1 H) |

TABLE 2-continued

| Ex # | Name | Structure | Ret. time | m/z | $^1$H NMR (400 MHz) |
|---|---|---|---|---|---|
| E277 | 7-((3-Chloro-4-fluorobenzyl)oxy)-3,4,11,11a-tetrahydro-1H-pyrazino[1',2':3,4]imidazo[1,2-c]pyrimidin-9(2H)-one | 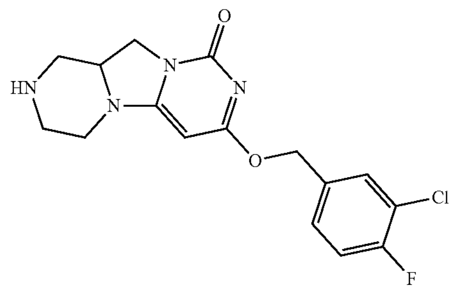 [SMILES: O=c1nc(OCc2ccc(F)c(Cl)c2)cc2n1CC1CNCCN21] | 0.61 | 351.3 | (CHLOROFORM-d) δ ppm 2.57 (br. s., 1 H) 2.71 (t, J = 11.29 Hz, 1 H) 2.81 (td, J = 12.05, 3.26 Hz, 1 H) 3.06 (d, J = 12.05 Hz, 1 H) 3.15-3.32 (m, 2 H) 3.44 (d, J = 13.05 Hz, 1 H) 3.69 (dd, J = 11.67, 6.40 Hz, 1 H) 3.91-4.04 (m, 1 H) 4.18 (dd, J = 11.29, 9.29 Hz, 1 H) 5.00 (s, 1 H) 5.28-5.41 (m, 2H) 7.13 (t, J = 8.66 Hz, 1 H) 7.24-7.33 (m, 1 H) 7.47 (d, J = 7.03 Hz, 1 H) |
| E278 | 2-Methoxy-5-(((9-oxo-2,3,4,9,11,11a-hexahydro-1H-pyrazino[1',2':3,4]imidazo[1,2-c]pyrimidin-7-yl)oxy)methyl)benzonitrile | 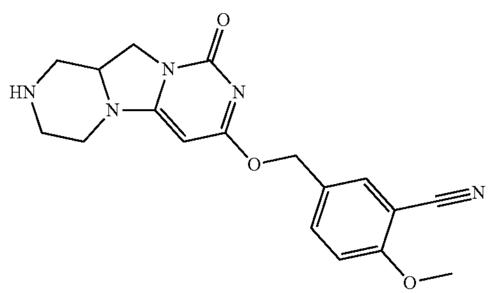 [SMILES: COc1ccc(COc2cc3n(c(=O)n2)CC2CNCCN32)cc1C#N] | 0.52 | 354.0 | (CHLOROFORM-d) δ ppm 1.84 (br. s., 1 H) 2.68 (t, J = 11.17 Hz, 1 H) 2.78 (td, J = 11.98, 2.89 Hz, 1 H) 3.02 (d, J = 11.80 Hz, 1 H) 3.12-3.28 (m, 2 H) 3.42 (d, J = 11.54 Hz, 1 H) 3.67 (dd, J = 11.67, 6.40 Hz, 1 H) 3.86-3.96 (m, 4 H) 4.05-4.25 (m, 1 H) 4.96 (s, 1 H) 5.25-5.40 (m, 2 H) 6.94 (d, J = 8.53 Hz, 1 H) 7.54-7.65 (m, 2 H) |
| E279 | 7-((3,5-Difluoro-4-((6-methylpyridin-3-yl)oxy)benzyl)oxy)-3,4,11,11a-tetrahydro-1H-pyrazino[1',2':3,4]imidazo[1,2-c]pyrimidin-9(2H)-one | 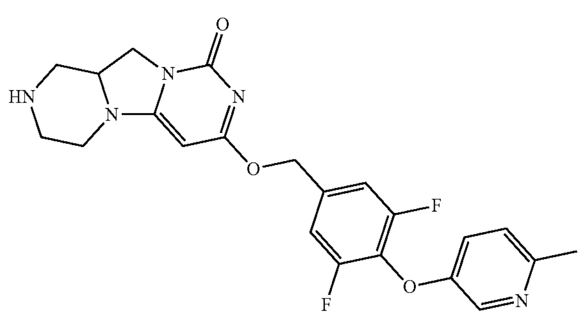 [SMILES: Cc1ccc(Oc2c(F)cc(COc3cc4n(c(=O)n3)CC3CNCCN43)cc2F)cn1] | 0.53 | 442.0 | (CHLOROFORM-d) δ ppm 1.15 (s, 1 H) 2.40 (s, 3 H) 2.57 (t, J = 11.54 Hz, 1 H) 2.67 (td, J = 12.17, 3.51 Hz, 1 H) 2.94 (dd, J = 12.42, 2.38 Hz, 1 H) 3.03-3.21 (m, 2 H) 3.38 (dd, J = 13.18, 2.64 Hz, 1 H) 3.55 (dd, J = 11.54, 6.78 Hz, 1 H) 3.81-3.91 (m, 1 H) 4.07 (dd, J = 11.42, 9.16 Hz, 1 H) 4.99 (s, 1 H) 5.17-5.29 (m, 2 H) 6.95-7.11 (m, 4 H) 8.08 (d, J = 2.76 Hz, 1 H) |

E280

Method A 5-(((2-Ethyl-9-oxo-2,3,4,9,11,11a-hexahydro-1H-pyrazino[1',2':3,4]imidazo[1,2-c]pyrimidin-7-yl)oxy)methyl)-2-fluorobenzonitrile

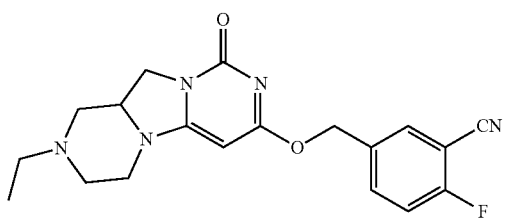 [SMILES: CCN1CCN2c3cc(OCc4ccc(F)c(C#N)c4)nc(=O)n3CC2C1]

To a solution of 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile (43 mg, 0.126 mmol) in DCM (0.4 mL) at 0° C. was added TEA (0.04 mL, 0.287 mmol) and bromoethane (0.02 mL, 0.27 mmol). The reaction was then warmed to room temperature and stirred for 92 hrs. The mixture was concentrated under a stream of nitrogen at 50° C., taken up in DCM, applied to isolute, and concentrated under a stream of nitrogen at 50° C. The crude product was purified on a Combiflash silica cartridge (4 g) [0-20% MeOH (1% NH$_4$OH)/DCM] then by prep reverse phase HPLC [0-50% CH$_3$CN/H$_2$O (0.1% NH$_4$OH)] to give the title compound E280 (22 mg, 0.060 mmol, 47.3% yield) as an amorphous white solid.

LC/MS: m/z 370.0 (M+H)$^+$, 0.55 min (ret. time).

$^1$H NMR (400 MHz, CDCl$_3$): δ 1.09 (t, J=7.03 Hz, 3H) 2.01 (t, J=11.04 Hz, 1H) 2.12 (td, J=11.67, 3.01 Hz, 1H) 2.49 (q, J=7 Hz, 2H) 2.87 (d, J=11.29 Hz, 1H) 3.00 (d, J=11.04 Hz, 1H) 3.24-3.39 (m, 1H) 3.40-3.55 (m, 1H) 3.73 (dd, J=11.54, 5.77 Hz, 1H) 3.93-4.08 (m, 1H) 4.10-4.26 (m, 1H) 4.99 (s, 1H) 5.31-5.47 (m, 2H) 7.19 (t, J=8.53 Hz, 1H) 7.56-7.71 (m, 2H).

E281

Method B 5-(((2-Acetyl-9-oxo-2,3,4,9,11,11a-hexahydro-1H-pyrazino[1',2':3,4]imidazo[1,2-c]pyrimidin-7-yl)oxy)methyl)-2-fluorobenzonitrile, trifluoroacetic Acid Salt

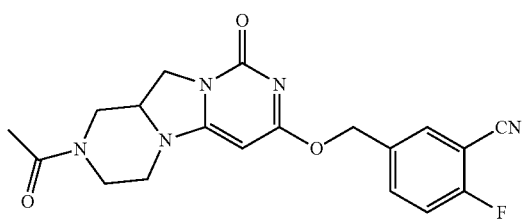 [SMILES: CC(=O)N1CCN2c3cc(OCc4ccc(F)c(C#N)c4)nc(=O)n3CC2C1]

To a solution of 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile (80 mg, 0.141 mmol) in DCM (1.3 mL) was added DIPEA (0.1 mL, 0.573 mmol), followed by acetyl chloride (0.01 mL, 0.140 mmol) in one portion at room temperature. The reaction was stirred for 45 min, diluted with DCM (2 mL), and washed with saturated NH$_4$Cl (1 mL×3), brine (1 mL), dried over anhydrous sodium sulfate, filtered and concentrated. The crude was purified on a Combiflash silica cartridge (4 g) (0-15% MeOH/DCM) then by prep reverse phase HPLC [10-90% CH$_3$CN/H$_2$O (0.1% TFA)] to give the title compound E281 (31 mg, 0.062 mmol, 44.4% yield) as an amorphous white solid.

LC/MS: m/z 384.0 (M+H)$^+$, 0.61 min (ret. time).

$^1$H NMR (400 MHz, CD$_3$OD): δ 2.15-2.23 (s, 3H) 2.69-2.89 (m, 1H) 3.22-3.46 (m, 2H) 3.79-4.39 (m, 5H) 4.70-4.93 (m, 1H) 5.33-5.45 (m, 3H) 7.38 (t, J=8.78 Hz, 1H) 7.75-7.88 (m, 2H)

E282

Method C tert-Butyl (2-(7-((3-cyano-4-fluorobenzyl)oxy)-9-oxo-3,4,11,11a-tetrahydro-1H-pyrazino[1',2':3,4]imidazo[1,2-c]pyrimidin-2(9H)-yl)-2-oxoethyl)carbamate

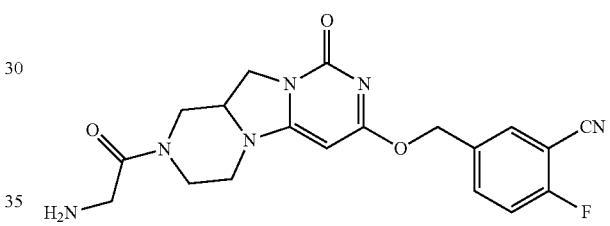

A solution of tert-butyl 7-((3-cyano-4-fluorobenzyl)oxy)-9-oxo-3,4,11,11a-tetrahydro-1H-pyrazino[1',2':3,4]imidazo[1,2-c]pyrimidine-2(9H)-carboxylate (81 mg, 0.183 mmol) and HCl (3M in CPME) (2.5 mL, 7.50 mmol) was stirred at room temperature for 3 hrs and then concentrated resulting in a tan powder. The powder was suspended in EtOAc (3 mL) and cooled to 0° C., TEA (0.3 mL, 2.152 mmol) was then added, followed by 2-((tert-butoxycarbonyl)amino)acetic acid (38 mg, 0.217 mmol) and T3P (50 wt % in EtOAc) (175 mg, 0.275 mmol). The resulting mixture was stirred a further 1.5 hrs and then concentrated. The crude product was purified on a Combiflash silica cartridge (12 g) (0-15% MeOH/DCM) to give the intermediate tert-butyl (2-(7-((3-cyano-4-fluorobenzyl)oxy)-9-oxo-3,4,11,11a-tetrahydro-1H-pyrazino[1',2':3,4]imidazo[1,2-c]pyrimidin-2(9H)-yl)-2-oxoethyl)carbamate (130 mg, 0.227 mmol, 124% yield) as an amorphous white solid. (LC/MS: m/z 499.2 (M+H)$^+$, 0.75 min (ret. time)). To this intermediate (130 mg, 0.261 mmol) was added HCl (3M in CPME) (3.5 mL, 10.50 mmol) and the reaction was stirred for 1 hr. The mixture was then concentrated and the crude was dissolved in DMSO:H$_2$O (2.1 mL), filtered through a 0.45 μm acrodisc, and purified by prep reverse phase HPLC [10-90% CH$_3$CN/H$_2$O (0.1% NH$_4$OH)] to give the title compound (11 mg, 0.028 mmol, 10.59% yield) as an amorphous white solid.

LC/MS: m/z 399.0 (M+H)$^+$, 0.49 min (ret. time).

$^1$H NMR (400 MHz, CD$_3$OD): δ 2.75 (m, 1H) 3.10-3.29 (m, 2H) 3.64-4.13 (m, 6H) 4.14-4.26 (m, 1H) 4.56-4.77 (m, 1H) 5.24-5.45 (m, 4H) 7.30 (t, J=8.91 Hz, 1H) 7.70-7.82 (m, 2H)

323

E283

Method D 5-(((2-(Ethylsulfonyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile

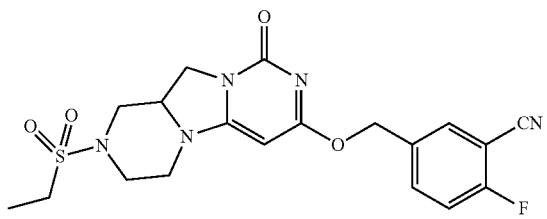 [SMILES: CCS(=O)(=O)N1CCN2c3cc(OCc4ccc(F)c(C#N)c4)nc(=O)n3CC2C1]

To a solution of 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile in DCM (1.373 mL) was added first DIPEA (0.1 mL, 0.573 mmol), followed by ethanesulfonyl chloride (0.02 mL, 0.179 mmol) in one portion at room temperature. The reaction was stirred for 1 h, diluted with DCM (2 mL), and washed with saturated $NH_4Cl$ (1 mL, three times), brine (1 mL), dried over anhydrous sodium sulfate, filtered, and concentrated. The crude was purified by prep reverse phase HPLC [10-90% $CH_3CN/H_2O$ (0.1% TFA)] then purified on a Combiflash silica cartridge (12 g) [0-10% (1% $NH_4OH/MeOH)/DCM$] to give the title compound (25 mg, 0.058 mmol, 38.6% yield) as an amorphous white solid.

LC/MS: m/z 434.1 $(M+H)^+$, 0.68 min (ret. time).

$^1$H NMR (400 MHz, $CD_3OD$, $CD_2Cl_2$) δ ppm 1.35 (t, J=7.40 Hz, 3H) 2.82-3.11 (m, 4H) 3.28-3.40 (m, 1H) 3.62-3.75 (m, 2H) 3.81 (dd, J=12.55, 1.51 Hz, 1H) 3.97 (dt, J=12.30, 1.76 Hz, 1H) 4.03-4.14 (m, 1H) 4.14-4.25 (m, 1H) 5.29-5.42 (m, 3H) 7.29 (t, J=8.78 Hz, 1H) 7.68-7.79 (m, 2H)

324

E284

Method E 5-(((2-(2-(Dimethylamino)acetyl)-9-oxo-2,3,4,9,11,11a-hexahydro-1H-pyrazino[1,2':3,4]imidazo[1,2-c]pyrimidin-7-yl)oxy)methyl)-2-fluorobenzonitrile

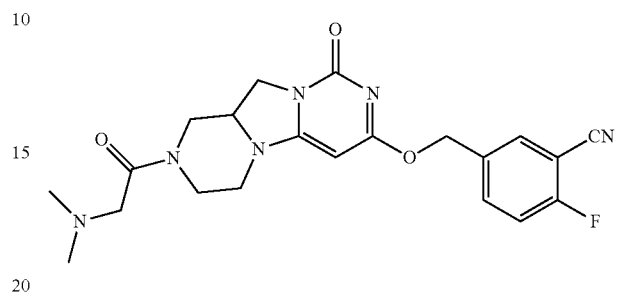

To a solution of E266 (44 mg, 0.129 mmol) and 2-(dimethylamino)acetic acid (17 mg, 0.165 mmol) in dichloromethane (DCM) (1 mL) at room temperature was added first DIPEA (0.03 mL, 0.172 mmol), followed by T3P (50 wt. % in EtOAc) (0.09 mL, 0.151 mmol). The reaction was stirred for 1 h at room temperature then diluted with DCM (3 mL), washed with saturated $NaHCO_3$ (2 mL, two times), brine (2 mL), dried over anhydrous sodium sulfate, filtered and concentrated. The crude product was purified on a Combiflash silica cartridge (12 g) [0-10% (1% $NH_4OH/MeOH)/DCM$] then by prep reverse phase HPLC [10-90% $CH_3CN/H_2O$ (0.1% $NH_4OH$)] to give the title compound (16 mg, 0.038 mmol, 29.1% yield) as an amorphous white solid.

LC/MS: m/z 427.3 $(M+H)^+$, 0.51 min (ret. time).

$^1$H NMR (400 MHz, $CD_3OD$): δ ppm 2.31 (s, 6H) 2.68-2.85 (m, 1H) 3.13-3.26 (m, 4H) 3.70-3.79 (m, 2H) 3.94-4.33 (m, 3H) 4.53-4.76 (m, 1H) 5.38 (m, 3H) 7.33-7.41 (m, 1H) 7.76-7.89 (m, 2H)

The following compounds E285-E308 listed in Table 3 were prepared by a procedure similar to that described for E280-E284 starting from the requisite fused piperazine and the requisite electrophile:

TABLE 3

| Ex # | Name | Structure | Method Used | LC/MS ret. Time (min) | MS | $^1$H NMR (400 MHz) |
|---|---|---|---|---|---|---|
| E285 | 5-(((2-Acetyl-11,11-dideutero-9-oxo-2,3,4,9,11,11a-hexahydro-1H-pyrazino[1',2':3,4]imidazo[1,2-c]pyrimidin-7-yl)oxy)methyl)-2-fluorobenzonitrile | 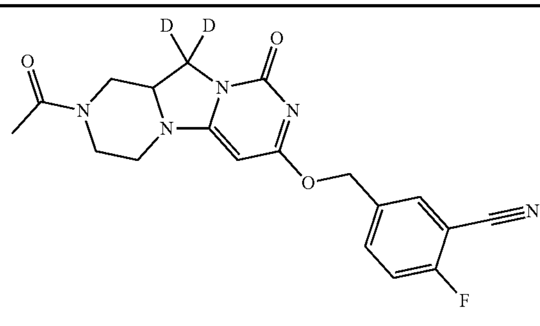 | B | 0.57 | 386.0 | ($CD_3OD$) δ ppm 2.11 (s, 3 H) 2.53-2.76 (m, 1 H) 3.06-3.31 (m, 2 H) 3.55-3.67 (m, 1 H) 3.89 (d, J = 10.04 Hz, 1 H) 3.94-4.11 (m, 1 H) 4.53-4.77 (m, 1 H) 5.18-5.38 (m, 3 H) 7.25 (t, J = 8.78 Hz, 1 H) 7.65-7.77 (m, 2 H) |

TABLE 3-continued

| Ex # | Name | Structure | Method Used | LC/MS ret. Time (min) | MS | $^1$H NMR (400 MHz) |
|---|---|---|---|---|---|---|
| E286 | 2-Fluoro-5-(((2-(methylsulfonyl)-9-oxo-2,3,4,9,11,11a-hexahydro-1H-pyrazino[1',2':3,4]imidazo[1,2-c]pyrimidin-7-yl)oxy)methyl)benzonitrile hydrochloride | 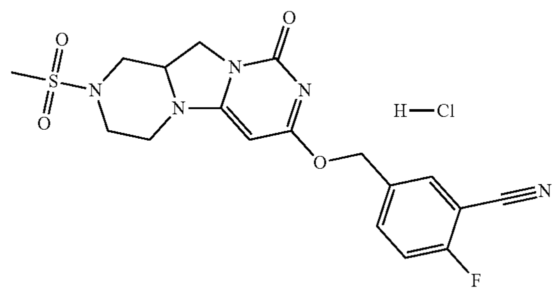 | D | 0.62 | 420.1 | (CDCl$_3$) δ ppm 2.75 (t, J = 11.29 Hz, 1 H) 2.83-2.94 (m, 4 H) 3.35-3.49 (m, 1 H) 3.60 (d, J = 12.80 Hz, 1 H) 3.78 (dd, J = 11.80, 5.52 Hz, 1 H) 3.87 (d, J = 12.30 Hz, 1 H) 3.98 (d, J = 10.54 Hz, 1 H) 4.12 (br. s., 1 H) 4.20-4.28 (m, 1 H) 5.06 (s, 1 H) 5.33-5.50 (m, 2 H) 7.21 (t, J = 8.66 Hz, 1 H) 7.60-7.71 (m, 2 H) |
| E287 | 5-(((11,11-Dideutero-2-(methylsulfonyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile | 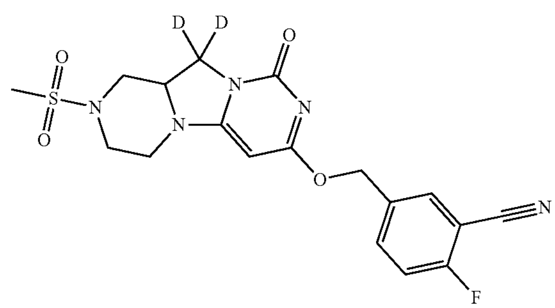 [SMILES: [2H]C1([2H])C2CN(S(C)(=O)=O)CCN2c2cc(OCc3ccc(F)c(C#N)c3)nc(=O)n21] | D | 0.64 | 422.0 | (CD$_3$OD) δ ppm 2.78-2.94 (m, 5 H) 3.36-3.41 (m, 1 H) 3.78 (br. s., 2 H) 3.91-3.99 (m, 1 H) 4.08-4.18 (m, 1 H) 5.27-5.39 (m, 3 H) 7.31 (s, 1 H) 7.80 (d, J = 6.53 Hz, 2 H) |
| E288 | 5-(((2-(3-Aminopropanoyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile | 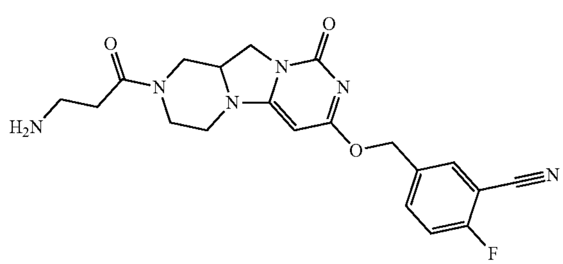 [SMILES: N#Cc1cc(COc2cc3n(c(=O)n2)CC2CN(C(=O)CCN)CCN32)ccc1F] | C | 0.49 | 413.1 | (CD$_3$OD) δ ppm 2.68-2.90 (m, 3 H) 3.08-3.33 (m, 4 H) 3.72-3.84 (m, 2 H) 3.97-4.29 (m, 3 H) 4.60-4.84 (m, 1 H) 5.34-5.45 (m, 3 H) 7.40 (t, J = 8.91 Hz, 1 H) 7.80-7.86 (m, 1 H) 7.89 (d, J = 5.77 Hz, 1 H) |

TABLE 3-continued

| Ex # | Name | Structure | Method Used | LC/MS ret. Time (min) | MS | ¹H NMR (400 MHz) |
|---|---|---|---|---|---|---|
| E289 | 2-Fluoro-5-(((9-oxo-2-propionyl-2,3,4,9,11,11a-hexahydro-1H-pyrazino[1',2':3,4]imidazo[1,2-c]pyrimidin-7-yl)oxy)methyl)benzonitrile 2,2,2-trifluoroacetate | 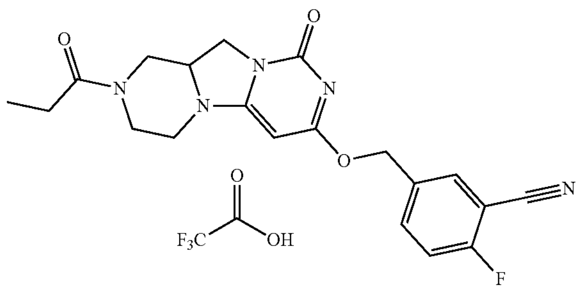 | B | 0.57 | 398.1 | (CD₃OD) δ ppm 1.17 (t, J = 7.40 Hz, 3 H) 2.53 (m, 2 H) 2.68 (s, 1 H) 2.86 (d, J = 11.80 Hz, 1 H) 3.35-3.55 (m, 1 H) 3.82-3.94 (m, 1 H) 4.09 (d, J = 13.05 Hz, 1 H) 4.14-4.45 (m, 3 H) 4.72-4.92 (m, 2 H) 5.43 (s, 2 H) 7.48 (t, J = 8.78 Hz, 1 H) 7.83-7.91 (m, 1 H) 7.94 (d, J = 5.77 Hz, 1 H) |
| E290 | 2-Fluoro-5-(((2-isobutyryl-9-oxo-2,3,4,9,11,11a-hexahydro-1H-pyrazino[1',2':3,4]imidazo[1,2-c]pyrimidin-7-yl)oxy)methyl)benzonitrile 2,2,2-trifluoroacetate | 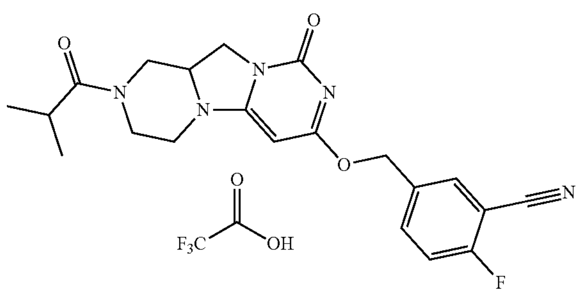 | B | 0.67 | 412.2 | (CD₃OD) δ ppm 1.17 (br. s., 6 H) 2.87 (m, 1 H) 3.04 (dt, J = 13.30, 6.65 Hz, 1 H) 3.37-3.53 (m, 2 H) 3.90 (dd, J = 10.92, 7.15 Hz, 1 H) 4.12 (d, J = 11.29 Hz, 1 H) 4.18-4.52 (m, 3 H) 4.69-4.96 (m, 2 H) 5.43 (s, 2 H) 7.48 (t, J = 8.91 Hz, 1 H) 7.76-8.02 (m, 2 H) |
| E291 | 5-(((2-Butyryl-9-oxo-2,3,4,9,11,11a-hexahydro-1H-pyrazino[1',2':3,4]imidazo[1,2-c]pyrimidin-7-yl)oxy)methyl)-2-fluorobenzonitrile 2,2,2-trifluoroacetate | 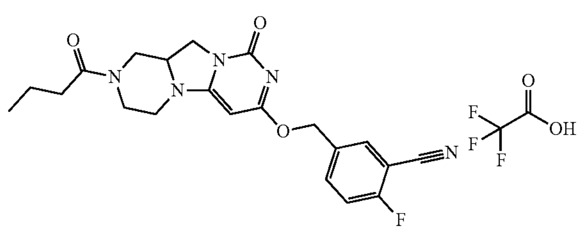 | B | 0.68 | 412.3 | (CD₃OD) δ ppm 0.92 (t, J = 7.40 Hz, 3 H) 1.47-1.70 (m, 2 H) 2.40 (t, J = 7.15 Hz, 2 H) 2.69-2.86 (m, 1 H) 3.26-3.46 (m, 2 H) 3.73-3.86 (m, 1 H) 4.01 (d, J = 13.05 Hz, 1 H) 4.12 (d, J = 12.55 Hz, 1 H) 4.19-4.37 (m, 2 H) 4.60-4.85 (m, 2 H) 5.34 (s, 2 H) 7.39 (t, |

TABLE 3-continued

| Ex # | Name | Structure | Method Used | LC/MS ret. Time (min) | MS | ¹H NMR (400 MHz) |
|---|---|---|---|---|---|---|
| | | | | | | J = 8.91 Hz, 1 H) 7.71-7.93 (m, 2 H) |
| E292 | 5-(((2-(cyclopropane-carbonyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile 2,2,2-trifluoroacetate | 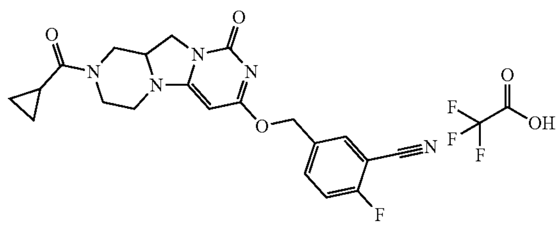 | B | 0.67 | 410.1 | (CD₃OD) δ ppm 0.75-0.97 (m, 4 H) 1.97 (m, 1 H) 2.60 (s, 1 H) 2.84 (br. s., 1 H) 3.35 (br. s., 2 H) 3.82 (br. s., 1 H) 3.92-4.36 (m, 3 H) 4.41-4.84 (m, 2 H) 5.35 (s, 2 H) 7.40 (t, J = 8.91 Hz, 1 H) 7.73-7.96 (m, 2 H) |
| E293 | 2-Fluoro-5-(((2-(3-methylbutanoyl)-9-oxo-2,3,4,9,11,11a-hexahydro-1H pyrazino[1',2':3,4]imidazo[1,2-c]pyrimidin-7-yl)oxy)methyl)benzonitrile | 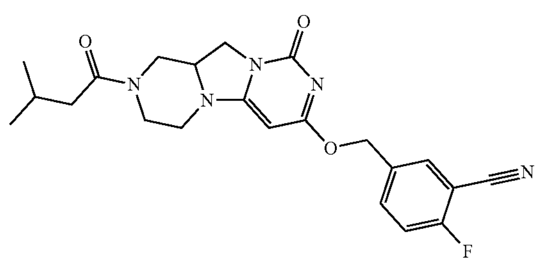 [SMILES: CC(C)CC(=O)N1CCN2c3cc(OCc4ccc(F)c(C#N)c4)nc(=O)n3CC2C1] | B | 0.75 | 426.1 | (CD₃OD) δ ppm 1.02 (d, J = 6.3 Hz, 6 H) 2.12 (sept, J = 6.3 Hz, 1 H) 2.31-2.46 (m, 2 H) 2.79-2.94 (m, 1 H) 3.30-3.53 (m, 2 H) 3.84-3.95 (m, 1 H) 4.10 (d, J = 13.05 Hz, 1 H) 4.23 (d, J = 11.29 Hz, 1 H) 4.27-4.46 (m, 2 H) 4.73-4.94 (m, 2 H) 5.43 (s, 2 H) 7.48 (t, J = 8.91 Hz, 1 H) 7.83-7.98 (m, 2 H) |
| E294 | 2-Fluoro-5-(((9-oxo-2-pivaloyl-2,3,4,9,11,11a-hexahydro-1H-pyrazino[1',2':3,4]imidazo[1,2-c]pyrimidin-7-yl)oxy)methyl)benzonitrile 2,2,2-trifluoroacetate | 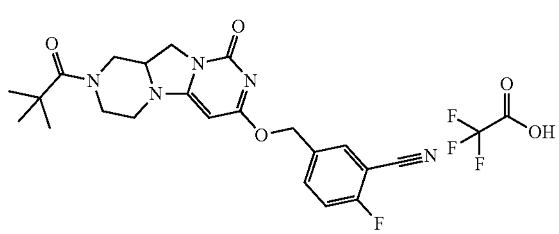 | B | 0.74 | 426.0 | (CD₃OD) δ ppm 1.33 (s, 9 H) 2.95-3.16 (m, 2 H) 3.33-3.42 (m, 1 H) 3.85 (dd, J = 11.80, 7.28 Hz, 1 H) 3.96 (br. d, J = 13.30 Hz, 1 H) 4.11-4.27 (m, 1 H) 4.28-4.39 (m, 1 H) 4.59 (br. d, J = 13.55 Hz, 1 H) 4.72-4.79 (m, 2 |

TABLE 3-continued

| Ex # | Name | Structure | Method Used | LC/MS ret. Time (min) | MS | ¹H NMR (400 MHz) |
|---|---|---|---|---|---|---|
| | | | | | | H) 5.40 (s, 2 H) 7.41 (t, J = 8.91 Hz, 1 H) 7.76-7.92 (m, 2 H) |
| E295 | 2-Fluoro-5-(((2-(isopropylsulfonyl)-9-oxo-2,3,4,9,11,11a-hexahydro-1H-pyrazino[1',2':3,4]imidazo[1,2-c]pyrimidin-7-yl)oxy)methyl)benzonitrile 2,2,2-trifluoroacetate | 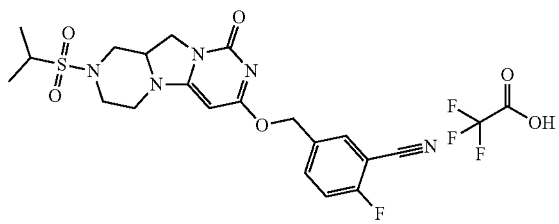 | D | 0.71 | 448.2 | (CD$_3$OD) δ ppm 1.37 (d, J = 6.78 Hz, 6 H) 3.11-3.27 (m, 2 H) 3.35-3.44 (m, 1 H) 3.44-3.56 (m, 1 H) 3.85 (m, 1 H) 3.90-4.02 (m, 1 H) 4.02-4.20 (m, 2 H) 4.27-4.44 (m, 2 H) 5.42 (s, 2 H) 7.48 (t, J = 8.78 Hz, 1 H) 7.87 (td, J = 5.52, 2.51 Hz, 1 H) 7.94 (d, J = 6.02 Hz, 1 H) |
| E296 | 5-(((2-(Cyclopropyl-sulfonyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile 2,2,2-trifluoroacetate | 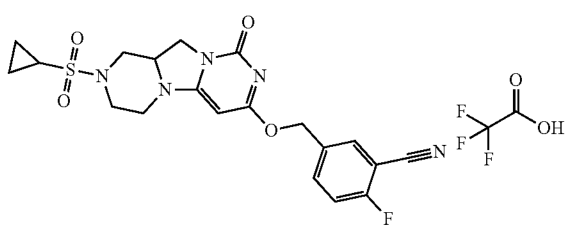 | D | 0.7 | 446.1 | (CD$_3$OD) δ ppm 1.00-1.19 (m, 4 H) 2.50-2.63 (m, 1 H) 3.06-3.20 (m, 2 H) 3.52 (td, J = 12.80, 3.51 Hz, 1 H) 3.84-3.97 (m, 2 H) 4.11 (d, J = 13.30 Hz, 2 H) 4.32-4.45 (m, 2 H) 5.36-5.48 (m, 2 H) 5.96 (s, 1 H) 7.47 (t, J = 8.91 Hz, 1 H) 7.83-7.90 (m, 1 H) 7.93 (d, J = 6.02 Hz, 1 H) |
| E297 | 5-(((2-(1-Aminocyclo-propanecarbonyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile 2,2,2-trifluoroacetate | 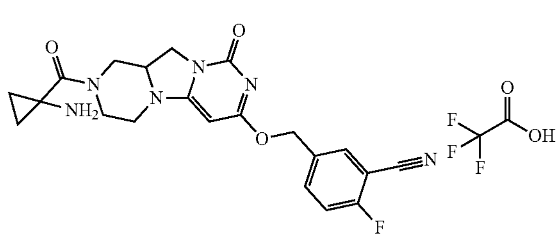 | C | 0.55 | 425.0 | (CD$_3$OD) δ ppm 1.36-1.50 (m, 4 H) 2.68 (s, 3H) 3.25 (m., 2H) 3.47-3.59 (m, 1 H) 3.91 (m, 1 H) 4.07-4.21 (m, 1 H) 4.30-4.45 (m, 2 H) 4.47- |

TABLE 3-continued

| Ex # | Name | Structure | Method Used | LC/MS ret. Time (min) | MS | 1H NMR (400 MHz) |
|---|---|---|---|---|---|---|
| | | | | | | 4.54 (m, 1 H) 4.61-4.72 (m, 1 H) 5.43 (s, 2 H) 6.07 (s, 1 H) 7.48 (t, J = 8.91 Hz, 1 H) 7.88 (m, 1 H) 7.95 (dd, J = 6.02, 2.26 Hz, 1 H) |
| E298 | 5-(((2-(3-Amino-3-methylbutanoyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile 2,2,2-trifluoroacetate | 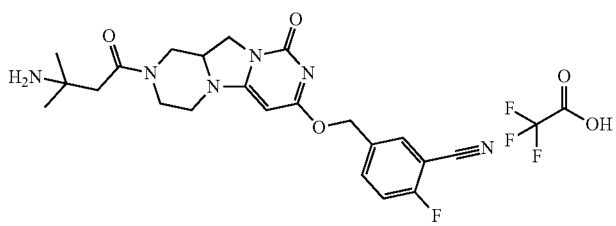 | C | 0.56 | 441.2 | (CD$_3$OD) δ ppm 1.33 (d, J = 8.53 Hz, 6 H) 2.55 (s, 3 H) 2.63-2.84 (m, 3 H) 3.22-3.42 (m, 2 H) 3.71-3.81 (m, 1 H) 3.94-4.31 (m, 4 H) 4.61-4.85 (m, 1 H) 5.29 (s, 2 H) 5.93 (d, J = 7.53 Hz, 1 H) 7.35 (t, J = 8.91 Hz, 1 H) 7.74 (ddd, J = 8.53, 5.14, 2.13 Hz, 1 H) 7.81 (dd, J = 6.02, 2.26 Hz, 1 H) |
| E299 | 2-Acetyl-7-((3,5-difluoro-4-((6-methylpyridin-3-yl)oxy)benzyl)oxy)-3,4,11,11a-tetrahydro-1H-pyrazino[1',2':3,4]imidazo[1,2-c]pyrimidin-9(2H)-one | 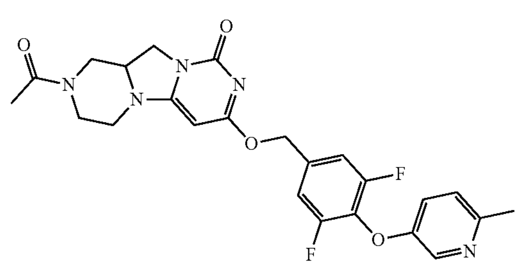 [SMILES: CC(=O)N1CCN2c3cc(OCc4cc(F)c(Oc5ccc(C)nc5)c(F)c4)nc(=O)n3CC2C1] | B | 0.59 | 484.1 | (CDCl$_3$) δ ppm 2.20 (s, 3 H) 2.54 (s, 3 H) 2.56-2.80 (m, 1 H) 3.11-3.36 (m, 2 H) 3.56 (m., 1 H) 3.80 (dd, J = 12.05, 6.27 Hz, 1 H) 3.84-4.06 (m, 2 H) 4.26 (d, J = 11.04 Hz, 1 H) 4.72-4.94 (m, 1 H) 5.11 (d, J = 10.79 Hz, 1 H) 5.41 (m, 2 H) 7.01-7.20 (m, 4 H) 8.29 (d, J = 2.51 Hz, 1 H) |

TABLE 3-continued

| Ex # | Name | Structure | Method Used | LC/MS ret. Time (min) | MS | ¹H NMR (400 MHz) |
|---|---|---|---|---|---|---|
| E300 | Methyl 7-((3,4-difluorobenzyl)oxy)-9-oxo-3,4,11,11a-tetrahydro-1H-pyrazino[1',2':3,4]imidazo[1,2-c]pyrimidine-2(9H)-carboxylate | 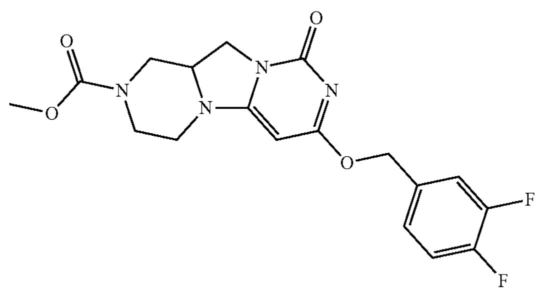 [SMILES: COC(=O)N1CCN2c3cc(OCc4ccc(F)c(F)c4)nc(=O)n3CC2C1] | B | 0.71 | 393.0 | (CDCl₃) δ ppm 2.76-3.02 (m, 2 H) 3.21 (m, 1 H) 3.46 (m, 1 H) 3.67-3.81 (m, 4 H) 3.91 (m, 1 H) 4.13-4.43 (m, 3 H) 5.04 (s, 1 H) 5.28-5.40 (m, 2 H) 7.10-7.26 (m, 3 H) |
| E301 | 7-((3,4-Difluorobenzyl)oxy)-N,N-dimethyl-9-oxo-3,4,11,11a-tetrahydro-1H-pyrazino[1',2':3,4]imidazo[1,2-c]pyrimidine-2(9H)-carboxamide | 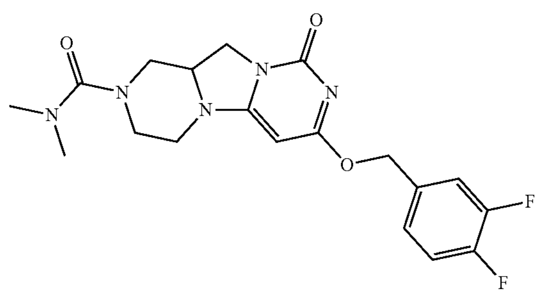 [SMILES: CN(C)C(=O)N1CCN2c3cc(OCc4ccc(F)c(F)c4)nc(=O)n3CC2C1] | B | 0.65 | 406.1 | (CDCl₃) δ ppm 2.77-3.02 (m, 8 H) 3.33 (dd, J = 12.05, 3.26 Hz, 1 H) 3.37-3.48 (m, 1 H) 3.64-3.82 (m, 3 H) 3.96-4.08 (m, 1 H) 4.21 (dd, J = 11.80, 8.78 Hz, 1 H) 5.02 (s, 1 H) 5.27-5.41 (m, 2 H) 7.11-7.26 (m, 3 H) |
| E302 | 5-(((2-(Cyclobutane-carbonyl)-9-oxo-2,3,4,9,11,11a-hexahydro-1H-pyrazino[1',2':3,4]imidazo[1,2-c]pyrimidin-7-yl)oxy)methyl)-2-fluorobenzonitrile | 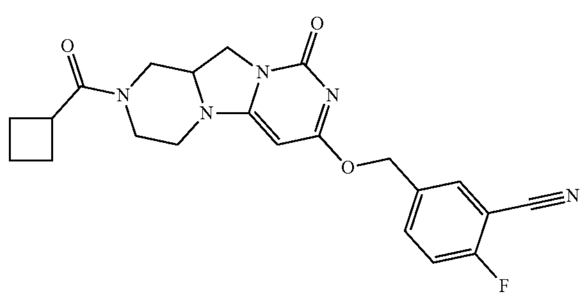 [SMILES: N#Cc1cc(COc2cc3n(c(=O)n2)CC2CN(C(=O)C4CCC4)CCN32)ccc1F] | E | 0.71 | 424.1 | (CDCl₃) δ ppm 1.85-2.12 (m, 2 H) 2.22 (m, 2 H) 2.38 (m, 2 H) 2.54-2.80 (m, 1 H) 3.00-3.38 (m, 3 H) 3.52 (d, J = 10.29 Hz, 1 H) 3.67-3.95 (m, 3 H) 4.23 (dd, J = 11.80, 8.53 Hz, 1 H) 4.67-4.94 (m, 1 H) 5.06 (d, J = 14.05 Hz, 1 H) 5.35-5.51 (m, 2 H) 7.22 (t, J = 8.53 Hz, 1 H) 7.61-7.72 (m, 2 H) |

TABLE 3-continued

| Ex # | Name | Structure | Method Used | LC/MS ret. Time (min) | MS | ¹H NMR (400 MHz) |
|---|---|---|---|---|---|---|
| E303 | 1-(7-((3,4-Difluorobenzyl)oxy)-9-oxo-3,4,11,11a-tetrahydro-1H-pyrazino[1',2':3,4]imidazo[1,2-c]pyrimidin-2(9H)-yl)-3-methylbutane-1,2-dione | 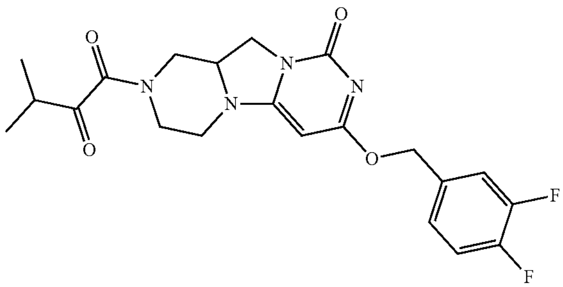 [SMILES: CC(C)C(=O)C(=O)N1CCN2c3cc(OCc4ccc(F)c(F)c4)nc(=O)n3CC2C1] | E | 0.83 | 433.2 | $(CD_2Cl_2)$ δ ppm 1.17 (t, J = 7.65 Hz, 6 H) 2.73-2.94 (m, 1 H) 3.08-3.34 (m, 3 H) 3.48-3.91 (m, 3 H) 3.91-4.08 (m, 1 H) 4.08-4.26 (m, 1 H) 4.57-4.77 (m, 1 H) 5.10 (m, 1 H) 5.30-5.36 (m, 2 H) 7.13-7.25 (m, 2 H) 7.25-7.35 (m, 1 H) |
| E304 | 7-((3,4-Difluorobenzyl)oxy)-2-propyl-3,4,11,11a-tetrahydro-1H-pyrazino[1',2':3,4]imidazo[1,2-c]pyrimidin-9(2H)-one | 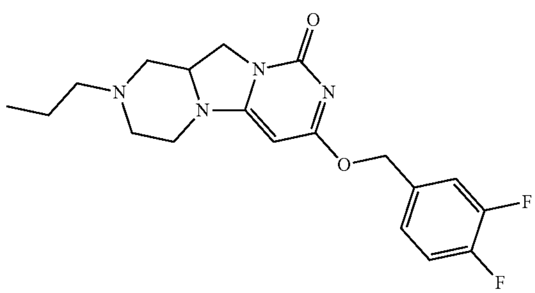 [SMILES: CCCN1CCN2c3cc(OCc4ccc(F)c(F)c4)nc(=O)n3CC2C1] | A | 0.63 | 377.1 | $(CD_2Cl_2)$ δ ppm 0.93 (t, J = 7.28 Hz, 3 H) 1.52 (sxt, J = 7.38 Hz, 2 H) 1.96-2.07 (m, 1 H) 2.12 (td, J = 11.67, 3.51 Hz, 1 H) 2.38 (m, 2 H) 2.85 (d, J = 11.54 Hz, 1 H) 2.99 (dd, J = 11.17, 2.38 Hz, 1 H) 3.29 (td, J = 12.55, 3.51 Hz, 1 H) 3.42-3.51 (m, 1 H) 3.67 (dd, J = 11.42, 5.65 Hz, 1 H) 3.95-4.07 (m, 1 H) 4.07-4.16 (m, 1 H) 5.02 (s, 1 H) 5.34 (m, 2 H) 7.07-7.26 (m, 2 H) 7.26-7.35 (m, 1 H) |
| E305 | 7-((3,4-Difluorobenzyl)oxy)-2-isobutyl-3,4,11,11a-tetrahydro-1H-pyrazino[1',2':3,4]imidazo[1,2-c]pyrimidin-9(2H)-one | 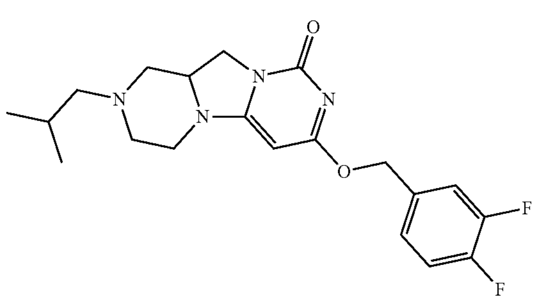 [SMILES: CC(C)CN1CCN2c3cc(OCc4ccc(F)c(F)c4)nc(=O)n3CC2C1] | A | 0.63 | 391.2 | $(CD_2Cl_2)$ δ ppm 0.93 (d, J = 6.53 Hz, 6 H) 1.75-1.87 (m, 1 H) 1.98-2.19 (m, 4 H) 2.78-2.85 (m, 1 H) 2.91-3.00 (m, 1 H) 3.25-3.34 (m, 1 |

TABLE 3-continued

| Ex # | Name | Structure | Method Used | LC/MS ret. Time (min) | MS | ¹H NMR (400 MHz) |
|---|---|---|---|---|---|---|
| | | | | | | H) 3.41-3.50 (m, 1 H) 3.61-3.72 (m, 1 H) 3.97-4.07 (m, 1 H) 4.06-4.16 (m, 1 H) 5.02 (s, 1 H) 7.15-7.24 (m, 2 H) 7.25-7.34 (m, 1 H); |
| E306 | Ethyl 7-((3,4-difluorobenzyl)oxy)-9-oxo-3,4,11,11a-tetrahydro-1H-pyrazino[1',2':3,4]imidazo[1,2-c]pyrimidine-2(9H)-carboxylate | 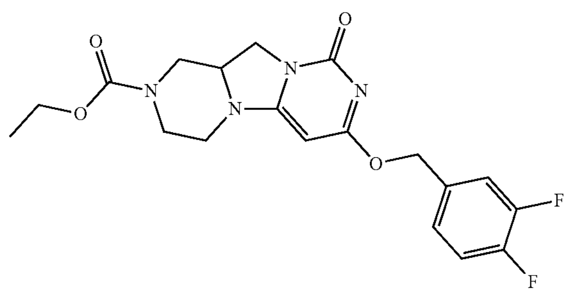 [SMILES: CCOC(=O)N1CCN2c3cc(OCc4ccc(F)c(F)c4)nc(=O)n3CC2C1] | B | 0.76 | 407.1 | (CDCl₃) δ ppm 1.25-1.35 (m, 3 H) 2.77-3.02 (m, 2 H) 3.22 (td, J = 12.61, 3.39 Hz, 1 H) 3.47 (m, 1 H) 3.75 (dd, J = 11.80, 6.53 Hz, 1 H) 3.84-3.98 (m, 1 H) 4.11-4.49 (m, 5 H) 5.05 (s, 1 H) 5.27-5.46 (m, 2 H) 7.09-7.28 (m, 3 H) |
| E307 | Isopropyl 7-((3,4-difluorobenzyl)oxy)-9-oxo-3,4,11,11a-tetrahydro-1H-pyrazino[1',2':3,4]imidazo[1,2-c]pyrimidine-2(9H)-carboxylate | 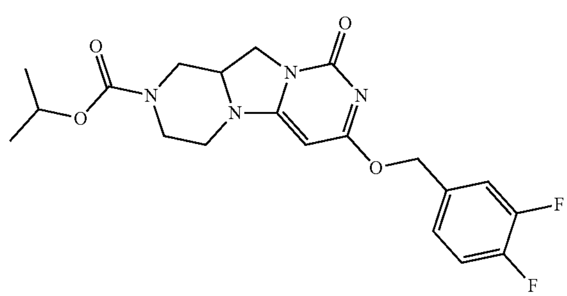 [SMILES: CC(C)OC(=O)N1CCN2c3cc(OCc4ccc(F)c(F)c4)nc(=O)n3CC2C1] | B | 0.82 | 421.3 | (CDCl₃) δ ppm 1.30 (d, J = 6.27 Hz, 6 H) 2.73-3.00 (m, 2 H) 3.14-3.28 (m, 1 H) 3.42-3.54 (m, 1 H) 3.75 (dd, J = 11.80, 6.53 Hz, 1 H) 3.85-3.98 (m, 1 H) 4.19-4.40 (m, 3 H) 4.93-5.02 (m, 1 H) 5.05 (s, 1 H) 5.37 (m, 2 H) 7.10-7.27 (m, 3 H) |

TABLE 3-continued

| Ex # | Name | Structure | Method Used | LC/MS ret. Time (min) | MS | ¹H NMR (400 MHz) |
|---|---|---|---|---|---|---|
| E308 | 7-((3,4-Difluorobenzyl)oxy)-2-(1-(methylamino)cyclopropane-carbonyl)-3,4,11,11a-tetrahydro-1H-pyrazino[1',2':3,4]imidazo[1,2-c]pyrimidin-9(2H)-one | 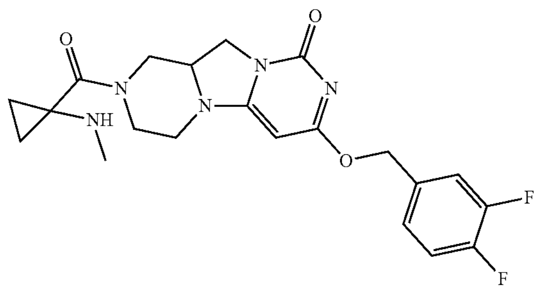 [SMILES: CNC1(C(=O)N2CCN3c4cc(OCc5ccc(F)c(F)c5)nc(=O)n4CC3C2)CC1] | C | 0.57 | 432.2 | (CD$_2$Cl$_2$) δ ppm 0.79 (br. s., 2 H) 1.07 (br. s., 2 H) 2.39 (s, 3 H) 2.79-3.05 (m, 2 H) 3.20-3.33 (m, 1 H) 3.47-3.59 (m, 1 H) 3.67-3.80 (m, 1 H) 3.91-4.05 (m, 1 H) 4.12-4.24 (m, 1 H) 4.59-4.73 (m, 1 H) 4.73-4.87 (m, 1 H) 5.08 (s, 1 H) 7.21 (m, 2 H) 7.25-7.36 (m, 1 H) |

E309

Method F 7-((3,4-Difluorobenzyl)amino)-2-(methylsulfonyl)-3,4,11,11a-tetrahydro-1H-pyrazino[1',2':3,4]imidazo[1,2-c]pyrimidin-9(2H)-one

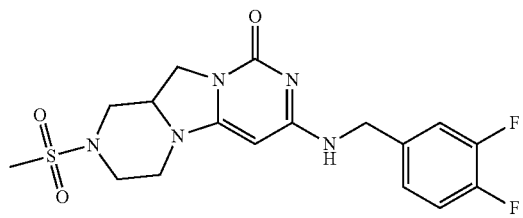 [SMILES: CS(=O)(=O)N1CCN2c3cc(NCc4ccc(F)c(F)c4)nc(=O)n3CC2C1]

To 7-chloro-3,4,11,11a-tetrahydro-1H-pyrazino[1',2':3,4]imidazo[1,2-c]pyrimidin-9(2H)-one (444 mg, 1.959 mmol) in DCM (15 mL) at 0° C. was added TEA (1.5 mL, 10.76 mmol) and then MsCl (0.19 mL, 2.438 mmol) dropwise. The reaction was stirred for 5 hrs, and then concentrated. The crude product was purified on a Combiflash silica cartridge (12 g) (0-5% MeOH/DCM) to give the intermediate 7-chloro-2-(methylsulfonyl)-3,4,11,11a-tetrahydro-1Hpyrazino[1',2':3,4]imidazo[1,2-c]pyrimidin-9(2H)-one (665 mg, 0.873 mmol, 44.6% yield) as an amorphous tan solid. (LC/MS: m/z 304.9 (M+H)⁺, 0.41 min (ret. time)) A mixture of the intermediate (0.151 mL, 0.368 mmol), (3,4-difluorophenyl)methanamine (0.13 mL, 1.099 mmol) and DIPEA (0.32 mL, 1.832 mmol) in 1-Butanol (1.8 mL) (in three portions), and added to a microwave vial and the reaction vessel was sealed and heated in Biotage Initiator using initial high to 120° C. for 30 min. After cooling the reaction, the mixture was concentrated The crude was purified on a Combiflash silica cartridge (12 g) [0-20% (10% NH$_4$OH/MeOH)/DCM] then by prep reverse phase HPLC [10-90% CH$_3$CN/H$_2$O (0.1% NH$_4$OH)] to give the title compound (18 mg, 0.044 mmol, 11.90% yield) as an amorphous white solid.

LC/MS: m/z 412.2 (M+H)⁺, 0.59 min (ret. time).

¹H NMR (400 MHz, CD$_3$OD): δ 2.76-2.97 (m, 5H) 3.25-3.31 (m, 1H) 3.64-3.77 (m, 3H) 3.90 (d, J=11.80 Hz, 1H) 3.99-4.18 (m, 2H) 4.52 (br. s., 2H) 5.08 (s, 1H) 7.08-7.31 (m, 3H)

E310

Method G 7-((3,4-Difluorobenzyl)oxy)-2-isobutyryl-3,4,11,11a-tetrahydro-1Hpyrazino[1',2':3,4] imidazo[1,2-c]pyrimidin-9(2H)-one

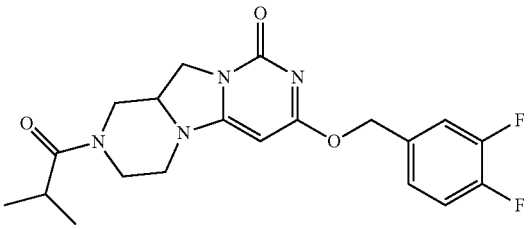 [SMILES: CC(C)C(=O)N1CCN2c3cc(OCc4ccc(F)c(F)c4)nc(=O)n3CC2C1]

The title compound was prepared by a procedure similar to that described for E310 starting from 7-chloro-3,4,11,11a-tetrahydro-1H-pyrazino[1',2':3,4]imidazo[1,2-c]pyrimidin-9(2H)-one and isobutyryl chloride.

LC/MS: m/z 405.0 (M+H)⁺, 0.73 min (ret. time).

¹H NMR (400 MHz, CD$_2$Cl$_2$) δ ppm 1.12 (br. s., 6H) 2.45-2.87 (m, 2H) 2.98-3.28 (m, 2H) 3.51 (d, J=10.54 Hz, 1H) 3.69 (dd, J=11.67, 6.40 Hz, 1H) 3.77-4.23 (m, 3H) 4.55-4.93 (m, 1H) 5.05 (s, 1H) 5.25-5.37 (m, 2H) 7.07-7.33 (m, 3H)

The following compounds E311-E315 listed in Table 4 were prepared by a procedure similar to that described for E309-E310 starting from the requisite acid chloride or sulfonyl chloride, and benzyl alcohol or benzyl amine:

TABLE 4

| Ex# | Name | Structure | Method Used | LC/MS ret. Time | MS | $^1$H NMR (400 MHz) |
|---|---|---|---|---|---|---|
| E311 | 7-((2,3-Difluoro-benzyl)amino)-2-(methyl-sulfonyl)-3,4,11,11a-tetrahydro-1H-pyrazino[1',2':3,4]imidazo[1,2-c]pyrimidin-9(2H)-one | 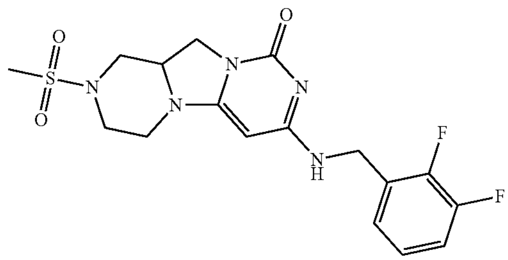 [SMILES: CS(=O)(=O)N1CCN2c3cc(NCc4cccc(F)c4F)nc(=O)n3CC2C1] | F | 0.59 | 412.2 | (CD$_3$OD) δ ppm 2.76-2.97 (m, 5 H) 3.27-3.31 (m, 1H) 3.65-3.79 (m, 3 H) 3.91 (d, J = 12.05 Hz, 1 H) 4.00-4.17 (m, 2 H) 4.64 (br. s., 2 H) 5.11 (br. s., 1 H) 7.06-7.25 (m, 3 H) |
| E312 | 2-Fluoro-5-(((2-(methyl-sulfonyl)-9-oxo-2,3,4,9,11,11a-hexahydro-1H-pyrazino[1',2':3,4]imidazo[1,2-c]pyrimidin-7-yl)amino)methyl)benzonitrile | 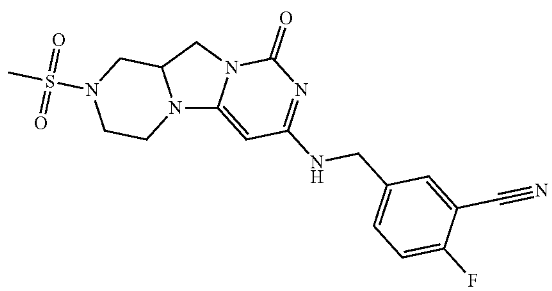 [SMILES: CS(=O)(=O)N1CCN2c3cc(NCc4ccc(F)c(C#N)c4)nc(=O)n3CC2C1] | F | 0.55 | 419.0 | (DMSO-d$_6$) δ ppm 2.67-2.87 (m, 2 H) 2.92 (s, 3 H) 3.15-3.25 (m, 1 H) 3.49-3.58 (m, 2 H) 3.61-3.75 (m, 2 H) 3.88-3.99 (m, 2 H) 4.42-4.54 (m, 2 H) 4.95-5.03 (m, 1 H) 7.46-7.54 (m, 1 H) 7.56-7.65 (m, 1 H) 7.66-7.73 (m, 1 H) 7.74-7.83 (m, 1 H) |
| E313 | 7-((3,4-Difluoro-benzyl)oxy)-2-(methyl-sulfonyl)-3,4,11,11a-tetrahydro-1H-pyrazino[1',2':3,4]imidazo[1,2-c]pyrimidin-9(2H)-one | 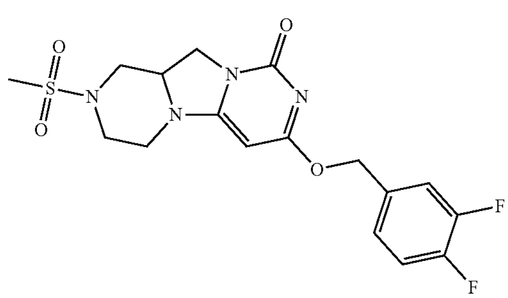 [SMILES: CS(=O)(=O)N1CCN2c3cc(OCc4ccc(F)c(F)c4)nc(=O)n3CC2C1] | G | 0.65 | 413.2 | (CHLOROFORM-d) δ ppm 2.70-2.95 (m, 5 H) 3.34-3.49 (m, 1 H) 3.59 (d, J = 13.30 Hz, 1 H) 3.80 (dd, J = 11.80, 5.52 Hz, 1 H) 3.87 (d, J = 11.04 Hz, 1 H) 3.98 (d, J = 12.05 Hz, 1 H) 4.04-4.19 (m, 1 H) 4.25 (dd, J = 11.42, 8.91 Hz, 1 H) 5.07 (s, 1 H) 5.30- |

TABLE 4-continued

| Ex# | Name | Structure | Method Used | LC/MS ret. Time | MS | ¹H NMR (400 MHz) |
|---|---|---|---|---|---|---|
| | | | | | | 5.45 (m, 2 H) 7.10-7.28 (m, 3 H) |
| E314 | 5-(((2-Acetyl-9-oxo-2,3,4,9,11,11a-hexahydro-1H-pyrazino[1',2':3,4]imidazo[1,2-c]pyrimidin-7-yl)amino)methyl)-2-fluoro-benzonitrile | 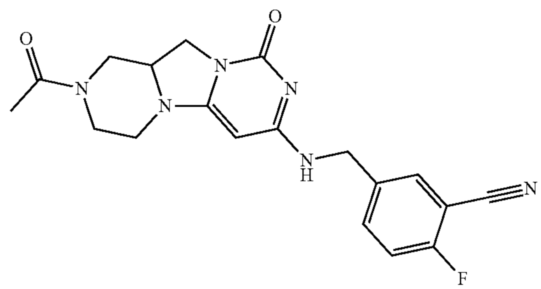 [SMILES: CC(=O)N1CCN2c3cc(NCc4ccc(F)c(C#N)c4)nc(=O)n3CC2C1] | F | 0.53 | 383.0 | (CD$_3$CN, D$_2$O) δ ppm 2.09 (s, 3 H) 2.61 (s, 1 H) 3.00-3.24 (m, 2 H) 3.54-3.64 (m, 2 H) 3.78-4.10 (m, 3 H) 4.47 (br. s., 3 H) 4.99 (br. s., 1 H) 7.31 (t, J = 8.91 Hz, 1 H) 7.61-7.76 (m, 2 H) |
| E315 | 2-Acetyl-7-((3,4-difluoro-benzyl)oxy)-3,4,11,11a-tetrahydro-1H-pyrazino[1',2':3,4]imidazo[1,2-c]pyrimidin-9(2H)-one | 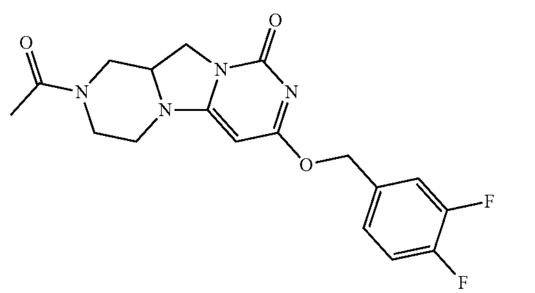 [SMILES: CC(=O)N1CCN2c3cc(OCc4ccc(F)c(F)c4)nc(=O)n3CC2C1] | G | 0.63 | 377.0 | (D$_2$O) δ ppm 2.55-2.63 (m, 1 H) 2.71 (s, 3 H) 3.21-3.41 (m, 1 H) 3.66-3.91 (m, 2 H) 4.16-4.34 (m, 2 H) 4.44-4.73 (m, 3 H) 4.99-5.23 (m, 1 H) 5.79-5.91 (m, 3 H) 7.80-8.00 (m, 3 H) |

E316

2-Cyclobutoxy-5-(((9-oxo-2,3,4,9,11,11a-hexahydro-1H-pyrazino[1',2':3,4]imidazo[1,2-c]pyrimidin-7-yl)oxy)methyl)benzonitrile

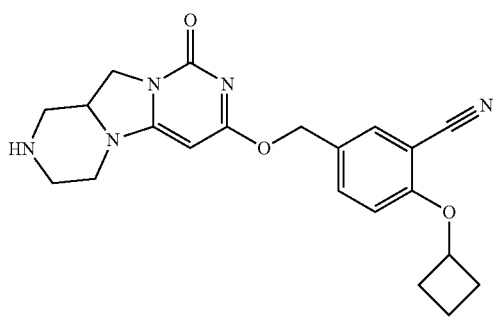 [SMILES: N#Cc1cc(COc2cc3n(c(=O)n2)CC2CNCCN32)ccc1OC1CCC1]

To an ice-cold solution of 2-cyclobutoxy-5-formylbenzonitrile (0.06 g, 0.298 mmol) in 2-MeTHF (0.550 mL) was added a fresh solution of NaBH$_4$ (0.017 g, 0.447 mmol) in 0.1% wt. NaOH in water (4.5 mL) and the reaction was stirred for 1 h. The mixture was quenched with saturated NH$_4$Cl. The aqueous layer was extracted with EtOAc (3 times). The combined organics were washed with brine, dried (anhydrous Na$_2$SO$_4$), filtered, and concentrated under reduced pressure to provide the benzyl alcohol. To a solution of the benzyl alcohol, tert-Butyl 7-chloro-9-oxo-3,4,11,11a-tetrahydro-1H-pyrazino[1',2':3,4]imidazo[1,2-c] pyrimidine-2(9H)-carboxylate (0.132 g, 0.298 mmol) in 2-MeTHF (1.832 mL) was added NaH (0.030 g, 0.745 mmol) and the reaction was stirred at room temperature for 1 h. The reaction was quenched by addition of saturated NH$_4$Cl. The layers were separated and the aqueous layer was extracted with EtOAc (3 times). The combined organic layers were concentrated. The crude was purified on a Combiflash silica cartridge (12 g) (0-15% MeOH/DCM) to give the intermediate tert-butyl 7-((3-cyano-4-cyclobutoxybenzyl)oxy)-9-oxo-3,4,11,11a-tetrahydro-1Hpyrazino[1',2':3,4]imidazo [1,2 c] pyrimidine-2(9H)-carboxylate (170 mg, 0.148 mmol, 49.7% yield) as a glassy solid film. (LC/MS: m/z 494.2 (M+H)$^+$, 0.96 min (ret. time)) To this intermediate (130 mg, 0.263 mmol) was added HCl (3M in CPME) (878 μl, 2.63 mmol). The mixture was stirred for 1 h and then concentrated. The crude was purified by prep reverse phase [10-90% CH$_3$CN/H$_2$O (0.1% NH$_4$OH)] to give the title compound (15 mg, 0.038 mmol, 14.47% yield) as an amorphous white powder.

LC/MS: m/z 394.1 (M+H)⁺, 0.68 min (ret. time).

¹H NMR (400 MHz, CDCl₃): δ ppm 1.63-1.81 (m, 2H) 1.91 (q, J=10.29 Hz, 1H) 2.26 (quin, J=9.85 Hz, 2H) 2.41-2.53 (m, 2H) 2.60-2.83 (m, 2H) 3.02 (d, J=12.05 Hz, 1H) 3.13-3.28 (m, 2H) 3.42 (d, J=11.54 Hz, 1H) 3.68 (dd, J=11.54, 6.53 Hz, 1H) 3.92 (d, J=8.78 Hz, 1H) 4.17 (dd, J=11.29, 9.03 Hz, 1H) 4.72 (quin, J=7.03 Hz, 1H) 4.96 (s, 1H) 5.24-5.39 (m, 2H) 6.78 (d, J=8.78 Hz, 1H) 7.53 (d, J=8.78 Hz, 1H) 7.59 (s, 1H)

E317

2-(Cyclopentyloxy)-5-(((9-oxo-2,3,4,9,11,11a-hexahydro-1H-pyrazino[1,2':3,4]imidazo[1,2-c]pyrimidin-7-yl)oxy)methyl)benzonitrile

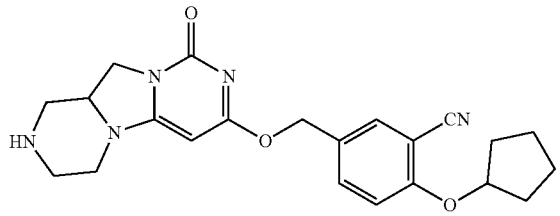 [SMILES: N#Cc1cc(COc2cc3n(c(=O)n2)CC2CNCCN32)ccc1OC1CCCC1]

The title compound was prepared by a procedure similar to that described for E316 starting from 2-(cyclopentyloxy)-5-formylbenzonitrile and tert-butyl 7-chloro-9-oxo-3,4,11,11a-tetrahydro-1H-pyrazino[1',2':3,4]imidazo[1,2-c]pyrimidine-2(9H)-carboxylate.

LC/MS: m/z 408.0 (M+H)⁺, 0.72 min (ret. time).

¹H NMR (400 MHz, CDCl₃): δ ppm 1.54-2.00 (m, 8H) 2.71-3.00 (m, 2H) 3.11-3.57 (m, 4H) 3.71 (d, J=6.02 Hz, 1H) 4.17 (d, J=9.54 Hz, 2H) 4.85 (br. s., 1H) 5.02 (s, 1H) 5.20-5.35 (m, 2H) 6.93 (d, J=8.78 Hz, 1H) 7.46-7.62 (m, 2H)

E318

7-(2,3-Difluorophenethyl)-3,4,11,11a-tetrahydro-1H-pyrazino[1',2':3,4]imidazo[1,2-c]pyrimidin-9(2H)-one

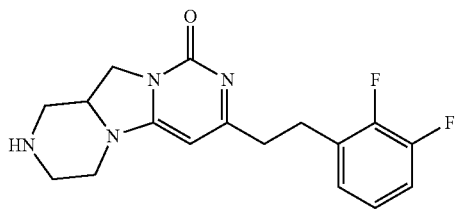 [SMILES: O=c1nc(CCc2cccc(F)c2F)cc2n1CC1CNCCN21]

A solution of tert-butyl 7-((2,3-difluorophenyl)ethynyl)-9-oxo-3,4,11,11a-tetrahydro-1H-pyrazino[1',2':3,4]imidazo[1,2-c]pyrimidine-2(9H)-carboxylate (40 mg, 0.093 mmol) and palladium on carbon (10%) (1.987 mg, 1.867 μmol) in methanol (5 mL) was placed under H₂ (balloon) at room temperature for 1 h. The reaction was filtered through celite. The filtrate was concentrated and then dissolved in TFA (0.5 mL, 6.49 mmol). The mixture was then stirred for 5 min at room temperature and concentrated. The crude was purified by reverse phase prep HPLC [10-90% CH₃CN/H₂O (0.1% TFA] to give the title compound (22 mg, 0.066 mmol, 70.9% yield) as an amorphous white solid.

LC/MS: m/z 333.3 (M+H)⁺, 0.45 min (ret. time).

¹H NMR (400 MHz, CDCl₃): δ ppm 1.81 (br. s., 1H) 2.61-2.82 (m, 4H) 2.97-3.14 (m, 3H) 3.13-3.30 (m, 2H) 3.38-3.53 (m, 1H) 3.72 (dd, J=12.05, 6.78 Hz, 1H) 3.87-4.05 (m, 1H) 4.21 (dd, J=11.80, 9.54 Hz, 1H) 5.31 (s, 1H) 6.88-7.08 (m, 3H)

E319

2-Fluoro-5-(((9-oxo-2,3,4,9,11,11a-hexahydro-1H-pyrazino[1',2':3,4]imidazo[1,2-c]pyrimidin-7-yl)amino)methyl)benzonitrile hydrochloride

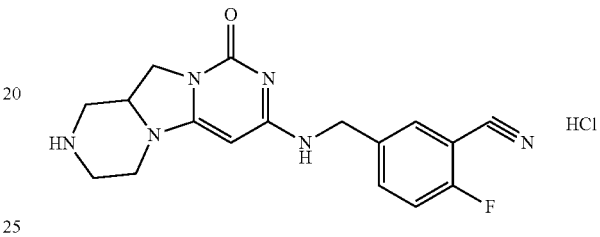

A mixture of tert-Butyl 7-chloro-9-oxo-3,4,11,11a-tetrahydro-1H-pyrazino[1',2':3,4]imidazo[1,2-c] pyrimidine-2(9H)-carboxylate (200 mg, 0.612 mmol), (3,4-difluorophenyl)methanamine (0.13 mL, 1.099 mmol) and DIPEA (0.32 mL, 1.832 mmol) in 1-butanol (3 mL) was added to a microwave vial and the reaction vessel was sealed and heated in Biotage Initiator to 120° C. for 30 min. After cooling to room temperature, the mixture was concentrated and the crude was purified on a Combiflash silica cartridge (12 g) [0-20% MeOH (10% NH₄OH)/DCM] to give the N-Boc protected product. The intermediate was dissolved in HCl (4N in dioxane) (1.530 mL, 6.12 mmol) and stirred for 30 min at room temperature. The reaction was concentrated and the crude was purified by reverse phase prep HPLC (10-90% CH₃CN/H₂O) to give the title compound (40 mg, 0.106 mmol, 17.34% yield) as a lightly colored amorphous solid.

LC/MS: m/z 341.0 (M+H)⁺, 0.32 min (ret. time).

¹H NMR (400 MHz, CD₃CN): δ 1.53 (d, J=5.27 Hz, 2H) 3.28-3.47 (m, 2H) 3.67-3.97 (m, 3H) 4.07 (dd, J=11.29, 6.78 Hz, 1H) 4.19 (dd, J=14.31, 3.01 Hz, 1H) 4.54 (t, J=10.42 Hz, 1H) 4.68 (d, J=9.03 Hz, 1H) 4.79 (s, 2H) 5.45 (br. s., 1H) 7.61 (t, J=8.78 Hz, 1H) 7.84-8.02 (m, 2H)

E320

7-((3,4-Difluorobenzyl)oxy)-2-methyl-3,4,11,11a-tetrahydro-1H-pyrazino[1,2':3,4]imidazo[1,2-c]pyrimidin-9(2H)-one

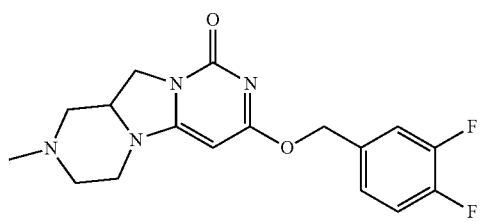 [SMILES: CN1CCN2c3cc(OCc4ccc(F)c(F)c4)nc(=O)n3CC2C1]

349

To a solution of 7-((3,4-difluorobenzyl)oxy)-3,4,11,11a-tetrahydro-1H-pyrazino[1',2':3,4]imidazo[1,2-c]pyrimidin-9(2H)-one (20 mg, 0.060 mmol) in DCM (0.5 mL) was added DIPEA (0.03 mL, 0.172 mmol) then MeI (0.01 mL, 0.160 mmol) at room temperature. The reaction was stirred at room temperature for 1.5 hrs, then diluted with DCM and quenched by addition of saturated NaHCO₃. Layers were separated and the organic layer was further washed with saturated NaHCO₃ (2 times). The organic layer was then dried over anhydrous Na₂SO₄, filtered, and concentrated. The crude was purified on a Combiflash silica cartridge (12 g) [0-10% (10% NH₄OH/MeOH)/DCM] to give the title compound (11 mg, 0.032 mmol, 52.8% yield) as an amorphous white powder.

LC/MS: m/z 349.0 (M+H)⁺, 0.55 min (ret. time).

¹H NMR (400 MHz, CDCl₃): δ ppm 2.02 (m, 2H) 2.36 (s, 3H) 2.74-2.84 (m, 1H) 2.88-2.99 (m, 1H) 3.27-3.38 (m, 1H) 3.41-3.51 (m, 1H) 3.71-3.80 (m, 1H) 3.99-4.10 (m, 1H) 4.17 (m, 1H) 5.01 (s, 1H) 5.36 (m, 2H) 7.11-7.26 (m, 3H)

E321

7-((3,5-Difluoro-4-((6-methylpyridin-3-yl)oxy)benzyl)oxy)-2-methyl-3,4,11,11a-tetrahydro-1Hpyrazino[1',2':3,4]imidazo[1,2-c]pyrimidin-9(2H)-one

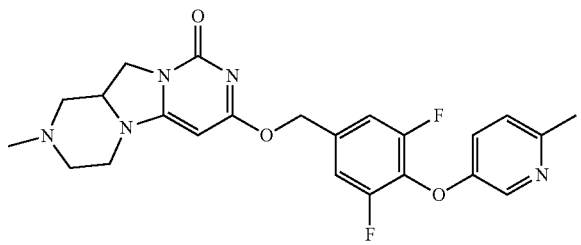

The title compound was prepared by a procedure similar to that described for 7-((3,4-difluorobenzyl)oxy)-2-methyl-3,4,11,11a-tetrahydro-1H-pyrazino[1',2':3,4] imidazo[1,2-c]pyrimidin-9(2H)-one starting from 7-Chloro-2-methyl-3,4,11,11a-tetrahydro-1H-pyrazino[1',2':3,4]imidazo[1,2-c]pyrimidin-9(2H)-one and (3,5-Difluoro-4-((6-methylpyridin-3-yl)oxy) phenyl)methanol LC/MS: m/z 456.1 (M+H)⁺, 0.56 min (ret. time).

¹H NMR (400 MHz, CDCl₃): δ ppm 1.98-2.09 (m, 1H) 2.09-2.20 (m, 1H) 2.37 (s, 3H) 2.54 (s, 3H) 2.77-2.87 (m, 1H) 2.89-2.99 (m, 1H) 3.29-3.40 (m, 1H) 3.44-3.53 (m, 1H) 3.70-3.81 (m, 1H) 3.99-4.12 (m, 1H) 4.14-4.24 (m, 1H) 5.05 (s, 1H) 5.41 (m, 2H) 7.04-7.19 (m, 4H) 8.30 (m, 1H)

E322

2-Fluoro-5-(((9-oxo-2-(2,2,2-trifluoroethyl)-2,3,4,9,11,11a-hexahydro-1H-pyrazino[1',2':3,4]imidazo[1,2-c]pyrimidin-7-yl)oxy)methyl)benzonitrile

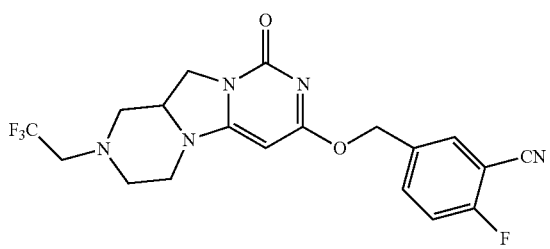 [SMILES: N#Cc1cc(COc2cc3n(c(=O)n2)CC2CN(CC(F)(F)F)CCN32)ccc1F]

350

To a solution of 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile (46 mg, 0.135 mmol) in THF (0.7 mL) and NMP (0.5 mL) was added lithium bis(trimethylsilyl)amide (1 M in THF) (0.14 mL, 0.140 mmol) at 0° C. slowly. After 15 min at 0° C., 2,2,2-trifluoroethyl trifluoromethanesulfonate (0.02 mL, 0.139 mmol) was added. After 1.25 h, DIPEA (0.024 mL, 0.135 mmol) and an additional aliquot of 2,2,2-trifluoroethyl trifluoromethanesulfonate (0.02 mL, 0.139 mmol) were added. After 42 hrs the reaction was concentrated and the residue was partitioned between saturated NaHCO₃ and EtOAc. The layers were separated and the aqeuous layer further extracted with EtOAc. The combined organic layers were washed with brine, then dried over anhydrous Na₂SO₄, filtered, and concentrated. The crude was purified on a Combiflash silica cartridge (24 g) [0-10% (10% NH₄OH/MeOH)/DCM] then by prep reverse phase HPLC [10-90% CH₃CN/H₂O to 90% CH₃CN/H₂O] to give the title compound (7 mg, 0.017 mmol, 12.27% yield) as an amorphous white solid.

LC/MS: m/z 424.1 (M+H)⁺, 0.78 min (ret. time).

¹H NMR (400 MHz, CDCl₃): δ ppm 2.54 (t, J=10.79 Hz, 1H) 2.64 (td, J=11.48, 2.89 Hz, 1H) 2.89-3.19 (m, 4H) 3.29-3.41 (m, 1H) 3.43-3.52 (m, 1H) 3.74 (dd, J=11.54, 5.77 Hz, 1H) 3.97-4.12 (m, 1H) 4.12-4.25 (m, 1H) 5.03 (s, 1H) 5.31-5.48 (m, 2H) 7.21 (t, J=8.53 Hz, 1H) 7.61-7.73 (m, 2H)

E323

2-Fluoro-5-(((9-oxo-2-(2,2,2-trifluoroacetyl)-2,3,4,9,11,11a-hexahydro-1H-pyrazino[1',2':3,4]imidazo[1,2-c]pyrimidin-7-yl)oxy)methyl)benzonitrile

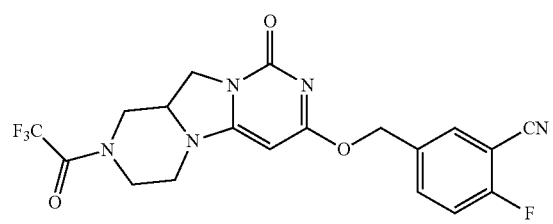 [SMILES: N#Cc1cc(COc2cc3n(c(=O)n2)CC2CN(C(=O)C(F)(F)F)CCN32)ccc1F]

To a solution of 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile (203 mg, 0.357 mmol) and 2-((tert-butoxycarbonyl)amino)-2-methylpropanoic acid (90 mg, 0.443 mmol) in DCM (3 mL) at room temperature was added first DIPEA (0.2 mL, 1.145 mmol) followed by T3P (50 wt. % in EtOAc) (0.25 mL, 0.420 mmol). The reaction was stirred for 16 h at room temperature then diluted with DCM (3 mL), washed with saturated NH₄Cl (2 mL, two times), saturated NaHCO₃ (2 mL, two times), brine (2 mL), dried over anhydrous sodium sulfate, filtered. The crude was purified by prep reverse phase HPLC [10-90% CH₃CN/H₂O (0.1% TFA)] to give the title compound (90 mg, 0.206 mmol, 57.7% yield) as a tan amorphous solid.

LC/MS: m/z 438.0 (M+H)⁺, 0.76 min (ret. time).

E324

2-(7-((3-Cyano-4-fluorobenzyl)oxy)-9-oxo-3,4,11,11a-tetrahydro-1H-pyrazino[1',2':3,4]imidazo[1,2-c]pyrimidin-2(9H)-yl)acetic acid, trifluoroacetic acid Salt

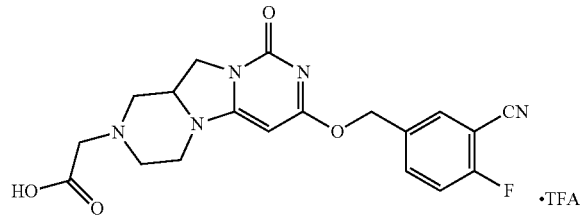 [SMILES: N#Cc1cc(COc2cc3n(c(=O)n2)CC2CN(CC(=O)O)CCN32)ccc1F]

To a solution of 2-fluoro-5-(((9-oxo-2,3,4,9,11,11a-hexahydro-1H-pyrazino[1',2':3,4]imidazo[1,2-c]pyrimidin-7-yl)oxy)methyl)benzonitrile (40 mg, 0.117 mmol) in DCM (0.4 mL) was added TEA (0.1 mL, 0.717 mmol) and tert-butyl 2-bromoacetate (0.03 mL, 0.203 mmol). After 18 h the reaction was diluted with DCM, then washed with H$_2$O (3 times) and brine, then dried over anhydrous Na$_2$SO$_4$, filtered and concentrated. Then anhydrous DCM (0.5 mL) was added by syringe followed by addition of TFA (0.5 mL, 6.49 mmol). The reaction was stirred for 30 min and concentrated. The residue was purified by prep reverse phase HPLC [10-90% CH$_3$CN/H$_2$O (0.1% TFA)] to afford the title compound (16 mg, 0.031 mmol, 26.6% yield) as a white amorphous.

LC/MS: m/z 399.9 (M+H)$^+$, 0.55 min (ret. time).

$^1$H NMR (400 MHz, CD$_3$OD): δ ppm 2.83-3.05 (m, 2H) 3.39 (m, 1H) 3.48-3.82 (m, 4H) 3.89 (dd, J=11.29, 7.28 Hz, 1H) 4.14 (m, 1H) 4.37 (t, J=10.79 Hz, 1H) 4.54 (m, 1H) 5.42 (s, 2H) 7.47 (t, J=8.91 Hz, 1H) 7.82-7.90 (m, 1H) 7.93 (d, J=6.02 Hz, 1H)

E325

3-(7-((3-Cyano-4-fluorobenzyl)oxy)-9-oxo-3,4,11,11a-tetrahydro-1H-pyrazino[1',2':3,4]imidazo[1,2-c]pyrimidin-2(9H)-yl)propanoic acid

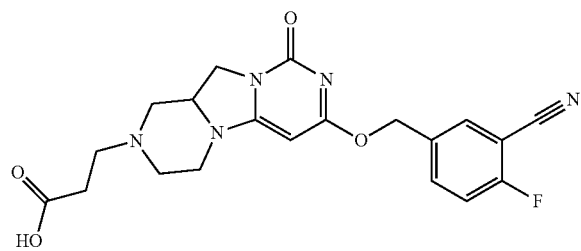 [SMILES: N#Cc1cc(COc2cc3n(c(=O)n2)CC2CN(CCC(=O)O)CCN32)ccc1F]

The title compound was prepared by a procedure similar to that described for E324 starting from tert-butyl 3-bromopropanoate.

LC/MS: m/z 415.0 (M+H)$^+$, 0.55 min (ret. time).

$^1$H NMR (400 MHz, D$_2$O): δ2.99 (t, J=6.65 Hz, 2H) 3.41 (t, J=11.92 Hz, 2H) 3.64 (t, J=6.78 Hz, 2H) 3.86 (m, 2H) 3.95-4.11 (m, 2H) 4.31 (d, J=14.81 Hz, 1H) 4.52 (t, J=11.04 Hz, 1H) 5.42 (s, 2H) 5.96 (s, 1H) 7.43 (t, J=8.91 Hz, 1H) 7.82 (m, 1H) 7.89 (d, J=5.77 Hz, 1H)

E326 and E327

E326: Isomer 1: Ethyl 2-(7-((3,4-difluorobenzyl)oxy)-9-oxo-3,4,11,11a-tetrahydro-1H-pyrazino[1',2':3,4] imidazo[1,2-c]pyrimidin-2(9H)-yl)propanoate (E326)

E327: Isomer 2: Ethyl 2-(7-((3,4-difluorobenzyl)oxy)-9-oxo-3,4,11,11a-tetrahydro-1H-pyrazino[1',2':3,4]imidazo[1,2-c]pyrimidin-2(9H)-yl)propanoate (E327)

E326 (isomer 1)

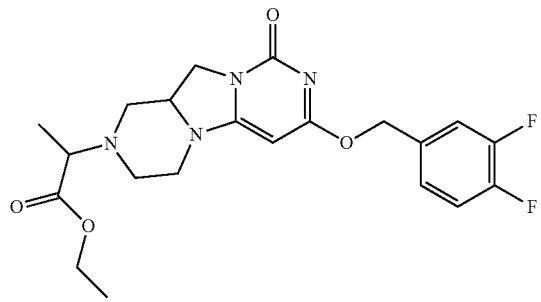

E327 (isomer 2)

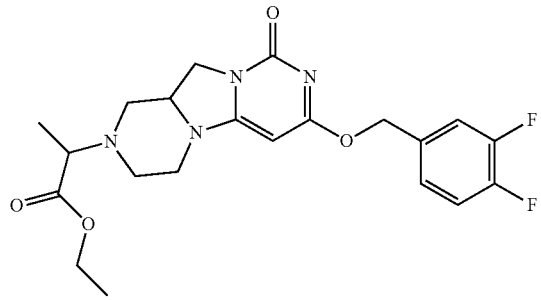

To a solution of 7-((3,4-difluorobenzyl)oxy)-3,4,11,11a-tetrahydro-1H-pyrazino[1',2':3,4]imidazo[1,2-c]pyrimidin-9(2H)-one (150 mg, 0.449 mmol) in DMF (1.3 mL) was added ethyl 2-bromopropanoate (0.070 mL, 0.538 mmol) and DIPEA (0.157 mL, 0.897 mmol) by syringe under argon. The reaction was heated to 110° C. with stirring for 3.75 hrs. The reaction was diluted with water and extracted with EtOAc. The combined organic layers were concentrated and the crude product was purified on a Combiflash silica cartridge (12 g) (0-15% MeOH/DCM) then by prep reverse phase HPLC [10-90% CH$_3$CN/H$_2$O (0.1% TFA)] to give the title compound of isomer 1 (15 mg, 0.035 mmol, 7.70% yield) as an amorphous white solid and the mixture of isomer 1 and isomer 2 (21 mg, 0.048 mmol, 10.77% yield) as a sticky solid.

E326 (isomer 1): LC/MS: m/z 435.1 (M+H)$^+$, 0.84 min (ret. time).

$^1$H NMR (400 MHz, CD$_2$Cl$_2$) δ ppm 1.16-1.35 (m, 6H) 2.30-2.65 (m, 2H) 2.83 (t, J=12.30 Hz, 1H) 3.01 (t, J=13.18 Hz, 1H) 3.10-3.26 (m, 1H) 3.32-3.45 (m, 2H) 3.51-3.62 (m, 1H) 3.77-3.96 (m, 1H) 3.99-4.19 (m, 3H) 4.70 (s, 1H) 4.93 (s, 2H) 7.01-7.13 (m, 1H) 7.17 (br. s., 1H) 7.21-7.33 (m, 1H).

E327 (isomer 2): LC/MS: m/z 435.2 (M+H)$^+$, 0.80 min (ret. time);

¹H NMR (400 MHz, CD₂Cl₂) δ ppm 1.17-1.35 (m, 6H) 2.47 (m, 2H) 2.75-2.91 (m, 1H) 2.92-3.07 (m, 1H) 3.14-3.31 (m, 1H) 3.32-3.49 (m, 2H) 3.59-3.70 (m, 1H) 3.87-4.18 (m, 4H) 4.98 (m, 1H) 7.15 (m, 2H) 7.21-7.31 (m, 1H).

E328

2-Cyclopropyl-2-(7-((3,4-difluorobenzyl)oxy)-9-oxo-3,4,11,11a-tetrahydro-1H-pyrazino[1',2':3,4]imidazo[1,2-c]pyrimidin-2(9H)-yl)acetic acid, trifluoroacetic acid Salt

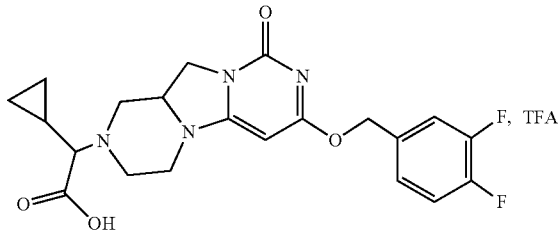 [SMILES: O=C(O)C(C1CC1)N1CCN2c3cc(OCc4ccc(F)c(F)c4)nc(=O)n3CC2C1]

To a solution of 7-((3,4-difluorobenzyl)oxy)-3,4,11,11a-tetrahydro-1H-pyrazino[1',2':3,4]imidazo[1,2-c]pyrimidin-9(2H)-one (50 mg, 0.150 mmol) and 2-cyclopropyl-2-oxoacetic acid (68 mg, 0.596 mmol) in dichloromethane (1 mL) was added acetic acid (4 µl, 0.070 mmol). The reaction was stirred for 30 min, then sodium triacetoxyborohydride (63 mg, 0.297 mmol) (100 µl) were added followed by water. The mixture was stirred for an additional 18 h. The reaction was diluted with H₂O (1 mL) and basified to pH 12 by addition of 1 N NaOH. The layers were separated and the aqeuous phase was washed with EtOAc (2×0.5 mL). The aqeuous phase was then acidified to pH 4 with 1 N HCl and washed with EtOAc (3×0.5 mL). The aqeuous layer was further acidified to pH 1 with 1N HCl, saturated with NaCl, and extracted with EtOAc 4 times). The combined organic layers were dried over anhydrous sodium sulfate, filtered, and concentrated. The crude was purified by prep reverse phase HPLC [10-90% CH₃CN/H₂O (0.1% TFA)] to give the title compound (12 mg, 0.022 mmol, 14.68% yield) as a 51:49 mixture of racemic diastereomers Isomer 1: LC/MS: m/z 433.1 (M+H)⁺, 0.62 min (ret. time);

Isomer 2 LC/MS: m/z 433.1 (M+H)⁺, 0.64 min (ret. time).

¹H NMR (400 MHz, DMSO-d₆) δ ppm 0.25-0.45 (m, 2H) 0.53-0.72 (m, 2H) 1.06 (d, J=3.76 Hz, 1H) 2.67 (m, 2H) 3.12-3.76 (m, 3H) 3.97 (br. s., 1H) 4.07-4.32 (m, 2H) 4.47 and 4.76 (s, 1H) 5.30 (s, 2H) 5.83 (br. s., 1H) 7.25-7.63 (m, 3H)

E329

2-Fluoro-5-(((9-oxo-1,3,4,9,11,11a-hexahydropyrimido[6',1':2,3]imidazo[5,1-c][1,4]oxazin-7-yl)oxy)methyl)benzonitrile

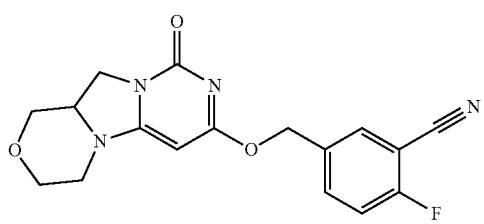 [SMILES: N#Cc1cc(COc2cc3n(c(=O)n2)CC2COCCN32)ccc1F]

To a solution of 7-chloro-3,4,11,11a-tetrahydropyrimido[6',1':2,3]imidazo[5,1-c][1,4]oxazin-9(1H)-one (100 mg, 0.439 mmol) and 2-fluoro-5-(hydroxymethyl)benzonitrile (66.4 mg, 0.439 mmol) in anhydrous 2-Me-THF (3 mL) was added NaH (49 mg, 1.225 mmol). The reaction was stirred at room temperature for 1.5 h and the mixture was quenched with saturated NH₄Cl (2 mL). The precipitate formed was filtered and the filtercake was washed with EtOAc (2×3 mL) and DCM (2×2 mL). The layers of the filtrate were separated, and the aqueous layer was extracted with EtOAc (2×2 mL). The filter cake was combined with the organic layers. Isolute was added to the combined organic layers, and the mixture was concentrated. The crude was then purified by flash chromatography and then reverse phase HPLC to give the title compound (57.5 mg, yield 37% as a white solid.

LC/MS: m/z 342.9 (M+H)⁺, 0.59 min (ret. time).

¹H NMR (400 MHz, CD₃OD): δ 7.79-7.68 (m, 2H), 7.27 (t, J=8.8 Hz, 1H), 5.40-5.31 (m, 3H), 4.17-3.85 (m, 4H), 3.66-3.33 (m, 5H)

E330

2-(Cyclopropanecarbonyl)-7-((3,4-difluorobenzyl)oxy)-3,4,11,11a-tetrahydro-1H-pyrazino[1',2':3,4]imidazo[1,2-c]pyrimidin-9(2H)-one

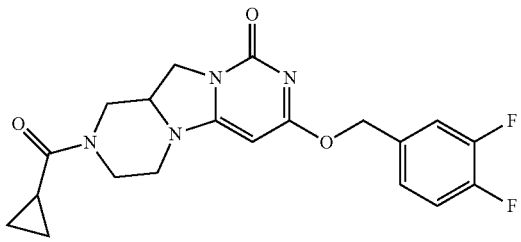 [SMILES: O=C(C1CC1)N1CCN2c3cc(OCc4ccc(F)c(F)c4)nc(=O)n3CC2C1]

Cyclopropanecarbonyl chloride (20 µl, 0.218 mmol) was added to a solution of 7-((3,4-difluorobenzyl)oxy)-3,4,11,11a-tetrahydro-1H-pyrazino[1',2':3,4]imidazo[1,2-c]pyrimidin-9(2H)-one (50 mg, 0.150 mmol) and TEA (60 µl, 0.430 mmol) in anhydrous DCM (1 mL). The reaction was stirred at room temperature for 40 min. Additional DCM (2 mL) was added, and the mixture was washed with 10% citric acid (1×1 mL) and saturated NaHCO₃ (1×1 mL). The mixture was concentrated and the crude was then purified by flash chromatography to give 15.3 mg (25%) of the title compound.

LC/MS: m/z 403.0 (M+H)⁺, 0.69 min (ret. time).

¹H NMR (400 MHz, CD₃CN): δ 7.48-7.26 (m, 3H), 5.31 (s, 2H), 5.21 (s, 1H), 4.84-4.34 (m, 2H), 4.24-3.61 (m, 4H), 3.34 (br. s., 2H), 2.93-2.68 (m, 2H), 0.95-0.70 (m, 4H)

E331

2-(Cyclopropylsulfonyl)-7-((3,4-difluorobenzyl)oxy)-3,4,11,11a-tetrahydro-1H-pyrazino[1',2':3,4]imidazo[1,2-c]pyrimidin-9(2H)-one

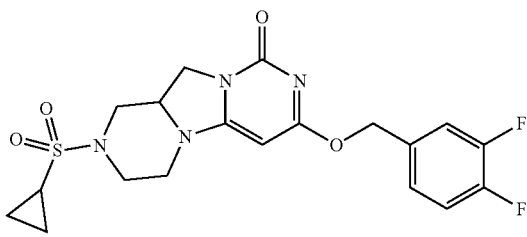 [SMILES: O=c1nc(OCc2ccc(F)c(F)c2)cc2n1CC1CN(S(=O)(=O)C3CC3)CCN21]

The title compound was prepared by a procedure similar to that described for E330 starting from cyclopropanesulfonyl chloride.

LC/MS: m/z 439.0 (M+H)$^+$, 0.76 min (ret. time).

$^1$H NMR (400 MHz, CD$_3$CN) δ 7.49-7.21 (m, 3H), 5.29 (br. s., 2H), 5.21 (br. s., 1H), 4.15 (br. s., 2H), 4.00-3.64 (m, 4H), 3.43-3.24 (m, 1H), 3.17-2.96 (m, 2H), 2.55 (br. s., 1H), 1.04 (br. s., 4H)

E332

7-((3,4-Difluorobenzyl)oxy)-2-pivaloyl-3,4,11,11a-tetrahydro-1H-pyrazino[1',2':3,4]imidazo[1,2-c]pyrimidin-9(2H)-one

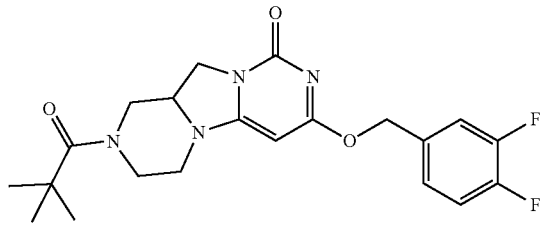 [SMILES: CC(C)(C)C(=O)N1CCN2c3cc(OCc4ccc(F)c(F)c4)nc(=O)n3CC2C1]

The title compound was prepared by a procedure similar to that described for E330 starting from pivaloyl chloride.

LC/MS: m/z 419.0 (M+H)$^+$, 0.79 min (ret. time).

$^1$H NMR (400 MHz, CD$_3$CN) δ 7.39-7.15 (m, 3H), 5.26 (s, 2H), 5.10 (s, 1H), 4.55-4.31 (m, 2H), 4.04 (dd, J=9.0, 11.5 Hz, 1H), 3.94-3.83 (m, 1H), 3.62 (dd, J=6.0, 11.8 Hz, 2H), 3.18-3.07 (m, 1H), 2.95-2.77 (m, 2H), 1.31-1.20 (m, 9H)

E333

2-(1-Aminocyclopropanecarbonyl)-7-((3,4-difluorobenzyl)oxy)-3,4,11,11a-tetrahydro-1H-pyrazino[1',2':3,4]imidazo[1,2-c]pyrimidin-9(2H)-one hydrochloride

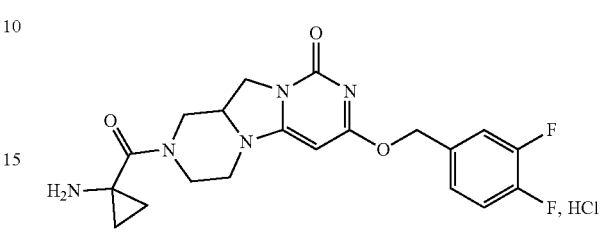

1H-Pyrazino[1',2':3,4]imidazo[1,2-c]pyrimidine-2-carbonyl)cyclopropyl)carbamate (33.5 mg, 0.065 mmol) was added to a solution of 4 M HCl in dioxane (1 mL, 4.00 mmol). The reaction was stirred at room temperature. After 20 min, the reaction mixture was concentrated to give 12.6 mg (41%) of the title compound.

LC/MS: m/z 418.0 (M+H)$^+$, 0.50 min (ret. time).

$^1$H NMR (400 MHz, CD$_3$OD): δ 7.51-7.42 (m, 1H), 7.38-7.32 (m, 2H), 6.05 (s, 1H), 5.38 (s, 2H), 4.67-4.60 (m, 1H), 4.47 (d, J=12.0 Hz, 1H), 4.40-4.33 (m, 2H), 4.20-4.10 (m, 1H), 3.89 (d, J=4.3 Hz, 1H), 3.76-3.71 (m, 1H), 3.70-3.67 (m, 1H), 3.49 (dd, J=3.6, 13.2 Hz, 1H), 1.50-1.43 (m, 2H), 1.41-1.35 (m, 2H)

Example E334

2-(3-Amino-3-methylbutanoyl)-7-((3,4-difluorobenzyl)oxy)-3,4,11,11a-tetrahydro-1H-pyrazino[1',2':3,4]imidazo[1,2-c]pyrimidin-9(2H)-one

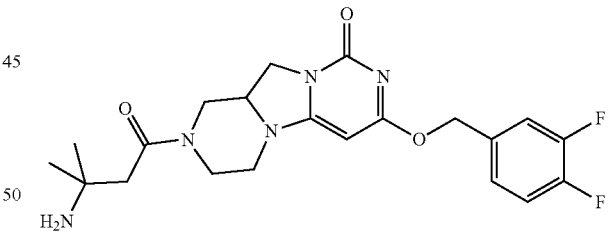

The title compound was prepared by a procedure similar to that described for E333 starting from 1H-pyrazino[1',2':3,4]imidazo[1,2-c]pyrimidin-2(9H)-yl)-2-methyl-4-oxobutan-2-yl)carbamate.

LC/MS: m/z 434.0 (M+H)$^+$, 0.55 min (ret. time).

$^1$H NMR (400 MHz, CD$_3$OD) δ 7.35 (dd, J=8.3, 10.8 Hz, 1H), 7.28-7.19 (m, 2H), 5.35 (d, J=6.8 Hz, 1H), 5.30 (d, J=4.3 Hz, 2H), 4.80-4.58 (m, 1H), 4.28-3.89 (m, 3H), 3.73 (dd, J=6.0, 10.8 Hz, 2H), 3.26-3.09 (m, 2H), 2.82-2.67 (m, 1H), 2.56 (s, 2H), 1.24 (d, J=3.8 Hz, 6H)

E335

2-(2-Amino-2-methylpropanoyl)-7-((3,4-difluorobenzyl)oxy)-3,4,11,11a-tetrahydro-1H-pyrazino[1,2':3,4]imidazo[1,2-c]pyrimidin-9(2H)-one

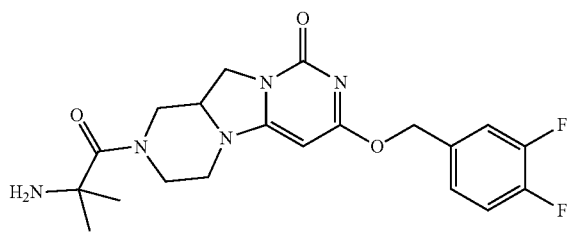 [SMILES: CC(C)(N)C(=O)N1CCN2c3cc(OCc4ccc(F)c(F)c4)nc(=O)n3CC2C1]

The title compound was prepared by a procedure similar to that described for E333 starting from tert-butyl (1-(7-((3,4-difluorobenzyl)oxy)-9-oxo-3,4,11,11a-tetrahydro-1H-pyrazino[1',2':3,4]imidazo[1,2-c]pyrimidin-2(9H)-yl)-2-methyl-1-oxopropan-2-yl).

LC/MS: m/z 420.1 (M+H)+, 0.58 min (ret. time).

$^1$H NMR (400 MHz, CD$_3$CN) δ 7.39-7.16 (m, 3H), 5.27 (s, 2H), 5.14-4.85 (m, 3H), 4.08-3.99 (m, 1H), 3.97-3.86 (m, 1H), 3.64-3.50 (m, 2H), 3.15 (dt, J=3.3, 12.7 Hz, 1H), 2.92-2.71 (m, 2H), 1.59 (s, 2H), 1.33 (s, 6H)

E336

7-((3,4-Difluorobenzyl)oxy)-3,4,11,11a-tetrahydropyrimido[6',1':2,3]imidazo[5,1-c][1,4] oxazin-9(1H)-one

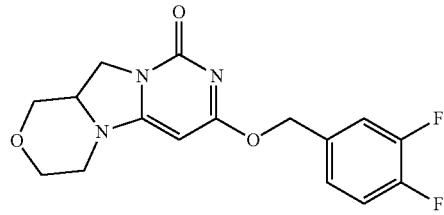 [SMILES: O=c1nc(OCc2ccc(F)c(F)c2)cc2n1CC1COCCN21]

The title compound was prepared by a procedure similar to that described for E329 starting from 7-chloro-3,4,11,11atetrahydropyrimido[6',1':2,3]imidazo[5,1-c][1,4]oxazin-9(1H)-one and (3,4-difluorophenyl)methanol.

LC/MS: m/z 336.1 (M+H)+, 0.60 min (ret. time).

$^1$H NMR (400 MHz, DMSO-d$_6$) δ 7.51-7.39 (m, 2H), 7.26 (br. s., 1H), 5.35 (s, 1H), 5.24 (s, 2H), 4.03 (d, J=4.8 Hz, 1H), 3.99-3.92 (m, 1H), 3.88 (dd, J=3.8, 11.3 Hz, 1H), 3.80 (dd, J=3.3, 11.3 Hz, 1H), 3.63 (d, J=13.3 Hz, 1H), 3.52 (dd, J=5.5, 11.3 Hz, 1H), 3.43-3.34 (m, 2H), 3.29-3.20 (m, 1H)

E337

7-((3,4-Difluorobenzyl)oxy)-2-(3-(dimethylamino)propanoyl)-3,4,11,11a-tetrahydro-1H-pyrazino[1,2':3,4]imidazo[1,2-c]pyrimidin-9(2H)-one

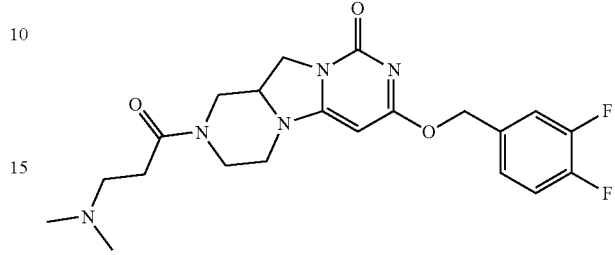

A solution of 50 wt % T$_3$P in EtOAc (0.11 mL, 0.185 mmol) was added dropwise to a solution of 3-(dimethylamino)propanoic acid hydrochloride (23 mg, 0.150 mmol), 7-((3,4-difluorobenzyl)oxy)-3,4,11,11a-tetrahydro-1H-pyrazino[1',2':3,4]imidazo[1,2-c]pyrimidin-9(2H)-one (50 mg, 0.150 mmol) and anhydrous TEA (0.08 mL, 0.577 mmol) in anhydrous DCM (1 mL). The reaction was stirred at room temperature. After 45 min, DCM (2 mL) was added, and the mixture was washed with saturated NaHCO$_3$ (1×1 mL). The organic layer was concentrated the crude was then purified by flash chromatography to give 31.7 mg (49%) of the title compound as a white solid.

LC/MS: m/z 434.2 (M+H)+ 0.54 min (ret. time).

$^1$H NMR (400 MHz, CD$_3$OD): δ 7.40-7.30 (m, 1H), 7.27-7.12 (m, 2H), 5.38-5.27 (m, 3H), 4.64-4.47 (m, 1H), 4.19 (t, J=8.5 Hz, 2H), 4.03 (d, J=10.3 Hz, 1H), 3.79-3.68 (m, 2H), 3.23-3.12 (m, 1H), 2.71-2.57 (m, 4H), 2.29 (s, 6H)

E338

7-((3,4-Difluorobenzyl)oxy)-2-(2,2,2-trifluoroethyl)-3,4,11,11a-tetrahydro-1H pyrazino[1',2':3,4]imidazo[1,2-c]pyrimidin-9(2H)-one trifluoroacetate

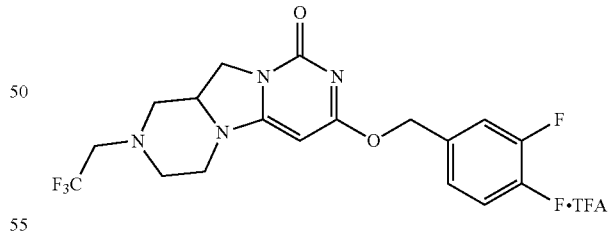

To a mixture of 7-((3,4-difluorobenzyl)oxy)-3,4,11,11atetrahydro-1H-pyrazino[1',2':3,4] imidazo[1,2-c]pyrimidin-9(2H)-one (50 mg, 0.150 mmol) and DIPEA (30 μl, 0.172 mmol) in anhydrous THF (0.5 mL) was added 2,2,2-trifluoroethyl trifluoromethanesulfonate (36.2 mg, 0.156 mmol) in anhydrous THF (500 μl). The vial was sealed, and the reaction was stirred at 70° C. The mixture was concentrated and the crude was then purified by flash chromatography and then reverse phase HPLC to give 14.9 mg (19%) of the title compound.

LC/MS: m/z 417.0 (M+H)+, 0.81 min (ret. time).

¹H NMR (400 MHz, CD₃OD): δ 7.47-7.39 (m, 1H), 7.37-7.22 (m, 2H), 5.80 (s, 1H), 5.33 (s, 2H), 4.34-4.22 (m, 2H), 3.91 (d, J=13.1 Hz, 1H), 3.82-3.71 (m, 1H), 3.44 (dt, J=3.8, 12.5 Hz, 1H), 3.23 (br. s., 3H), 3.08 (d, J=10.5 Hz, 1H), 2.73-2.57 (m, 2H)

E339

2-((S)-azetidine-2-carbonyl)-7-((3,4-difluorobenzyl) oxy)-3,4,11,11a-tetrahydro-1H-pyrazino[1',2':3,4] imidazo[1,2-c]pyrimidin-9(2H)-one

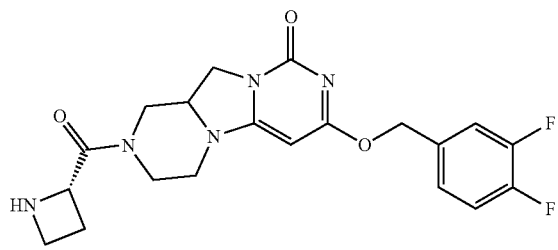 [SMILES: O=C([C@@H]1CCN1)N1CCN2c3cc(OCc4ccc(F)c(F)c4)nc(=O)n3CC2C1]

The title compound was prepared by a procedure similar to that described for E333 starting from (2S)-tert-butyl 2-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)azetidine-1-carboxylate.

LC/MS: m/z 418.1 (M+H)⁺, 0.59 min (ret. time).
¹H NMR (400 MHz, CD₃OD): δ 7.41-7.31 (m, 1H), 7.27-7.16 (m, 2H), 5.39-5.33 (m, 1H), 5.30 (d, J=4.8 Hz, 2H), 4.74 (d, J=9.8 Hz, 1H), 4.65-4.48 (m, 1H), 4.26-4.11 (m, 1H), 4.01 (d, J=6.3 Hz, 1H), 3.81-3.68 (m, 2H), 3.62-3.45 (m, 2H), 3.25-3.07 (m, 2H), 2.93-2.72 (m, 2H), 2.53-2.29 (m, 1H)

E340

7-((3,4-Difluorobenzyl)oxy)-2-((S)-pyrrolidine-2-carbonyl)-3,4,11,11a-tetrahydro-1H-pyrazino[1,2':3,4]imidazo[1,2-c]pyrimidin-9(2H)-one

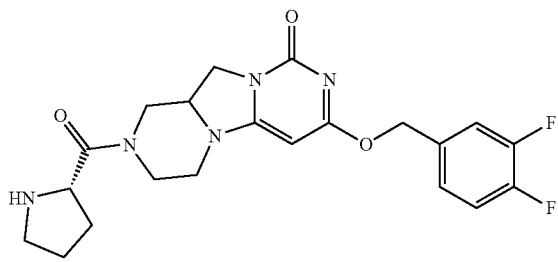 [SMILES: O=C([C@@H]1CCCN1)N1CCN2c3cc(OCc4ccc(F)c(F)c4)nc(=O)n3CC2C1]

The title compound was prepared by a procedure similar to that described for E333 starting from (2S)-tert-butyl 2-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)pyrrolidine-1-carboxylate.

LC/MS: m/z 432.1 (M+H)⁺, 0.60 min (ret. time).
¹H NMR (400 MHz, CD₃OD): δ 7.40-7.30 (m, 1H), 7.28-7.17 (m, 2H), 5.40-5.28 (m, 3H), 4.73 (d, J=15.1 Hz, 1H), 4.57 (d, J=13.6 Hz, 1H), 4.19 (t, J=10.3 Hz, 2H), 4.11-3.89 (m, 2H), 3.81-3.68 (m, 2H), 3.23-3.08 (m, 2H), 2.89-2.70 (m, 2H), 2.21 (br. s., 1H), 1.91-1.59 (m, 3H)

E341

7-((3,4-Difluorobenzyl)oxy)-2-((2S,4S)-4-fluoropyrrolidin-2-carbonyl)-3,4,11,11a-tetrahydro-1H-pyrazino[1',2':3,4]imidazo[1,2-c]pyrimidin-9(2H)-one

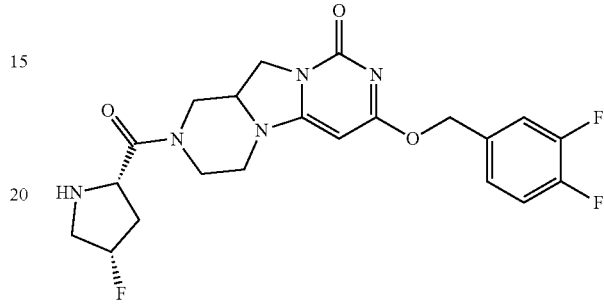

The title compound was prepared by a procedure similar to that described for E333 starting from (2S,4S)-tert-butyl 2-(7-((3,4-difluorobenzyl)oxy)-9-oxo-2,3,4,9,11,11a-hexahydro-1H-pyrazino[1',2': 3,4]imidazo[1,2-c]pyrimidine-2-carbonyl)-4-fluoropyrrolidine-1-carboxylate.

LC/MS: m/z 450.0 (M+H)⁺, 0.60 min (ret. time).
¹H NMR (400 MHz, CD₃OD) δ 7.36 (dd, J=7.7, 10.7 Hz, 1H), 7.26 (br. s., 2H), 5.42-5.21 (m, 3H), 5.13 (d, J=10.0 Hz, 1H), 4.74 (d, J=13.1 Hz, 1H), 4.57 (d, J=10.0 Hz, 1H), 4.28-3.88 (m, 4H), 3.76 (dd, J=5.8, 11.5 Hz, 2H), 3.46-3.34 (m, 1H), 3.21 (d, J=8.0 Hz, 1H), 2.93-2.70 (m, 2H), 2.64-2.39 (m, 1H), 2.10-1.83 (m, 1H)

E342

7-((3,4-Difluorobenzyl)oxy)-2-((S)-4,4-difluoropyrrolidin-2-carbonyl)-3,4,11,11a-tetrahydro-1H-pyrazino[1,2':3,4]imidazo[1,2-c]pyrimidin-9(2H)-one

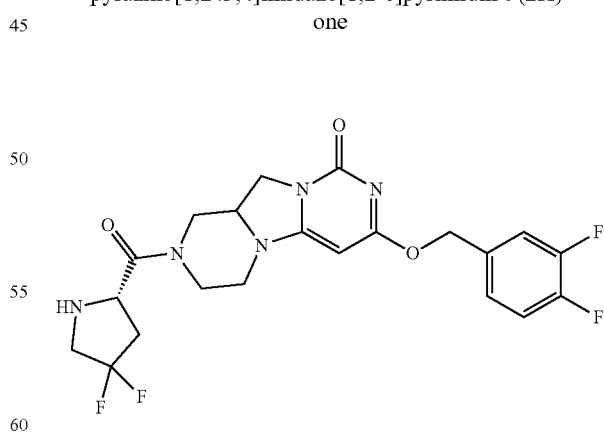

The title compound was prepared by a procedure similar to that described for E333 starting from (2S)-tert-butyl 2-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)-4,4-difluoropyrrolidine-1-carboxylate.

LC/MS: m/z 468.0 (M+H)⁺, 0.61 min (ret. time).

¹H NMR (400 MHz, CD₃OD): δ 7.36 (dd, J=8.0, 10.8 Hz, 1H), 7.28-7.19 (m, 2H), 5.40-5.27 (m, 3H), 4.77-4.50 (m, 1H), 4.38-4.27 (m, 1H), 4.23-3.93 (m, 3H), 3.80-3.69 (m, 2H), 3.28-3.03 (m, 4H), 2.90-2.72 (m, 1H), 2.72-2.49 (m, 1H), 2.38 (dt, J=7.7, 15.5 Hz, 1H)

E343

7-((3,4-Difluorobenzyl)oxy)-2-((R)-pyrrolidine-2-carbonyl)-3,4,11,11a-tetrahydro-1H-pyrazino[1,2':3,4]imidazo[1,2-c]pyrimidin-9(2H)-one

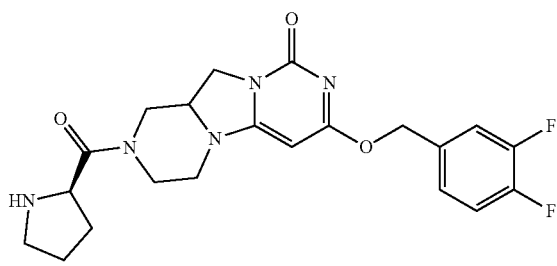 [SMILES: O=C([C@H]1CCCN1)N1CCN2c3cc(OCc4ccc(F)c(F)c4)nc(=O)n3CC2C1]

The title compound was prepared by a procedure similar to that described for E333 starting from (2R)-tert-butyl 2-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)pyrrolidine-1-carboxylate.

LC/MS: m/z 432.1 (M+H)⁺, 0.60 min (ret. time).

¹H NMR (400 MHz, CD₃OD): δ 7.41-7.32 (m, 1H), 7.28-7.15 (m, 2H), 5.40-5.26 (m, 3H), 4.78-4.50 (m, 1H), 4.26-3.89 (m, 4H), 3.81-3.69 (m, 2H), 3.27-3.09 (m, 3H), 2.90-2.71 (m, 2H), 2.20 (d, J=4.5 Hz, 1H), 1.93-1.56 (m, 3H)

E344

2-(1-Aminocyclobutanecarbonyl)-7-((3,4-difluorobenzyl)oxy)-3,4,11,11a-tetrahydro-1H-pyrazino[1,2':3,4]imidazo[1,2-c]pyrimidin-9(2H)-one

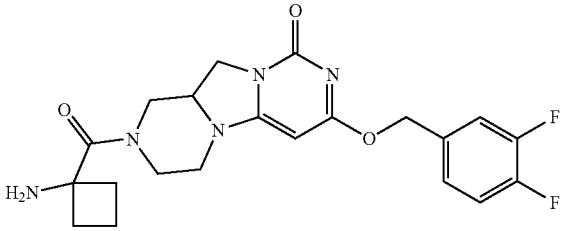 [SMILES: NC1(C(=O)N2CCN3c4cc(OCc5ccc(F)c(F)c5)nc(=O)n4CC3C2)CCC1]

The title compound was prepared by a procedure similar to that described for E333 starting from tert-butyl (1-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)cyclobutyl)carbamate.

LC/MS: m/z 432.1 (M+H)⁺, 0.62 min (ret. time).

¹H NMR (400 MHz, CD₃OD) δ 7.36 (dd, J=7.9, 10.7 Hz, 1H), 7.28-7.15 (m, 2H), 5.42-5.27 (m, 3H), 4.53 (br. s., 1H), 4.31-3.92 (m, 3H), 3.81-3.67 (m, 2H), 3.13 (br. s., 2H), 2.66 (s, 3H), 2.01 (br. s., 3H), 1.76-1.58 (m, 1H)

E345

2-(4-Aminotetrahydro-2H-pyran-4-carbonyl)-7-((3,4-difluorobenzyl)oxy)-3,4,11,11a-tetrahydro-1H-pyrazino[1,2':3,4]imidazo[1,2-c]pyrimidin-9(2H)-one

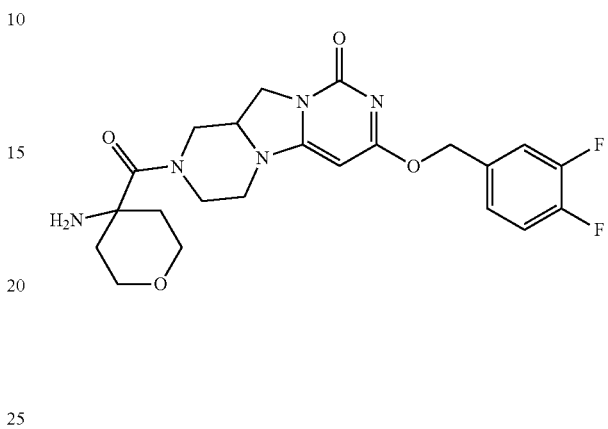

The title compound was prepared by a procedure similar to that described for E333 starting from tert-butyl (4-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)tetrahydro-2H-pyran-4-yl)carbamate.

LC/MS: m/z 462.1 (M+H)⁺, 0.60 min (ret. time).

¹H NMR (400 MHz, CD₃OD): δ 7.36 (dd, J=7.8, 10.8 Hz, 1H), 7.29-7.13 (m, 2H), 5.38-5.27 (m, 3H), 5.05 (br. s., 1H), 4.23-4.13 (m, 1H), 4.07 (d, J=4.5 Hz, 1H), 3.85-3.66 (m, 6H), 3.28-3.19 (m, 2H), 3.02-2.84 (m, 2H), 2.17 (d, J=7.0 Hz, 2H), 1.62 (d, J=3.3 Hz, 2H)

E346

7-((3,4-Difluorobenzyl)oxy)-2-(2-(dimethylamino)acetyl)-3,4,11,11a-tetrahydro-1H-pyrazino[1,2':3,4]imidazo[1,2-c]pyrimidin-9(2H)-one

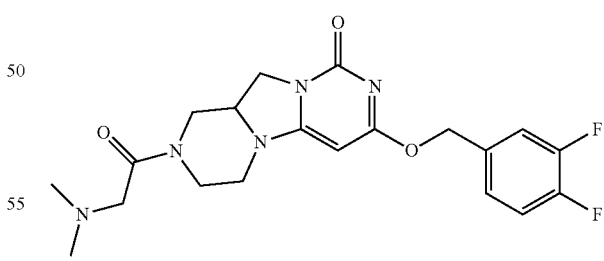

The title compound was prepared by a procedure similar to that described for E337 starting from 2-(dimethylamino)acetic acid.

LC/MS: m/z 420.1 (M+H)⁺ 0.55 min (ret. time).

¹H NMR (400 MHz, CD₃CN) δ 7.38-7.17 (m, 3H), 5.27 (s, 2H), 5.10 (s, 1H), 4.66-4.38 (m, 1H), 4.34-4.09 (m, 1H), 4.09-3.78 (m, 2H), 3.60 (s, 2H), 3.24-2.95 (m, 4H), 2.72-2.52 (m, 1H), 2.21 (s, 6H)

E347

2-(1-Aminocyclohexanecarbonyl)-7-((3,4-difluorobenzyl)oxy)-3,4,11,11a-tetrahydro-1H-pyrazino[1,2':3,4]imidazo[1,2-c]pyrimidin-9(2H)-one

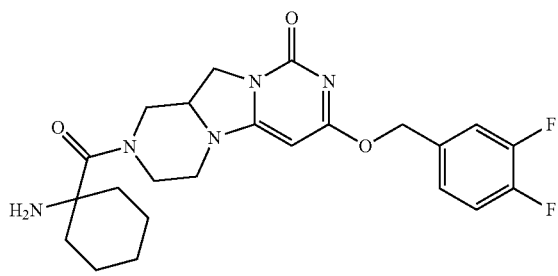 [SMILES: NC1(C(=O)N2CCN3c4cc(OCc5ccc(F)c(F)c5)nc(=O)n4CC3C2)CCCCC1]

The title compound was prepared by a procedure similar to that described for E333 starting from tert-butyl (1-(7-((3,4-difluorobenzyl)oxy)-9-oxo-2,3,4,9,11,11a-hexahydro-1H-pyrazino[1',2':3,4]imidazo[1,2-c]pyrimidine-2-carbonyl)cyclohexyl)carbamate.

LC/MS: m/z 460.1 (M+H)$^+$, 0.63 min (ret. time).

$^1$H NMR (400 MHz, CD$_3$CN): δ 7.40-7.16 (m, 3H), 5.26 (s, 2H), 5.09 (s, 3H), 4.07-3.98 (m, 1H), 3.96-3.85 (m, 1H), 3.60 (s, 3H), 3.20-3.06 (m, 1H), 2.88-2.70 (m, 2H), 1.65-1.40 (m, 8H), 1.37-1.25 (m, 1H)

E348

7-((2,3-Difluorobenzyl)oxy)-11,11a-dihydro-1H-pyrazino[1',2':3,4]imidazo[1,2-c]pyrimidine-3,9(2H,4H)-dione

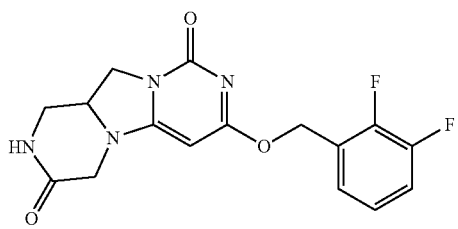 [SMILES: O=C1CN2c3cc(OCc4cccc(F)c4F)nc(=O)n3CC2CN1]

To a solution of 7-chloro-11,11a-dihydro-1H-pyrazino[1',2':3,4]imidazo[1,2-c]pyrimidine-3,9(2H,4H)-dione (34 mg, 0.141 mmol) and (2,3-difluorophenyl)methanol (30.5 mg, 0.212 mmol) in DMF (4 mL) at 23° C. was added sodium hydride (16.95 mg, 0.424 mmol). The mixture was stirred at 23° C. for 40 minutes and then quenched with aq. NH$_4$Cl. The mixture was concentrated and EA and water was added. The layers were separated and the water layer was extracted with EA for 6 times. The combined organic Iyer was concentrated and the crude was purified using CombiFlash Rf 200 with a gradient of 100% DCM to 10% MeOH in DCM then neutral Gilson at a gradient of 10% to 85% water/MeCN to give 5 mg of the title compound.

LC/MS: m/z 349.0 (M+H)$^+$, 0.57 min(ret. time).

$^1$H NMR (400 MHz, DMSO-d$_6$): δ 3.24-3.43 (m, 2H) 3.71 (dd, J=11.54, 6.02 Hz, 1H) 3.81 (d, J=17.57 Hz, 1H) 4.01-4.27 (m, 3H) 5.36 (s, 3H) 7.19-7.36 (m, 2H) 7.44 (d, J=8.78 Hz, 1H) 8.17 (br. s., 1H)

E349 and E350

5-(((3,9-Dioxo-2,3,4,9,11,11a-hexahydro-1H-pyrazino[1',2':3,4]imidazo[1,2-c]pyrimidin-7-yl)oxy)methyl)-2-fluorobenzonitrile (E349)

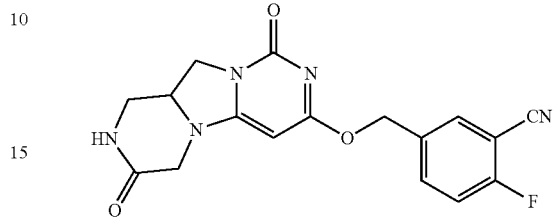

5-((2-cyano-4-(((3,9-dioxo-2,3,4,9,11,11a-hexahydro-1H-pyrazino[1',2':3,4]imidazo[1,2-c]pyrimidin-7-yl)oxy)methyl)phenoxy)methyl)-2-fluorobenzonitrile (E350)

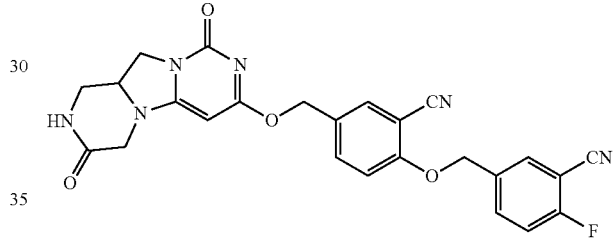

To a solution of 7-chloro-11,11a-dihydro-1H-pyrazino[1',2':3,4]imidazo[1,2-c]pyrimidine-3,9(2H,4H)-dione (318 mg, 1.321 mmol) and 2-fluoro-5-(hydroxymethyl)benzonitrile (200 mg, 1.321 mmol) in DMSO (10 mL) was added sodium hydride (132 mg, 3.30 mmol) at room temperature and the mixture was stirred for 60 minutes. Then water was added to quench the reaction and the mixture was concentrated. Water and EA were added and the water layer was extracted with EA for 5 times. The combined organic layer was concentrated and the crude was purified using CombiFlash Rf 200 with a gradient of 100% DCM to 10% MeOH in DCM and then purified again using neutral Gilson at a gradient of 10% to 80% water/MeCN to give the title compound 5-(((3,9-Dioxo-2,3,4,9,11,11a-hexahydro-1H-pyrazino[1',2':3,4]imidazo[1,2-c]pyrimidin-7-yl)oxy)methyl)-2-fluorobenzonitrile (13 mg) and 5-((2-cyano-4-(((3,9-dioxo-2,3,4,9,11,11a-hexahydro-1H-pyrazino[1',2':3,4]imidazo[1,2-c]pyrimidin-7-yl)oxy)methyl)phenoxy)methyl)-2-fluorobenzonitrile (3 mg).

E349

LC/MS: m/z 356.0 (M+H)$^+$, 0.51 min(ret. time).

$^1$H NMR (400 MHz, DMSO-d$_6$): δ ppm 3.22-3.42 (m, 4H) 3.71 (dd, J=11.54, 6.02 Hz, 1H) 3.82 (d, J=17.57 Hz, 1H) 4.02-4.31 (m, 3H) 7.56 (t, J=9.03 Hz, 1H) 7.83 (t, J=6.90 Hz, 1H) 7.96 (d, J=6.27 Hz, 1H) 8.16 (d, J=3.76 Hz, 1H)

E350

LC/MS: m/z 387.1 (M+H)⁺, 0.76 min(ret. time).

¹H NMR (400 MHz, DMSO-d₆): δ ppm 3.23-3.43 (m, 2H) 3.64-3.86 (m, 2H) 4.02-4.27 (m, 3H) 5.23 (s, 2H) 5.33 (s, 3H) 7.36 (d, J=8.78 Hz, 1H) 7.63 (t, J=8.91 Hz, 1H) 7.72 (d, J=8.53 Hz, 1H) 7.80 (s, 1H) 7.91 (br. s., 1H) 8.06 (d, J=6.27 Hz, 1H) 8.15 (br. s., 1H)

E351

7-((3,5-Difluoro-4-((2-(trifluoromethyl)pyridin-4-yl)oxy)benzyl)oxy)-11,11a-dihydro-1H-pyrazino[1',2':3,4]imidazo[1,2-c]pyrimidine-3,9(2H,4H)-dione

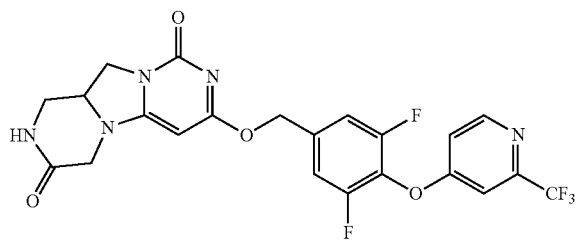 [SMILES: O=C1CN2c3cc(OCc4cc(F)c(Oc5ccnc(C(F)(F)F)c5)c(F)c4)nc(=O)n3CC2CN1]

The title compound was prepared by a procedure similar to that described for E348 starting from 7-chloro-11,11a-dihydro-1H-pyrazino[1',2':3,4]imidazo[1,2-c]pyrimidine-3,9(2H,4H)-dione and (3,5-difluoro-4-((2-(trifluoromethyl)pyridin-4-yl)oxy)phenyl)methanol.

LC/MS: m/z 510.0 (M+H)⁺, 0.81 min (ret. time).

¹H NMR (400 MHz, CD₃OD): δ ppm 3.40-3.62 (m, 2H) 3.86 (dd, J=11.29, 6.02 Hz, 1H) 4.00 (d, J=17.82 Hz, 1H) 4.18-4.41 (m, 3H) 5.42 (s, 3H) 7.18 (d, J=5.02 Hz, 1H) 7.34 (d, J=8.78 Hz, 2H) 7.44 (s, 1H) 8.63 (d, J=5.77 Hz, 1H)

E352

7-((3,5-Difluoro-4-((5-(trifluoromethyl)pyridin-3-yl)oxy)benzyl)oxy)-11,11a-dihydro-1H-pyrazino[1,2':3,4]imidazo[1,2-c]pyrimidine-3,9(2H,4H)-dione

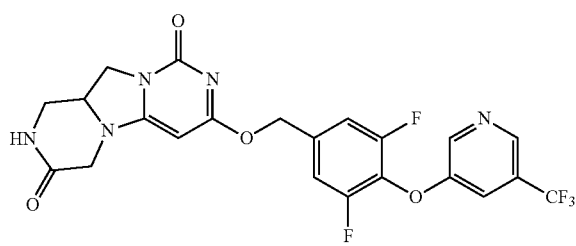 [SMILES: O=C1CN2c3cc(OCc4cc(F)c(Oc5cncc(C(F)(F)F)c5)c(F)c4)nc(=O)n3CC2CN1]

The title compound was prepared by a procedure similar to that described for E348 starting from 7-chloro-11,11a-dihydro-1H-pyrazino[1',2':3,4]imidazo[1,2-c]pyrimidine-3,9(2H,4H)-dione and (3,5-difluoro-4-((5-(trifluoromethyl)pyridin-3-yl)oxy)phenyl)methanol.

LC/MS: m/z 510.0 (M+H)⁺, 0.80 min (ret. time).

¹H NMR (400 MHz, DMSO-d₆): δ ppm 3.24-3.46 (m, 3H) 3.72 (dd, J=11.80, 6.27 Hz, 1H) 3.83 (d, J=17.57 Hz, 1H) 4.02-4.30 (m, 3H) 5.34 (s, 2H) 5.40 (s, 1H) 7.41 (d, J=9.29 Hz, 2H) 7.94 (br. s., 1H) 8.18 (br. s., 1H) 8.78 (d, J=15.56 Hz, 1H)

E353

7-((3,4-Difluorobenzyl)amino)-11,11a-dihydro-1H-pyrazino[1',2':3,4]imidazo[1,2-c]pyrimidine-3,9(2H,4H)-dione

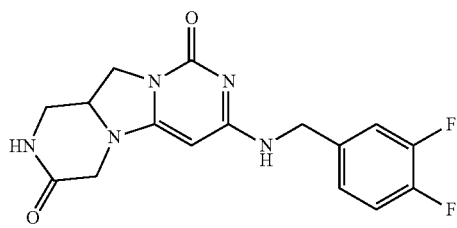 [SMILES: O=C1CN2c3cc(NCc4ccc(F)c(F)c4)nc(=O)n3CC2CN1]

A solution of 7-chloro-11,11a-dihydro-1H-pyrazino[1',2':3,4]imidazo[1,2-c]pyrimidine-3,9(2H,4H)-dione (98 mg, 0.407 mmol), (3,4-difluorophenyl)methanamine (0.053 mL, 0.448 mmol) and TEA (0.114 mL, 0.814 mmol) in DMSO (3 mL) in a microwave vial was heated to 160° C. using Microwave for 30 minutes. The crude product was purified using neutral Gilson at a gradient of 10% to 80% water/MeCN to give the title compound (75 mg).

LC/MS: m/z 347.9 (M+H)⁺, 0.50 min (ret. time).

¹H NMR (400 MHz, CD₃OD): δ 3.41 (dd, J=12.17, 10.16 Hz, 1H) 3.48-3.59 (m, 1H) 3.74 (d, J=5.02 Hz, 1H) 3.86-3.97 (m, 1H) 4.03-4.27 (m, 3H) 4.54 (br. s., 2H) 5.04 (s, 1H) 7.02-7.31 (m, 3H)

E354

5-(((3,9-dioxo-2,3,4,9,11,11a-hexahydro-1H-pyrazino[1',2':3,4]imidazo[1,2-c]pyrimidin-7-yl)amino)methyl)-2-fluorobenzonitrile, trifluoroacetic acid salt

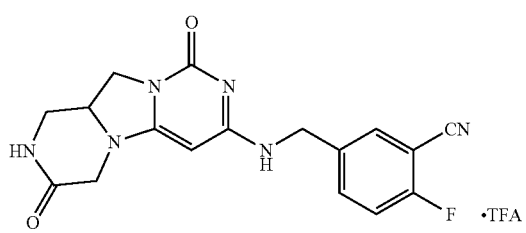 [SMILES: N#Cc1cc(CNc2cc3n(c(=O)n2)CC2CNC(=O)CN32)ccc1F]

The title compound was prepared by a procedure similar to that described for E353 starting from 7-chloro-11,11a-dihydro-1H-pyrazino[1',2':3,4]imidazo[1,2-c]pyrimidine-3,9(2H,4H)-dione and 5-(aminomethyl)-2-fluorobenzonitrile.

LC/MS: m/z 355.0 (M+H)⁺, 0.53 min (ret. time).

¹H NMR (400 MHz, CD₃OD): δ ppm 3.40-3.66 (m, 2H) 3.89 (dd, J=11.29, 6.53 Hz, 1H) 4.07 (d, J=17.82 Hz, 1H) 4.25-4.39 (m, 2H) 4.45 (br. s., 1H) 4.62 (s, 2H) 5.35 (m, 1H) 7.42 (t, J=8.78 Hz, 1H) 7.69-7.85 (m, 1H)

E355

7-((2,3-Difluorobenzyl)amino)-11,11a-dihydro-1H-pyrazino[1',2':3,4]imidazo[1,2-c]pyrimidine-3,9(2H,4H)-dione

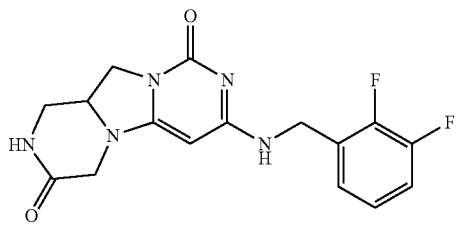 [SMILES: O=C1CN2c3cc(NCc4cccc(F)c4F)nc(=O)n3CC2CN1]

The title compound was prepared by a procedure similar to that described for E353 starting from 7-chloro-11,11a-dihydro-1H-pyrazino[1',2':3,4]imidazo[1,2-c]pyrimidine-3,9(2H,4H)-dione and (2,3-difluorophenyl)methanamine.

LC/MS: m/z 348.1 (M+H)$^+$, 0.49 min (ret. time).

$^1$H NMR (400 MHz, DMSO-d$_6$): δ ppm 3.17-3.44 (m, 4H) 3.57 (dd, J=11.04, 6.27 Hz, 1H) 3.71-3.83 (m, 1H) 3.86-4.02 (m, 2H) 4.02-4.14 (m, 1H) 4.95 (br. s., 1H) 7.07-7.23 (m, 2H) 7.24-7.36 (m, 1H) 7.60 (br. s., 1H) 8.14 (d, J=4.77 Hz, 1H)

E356

7-((3,4-difluorobenzyl)oxy)-11,11a-dihydro-1H-pyrazino[1',2':3,4]imidazo[1,2-c]pyrimidine-3,9(2H,4H)-dione

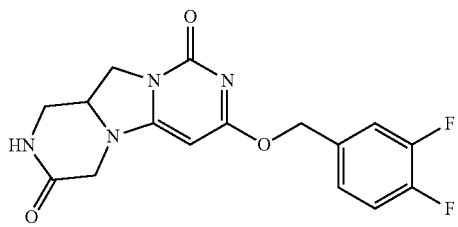 [SMILES: O=C1CN2c3cc(OCc4ccc(F)c(F)c4)nc(=O)n3CC2CN1]

The title compound was prepared by a procedure similar to that described for E348 starting from 7-chloro-11,11a-dihydro-1H-pyrazino[1',2':3,4]imidazo[1,2-c]pyrimidine-3,9(2H,4H)-dione and (3,4-difluorophenyl)methanol.

LC/MS: m/z 349.0 (M+H)$^+$, 0.58 min (ret. time).

$^1$H NMR (400 MHz, DMSO-d$_6$): δ 3.22-3.44 (m, 3H) 3.64-3.87 (m, 2H) 3.99-4.29 (m, 3H) 5.26 (s, 2H) 5.35 (s, 1H) 7.27 (br. s., 1H) 7.36-7.55 (m, 2H) 8.16 (d, J=3.76 Hz, 1H).

E357

2-Fluoro-5-(((2-methyl-3,9-dioxo-2,3,4,9,11,11a-hexahydro-1H-pyrazino[1',2':3,4]imidazo[1,2-c]pyrimidin-7-yl)oxy)methyl)benzonitrile

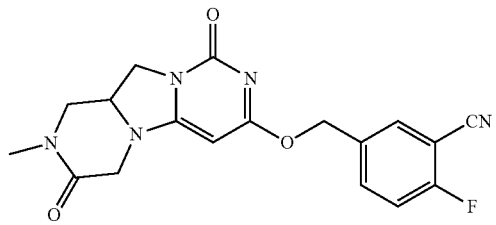 [SMILES: CN1CC2Cn3c(cc(OCc4ccc(F)c(C#N)c4)nc3=O)N2CC1=O]

The title compound was prepared by a procedure similar to that described for E348 starting from 7-chloro-2-methyl-11,11a-dihydro-1H-pyrazino[1',2':3,4]imidazo[1,2-c]pyrimidine-3,9(2H,4H)-dione and 2-fluoro-5-(hydroxymethyl)

LC/MS: m/z 370.0 (M+H)$^+$, 0.59 min (ret. time).

$^1$H NMR (400 MHz, DMSO-d$_6$): δ 2.89 (s, 3H) 3.38-3.60 (m, 2H) 3.76 (d, J=5.52 Hz, 1H) 3.88 (d, J=17.57 Hz, 1H) 4.04-4.24 (m, 2H) 4.26-4.40 (m, 1H) 5.30 (s, 2H) 5.40 (s, 1H) 6.52 (s, 1H) 7.52-7.61 (m, 1H) 7.83 (br. s., 1H) 7.96 (d, J=4.52 Hz, 1H).

E358

7-((3,4-Difluorobenzyl)oxy)-2-(2,2,2-trifluoroethyl)-11,11a-dihydro-1Hpyrazino[1',2':3,4] imidazo[1,2-c] pyrimidine-3,9(2H,4H)-dione

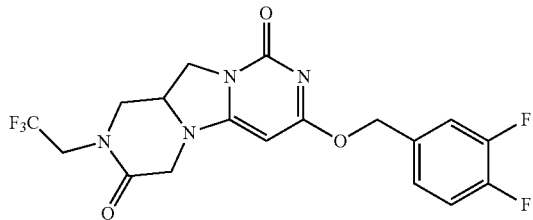 [SMILES: O=C1CN2c3cc(OCc4ccc(F)c(F)c4)nc(=O)n3CC2CN1CC(F)(F)F]

To a stirred suspension of 7-((3,4-difluorobenzyl)oxy)-11,11a-dihydro-1Hpyrazino[1',2':3,4]imidazo[1,2-c]pyrimidine-3,9(2H,4H)-dione (83 mg, 0.238 mmol) in THF (5 mL) and NMP (3 mL) at 0° C. was added lithium bis(trimethylsilyl)amide (1.0 M in THF) (0.274 mmol) dropwise, the resulting mixture was stirred at 0° C. for 15 min, then 2,2,2-trifluoroethyl trifluoromethanesulfonate (0.039 mL, 0.274 mmol) was added dropwise. The mixture was allowed to warm to RT and stirred for 1 hour. The resulting mixture was partitioned between 20 mL aq. NaHCO$_3$ and EA (30 mL). The combined organic layer was concentrated and the crude was purified using CombiFlash Rf 200 with a gradient of 100% DCM to 10% MeOH in DCM and then purified again using neutral Gilson at a gradient of 10% to 90% water/MeCN to give the title compound (46 mg) as a white solid.

LC/MS: m/z 431.0 (M+H)$^+$, 0.75 min (ret. time).

$^1$H NMR (400 MHz, DMSO-d$_6$): δ 3.58-3.71 (m, 2H) 3.76 (dd, J=11.80, 6.02 Hz, 1H) 4.02 (d, J=17.82 Hz, 1H)

4.07-4.22 (m, 2H) 4.27-4.41 (m, 3H) 5.26 (s, 2H) 5.40 (s, 1H) 7.27 (br. s., 1H) 7.37-7.53 (m, 2H)

E359

7-((3,4-Difluorobenzyl)oxy)-2-methyl-11,11a-dihydro-1H-pyrazino[1,2':3,4]imidazo[1,2-c]pyrimidine-3,9(2H,4H)-dione

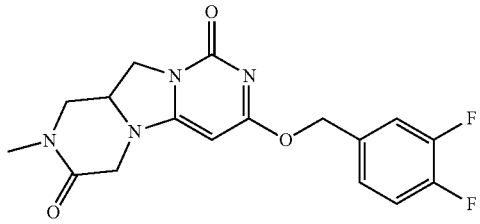 [SMILES: CN1CC2Cn3c(cc(OCc4ccc(F)c(F)c4)nc3=O)N2CC1=O]

To a solution of 7-((3,4-difluorobenzyl)oxy)-11,11a-dihydro-1H-pyrazino[1',2':3,4]imidazo[1,2-c]pyrimidine-3,9(2H,4H)-dione (71 mg, 0.204 mmol) and 18-crown-6 (2.55 mg, 10.19 µmol) in THF (10 mL) and DMSO (2 mL) at 0° C. was added sodium hydride (16.31 mg, 0.408 mmol). The reaction mixture was then stirred for 20 minutes at RT, then at 0° C., iodomethane (0.020 mL, 0.326 mmol) was added. The mixture was stirred at RT for two hours. Water was added to quench the reaction. The mixture was then concentrated and the crude was purified using CombiFlash Rf 200 with a gradient of 100% DCM to 20% MeOH in DCM, the product came out about 12% MeOH in DCM and then purified again using neutral Gilson at a gradient of 10% to 85% water/MeCN to give 58 mg of the title compound as a white solid.

LC/MS: m/z 363.0 (M+H)$^+$, 0.61 min (ret. time).
$^1$H NMR (400 MHz, DMSO-d$_6$): δ 2.88 (s, 3H) 3.38-3.58 (m, 2H) 3.73 (dd, J=11.54, 5.77 Hz, 1H) 3.87 (d, J=17.32 Hz, 1H) 4.09 (dd, J=11.54, 9.03 Hz, 1H) 4.18 (d, J=17.57 Hz, 1H) 4.31 (dd, J=9.29, 4.77 Hz, 1H) 5.26 (s, 2H) 5.38 (s, 1H) 7.26 (br. s., 1H) 7.36-7.53 (m, 1H)

E360

7-((3,5-difluoro-4-((6-methylpyridin-3-yl)oxy)benzyl)oxy)-2-methyl-11,11a-dihydro-1H-pyrazino[1',2':3,4]imidazo[1,2-c]pyrimidine-3,9(2H,4H)-dione, trifluoroacetic acid salt

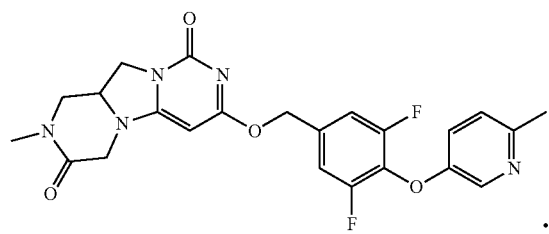

The title compound was prepared by a procedure similar to that described for E348 starting from 7-chloro-2-methyl-11,11a-dihydro-1H-pyrazino[1',2':3,4]imidazo[1,2-c]pyrimidine-3,9(2H,4H)-dione and (3,5-difluoro-4-((6-methylpyridin-3-yl)oxy)phenyl)methanol.

LC/MS: m/z 470.0 (M+H)$^+$, 0.60 min (ret. time).
$^1$H NMR (400 MHz, DMSO-d$_6$): δ 2.47 (s, 3H) 2.90 (s, 3H) 3.42-3.53 (m, 1H) 3.53-3.66 (m, 1H) 3.83 (dd, J=11.80, 5.77 Hz, 1H) 4.00 (d, J=17.57 Hz, 1H) 4.09-4.24 (m, 1H) 4.35 (d, J=17.57 Hz, 2H) 5.35 (s, 2H) 5.76 (s, 1H) 7.01 (s, 1H) 7.14 (s, 1H) 7.26 (s, 1H) 7.29-7.37 (m, 1H) 7.42 (d, J=8.78 Hz, 2H) 8.34 (d, J=2.76 Hz, 1H)

E361

7-((2,3-Difluorobenzyl)oxy)-3,4,11,11a-tetrahydropyrimido[6',1':2,3]imidazo[5,1-c][1,4] thiazin-9(1H)-one

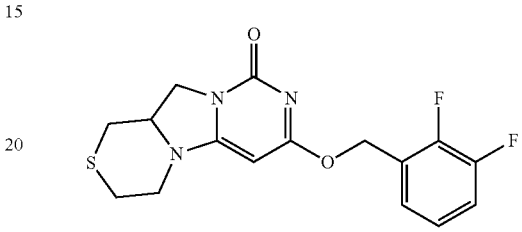

The title compound was prepared by a procedure similar to that described for E348 starting from 7-chloro-3,4,11,11a-tetrahydropyrimido[6',1':2,3]imidazo[5,1-c][1,4]thiazin-9(1H)-one and (2,3-difluorophenyl)methanol.

LC/MS: m/z 352 (M+H)$^+$, 0.706 min (ret. time).
$^1$H NMR (400 MHz, DMSO-d$_6$) δ ppm 2.54-2.61 (m, 1H) 2.66-2.83 (m, 3H) 3.17 (t, J=12.55 Hz, 1H) 3.52-3.59 (m, 1H) 3.95-4.15 (m, 3H) 5.34 (br. s., 1H) 5.35 (br. s., 2H) 7.19-7.28 (m, 1H) 7.28-7.35 (m, 1H) 7.38-7.49 (m, 1H).

E362 and E363

7-((2,3-Difluorobenzyl)oxy)-3,4,11,11a-tetrahydropyrimido[6',1':2,3]imidazo[5,1-c][1,4] thiazin-9(1H)-one 2-oxide (E362)

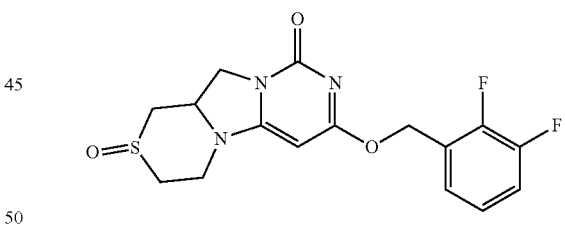

7-((2,3-Difluorobenzyl)oxy)-3,4,11,11a-tetrahydropyrimido[6',1':2,3]imidazo[5,1-c][1,4] thiazin-9(1H)-one 2,2-dioxide (E363)

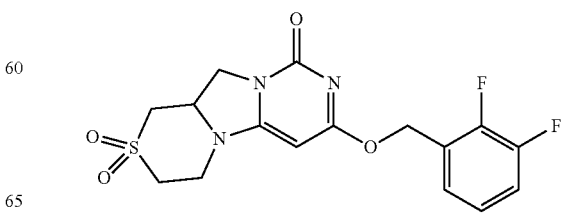

To a solution of 7-((2,3-difluorobenzyl)oxy)-3,4,11,11a-tetrahydropyrimido[6',1':2,3]imidazo[5,1-c][1,4] thiazin-9(1H)-one (142 mg, 0.40 mmol, 1.0 equiv) in THF (3 mL) and water (1 mL) was added oxone (248 mg, 0.40 mmol, 1.0 equiv) and the reaction was stirred at rt for 1 h. The mixture was quenched with saturated NaHCO₃ dropwise and then concentrated. The residue was re-dissolved in saturated NaHCO₃ (3 mL) and water (15 mL), and 10% MeOH in DCM (20 mL). The mixture was filtered through celite. The celite cake was repeatedly washed with 10% MeOH in DCM (20 mL). The combined filtrate was phase separated. The aqueous portion was back extracted with 10% MeOH in DCM (20 mL). The combined organic was concentrated and purified by Gilson HPLC (Sunfire 5 μm C18 OBD 19×100 mm, 10%-90% CH₃CN/H₂O (0.1% TFA) preparatory column) to give the title compound E362 (70 mg) as a white solid and E363 (152 mg) as a white solid.

E362: LC/MS: m/z 367.9 (M+H)⁺, 0.61 min (ret. time).
¹H NMR (400 MHz, DMSO-d₆) δ ppm 2.75-2.85 (m, 1H) 2.88-2.96 (m, 2H) 3.11 (d, J=14.05 Hz, 1H) 3.67 (dd, J=11.54, 6.53 Hz, 1H) 3.71-3.80 (m, 1H) 3.81-3.89 (m, 1H) 4.12 (t, J=10.29 Hz, 1H) 4.50-4.62 (m, 1H) 5.30-5.40 (m, 2H) 5.45 (s, 1H) 7.18-7.27 (m, 1H) 7.27-7.34 (m, 1H) 7.37-7.48 (m, 1H).

E363: LC/MS: m/z 383.9 (M+H)⁺, 0.66 min (ret. time).
¹H NMR (400 MHz, DMSO-d₆): δ ppm 3.22-3.34 (m, 3H) 3.41 (d, J=6.02 Hz, 1H) 3.49-3.58 (m, 1H) 3.72 (dd, J=11.80, 6.02 Hz, 1H) 4.07-4.16 (m, 1H) 4.20 (d, J=14.05 Hz, 1H) 4.33-4.44 (m, 1H) 5.31-5.42 (m, 2H) 5.49 (s, 1H) 7.20-7.28 (m, 1H) 7.29-7.36 (m, 1H) 7.44 (q, J=9.03 Hz, 1H).

The following compounds E364-E373 listed in Table 5 were prepared by a procedure similar to that described for E362 and E363 starting from the requisite benzyl alcohols and intermediates:

TABLE 5

| Ex # | Name | Structure | LCMS | ¹HNMR (400 MHz) |
|---|---|---|---|---|
| E364 | 2-Fluoro-5-(((9-oxo-1,3,4,9,11,11a-hexahydropyrimido[6',1':2,3]imidazo[5,1-c][1,4]thiazin-7-yl)oxy)methyl)benzonitrile | 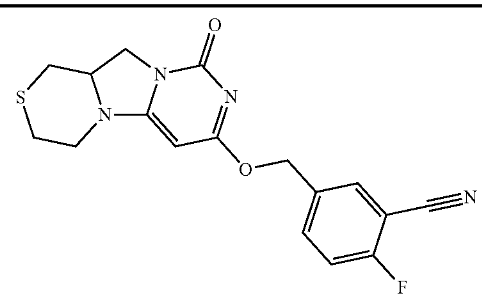 | m/z 359 (M + H)⁺, 0.689 min (ret. time) | DMSO-d6: δ ppm 2.55-2.63 (m, 1 H) 2.65-2.85 (m, 3 H) 3.12-3.25 (m, 1 H) 3.51-3.60 (m, 1 H) 3.95-4.16 (m, 3 H) 5.29 (s, 2 H) 5.35 (s, 1 H) 7.56 (t, J = 9.03 Hz, 1 H) 7.78-7.87 (m, 1 H) 7.96 (dd, J = 6.27, 2.26 Hz, 1 H). |
| E365 | 5-((2-Cyano-4-(((9-oxo-1,3,4,9,11,11a-hexahydropyrimido[6',1':2,3]imidazo[5,1-c][1,4]thiazin-7-yl)oxy)methyl)phenoxy)methyl)-2-fluorobenzonitrile | 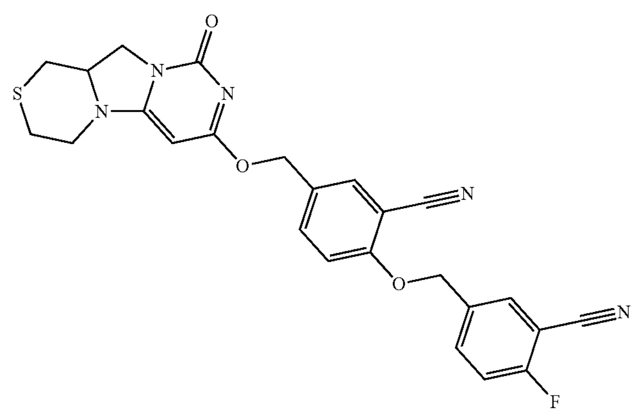 [SMILES: N#Cc1cc(COc2ccc(COc3cc4n(c(=O)n3)CC3CSCCN43)cc2C#N)ccc1F] | m/z 490 (M + H)⁺, 0.854 min (ret. time). | DMSO-d6: δ ppm 2.54-2.62 (m, 1 H) 2.66-2.84 (m, 3 H) 3.11-3.23 (m, 1 H) 3.55 (dd, J = 10.79, 6.53 Hz, 1 H) 3.95-4.15 (m, 3 H) 5.22 (s, 2 H) 5.31 (s, 1 H) 5.33 (s, 2 H) 7.36 (d, J = 8.78 Hz, 1 H) 7.63 (t, J = 9.03 Hz, 1 H) 7.72 (dd, J = 8.66, 2.13 Hz, 1 H) 7.80 (d, J = 2.01 Hz, 1 H) 7.91 (ddd, J = 8.47, 5.58, 2.26 Hz, 1 H) 8.06 (dd, J = 6.27, 2.26 Hz, 1 H) |
| E366 | 2-Fluoro-5-(((2-oxido-9-oxo-1,3,4,9,11,11a-hexahydropyrimido[6',1':2,3]imidazo[5,1-c][1,4]thiazin-7-yl)oxy)methyl)benzonitrile | 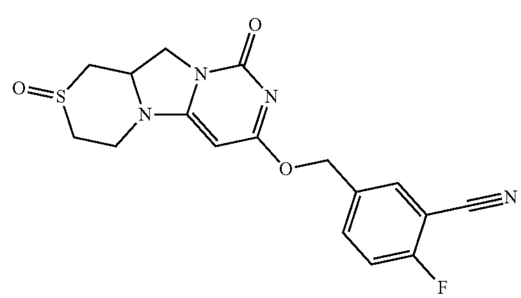 [SMILES: N#Cc1cc(COc2cc3n(c(=O)n2)CC2CS(=O)CCN32)ccc1F] | m/z 374.9 (M + H)⁺, 0.56 min (ret. time). | DMSO-d6, selected signals: δ ppm 2.75-2.87 (m, 1 H) 2.87-2.97 (m, 1 H) 3.07-3.15 (m, 2 H) 3.67 (dd, J = 11.54, 6.53 Hz, 1 H) 3.71-3.77 (m, 1 H) 3.80 (d, J = 9.54 Hz, 1 H) 4.08-4.18 (m, 1 H) 4.56 (d, J = 8.78 Hz, 1 H |

TABLE 5-continued

| Ex # | Name | Structure | LCMS | ¹HNMR (400 MHz) |
|---|---|---|---|---|
| | | | | 5.29 (s, 2 H) 5.43 (s, 1 H) 7.53 (t, J = 9.03 Hz, 1 H) 7.81 (t, J = 5.90 Hz, 1 H) 7.94 (d, J = 6.27 Hz, 1 H). |
| E367 | 5-(((2,2-Dioxido-9-oxo-1,3,4,9,11,11a-hexahydro-pyrimido[6',1':2,3]imidazo[5,1-c][1,4]thiazin-7-yl)oxy)methyl)-2-fluoro-benzonitrile | 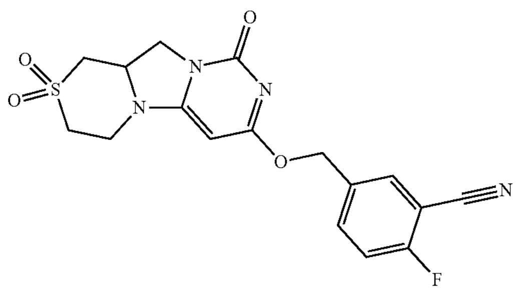 [SMILES: N#Cc1cc(COc2cc3n(c(=O)n2)CC2CS(=O)(=O)CCN32)ccc1F] | m/z 390.9 (M + H)+, 0.65 min (ret. time) | DMSO-d6: δ ppm 3.26 (d, J = 5.02 Hz, 2 H) 3.40-3.49 (m, 2 H) 3.49-3.57 (m, 1 H) 3.71 (dd, J = 11.54, 6.02 Hz, 1 H) 4.09-4.16 (m, 1 H) 4.20 (d, J = 14.31 Hz, 1 H) 4.37 (br. s., 1 H) 5.31 (s, 2 H) 5.51 (s, 1 H) 7.57 (t, J = 9.03 Hz, 1 H) 7.79-7.87 (m, 1 H) 7.96 (d, J = 6.27 Hz, 1 H). |
| E368 | 7-((3,5-Difluoro-4-((2-(trifluoro-methyl)pyridin-4-yl)oxy)benzyl)oxy)3,4,11,11a-tetrahydro-pyrimido[6',1':2,3]imidazo[5,1-c][1,4]thiazin-9(1H)-one | 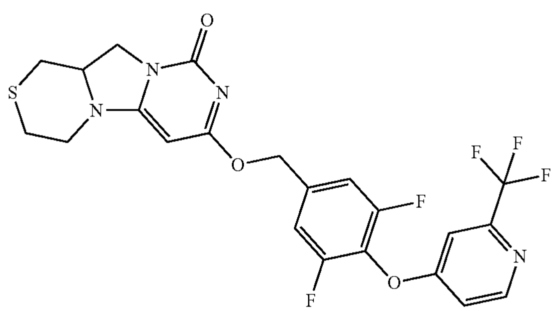 [SMILES: O=c1nc(OCc2cc(F)c(Oc3ccnc(C(F)(F)F)c3)c(F)c2)cc2n1CC1CSCCN21] | m/z 513 (M + H)+, 0.937 min (ret. time | DMSO-d6: δ ppm 2.55-2.64 (m, 1 H) 2.66-2.85 (m, 3 H) 3.20 (t, J = 11.67 Hz, 1 H) 3.55-3.59 (m, 1 H) 3.98-4.17 (m, 3 H) 5.34 (s, 2 H) 5.39 (s, 1 H) 7.32 (d, J = 4.02 Hz, 1 H) 7.44 (d, J = 9.03 Hz, 2 H) 7.67 (s, 1 H) 8.69 (d, J = 5.77 Hz, 1 H). |
| E369 | 7-((3,5-Difluoro-4-((2-(trifluoro-methyl)pyridin-4-yl)oxy)benzyl)oxy)-3,4,11,11a-tetrahydro-pyrimido[6',1':2,3]imidazo[5,1-c][1,4]thiazin-9(1H)-one 2-oxide | 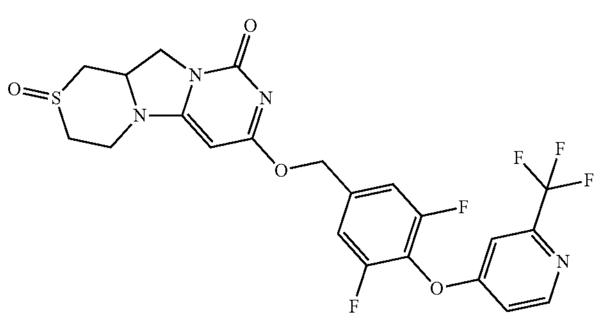 [SMILES: O=c1nc(OCc2cc(F)c(Oc3ccnc(C(F)(F)F)c3)c(F)c2)cc2n1CC1CS(=O)CCN21] | m/z 528.9 (M + H)+, 0.81 min (ret. time). | DMSO-d6: δ ppm 3.23-3.28 (m, 2 H) 3.40-3.47 (m, 2 H) 3.47-3.57 (m, 1 H) 3.71 (dd, J = 11.67, 5.90 Hz, 1 H) 4.08-4.17 (m, 1 H) 4.21 (d, J = 14.30 Hz, 1 H) 4.38 (d, J = 8.03 Hz, 1 H) 5.34 (s, 2 H) 5.53 (s, 1 H) 7.39 (d, J = 9.03 Hz, 2 H) 7.91 (br. s., 1 H) 8.74 (s, 1 H) 8.79 (s, 1 H). |

TABLE 5-continued

| Ex # | Name | Structure | LCMS | ¹HNMR (400 MHz) |
|---|---|---|---|---|
| E370 | 7-((3,5-Difluoro-4-((2-(trifluoromethyl)pyridin-4-yl)oxy)benzyl)oxy)-3,4,11,11a-tetrahydropyrimido[6',1':2,3]imidazo[5,1-c][1,4]thiazin-9(1H)-one-2,2-dioxide | 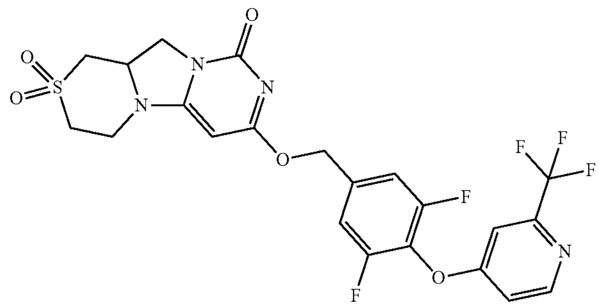 [SMILES: O=c1nc(OCc2cc(F)c(Oc3ccnc(C(F)(F)F)c3)c(F)c2)cc2n1CC1CS(=O)(=O)CCN21] | m/z 544.9 (M + H)+, 0.90 min (ret. time). | DMSO-d6: δ ppm 3.23-3.28 (m, 2 H) 3.40-3.47 (m, 2 H) 3.47-3.57 (m, 1 H) 3.71 (dd, J = 11.67, 5.90 Hz, 1 H) 4.08-4.17 (m, 1 H) 4.21 (d, J = 14.30 Hz, 1 H) 4.38 (d, J = 8.03 Hz, 1 H) 5.34 (s, 2 H) 5.53 (s, 1 H) 7.39 (d, J = 9.03 Hz, 2 H) 7.91 (br. s., 1 H) 8.74 (s, 1 H) 8.79 (s, 1 H). |
| E371 | 7-((3,5-Difluoro-4-((5-(trifluoromethyl)pyridin-3-yl)oxy)benzyl)oxy)-3,4,11,11a-tetrahydropyrimido[6',1':2,3]imidazo[5,1-c][1,4]thiazin-9(1H)-one | 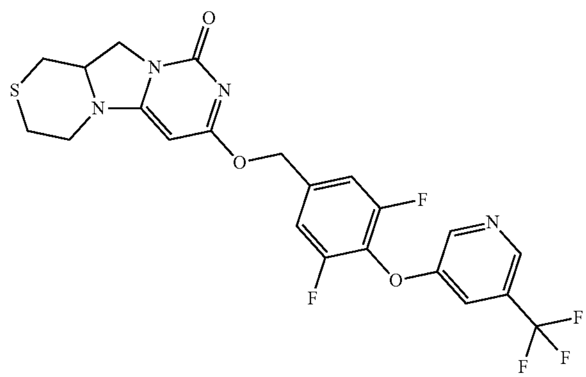 [SMILES: O=c1nc(OCc2cc(F)c(Oc3cncc(C(F)(F)F)c3)c(F)c2)cc2n1CC1CSCCN21] | m/z 513 (M + H)+, 0.924 min (ret. time). | DMSO-d6: δ ppm 3.23-3.28 (m, 2 H) 3.40-3.47 (m, 2 H) 3.47-3.57 (m, 1 H) 3.71 (dd, J = 11.67, 5.90 Hz, 1 H) 4.08-4.17 (m, 1 H) 4.21 (d, J = 14.30 Hz, 1 H) 4.38 (d, J = 8.03 Hz, 1 H) 5.34 (s, 2 H) 5.53 (s, 1 H) 7.39 (d, J = 9.03 Hz, 2 H) 7.91 (br. s., 1 H) 8.74 (s, 1 H) 8.79 (s, 1 H). |
| E372 | 7-((3,5-Difluoro-4-((5-(trifluoromethyl)pyridin-3-yl)oxy)benzyl)oxy)-3,4,11,11a-tetrahydropyrimido[6',1':2,3]imidazo[5,1-c][1,4]thiazin-9(1H)-one 2-oxide | 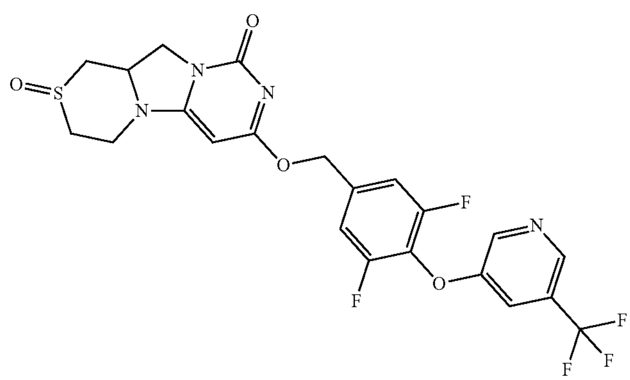 [SMILES: O=c1nc(OCc2cc(F)c(Oc3cncc(C(F)(F)F)c3)c(F)c2)cc2n1CC1CS(=O)CCN21] | m/z 528.9 (M + H)+, 0.81 min (ret. time). | DMSO-d6: δ ppm 3.23-3.28 (m, 2 H) 3.40-3.47 (m, 2 H) 3.47-3.57 (m, 1 H) 3.71 (dd, J = 11.67, 5.90 Hz, 1 H) 4.08-4.17 (m, 1 H) 4.21 (d, J = 14.30 Hz, 1 H) 4.38 (d, J = 8.03 Hz, 1 H) 5.34 (s, 2 H) 5.53 (s, 1 H) 7.39 (d, J = 9.03 Hz, 2 H) 7.91 (br. s., 1 H) 8.74 (s, 1 H) 8.79 (s, 1 H). |
| E373 | 7-((3,5-Difluoro-4-((5-(trifluoromethyl)pyridin-3-yl)oxy)benzyl)oxy)-3,4,11,11a-tetrahydropyrimido[6',1':2,3]imidazo[5,1-c][1,4]thiazin-9(1H)-one 2,2-dioxide | 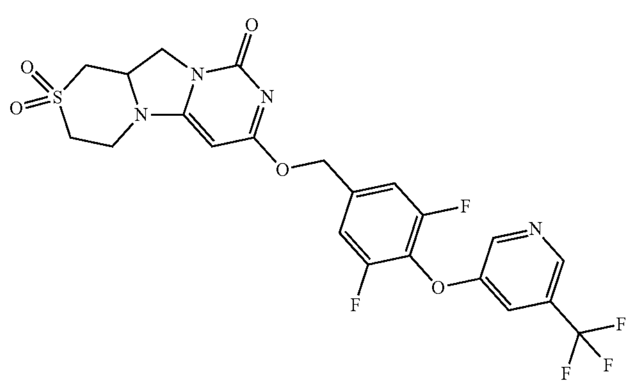 [SMILES: O=c1nc(OCc2cc(F)c(Oc3cncc(C(F)(F)F)c3)c(F)c2)cc2n1CC1CS(=O)(=O)CCN21] | m/z 544.9 (M + H)+, 0.89 min (ret. time). | DMSO-d6: δ ppm 3.23-3.28 (m, 2 H) 3.40-3.47 (m, 2 H) 3.47-3.57 (m, 1 H) 3.71 (dd, J = 11.67, 5.90 Hz, 1 H) 4.08-4.17 (m, 1 H) 4.21 (d, J = 14.30 Hz, 1 H) 4.38 (d, J = 8.03 Hz, 1 H) 5.34 (s, 2 H) 5.53 (s, 1 H) 7.39 (d, J = 9.03 Hz, 2 H) 7.91 (br. s., 1 H) 8.74 (s, 1 H) 8.79 (s, 1 H). |

E374

7-((3,4-Difluorobenzyl)amino)-3,4,11,11a-tetrahydropyrimido[6',1':2,3]imidazo[5,1-c][1,4]thiazin-9(1H)-one

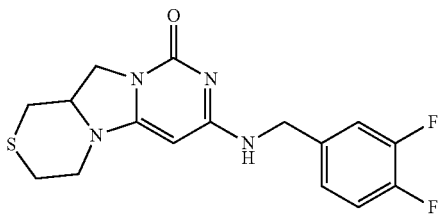 [SMILES: O=c1nc(NCc2ccc(F)c(F)c2)cc2n1CC1CSCCN21]

A mixture of 7-chloro-3,4,11,11a-tetrahydropyrimido[6',1':2,3]imidazo[5,1-c][1,4]thiazin-9(1H)-one (109 mg, 0.45 mmol, 1 equiv) and (3,4-difluorobenzylamine (77 mg, 0.54 mmol, 1.2 equiv) and $K_2CO_3$ (185 mg, 1.34 mmol, 3 equiv) in (2 mL) was heated at 100° C. for 16 hrs. The mixture was acidified with 0.5 mL of 6N HCl and filtered. The filtrate was concentrated and purified on a Gilson HPLC (Sunfire 5 μm C18 OBD 19×100 mm, 10%-90% $CH_3CN/H_2O$ (0.1% TFA)) to give the title compound (52 mg) as a white solid.

LC/MS: m/z 350.9 (M+H)$^+$, 0.67 min (ret. time).

$^1$H NMR (400 MHz, DMSO-$d_6$): δ ppm 2.53-2.61 (m, 1H) 2.65-2.77 (m, 3H) 3.08-3.14 (m, 1H) 3.41 (t, J=9.29 Hz, 1H) 3.89 (br. s., 1H) 3.96-4.04 (m, 1H) 4.06 (q, J=5.27 Hz, 1H) 4.42 (br. s., 2H) 4.90 (br. s., 1H) 7.11 (br. s., 1H) 7.24-7.43 (m, 2H) 7.54 (br. s., 1H).

E375

7-((3,4-Difluorobenzyl)amino)-3,4,11,11a-tetrahydropyrimido[6',1':2,3]imidazo[5,1-c][1,4]thiazin-9(1H)-one 2-oxide

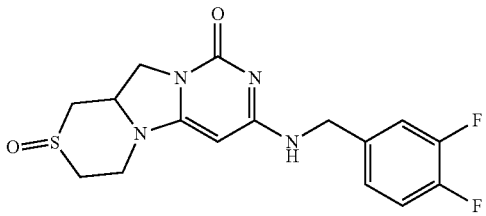 [SMILES: O=c1nc(NCc2ccc(F)c(F)c2)cc2n1CC1CS(=O)CCN21]

To a solution of 7-((3,4-Difluorobenzyl)amino)-3,4,11,11a-tetrahydropyrimido[6',1':2,3]imidazo[5,1-c][1,4]thiazin-9(1H)-one (97 mg, 0.28 mmol, 1.0 equiv) in 3 mL of THF, 0.5 mL of 1N HCl and 0.5 mL of water at rt was added oxone (42 mg) in one portion. The mixture was stirred at room temperature for 3.5 hrs and concentrated to remove THF. The resulting slurry was basified with saturated $NaHCO_3$ solution to pH=8/9. The mixture was diluted with water (8 mL) and 10% MeOH in DCM (30 mL), and filtered through celite. The filtrate was phase separated and the aqueous was extracted with 10% MeOH in DCM (3×10 mL). The combined organic layer was dried over $Na_2SO_4$, filtered, and concentrated. The crude was purified by Combiflash system (24 g silica gel cartridge) to give 83 mg of the title compound as diastereomers (3:7 roughly).

LC/MS: m/z 366.9 (M+H)$^+$, 0.54 min (ret. time).

$^1$H NMR (400 MHz, DMSO-$d_6$): δ ppm 2.58-2.73 (m, 1H) 2.74-2.86 (m, 2H) 2.86-2.95 (m, 1H) 3.09 (d, J=13.55 Hz, 1H) 3.53 (dd, J=11.17, 6.65 Hz, 1H) 3.57-3.65 (m, 1H) 3.65-3.77 (m, 1H) 3.92-4.09 (m, 2H) 4.32-4.54 (m, 2H) 4.99 (br. s., 1H) 7.12 (br. s., 1H) 7.24-7.34 (m, 2H) 7.34-7.42 (m, 1H) 7.58 (br. s., 1H).

E376

7-((3,4-difluorobenzyl)amino)-3,4,11,11a-tetrahydropyrimido[6',1':2,3]imidazo[5,1-c][1,4]thiazin-9(1H)-one 2,2-dioxide

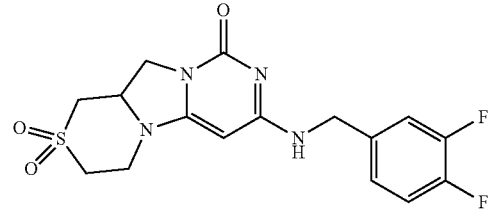 [SMILES: O=c1nc(NCc2ccc(F)c(F)c2)cc2n1CC1CS(=O)(=O)CCN21]

To a cloudy mixture of 7-((3,4-difluorobenzyl)amino)-3,4,11,11a-tetrahydropyrimido[6',1':2,3]imidazo[5,1-c][1,4]thiazin-9(1H)-one (250 mg, 0.71 mmol, 1.0 equiv) in THF (6 mL) and water (2 mL) at rt was added oxone (136 mg) in one portion. The reaction was monitored by LCMS every 0.5-1.0 h, followed by addition of incremental amounts of oxone (181 and 50 mg). After 4.5 h at rt, the mixture was concentrated to remove THF. The resulting slurry was basified with saturated $NaHCO_3$ solution to pH=8/9. The mixture was diluted with water (15 mL) and 10% MeOH in DCM (30 mL), and filtered through celite. The filtrate was phase separated and the aqueous layer was extracted with 10% MeOH in DCM (3×10 mL). The combined organic was dried over $Na_2SO_4$, filtered, and concentrated. The crude was purified by Gilson HPLC (Sunfire 5 μm C18 OBD 19×100 mm, 10%-80% $CH_3CN/H_2O$ (0.1% TFA)) and then Redi-Sep 12 g silica gel cartridge to give the title compound (34 mg) as a white solid.

LC/MS: m/z 382.9 (M+H)$^+$, 0.50 min (ret. time).

$^1$H NMR (400 MHz, DMSO-$d_6$): δ ppm 3.18-3.27 (m, 2H) 3.34-3.46 (m, 3H) 3.57 (dd, J=11.29, 6.53 Hz, 1H) 3.91-4.05 (m, 2H) 4.17-4.27 (m, 1H) 4.44 (br. s., 2H) 5.01 (br. s., 1H) 7.12 (br. s., 1H) 7.24-7.33 (m, 1H) 7.37 (dt, J=10.79, 8.53 Hz, 1H) 7.62 (br. s., 1H).

The following compounds E377-E379 listed in Table 6 were prepared by a procedure similar to that described for E375 and E376 starting from the requisite benzyl amines and intermediates:

TABLE 6

| Ex # | Name | Structure | LCMS | ¹HNMR (400 MHz) |
|---|---|---|---|---|
| E377 | 7-((2,3-Difluoro-benzyl)amino)-3,4,11,11a-tetrahydro-pyrimido[6',1':2,3]imidazo[5,1-c][1,4]thiazin-9(1H)-one | 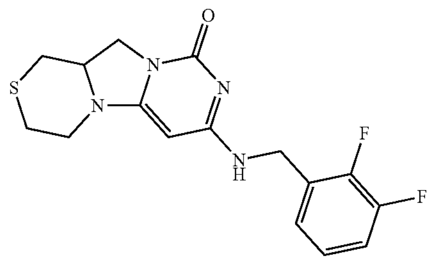 [SMILES: O=c1nc(NCc2cccc(F)c2F)cc2n1CC1CSCCN21] | 350.9 (M + H)⁺, 0.64 min (ret. time). | DMSO-d6: δ ppm 2.56 (d, J = 13.30 Hz, 1 H) 2.64-2.77 (m, 3 H) 3.06-3.14 (m, 1 H) 3.39 (dd, J = 10.67, 7.91 Hz, 1 H) 3.77 (d, J = 13.55 Hz, 1 H) 3.82-3.92 (m, 1 H) 3.95-4.03 (m, 1 H) 4.52 (br. s., 2 H) 4.92 (br. s., 1 H) 7.08-7.20 (m, 2 H) 7.23-7.35 (m, 1 H) 7.49 (br. s., 1 H). |
| E378 | 7-((2,3-Difluoro-benzyl)amino)-3,4,11,11a-tetrahydro-pyrimido[6',1':2,3]imidazo[5,1-c][1,4]thiazin-9(1H)-one-2-oxide | 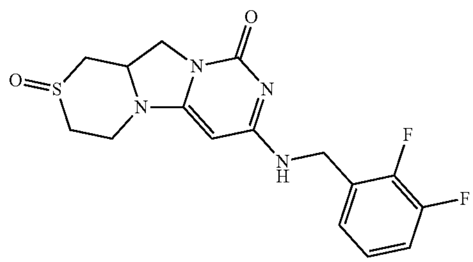 [SMILES: O=c1nc(NCc2cccc(F)c2F)cc2n1CC1CS(=O)CCN21] | m/z 366.9 (M + H)⁺, 0.52 min (ret. time). | DMSO-d6, selected signals: δ ppm 2.87-2.95 (m, 1 H) 3.03-3.13 (m, 1 H) 3.53 (dd, J = 11.17, 6.65 Hz, 1 H) 3.56-3.63 (m, 1 H) 3.65-3.76 (m, 1 H) 4.00 (dd, J = 11.17, 8.66 Hz, 1 H) 4.32-4.44 (m, 1 H) 4.53 (br. s., 2 H) 5.01 (br. s., 1 H) 7.08-7.20 (m, 2 H) 7.25-7.36 (m, 1 H) 7.62 (br. s., 1 H). |
| E379 | 7-((2,3-Difluoro-benzyl)amino)-3,4,11,11a-tetrahydro-pyrimido[6',1':2,3]imidazo[5,1-c][1,4]thiazin-9(1H)-one-2,2-dioxide | 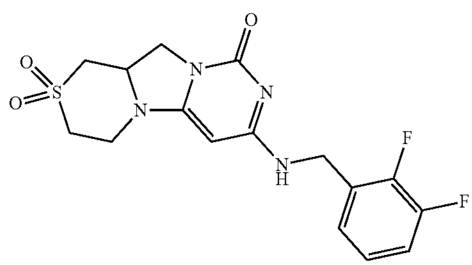 [SMILES: O=c1nc(NCc2cccc(F)c2F)cc2n1CC1CS(=O)(=O)CCN21] | m/z 382.9 (M + H)⁺, 0.57 min (ret. time). | DMSO-d6: δ ppm 3.19-3.27 (m, 2 H) 3.33-3.46 (m, 3 H) 3.57 (dd, J = 11.29, 6.53 Hz, 1 H) 3.94-4.04 (m, 2 H) 4.16-4.27 (m, 1 H) 4.53 (br. s., 2 H) 5.03 (br. s., 1 H) 7.07-7.21 (m, 2 H) 7.25-7.36 (m, 1 H) 7.61 (br. s., 1 H). |

E380

7-(2,3-Difluorophenethyl)-3,4,11,11a-tetrahydropy-rimido[6',1':2,3]imidazo[5,1-c][1,4]thiazin-9(1H)-one

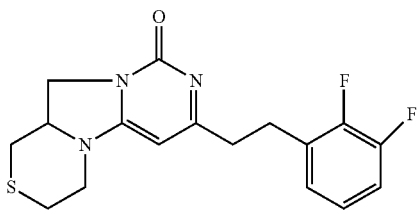 [SMILES: O=c1nc(CCc2cccc(F)c2F)cc2n1CC1CSCCN21]

A solution of 7-((2,3-difluorophenyl)ethynyl)-3,4,11,11a-tetrahydropyrimido[6',1':2,3]imidazo[5,1-c][1,4]thiazin-9 (1H)-one (100 mg) in EtOH (30 mL) and of MeOH (70 mL) was treated in the H-Cube using a 20% Pd(OH)₂/C cartridge under 90 Bar and was stirred at 55° C. for 9 hrs. The mixture was filtered and concentrated. The crude was purified by Gilson HPLC (Sunfire 5 μm C18 OBD 19×100 mm, 10%-90% CH₃CN/H₂O (0.1% TFA)) to give the title compound (25 mg) as a light yellowish oily residue.

LC/MS: m/z 350 (M+H)⁺, 0.610 min (ret. time).

¹H NMR (400 MHz, 1:1 CD₂Cl₂: CD₃OD): δ ppm 2.50-2.61 (m, 1H) 2.67-2.86 (m, 5H) 3.00 (t, J=7.65 Hz, 2H) 3.32-3.43 (m, 1H) 3.69-3.71 (m, 1H) 3.92-3.95 (m, 1H) 4.13-4.23 (m, 1H) 4.24-4.33 (m, 1H) 5.60 (s, 1H) 6.94-7.09 (m, 3H).

E381

2-Fluoro-5-((((7R,8aR)-7-hydroxy-1-oxo-1,6,7,8,8a,9-hexahydropyrrolo[1',2':3,4]imidazo[1,2-c]pyrimi-din-3-yl)oxy)methyl)benzonitrile

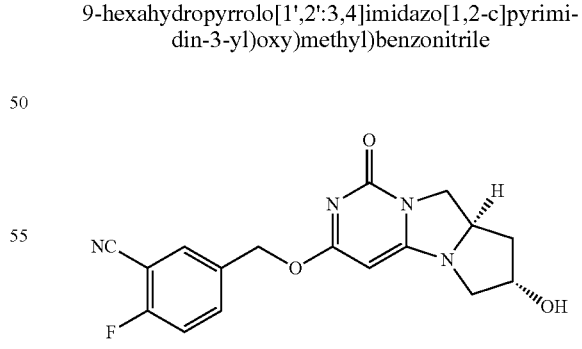

To a solution of (7R,8aR)-7-((tert-Butyldimethylsilyl)oxy)-3-chloro-7,8,8a,9 tetrahydropyrrolo[1',2':3,4] imidazo[1,2-c]pyrimidin-1(6H)-one (30 mg, 0.088 mmol) and 2-fluoro-5-(hydroxymethyl)benzonitrile (13.26 mg, 0.088 mmol) in THF (627 μl) was added NaH (8.77 mg, 0.219 mmol). After 40 min at room temperature, the reaction was quenched with MeOH and concentrated. The crude was purified by reverse-phase HPLC (10-70% CH₃CN:H₂O, 0.1% TFA as modifier) to TBS-protected intermediate as a white solid (LC/MS: m/z 457.2 (M+H)⁺, 1.10 min (ret. time)). To this intermediate in THF (850 µl) at 0° C. was added TBAF (1.0 M in THF) (44.4 mg, 0.170 mmol) dropwise and the reaction was stirred for 20 min. The mixture was then diluted with saturated NH₄Cl and extracted EtOAc for three times. The combined organic layer was dried over Na₂SO₄, filtered and concentrated. The crude was purified by reverse-phase HPLC (10-60% CH₃CN:H₂O, 0.1% TFA as modifier) and then 4 g Combi-Flash column (0-5% MeOH: DCM) to give the title compound as a white solid.

LC/MS: m/z 343.0 (M+H)⁺, 0.57 min (ret. time).

¹H NMR (400 MHz, CD₃OD): δ ppm 1.72 (d, J=13.30 Hz, 1H) 2.30-2.44 (m, 1H) 3.36 (d, J=4.02 Hz, 1H) 3.40-3.49 (m, 1H) 3.91-4.01 (m, 1H) 4.21-4.34 (m, 2H) 4.48 (br. s., 1H) 5.35 (d, J=6.78 Hz, 2H) 5.41 (s, 1H) 7.35 (t, J=8.91 Hz, 1H) 7.75-7.82 (m, 1H) 7.85 (d, J=5.77 Hz, 1H)

The following compounds E382-E385 listed in Table 7 were prepared by a procedure similar to that described for E381 starting from the requisite 4-hydroxyproline and benzyl alcohol:

TABLE 7

| Ex # | Name | Structure | LCMS | ¹H NMR (400 MHz) |
|---|---|---|---|---|
| E382 | 2-Fluoro-5-((((7S,8aS)-7-hydroxy-1-oxo-1,6,7,8,8a,9-hexahydropyrrolo[1',2':3,4]imidazo[1,2-c]pyrimidin-3-yl)oxy)methyl)benzonitrile | 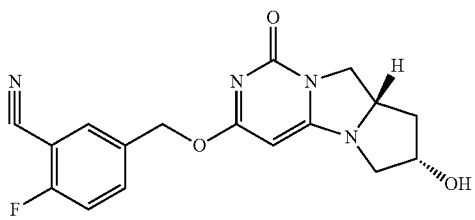 [SMILES: N#Cc1cc(COc2cc3n(c(=O)n2)C[C@@H]2C[C@H](O)CN32)ccc1F] | m/z 343.0 (M + H)⁺, 0.57 min (ret. time) | CD₃OD: δ ppm 1.74 (d, J = 13.30 Hz, 1 H) 2.34-2.45 (m, 1 H) 3.39 (d, J = 4.02 Hz, 1 H) 3.43-3.51 (m, 1 H) 3.99 (d, J = 6.53 Hz, 1 H) 4.24-4.38 (m, 2 H) 4.50 (br. s., 1 H) 5.37 (d, J = 6.78 Hz, 2 H) 5.43 (s, 1 H) 7.37 (t, J = 8.78 Hz, 1 H) 7.78-7.85 (m, 1 H) 7.87 (d, J = 5.52 Hz, 1 H) |
| E383 | (7S,8aS)-3-((3,5-Difluoro-4-((2-(trifluoromethyl)pyridin-4-yl)oxy)benzyl)oxy)-7-hydroxy-7,8,8a,9-tetrahydropyrrolo[1',2':3,4]imidazo[1,2-c]pyrimidin-1(6H)-one | 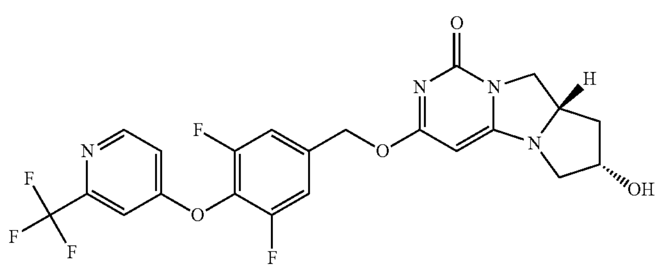 [SMILES: O=c1nc(OCc2cc(F)c(Oc3ccnc(C(F)(F)F)c3)c(F)c2)cc2n1C[C@@H]1C[C@H](O)CN21] | m/z 497.0 (M + H)⁺, 0.86 min (ret. time) | CD₃OD: δ ppm 1.73 (d, J = 13.55 Hz, 1 H) 2.31-2.46 (m, 1 H) 3.33-3.40 (m, 1 H) 3.42-3.51 (m, 1 H) 3.98 (d, J = 6.53 Hz, 1 H) 4.29 (q, J = 10.04 Hz, 2 H) 4.49 (br. s., 1 H) 5.39 (d, J = 6.02 Hz, 2 H) 5.46 (s, 1 H) 7.16 (d, J = 4.77 Hz, 1 H) 7.32 (d, J = 8.78 Hz, 2 H) 7.42 (s, 1 H) 8.61 (d, J = 5.52 Hz, 1 H) |
| E384 | (7R,8aR)-3-((3,5-Difluoro-4-((2-(trifluoromethyl)pyridin-4-yl)oxy)benzyl)oxy)-7-hydroxy-7,8,8a,9-tetrahydropyrrolo[1',2':3,4]imidazo[1,2-c]pyrimidin-1(6H)-one | 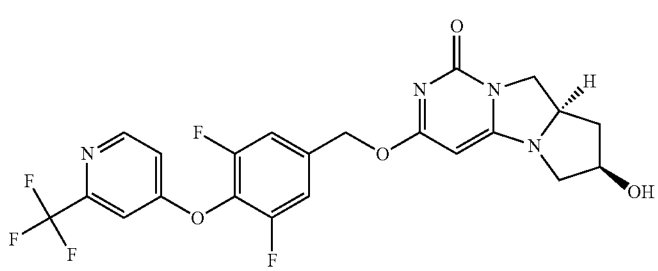 [SMILES: O=c1nc(OCc2cc(F)c(Oc3ccnc(C(F)(F)F)c3)c(F)c2)cc2n1C[C@H]1C[C@@H](O)CN21] | m/z 497.0 (M + H)⁺, 0.86 min (ret. time) | CD₃OD: δ ppm 1.73 (d, J = 13.30 Hz, 1 H) 2.33-2.47 (m, 1 H) 3.33-3.40 (m, 1 H) 3.43-3.53 (m, 1 H) 3.93-4.03 (m, 1 H) 4.23-4.36 (m, 2 H) 4.49 (br. s., 1 H) 5.39 (d, J = 6.02 Hz, 2 H) 5.46 (s, 1 H) 7.16 (d, J = 5.02 Hz, 1 H) 7.32 (d, J = 8.78 Hz, 2 H) 7.42 (s, 1 H) 8.61 (d, J = 5.52 Hz, 1 H) |

TABLE 7-continued

| Ex # | Name | Structure | LCMS | ¹H NMR (400 MHz) |
|---|---|---|---|---|
| E385 | (7S,8aS)-3-((3,5-Difluoro-4-((6-methyl-pyridin-3-yl)oxy)benzyl)oxy)-7-hydroxy-7,8,8a,9-tetrahydro-pyrrolo[1',2':3,4]imidazo[1,2-c]pyrimidin-1(6H)-one | 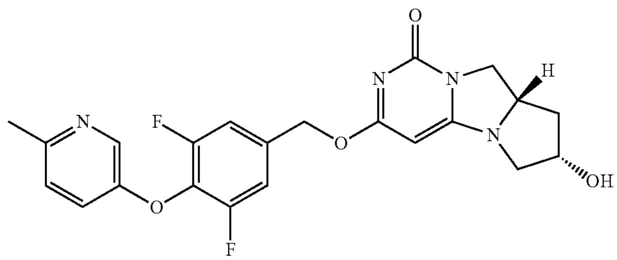 [SMILES: Cc1ccc(Oc2c(F)cc(COc3cc4n(c(=O)n3)C[C@@H]3C[C@H](O)CN43)cc2F)cn1] | m/z 443.1 (M + H)⁺, 0.61 min (ret. time) | CDCl₃: δ ppm 1.78-1.85 (m, 1 H) 2.38-2.48 (m, 1 H) 2.53 (s, 3 H) 3.43 (s, 2 H) 4.04-4.12 (m, 1 H) 4.30 (s, 3 H) 4.60-4.69 (m, 1 H) 5.22 (s, 1 H) 5.38 (s, 2 H) 7.08 (d, J = 8.53 Hz, 3 H) 7.12 (d, J = 3.01 Hz, 1 H) 8.29 (d, J = 2.76 Hz, 1 H) |

E386

5-(((((7S,8aR)-7-Amino-1-oxo-1,6,7,8,8a,9-hexahydropyrrolo[1,2':3,4]imidazo[1,2-c] pyrimidin-3-yl)oxy)methyl)-2-fluorobenzonitrile

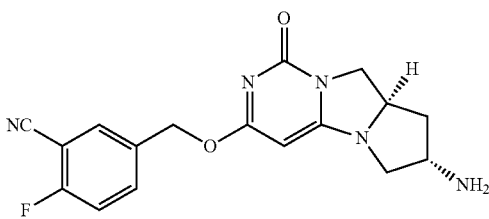 [SMILES: N#Cc1cc(COc2cc3n(c(=O)n2)C[C@H]2C[C@H](N)CN32)ccc1F]

To a suspension of tert-butyl ((7S,8aR)-3-chloro-1-oxo-1,6,7,8,8a,9-hexahydropyrrolo[1',2':3,4]imidazo[1,2-c]pyrimidin-7-yl)carbamate (52.1 mg, 0.159 mmol) and 2-fluoro-5-(hydroxymethyl)benzonitrile (24.10 mg, 0.159 mmol) in tetrahydrofuran (THF) (1139 μl) was added NaH (15.94 mg, 0.399 mmol) and the reaction was stirred at room temperature for 30 min. The mixture was diluted with 5 mL saturated NH₄Cl and extracted with EtOAc (10 mL×3). The combined organic layer was dried over Na₂SO₄, filtered and concentrated. The crude was purified by HPLC (12 g CombiFlash column, 0-5% MeOH: DCM) to give Boc-protected intermediate as a white solid (LC/MS: m/z 442.0 (M+H)⁺, 0.86 min (ret. time)). To this intermediate (51.4 mg, 0.116 mmol) in DCM (554 μl) was added trifluoroacetic acid (TFA) (277 μl). After 30 min at RT, the mixture was concentrated and the crude was purified by reverse-phase HPLC (0-60% CH₃CN:H₂O, 0.1% TFA as modifier) to give the title compound as a white solid.

LC/MS: m/z 342.0 (M+H)⁺, 0.51 min (ret. time).

¹H NMR (400 MHz, CDCl₃): δ ppm 1.63-1.72 (m, 1H) 1.95 (dd, J=12.80, 5.77 Hz, 1H) 3.10 (d, J=11.29 Hz, 1H) 3.54 (dd, J=11.29, 6.02 Hz, 1H) 3.89 (br. s., 1H) 4.02 (dd, J=12.05, 4.02 Hz, 1H) 4.22 (dd, J=11.80, 9.03 Hz, 1H) 4.48 (tt, J=9.54, 4.77 Hz, 1H) 5.11 (s, 1H) 5.31 (s, 1H) 5.35 (d, J=13.30 Hz, 1H) 5.44 (d, J=13.30 Hz, 1H) 7.20 (t, J=8.53 Hz, 1H) 7.60-7.66 (m, 1H) 7.68 (d, J=6.02 Hz, 1H)

The following compounds E387-E392 listed in Table 8 were prepared by a procedure similar to that described for E386 starting from the requisite aminoalcohol and benzyl alcohol:

TABLE 8

| Ex # | Name | Structure | LCMS | ¹H NMR (400 MHz) |
|---|---|---|---|---|
| E387 | (7R,8aR)-7-Amino-3-((3,5-difluoro-4-((2-(trifluoromethyl)pyridin-4-yl)oxy)benzyl)oxy)-7,8,8a,9-tetrahydro-pyrrolo[1',2':3,4]imidazo[1,2-c]pyrimidin-1(6H)-one | 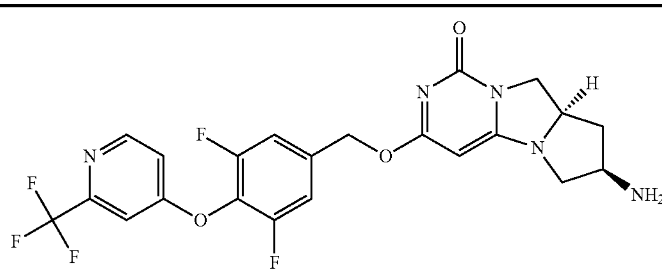 | m/z 496.0 (M + H)⁺, 0.75 min (ret. time) | CD₃OD: δ ppm 1.47 (dt, J = 12.05, 9.66 Hz, 1 H) 2.35 (dt, J = 11.98, 5.93 Hz, 1 H) 3.02 (dd, J = 10.67, 6.90 Hz, 1 H) 3.64 (dd, J = 10.54, 7.53 Hz, 1 H) 3.70-3.80 (m, 1 H) 3.94-4.03 (m, 1 H) 4.14-4.23 (m, 1 H) 4.23-4.32 (m, 1 H) 5.38 (s, 2 H) 5.41 (s, 1 H) 7.16 (dd, J = 5.65, 2.38 |

TABLE 8-continued

| Ex # | Name | Structure | LCMS | ¹H NMR (400 MHz) |
|---|---|---|---|---|
| | | | | Hz, 1 H) 7.28-7.36 (m, 2 H) 7.43 (d, J = 2.51 Hz, 1 H) 8.61 (d, J = 5.77 Hz, 1 H) |
| E388 | (7S,8aR)-7-Amino-3-((3,5-difluoro-4-((2-(trifluoromethyl)pyridin-4-yl)oxy)benzyl)oxy)-7,8,8a,9-tetrahydropyrrolo[1',2':3,4]imidazo[1,2-c]pyrimidin-1(6H)-one | 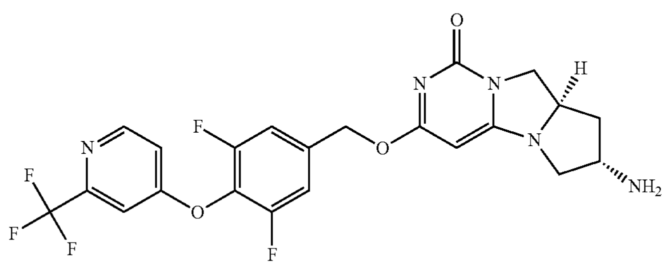 [SMILES: N[C@H]1C[C@@H]2Cn3c(cc(OCc4cc(F)c(Oc5ccnc(C(F)(F)F)c5)c(F)c4)nc3=O)N2C1] | m/z 496.1 (M + H)⁺, 0.76 min (ret. time) | CDCl₃: δ ppm 1.27 (br. s., 1 H) 1.96 (dd, J = 12.05, 5.27 Hz, 1 H) 3.12 (d, J = 11.04 Hz, 1 H) 3.55 (dd, J = 11.17, 5.90 Hz, 1 H) 3.90 (br. s., 1 H) 4.03 (dd, J = 11.92, 3.64 Hz, 1 H) 4.19-4.28 (m, 1 H) 4.48 (d, J = 4.27 Hz, 1 H) 5.15 (s, 1 H) 5.38 (d, J = 13.80 Hz, 1 H) 5.46 (d, J = 13.30 Hz, 1 H) 6.99 (d, J = 3.76 Hz, 1 H) 7.13 (d, J = 8.53 Hz, 2 H) 8.61 (d, J = 5.52 Hz, 1 H) |
| E389 | 5-((((7R,8aR)-7-Amino-1-oxo-1,6,7,8,8a,9-hexahydropyrrolo[1',2':3,4]imidazo[1,2-c]pyrimidin-3-yl)oxy)methyl)-2-fluorobenzonitrile | 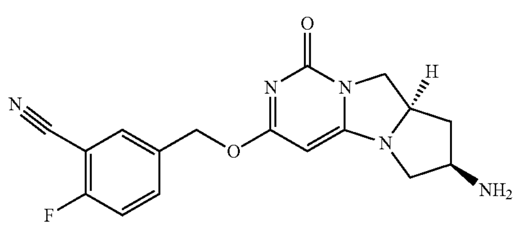 [SMILES: N#Cc1cc(COc2cc3n(c(=O)n2)C[C@H]2C[C@@H](N)CN32)ccc1F] | m/z 342.1 (M + H)⁺, 0.50 min (ret. time) | CDCl₃: δ ppm 1.40-1.50 (m, 1 H) 2.37 (dt, J = 12.17, 5.96 Hz, 1 H) 3.00 (dd, J = 10.79, 5.52 Hz, 1 H) 3.55 (dd, J = 11.04, 6.53 Hz, 1 H) 3.85 (quin, J = 6.27 Hz, 1 H) 4.01-4.09 (m, 1 H) 4.17-4.29 (m, 2 H) 5.12 (s, 1 H) 5.34-5.46 (m, 2 H) 7.20 (t, J = 8.53 Hz, 1 H) 7.64 (d, J = 5.27 Hz, 1 H) 7.67-7.72 (m, 1 H) |
| E390 | (7S,8aS)-7-Amino-3-((3,5-difluoro-4-((2-(trifluoromethyl)pyridin-4-yl)oxy)benzyl)oxy)-7,8,8a,9-tetrahydropyrrolo[1',2':3,4]imidazo[1,2-c]pyrimidin-1(6H)-one | 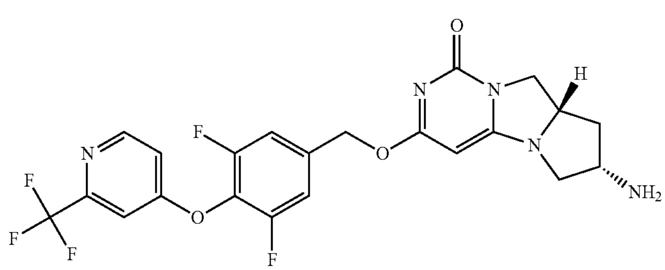 [SMILES: N[C@H]1C[C@H]2Cn3c(cc(OCc4cc(F)c(Oc5ccnc(C(F)(F)F)c5)c(F)c4)nc3=O)N2C1] | m/z 496.0 (M + H)⁺, 0.76 min (ret. time) | CDCl₃ δ ppm 1.41-1.51 (m, 1 H) 2.32-2.45 (m, 1 H) 2.97-3.06 (m, 1 H) 3.56 (dd, J = 10.79, 6.53 Hz, 1 H) 3.86 (d, J = 5.77 Hz, 1 H) 4.06 (d, J = 7.28 Hz, 1 H) 4.25 (d, J = 10.54 Hz, 2 H) 5.17 (s, 1 H) 5.43 (s, 2 |

TABLE 8-continued

| Ex # | Name | Structure | LCMS | ¹H NMR (400 MHz) |
|---|---|---|---|---|
| | | | | H) 6.99 (d, J = 3.51 Hz, 1 H) 7.14 (d, J = 8.28 Hz, 2 H) 8.61 (d, J = 5.77 Hz, 1 H) |
| E391 | 5-((((7S,8aS)-7-Amino-1-oxo-1,6,7,8,8a,9-hexahydro-pyrrolo[1',2':3,4]imidazo[1,2-c]pyrimidin-3-yl)oxy)methyl)-2-fluorobenzo-nitrile | 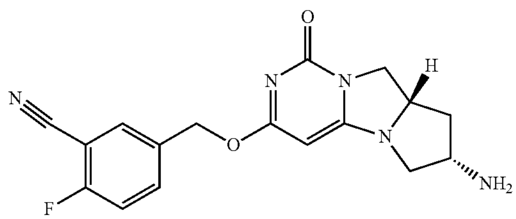 [SMILES: N#Cc1cc(COc2cc3n(c(=O)n2)C[C@@H]2C[C@H](N)CN32)ccc1F] | m/z 342.0 (M + H)⁺, 0.54 min (ret. time) | CDCl₃: δ ppm 1.45 (dt, J = 12.42, 7.84 Hz, 1 H) 2.37 (dt, J = 12.23, 6.05 Hz, 1 H) 3.00 (dd, J = 11.04, 5.52 Hz, 1 H) 3.55 (dd, J = 10.92, 6.65 Hz, 1 H) 3.85 (t, J = 6.53 Hz, 1 H) 4.01-4.09 (m, 1 H) 4.16-4.30 (m, 2 H) 5.13 (s, 1 H) 5.33-5.47 (m, 2 H) 7.21 (t, J = 8.66 Hz, 1 H) 7.61-7.67 (m, 1 H) 7.67-7.71 (m, 1 H) |
| E392 | (7R,8aS)-7-Amino-3-((3,5-difluoro-4-((2-(trifluoromethyl)pyridin-4-yl)oxy)benzyl)oxy)-7,8,8a,9-tetrahydro-pyrrolo[1',2':3,4]imidazo[1,2-c]pyrimidin-1(6H)-one | 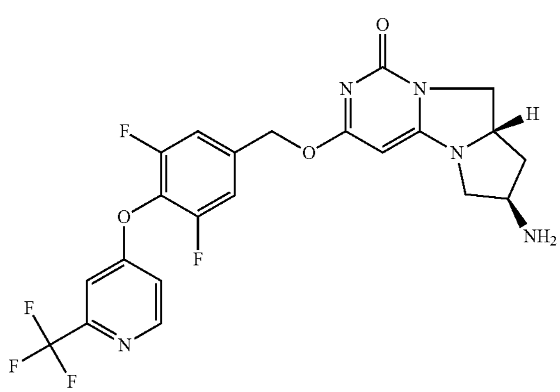 [SMILES: N[C@@H]1C[C@H]2Cn3c(cc(OCc4cc(F)c(Oc5ccnc(C(F)(F)F)c5)c(F)c4)nc3=O)N2C1] | m/z 496.2 (M + H)⁺, 0.79 min (ret. time) | DMSO-d6: δ ppm 1.52-1.67 (m, 1 H) 1.88 (br. s., 1 H) 3.18 (m, 2 H) 3.53 (dd, J = 11.42, 6.40 Hz, 1 H) 3.75-3.87 (m, 1 H) 3.99-4.10 (m, 2 H) 4.31 (br. s., 1 H) 4.69 (br. s., 1 H) 5.34 (m, 3 H) 7.32 (br. s., 1 H) 7.46 (d, J = 8.78 Hz, 2 H) 7.68 (br. s., 1 H) 8.69 (d, J = 5.52 Hz, 1 H) |

E393

7-((3,5-Difluoro-4-(0-methyl-1H-pyrazol-4-yl)oxy)benzyl)oxy)-1H-spiro[imidazo[1,2-c]pyrimidine-2,3'-oxetan]-5(3H)-one

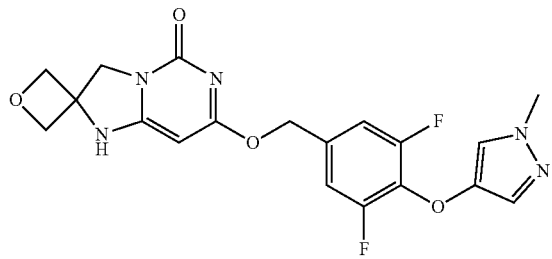 [SMILES: Cn1cc(Oc2c(F)cc(COc3cc4n(c(=O)n3)CC3(COC3)N4)cc2F)cn1]

NaH (60% wt, 40 mg, 1.00 mmol, 3.7 equiv) was added as solids in one portion to a chilled solution of (3,5-difluoro-4-((1-methyl-1H-pyrazol-4-yl)oxy)phenyl)methanol (96 mg, 0.40 mmol, 1.5 equiv) in 3 mL of 2-MeTHF. The resulting mixture was stirred in the ice bath for 5 min, followed by addition of tert-butyl 7-chloro-5-oxo-3,5-dihydro-1H-spiro[imidazo[1,2-c]pyrimidine-2,3'-oxetane]-1-carboxylate (84 mg, 0.27 mmol, 1 equiv) as solids in one portion. The mixture was stirred in the ice bath for 15 min, and followed by removal of the cooling bath. The mixture was stirred at ambient temperature for a total of 3 h. The mixture was rechilled in the ice bath, and followed by addition of 0.5 mL of saturated $NH_4Cl$. The resulting mixture was diluted with 1 mL of water, and followed by phase separation. The aqueous was extracted with 10% MeOH in DCM (2×4 mL). The combined organic was dried over $Na_2SO_4$, filtered, and evaporated under a stream of nitrogen at 50° C. as a yellowish oily residue. This residue was redissolved in 10% MeOH in DCM and adsorbed onto Isolute. Purification was performed on a Teledyne-Isco Combiflash Rf purification system using a GOLD Redi-Sep 24 g silica gel cartridge with gradient elution of 0% A in DCM to 100% A in DCM over a 60 min period (A was a mixture of 80/800/3200 $NH_4OH$/MeOH/DCM, flow rate at 35 mL/min, UV at 254 nm). The desired product eluted at 17 min. Appropriate fractions were combined and concentrated to give the title compound (34 mg) as white solids.

LC/MS: m/z 418.1 $(M+H)^+$, 0.61 min (ret. time).

$^1$H NMR (400 MHz, DMSO-$d_6$) δ ppm 3.72 (s, 3H) 4.27 (s, 2H) 4.66 (d, J=7.03 Hz, 2H) 4.71 (d, J=7.28 Hz, 2H) 5.09 (s, 1H) 5.24 (s, 2H) 7.22-7.32 (m, 3H) 7.59 (s, 1H).

The following compounds in Table 9 were prepared from the requisite benzyl alcohols and intermediate (e.g., tert-butyl 7-chloro-5-oxo-3,5-dihydro-1H-spiro[imidazo[1,2-c]pyrimidine-2,3'-oxetane]-1-carboxylate) via a reaction sequence analogous to that described in Scheme 10:

TABLE 9

| Ex # | Name | Structure | LCMS | $^1$HNMR (400 MHz) |
|---|---|---|---|---|
| E394 | 7-((3,5-Difluoro-4-((6-methylpyridin-3-yl)oxy)benzyl)oxy)-1H-spiro[imidazo[1,2-c]pyrimidine-2,3'-oxetan]-5(3H)-one | 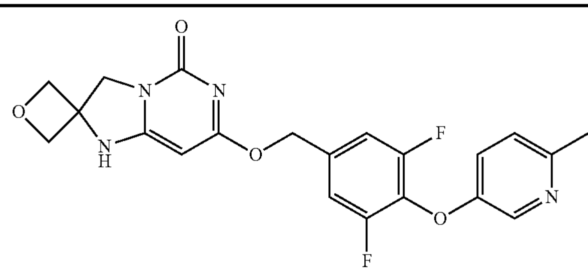 | m/z 429.2 $(M + H)^+$, 0.54 min (ret. time). | DMSO-d6: δ ppm 2.43 (s, 3 H) 4.28 (s, 2 H) 4.67 (d, J = 7.28 Hz, 2 H) 4.71 (d, J = 7.28 Hz, 2 H) 5.11 (s, 1 H) 5.28 (s, 2 H) 7.21-7.31 (m, 2 H) 7.35 (d, J = 9.03 Hz, 2 H) 8.25 (d, J = 2.76 Hz, 1 H) 9.18 (br. s., 1 H). |
| E395 | 7-((3,5-difluoro-4-((2-(trifluoromethyl)pyridin-4-yl)oxy)benzyl)oxy)-1H-spiro[imidazo[1,2-c]pyrimidine-2,3'-oxetan]-5(3H)-one | 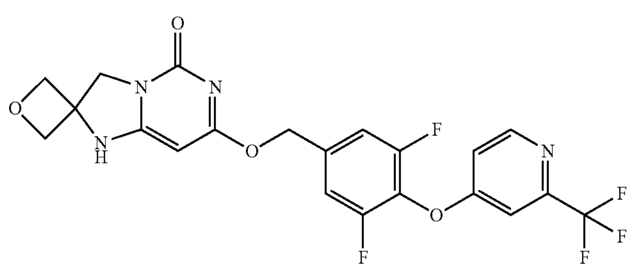 [SMILES: O=c1nc(OCc2cc(F)c(Oc3ccnc(C(F)(F)F)c3)c(F)c2)cc2n1CC1(COC1)N2] | m/z 482.9 $(M + H)^+$, 1.96 min (ret. time). | |
| E396 | 7-((3,4-difluorobenzyl)oxy)-1H-spiro[imidazo[1,2-c]pyrimidine-2,3'-oxetan]-5(3H)-one | 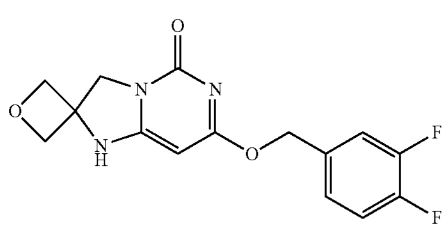 [SMILES: O=c1nc(OCc2ccc(F)c(F)c2)cc2n1CC1(COC1)N2] | m/z 322.0 $(M + H)^+$, 0.57 min (ret. time). | DMSO-$d_6$: δ ppm 4.26 (s, 2 H) 4.61-4.74 (m, 4 H) 5.05 (s, 1 H) 5.22 (s, 2 H) 7.24 (br. s., 1 H) 7.37-7.50 (m, 2 H) 9.13 (br. s., 1 H). |

E397

7-((3,5-Difluoro-4-((1-methyl-1H-pyrazol-4-yl)oxy)benzyl)oxy)-1-methyl-1H-spiro[imidazo[1,2-c]pyrimidine-2,3'-oxetan]-5(3H)-one

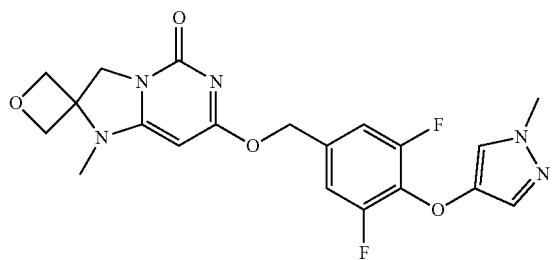 [SMILES: CN1c2cc(OCc3cc(F)c(Oc4cnn(C)c4)c(F)c3)nc(=O)n2CC12COC2]

(3,5-Difluoro-4-((1-methyl-1H-pyrazol-4-yl)oxy)phenyl)methanol (98 mg, 0.41 mmol, 1.5 equiv) was dissolved in 1.5 mL of 2-MeTHF in a 20 mL vial, followed by cooling in an ice bath. To this was added NaH (60% wt, 38 mg, 0.95 mmol, 3.5 equiv) in one portion. The mixture was stirred in the ice bath for 5 min, followed by addition of 7-chloro-1-methyl-1H-spiro[imidazo[1,2-c]pyrimidine-2,3'-oxetan]-5(3H)-one (62 mg, 0.27 mmol, 1 equiv) in one portion as solids. The mixture was stirred in the ice bath for 30 min, followed by removing the ice bath. The mixture was stirred at ambient temperature for another 1 h. The mixture was rechilled in the ice bath, followed by addition of 0.5 mL of saturated NH$_4$Cl. The mixture was diluted with 2 mL of water and phase separated. The aqueous was extracted with 10% MeOH in DCM (2×4 mL). The combined organic was dried over Na$_2$SO$_4$, filtered and evaporated under a stream of nitrogen at 50° C. to give a pale yellowish residue. This residue was redissolved in 10% MeOH in DCM and adsorbed onto Isolute. Purification was performed on a Teledyne-Isco Combiflash Rf purification system using a GOLD Redi-Sep 24 g silica gel cartridge with gradient elution of 0% A in DCM to 100% A in DCM over a 60 min period (A was a mixture of 80/800/3200 NH$_4$OH/MeOH/DCM, flow rate at 35 mL/min, UV at 254 nm). The desired product eluted at 15 min. Appropriate fractions were combined and concentrated to give the title compound (49 mg) as a white powdery solid.

LC/MS: m/z 432.1 (M+H)$^+$, 0.68 min (ret. time).

$^1$H NMR (400 MHz, DMSO-d$_6$) δ ppm 3.11 (s, 3H) 3.72 (s, 3H) 4.27 (s, 2H) 4.66 (d, J=8.03 Hz, 2H) 4.91 (d, J=7.78 Hz, 2H) 5.26 (s, 2H) 5.29 (s, 1H) 7.22-7.30 (m, 3H) 7.59 (s, 1H).

The following compounds in table 10 were prepared from the requisite benzyl alcohols and intermediate (e.g., 7-chloro-1-methyl-1H-spiro[imidazo[1,2-c]pyrimidine-2,3'-oxetan]-5(3H)-one) via a reaction sequence analogous to that described in Scheme 12:

TABLE 10

| Ex # | Name | Structure | LCMS | $^1$HNMR (400 MHz) |
|---|---|---|---|---|
| E398 | 7-((3,4-Difluorobenzyl)oxy)-1-methyl-1H-spiro[imidazo[1,2-c]pyrimidine-2,3'-oxetan]-5(3H)-one | 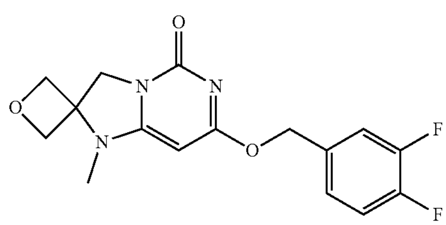 [SMILES: CN1c2cc(OCc3ccc(F)c(F)c3)nc(=O)n2CC12COC2] | m/z 336.0 (M + H)$^+$, 0.64 min (ret. time). | DMSO-d$_6$: δ ppm 3.10 (s, 3 H) 4.27 (s, 2 H) 4.66 (d, J = 7.78 Hz, 2 H) 4.91 (d, J = 7.78 Hz, 2 H) 5.24 (s, 2 H) 5.27 (s, 1 H) 7.24 (ddd, J = 6.15, 3.76, 2.38 Hz, 1 H) 7.39-7.51 (m, 2 H). |
| E399 | 3-Fluoro-5-(((1-methyl-5-oxo-3,5-dihydro-1H-spiro[imidazo[1,2-c]pyrimidine-2,3'-oxetan]-7-yl)oxy)methyl)-2-((6-methylpyridin-3-yl)oxy)benzonitrile | 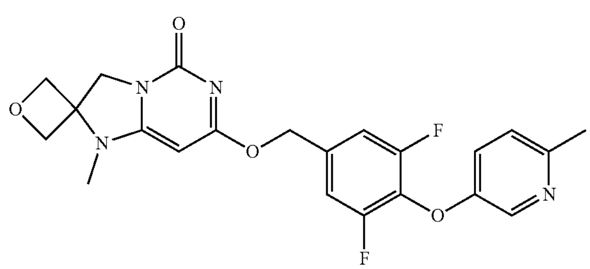 | m/z 450.2 (M + H)$^+$, 2.93 min (ret. time). | |
| E400 | 7-((3,5-Difluoro-4-((6-methylpyridin-3-yl)oxy)benzyl)oxy)-1-methyl-1H-spiro[imidazo[1,2-c]pyrimidine-2,3'-oxetan]-5(3H)-one | 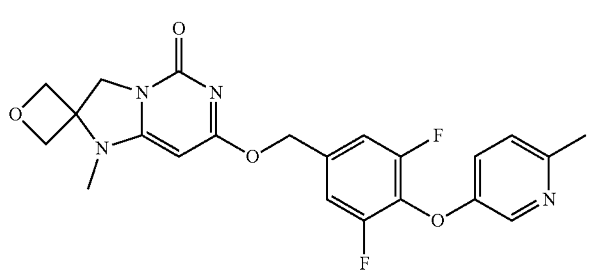 [SMILES: Cc1ccc(Oc2c(F)cc(COc3cc4n(c(=O)n3)CC3(COC3)N4C)cc2F)cn1] | m/z 443.0 (M + H)$^+$, 3.21 min (ret. time). | |

E401

7-((3,5-Difluoro-4-((5-(trifluoromethyl)pyridin-3-yl)oxy)benzyl)oxy)-2',3',5',6'-tetrahydro-1H-spiro[imidazo[1,2-c]pyrimidine-2,4'-pyran]-5(3H)-one

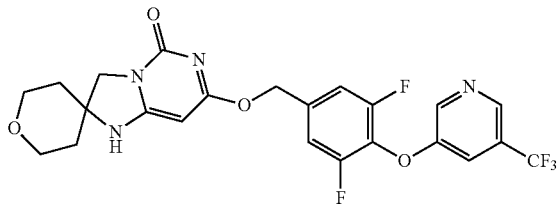 [SMILES: O=c1nc(OCc2cc(F)c(Oc3cncc(C(F)(F)F)c3)c(F)c2)cc2n1CC1(CCOCC1)N2]

To a 5 mL microwave vial was added (3,5-difluoro-4-((5-(trifluoromethyl)pyridin-3-yl)oxy)phenyl)methanol (25.9 mg, 0.085 mmol in THF (2 mL) and this was cooled in ice and stirred for 15 min. To this was added sodium hydride (4.07 mg, 0.170 mmol) and solution was stirred in ice for 15 min and tert-butyl 7-chloro-5-oxo-2',3,3',5,5',6'-hexahydro-1H-spiro[imidazo[1,2-c]pyrimidine-2,4'-pyran]-1-carboxylate (29 mg, 0.085 mmol) was added at 0° C. and then allowed to warm slowly to RT overnight. The reaction vessel was sealed and irradiated in a Biotage Initiator microwave using normal power setting to 150° C. for 1 hour then allowed to stir at RT over 2 days. LCMS shows reaction complete with removal of boc group. The solution was diluted with ethyl acetate and water and the layers were separated, and the aqueous layer was extracted with EtOAc (3×10 mL). The combined organic layers were washed with saturated NaCl (1×10 mL), dried (MgSO$_4$), and concentrated under reduced pressure. The crude product was dissolved in DMSO (1 mL), filtered through a 0.45 m acrodisc, and purified on a Gilson HPLC (YMC C18 S-5 m/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min to yield 7-((3,5-difluoro-4-((5-(trifluoromethyl)pyridin-3-yl)oxy)benzyl)oxy)-2',3',5',6'-tetrahydro-1H-spiro[imidazo[1,2-c]pyrimidine-2,4'-pyran]-5(3H)-one (7.4 mg, 0.014 mmol, 6.07% yield as a white powder.

$^1$H NMR (400 MHz, CDCl$_3$) δ ppm 1.76 (br. s., 2H) 1.90 (br. s., 2H) 2.60 (s, 1H) 3.51 (d, J=8.03 Hz, 2H) 3.75-3.84 (m, 2H) 3.88 (s, 2H) 5.17 (s, 2H) 5.90 (s, 1H) 7.03 (d, J=7.78 Hz, 2H) 7.39 (br. s., 1H) 8.39 (s, 1H) 8.51 (s, 1H);
LCMS: (MH+)=511 RT=0.86 min.

E402

7-((3,4-Difluorobenzyl)oxy)-2',3',5',6'-tetrahydro-1H-spiro[imidazo[1,2-c]pyrimidine-2,4'-pyran]-5(3H)-one

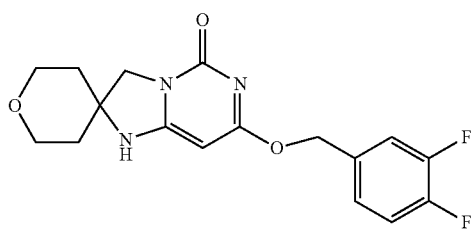 [SMILES: O=c1nc(OCc2ccc(F)c(F)c2)cc2n1CC1(CCOCC1)N2]

To a 25 mL round bottomed flask was added (3,4-difluorophenyl)methanol (100 □mL, 0.878 mmol) in THF (4 mL) and this was cooled in ice and stirred for 15 min. To this was added 60% sodium hydride (117 mg, 2.93 mmol) and solution was stirred in ice for 15 min. Solid tert-butyl 7-chloro-5-oxo-2',3,3',5,5',6'-hexahydro-1H-spiro[imidazo[1,2-c]pyrimidine-2,4'-pyran]-1-carboxylate (200 mg, 0.586 mmol) was added then stirred for 30 min in ice. The mixture was treated with water and then ethyl acetate and the organics were washed with brine and then evaporated to a white powder. The powder was triturated with hexanes to yield a white powder (92.3 mg, 45%).

$^1$H NMR (400 MHz, DMSO-d$_6$) δ ppm 1.59-1.84 (m, 4H) 3.53 (t, J=8.66 Hz, 2H) 3.67-3.78 (m, 2H) 3.81 (s, 2H) 4.96-5.07 (m, 1H) 5.23 (s, 2H) 7.26 (br. s., 1H) 7.37-7.57 (m, 2H) 8.54 (s, 1H); LCMS: (MH+)=350 rt=0.58 min.

E403

7-((3,5-Difluoro-4-((6-methylpyridin-3-yl)oxy)benzyl)oxy)-2',3',5',6'-tetrahydro-1H-spiro[imidazo[1,2-c]pyrimidine-2,4'-pyran]-5(3H)-one

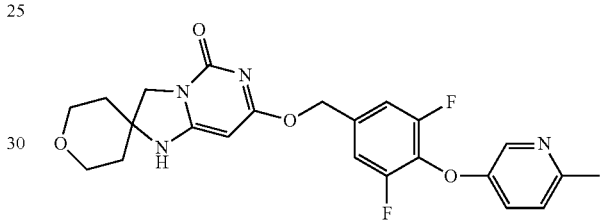

To a 5 mL microwave vial was added (3,5-difluoro-4-((6-methylpyridin-3-yl)oxy)phenyl)methanol (73.5 mg, 0.293 mmol in tetrahydrofuran (THF) (1 mL) and this was cooled in ice and stirred for 15 min. To this was added 60% sodium hydride (23.40 mg, 0.585 mmol) and solution was stirred in ice for 15 min. To a separate 5 mL microwave vial was added tert-butyl 7-chloro-5-oxo-2',3,3',5,5',6'-hexahydro-1H-spiro[imidazo[1,2-c]pyrimidine-2,4'-pyran]-1-carboxylate (100 mg, 0.293 mmol) in tetrahydrofuran (THF) (1 mL) and solution was cooled in ice and stirred 30 min. The alkoxide solution was added dropwise via glass pipette and solution was then stirred for 30 min in ice and allowed to warm to RT and stirred 30 min. The reaction vessel was sealed and irradiated in a Biotage Initiator microwave using normal power setting to 100° C. for 10 min The solution was diluted with ethyl acetate and water and the layers were separated, and the aqueous layer was extracted with EtOAc (3×10 mL). The combined organic layers were washed with saturated NaCl (1×10 mL), dried (MgSO$_4$), and concentrated under reduced pressure. The crude product was dissolved in methanol (1.2 mL), filtered through a 0.45 m acrodisc, and purified on a Gilson HPLC (Sunfire 5 m C18 OBD 19×100 mm preparatory column), eluting at 20 mL/min with a linear gradient running from 5% CH$_3$CN/H$_2$O (0.1% TFA) to 50% CH$_3$CN/H$_2$O (0.1% TFA) over 12 min. The desired fractions were concentrated to an oil which was lyophilized to a white powder: 7-((3,5-difluoro-4-((6-methylpyridin-3-yl)oxy)benzyl)oxy)-2',3',5',6'-tetrahydro-1H-spiro[imidazo[1,2-c]pyrimidine-2,4'-pyran]-5(3H)-one (13.2 mg, 0.029 mmol, 9.88% yield).

$^1$H NMR (400 MHz, CD$_3$OD) δ ppm 1.85-2.04 (m, 4H) 2.63 (s, 3H) 3.62-3.74 (m, 2H) 3.83-3.92 (m, 2H) 4.12 (s, 2H) 5.42 (s, 2H) 5.56-5.64 (m, 1H) 7.37 (d, J=8.53 Hz, 2H)

7.55 (d, J=8.53 Hz, 1H) 7.68 (dd, J=8.78, 3.01 Hz, 1H) 8.36 (d, J=2.76 Hz, 1H); LCMS: (MH+)=457 RT=0.58 min.

E404

2-Fluoro-5-(2-((5-oxo-2',3,3',5,5',6'-hexahydro-1H-spiro[imidazo[1,2-c]pyrimidine-2,4'-pyran]-7-yl)oxy)ethyl)benzonitrile

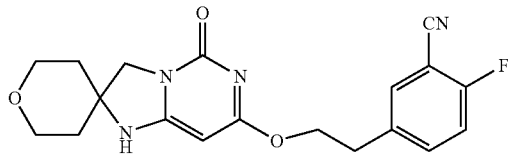 [SMILES: N#Cc1cc(CCOc2cc3n(c(=O)n2)CC2(CCOCC2)N3)ccc1F]

To a 20 mL scintillation vial was added 2-fluoro-5-(2-hydroxyethyl)benzonitrile (72.5 mg, 0.439 mmol) in tetrahydrofuran (THF) (2 mL) and this was cooled in ice and stirred for 15 min. To this was added 60% NaH (58.5 mg, 1.463 mmol) and solution was stirred in ice for 15 min. Solid tert-butyl 7-chloro-5-oxo-2',3,3',5,5',6'-hexahydro-1H-spiro[imidazo[1,2-c]pyrimidine-2,4'-pyran]-1-carboxylate (100 mg, 0.293 mmol) was added then stirred for 1 h in ice, solution was allowed to warm to RT and stirred 1 h. The mixture was treated with water and then ethyl acetate and the organics were washed with brine and then evaporated to an oil. The crude product was dissolved in DMSO (1.2 mL), filtered through a 0.45 mm acrodisc, and purified on a Gilson HPLC (Sunfire 5 mm C18 OBD 19×100 mm preparatory column), eluting at 20 mL/min with a linear gradient running from 10% CH$_3$CN/H$_2$O (0.1% TFA) to 50% CH$_3$CN/H$_2$O (0.1% TFA) over 12 min. The desired fractions were concentrated by rotovap to an oil which was lyophilized to a white powder 2-fluoro-5-(2-((5-oxo-2',3,3',5,5',6'-hexahydro-1H-spiro[imidazo[1,2-c]pyrimidine-2,4'-pyran]-7-yl)oxy)ethyl)benzonitrile (35 mg, 0.094 mmol, 32.0% yield).

$^1$H NMR (400 MHz, CDCl$_3$) δ ppm 1.92-2.09 (m, 4H) 3.12 (t, J=6.27 Hz, 2H) 3.66 (br. s., 2H) 3.93-4.05 (m, 4H) 4.52 (t, J=6.27 Hz, 2H) 6.04 (s, 1H) 7.20 (s, 1H) 7.55 (d, J=6.53 Hz, 2H); LCMS: (MH+)=341 rt=0.56 min.

E405

7-((3,5-Difluoro-4-((6-methylpyridin-3-yl)oxy)benzyl)oxy)-1-methyl-2',3',5',6'-tetrahydro-1H-spiro[imidazo[1,2-c]pyrimidine-2,4'-pyran]-5(3H)-one

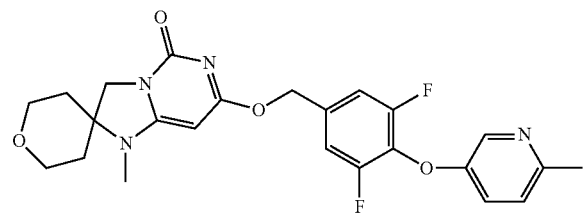 [SMILES: Cc1ccc(Oc2c(F)cc(COc3cc4n(c(=O)n3)CC3(CCOCC3)N4C)cc2F)cn1]

To a 5 mL microwave vial was added (3,5-difluoro-4-((6-methylpyridin-3-yl)oxy)phenyl)methanol (73.7 mg, 0.293 mmol) in THF (1 mL) and this was cooled in ice and stirred for 15 min. To this was added 60% sodium hydride (23.46 mg, 0.587 mmol) and solution was stirred in ice for 15 min.

To a separate 5 mL microwave vial was added 7-chloro-1-methyl-2',3',5',6'-tetrahydro-1H-spiro[imidazo[1,2-c]pyrimidine-2,4'-pyran]-5(3H)-one (75 mg, 0.293 mmol) in tetrahydrofuran (THF) (1.000 mL) and solution was cooled in ice and stirred 30 min. The alkoxide solution was added dropwise via glass pipette and solution was then stirred for 30 min in ice; reaction complete by 1 cms. The solution was diluted with ethyl acetate and water and the layers were separated, and the aqueous layer was extracted with EtOAc (3×10 mL). The combined organic layers were washed with saturated NaCl (1×10 mL), dried (MgSO$_4$), and concentrated under reduced pressure. The crude product was dissolved in methanol (1.2 mL), filtered through a 0.45 μm acrodisc, and purified on a Gilson HPLC (Sunfire 5 m C18 OBD 19×100 mm preparatory column), eluting at 20 mL/min with a linear gradient running from 5% CH$_3$CN/H$_2$O (0.1% TFA) to 50% CH$_3$CN/H$_2$O (0.1% TFA) over 12 min. The desired fractions were not pure. The residue was dissolved in THF (1.000 mL) and treated with 60% sodium hydride (23.46 mg, 0.587 mmol) and stirred for 30 min at RT. To this was added Boc-anhydride (0.068 mL, 0.293 mmol) and solution was stirred for 30 min. The Boc group was added to the impurity (alcohol) which enabled separation of desired compound. Solution was diluted with 2 mL of methanol and evaporated, and residue was dissolved in 1 mL of DMF, filtered through an acrodisk (0.45) and was purified on a Gilson HPLC (Sunfire 5 m C18 OBD 19×100 mm preparatory column), eluting at 20 mL/min with a linear gradient running from 10% CH$_3$CN/H$_2$O (0.1% TFA) to 90% CH$_3$CN/H$_2$O (0.1% TFA) over 12 min. The fraction was evaporated and lyophilized to yield 7-((3,5-difluoro-4-((6-methylpyridin-3-yl)oxy)benzyl)oxy)-1-methyl-2',3',5',6'-tetrahydro-1H-spiro[imidazo[1,2-c]pyrimidine-2,4'-pyran]-5(3H)-one (8 mg, 0.017 mmol, 5.68% yield) as a white powder.

$^1$H NMR (400 MHz, CD$_3$OD) δ ppm 1.74 (d, J=13.05 Hz, 2H) 2.22 (td, J=12.80, 5.27 Hz, 2H) 2.71 (s, 3H) 3.17 (s, 3H) 3.55 (t, J=12.30 Hz, 2H) 4.07 (dd, J=12.05, 4.77 Hz, 2H) 4.23 (s, 2H) 5.46 (s, 2H) 5.91 (s, 1H) 7.41 (d, J=8.53 Hz, 2H) 7.74 (d, J=8.78 Hz, 1H) 7.93 (dd, J=8.78, 2.76 Hz, 1H) 8.54 (d, J=3.01 Hz, 1H);

LCMS: (MH+)=471, RT=0.66 min.

E406

7-((3,4-Difluorobenzyl)oxy)-1H-spiro[imidazo[1,2-c]pyrimidine-2,4'-piperidin]-5(3H)-one

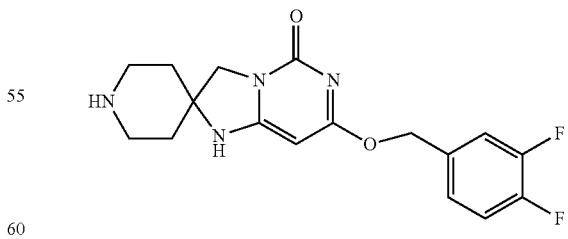

To a 25 mL round bottomed flask was added tert-butyl 7-((3,4-difluorobenzyl)oxy)-5-oxo-3,5-dihydro-1H-spiro[imidazo[1,2-c]pyrimidine-2,4'-piperidine]-1'-carboxylate (93 mg, 0.207 mmol) and 4M HCl in dioxane (2 mL, 8 mmol) then stirred for 1 h at RT. The solution was evaporated to yield 7-((3,4-difluorobenzyl)oxy)-1H-spiro[imidazo

[1,2-c]pyrimidine-2,4'-piperidin]-5(3H)-one (56 mg, 0.154 mmol, 74.4% yield) as a white solid.

$^1$H NMR (400 MHz, CD$_3$OD) δ ppm 2.07-2.31 (m, 4H) 3.40-3.51 (m, 2H) 3.64-3.81 (m, 1H) 4.09-4.24 (m, 2H) 5.37 (s, 2H) 5.65 (s, 1H) 7.27-7.40 (m, 2H) 7.41-7.52 (m, 1H); LCMS: (MH+)=349 rt=0.51 min.

E407 and E408

1-Acetyl-7-((3,4-difluorobenzyl)oxy)-1H-spiro[imidazo[1,2-c]pyrimidine-2,4'-piperidin]-5(3H)-one (E407)

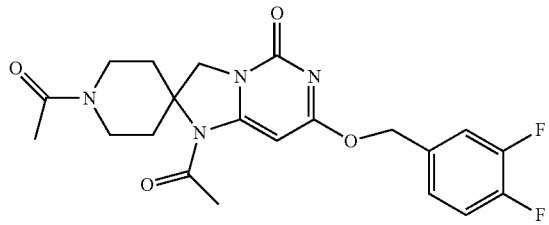 [SMILES: CC(=O)N1CCC2(CC1)Cn1c(cc(OCc3ccc(F)c(F)c3)nc1=O)N2C(C)=O]

and 1,1-(7-((3,4-difluorobenzyl)oxy)-5-oxo-1H-spiro[imidazo[1,2-c]pyrimidine-2,4'-piperidin]-1,1'(3H,5H)-diyl)diethanone (E408)

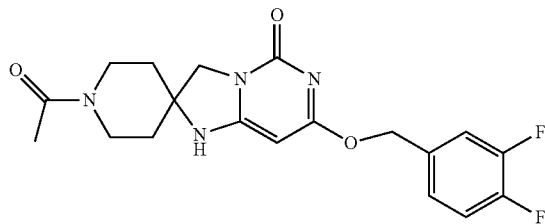 [SMILES: CC(=O)N1CCC2(CC1)Cn1c(cc(OCc3ccc(F)c(F)c3)nc1=O)N2]

To a 2 mL microwave vial was added tert-butyl 7-((3,4-difluorobenzyl)oxy)-5-oxo-3,5-dihydro-1H-spiro[imidazo[1,2-c]pyrimidine-2,4'-piperidine]-t-carboxylate (25 mg, 0.063 mmol) in DCM (2 mL). To this was added DIEA (72 L, 0.431 mmol) and then acetyl chloride (16 L, 0.215 mmol) at RT. Upon addition of acetyl chloride solution turned from cloudy to clear with a slight warming observed. Stirring for 10 min and check by 1 cms shows 2:1 ratio of diacetylated to monoacetylated products. The solution was evaporated and purified by Gilson (sunfire-c18-small-gradient: 10% Acetonitrile/water to 60% over 10 min. The residues were individually lyophilzed to yield:

1'-acetyl-7-((3,4-difluorobenzyl)oxy)-1H-spiro[imidazo[1,2-c]pyrimidine-2,4'-piperidin]-5(3H)-one (10 mg, 34%) as a white powder.

$^1$H NMR (400 MHz, CD$_3$OD) δ ppm 1.76-2.08 (m, 4H) 2.16 (s, 3H) 3.50-3.66 (m, 2H) 3.74 (dd, J=13.55, 6.78 Hz, 1H) 3.87 (dd, J=14.68, 6.15 Hz, 1H) 5.36 (s, 2H) 7.26-7.52 (m, 3H); LCMS: (MH+)=391 rt=0.61 min, and 1,1'-(7-((3,4-difluorobenzyl)oxy)-5-oxo-1H-spiro[imidazo[1,2-c]pyrimidine-2,4'-piperidin]-1,1'(3H,5H)-diyl)diethanone (14 mg, 41%) as a white powder.

$^1$H NMR (400 MHz, CD$_3$OD) δ ppm 1.82 (dd, J=17.07, 12.30 Hz, 2H) 2.16 (s, 3H) 2.37-2.52 (m, 3H) 2.65-2.77 (m, 2H) 2.79-2.87 (m, 1H) 3.20-3.30 (m, 1H) 4.02 (d, J=14.30 Hz, 1H) 4.16 (s, 2H) 4.63 (d, J=8.78 Hz, 1H) 5.34-5.42 (m, 2H) 5.99 (s, 1H) 7.21-7.32 (m, 2H) 7.36-7.49 (m, 1H); LCMS: (MH+)=433 rt=0.81 min.

E409

1-(Cyclopropanecarbonyl)-7-((3,4-difluorobenzyl)oxy)-1H-spiro[imidazo[1,2-c]pyrimidine-2,4'-piperidin]-5(3H)-one

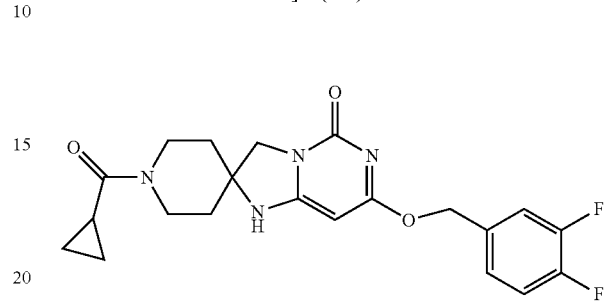

To a 2 mL microwave vial was added 7-((3,4-difluorobenzyl)oxy)-1H-spiro[imidazo[1,2-c]pyrimidine-2,4'-piperidin]-5(3H)-one (20 mg, 0.057 mmol) in DCM (2 mL). To this was added DIEA (72 L, 0.431 mmol) and then portionwise addition of cyclopropanecarbonyl chloride (5.78 μl, 0.063 mmol) [60 ml dissolved in 1 mL DCM-add 100 mL (4×25 mL batches)] at 0° C. Upon addition of acid chloride solution turned from cloudy to clear; after 30 min solution was evaporated under a stream of nitrogen. The crude product was dissolved in DMSO (1 mL), filtered through a 0.45 mm acrodisc, and purified on a Gilson HPLC (YMC C18 S-5 mm/12 nm 50×20 mm preparatory column), eluting at 20 mL/min with a linear gradient running from 10% CH$_3$CN/H$_2$O (0.1% TFA) to 90% CH$_3$CN/H$_2$O (0.1% TFA) over 10 min. The desired fractions were concentrated under a stream of nitrogen at 50° C., giving an oil which was lyophilized to a white powder 1'-(cyclopropanecarbonyl)-7-((3,4-difluorobenzyl)oxy)-1H-spiro[imidazo[1,2-c]pyrimidine-2,4'-piperidin]-5(3H)-one (9.3 mg, 0.022 mmol, 38.5% yield).

$^1$H NMR (400 MHz, CD$_3$OD) δ ppm 0.75-0.98 (m, 4H) 1.79-2.08 (m, 4H) 3.56 (br. s., 1H) 3.75-4.02 (m, 4H) 4.08 (s, 2H) 5.29-5.39 (m, 2H) 5.46 (s, 1H) 7.33 (d, J=9.54 Hz, 1H) 7.39-7.49 (m, 1H); LCMS: (MH+)=417 rt=0.67 min.

E410

1'-(Cyclopropylsulfonyl)-7-((3,4-difluorobenzyl)oxy)-1H-spiro[imidazo[1,2-c]pyrimidine-2,4'-piperidin]-5(3H)-one

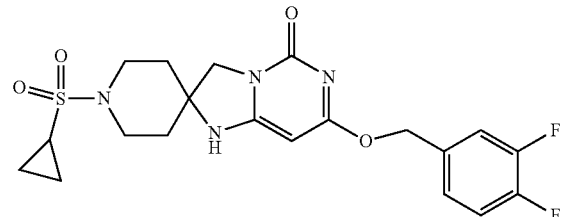

To a 2 mL microwave vial was added tert-butyl 7-((3,4-difluorobenzyl)oxy)-5-oxo-3,5-dihydro-1H-spiro[imidazo

[1,2-c]pyrimidine-2,4'-piperidine]-1'-carboxylate (36 mg, 0.080 mmol) and 4 M HCl (0.803 mL, 3.21 mmol) and solution was stirred overnight, then solution was evaporated. The residue was dissolved in DCM (2 mL) and DIEA (0.084 mL, 0.482 mmol) was added followed by portionwise addition of cyclopropanesulfonyl chloride (9.81 µl, 0.096 mmol) [98 ml dissolved in 1 mL DCM-add 100 mL (4×25 mL batches)] at 0° C. Solution was allowed to warm to RT and stirred 1 h. The crude product was dissolved in DMSO (1 mL), filtered through a 0.45 mm acrodisc, and purified on a Gilson HPLC (YMC C18 S-5 mm/12 nm 50×20 mm preparatory column), eluting at 20 mL/min with a linear gradient running from 10% $CH_3CN/H_2O$ (0.1% TFA) to 90% $CH_3CN/H_2O$ (0.1% TFA) over 10 min. The desired fractions were concentrated by rotovap giving an oil which was lyophilized to a white powder 1'-(cyclopropylsulfonyl)-7-((3,4-difluorobenzyl)oxy)-1H-spiro[imidazo[1,2-c]pyrimidine-2,4'-piperidin]-5(3H)-one (17.5 mg, 0.037 mmol, 45.8% yield).

$^1$H NMR (400 MHz, $CD_3OD$) δ ppm 1.00-1.15 (m, 4H) 1.97-2.12 (m, 4H) 2.53 (t, J=5.77 Hz, 1H) 3.37 (d, J=8.78 Hz, 2H) 3.49-3.64 (m, 2H) 4.09 (s, 2H) 5.35 (s, 2H) 5.59 (s, 1H) 7.25-7.51 (m, 3H); LCMS: (MH+)=453 rt=0.70 min.

E411

1'-Benzyl-7-((3,5-difluoro-4-((5-(trifluoromethyl)pyridin-3-yl)oxy)benzyl)oxy)-1H-spiro[imidazo[1,2-c]pyrimidine-2,4'-piperidin]-5(3H)-one To a 5 mL microwave vial was added (3,5-difluoro-4-((5-(trifluoromethyl)pyridin-3-yl)oxy)phenyl)methanol (177 mg, 0.580 mmol) in THF (3 mL) and to this was added 60% sodium hydride (46.4 mg, 1.160 mmol) and solution was stirred for 15 min and tert-butyl 1'-benzyl-7-chloro-5-oxo-3,5-dihydro-1H-spiro[imidazo[1,2-c]pyrimidine-2,4'-piperidine]-1-carboxylate (250 mg, 0.580 mmol) was added at rt and then was stirred 1 h. The solution was diluted with ethyl acetate and water and the layers were separated, and the aqueous layer was extracted with EtOAc. The combined organic layers were washed with saturated NaCl, dried ($MgSO_4$), and concentrated under reduced pressure. The crude product was dissolved in methanol (2 mL), filtered through a 0.45 m acrodisc, and purified on a Gilson HPLC (YMC C18 S-5 m/12 nm 50×20 mm preparatory column), eluting at 20 mL/min with a linear gradient running from 30% $CH_3CN/H_2O$ (0.1% TFA) to 90% $CH_3CN/H_2O$ (0.1% TFA) over 10 min. The desired fractions were concentrated by rotovap to yield tert-butyl 1'-benzyl-7-((3,5-difluoro-4-((5-(trifluoromethyl)pyridin-3-yl)oxy)benzyl)oxy)-5-oxo-3,5-dihydro-1H-spiro[imidazo[1,2-c]pyrimidine-2,4'-piperidine]-1-carboxylate (164 mg, 0.234 mmol, 40.4% yield) as a white solid. $^1$H NMR (400 MHz, $CDCl_3$) δ ppm 1.50 (br. s., 9H) 1.86 (d, J=13.05 Hz, 2H) 2.98-3.31 (m, 4H) 3.64 (d, J=10.04 Hz, 2H) 4.22 (s, 2H) 4.40 (s, 2H) 5.22 (s, 2H) 6.31 (br. s., 1H) 6.91 (d, J=8.28 Hz, 2H) 7.28-7.50 (m, 6H) 8.45 (br. s., 1H) 8.57 (s, 1H); LCMS: (MH+)=700 RT=1.13 min. To a 4 mL screw cap vial was added tert-butyl 1-benzyl-7-((3,5-difluoro-4-((5-(trifluoromethyl)pyridin-3-yl)oxy)benzyl)oxy)-5-oxo-3,5-dihydro-1H-spiro[imidazo[1,2-c]pyrimidine-2,4'-piperidine]-1-carboxylate (35 mg, 0.050 mmol) and 4 M HCl in dioxane (1 mL, 4.00 mmol) and solution was stirred at RT for 4 h. The solution was evaporated under a stream of nitrogen and the residue was lyophilized to yield 1-benzyl-7-((3,5-difluoro-4-((5-(trifluoromethyl)pyridin-3-yl)oxy)benzyl)oxy)-1H-spiro[imidazo[1,2-c]pyrimidine-2,4'-piperidin]-5(3H)-one (16.2 mg, 0.027 mmol, 54.0% yield) as a white solid. $^1$H NMR (400 MHz, $CD_3OD$) δ ppm 2.22 (br. s., 4H) 3.42-3.53 (m, 4H) 3.62-3.69 (m, 2H) 4.00 (s, 1H) 4.18 (s, 1H) 4.33 (d, J=18.82 Hz, 2H) 5.36 (d, J=5.02 Hz, 2H) 5.67-5.82 (m, 1H) 7.32 (dd, J=8.16, 4.14 Hz, 2H) 7.42 (br. s., 3H) 7.53 (br. s., 2H) 7.80 (d, J=9.03 Hz, 1H) 8.62 (br. s., 1H); LCMS: (MH+)=600 RT=0.86 min.

E412

5-(((1'-Benzyl-5-oxo-3,5-dihydro-1H-spiro[imidazo[1,2-c]pyrimidine-2,4'-piperidin]-7-yl)oxy)methyl)-2-fluorobenzonitrile

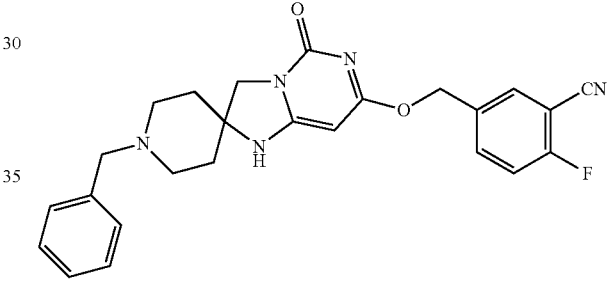

To a 5 mL microwave vial was added 2-fluoro-5-(hydroxymethyl)benzonitrile (88 mg, 0.580 mmol) in tetrahydrofuran (THF) (3 mL) and to this was added 60% sodium hydride (46.4 mg, 1.160 mmol) and solution was stirred for 15 min and then added to reaction vessel and stirred at RT for 1 h. The solution was diluted with ethyl acetate and water and the layers were separated, and the aqueous layer was extracted with EtOAc. The combined organic layers were washed with saturated NaCl, dried over $MgSO_4$ and concentrated under reduced pressure. The crude product was dissolved in methanol (2 mL), filtered through a 0.45 m acrodisc, and purified on a Gilson HPLC (YMC C18 S-5 m/12 nm 50×20 mm preparatory column), eluting at 20 mL/min with a linear gradient running from 10% $CH_3CN/H_2O$ (0.1% TFA) to 90% $CH_3CN/H_2O$ (0.1% TFA) over 10 min. The desired fractions were concentrated by rotovap to yield tert-butyl 1'-benzyl-7-((3-cyano-4-fluorobenzyl)oxy)-5-oxo-3,5-dihydro-1H-spiro[imidazo[1,2-c]pyrimidine-2,4'-piperidine]-1-carboxylate (22 mg, 0.040 mmol, 6.95% yield) as an oil. $^1$H NMR (400 MHz, $CDCl_3$) δ ppm 1.49 (br. s., 9H) 1.84 (d, J=13.30 Hz, 2H) 3.00 (d, J=13.05 Hz, 2H) 3.06-3.18 (m, 2H) 3.67 (d, J=11.80 Hz, 2H) 4.13 (s, 2H) 4.31 (br. s., 2H) 5.25 (s, 2H) 6.25 (br. s., 1H) 7.09 (t, J=8.66 Hz, 1H) 7.19 (s, 1H) 7.33-7.42 (m, 5H) 7.46 (br. s., 1H) 7.52 (d, J=5.02 Hz, 1H); LCMS: (MH+)=546 RT=0.93 min. To a 4 mL screw cap vial was added tert-butyl 1'-benzyl-7-((3-cyano-4-fluorobenzyl)oxy)-5-oxo-3,5-dihydro-1H-spiro

[imidazo[1,2-c]pyrimidine-2,4'-piperidine]-1-carboxylate (22 mg, 0.040 mmol) and 4 M HCl in dioxane (1 mL, 4.00 mmol) and solution was stirred at RT overnight. Solution was evaporated under a stream of nitrogen and the residue was lyophilized to yield 5-((r-benzyl-5-oxo-3,5-dihydro-1H-spiro[imidazo[1,2-c]pyrimidine-2,4'-piperidin]-7-yl)oxy)methyl)-2-fluorobenzonitrile (8.7 mg, 0.020 mmol, 48.4% yield) as a white solid. $^1$H NMR (400 MHz, CD$_3$OD) δ ppm 3.45-3.51 (m, 4H) 3.54-3.59 (t, 2H) 3.62-3.67 (m, 2H) 3.98 (br. s., 1H) 4.16 (br. s., 1H) 4.26-4.37 (m, 2H) 5.32 (d, J=5.27 Hz, 2H) 5.60-5.82 (m, 1H) 7.34-7.39 (m, 1H) 7.42 (br. s., 3H) 7.50 (br. s., 2H) 7.76 (br. s., 1H) 7.83 (br. s., 1H); LCMS: (MH+)=445 RT=0.61 min.

Table 11 provides more exemplary compounds. Example Nos. 413-430 were prepared according to methods similar to the above described reactions.

TABLE 11

| Example No. | Compound name | Analytical data |
|---|---|---|
| 413 | 7'((3-fluorobenzyhoxy)-1'-methyl-1'H-spiro[cyclobutane-1,2'-imidazo[1,2-c]pyrimidin]-5'(3'H)-one | LCMS: Rt = 3.472 min, [M + H]$^+$ = 316 |
| 414 | 1'-methyl-7'-((3,4,5-trifluorobenzyl)oxy)-1'H-spiro[cyclopentane-1,2'-imidazo[1,2-c]pyrimidin]-5'(3'H)-one | LCMS: Rt = 4.417 min, [M + H]$^+$ = 366 |
| 415 | 1-methyl-7'-((2,4,5-trifluorobenzyl)oxy)-1'H-spiro[cyclopentane-1,2'-imidazo[1,2-c]pyrimidin]-5'(3'H)-one | LCMS: Rt = 3.359 min, [M + H]$^+$ = 366 |
| 416 | 7'4(2,4-difluorobenzyhoxy)-1-methyl-1H-spiro[cyclobutane-1,2'-imidazo[1,2-c]pyrimidin]-5'(3'H)-one | LCMS: Rt = 3.524 min, [M + H]$^+$ = 334 |
| 417 | 7'((3-fluorobenzyhoxy)-1'-methyl-1'H-spiro[cyclohexane-1,2'-imidazo[1,2-c]pyrimidin]-5'(3'H)-one | LCMS: Rt = 3.832 min, [M + H]$^+$ = 344 |
| 418 | 7'((3-fluorobenzyhoxy)-1'-methyl-1'H-spiro[cyclopentane-1,2'-imidazo[1,2-c]pyrimidin]-5'(3'H)-one | LCMS: Rt = 4.150 min, [M + H]$^+$ = 330 |
| 419 | 7'4(2,4-difluorobenzyhoxy)-1-methyl-1H-spiro[cyclopentane-1,2'-imidazo[1,2-c]pyrimidin]-5'(3'H)-one | LCMS: Rt = 3.105 min, [M + H]$^+$ = 348 |
| 420 | 7'4(2,3-difluorobenzyhoxy)-1-methyl-1H-spiro[cyclobutane-1,2'-imidazo[1,2-c]pyrimidin]-5'(3'H)-one | LCMS: Rt = 3.995 min, [M + H]$^+$ = 334 |
| 421 | 4-(((1'-methyl-5'-oxo-3',5'-dihydro-1'H-spiro[cyclobutane-1,2'-imidazo[1,2-c]pyrimidin]-7'-yl)oxy)methyl)benzonitrile | LCMS: Rt = 3.777 min, [M + H]$^+$ = 323 |
| 422 | 1'-methyl-7'-((3,4,5-trifluorobenzyl)oxy)-1'H-spiro[cyclohexane-1,2'-imidazo[1,2-c]pyrimidin]-5'(3'H)-one | LCMS: Rt = 4.063 min, [M + H]$^+$ = 380 |
| 423 | 1'-methyl-7'-((3,4,5-trifluorobenzyl)oxy)-1'H-spiro[cyclobutane-1,2'-imidazo[1,2-c]pyrimidin]-5'(3'H)-one | LCMS: Rt = 4.165 min, [M + H]$^+$ = 352 |
| 424 | 4-(((1'-methyl-5'-oxo-3',5'-dihydro-1'H-spiro[cyclopentane-1,2'-imidazo[1,2-c]pyrimidin]-7'-yl)oxy)methyl)benzonitrile | LCMS: Rt = 3.884 min, [M + H]$^+$ = 337 |
| 425 | 7'4(2,3-difluorobenzyhoxy)-1-methyl-1H-spiro[cyclohexane-1,2'-imidazo[1,2-c]pyrimidin]-5'(3'H)-one | LCMS: Rt = 3.876 min, [M + H]$^+$ = 362 |
| 426 | 7'4(2,3-difluorobenzyhoxy)-1-methyl-1H-spiro[cyclopentane-1,2'-imidazo[1,2-c]pyrimidin]-5'(3'H)-one | LCMS: Rt = 3.133 min, [M + H]$^+$ = 348 |
| 427 | 7'4(2,4-difluorobenzyhoxy)-1-methyl-1H-spiro[cyclohexane-1,2'-imidazo[1,2-c]pyrimidin]-5'(3'H)-one | LCMS: Rt = 3.871 min, [M + H]$^+$ = 362 |
| 428 | 1-methyl-7'-((2,4,5-trifluorobenzyl)oxy)-1'H-spiro[cyclohexane-1,2'-imidazo[1,2-c]pyrimidin]-5'(3'H)-one | LCMS: Rt = 3.982 min, [M + H]$^+$ = 380 |
| 429 | 1-methyl-7'-((2,4,5-trifluorobenzyl)oxy)-1'H-spiro[cyclobutane-1,2'-imidazo[1,2-c]pyrimidin]-5'(3'H)-one | LCMS: Rt = 3.647 min, [M + H]$^+$ = 352 |
| 430 | 4-(((1'-methyl-5'-oxo-3',5'-dihydro-1'H-spiro[cyclohexane-1,2'-imidazo[1,2-c]pyrimidin]-7'-yl)oxy)methyl)benzonitrile | LCMS: Rt = 4.042 min, [M + H]$^+$ = 351 |

D. Biological Assays and Data

The compounds of present invention are Lp-PLA$_2$ inhibitors, and may be useful in the treatment and prevention of diseases mediated by Lp-PLA$_2$. The biological activities of the compounds of present invention can be determined by using any suitable assay for determining the activity of a compound as a Lp-PLA$_2$ inhibitor, as well as tissue and in vivo models.

The biological activity data for each compound was either reported in at least one experiment or the average of multiple experiments. It is understood that the data described herein may have reasonable variations depending on the specific conditions and procedures used by the person conducting the experiments.

Lipoprotein-Associated Phospholipase A2 (Lp-PLA$_2$) Biochemical Assay
(1) Recombinant Human Lp-PLA$_2$ Assays (rhLp-PLA$_2$)
(1a) PED6 Assay N-((6-(2,4-Dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labeled phospholipid, which is commercially available from Invitrogene and Molecular Probes. There is a quenching para-nitro phenyl (PNP) group in the sn3 position and a Bodipy fluorescein (FL) group in the sn2 position. Upon cleavage with Lp-PLA$_2$, the Bodipy FL group is liberated and then may result in an increase in fluorescence. Inhibitors of Lp-PLA$_2$ therefore prevent this cleavage and no fluorescent increase is observed.

The PED6 assay was run as an unquenched 10 μL assay. The source plate containing the compounds to be tested was prepared by making 1:3 (by volume) serial dilution of the compounds within DMSO on 384-well microplate. Then, 0.01 μL of the compounds on compound source plate were transferred into 384 well Greiner 784076 (black) plates using ECHO liquid dispenser. 5 μL of recombinant human Lp-PLA$_2$ enzyme (4 nM) rhLp-PLA$_2$ in assay buffer of 50 mM HEPES, pH 7.4, 150 mM NaCl, 1 mM CHAPS) was added to each well of the plate. Plates were centrifuged for 10 sec at 500 rpm. After 30 minutes preincubation, 5 μL of substrate (4 μM PED6 [from 5 mM DMSO stock] in assay buffer of 50 mM HEPES, pH 7.4, 150 mM NaCl, 1 mM CHAPS) was added to 384 well Greiner 784076 (black) plates. Plates were centrifuged for 10 sec at 500 rpm. The plate was covered to protect it from light and incubated for 20 min at room temperature. The plates were read for fluorescence intensity at ex: 480/em: 540 using ViewLux microplate imager for Envision spectrofluroimeters. pIC50 data, curve and QC analysis was conducted by using XL fit module in Excel.

(1b) hrThioPAF Assay

1-O-Hexadecyl-2-deoxy-2-thio-S-acetyl-sn-glyceryl-3-phosphorylcholine (2-thio-PAF) is a substrate for PAF-hydrolases (PAF-AH) commercially available from Cayman Chemical. Upon cleavage with PAF-AH, the free thiol is released at the sn-2 position and can then react with 7-diethylamino-3-(4'-maleimidylphenyl)-4-methylcoumarin (CPM) a thiol-reactive coumarin. This reaction (Michael addition) results in an increase in fluorescence. Inhibitors of Lp-PLA$_2$ therefore prevent this cleavage and no fluorescent increase is observed.

The Thio-PAF assay was run as an unquenched 20 μL assay. The source plate containing the compounds to be tested was prepared by making 1:3 (by volume) serial dilution of the compounds within DMSO on 384-well microplate. Then, 5 μL of the compounds on compound source plate were transferred into 384 well Greiner 784076 (black) plates using STAR+(Hamilton) liquid dispenser. 10 μL of recombinant human Lp-PLA$_2$ enzyme (20 pM rhLp-PLA$_2$ in assay buffer of 50 mM HEPES, pH 7.4, 150 mM NaCl, 1 mM CHAPS) was added to each well of the plate. 5 μL of substrate comprising 40 μM 2-thio-PAF [from ethanol stock], 40 μM CPM [from a DMSO stock] and 400 μM NEM (N-ethylmaleimide) [made fresh daily in DMSO] in assay buffer (50 mM HEPES, pH 7.4, 150 mM NaCl, 1 mM CHAPS) was added to 384 well Greiner 784076 black plates. Plates were vortexed for 10 sec. The plate was covered to protect it from light and incubated for 20 min at 25° C. The plates were read for fluorescence intensity at ex: 380 nm/em: 485 nm using Envision plate reader (Perkin Elmer). Raw data were transferred to Excel software and pIC50 data, curve and QC analysis was conducted by using XL fit module in Excel.

(1c) Alternative PED6 assay

N-((6-(2,4-Dinitrophenyl)amino)-hexanoyl)-2-(4,4-difluoro-5,7-dimethyl-4-bora-3a,4a-diaza-s-indacene-3-pentanoyl)-1-hexadecanoyl-sn-glycero-3-phosphoethanolamine, triethylammonium salt (PED6) is a commercially available fluorescently-labeled phospholipid, which is commercially available from Invitrogene and Molecular Probes. There is a quenching para-nitro phenyl (PNP) group in the sn3 position and a Bodipy fluorescein (FL) group in the sn2 position. Upon cleavage with Lp-PLA$_2$, the Bodipy FL group is liberated and then may result in an increase in fluorescence. Inhibitors of Lp-PLA$_2$ therefore prevent this cleavage and no fluorescent increase is observed.

The PED6 assay was run as an unquenched 10 μL assay. The source plate containing the compounds to be tested was prepared at 10 mM in DMSO on 384-well microplate. Then, 0.01 μL of the compounds on compound source plate were transferred into 384 well Greiner 784076 (black) plates using ECHO liquid dispenser (the final concentration of compound is 10 uM). 5 μL of recombinant human Lp-PLA$_2$ enzyme (final concentration is 110 pM) rhLp-PLA$_2$ in assay buffer of 50 mM HEPES, pH 7.4, 150 mM NaCl, 1 mM CHAPS) was added to each well of the plate. Plates were centrifuged for 10 sec at 500 rpm. After 30 minutes preincubation, 5 μL of substrate (final concentration is 5 μM) PED6 [from 5 mM DMSO stock] in assay buffer of 50 mM HEPES, pH 7.4, 150 mM NaCl, 1 mM CHAPS) was added to 384 well Greiner 784076 (black) plates. Plates were centrifuged for 10 sec at 500 rpm. The plate was covered to protect it from light and incubated for 20 min at room temperature. The plates were read for fluorescence intensity at ex: 480/em: 540 using ViewLux microplate imager for Envision spectrofluroimeters. This assay was used to qualitatively measure whether the tested compound demonstrates inhibition activity.

Examples 1-167 and 413-430 were tested in the (1a) PED6 assay, Examples 168-265 were tested in (1c) alternative PED6 assay, and Example 266-412, was tested in (1 b) hrThioPAF assay. All tested Examples except Examples 318, 355, 376, 378, 379, and 380, 421, 424 and 430 were found to demonstrate inhibition activity to Lp-PLA$_2$. The pIC$_{50}$ value for compounds tested under (1a) and (1b) was either reported in at least one experiment or the average of multiple experiments. (1c) alternative PED6 assay was used to test whether the compounds have inhibition activity to Lp-PLA$_2$, but not the actual pIC$_{50}$ value.

The pIC$_{50}$ values in the recombinant human Lp-PLA$_2$ assay ((1a) and (1 b)) for Examples 1-167, 266-317, 319-354, 356-375, 377, 381-412, 413-420, 422, 423, and 425-429 were at least 5.0.

The pIC$_{50}$ values in the recombinant human Lp-PLA$_2$ assay ((1a) and (1 b)) for Examples 1-3, 5, 6, 8, 10-12, 14-167, 266, 267, 269-271, 273, 274, 279-308, 310, 313, 315, 317, 320-325, 327-347, 349-352, 356-361, 364, 366-373, 381-388, 390-392 393-403, 405, 407-412, 413-420, 422, 423, and 425-429 were at least 7.0.

The pIC$_{50}$ values in the recombinant human Lp-PLA$_2$ assay ((1a) and (1 b)) for Examples 10-12, 17, 19-26, 28, 37-42, 44-49, 67, 71, 75, 77-79, 81, 83, 85, 87, 88, 90, 91, 107, 110-113, 115, 118, 119, 124, 125, 134, 135, 141, 142, 149, 151, 154, 162, 164, 166, 273, 351, 352, 368, 371, 372, 383, 388, 395, 401 and 409-411 were at least 9.0.

For example, the pIC50 values of recombinant human Lp-PLA$_2$ assay ((1a) and (1b)) for following examples are:

| Example No. | rhLp-PLA$_2$ (pIC50) |
|---|---|
| 67 | 9.8 |
| 71 | 9.5 |
| 107 | 10.4 |
| 109 | 8.9 |
| 110 | 9.3 |
| 113 | 10.5 |
| 115 | 9.0 |
| 124 | 9.3 |
| 125 | 10.2 |
| 128 | 8.0 |
| 338 | 8.0 |
| 352 | 9.3 |
| 395 | 9.1 |
| 401 | 9.2 |

(2) PLA2 VIIB Assay (2a) PLA2 VIIB Assay

PLA2 VIIB (also known as Novel Serine Dependent Lipase, NSDL) is a serine hydrolase with 40% amino acid identity with human Lp-PLA$_2$. Sequence comparisons indicate that the PLA VIIB active site catalytic triad positions are similar to those of Lp-PLA$_2$. Similar to Lp-PLA$_2$, it is capable of hydrolyzing oxidatively modified phospholipids and may be assayed using known Lp-PLA$_2$ substrates.

Upon cleavage by a phopholipase, PLA2 VIIB liberates a fluorescent Bodipy group. Recombinant human PLA2 VIIB is used as the phospholipase source in this assay, and compounds are screened to test their degree of inhibition in this assay. The assay is used to determine the degree of selectivity of the testing compounds between PLA2 VIIB and Lp-PLA$_2$.

The PLA2 VIIB assay was applied as an unquenched 10 μL assay. The source plate containing the compounds is prepared by making 1:3 (by volume) serial dilution of the compounds with pure DMSO on 384-well microplate. 0.01 μL of compounds on the compound source plate were transferred into 384 well Greiner 784076 (black) plates by ECHO liquid dispenser. 5 μL of Novel Serine Dependent Lipase (NSDL) enzyme (5 nM NSDL in assay buffer of 50 mM HEPES, pH 7.4, 150 mM NaCl, 1 mM CHAPS) was added to each well. Alternatively, in some instances, this step was carried out by adding 10 μL of recombinant human PLA2 VIIB (200 pM rhPLA$_2$ VIIB in assay buffer of 50 mM HEPES, pH 7.4, 150 mM NaCl, 1 mM CHAPS) to each well. Plates were centrifuged for 10 sec at 500 rpm. After 30 minutes preincubation, 5 μL of substrate (5 μM PED6 [from 5 mM DMSO stock] in assay buffer of 50 mM HEPES, pH 7.4, 150 mM NaCl, 1 mM CHAPS) was added to 384 well Greiner 784076 (black) low-volume plates. Plates were kinetic read by starting read immediately after PED6 addition at ex: 480/em: 540 using ViewLux microplate reader or Envision spectrofluorimeters. IC 50 data (which may be converted to pIC50 data), curve and QC analysis was conducted using XLfit module in Excel.

(2b) Alternative PLA2 VIIB Assay

1-O-hexadecyl-2-deoxy-2-thio-S-acetyl-sn-glyceryl-3-phosphorylcholine (2-thio-PAF) is a substrate for PAF-hydrolases (PAF-AH) commercially available from Cayman Chemical. Upon cleavage with PAF-AH, the free thiol is released at the sn-2 position and can then react with 7-diethylamino-3-(4'-maleimidylphenyl)-4-methylcoumarin (CPM) a thiol-reactive coumarin. This reaction (Michael addition) results in an increase in fluorescence. Inhibitors of $PLA_2$-VIIB therefore prevent this cleavage and no fluorescent increase is observed.

The Thio-PAF assay was run as an unquenched 20 µL assay. The source plate containing the compounds to be tested was prepared by making 1:3 (by volume) serial dilution of the compounds within DMSO on 384-well microplate. Then, 5 µL of the compounds on compound source plate were transferred into 384 well Greiner 784076 (black) plates using STAR+(Hamilton) liquid dispenser. 10 µL of recombinant human $PLA_2$-VIIB enzyme (200 pM rh$PLA_2$-VIIB in assay buffer of 50 mM HEPES, pH 7.4, 150 mM NaCl, 1 mM CHAPS) was added to each well of the plate. 5 µL of substrate comprising 40 µM 2-thio-PAF [from ethanol stock], 40 µM CPM [from a DMSO stock] and 400 µM NEM (N-ethylmaleimide) [made fresh daily in DMSO] in assay buffer (50 mM HEPES, pH 7.4, 150 mM NaCl, 1 mM CHAPS) was added to 384 well Greiner 784076 black plates. Plates were vortexed for 10 sec. The plate was covered to protect it from light and incubated for 20 min at 25° C. The plates were read for fluorescence intensity at ex: 380 nm/em: 485 nm using Envision plate reader (Perkin Elmer). Raw data were transferred to Excel software and pIC50 data, curve and QC analysis was conducted by using XL fit module in Excel.

Examples 1-9, 11-105, 107-193, 203-259 and 413-430 were tested in (2a) PLA2 VIIB assay described above. Examples 266-412 were tested in (2b) alternative PLA2 VIIB assay described above. Examples 1-3, 5, 6, 8, 11-12, 15, 17-28, 30-34, 36-52, 54-72, 74-83, 85-105, 107-119, 121, 122, 124-132, 134-152, 154-167, 266, 267, 269-271, 273, 274, 279-308, 310, 313, 315, 317, 320-325, 327-352, 356-361, 364, 366-373, 381-386, 388, and 390-396, 398-403, 405, 407-412, 413-420, 422, 423, and 425-429 had at least 100 fold selectivity between human recombinant Lp-$PLA_2$ and PLA2 VIIB.

(3) Lipoprotein-Associated Phospholipase A2 (Lp-$PLA_2$) Human Plasma Assay (3a) Thio-PAF Assay The human plasma assay utilizes a thioester analog of PAF (phosphatidylcholine), where hydrolysis yields to the formation of a phospholipid containing a free thiol group. The amount of thiol is quantitated continuously by reacting with CPM (7-diethylamino-3-(4'-maleimidylphenyl)-4-methylcoumarin), a maleimide which increases in fluorescence after Michael addition of thiols. This assay may detect the activity of Lp-$PLA_2$ in human plasma, as determined by specific inhibition by Lp-$PLA_2$ inhibitors.

The thio-PAF assay was run as a quenched 15 µL assay. Compounds source plate was prepared by making 1:3 (by volume) serial dilution of the compounds into pure DMSO on 384-well microplate. 0.01 µL of compounds on compound source plate were transferred to 384 well Greiner 784076 (black) low-volume plates by ECHO liquid dispenser. 8 µL pooled human plasma, which was previously aliquoted and frozen, was added. Plates were centrifuged for 10 sec at 500 rpm. After 30 minutes preincubation, 2 µL of substrate solution comprising 2.5 mM 2-thio-PAF [from ethanol stock], 32 µM CPM [from a DMSO stock] and 3.2 mM NEM (N-ethylmaleimide) [made fresh daily in DMSO] in assay buffer of 50 mM HEPES, pH 7.4, 150 mM NaCl, 1 mM CHAPS was added to 384 well Greiner 784076 (black) low-volume plates by BRAVO liquid handling station. After 2 mins, reaction was quenched with 5 µL of 5% aqueous trifluoroacetic acid (TFA). Plates were covered to protect from light and incubated for 40 min at room temperature. Plates were read at ex: 380/em: 485 using Envision microplate reader. PIC50 data, curve and QC analysis were conducted by using XLFit module in Excel.

(3b) Alternative Thio-PAF Assay

The human plasma assay utilizes the same thioester analog of PAF as described in (1b) "hr ThioPAF" assay. This assay may detect the activity of Lp-$PLA_2$ in human plasma, as determined by specific inhibition by Lp-$PLA_2$ inhibitors.

The thio-PAF assay was run as a quenched 20 µL assay. Compounds source plate was prepared by making 1:3 (by volume) serial dilution of the compounds into pure DMSO on 96-well microplate. 5 µL of compounds on compound source plate were transferred to 96-well Corning 3686 (black) low-volume plates by STAR+(Hamilton) liquid dispenser. 10 µL pooled human plasma, which was previously aliquoted and frozen, was added. Plates were centrifuged for 30 sec at 1000 rpm. After 15 minutes preincubation at room temperature, 5 µL of substrate solution comprising 2 mM 2-thio-PAF [from ethanol stock], 52 µM CPM [from a DMSO stock] and 2.5 mM NEM (N-ethylmaleimide) [made fresh daily in DMSO] in assay buffer (50 mM HEPES, pH 7.4, 150 mM NaCl, 1 mM CHAPS) was added to 96-well Corning 3686 (black) low-volume plates. After 3 mins, reaction was quenched with 10 µL of 5% aqueous trifluoroacetic acid (TFA). Plates were centrifuged 30 sec at 1000 rpm, covered to protect from light and incubated for 10 min at room temperature. Plates were read at ex: 380 nm/em: 485 nm using Envision plate reader (Perkin Elmer). Raw data were transferred to Excel software and pIC50 data, curve and QC analysis was conducted by using XL fit module in Excel.

Examples 1-265 and 413-430 were tested in the Thio-PAF assay described in (3a) and Examples 266-274, 279-309, 310, 313, 315, 317, 320-325, 327, 329-352, 356-361, 364-373, 381-388, 390-403, and 405-412 were tested in the alternative Thio-PAF assay described in (3b). The $pIC_{50}$ value for all tested compounds was either reported in at least one experiment or the average of multiple experiments.

The $pIC_{50}$ values in the Lp-$PLA_2$ human plasma assays ((3a) and 3(b)) for Examples 1-3, 5, 6, 8, 10-12, 14-60, 62-169, 171-177, 180-184, 186-189, 191, 193, 195, 197, 200, 205-207, 209, 211-212, 214-216, 218-221, 225, 246, 248, 249, 254-258, 262, 266-274, 279-308, 310, 313, 315, 317-320-326, 327, 329-352, 356-361, 364-373, 381-388, 390-403, 405-408, 411-420, 422, 423, and 425-429 were at least 5.0.

The $pIC_{50}$ values in the Lp-$PLA_2$ human plasma assays ((3a) and 3(b)) for Examples 2, 5, 10-12, 17, 19-21, 23-26, 28, 30, 37-47, 49, 52, 54, 67, 69-71, 75, 77-79, 81, 83, 85, 87, 90, 91, 107-119, 124, 125, 127-129, 131, 134, 135, 139, 141, 142, 146, 149-152, 154, 162, 164-166, 221, 266, 267, 269, 270, 272-274, 279-308, 310, 313, 315, 320-325, 327, 329-347, 349, 351, 352, 356-360, 364, 366-373, 382-384, 386-388, 390-392, 394-403, 405-408, 411, 414, 418, 423, and 426 were at least 7.0.

E. Methods of Use

The compounds of the invention are inhibitors of Lp-PLA$_2$. Therefore, these compounds may be used in therapy, for example, in the treatment or prevention of diseases associated with the activity of Lp-PLA$_2$, which comprises treating a subject in need thereof with a therapeutically effective amount of an inhibitor of Lp-PLA$_2$. Accordingly, one aspect of the invention is directed to methods of treating or preventing diseases associated with the activity of Lp-PLA$_2$. As will be appreciated by those skilled in the art, a particular disease or its treatment may involve one or more underlying mechanisms associated with Lp-PLA$_2$ activity, including one or more of the mechanisms described herein.

In some embodiments, an inhibitor of Lp-PLA$_2$ according to the invention may be used in treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the compounds of the present invention may be used to treat or prevent any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the compounds of the present invention may be used to treat or prevent any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the compounds of the present invention may be used to lower the chances of having a cardiovascular event (such as a heart attack, myocardial infarction or stroke) in a patient with coronary heart disease.

In certain embodiments, the compounds of the present invention may be used to treat or prevent diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the compounds of the invention may be used for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides methods of treating or preventing a neurological disease associated with an abnormal blood brain barrier (BBB) function, inflammation, and/or microglia activation in a subject in need thereof. In some embodiments, the present invention provides methods of treating a neurological disease associated with an abnormal blood brain barrier (BBB) function, inflammation, and/or microglia activation in a subject in need thereof. The methods comprise administering to the subject a therapeutically effective amount of a compound of the present invention. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides methods of treating or preventing disease associated with a subject with blood brain barrier (BBB) leakage. In some embodiments, the present invention provides methods of treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the compounds of the present invention may be used to treat or prevent a neurodegeneration disease in a subject. The methods comprise administering to a subject in need thereof a compound of the invention, e.g., as a pharmaceutical composition comprising a compound of the invention. In one embodiment, the compounds of the present invention may be used to treat a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier. In one embodiment, the subject which is administered an agent that inhibits the activity of Lp-PLA$_2$ is a human.

In one embodiment, the present invention provides methods of treating or preventing a subject with or at risk of vascular dementia. The methods comprise administering to the subject a compound of the invention, e.g., as a pharmaceutical composition comprising a therapeutically effective amount of a compound of the present invention. In one embodiment, the present invention provides methods of treating a subject with or at risk of vascular dementia. In a certain embodiment, the vascular dementia is associated with Alzheimer's disease.

In certain embodiments, the present invention provides methods of decreasing beta amyloid, referred to as "Aβ" accumulation in the brain of a subject. The methods comprise administering to a subject in need thereof a pharmaceutical composition comprising a therapeutically effective amount of a compound of the present invention. In a further embodiment, the beta amyloid is Abeta-42.

In certain embodiments, when a subject is administered a therapeutically effective amount of a compound of the present invention, the methods may further comprise administering to the subject another therapeutic agent that may be useful in treating the neurodegenerative disease for which the subject is being treated, or that may be a co-morbidity. In one embodiment, the present invention provides methods of slowing or delaying the progression of cognitive and function decline in patients with mild Alzheimer's disease. In certain embodiment, the compounds of the present invention described herein may be used as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides methods of slowing or delaying the progression of cognitive or function decline in a patient with mild or moderate Alzheimer's disease and/or cerebrovascular disease (CVD) comprise administering a therapeutically effective amount of a compound of the present invention to the patient who has been administered an agent used to provide symptomatic treatment to Alzheimer's disease (e.g., ARICEPT® or memantine) for 6 months or longer.

In certain embodiments, the present invention relates to methods of treating or preventing metabolic bone diseases by administering to the subject in need thereof a therapeutically effective amount of a compound of the present invention. In some embodiments, the present invention relates to methods of treating metabolic bone diseases by administering to the subject in need thereof a therapeutically effective amount of a compound of the present invention. Exemplary metabolic bone diseases include, diseases associated with loss of bone mass and density including, but are not limited to, osteoporosis and osteopenic diseases. Exemplary osteoporosis and osteopenic diseases include, but are not limited to, bone marrow abnormalities, dyslipidemia, Paget's diseases, type II diabetes, metabolic syndrome, insulin resistance, hyperparathyroidism and related diseases. In a further embodiment, the subject in need thereof is a human.

It is believed that methods of preventing osteoporosis and/or osteopenic diseases described herein may be affected by inhibiting the expression of Lp-PLA$_2$ and/or inhibiting the protein activity of Lp-PLA$_2$. Accordingly, some embodiments of the present invention provide methods for inhibiting Lp-PLA$_2$ by blocking enzyme activity. In a further embodiment, methods for inhibiting Lp-PLA$_2$ by reducing and/or down-regulating the expression of Lp-PLA$_2$ RNA are provided. In a further embodiment, preventing and/or reducing loss of bone mass and/or loss of bone density leads to preventing or reducing symptoms associated with metabolic bone diseases such as osteoporosis and/or osteopenic diseases.

In certain embodiments, the methods further comprise administering to a subject in need thereof additional therapeutic agents used in the treatment of metabolic bone diseases. For example, when the metabolic bone disease is osteoporosis additional therapeutic agents such as bisphosphates (e.g., alendronate, ibandronate, risedronate, calcitonin, raloxifene), a selective estrogen modulator (SERM), estrogen therapy, hormone replacement therapy (ET/HRT) and teriparatide may be used.

One aspect of the present invention provides methods for treating and/or preventing ocular diseases by administering a therapeutically effective amount of a compound of the present invention. In some embodiments, the present invention provides methods for treating ocular diseases by administering a therapeutically effective amount of a compound of the present invention. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. Further, in one embodiment, the present invention relates to methods for treating ocular diseases by administering a compound of the present invention to inhibit Lp-PLA$_2$. Exemplary ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-PLA$_2$ inhibitor to treat eye diseases are provided in WO2012/080497, which is incorporated by reference herein.

Further, some embodiments of the present invention provide methods for treating or preventing diabetic macular edema in a subject. In some embodiments, the present invention provides methods for treating diabetic macular edema in a subject. The method comprises administering to a subject in need thereof a therapeutically effective amount of a compound of the present invention.

In certain embodiments, the present invention provides methods of treating or preventing a subject with or at risk of macular edema. In some embodiments, the present invention provides methods of treating a subject with or at risk of macular edema. The methods comprise administering to the subject a therapeutically effective amount of a compound of the present invention. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides methods of treating or preventing glaucoma or macular degeneration. In some embodiments, the present invention provides methods of treating glaucoma or macular degeneration. The methods comprise administering to the subject a therapeutically effective amount of a compound of the present invention.

In one embodiment, the present invention provides methods of treating or preventing a disease associated with the breakdown of the inner blood-retinal barrier in a subject in need thereof. In one embodiment, the present invention provides methods of treating a disease associated with the breakdown of the inner blood-retinal barrier in a subject in need thereof. The methods comprise administering to the subject a therapeutically effective amount of a compound of the present invention.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. The present invention relates to methods for treating or preventing posterior uveitis or any of these systemic inflammatory diseases by administering a therapeutically effective amount of a compound of the present invention. In one embodiment, the present invention provides methods for treating posterior uveitis or any of these systemic inflammatory diseases by administering a therapeutically effective amount of a compound of the present invention.

It is believed that Lp-PLA$_2$ inhibitors may have beneficial effects on diseases associated with M1/M2 macrophage polarization. The belief is based on the following studies. A study was carried out by GSK to investigate the relationship between M1/M2 macrophage polarization and different diseases. 94 human markers described in Martinez F O et al., which distinguished M1 and M2 phenotypes was used against a GSK subscribed GeneLogic database. (See Martinez F O et al. (2006) J Immunol 177, 7303-7311.) The Connectivity Map methodology described in Lamb J et al. was used to identify the fraction of samples in each disease state having expression characteristics consistent with a M1-favoring or M2-favoring macrophage population. (See Lamb J et al. (2006) Science 313, 1929-1935) (PMID 17008526)). The study showed that liver cirrhosis, skin psoriasis, atopic dermatitis, pulmonary emphysema, chronic pancreatitis, chronic gastritis, and aortic aneurysm have M1/M2 imbalance.

A further study was carried out to study the impact of Lp-PLA$_2$ inhibitors on modulating M1/M2 imbalance. In this study, rats were induced to develop experimental autoimmune encephalomyelitis (EAE) by immunization with myelin basic protein (MBP) antigen and treated with a known Lp-PLA$_2$ inhibitor: 5-((9-Methoxy-4-oxo-6,7-dihydro-4H-pyrimido[6,1-a]isoquinolin-2-yl)oxy)-2-(3-(trifluoromethyl)phenoxy)benzonitrile (See PCT application no. PCT/CN2011/001597). In this preventive treatment model, the compound was administered at day 0 (day of immunization) and continued to administer until day 22. The study lasted for 25 days. Rats were subsequently monitored for symptoms of EAE. Rats were immunized with MBP to develop EAE and symptoms were monitored daily. Plasma Lp-PLA$_2$ activity, OxLDL, and LysoPC concentration were determined at different time points through the course of EAE. The results showed that plasma Lp-PLA$_2$ activity, OxLDL, and LysoPC concentrations increased as the clinical EAE disease progressed in the model, which indicates that they played a role in the pathology development. Lp-PLA$_2$ inhibitor treatment led to reduction in clinical disease associated with decreased Lp-PLA$_2$ activity and LysoPC levels in rat EAE plasma. Hence, inhibition of Lp-PLA$_2$ activity is beneficial in ameliorating disease in the rat EAE model.

Ex vivo analysis of proinflammatory (M1) and anti-inflammatory (M2) markers in control and compound treated EAE rats. Splenic macrophages were harvested at day 13 post MBP-immunization and assayed for expression of a variety of markers by realtime PCR. CNS infiltrating cells were harvested and macrophages were analyzed for expression of M1 and M2 markers by realtime PCR. Treatment with compound resulted in the decrease in M1 markers and increase in M2 markers, which potentially indicated the possibility of anti-inflammation and tissue repair.

Therefore, in certain embodiments, the present invention provides methods of treating or preventing disease associated with macrophage polarization, for example, M1/M2 macrophage polarization. In some embodiments, the present invention provides methods of treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS), ischemic cardiomyopathy, chronic heart failure post myocardial infarction (MI) and other autoimmune diseases that are associated with macrophage polarization.

Treatment and or prevention of a disease associated with Lp-PLA$_2$ activity may be achieved using a compound of this invention as a monotherapy, or in dual or multiple combination therapy. For example, the compounds of the present invention may be used to treat or prevent the disease described herein in combination with an anti-hyperlipidaemic, anti-atherosclerotic, anti-diabetic, anti-anginal, anti-inflammatory, or anti-hypertension agent or an agent for lowering Lipoprotein (a) (Lp(a)). Examples of the above include, but are not limited to, cholesterol synthesis inhibitors such as statins, antioxidants such as probucol, insulin sensitizers, calcium channel antagonists, and anti-inflammatory drugs such as non-steroidal anti-inflammatory Drugs (NSAIDs). Examples of agents for lowering Lp(a) include the aminophosphonates described in WO 97/02037, WO 98/28310, WO 98/28311 and WO 98/28312. In one embodiment, the compounds of the present invention may be used with one or more statins. The statins are a well-known class of cholesterol lowering agents and include atorvastatin, simvarstatin, pravastatin, cerivastatin, fluvastatin, lovastatin and rosuvastatin. In a certain embodiment, the compounds of the present invention may be used with an anti-diabetic agent or an insulin sensitizer. In one embodiment, a compound of the present invention may be used with PPAR gamma activators, for instance G1262570 (GlaxoSmithKline) and the glitazone class of compounds such as rosiglitazone, troglitazone and pioglitazone. Such agents may be administered in therapeutically effective amounts, e.g., as is known in the art, or lesser or greater amounts than known in the art provided that the amount administered is therapeutically effective.

Combination therapy includes administration of the therapeutic agents in separate dosage forms or together in a single dosage form. Combination therapy may involve simultaneous administration or separate administration of the therapeutic agents, which may be substantially simultaneous or substantially separate administration. Typically, combination therapy will involve administration of each agent such that therapeutically effective amounts of each agent are present in the subject's body in at least an overlapping period.

One aspect of the present invention provides the use of a compound of the present invention for the preparation of a medicament for carrying out a method described herein.

In some embodiments, the present invention provides the use of a compound of the present invention for the preparation of a medicament for treating or preventing diseases associated with the activity of Lp-PLA$_2$.

In some embodiments, it provides the use of a compound of the present invention for preparation of a medicament for treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/

042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the present invention provides the use of a compound of the present invention for the preparation of a medicament for treating or preventing any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the present invention provides the use of a compound of the present invention for the preparation of a medicament for treating or preventing any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the present invention provides the use of a compound of the present invention for the preparation of a medicament for lowering the chances of having a cardiovascular event (such as a heart attack, myocardial infarction or stroke) in a patient with coronary heart disease.

In certain embodiments, the present invention provides the use of a compound of the present invention for the preparation of a medicament for treating or preventing diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the present invention provides the use of a compound of the present invention for the preparation of a medicament for the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides the use of a compound of the present invention for the preparation of a medicament for treating or preventing a neurological disease associated with an abnormal blood brain barrier (BBB) function, inflammation, and/or microglia activation in a subject in need thereof. In some embodiments, the present invention provides the use of a compound of the present invention for the preparation of a medicament for treating a neurological disease associated with an abnormal blood brain barrier (BBB) function, inflammation, and/or microglia activation in a subject in need thereof. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides use of a compound of the present invention for the preparation of a medicament for treating or preventing disease associated with a subject with blood brain barrier (BBB) leakage. In some embodiments, the present invention provides the use of a compound of the present invention for the preparation of a medicament for treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the present invention provides the use of a compound of the present invention for the preparation of a medicament for treating or preventing a neurodegeneration disease in a subject. In one embodiment, the present invention provides the use of a compound of the present invention for the preparation of a medicament for treating a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier.

In one embodiment, the present invention provides the use of a compound of the present invention for the preparation of a medicament for treating or preventing a subject with or at risk of vascular dementia. In one embodiment, the present invention provides the use of a compound of the present invention for the preparation of a medicament for treating a subject with or at risk of vascular dementia. In a certain embodiment, the vascular dementia is associated with Alzheimer's disease.

In certain embodiments, the present invention provides the use of a compound of the present invention for the preparation of a medicament for decreasing beta amyloid, referred to as "Aβ" accumulation in the brain of a subject. In a further embodiment, the beta amyloid is Abeta-42.

In one embodiment, the present invention provides the use of a compound of the present invention for the preparation of a medicament for slowing or delaying the progression of cognitive function decline in patients with mild Alzheimer's disease. In certain embodiment, the present invention provides the use of a compound of the present invention for the preparation of a medicament as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides the use of a compound of the present invention for the preparation of a medicament for slowing or delaying the progression of cognitive function decline in a patient with mild or moderate Alzheimer's disease and/or cerebrovascular disease (CVD), wherein the patient who has been administered an agent used to provide symptomatic treatment to Alzheimer's disease (e.g., ARICEPT® or memantine) for 6 months or longer. In certain embodiments, the present invention provides the use of a compound of the present invention for the preparation of a medicament for slowing or delaying the progression of cognitive function decline in a patient with mild or moderate Alzheimer's disease and cerebral small vessel disease (SVD), wherein the patient who has been administered an agent used to provide symptomatic treatment to Alzheimer's disease (e.g., ARICEPT® or memantine) for 6 months or longer.

In certain embodiments, the present invention provides the use of a compound of the present invention for the preparation of a medicament for treating or preventing metabolic bone diseases. In some embodiments, the present invention provides the use of a compound of the present invention for the preparation of a medicament for treating metabolic bone diseases. Exemplary metabolic bone diseases include, diseases associated with loss of bone mass and density including, but are not limited to, osteoporosis and osteopenic diseases. Exemplary osteoporosis and osteopenic diseases include, but are not limited to, bone marrow abnormalities, dyslipidemia, Paget's diseases, type II diabetes, metabolic syndrome, insulin resistance, hyperparathyroidism and related diseases. In a further embodiment, the present invention provides the use of a compound of the present invention for the preparation of a medicament for preventing and/or reducing loss of bone mass and/or loss of bone density leads to preventing or reducing symptoms associated with metabolic bone diseases such as osteoporosis and/or osteopenic diseases.

In certain embodiments, the present invention provides the use of a compound of the present invention for the preparation of a medicament for treating metabolic bone diseases, wherein the medicament is used with additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene), a selective estrogen modulator (SERM), estrogen therapy, hormone replacement therapy (ET/HRT) and teriparatide may be used.

One aspect of the present invention provides the use of a compound of the present invention for the preparation of a medicament for treating and/or preventing ocular diseases. In some embodiments, the present invention provides the use of a compound of the present invention for the preparation of a medicament for treating ocular diseases. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. More ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-PLA$_2$ inhibitor to treat eye diseases are provided in WO2012/080497, which is incorporated by reference herein.

Further, some embodiments of the present invention provide the use of a compound of the present invention for the preparation of a medicament for treating or preventing diabetic macular edema in a subject. In some embodiments, the present invention provides the use of a compound of the present invention for treating diabetic macular edema in a subject.

In certain embodiments, the present invention provides the use of a compound of the present invention for the preparation of a medicament for treating or preventing a subject with or at risk of macular edema. In some embodiments, the present invention provides the use of a compound of the present invention for the preparation of a medicament for treating a subject with or at risk of macular edema. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides the use of a compound of the present invention for the preparation of a medicament for treating or preventing glaucoma or macular degeneration. In some embodiments, the present invention provides the use of a compound of the present invention for the preparation of a medicament for treating glaucoma or macular degeneration.

In one embodiment, the present invention provides the use of a compound of the present invention for the preparation of a medicament for treating or preventing a disease associated with the breakdown of the inner blood-retinal barrier in a subject in need thereof. In one embodiment, the present invention provides the use of a compound of the present invention for the preparation of a medicament for treating a disease associated with the breakdown of the inner blood-retinal barrier in a subject in need thereof.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. In one embodiment, the present invention provides the use of a compound of the present invention for the preparation of a medicament for treating posterior uveitis or any of these systemic inflammatory diseases.

In certain embodiments, the present invention provides the use of a compound of the present invention for the preparation of a medicament for treating or preventing disease associated with macrophage polarization, for example, M1/M2 macrophage polarization. In some embodiments, the present invention provides the use of a compound of the present invention for the preparation of a medicament for treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS), ischemic cardiomyopathy, chronic heart failure post myocardial infarction (MI) and other autoimmune diseases that are associated with macrophage polarization.

Another aspect of the present invention provides a compound of the present invention for use in carrying out methods of treatment or prevention described herein. A further aspect of the present invention provides a compound described herein or a pharmaceutically acceptable salt thereof, for use in therapy.

In some embodiments, the present invention provides a compound of the present invention for use in treating or preventing diseases associated with the activity of Lp-PLA$_2$.

In some embodiments, the present invention provides a compound of the present invention for use in treating or preventing any of diseases disclosed in the following published patent applications: WO96/13484, WO96/19451, WO97/02242, WO97/12963, WO97/21675, WO97/21676, WO 97/41098, WO97/41099, WO99/24420, WO00/10980, WO00/66566, WO00/66567, WO00/68208, WO01/60805, WO02/30904, WO02/30911, WO03/015786, WO03/016287, WO03/041712, WO03/042179, WO03/042206, WO03/042218, WO03/086400, WO03/87088, WO08/048867, US 2008/0103156, US 2008/0090851, US 2008/0090852, WO08/048866, WO05/003118 CA 2530816A1), WO06/063811, WO06/063813, WO 2008/141176, JP 200188847, US 2008/0279846 A1, US 2010/0239565 A1, and US 2008/0280829 A1.

In certain embodiments, the present invention provides a compound of the present invention for use in treating or preventing any diseases that involve endothelial dysfunction, for example, atherosclerosis, (e.g. peripheral vascular atherosclerosis and cerebrovascular atherosclerosis), diabetes, hypertension, angina pectoris and after ischaemia and reperfusion.

In certain embodiments, the present invention provides a compound of the present invention for use in treating or preventing any disease that involves lipid oxidation in conjunction with enzyme activity, for example, in addition to conditions such as atherosclerosis and diabetes, other conditions such as rheumatoid arthritis, stroke, inflammatory conditions of the brain such as Alzheimer's Disease, various neuropsychiatric disorders such as schizophrenia, myocardial infarction, ischaemia, reperfusion injury, sepsis, and acute and chronic inflammation.

In certain embodiments, the present invention provides a compound of the present invention for use in lowering the chances of having a cardiovascular event (such as a heart attack, myocardial infarction or stroke) in a patient with coronary heart disease.

In certain embodiments, the present invention provides a compound of the present invention for use in treating or preventing diseases that involve activated monocytes, macrophages or lymphocytes, as all of these cell types express Lp-PLA$_2$ including diseases involving activated macrophages such as M1, dendritic and/or other macrophages which generate oxidative stress. Exemplary diseases include, but are not limited to, psoriasis, rheumatoid arthritis, wound healing, chronic obstructive pulmonary disease (COPD), liver cirrhosis, atopic dermatitis, pulmonary emphysema, chronic pancreatitis, chronic gastritis, aortic aneurysm, atherosclerosis, multiple sclerosis, Alzheimer's disease, and autoimmune diseases such as lupus.

In other embodiments, the present invention provides a compound of the present invention for use in the primary or secondary prevention of acute coronary events, e.g. caused by atherosclerosis; adjunctive therapy in the prevention of restenosis; or delaying the progression of diabetic or hypertensive renal insufficiency. Prevention includes treating a subject at risk of having such conditions.

In certain embodiments, the present invention provides a compound of the present invention for use in treating or preventing a neurological disease associated with an abnormal blood brain barrier (BBB) function, inflammation, and/or microglia activation in a subject in need thereof. In some embodiments, the present invention provides a compound of the present invention for use in treating a neurological disease associated with an abnormal blood brain barrier (BBB) function, inflammation, and/or microglia activation. In a further embodiment, the abnormal BBB is a permeable BBB. In yet a further embodiment, the disease is a neurodegeneration disease. Such neurodegeneration diseases are, for example, but are not limited to, vascular dementia, Alzheimer's disease, Parkinson's disease and Huntington's disease. In one embodiment, the present invention provides a compound of the present invention for use in treating or preventing disease associated with a subject with blood brain barrier (BBB) leakage. In some embodiments, the present invention provides a compound of the present invention for use in treating disease associated with a subject with blood brain barrier (BBB) leakage. Exemplary diseases include, but are not limited to, brain hemorrhage, cerebral amyloid angiopathy. In one embodiment, the neurodegeneration disease is Alzheimer's disease. In a certain embodiment, the neurodegeneration disease is vascular dementia. In one embodiment, the neurodegeneration disease is multiple sclerosis (MS).

In one embodiment, the present invention provides a compound of the present invention for use in treating or preventing a neurodegeneration disease in a subject. In one embodiment, the present invention provides a compound of the present invention for use in treating a neurodegeneration disease in a subject. Exemplary neurodegeneration diseases include, but are not limited to, Alzheimer's disease, vascular dementia, Parkinson's disease and Huntington's disease. In a certain embodiment, the neurodegeneration disease described herein is associated with an abnormal blood brain barrier.

In one embodiment, the present invention provides a compound of the present invention for use in treating or preventing a subject with or at risk of vascular dementia. In one embodiment, the present invention provides a compound of the present invention for use in treating a subject with or at risk of vascular dementia. In a certain embodiment, the vascular dementia is associated with Alzheimer's disease.

In certain embodiments, the present invention provides a compound of the present invention for use in decreasing beta amyloid, referred to as "Aβ" accumulation in the brain of a subject. In a further embodiment, the beta amyloid is Abeta-42.

In one embodiment, the present invention provides a compound of the present invention for use in slowing or delaying the progression of cognitive function decline in patients with mild Alzheimer's disease. In certain embodiment, the present invention provides a compound of the present invention for use as an adjunct to an agent that used to provide symptomatic treatment to patients with Alzheimer's disease. For example, when the neurodegenerative disease is or is similar to Alzheimer's disease, the subject may be treated with other agents targeting Alzheimer's disease such as ARICEPT® or donepezil, COGNEX® or tacrine, EXELON® or rivastigmine, REMINYL® or galantamine, anti-amyloid vaccine, Abeta-lowering therapies, mental exercise or stimulation. In certain embodiments, the present invention provides a compound of the present invention for use in slowing or delaying the progression of cognitive function decline in a patient with mild or moderate Alzheimer's disease and/or cerebrovascular disease (CVD), wherein the patient who has been administered an agent used to provide symptomatic treatment to Alzheimer's disease (e.g., ARICEPT® or memantine) for 6 months or longer. In certain embodiments, the present invention provides a compound of the present invention for use in slowing or delaying the progression of cognitive function decline in a patient with mild or moderate Alzheimer's disease and cerebral small vessel disease (SVD), wherein the patient who has been administered an agent used to provide symptomatic treatment to Alzheimer's disease (e.g., ARICEPT® or memantine) for 6 months or longer.

In certain embodiments, the present invention provides a compound of the present invention for use in treating or preventing metabolic bone diseases. In some embodiments, the present invention provides a compound of the present invention for use in treating metabolic bone diseases. Exemplary metabolic bone diseases include, diseases associated with loss of bone mass and density including, but are not limited to, osteoporosis and osteopenic diseases. Exemplary osteoporosis and osteopenic diseases include, but are not limited to, bone marrow abnormalities, dyslipidemia, Paget's diseases, type II diabetes, metabolic syndrome, insulin resistance, hyperparathyroidism and related diseases. In a further embodiment, the present invention provides a compound of the present invention for use in preventing and/or reducing loss of bone mass and/or loss of bone density leads to preventing or reducing symptoms associated with metabolic bone diseases such as osteoporosis and/or osteopenic diseases.

In certain embodiments, the present invention provides a compound of the present invention for use in treating metabolic bone diseases, wherein the medicament is used with additional therapeutic agents used in the treatment of metabolic bone diseases. For example, when the metabolic bone disease is osteoporosis additional therapeutic agents such as bisphosphates (e.g., alendronate, ibandromate, risedronate, calcitonin, raloxifene), a selective estrogen modulator (SERM), estrogen therapy, hormone replacement therapy (ET/HRT) and teriparatide may be used.

One aspect of the present invention provides a compound of the present invention for use the use in treating and/or preventing ocular diseases. In some embodiments, the present invention provides a compound of the present invention for use in treating ocular diseases. Ocular diseases applicable in the present invention may be associated with the breakdown of the inner blood-retinal barrier (iBRB). Exemplary ocular diseases relate to diabetic ocular, which include macular edema, diabetic retinopathy, posterior uveitis, retinal vein occlusion and the like. More ocular diseases include, but are not limited to, central retinal vein occlusion, branched retinal vein occlusion, Irvine-Gass syndrome (post cataract and post-surgical), retinitis pigmentosa, pars planitis, birdshot retinochoroidopathy, epiretinal membrane, choroidal tumors, cystic macular edema, parafoveal telengiectasis, tractional maculopathies, vitreomacular traction syndromes, retinal detachment, neuroretinitis, idiopathic macular edema, and the like. More details of using Lp-PLA$_2$ inhibitor to treat eye diseases are provided in WO2012/080497, which is incorporated by reference herein.

Further, some embodiments of the present invention provide a compound of the present invention for use in treating or preventing diabetic macular edema in a subject. In some embodiments, the present invention provides a compound of the present invention for use in treating diabetic macular edema in a subject.

In certain embodiments, the present invention provides a compound of the present invention for use in treating or preventing a subject with or at risk of macular edema. In some embodiments, the present invention provides a compound of the present invention for use in treating a subject with or at risk of macular edema. In a further embodiment, the macular edema is associated with diabetic ocular disease, for example, diabetic macular edema or diabetic retinopathy. In yet a further embodiment, the macular edema is associated with posterior uveitis.

In certain embodiments, the present invention provides a compound of the present invention for use in treating or preventing glaucoma or macular degeneration. In some embodiments, the present invention provides a compound of the present invention for use in treating glaucoma or macular degeneration.

In one embodiment, the present invention provides a compound of the present invention for use in treating or preventing a disease associated with the breakdown of the inner blood-retinal barrier in a subject in need thereof. In one embodiment, the present invention provides a compound of the present invention for use in treating a disease associated with the breakdown of the inner blood-retinal barrier in a subject in need thereof.

In one embodiment, systemic inflammatory diseases such as, juvenile rheumatoid arthritis, inflammatory bowel disease, Kawasaki disease, multiple sclerosis, sarcoidosis, polyarteritis, psoriatic arthritis, reactive arthritis, systemic lupus erythematosus, Vogt-Koyanagi-Harada syndrome, Lyme disease, Bechet's disease, ankylosing sponsylitis, chronic granulomatous disease, enthesitis, may be the underlying cause of posterior uveitis affecting the retina, and which can result in macula edema. In one embodiment, the present invention provides a compound of the present invention for use in treating posterior uveitis or any of these systemic inflammatory diseases.

In certain embodiments, the present invention provides a compound of the present invention for use in treating or preventing disease associated with macrophage polarization, for example, M1/M2 macrophage polarization. In some embodiments, the present invention provides the use of a compound of the present invention for the preparation of a medicament for treating disease associated with macrophage polarization, for example, M1/M2 macrophage polarization. Exemplary diseases associated with macrophage polarization include, but are not limited to, liver cirrhosis, skin psoriasis, atopic dermatitis, pulmonary emphysema, chronic pancreatitis, chronic gastritis, aortic aneurysm, atherosclerosis, multiple sclerosis, amyotrophic lateral sclerosis (ALS), ischemic cardiomyopathy, chronic heart failure post myocardial infarction (MI) and other autoimmune diseases that are associated with macrophage polarization.

F. Composition

The compounds of the present invention may be formulated into pharmaceutical compositions prior to administration to a subject. Accordingly, one aspect of the invention is directed to pharmaceutical compositions comprising a compound of the invention and a pharmaceutically acceptable excipient. In accordance with another aspect of the invention, a process is provided for the preparation of a pharmaceutical composition including admixing a compound of the above referenced formulas or salts thereof, solvates etc thereof, with one or more pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the condition being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of the present invention will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of present invention for the treatment of the disease described herein will generally be in the range of 0.1 to 100 mg/kg body weight of recipient per day and more usually in the range of 1 to 10 mg/kg body weight per day. Thus, for example, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. It is envisaged that similar dosages would be appropriate for treatment of the other conditions referred to above.

The pharmaceutical compositions of the invention may contain one or more compounds of the invention. In some embodiments, the pharmaceutical compositions may contain more than one compound of the invention. For example, in some embodiments, the pharmaceutical compositions may contain two or more compounds of the invention. In addition, the pharmaceutical compositions may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of the above referenced formulas with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically acceptable excipients may vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more compounds of the above referenced formulas described herein or a pharmaceutically acceptable salt thereof and 0.01 to 5 g of one or more pharmaceutically acceptable excipients.

In another embodiment, the present invention is directed a pharmaceutical composition for the treatment of neurodegeneration disease comprising a compound described herein or a pharmaceutically acceptable salt thereof.

What is claimed is:

1. A compound or a pharmaceutically acceptable salt thereof having the structure of Formula (I-4)

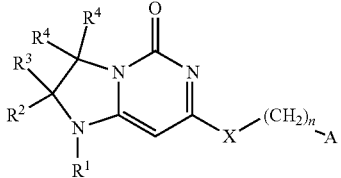

Formula (I-4)

wherein
  $R^1$ is selected from the group consisting of H, $C_{1-3}$alkyl, and —C(O)—$C_{1-3}$alkyl; and
  $R^2$ and $R^3$ together with the carbon to which they are attached form a 4-, 5- or 6-membered saturated ring, which ring
    optionally contains one heteroatom ring member selected from N or O, and
    is optionally substituted with one substituent of -L-K, wherein
      L is selected from the group consisting of C(O), $CH_2$, and $S(O)_2$, and
      K is selected from the group consisting of $C_{1-3}$alkyl, phenyl, and $C_{3-6}$cycloalkyl;
  or $R^1$ and $R^2$ together with the nitrogen and carbon to which they are attached form a 6-membered saturated ring, which ring
    optionally contains one or two additional heteroatom ring members independently selected from the group consisting of N, O, C(O), S, S(O), and $S(O)_2$, and
    is optionally substituted with one or more substituents independently selected from the group consisting of OH, halo, $NR^{1a}R^{1b}$, COOH, and —Y—$R^c$, wherein
      Y is absent or is selected from the group consisting of C(O), $S(O)_2$, —C(O)—C(O)—, and $CH_2$, and
      $R^c$ is selected from the group consisting of
        $C_{1-5}$alkyl optionally substituted with one or more substituents independently selected from the group consisting of $NR^{2a}R^{2b}$, $C_{3-6}$ cycloalkyl, and —COOH,
        $C_{1-3}$haloalkyl,
        $C_{1-3}$alkoxyl,
        $NR^{3a}R^{3b}$,
        —$(CH_2)_p$—C(O)—O—$C_{1-3}$alkyl, wherein p is 1, 2, or 3 and the —$(CH_2)_p$— is optionally substituted by one or more methyl,
        —$(CH_2)_q$—$C_{3-6}$ cycloalkyl, wherein q is 1, 2, or 3, the cycloalkyl is optionally substituted with $NR^{4a}R^{4b}$, and the —$(CH_2)_q$— is optionally substituted by one or more methyl, and
        heterocyclyl optionally substituted with one or more substituents independently selected from the group consisting of halo and $NR^{5a}R^{5b}$,
      wherein $R^{1a}$, $R^{1b}$, $R^{2a}$, $R^{2b}$, $R^{3a}$, $R^{3b}$, $R^{4a}$, $R^{4b}$, $R^{5a}$, and $R^{5b}$ are independently H or $C_{1-3}$alkyl; and
  $R^3$ is H;
  each occurrence of $R^4$ is independently H or D;
  X is absent or is selected from the group consisting of
    —O—,
    —NH—, and
    —N($C_{1-3}$ alkyl)-,
  n is 1 or 2; or
  X is —O—$CH_2$-bicyclo[1.1.1]pentanyl-$CH_2$—O— and n is 0; and
  A is unsubstituted thiophenyl, or
  A is

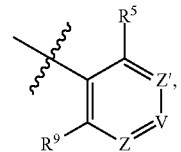

wherein
  $R^5$ and $R^9$ are independently H or halo,
  Z' is N or $CR^6$,
  Z is N or $CR^8$,
    wherein $R^6$ and $R^8$ are independently selected from the group consisting of H, CN, halo, $C_{1-3}$alkyl, $C_{1-3}$haloalkyl, —$S(O)_2$—$C_{1-3}$alkyl and —S(O)—$C_{1-3}$alkyl, and
  V is $CR^7$, wherein $R^7$ is -Q-$(CH_2)_m$—W, wherein
    Q is O, N, or $CH_2$,
    m is 0 or 1, and
    W is pyridyl, and
    wherein said pyridyl is optionally substituted with one or more substituents independently selected from the group consisting of $C_{1-3}$haloalkyl, CN, halo, and $C_{1-5}$ alkyl.

2. The compound or a pharmaceutically acceptable salt thereof according to claim 1, wherein
  $R^1$ and $R^2$ together with the nitrogen and carbon to which they are attached form a 6-membered saturated, unsubstituted ring, which ring contains one additional heteroatom ring member selected from the group consisting of N, O, and C(O); and
  $R^3$ is H;
  each $R^4$ is H;
  X is O;
  n is 1 or 2; and
  A is

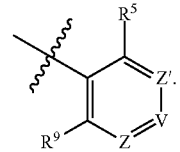

3. The compound or a pharmaceutically acceptable salt thereof according to claim 1, wherein $R^1$ and $R^2$ together with the nitrogen and carbon to which they are attached form a 6-membered saturated ring, which ring optionally contains one additional heteroatom ring member selected from the group consisting of N, O, and C(O), and $R^3$ is H.

4. The compound or a pharmaceutically acceptable salt thereof according to claim 1, wherein $R^4$ is H.

5. The compound or a pharmaceutically acceptable salt thereof according to claim 1, wherein X is O.

6. The compound or a pharmaceutically acceptable salt thereof according to claim 1, wherein n is 1.

7. The compound or a pharmaceutically acceptable salt thereof according to claim 1, wherein A is

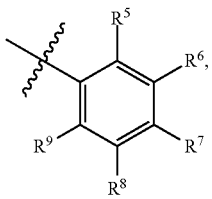

wherein
$R^5$ and $R^9$ are independently H or F, and
$R^6$ and $R^8$ are independently selected from the group consisting of H, CN, and F, and
$R^7$ is —O—W.

8. The compound or a pharmaceutically acceptable salt thereof according to claim 1, wherein A is

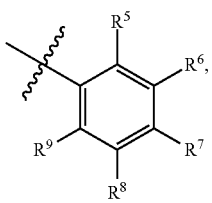

wherein
$R^5$ and $R^9$ are independently H or F, and
$R^6$ and $R^8$ are independently selected from the group consisting of H, CN, and F, and
$R^7$ is —O—W, wherein W is pyridyl, and said pyridyl is optionally substituted with one or more substituents independently selected from the group consisting of $CF_3$ and $CH_3$.

9. The compound or a pharmaceutically acceptable salt thereof according to claim 1 having the structure of Formula (A-4), Formula (A-4)

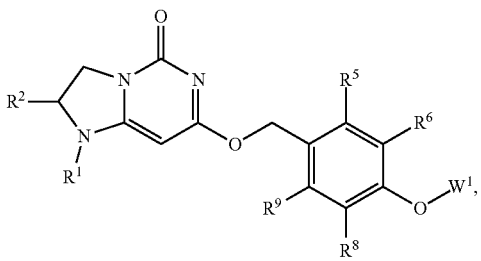

wherein
$R^1$ and $R^2$ together with the nitrogen and carbon to which they are attached form a 6-membered saturated ring, which ring contains one additional heteroatom ring member selected from the group consisting of N, O, and C(O), and which ring has no further substitution;

$R^5$ and $R^9$ are independently H or F;

$R^6$ and $R^8$ are independently selected from the group consisting of H or F; and $W^1$ is pyridyl, wherein said pyridyl is optionally substituted with one or two substituents independently selected from the group consisting of $CF_3$ and $CH_3$.

10. The compound or a pharmaceutically acceptable salt thereof according to claim 1 having the structure of Formula (A-5), Formula (A-5)

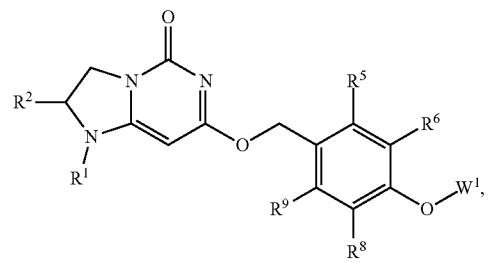

wherein
$R^1$ and $R^2$ together with the nitrogen and carbon to which they are attached form a 6-membered saturated ring, which ring contains one additional heteroatom ring member O and which ring has no further substitution;

$R^5$ and $R^9$ are independently H or F;

$R^6$ and $R^8$ are independently selected from the group consisting of H or F; and $W^1$ is pyridyl, wherein said pyridyl is optionally substituted with one or two substituents independently selected from the group consisting of $CF_3$ and $CH_3$.

11. A pharmaceutical composition comprising the compound or a pharmaceutically acceptable salt thereof according to claim 1, and a pharmaceutically acceptable excipient.

12. A method for treating neurodegeneration disease in a subject in need thereof comprising administering to the subject a therapeutically effective amount of the compound or a pharmaceutically acceptable salt thereof according to claim 1.

13. The method according to claim 12, wherein the neurodegeneration disease is Alzheimer's disease.

14. A method for treating atherosclerosis in a subject in need thereof comprising administering to the subject a therapeutically effective amount of the compound or a pharmaceutically acceptable salt thereof according to claim 1.

* * * * *